United States Patent
Inayama et al.

(10) Patent No.: US 11,706,977 B2
(45) Date of Patent: Jul. 18, 2023

(54) HETEROCYCLIC COMPOUND, COMPOSITION INCLUDING THE SAME, AND ORGANIC LIGHT-EMITTING DEVICE INCLUDING THE HETEROCYCLIC COMPOUND

(71) Applicant: Samsung Electronics Co., Ltd., Suwon-si (KR)

(72) Inventors: Satoshi Inayama, Kanagawa (JP); Shiro Irisa, Kanagawa (JP); Keisuke Korai, Kanagawa (JP); Rie Sakurai, Suwon-si (KR); Mitsunori Ito, Kanagawa (KR); Masaki Numata, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 629 days.

(21) Appl. No.: 16/244,339

(22) Filed: Jan. 10, 2019

(65) Prior Publication Data
US 2019/0214570 A1    Jul. 11, 2019

(30) Foreign Application Priority Data

Jan. 11, 2018 (JP) .................................. 2018-002610
Nov. 23, 2018 (KR) ........................ 10-2018-0146761

(51) Int. Cl.
*H10K 85/60*    (2023.01)
*C07D 403/14*    (2006.01)
(Continued)

(52) U.S. Cl.
CPC ......... *H10K 85/654* (2023.02); *C07D 403/14* (2013.01); *H10K 85/6572* (2023.02);
(Continued)

(58) Field of Classification Search
CPC ..................... H10K 85/654; H10K 85/6572
See application file for complete search history.

(56) References Cited

U.S. PATENT DOCUMENTS 9,406,892 B2    8/2016    Zeng et al.
2005/0127823 A1    6/2005    Iwakuma et al.
(Continued)

FOREIGN PATENT DOCUMENTS

EP    2818468 A2    12/2014
JP    2010199067 A    9/2010
(Continued)

OTHER PUBLICATIONS

STN Structure search conducted by the Examiner for U.S. Appl. No. 16/244,339. 2021. All Pages. (Year: 2021).*

(Continued)

*Primary Examiner* — Daniel P Malley, Jr.
(74) *Attorney, Agent, or Firm* — Cantor Colburn LLP

(57) ABSTRACT

A heterocyclic compound represented by Formula 1:

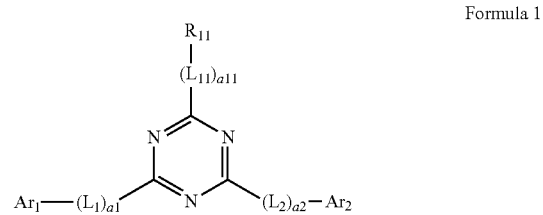

Formula 1 wherein, in Formula 1, groups and variables are the same as described in the specification.

17 Claims, 1 Drawing Sheet

(51) Int. Cl.
- *H10K 50/11* (2023.01)
- *H10K 50/15* (2023.01)
- *H10K 50/16* (2023.01)
- *H10K 50/17* (2023.01)
- *H10K 50/82* (2023.01)
- *H10K 50/813* (2023.01)
- *H10K 71/00* (2023.01)
- *H10K 71/12* (2023.01)
- *H10K 71/16* (2023.01)
- *H10K 101/10* (2023.01)
- *H10K 101/30* (2023.01)
- *H10K 101/40* (2023.01)
- *H10K 102/00* (2023.01)
- *H10K 102/10* (2023.01)

(52) U.S. Cl.
CPC .............. *H10K 50/11* (2023.02); *H10K 50/15* (2023.02); *H10K 50/16* (2023.02); *H10K 50/17* (2023.02); *H10K 50/171* (2023.02); *H10K 50/813* (2023.02); *H10K 50/82* (2023.02); *H10K 71/00* (2023.02); *H10K 71/12* (2023.02); *H10K 71/164* (2023.02); *H10K 85/6574* (2023.02); *H10K 2101/10* (2023.02); *H10K 2101/30* (2023.02); *H10K 2101/40* (2023.02); *H10K 2102/00* (2023.02); *H10K 2102/103* (2023.02); *H10K 2102/351* (2023.02)

(56) References Cited

U.S. PATENT DOCUMENTS

| | | |
|---|---|---|
| 2008/0145699 A1 | 6/2008 | Yabe et al. |
| 2009/0236973 A1 | 9/2009 | Yabe et al. |
| 2010/0213438 A1 | 8/2010 | Cho et al. |
| 2012/0241732 A1 | 9/2012 | Endo et al. |
| 2013/0140549 A1 | 6/2013 | Xia et al. |
| 2013/0248845 A1 | 9/2013 | Ogawa et al. |
| 2014/0131665 A1 | 5/2014 | Xia et al. |
| 2014/0209885 A1 | 7/2014 | Tada et al. |
| 2015/0025239 A1 | 1/2015 | Ahn et al. |
| 2015/0171340 A1* | 6/2015 | Lee ..................... H01L 51/0067 257/40 |
| 2015/0249215 A1 | 9/2015 | Ono et al. |
| 2015/0318487 A1 | 11/2015 | Ito et al. |
| 2015/0318510 A1 | 11/2015 | Ito et al. |
| 2015/0336937 A1 | 11/2015 | Lee et al. |
| 2015/0337197 A1 | 11/2015 | Jatsch et al. |
| 2015/0357582 A1 | 12/2015 | Hirata et al. |
| 2016/0020397 A1 | 1/2016 | Sannomiya et al. |
| 2017/0062733 A1 | 3/2017 | Yamaki et al. |
| 2017/0141323 A1 | 5/2017 | Miyazaki et al. |
| 2017/0170409 A1 | 6/2017 | Xia et al. |
| 2017/0194574 A1 | 7/2017 | Ishidai et al. |
| 2017/0237017 A1 | 8/2017 | Parham et al. |
| 2018/0254426 A1 | 9/2018 | Ikenaga et al. |
| 2018/0337348 A1* | 11/2018 | Jung ..................... H10K 50/11 |
| 2020/0176689 A1* | 6/2020 | Jung ..................... C07D 405/14 |
| 2021/0070717 A1* | 3/2021 | Li ..................... H01L 51/0067 |

FOREIGN PATENT DOCUMENTS

| | | |
|---|---|---|
| JP | 2014521604 A | 8/2014 |
| JP | 2015512875 A | 4/2015 |
| JP | 2016506399 A | 3/2016 |
| JP | 2016128432 A | 7/2016 |
| JP | 2017092277 A | 5/2017 |
| JP | 2017530945 A | 10/2017 |
| JP | 6249150 B2 | 12/2017 |
| KR | 1020100094415 A | 8/2010 |
| KR | 1020120098561 A | 9/2012 |
| KR | 1020130077471 A | 7/2013 |
| KR | 1020140034710 A | 3/2014 |
| KR | 1020130085364 A | 1/2015 |
| KR | 1020150010387 A | 1/2015 |
| KR | 1020150077220 A | 7/2015 |
| KR | 1020150106668 A | 9/2015 |
| KR | 1020150107442 A | 9/2015 |
| KR | 20150124637 A | 11/2015 |
| KR | 20160066308 A | 6/2016 |
| KR | 20160079415 A | 7/2016 |
| KR | 20170134490 A | 12/2017 |
| KR | 20170126812 A | 7/2018 |
| WO | 2003078541 A1 | 9/2003 |
| WO | 2006062062 A1 | 6/2006 |
| WO | 2006067976 A1 | 6/2006 |
| WO | 2011070963 A1 | 6/2011 |
| WO | 2012023947 A1 | 2/2012 |
| WO | 2012077520 A | 6/2012 |
| WO | 2012077520 A1 | 6/2012 |
| WO | 2013012298 A1 | 1/2013 |
| WO | 2013038804 A1 | 3/2013 |
| WO | 2013122402 A1 | 8/2013 |
| WO | 20130122402 A1 † | 8/2013 |
| WO | 20130137001 A1 † | 9/2013 |
| WO | 2014042265 A1 | 3/2014 |
| WO | 2014094963 A1 | 6/2014 |
| WO | 2014128945 A1 | 8/2014 |
| WO | 2014132922 A | 9/2014 |
| WO | 2015009102 A1 | 1/2015 |
| WO | 2015137472 A1 | 9/2015 |
| WO | 20160023608 A1 † | 2/2016 |
| WO | 2016105161 A2 | 6/2016 |
| WO | 2016105165 A2 | 6/2016 |
| WO | 2017016630 A1 | 2/2017 |
| WO | 2017043770 A1 | 3/2017 |
| WO | 2018016742 A1 | 1/2018 |

OTHER PUBLICATIONS

STN structure search for U.S. Appl. No. 16/244,339 conducted by the Examiner Jan. 7, 2022. All Pages. (Year: 2022).*
STN structure search for application U.S. Appl. No. 16/22,339 conducted by the Examiner Apr. 21, 2022, All Pages. (Year: 2022).*
STN structure search for U.S. Appl. No. 16/244,339 conducted by the Examiner on Oct 17, 2022, All Pages. (Year: 2022).*
STN Structure search conducted by the Examiner for U.S. Appl. No. 16/244,339. All Pages, 2023. (Year: 2023).*
English Translation of Office Action dated Dec. 7, 2021, issued in corresponding JP Patent Application No. 2018-002610, 9 pp.
Office Action dated Dec. 7, 2021, issued in corresponding JP Patent Application No. 2018-002610, 8 pp.

* cited by examiner
† cited by third party

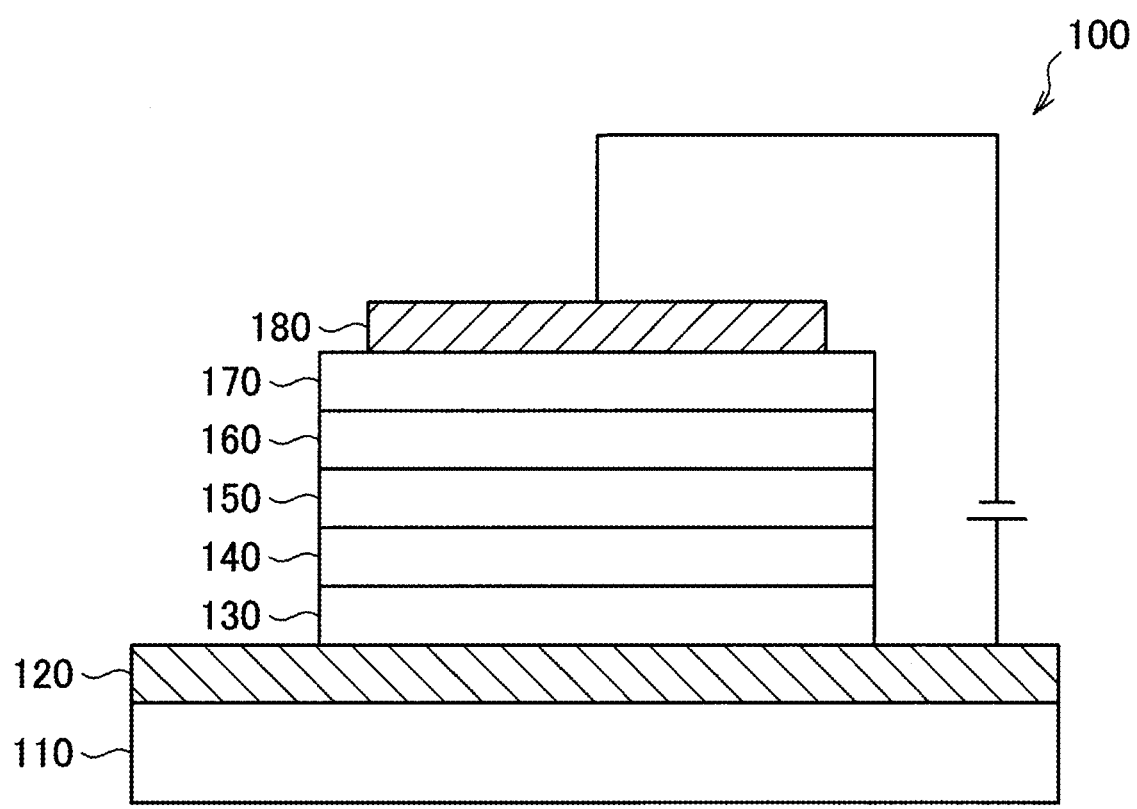

HETEROCYCLIC COMPOUND, COMPOSITION INCLUDING THE SAME, AND ORGANIC LIGHT-EMITTING DEVICE INCLUDING THE HETEROCYCLIC COMPOUND

CROSS-REFERENCE TO RELATED APPLICATIONS

This application claims priority to Japanese Patent Application No. 2018-002610, filed on Jan. 11, 2018 in the Japanese Patent Office, and Korean Patent Application No. 10-2018-0146761, filed on Nov. 23, 2018, 2018 in the Korean Intellectual Property Office, and all the benefits accruing therefrom under 35 U.S.C. § 119, the contents of which are incorporated herein in their entireties by reference.

BACKGROUND

1. Field

One or more embodiments relate to a heterocyclic compound, a material for an organic light-light-emitting device including the heterocyclic compound, and an organic light-emitting device including the material.

2. Description of the Related Art

Organic light-emitting devices (OLEDs) are self-emission devices that produce full-color images, and that also have wide viewing angles, high contrast ratios, short response times, and excellent characteristics in terms of brightness, driving voltage, and response speed.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in an emission layer region to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Aspects of the present disclosure provide a heterocyclic compound, a composition including the heterocyclic compound, and an organic light-emitting device including the heterocyclic compound.

The organic light-emitting device including the heterocyclic compound may provide high current efficiency and a long lifespan. In addition, the heterocyclic compound may provide characteristics suitable for use in solution coating.

Additional aspects will be set forth in part in the description which follows and, in part, will be apparent from the description, or may be learned by practice of the presented embodiments.

An aspect of the present disclosure provides a heterocyclic compound represented by Formula 1:

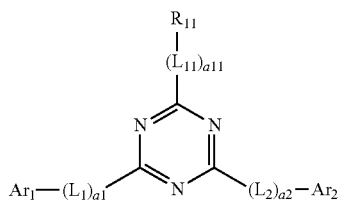

Formula 1

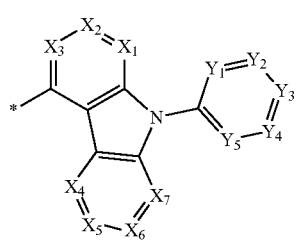

Formula 2-1

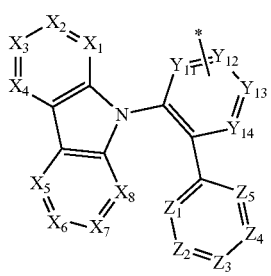

Formula 2-2

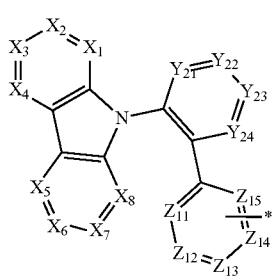

Formula 2-3

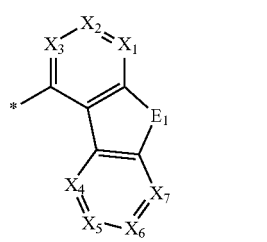

Formula 2-4

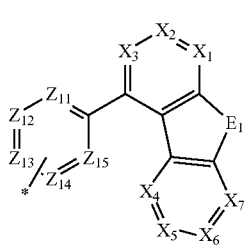

Formula 2-5

-continued

Formula 2-6

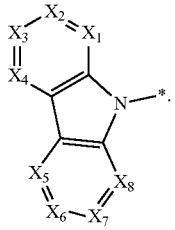

In Formulae 1 and 2-1 to 2-6,
$L_1$, $L_2$, and $L_{11}$ may each independently be selected from a single bond, a substituted or unsubstituted $C_5$-$C_{60}$ carbocyclic group, and a substituted or unsubstituted $C_1$-$C_{60}$ heterocyclic group,
a1, a2, and a11 may each independently be an integer from 1 to 10,
$Ar_1$ may be selected from groups represented by Formulae 2-1 to 2-5,
$Ar_2$ may be selected from groups represented by Formulae 2-1 to 2-6,
$X_1$ to $X_8$ may each independently be C(R12) or N,
$Y_1$ to $Y_5$ may each independently be C($R_{13}$) or N,
$Z_1$ to $Z_5$ may each independently be C($R_{14}$) or N,
$Y_{11}$ to $Y_{14}$ may each independently be selected from C($R_{16}$), N, and carbon linked to $L_1$ or $L_2$,
$Z_{11}$ to $Z_{15}$ may each independently be selected from C($R_{16}$), N, and carbon linked to $L_1$ or $L_2$,
$Y_{21}$ to $Y_{24}$ may each independently be C($R_{17}$) or N,
$E_1$ may be selected from C($R_{21}$)(R22), Si($R_{23}$)($R_{24}$), N($R_{25}$), O, and S,
wherein one selected from $Y_{11}$ to $Y_{14}$ may be carbon linked to $L_1$ or $L_2$, and
one selected from $Z_{11}$ to $Z_{15}$ may be carbon linked to $L_1$ or $L_2$,
$R_1$, $R_{11}$ to $R_{17}$, and $R_{21}$ to $R_{25}$ may each independently be selected from hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)(Q2)($Q_3$), and —N($Q_1$)($Q_2$),
any neighboring groups selected from $R_{12}$ to $R_{17}$ and $R_{21}$ to $R_{25}$ may optionally be linked to form a substituted or unsubstituted $C_5$-$C_{30}$ carbocyclic group or a substituted or unsubstituted $C_2$-$C_{30}$ heterocyclic group,
wherein each of $R_{15}$ and $R_{17}$ is not a substituted or unsubstituted carbazolyl group, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_3$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the unsubstituted $C_7$-$C_{60}$ alkylaryl group, the substituted $C_6$-$C_{60}$ aryloxy group, the substituted $C_6$-$C_{60}$ arylthio group, the substituted $C_1$-$C_{60}$ heteroaryl group, the substituted $C_2$-$C_{60}$ alkylheteroaryl group, the substituted $C_1$-$C_{60}$ heteroaryloxy group, the substituted $C_1$-$C_{60}$ heteroarylthio group, the substituted monovalent non-aromatic condensed polycyclic group, the substituted monovalent non-aromatic condensed heteropolycyclic group, the substituted $C_5$-$C_{30}$ carbocyclic group, and the substituted $C_2$-$C_{30}$ heterocyclic group may be selected from:
deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{50}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_9$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), and —C(=O)($Q_{11}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), and —C(=O)($Q_{21}$); and —Si($Q_{31}$)($Q_{32}$)($Q_{33}$), —N($Q_{31}$)($Q_{32}$), and —C(=O)($Q_{31}$), $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenyl pyridinyl group, a phenyl pyrimidinyl group, a phenyl triazinyl group, a diphenyl pyridinyl group, a diphenyl pyrimidinyl group, a diphenyl triazinyl group, a pyridinyl phenyl group, a dipyridinyl phenyl group, a pyrimidinyl phenyl group, a dipyrimidinyl phenyl group, a triazinyl phenyl group, a ditriazinyl phenyl group, a fluorenyl group, a spiro-bifluorenyl group, a dimethylfluorenyl group, a diphenyl fluorenyl group, a carbazolyl group, a phenylcarbazolyl group, a biphenylcarbazolyl group, a dibenzofuranyl group, a phenyl dibenzofuranyl group, a diphenyl dibenzofuranyl group, a dibenzothiophenyl group, a phenyl dibenzothiophenyl group, and a diphenyl dibenzothiophenyl group, and

* indicates a binding site to a neighboring atom.

Another aspect of the present disclosure provides a composition including at least one of a heterocyclic compound represented by Formula 1.

Another aspect of the present disclosure provides an organic light-emitting device including:
a first electrode;
a second electrode; and
an organic layer disposed between the first electrode and the second electrode,
wherein the organic layer includes an emission layer, and
wherein the organic layer includes at least one heterocyclic compound.

BRIEF DESCRIPTION OF THE DRAWING

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Heterocyclic Compound

In an embodiment, a heterocyclic compound represented by Formula 1 is provided. The heterocyclic compound represented by Formula 1 according to an embodiment may be described as follows:

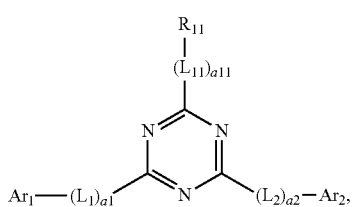

Formula 1

In Formula 1, $L_1$ to $L_2$ and $L_{11}$ may each independently be selected from a single bond, a substituted or unsubstituted $C_5$-$C_{50}$ carbocyclic group, and a substituted or unsubstituted $C_1$-$C_{60}$ heterocyclic group.

For example, $L_1$ to $L_2$ and $L_{11}$ may each independently be selected from:
 a single bond, a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group; and
 a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group, each substituted with at least one selected from deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_3$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a curmarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonyl group, and a thioxanthonyl group.

In Formula 1, a1 to a2 and a11 may each independently be an integer from 1 to 10.

For example, a1 to a2 and a11 may each independently be an integer from 1 to 2, but embodiments of the present disclosure are not limited thereto.

In Formula 1, $Ar_1$ may be selected from groups represented by Formulae 2-1 to 2-5, and $Ar_2$ may be selected from groups represented by Formulae 2-1 to 2-6:

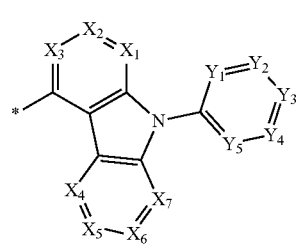

Formula 2-1

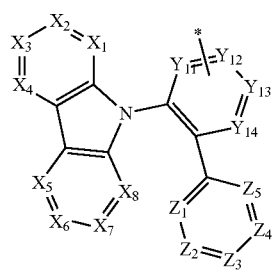

Formula 2-2

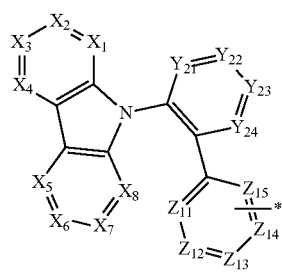

Formula 2-3

-continued

Formula 2-4

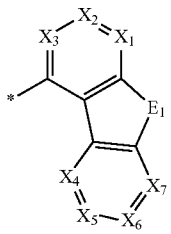

Formula 2-5

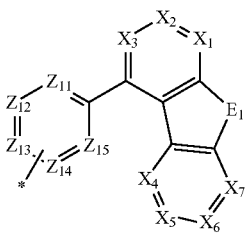

Formula 2-6

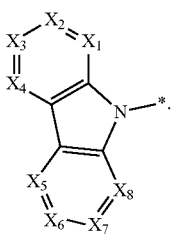

For example, in Formula 1, $Ar_1$ may be selected from groups represented by Formulae 2-1 to 2-3, and $Ar_2$ may be selected from groups represented by Formulae 2-1 to 2-3 and 2-6.

In Formulae 2-1 to 2-6, $X_1$ to $X_8$ may each independently be $C(R_{12})$ or N.

For example, $X_1$ to $X_8$ may each independently be $C(R_{12})$, but embodiments of the present disclosure are not limited thereto.

In Formulae 2-1 to 2-6, $Y_1$ to $Y_5$ may each independently be $C(R_{13})$ or N.

For example, i) $Y_1$ to $Y_5$ may be $C(R_{13})$, ii) $Y_1$ to $Y_2$ and $Y_4$ to $Y_5$ may be $C(R_{13})$, and $Y_3$ may be N, iii) $Y_1$ to $Y_3$ and $Y_5$ may be $C(R_{13})$, and $Y_4$ may be N, or iv) $Y_1$ to $Y_4$ may be $C(R_{13})$, and $Y_5$ may be N, but embodiments of the present disclosure are not limited thereto.

For example, when $Y_3$ and $Y_4$ are $C(R_{13})$, neighboring groups $R_{13}$ may be linked to form a benzene group, a benzofuran group, or a benzothiophene group.

In Formulae 2-1 to 2-6, $Z_1$ to $Z_5$ may each independently be $C(R_{14})$ or N.

For example, i) $Z_1$ to $Z_5$ may be $C(R_{14})$, ii) $Z_1$ to $Z_2$ and $Z_4$ to $Z_5$ may be $C(R_{14})$, and $Z_3$ may be N, iii) $Z_1$ to $Z_3$ and $Z_5$ may be $C(R_{14})$, and $Z_4$ may be N, or iv) $Z_1$ to $Z_4$ may be $C(R_{14})$, and $Z_5$ may be N, but embodiments of the present disclosure are not limited thereto.

For example, when $Z_3$ and $Z_4$ are $C(R_{14})$, neighboring groups $R_{14}$ may be linked to form a benzene group, a benzofuran group, or a benzothiophene group.

In Formulae 2-1 to 2-6, $Y_{11}$ to $Y_{14}$ may each independently be selected from $C(R_{15})$, N, and carbon linked to $L_1$ or $L_2$, wherein one selected from $Y_{11}$ to $Y_{14}$ may be carbon linked to $L_1$ or $L_2$.

For example, i) $Y_{12}$ may be carbon linked to $L_1$ or $L_2$, and each of $Y_{11}$, $Y_{13}$, and $Y_{14}$ may be $C(R_{15})$, ii) $Y_{12}$ may be carbon linked to $L_1$ or $L_2$, and one selected from $Y_{11}$, $Y_{13}$, and $Y_{14}$ may be N, iii) $Y_{13}$ may be carbon linked to $L_1$ or $L_2$, and each of $Y_{11}$, $Y_{12}$, and $Y_{14}$ may be $C(R_{15})$, or iv) $Y_{13}$ may be carbon linked to $L_1$ or $L_2$, and one selected from $Y_{11}$, $Y_{12}$, and $Y_{14}$ may be N, but embodiments of the present disclosure are not limited thereto.

In Formulae 2-1 to 2-6, $Z_{11}$ to $Z_{15}$ may each independently be selected from $C(R_{16})$, N, and carbon linked to $L_1$ or $L_2$, wherein one selected from $Z_{11}$ to $Z_{15}$ may be carbon linked to $L_1$ or $L_2$.

For example, i) $Z_{13}$ may be carbon linked to $L_1$ or $L_2$, and each of $Z_{11}$, $Z_{12}$, $Z_{14}$, and $Z_{15}$ may be $C(R_{16})$, ii) $Z_{13}$ may be carbon linked to $L_1$ or $L_2$, and one selected from $Z_{11}$, $Z_{12}$, $Z_{14}$, and $Z_{15}$ may be N, iii) $Z_{14}$ may be carbon linked to $L_1$ or $L_2$, and each of $Z_{11}$ to $Z_{13}$ and $Z_{15}$ may be $C(R_{16})$, iv) $Z_{14}$ may be carbon linked to $L_1$ or $L_2$, and one selected from $Z_{11}$ to $Z_{13}$ and $Z_{15}$ may be N, or v) $Z_{13}$ and $Z_{14}$ may be $C(R_{16})$, neighboring groups $R_{16}$ may be linked to form a substituted or unsubstituted $C_5$-$C_{30}$ carbocyclic group or a substituted or unsubstituted $C_2$-$C_{30}$ heterocyclic group, and any carbon in the substituted or unsubstituted $C_5$-$C_{30}$ carbocyclic group or the substituted or unsubstituted $C_2$-$C_{30}$ heterocyclic group may be carbon linked to $L_1$ or $L_2$, but embodiments of the present disclosure are not limited thereto.

For example, when $Z_{13}$ and $Z_{14}$ are $C(R_{16})$, neighboring groups $R_{16}$ may be linked to form a benzene group, a benzofuran group, or a benzothiophene group.

In Formulae 2-1 to 2-6, $Y_{21}$ to $Y_{24}$ may each independently be $C(R_{17})$ or N.

For example, i) $Y_{21}$ to $Y_{24}$ may be $C(R_{17})$, or ii) one selected from $Y_{21}$ to $Y_{24}$ may be N, and the others thereof may be $C(R_{17})$, but embodiments of the present disclosure are not limited thereto.

In Formulae 2-1 to 2-6, $E_1$ may be selected from $C(R_{21})(R_{22})$, $Si(R_{23})(R_{24})$, $N(R_{25})$, O, and S.

For example, when $Ar_1$ or $Ar_2$ is a group represented by Formula 2-1, $L_1$ or $L_2$ which is linked to the group represented by Formula 2-1, respectively, may be selected from:
  a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group; and
  a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group, each substituted with at least one selected from deuterium, a cyano group, a phenyl group, a naphthyl group, and a pyridinyl group, but embodiments of the present disclosure are not limited thereto.

For example, when $Ar_1$ or $Ar_2$ is a group represented by Formula 2-1, $L_1$ or $L_2$ which is linked to the group represented by Formula 2-1, respectively, may be selected from groups represented by Formulae 3-1 to 3-5, but embodiments of the present disclosure are not limited thereto:

3-1

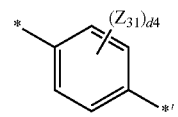

3-2

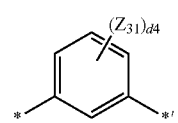

-continued

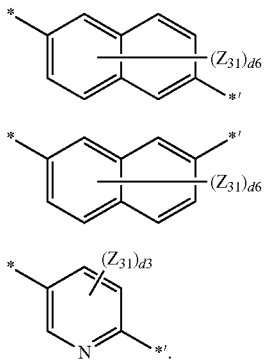

In Formulae 3-1 to 3-5, $Z_{31}$ may be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzosilolyl group, and —Si($Q_{31}$)($Q_{32}$)($Q_{33}$), d4 may be an integer from 0 to 3,
d4 may be an integer from 0 to 4,
d6 may be an integer from 0 to 6, and
* and *' each indicate a binding site to a neighboring atom.

For example, i) in Formulae 2-1 and 2-4, $X_3$ may be $C(R_{12})$ or N, and $R_{12}$ may be hydrogen or deuterium,
ii) in Formula 2-2, iia) when $Y_{11}$ is carbon linked to $L_1$ or $L_2$, $Y_{12}$ may be $C(R_{15})$ or N, and $R_{15}$ may be hydrogen or deuterium, iib) when $Y_{12}$ is carbon linked to $L_1$ or $L_2$, $Y_{11}$ and $Y_{13}$ may each independently be $C(R_{15})$ or N, and $R_{15}$ may be hydrogen or deuterium, iic) when $Y_{13}$ is carbon linked to $L_1$ or $L_2$, $Y_{12}$ and $Y_{14}$ may each independently be $C(R_{15})$ or N, and $R_{15}$ may be hydrogen or deuterium, and iid) when $Y_{14}$ is carbon linked to $L_1$ or $L_2$, $Y_{13}$ may be $C(R_{15})$ or N, and $R_{15}$ may be hydrogen or deuterium, and
iii) in Formulae 2-3 and 2-5, iiia) when $Z_{11}$ is carbon linked to $L_1$ or $L_2$, $Z_{12}$ may be $C(R_{16})$ or N, and $R_{16}$ may be hydrogen or deuterium, iiib) when $Z_{12}$ is carbon linked to $L_1$ or $L_2$, $Z_{11}$ and $Z_{13}$ may each independently be $C(R_{16})$ or N, and $R_{16}$ may be hydrogen or deuterium, iiic) when $Z_{13}$ is carbon linked to $L_1$ or $L_2$, $Z_{12}$ and $Z_{14}$ may each independently be $C(R_{16})$ or N, and $R_{16}$ may be hydrogen or deuterium, iiid) when $Z_{14}$ is carbon linked to $L_1$ or $L_2$, $Z_{13}$ and $Z_{15}$ may each independently be $C(R_{16})$ or N, and $R_{16}$ may be hydrogen or deuterium, and iiie) when $Z_{15}$ is carbon linked to $L_1$ or $L_2$, $Z_{14}$ may be $C(R_{16})$ or N, and $R_{16}$ may be hydrogen or deuterium.

For example, i) when $Ar_1$ or $Ar_2$ is a group represented by Formula 2-2, $Y_{12}$ or $Y_{13}$ may be carbon linked to $L_1$ or $L_2$, and ii) when $Ar_1$ or $Ar_2$ is a group represented by Formula 2-3, iia) $Z_{13}$ or $Z_{14}$ may be carbon linked to $L_1$ or $L_2$, or iib) $Z_{13}$ and $Z_{14}$ may be $C(R_{16})$, and neighboring groups $R_{16}$ may be linked to form a benzene group, a benzofuran group, or a benzothiophene group.

In this embodiment, when $Z_{13}$ and $Z_{14}$ are $C(R_{16})$ and neighboring groups $R_{16}$ are linked to form a benzene group, a benzofuran group, or a benzothiophene group, any carbon in the benzene group, the benzofuran group, or the benzothiophene group may be carbon linked to $L_1$ or $L_2$.

For example, when $Ar_1$ or $Ar_2$ is a group represented by Formula 2-1, $X_5$ may be $C(R_{12})$, and $R_{12}$ may be selected from: hydrogen, a phenyl group, a naphthyl group, a pyridinyl group, a pyrazinyl group, a pyrimidinyl group, and a pyridazinyl group; and a phenyl group, a naphthyl group, a pyridinyl group, a pyrazinyl group, a pyrimidinyl group, and a pyridazinyl group, each substituted with at least one selected from deuterium, —F, —Cl, —Br, —I, a cyano group, a phenyl group, a naphthyl group, a pyridinyl group, a pyrazinyl group, a pyrimidinyl group, and a pyridazinyl group.

For example, when $Ar_1$ or $Ar_2$ is a group represented by Formula 2-1 or 2-2, $Y_2$ or $Y_3$ may be $C(R_{13})$, or $Y_{12}$ or $Y_{13}$ may be $C(R_{15})$, and $R_{13}$ or $R_{15}$ may be a substituted or unsubstituted $C_6$-$C_{60}$ aryl group or a substituted or unsubstituted $C_6$-$C_{60}$ heteroaryl group, but embodiments of the present disclosure are not limited thereto.

For example, when $Ar_2$ is a group represented by Formula 2-6 and $L_2$ is a single bond, $X_1$ may be $C(R_{12})$, and $R_{12}$ may be a substituted or unsubstituted $C_6$-$C_{60}$ aryl group or a substituted or unsubstituted $C_1$-$C_{60}$ heteroaryl group, but embodiments of the present disclosure are not limited thereto.

For example, i) $Ar_1$ may be selected from groups represented by Formulae 2-1 to 2-3, and $Ar_2$ may be a group represented by Formula 2-2 or 2-6; or
ii) $Ar_1$ may be a group represented by Formula 2-3, and $Ar_2$ may be a group represented by Formula 2-3.

In an embodiment, $Ar_1$ may be selected from groups represented by Formulae 2-1(1) to 2-1(6), 2-2(1) to 2-2(18), and 2-3(1) to 2-3(13), and
$Ar_2$ may be selected from groups represented by Formulae 2-1(1) to 2-1(6), 2-2(1) to 2-2(18), 2-3(1) to 2-3(13), and 2-6(1) to 2-6(11), but embodiments of the present disclosure are not limited thereto:

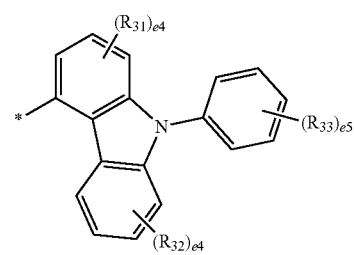

2-1(1)

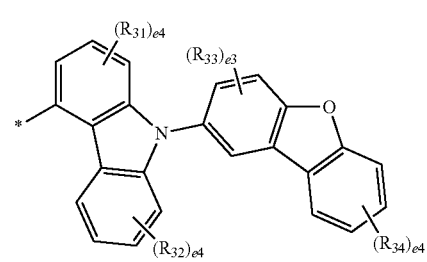

2-1(2)

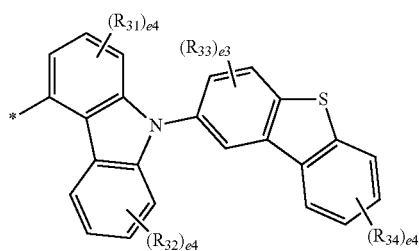
2-1(3)
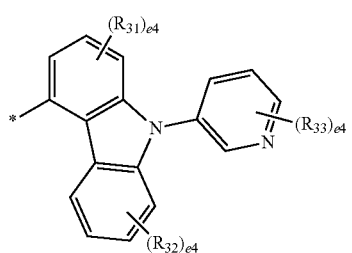
2-1(4)
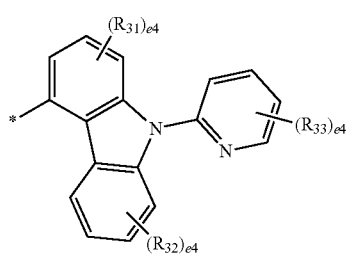
2-1(5)
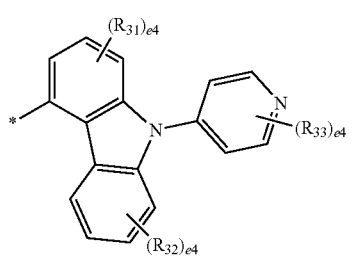
2-1(6)
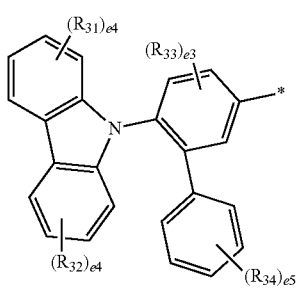
2-2(1)
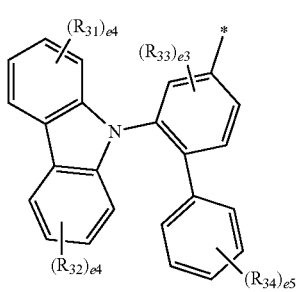
2-2(2)
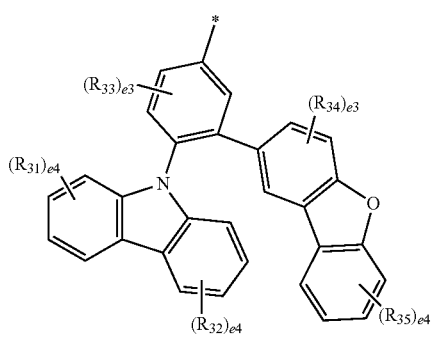
2-2(3)
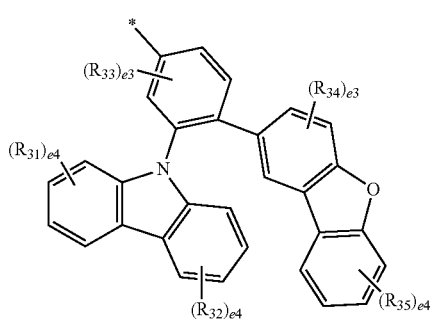
2-2(4)
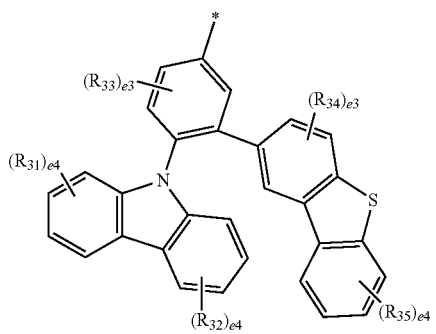
2-2(5)
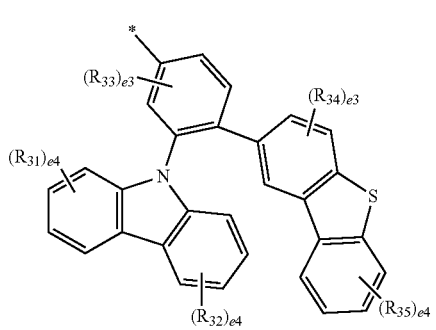
2-2(6)
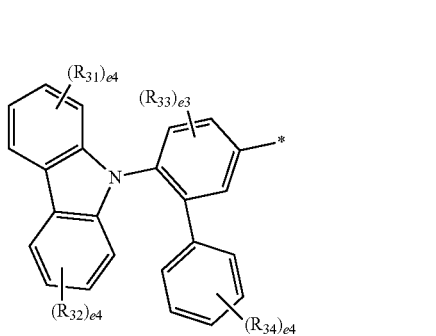
2-2(7)

2-2(8)
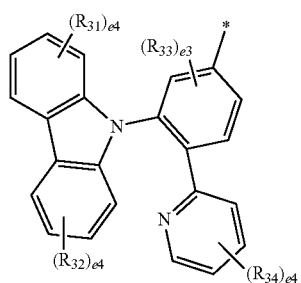
2-2(9)
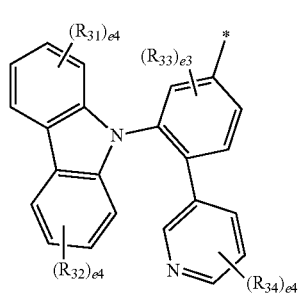
2-2(10)
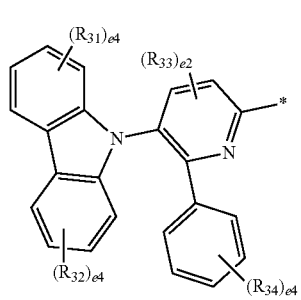
2-2(11)
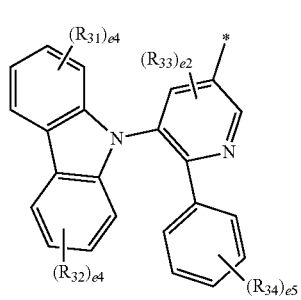
2-2(12)
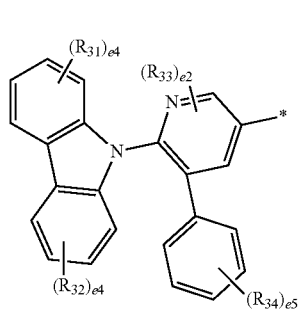
2-2(13)
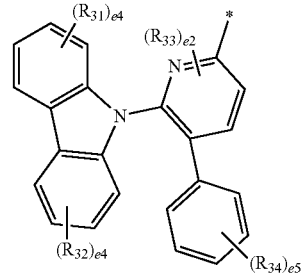
2-2(14)
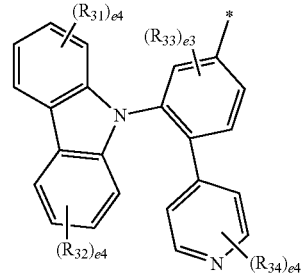
2-2(15)
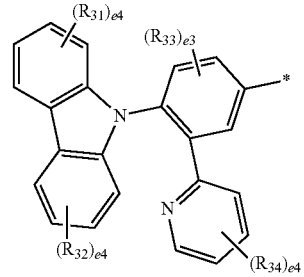
2-2(16)
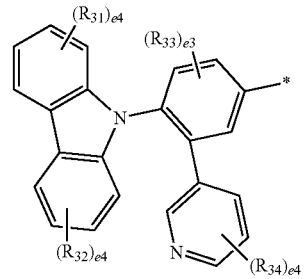
2-2(17)
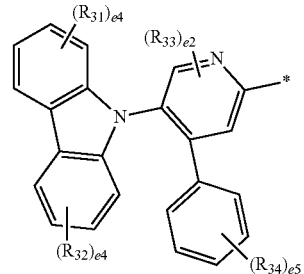

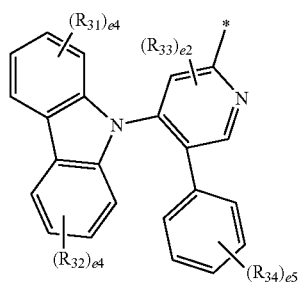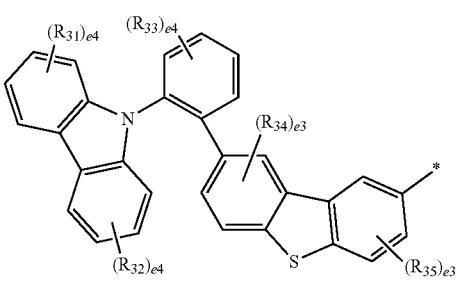

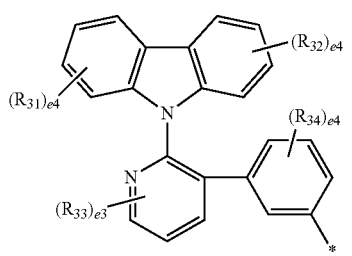
2-3(12)
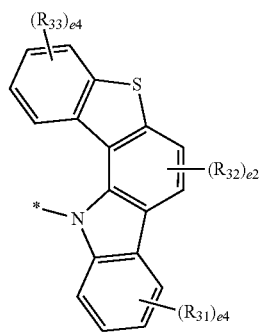
2-6(4)
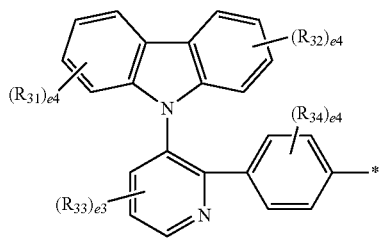
2-3(13)
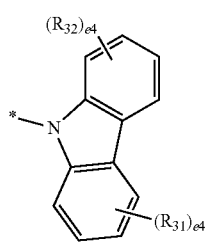
2-6(1)
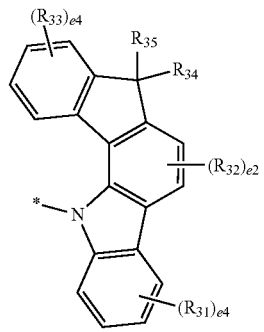
2-6(5)
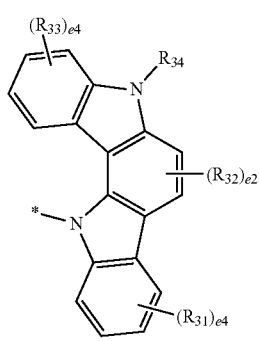
2-6(2)
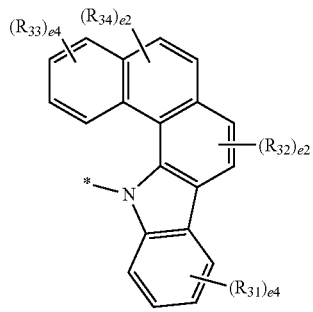
2-6(6)
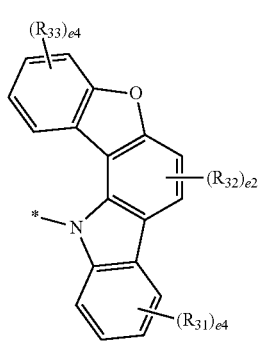
2-6(3)
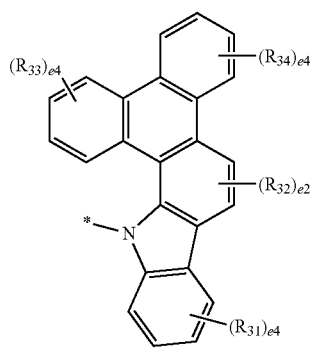
2-6(7)

-continued

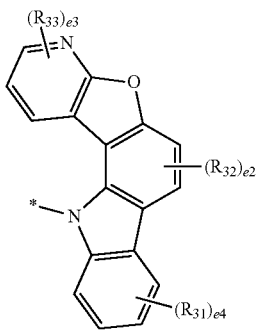
2-6(8)

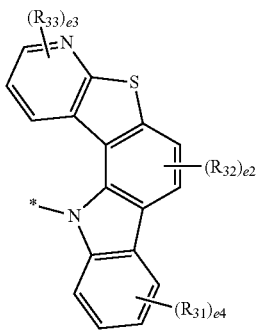
2-6(9)

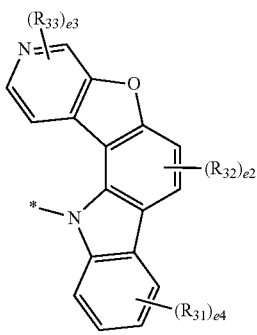
2-6(10)

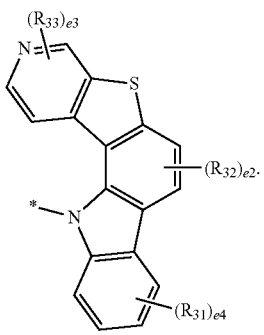
2-6(11)

In Formulae 2-1(1) to 2-1(6), 2-2(1) to 2-2(18), 2-3(1) to 2-3(13), and 2-6(1) to 2-6(11), $R_{31}$ to $R_{36}$ may each independently be the same as described in connection with $R_1$, $R_{11}$ to $R_{17}$, and $R_{21}$ to $R_{25}$ in Formula 1, e2 may be an integer from 0 to 2, e3 may be an integer from 0 to 3, e4 may be an integer from 0 to 4, e5 may be an integer from 0 to 5, e6 may be an integer from 0 to 6, and

* indicates a binding site to a neighboring atom.

For example, in Formulae 2-1(1) to 2-1(6), $R_{31}$ and $R_{32}$ may each independently be the same as described in connection with $R_{12}$ in Formula 1, and $R_{33}$ and $R_{34}$ may each independently be the same as described in connection with $R_{13}$ in Formula 1, in Formulae 2-2(1) to 2-2(18), $R_{31}$ and $R_{32}$ may each independently be the same as described in connection with $R_{12}$ in Formula 1, $R_{33}$ may be the same as described in connection with $R_{15}$ in Formula 1, and $R_{34}$ and $R_{35}$ may each independently be the same as described in connection with $R_{14}$ in Formula 1, in Formulae 2-3(1) to 2-3(13), $R_{31}$ and $R_{32}$ may each independently be the same as described in connection with $R_{12}$ in Formula 1, $R_{33}$ may be the same as described in connection with $R_{17}$ in Formula 1, and $R_{34}$ and $R_{35}$ may each independently be the same as described in connection with $R_{16}$ in Formula 1, and in Formulae 2-6(1) to 2-6(11), $R_{31}$ to $R_{35}$ may each independently be the same as described in connection with $R_{12}$ in Formula 1.

For example, *-$(L_1)_{a1}$-$Ar_1$, *-$(L_2)_{a2}$-$Ar_2$, and *-$(L_{11})_{a11}$-$R_{11}$ may be different from each other, but embodiments of the present disclosure are not limited thereto.

For example, two structures in *-$(L_1)_{a1}$-$Ar_1$, *-$(L_2)_{a2}$-$Ar_2$, and *-$(L_{11})_{a11}$-$R_{11}$ may be identical to each other, and the other thereof may be different, but embodiments of the present disclosure are not limited thereto.

In Formulae 2-1 to 2-6, $R_{11}$ to $R_{17}$, and $R_{21}$ to $R_{25}$ may each independently be selected from hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, and —$N(Q_1)(Q_2)$, any neighboring groups selected from $R_{12}$ to $R_{17}$ and $R_{21}$ to $R_{25}$ may optionally be linked to each other to form a substituted or unsubstituted $C_5$-$C_{30}$ carbocyclic group or a substituted or unsubstituted $C_2$-$C_{30}$ heterocyclic group, wherein each of $R_{15}$ and $R_{17}$ is not a substituted or unsubstituted carbazolyl group.

For example, $R_1$, $R_{11}$ to $R_{17}$, and $R_{21}$ to $R_{25}$ may each independently be selected from:

a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group; and a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group, but embodiments of the present disclosure are not limited thereto.

For example, the heterocyclic compound may have three or less carbazole moieties, but embodiments of the present disclosure are not limited thereto.

In an embodiment, the heterocyclic compound may be selected from Compounds 1 to 509, but embodiments of the present disclosure are not limited thereto:

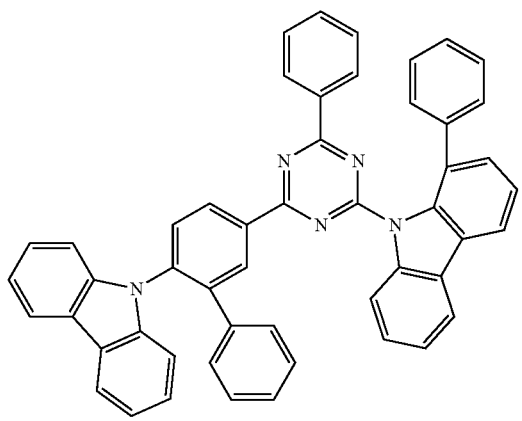

1

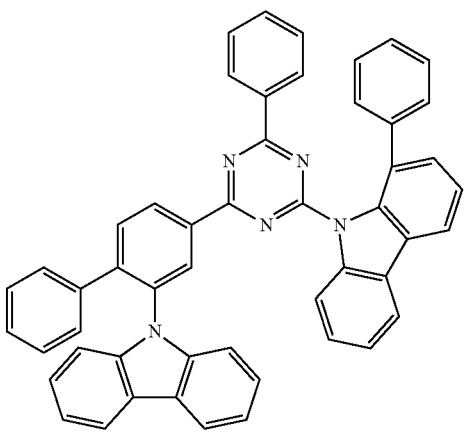 [SMILES: c1ccc(-c2nc(-c3ccc(-c4ccccc4)c(-n4c5ccccc5c5ccccc54)c3)nc(-n3c4ccccc4c4cccc(-c5ccccc5)c43)n2)cc1]

2

-continued
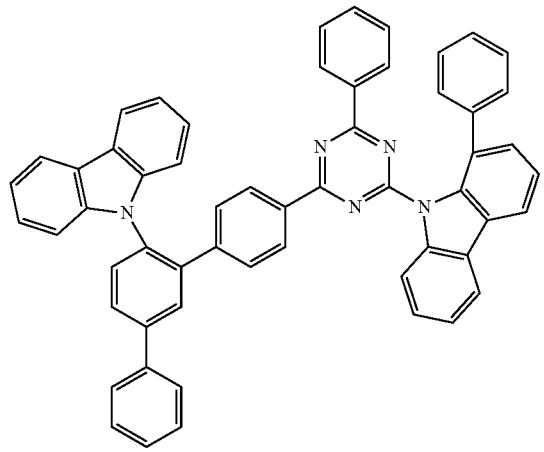 [SMILES: c1ccc(-c2ccc(-n3c4ccccc4c4ccccc43)c(-c3ccc(-c4nc(-c5ccccc5)nc(-n5c6ccccc6c6cccc(-c7ccccc7)c65)n4)cc3)c2)cc1]
3
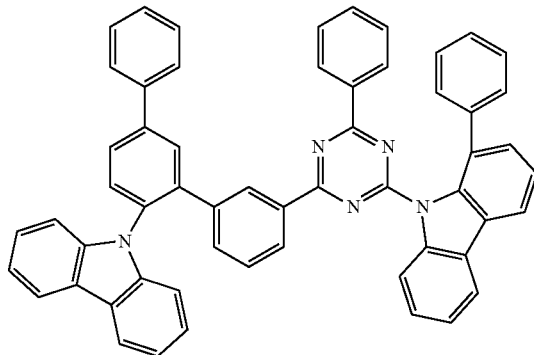
4
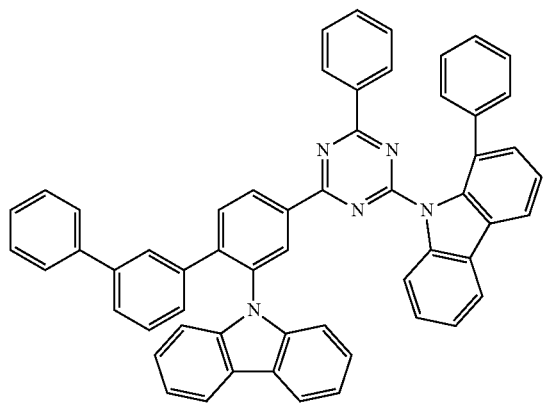 [SMILES: c1ccc(-c2cccc(-c3ccc(-c4nc(-c5ccccc5)nc(-n5c6ccccc6c6cccc(-c7ccccc7)c65)n4)cc3-n3c4ccccc4c4ccccc43)c2)cc1]
5
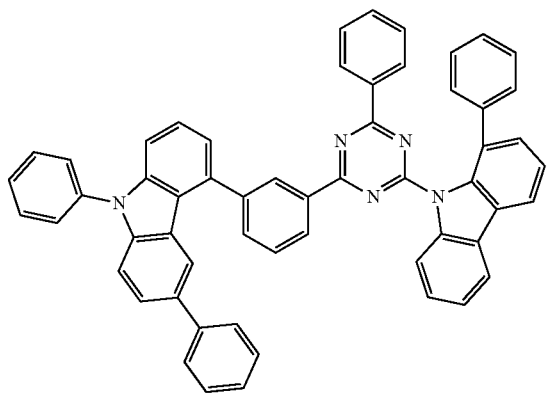 [SMILES: c1ccc(-c2ccc3c(c2)c2c(-c4cccc(-c5nc(-c6ccccc6)nc(-n6c7ccccc7c7cccc(-c8ccccc8)c76)n5)c4)cccc2n3-c2ccccc2)cc1]
6
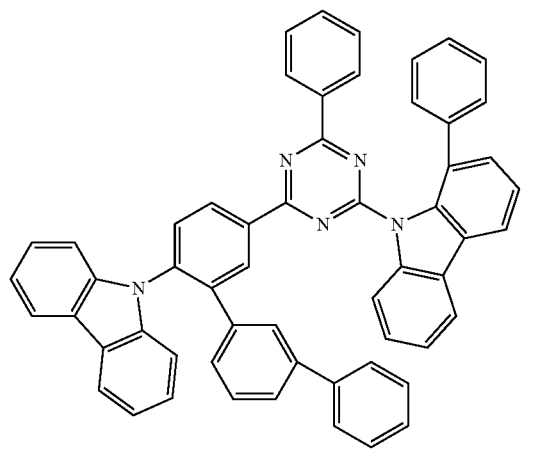
7
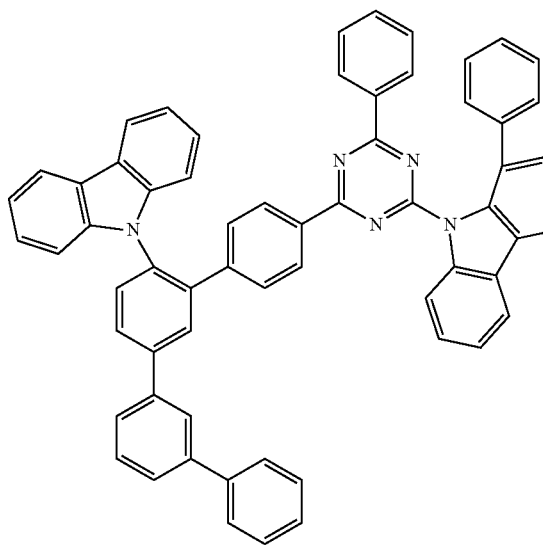
8

-continued
9
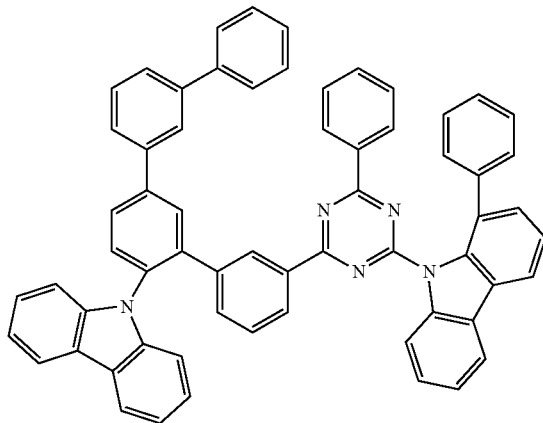
10
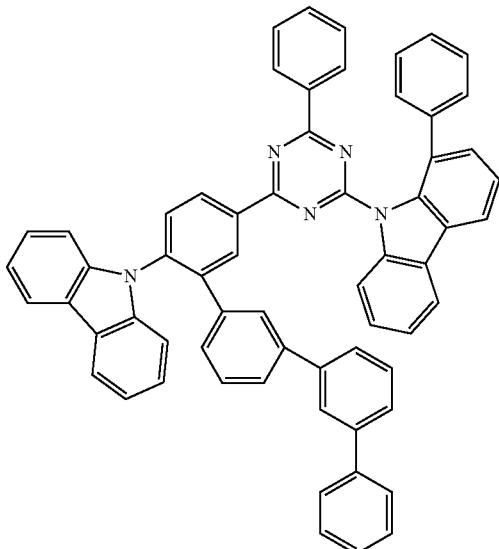
11
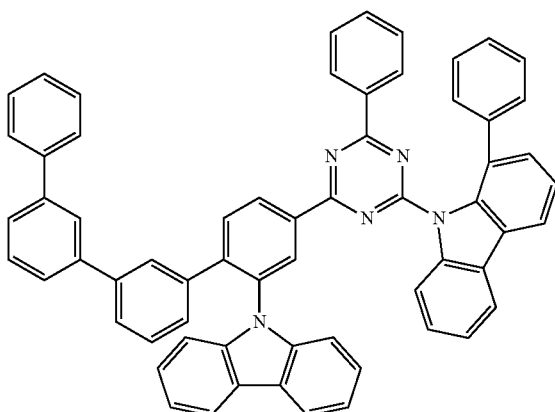
12
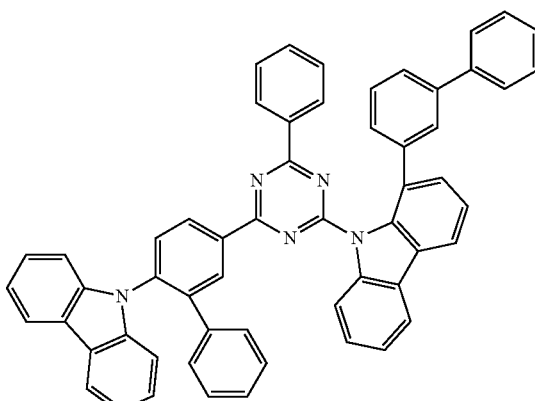
13
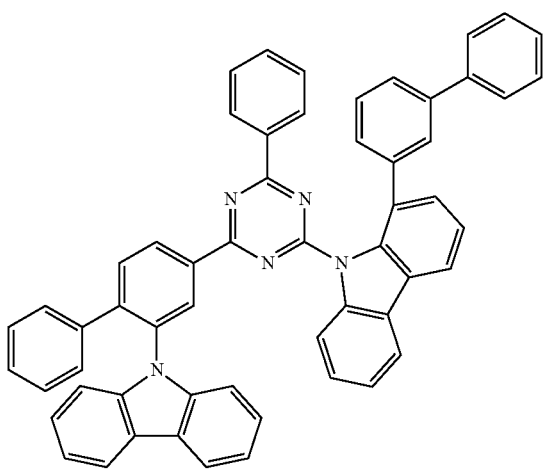
14
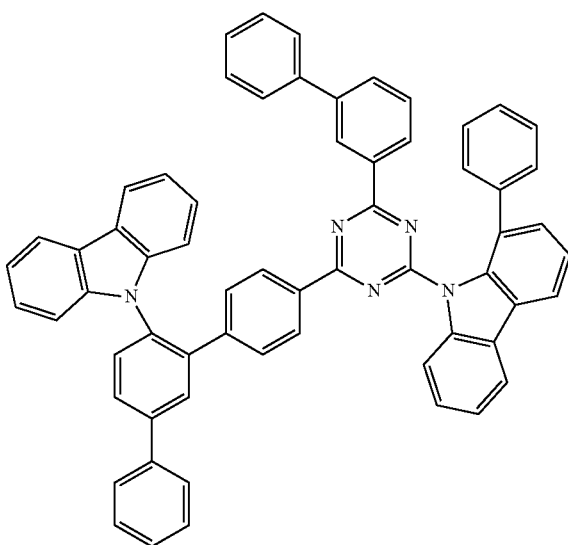

-continued
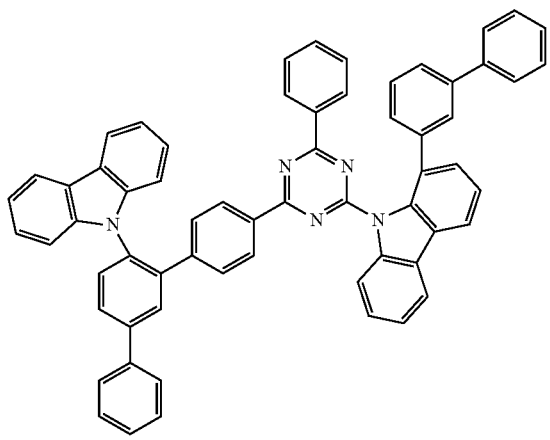
15
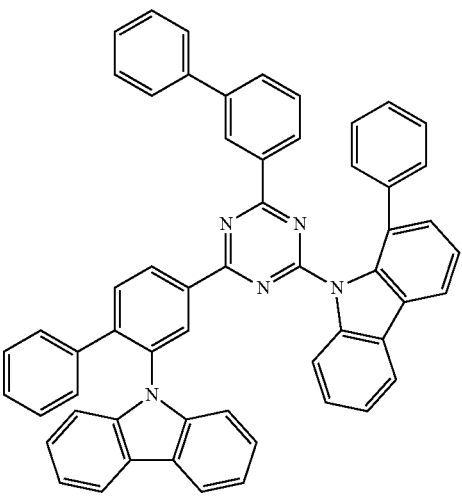
16
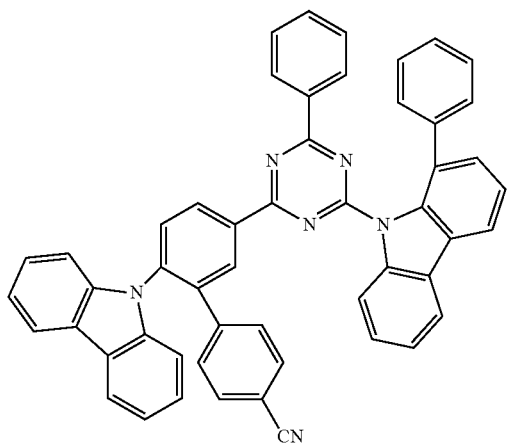
17
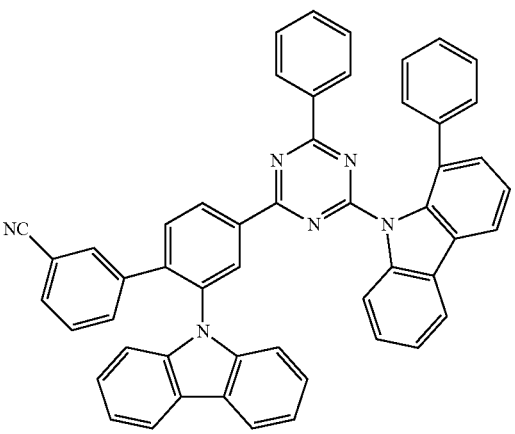
18
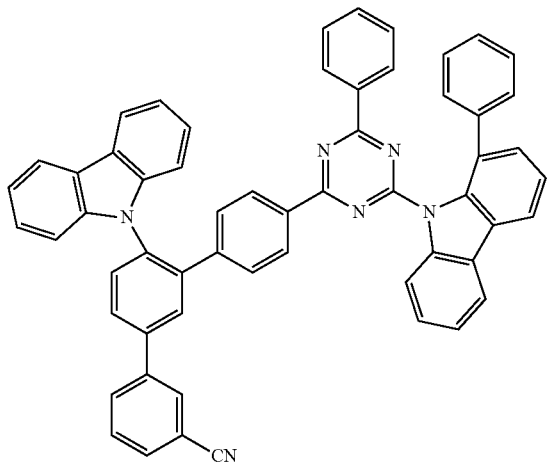
19
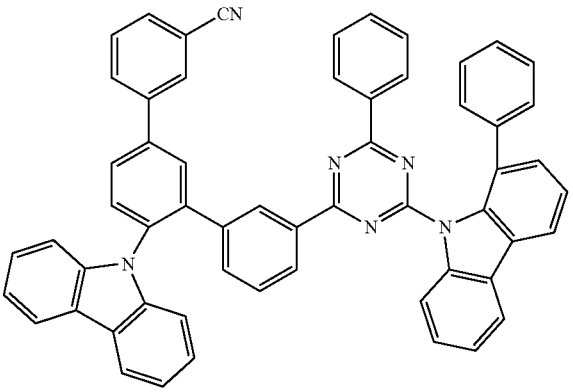
20

-continued
21
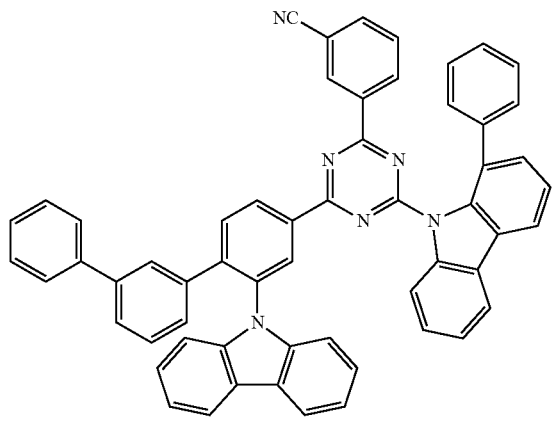
22
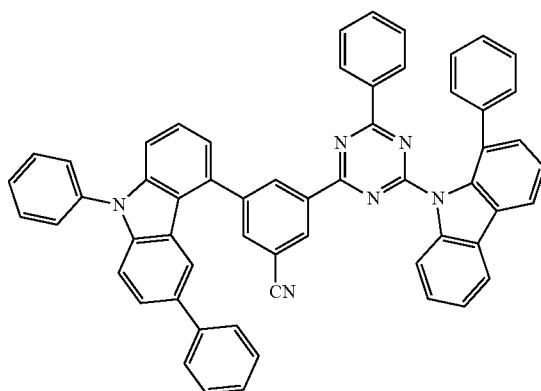
23
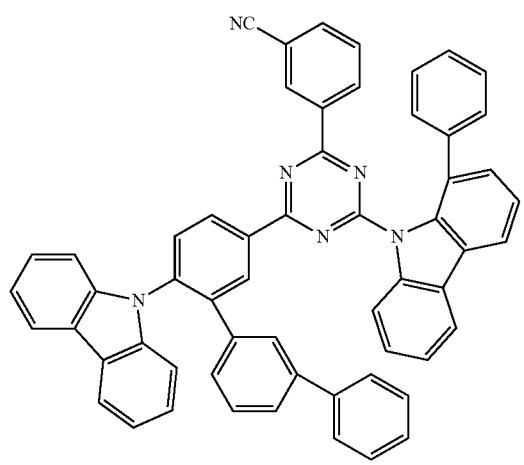
24
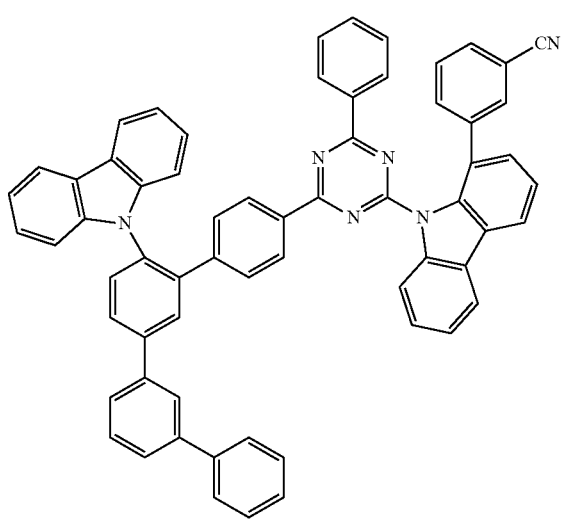
25
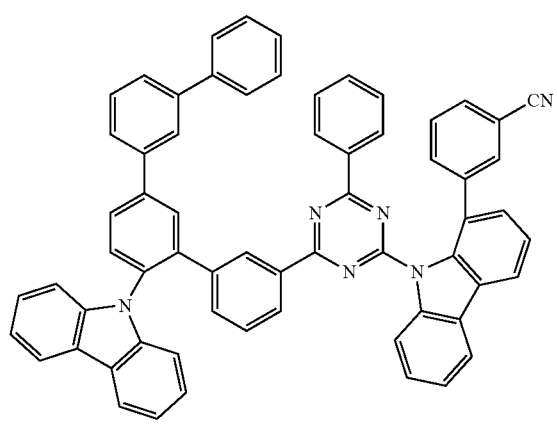
26
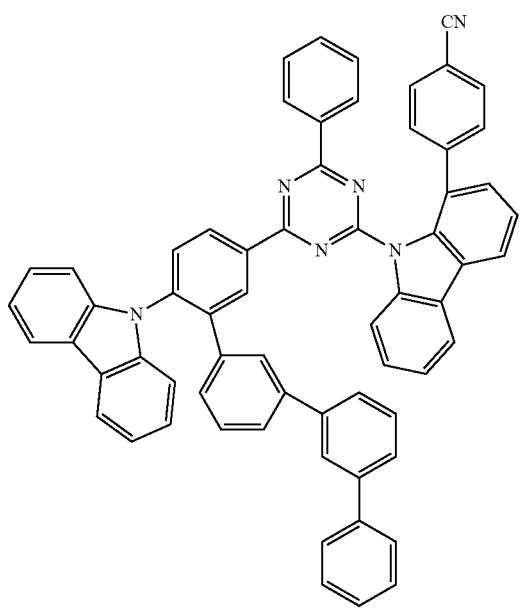

-continued
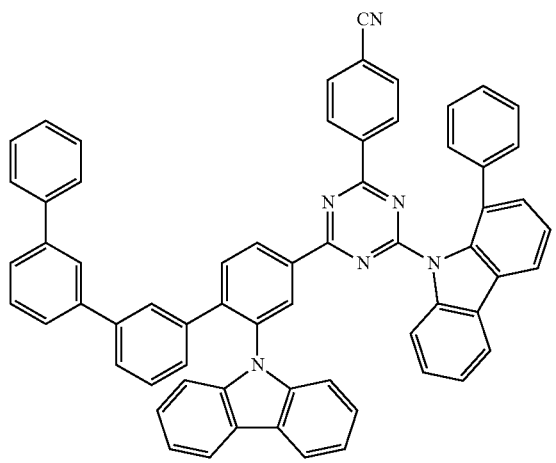
27
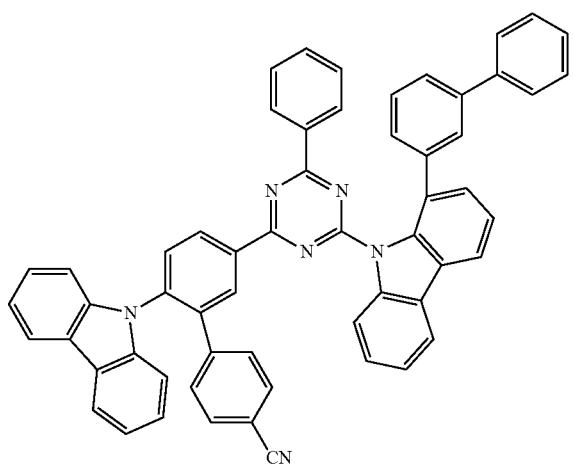
28
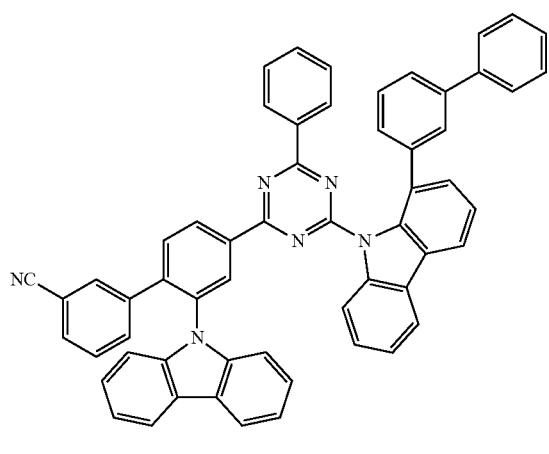
29
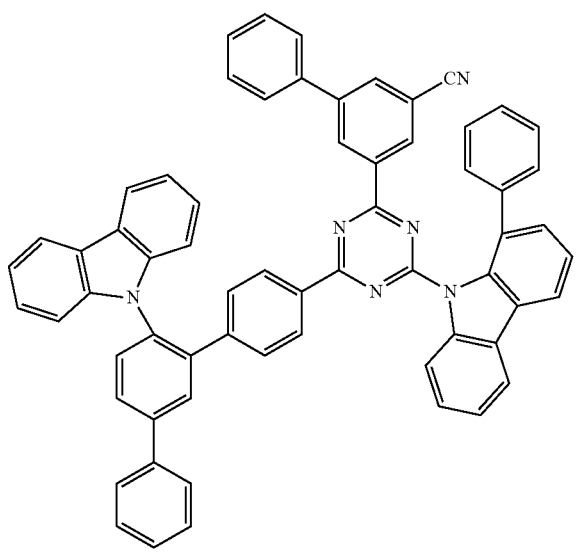
30
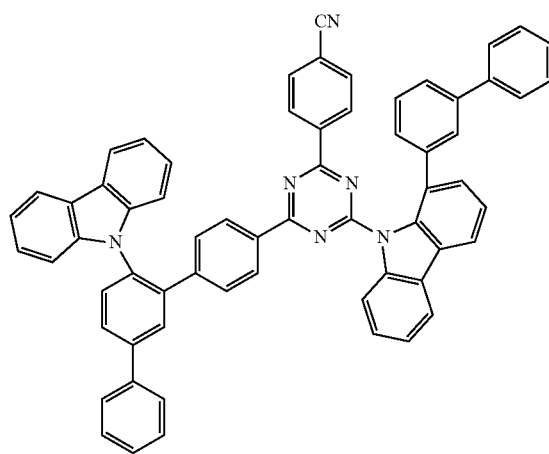
31
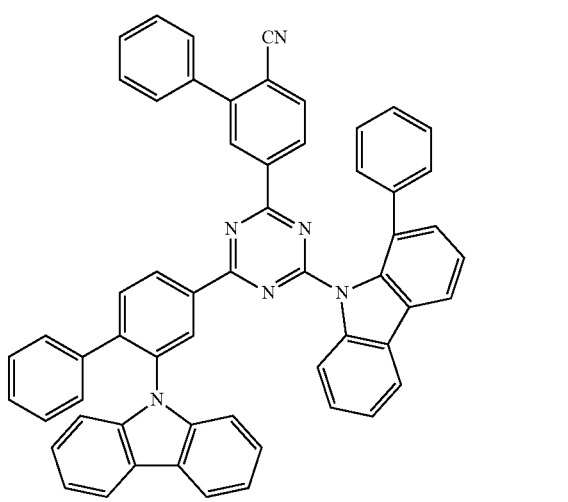
32

-continued
33
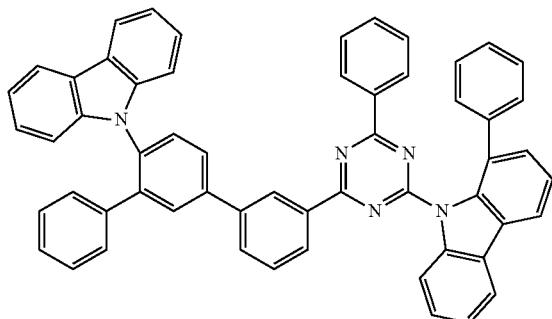
34
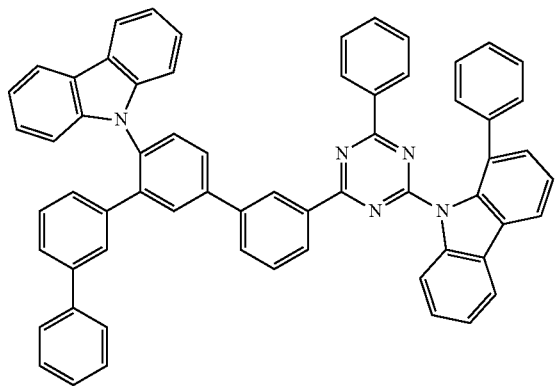
35
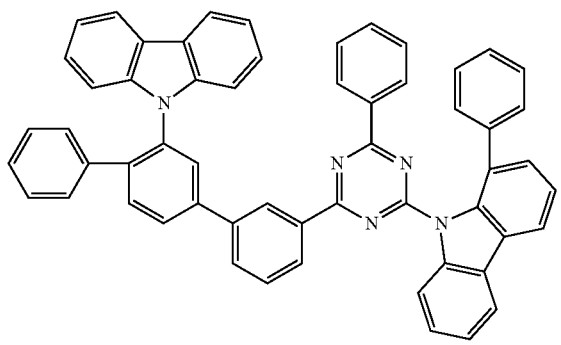
36
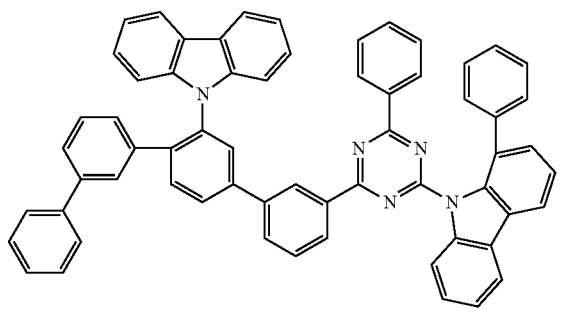
37
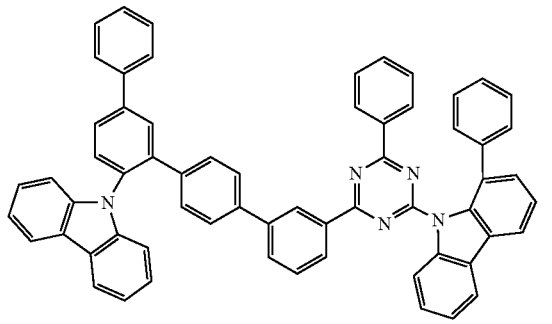
38
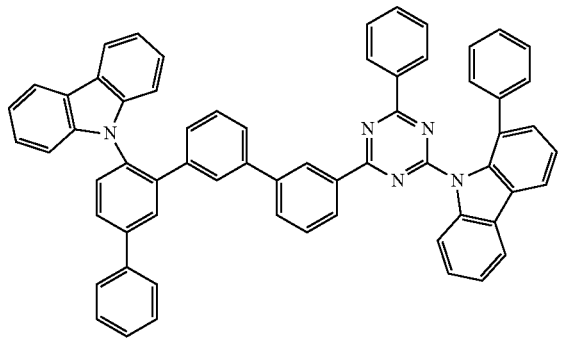
39
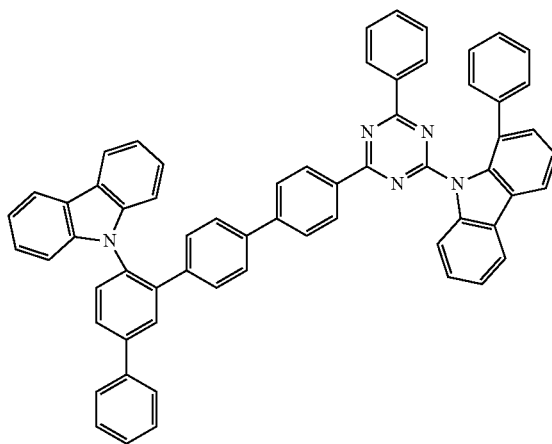
40
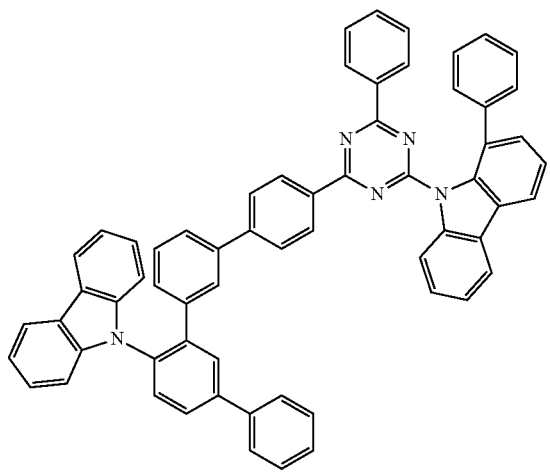

-continued
41
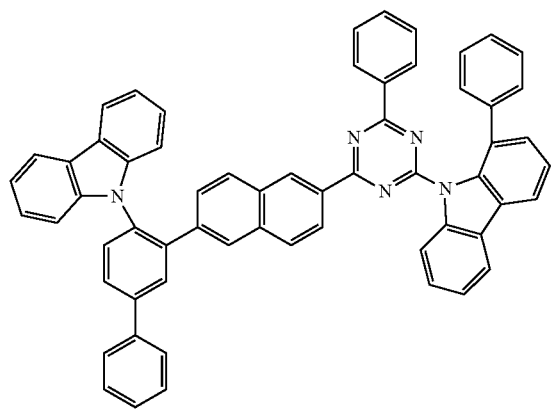
42
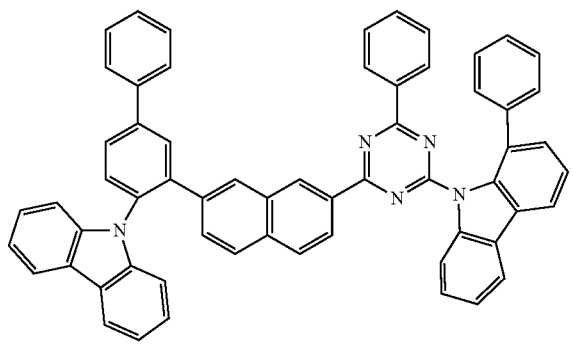
43
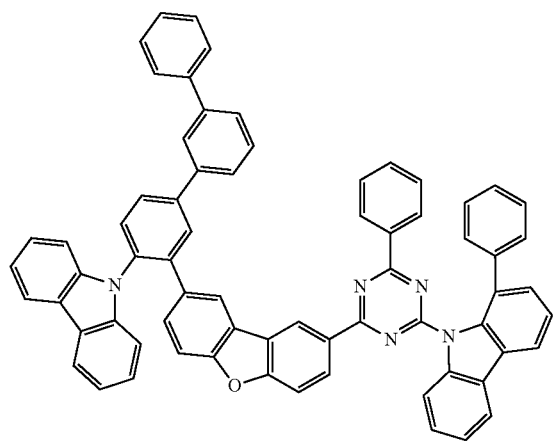
44
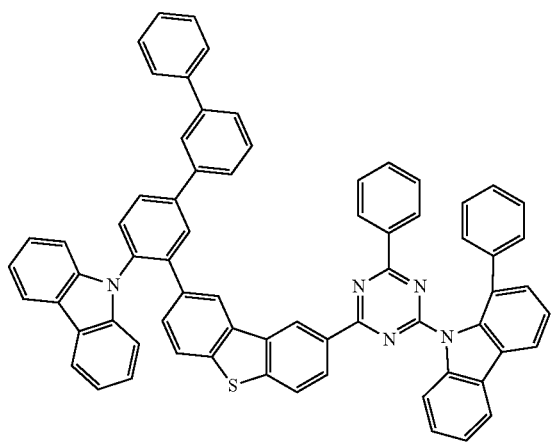
45
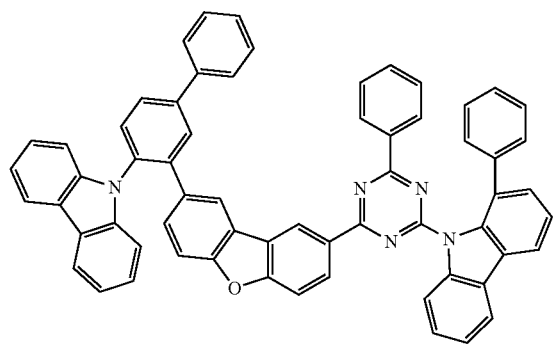
46
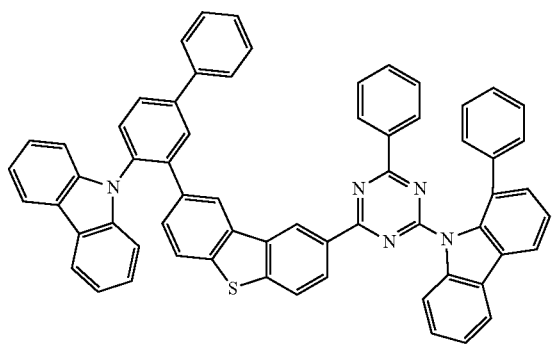

47
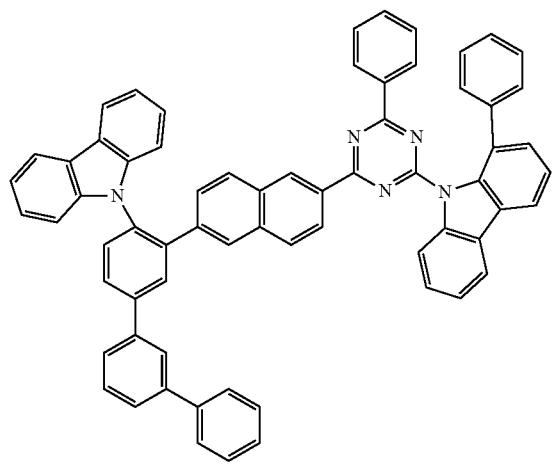
48
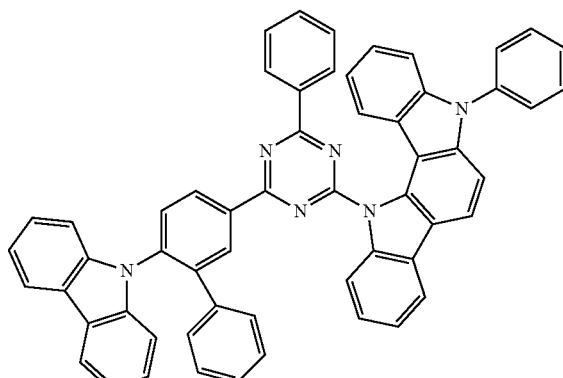
49
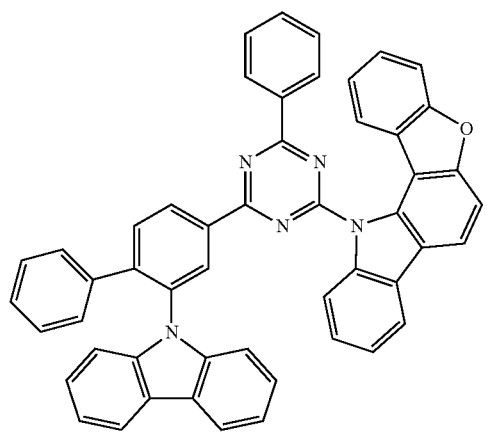
50
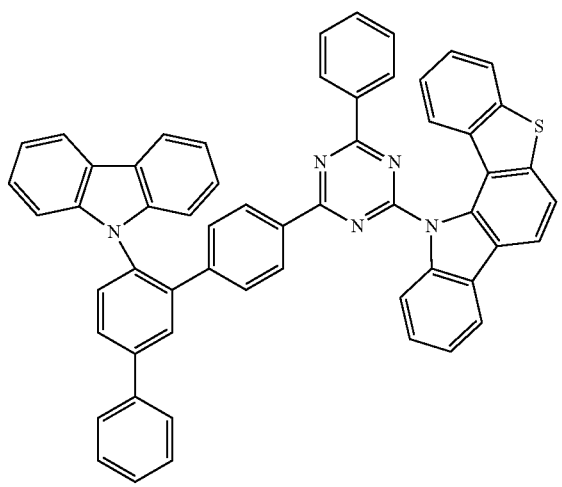
51
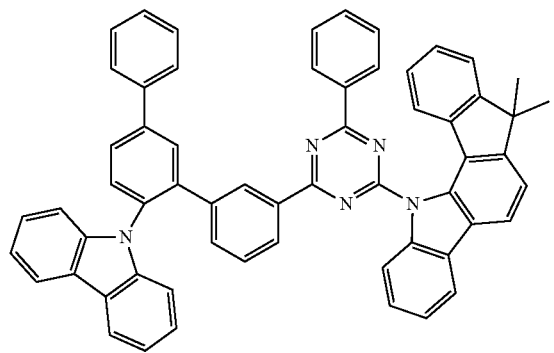
52
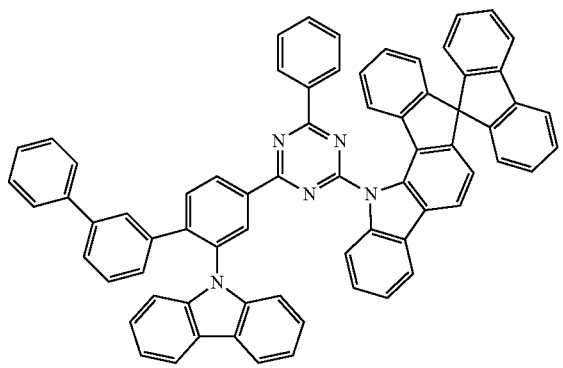

-continued
53
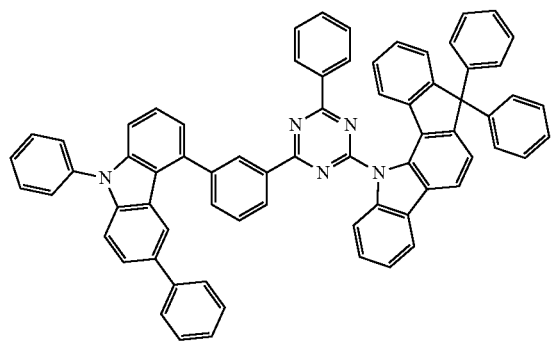
54
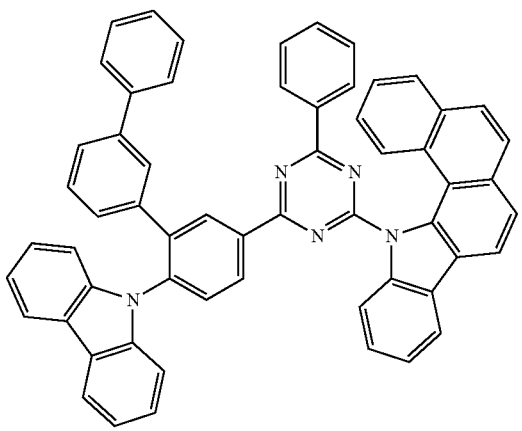
55
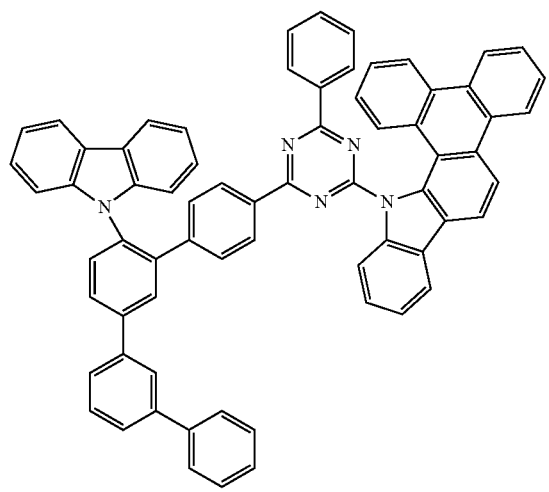
56
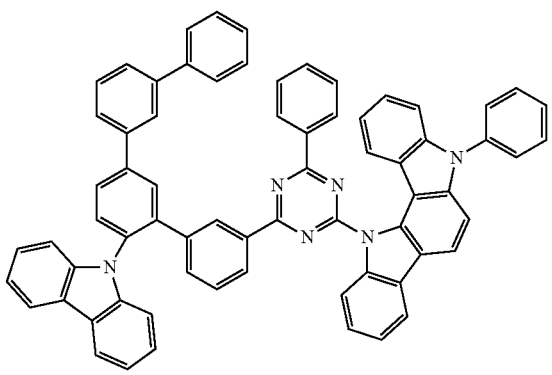
57
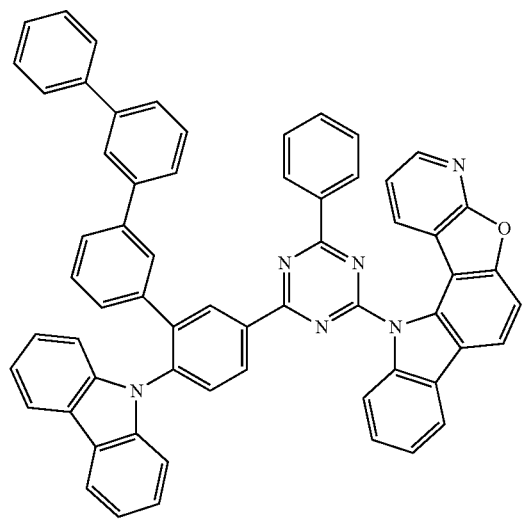
58
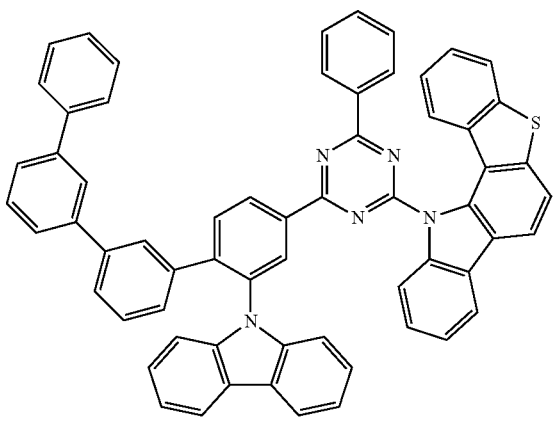

-continued
59
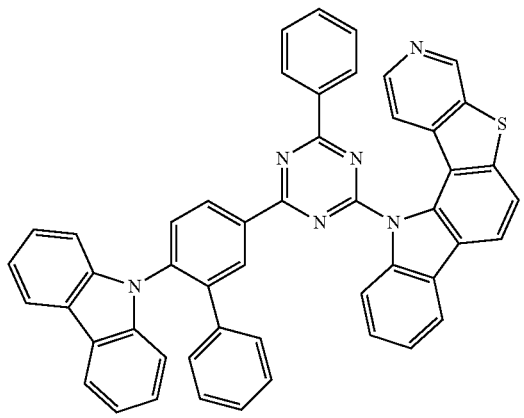
60
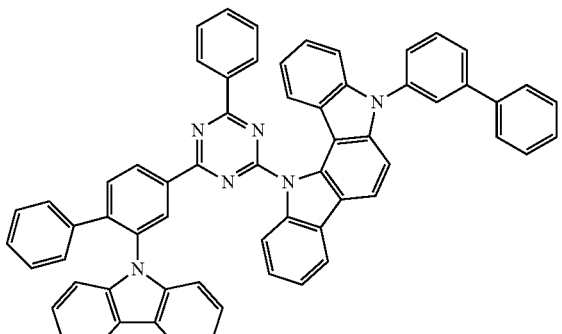
61
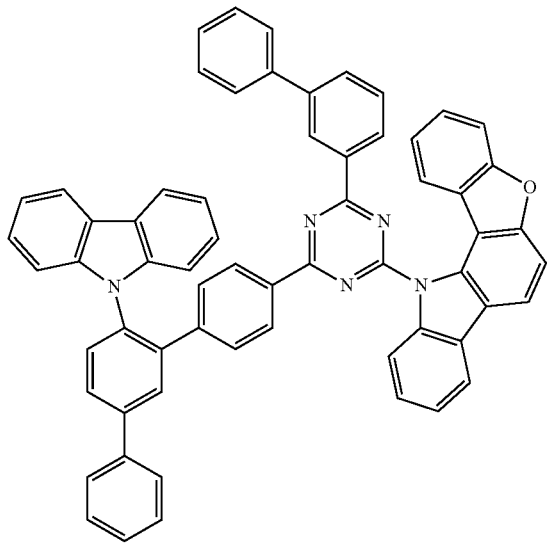
62
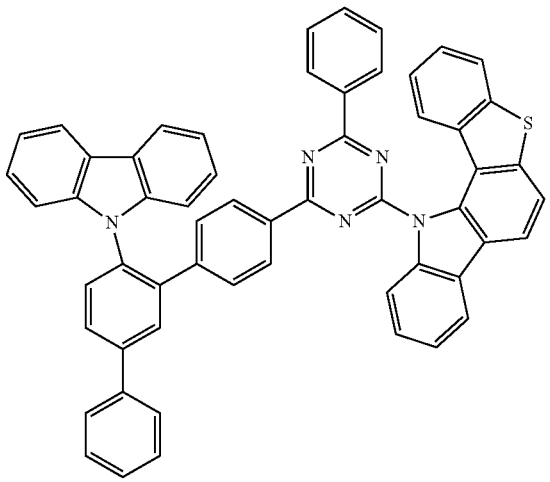
63
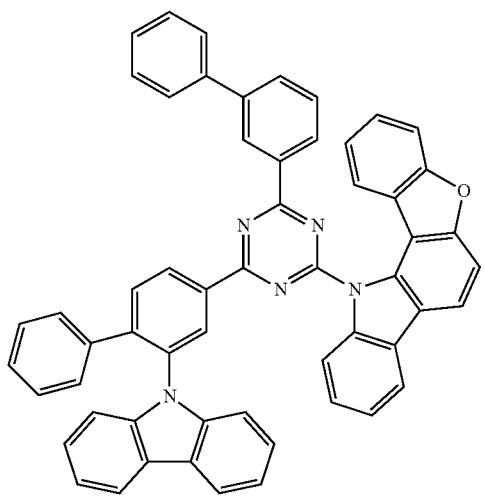
64
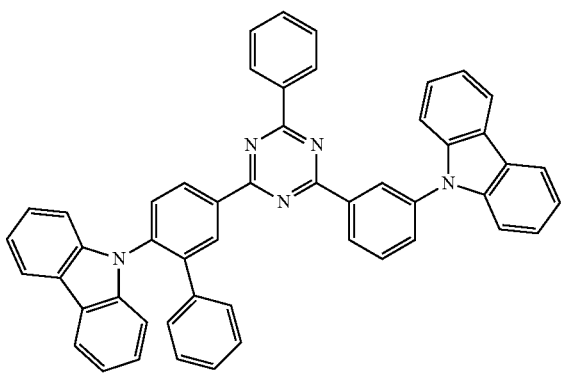

-continued
65
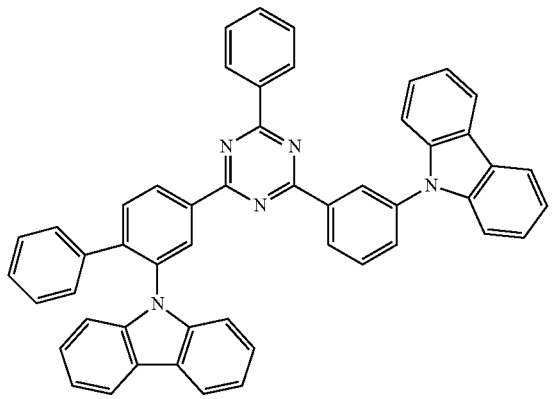
66
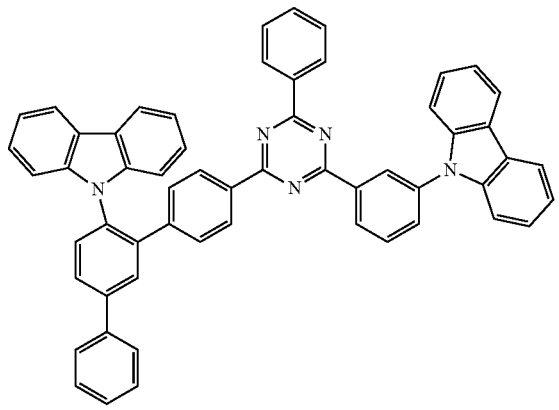
67
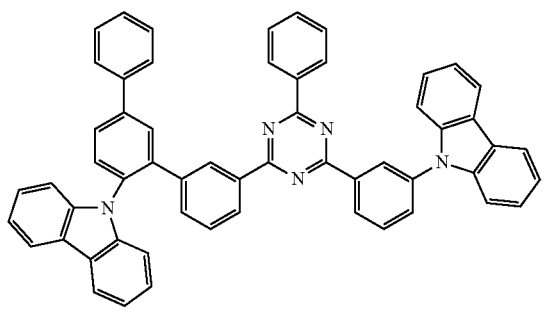
68
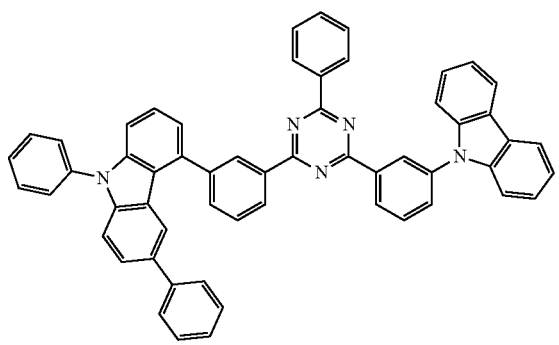
69
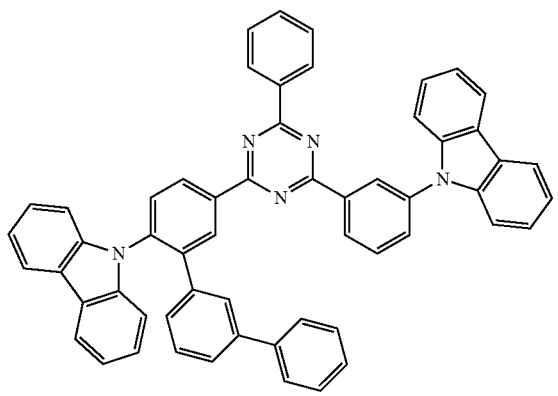
70
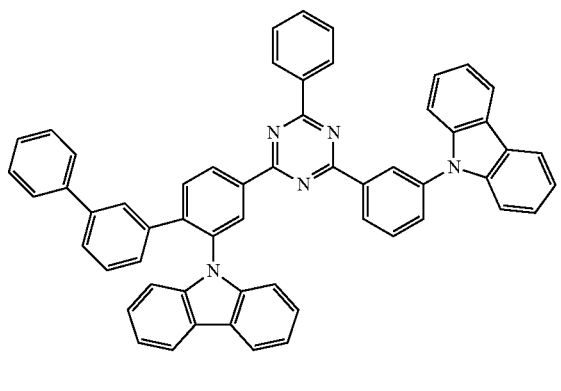

-continued
71
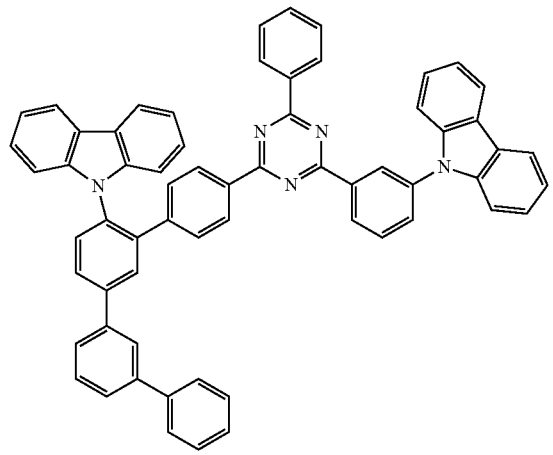
72
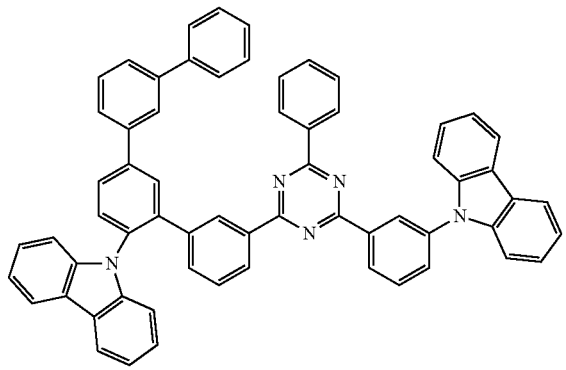
73
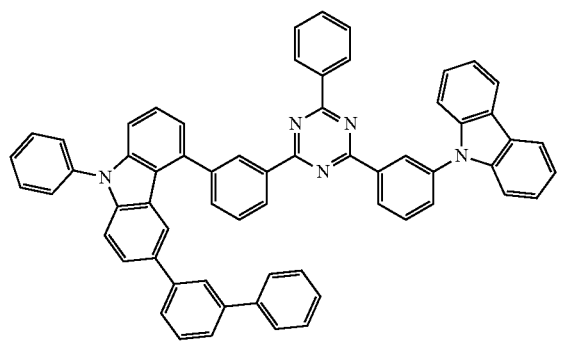
74
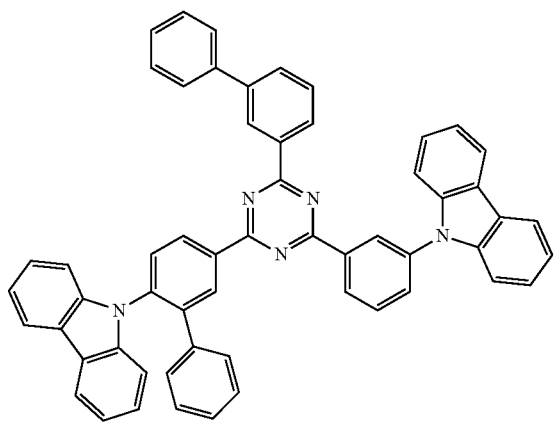
75
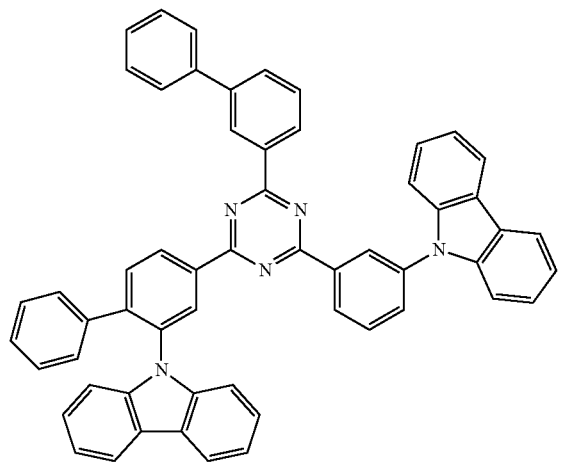
76
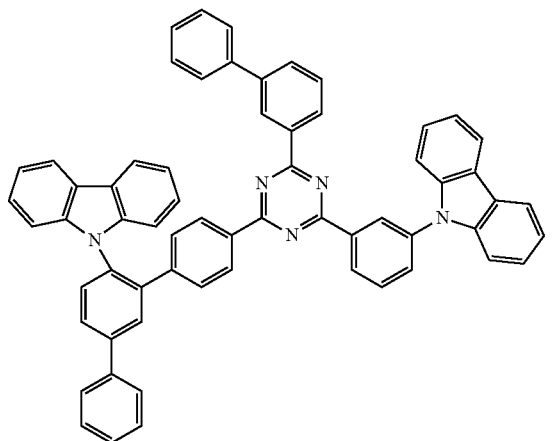

77
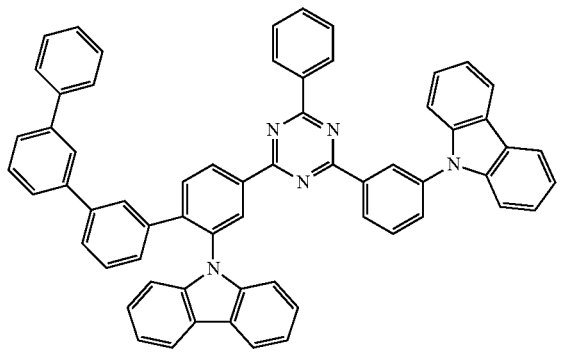
78
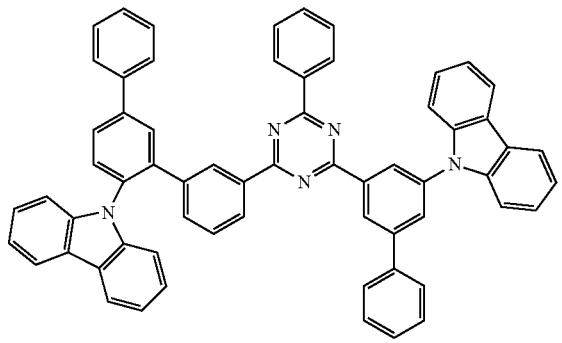
79
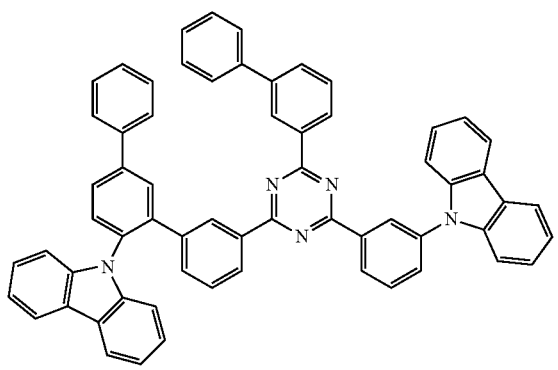
80
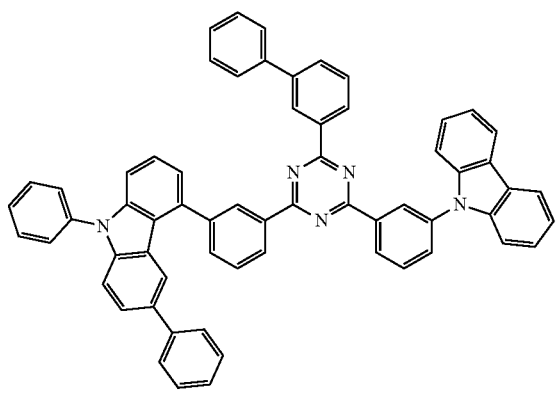
81
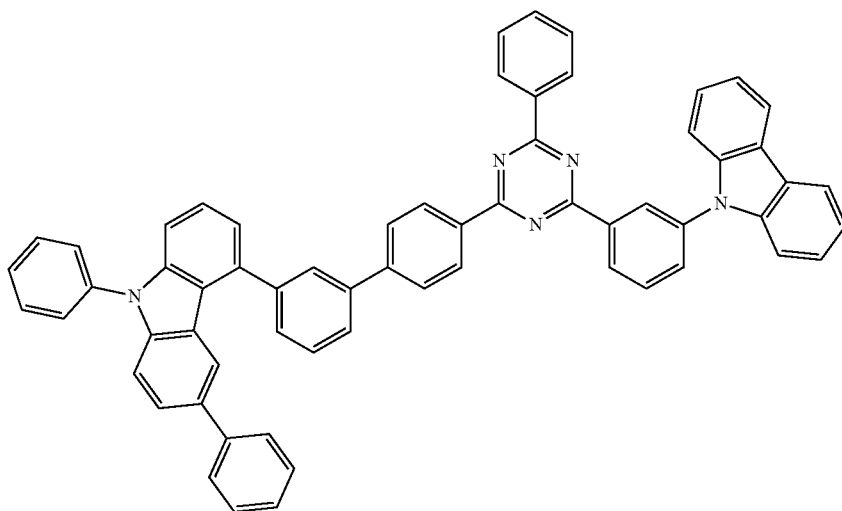

-continued
82
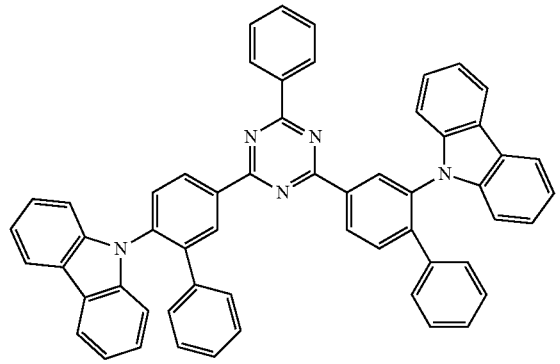
83
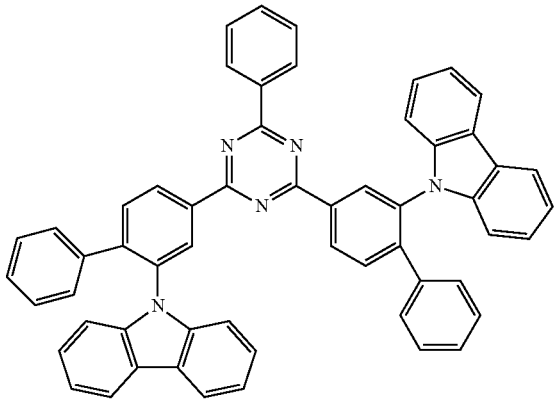
84
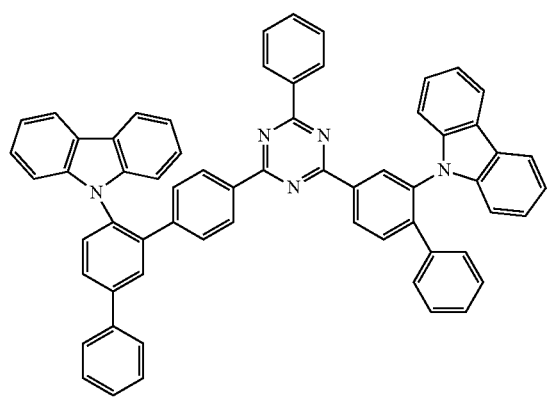
85
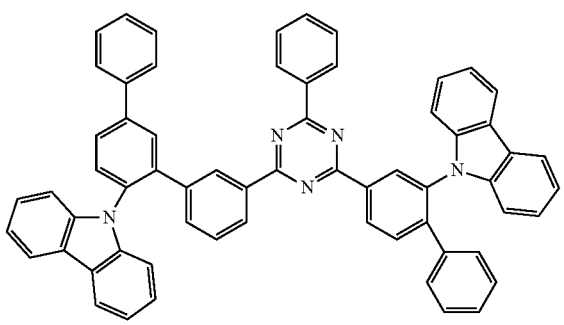
86
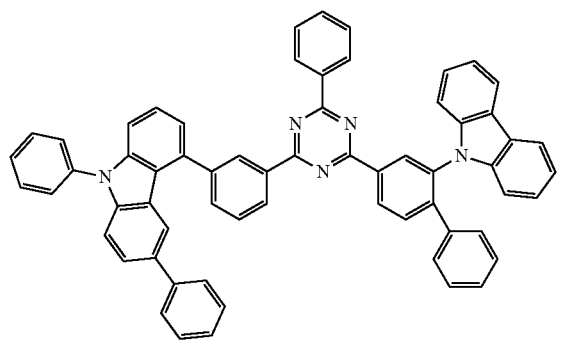
87
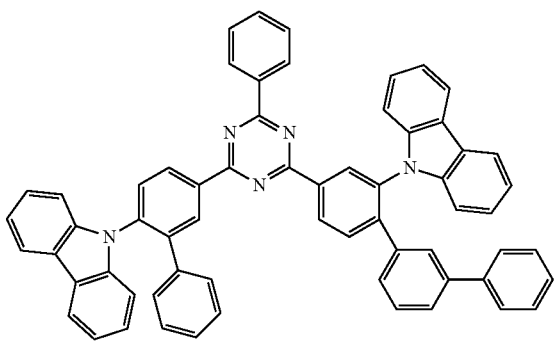
88
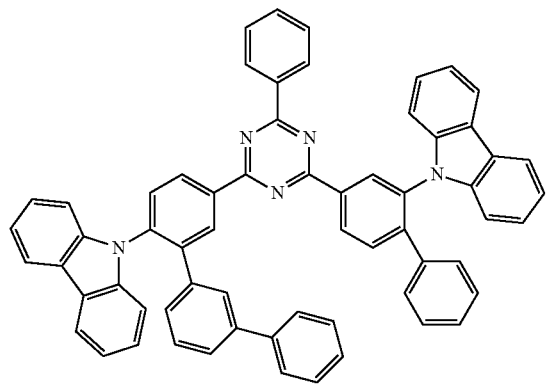
89
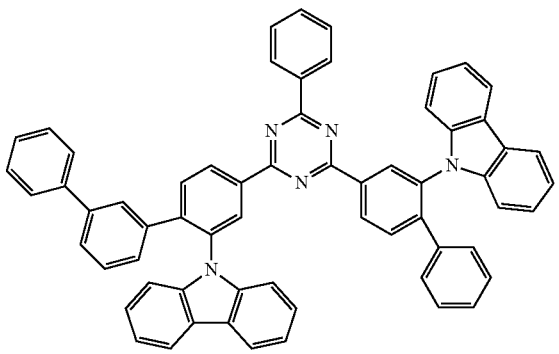

-continued
90
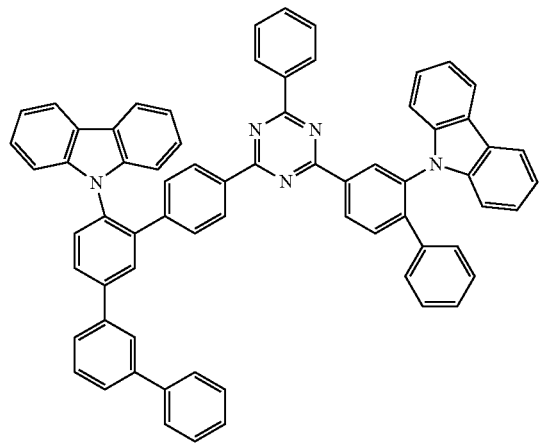
91
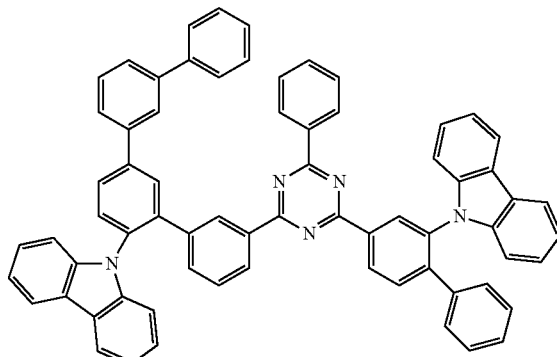
92
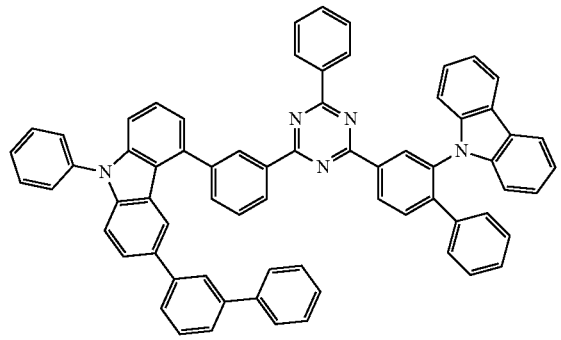
93
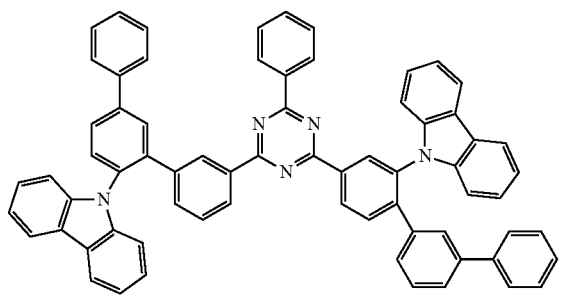
94
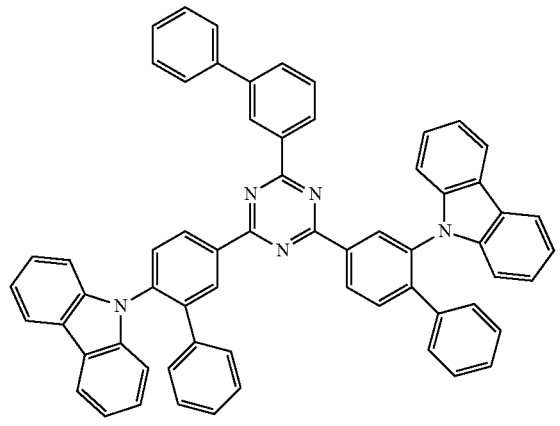
95
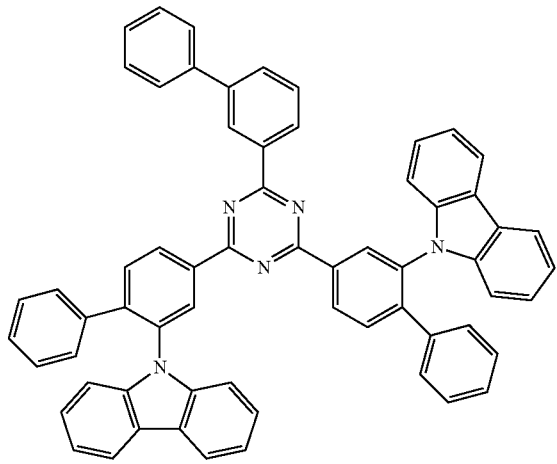

96
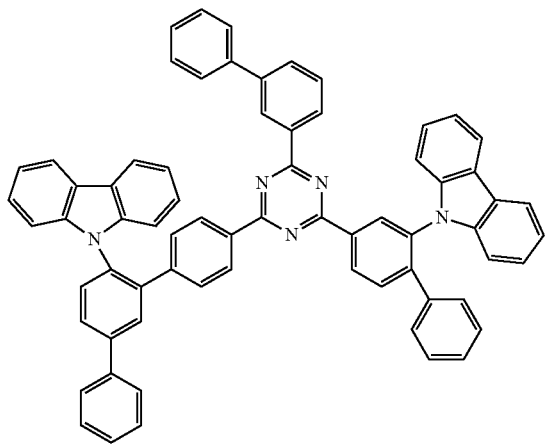
97
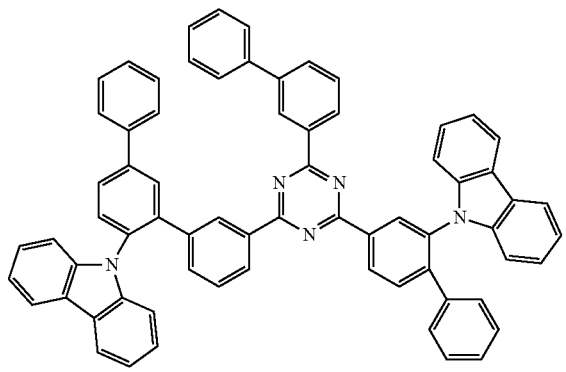
98
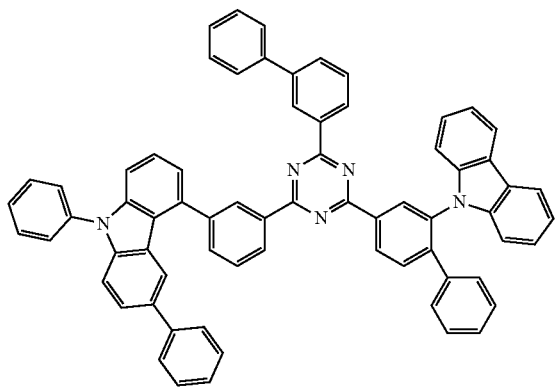
99
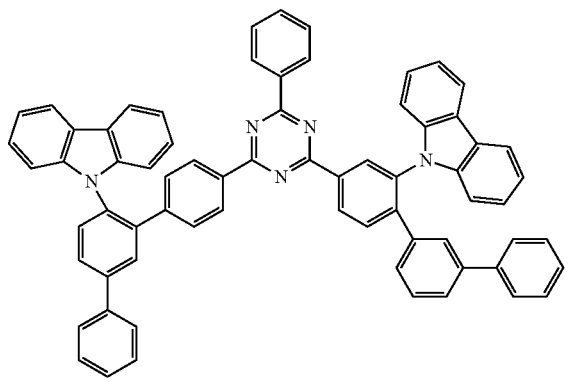
100
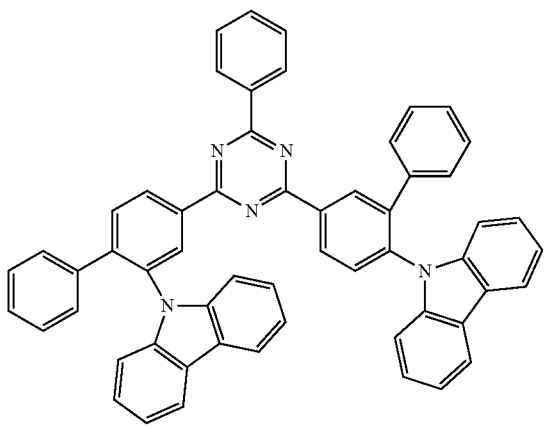
101
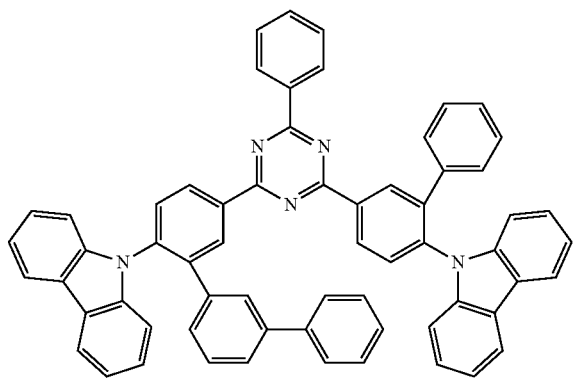

-continued
102
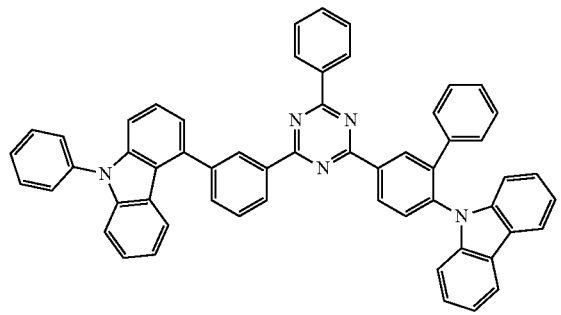
103
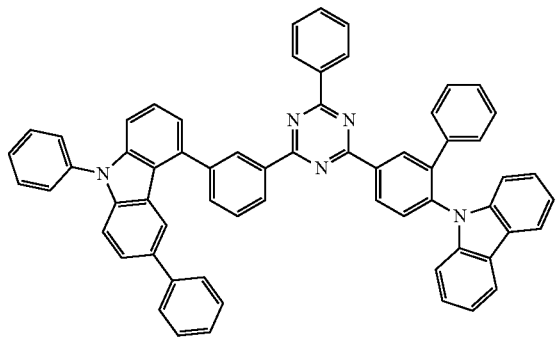
104
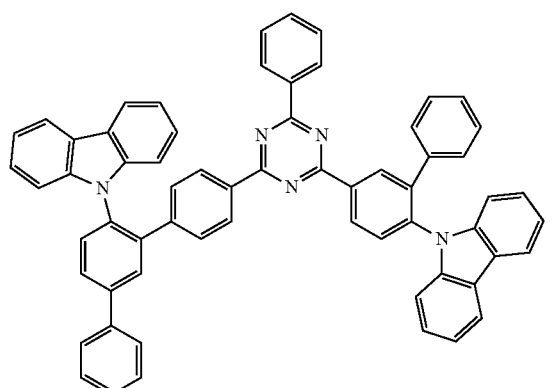
105
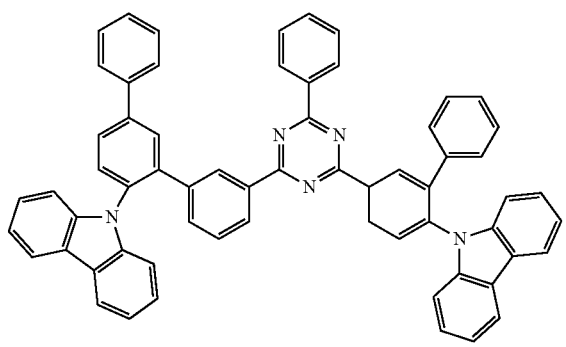
106
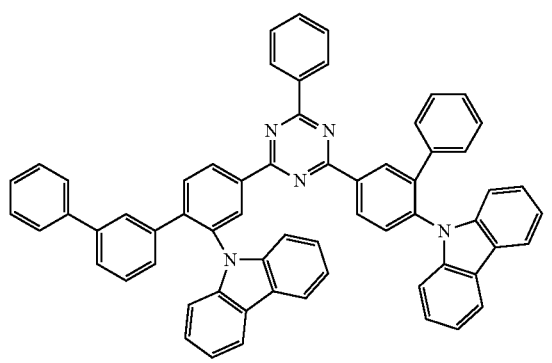
107
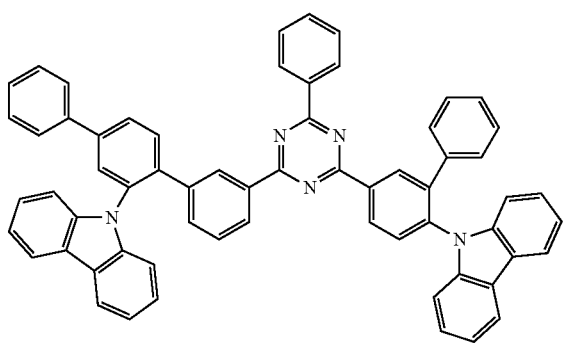
108
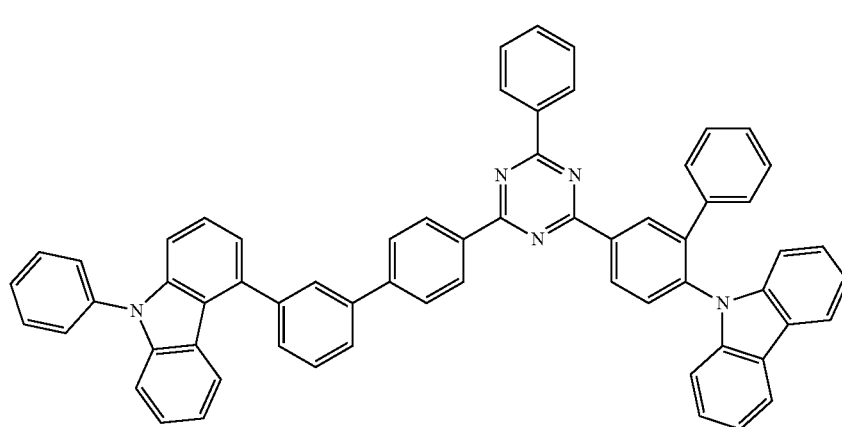

-continued
109
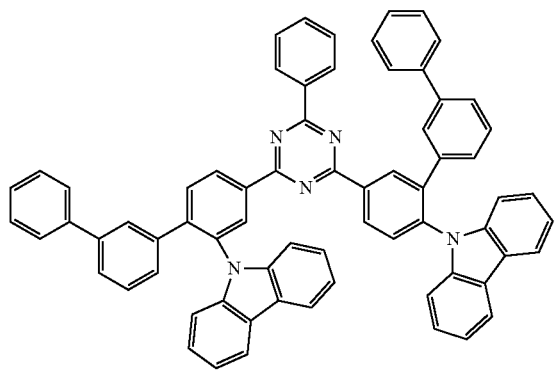
110
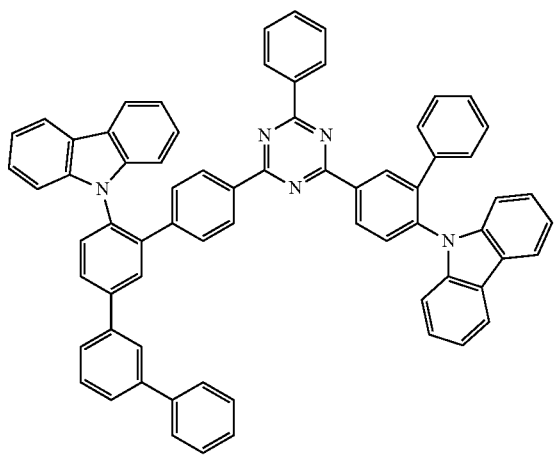
111
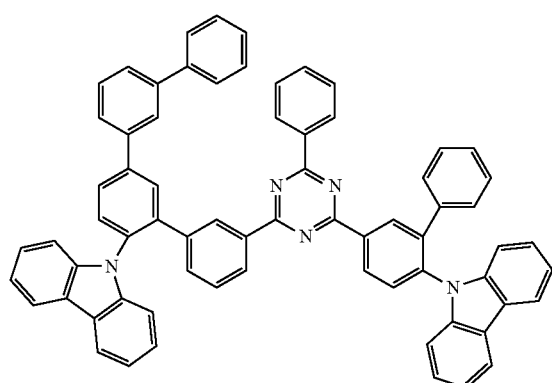
112
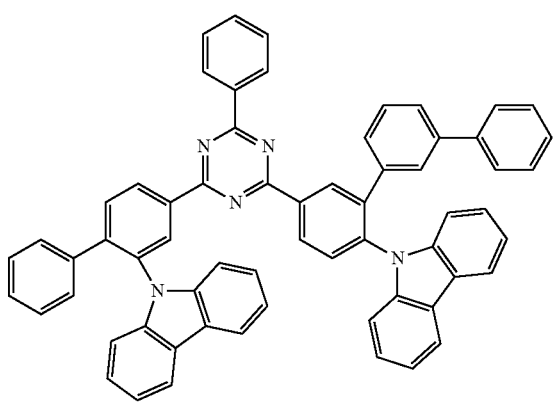
113
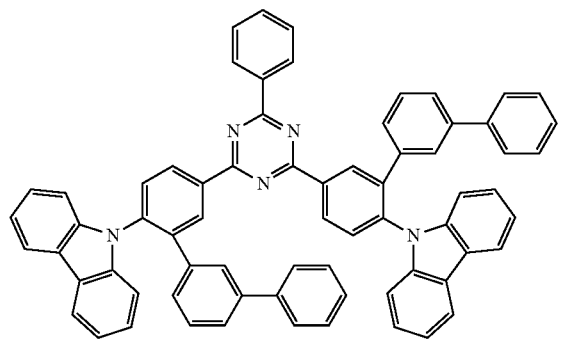
114
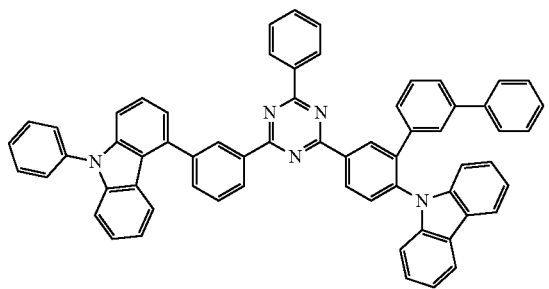
115
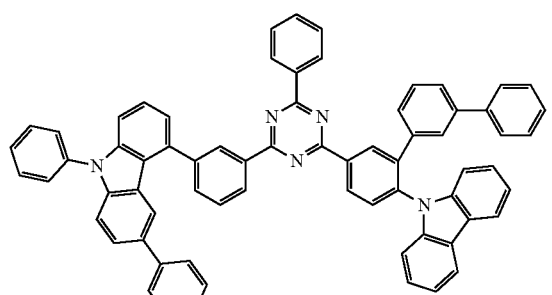
116
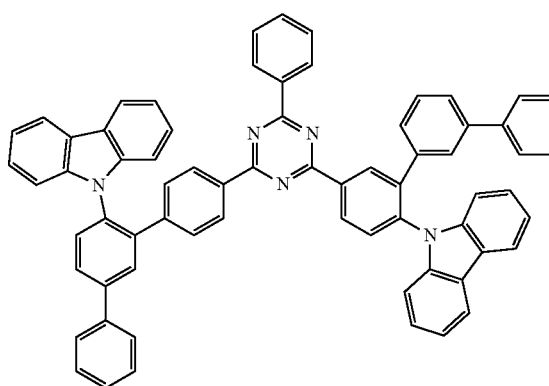

117
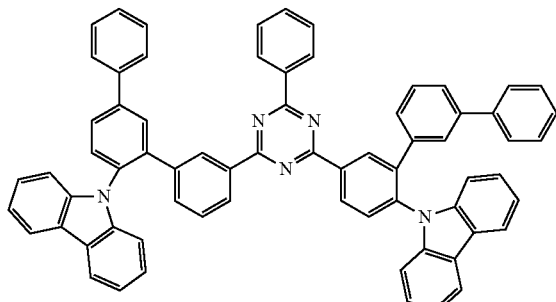
118
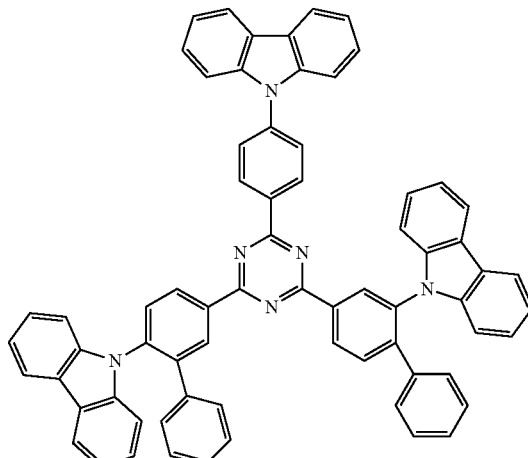
119
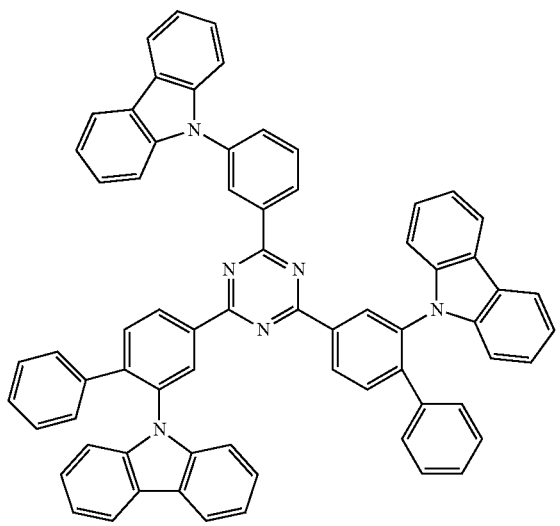
120
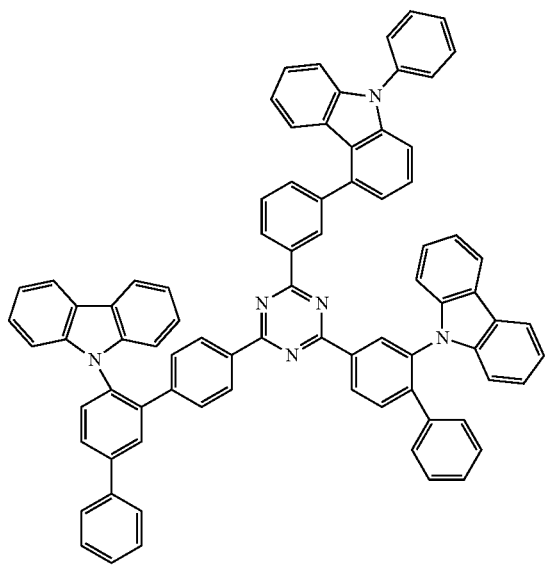
121
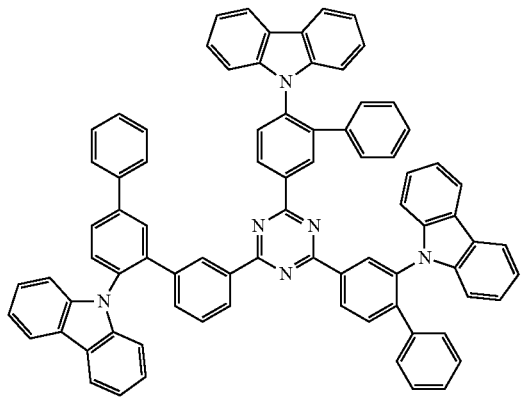
122
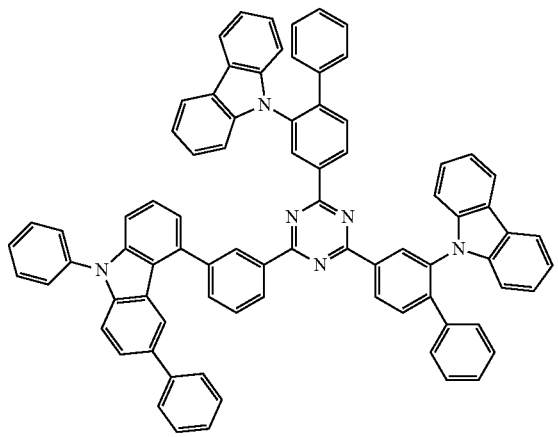

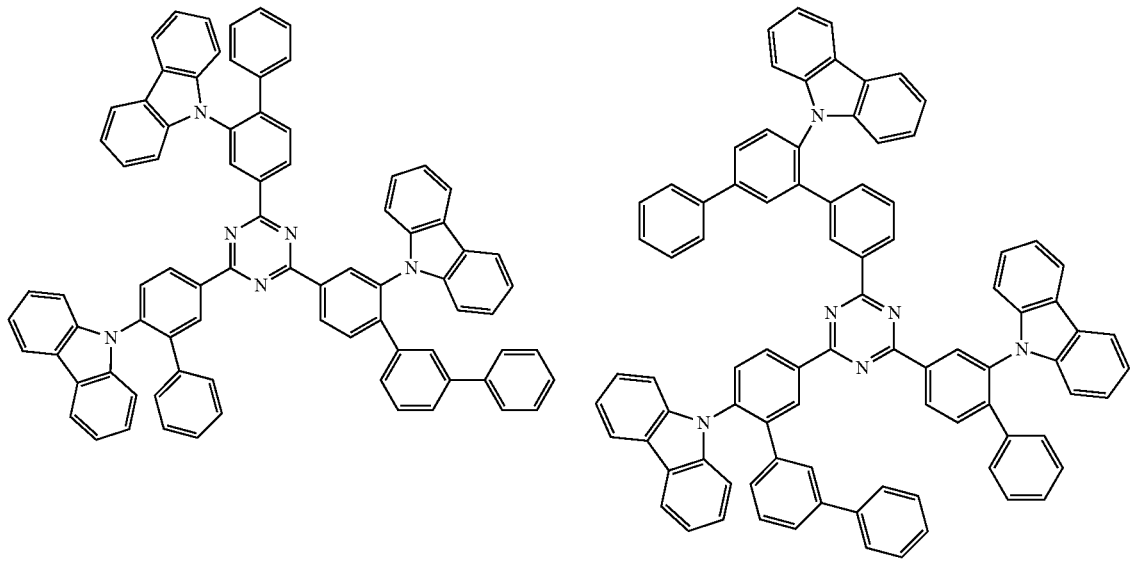
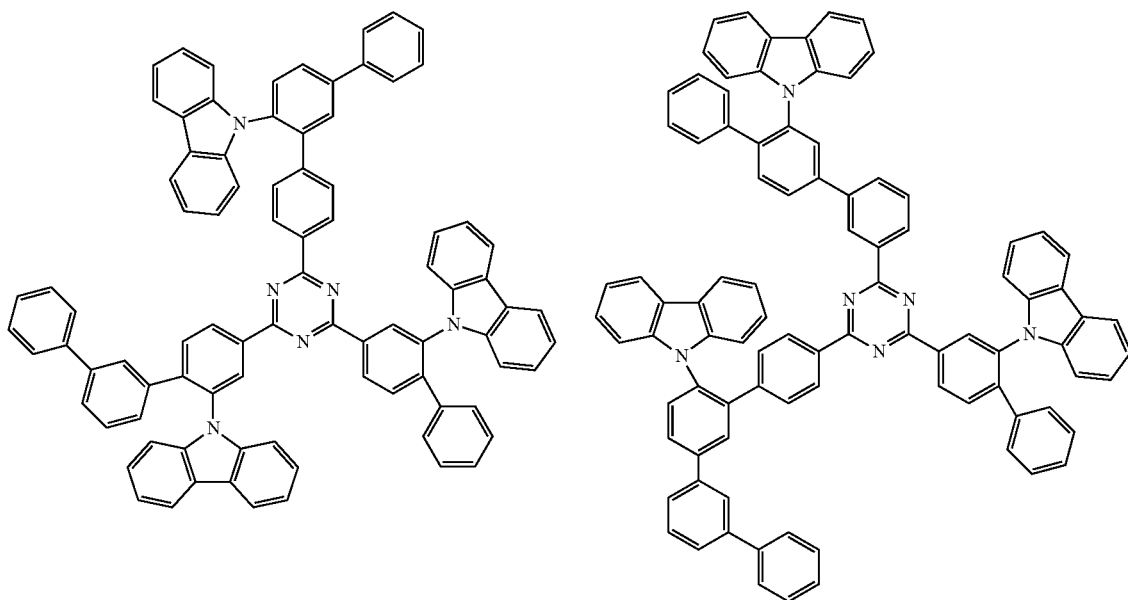

-continued
127
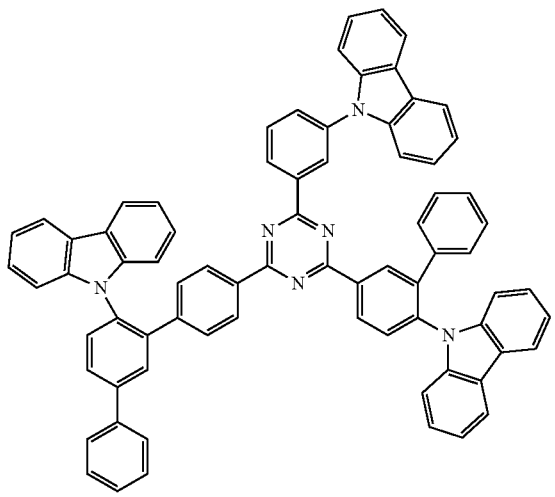
128
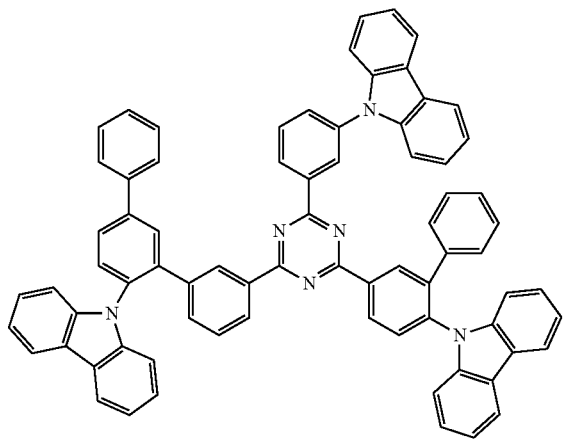
129
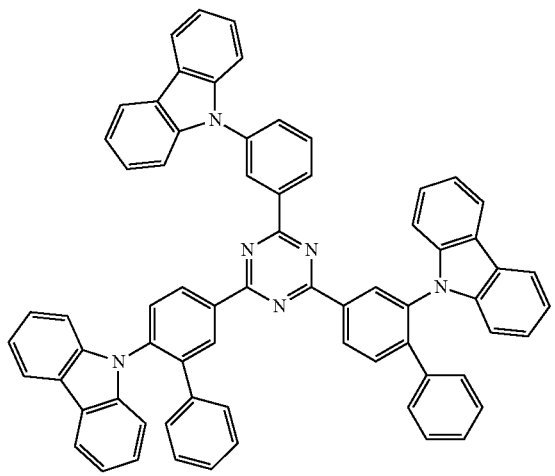
130
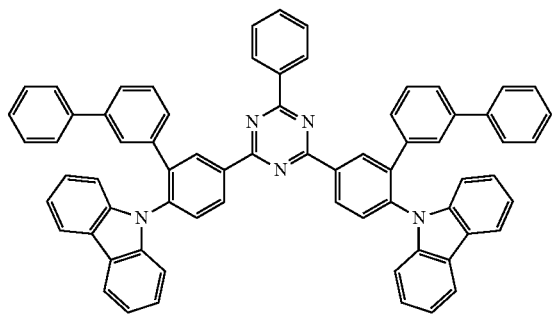
131
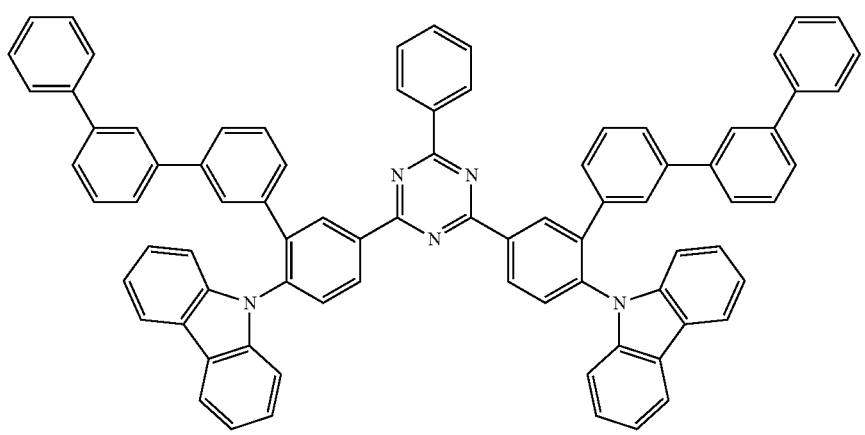

-continued
132
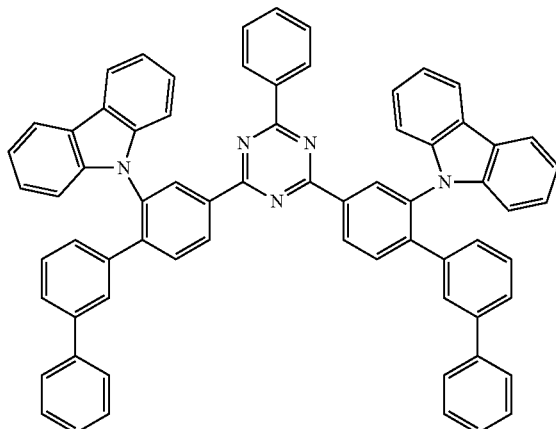
133
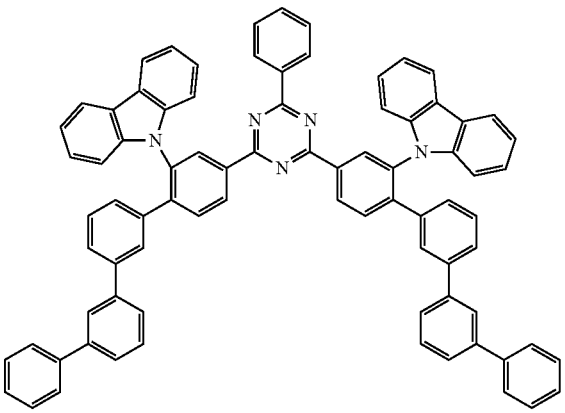
134
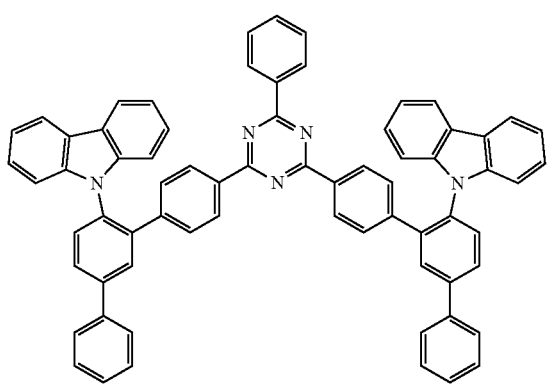
135
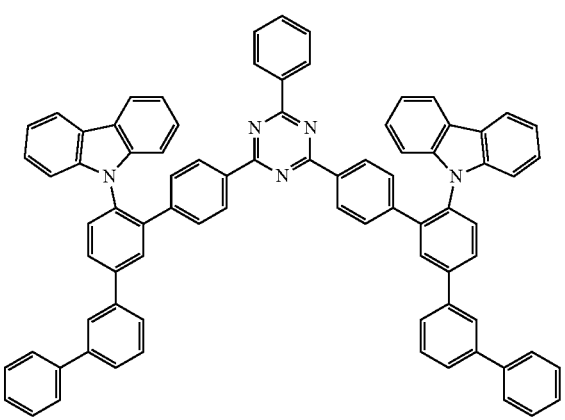
136
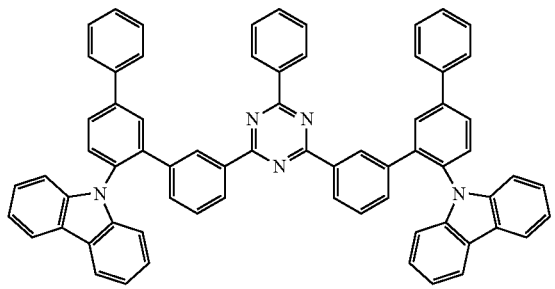
137
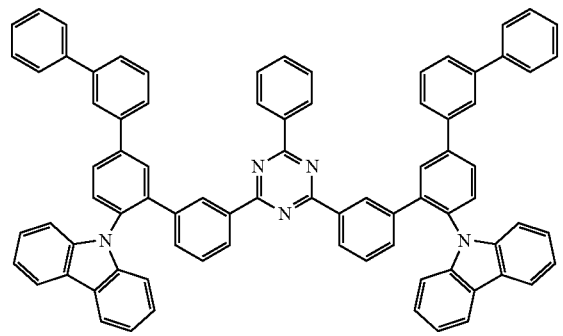
138
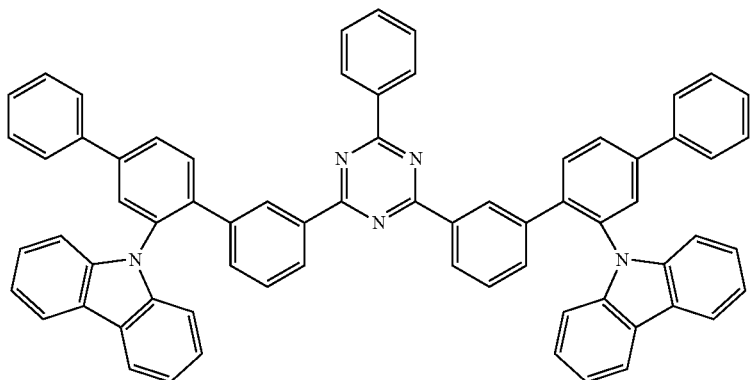

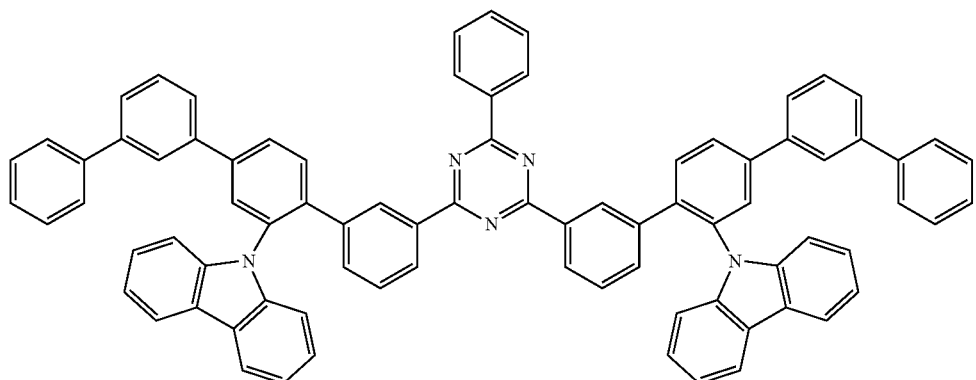
139
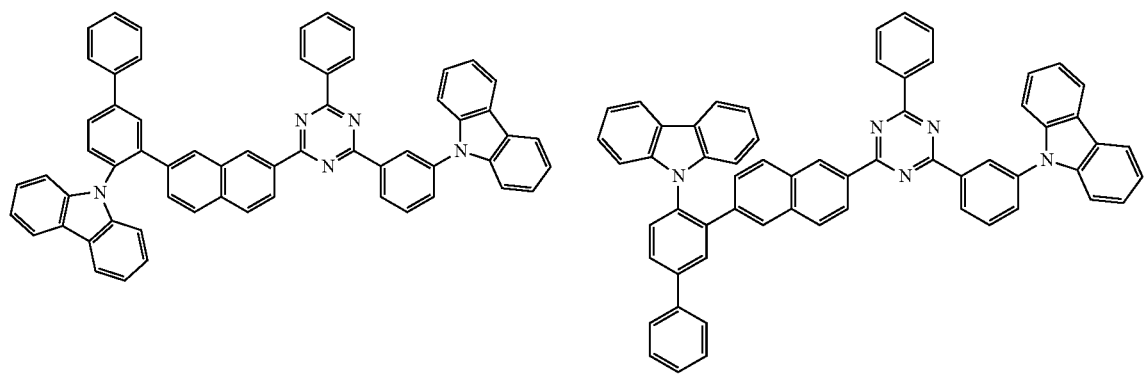
140 141
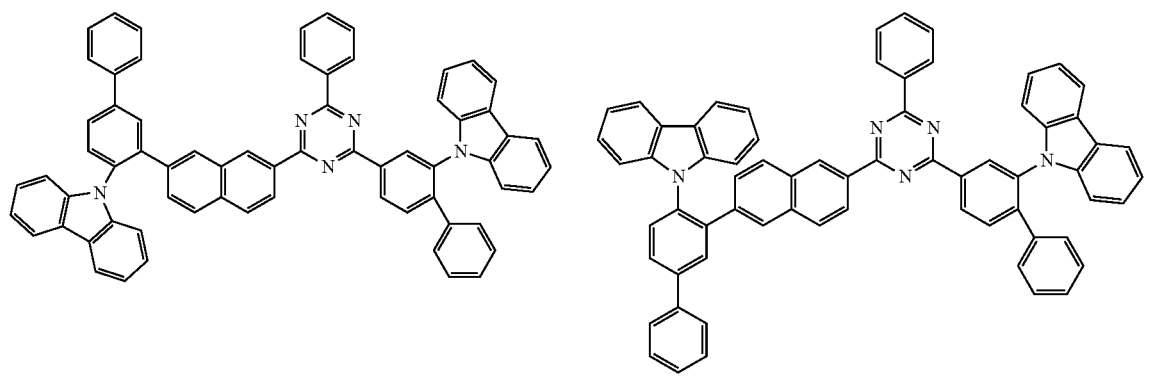
142 143
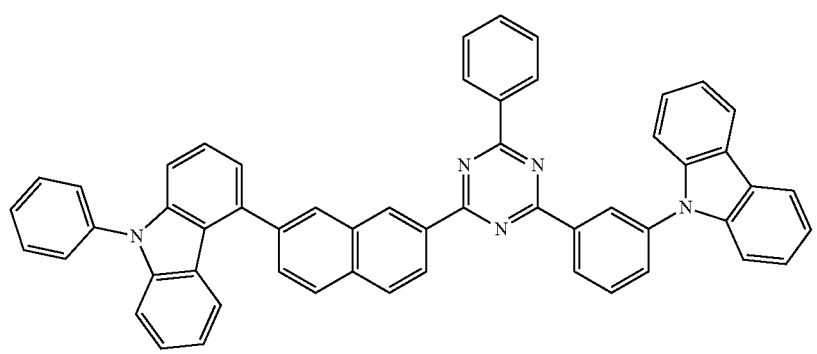
144

-continued
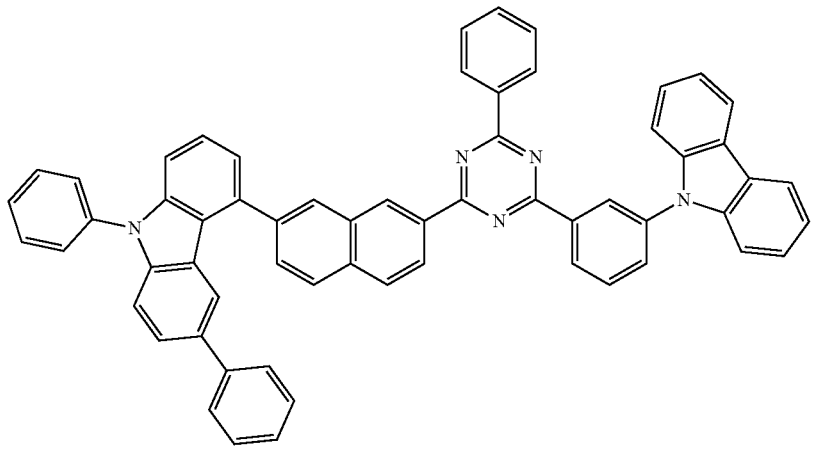
145
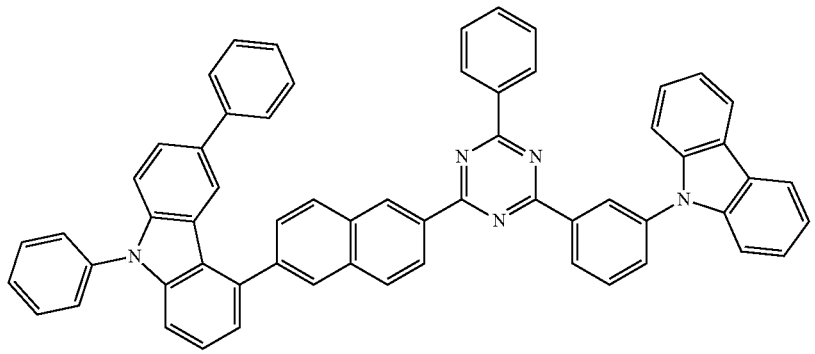
146
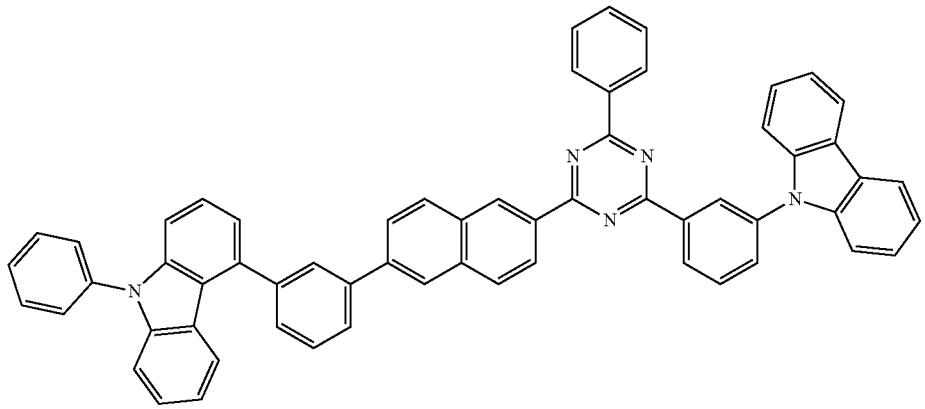
147
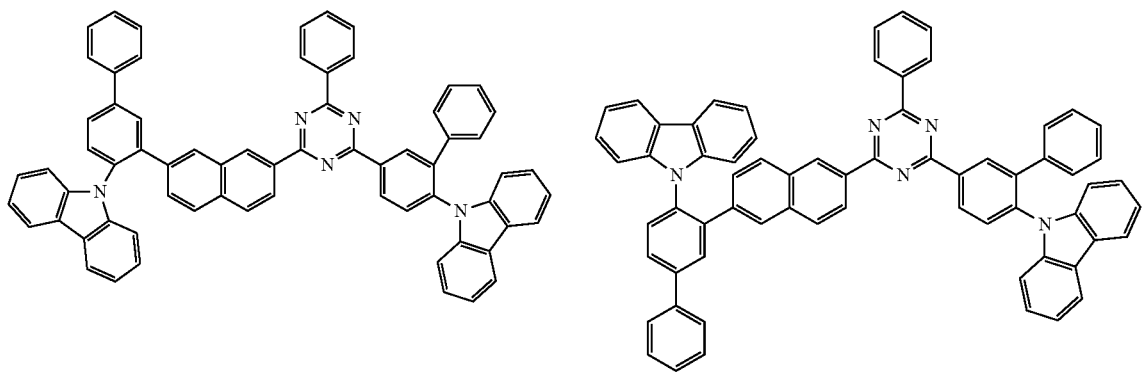
148  149

-continued
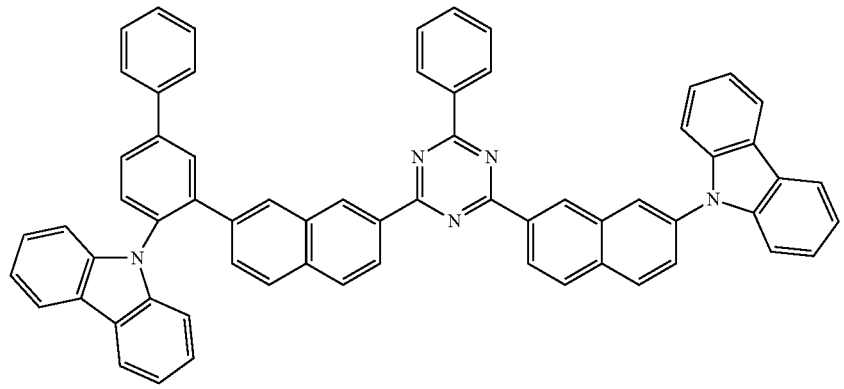
150
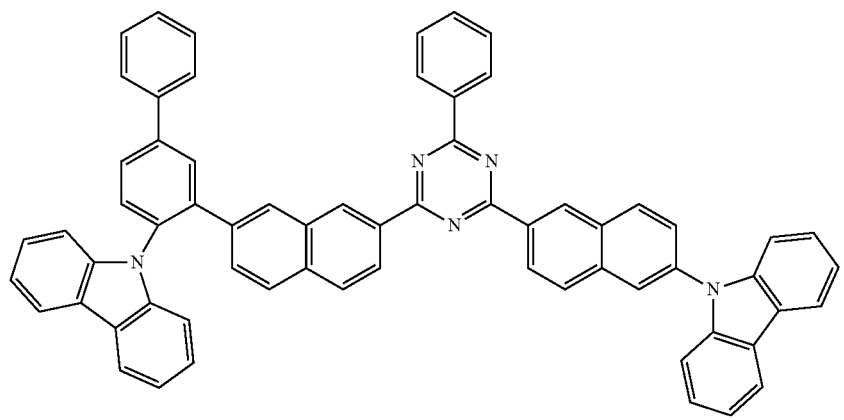
151
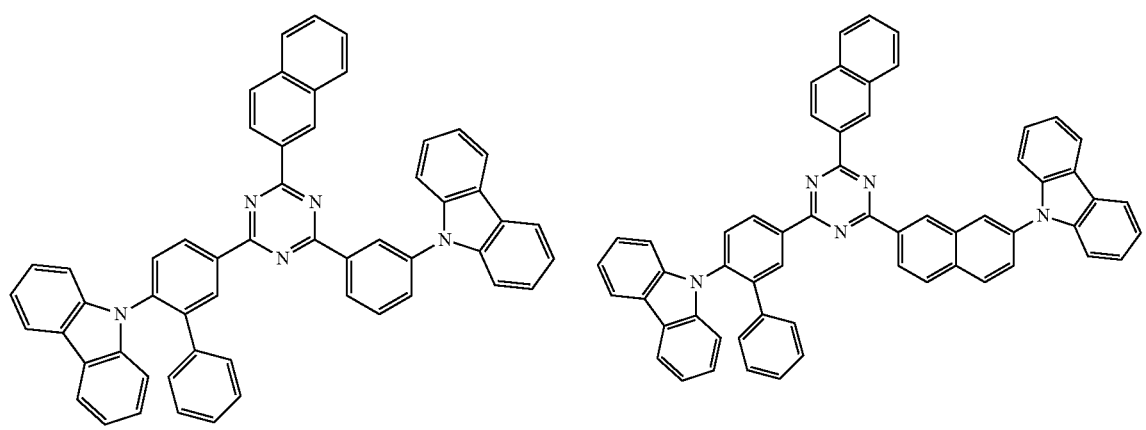
152    153

154
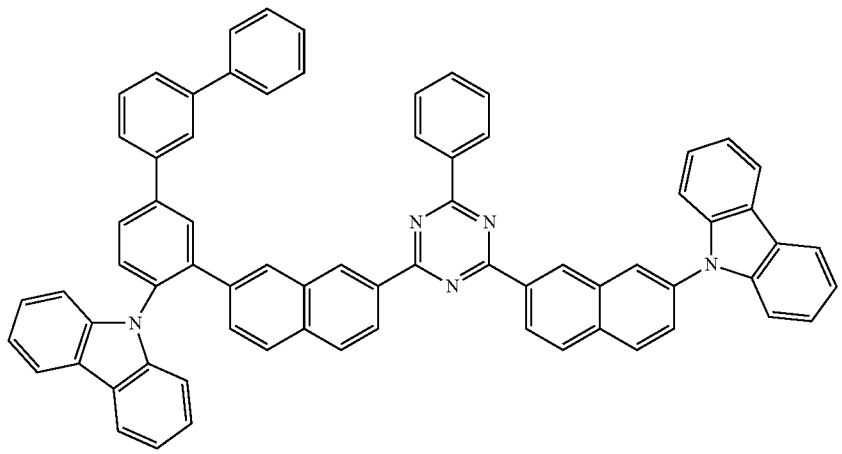
155
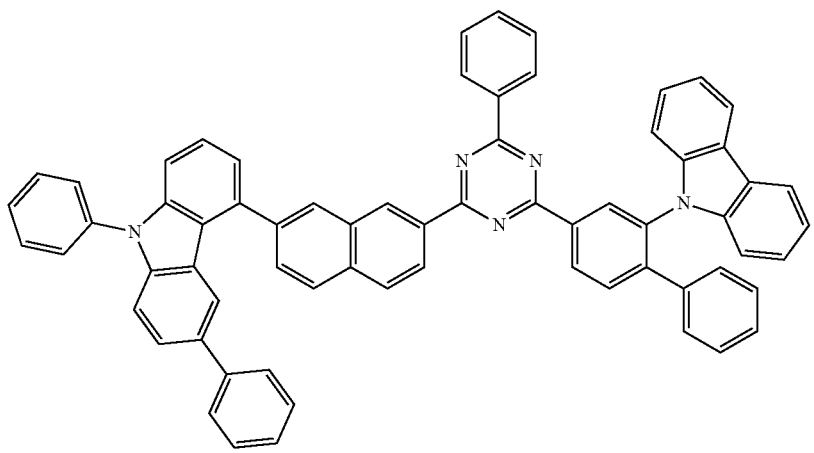
156
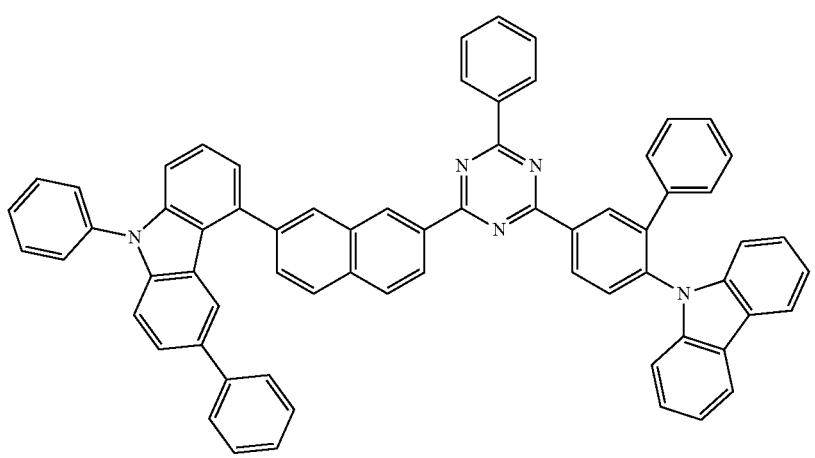

157
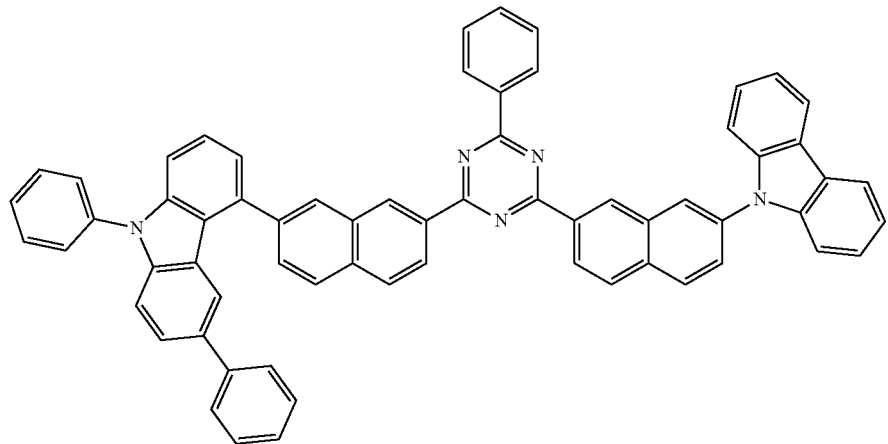
158
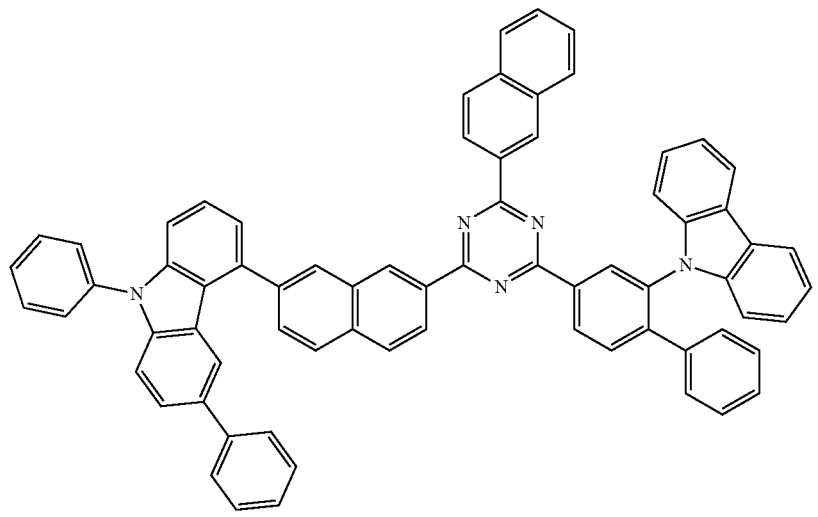
159
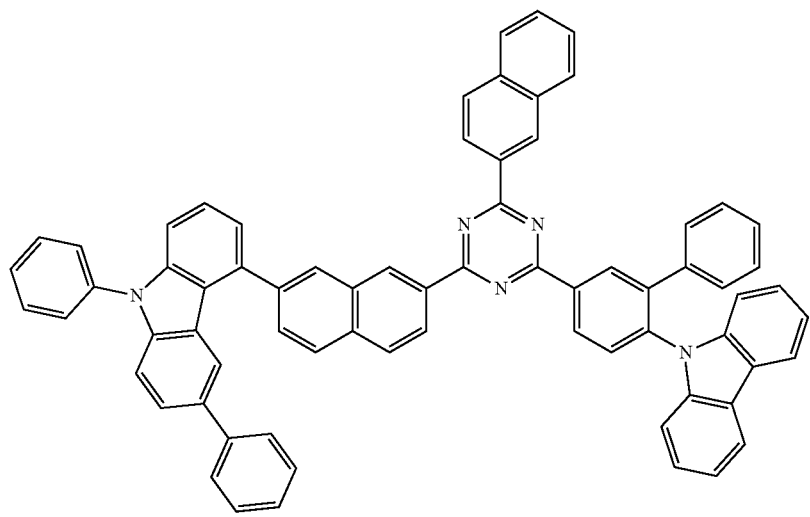

160
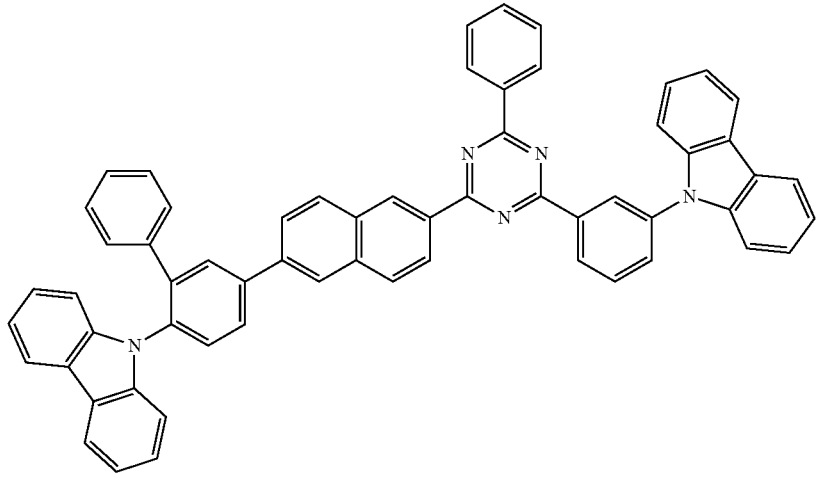
161
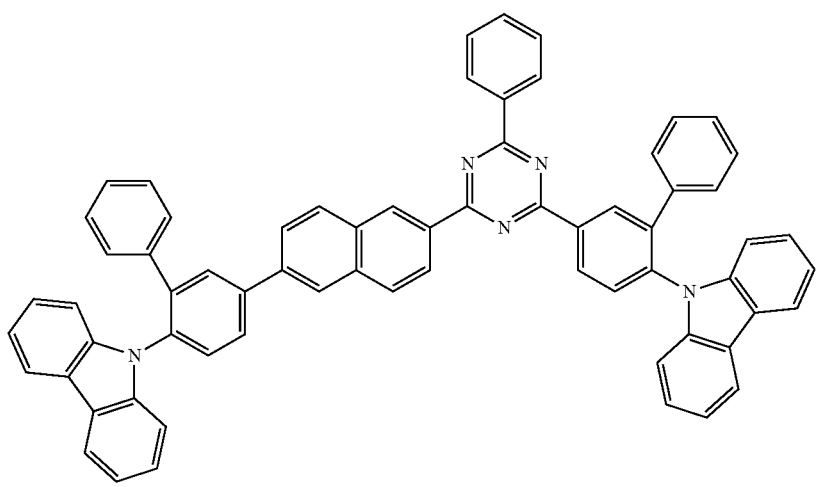
162
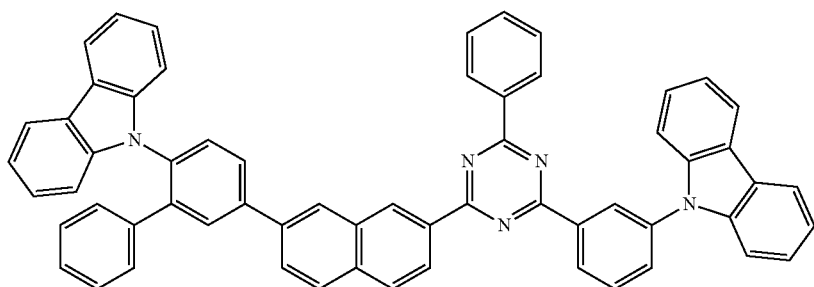

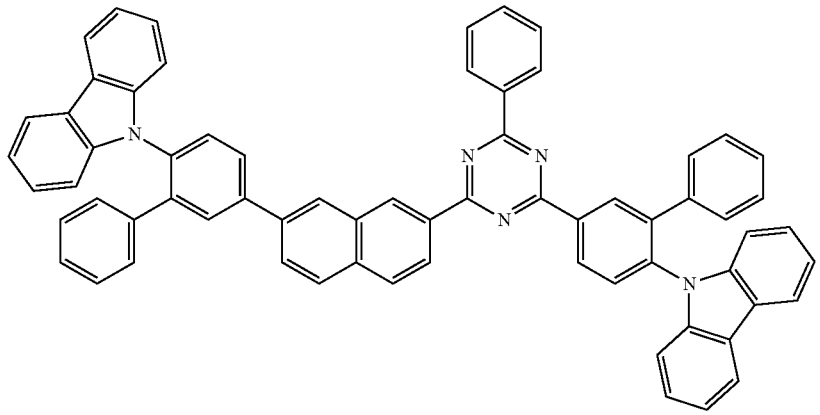
163
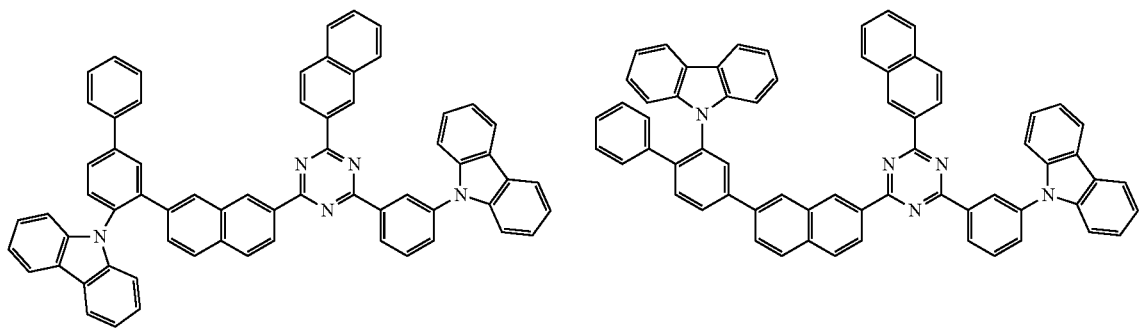
164 165
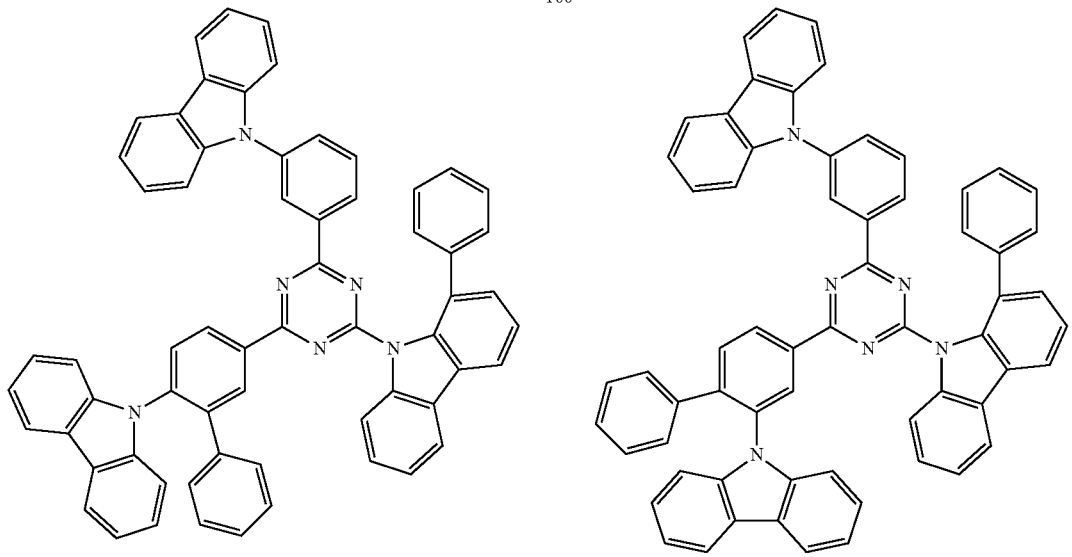
166 167

-continued
168
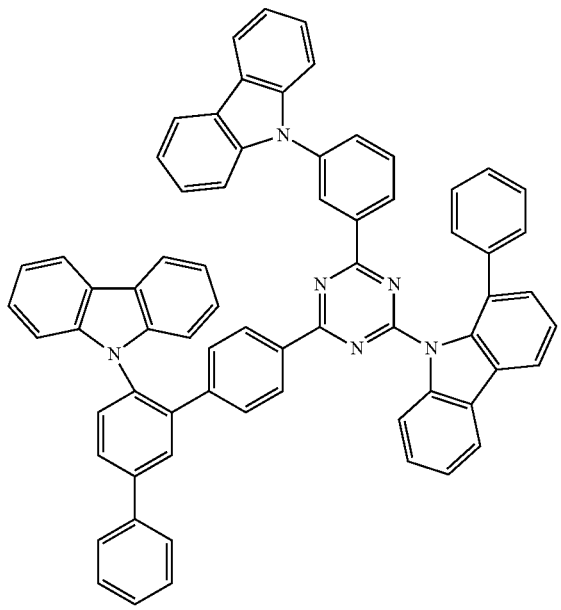
169
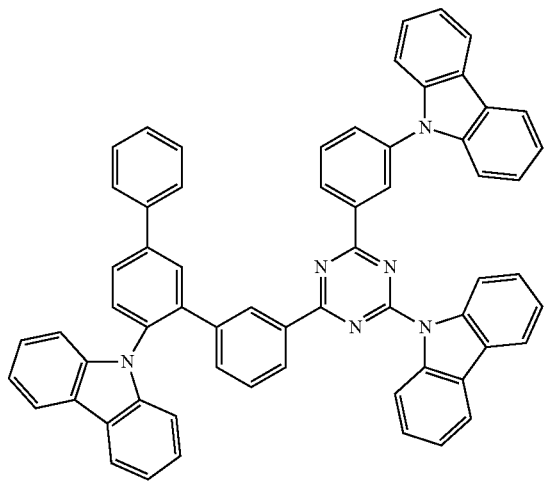
170
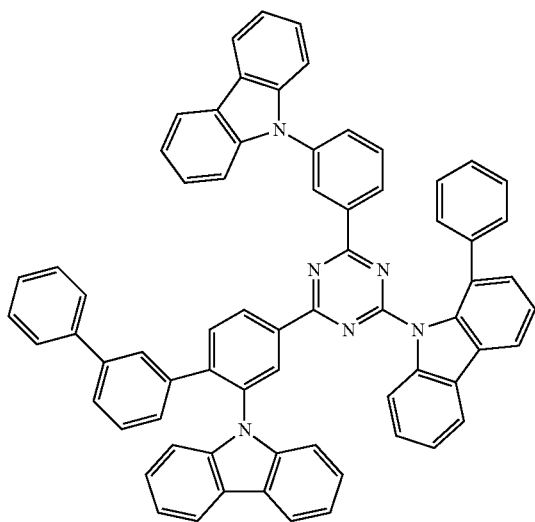
171
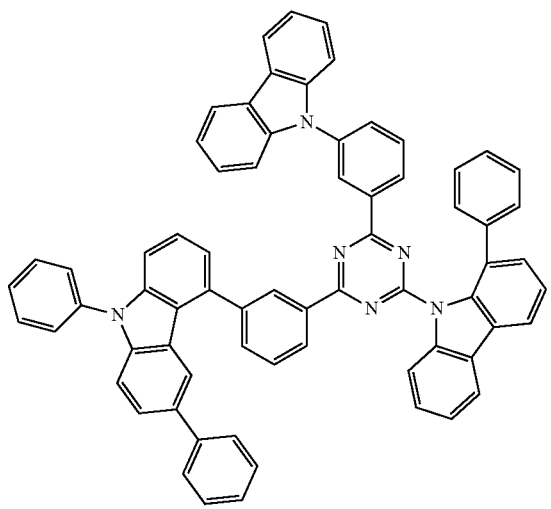

-continued
172
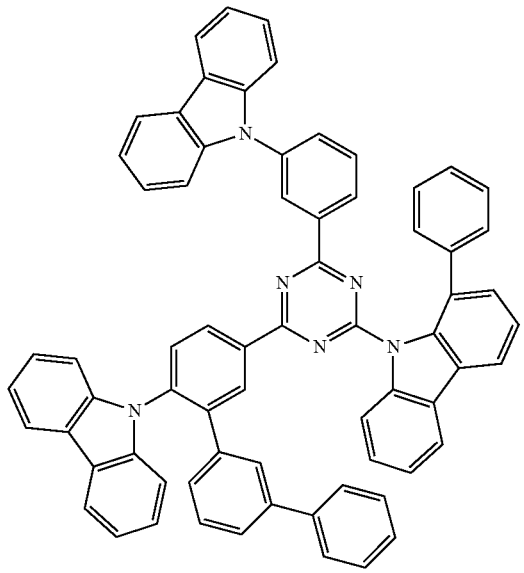
173
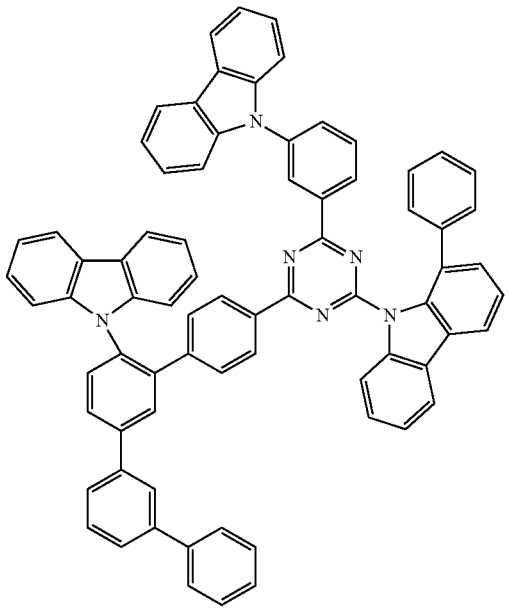
174
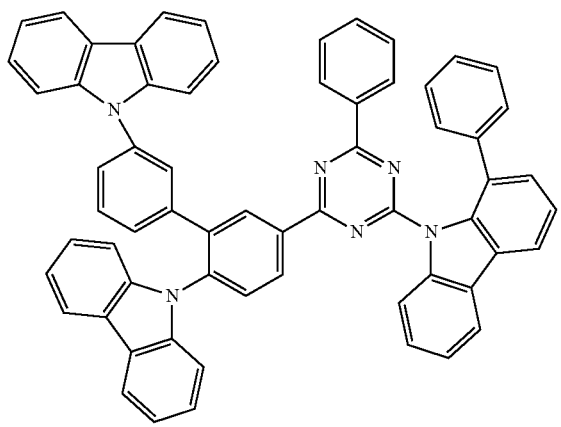
175
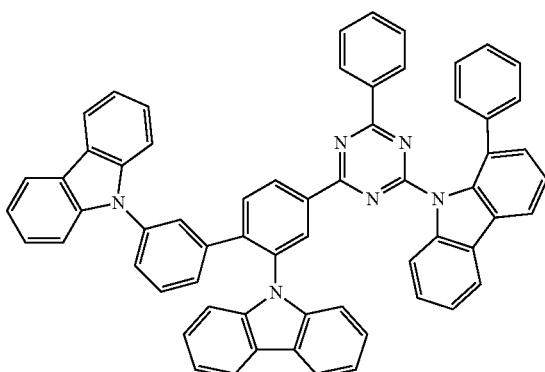
176
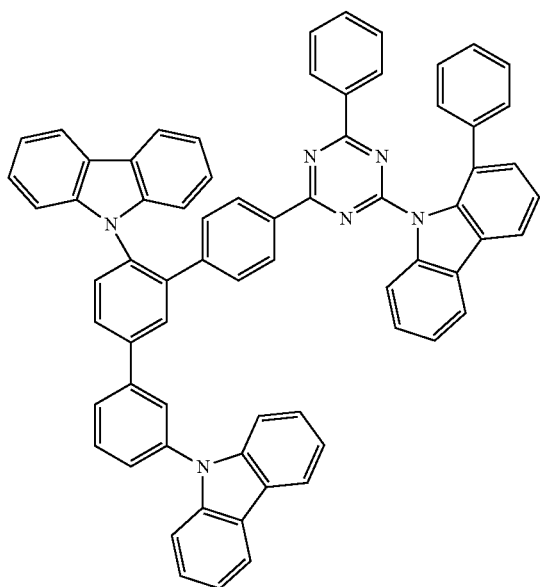
177
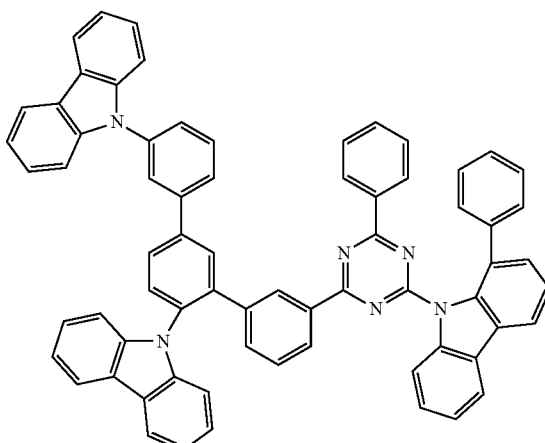

-continued
178
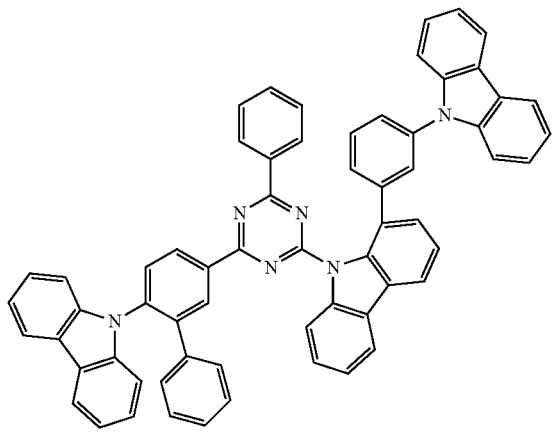
179
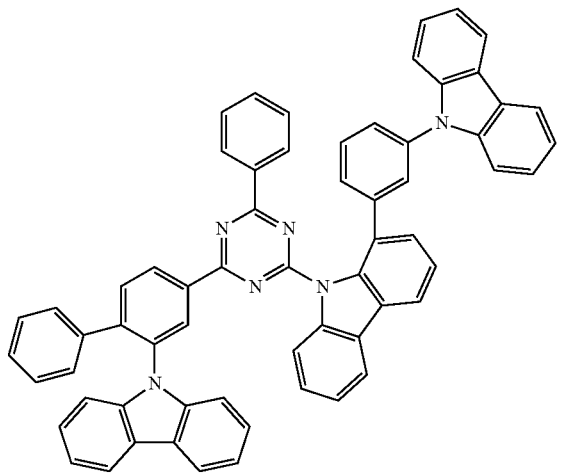
180
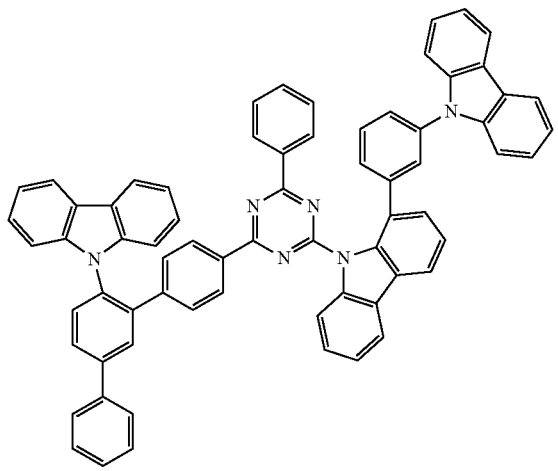
181
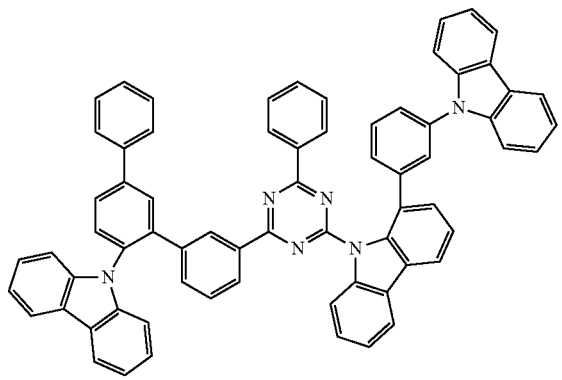
182
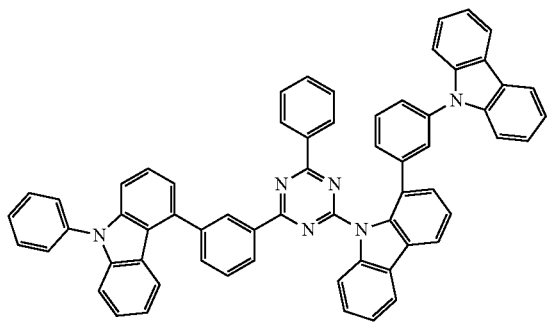
183
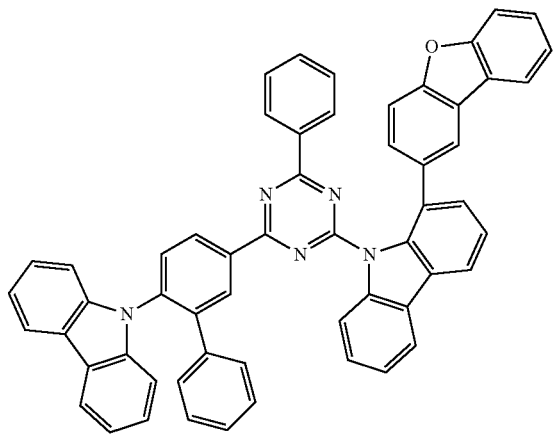

-continued
184
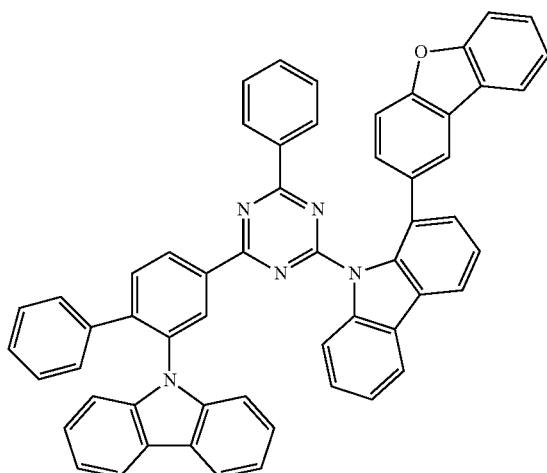
185
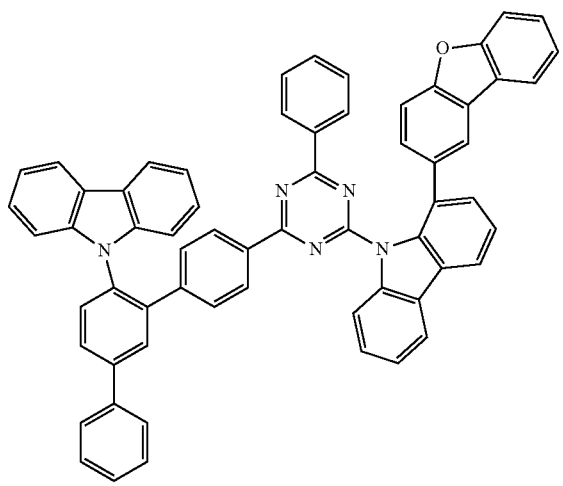
186
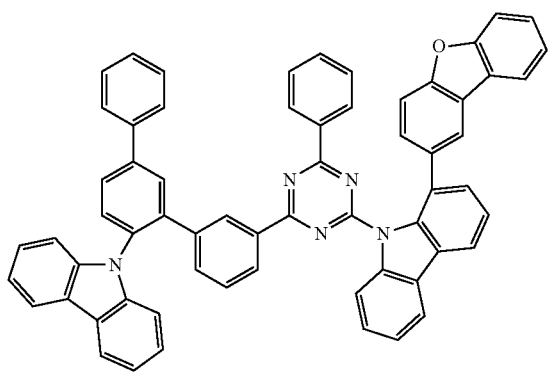
187
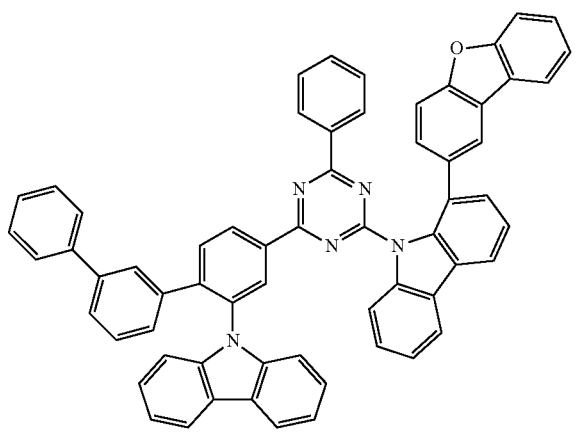
188
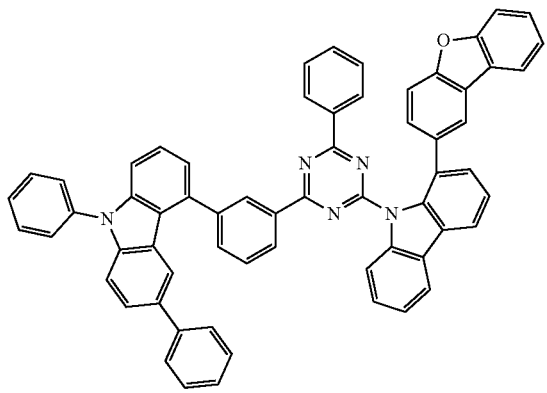
189
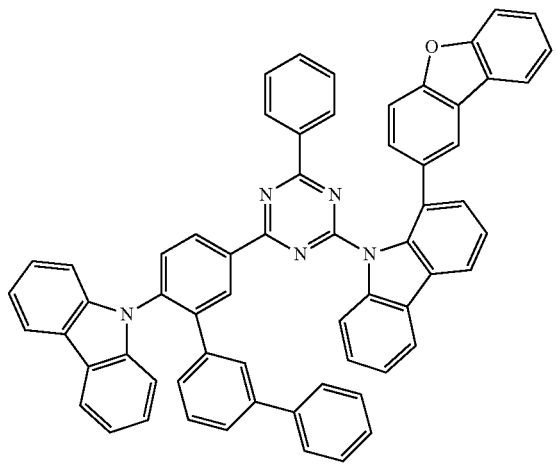

-continued
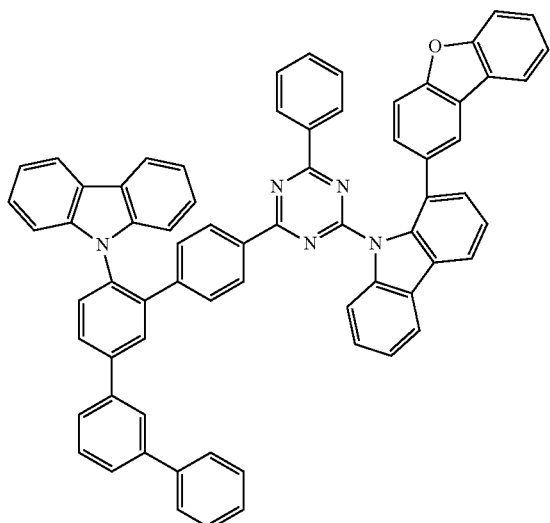
190
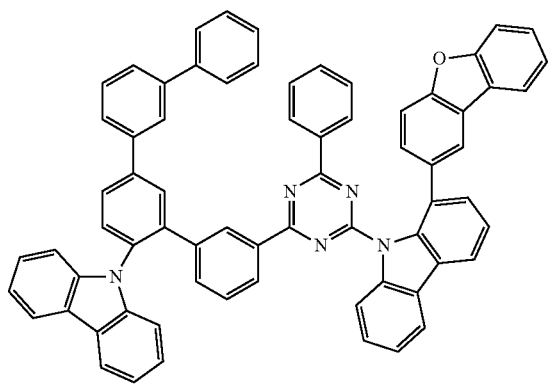
191
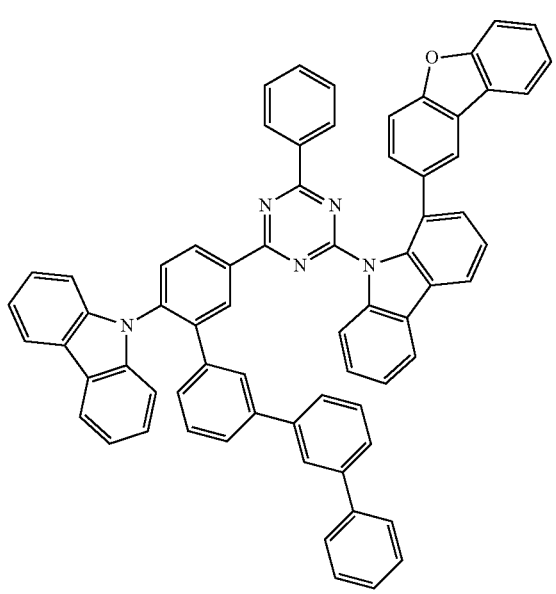
192
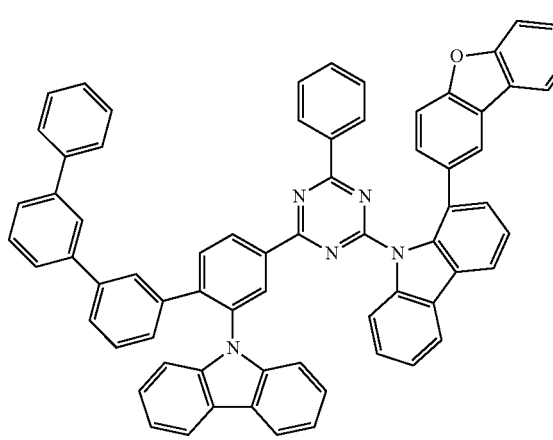
193
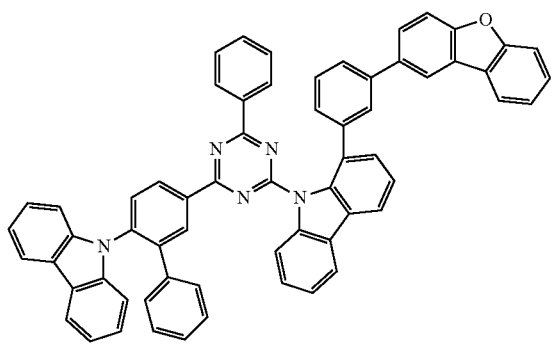
194
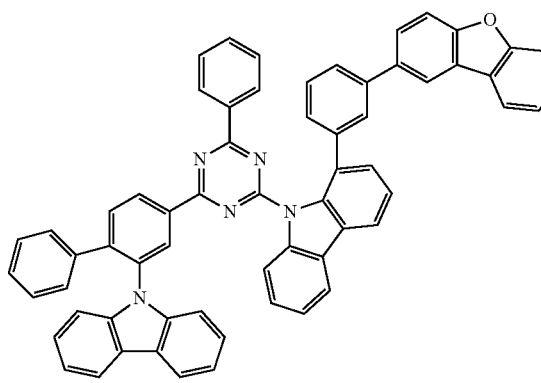
195

-continued
196
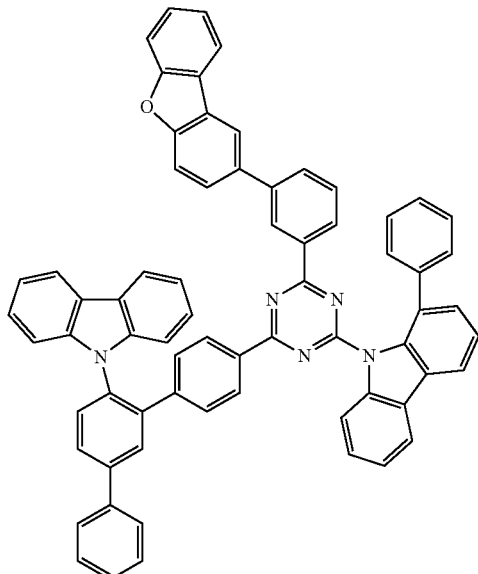
197
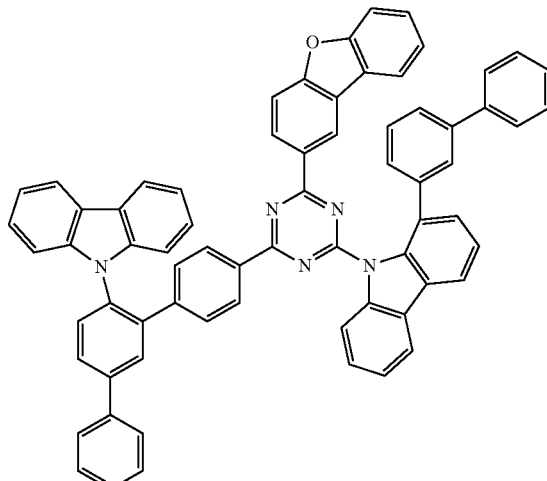
198
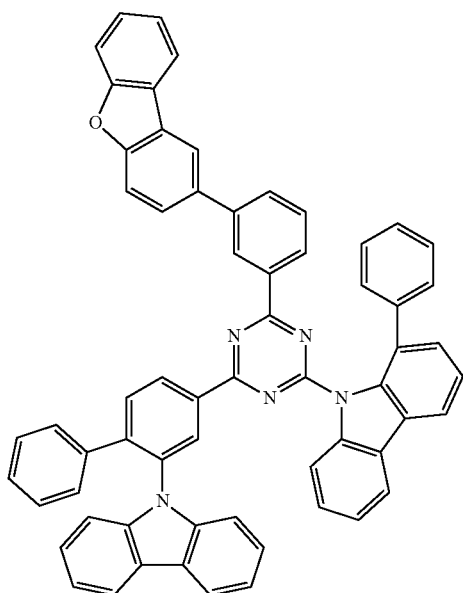
199
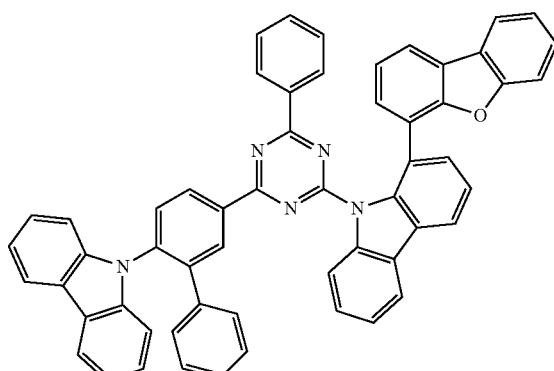
200
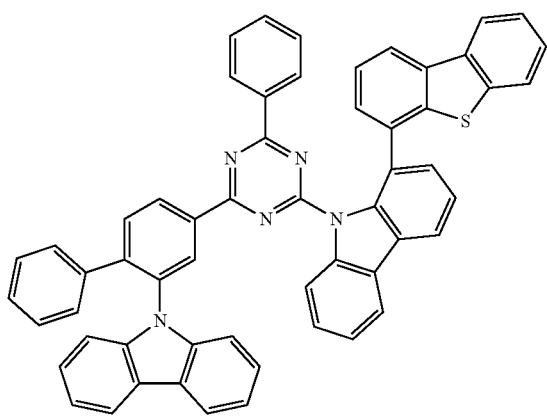
201
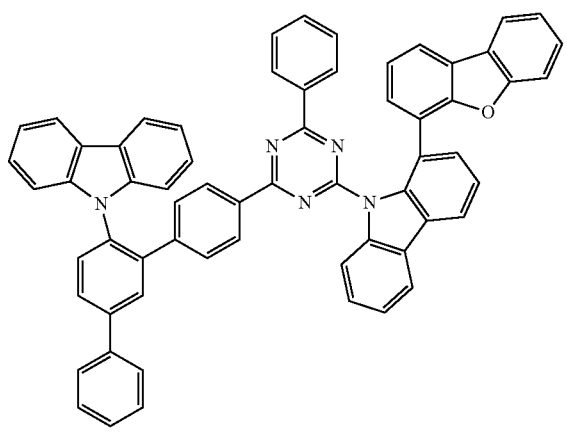

-continued
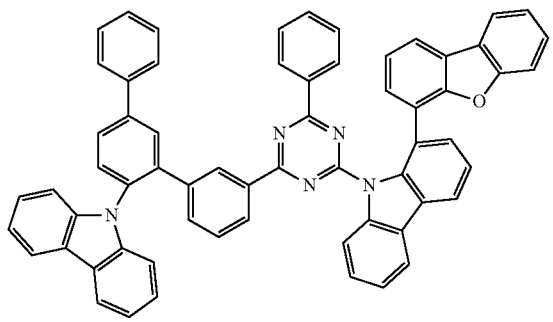
202
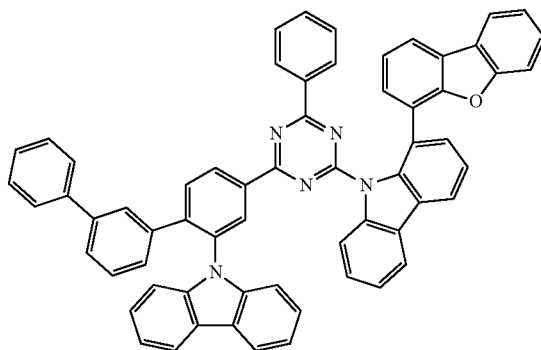
203
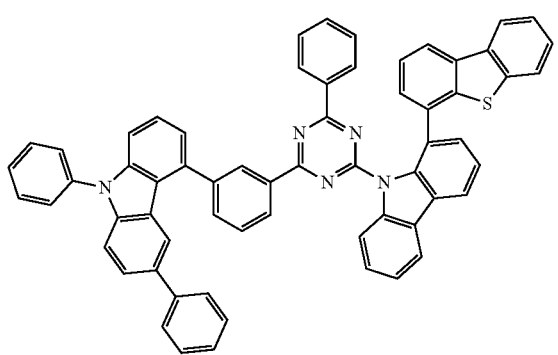
204
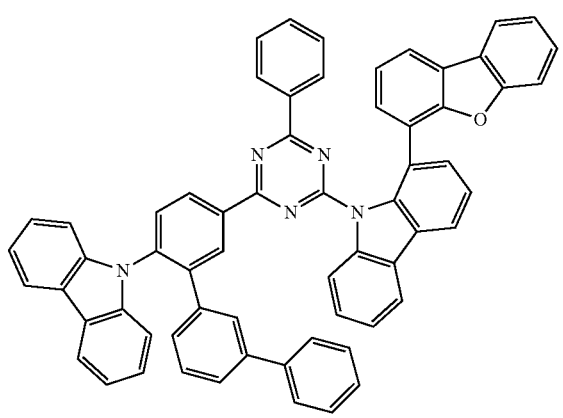
205
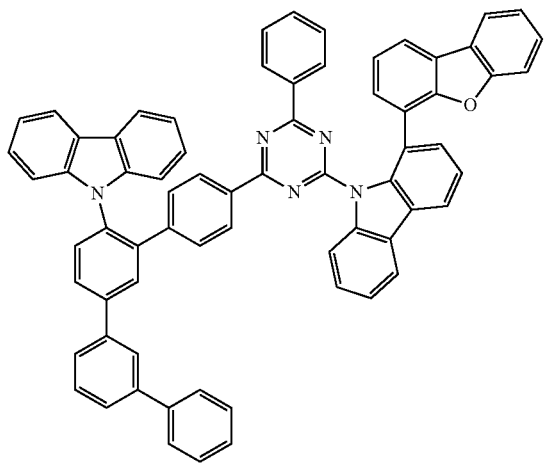
206
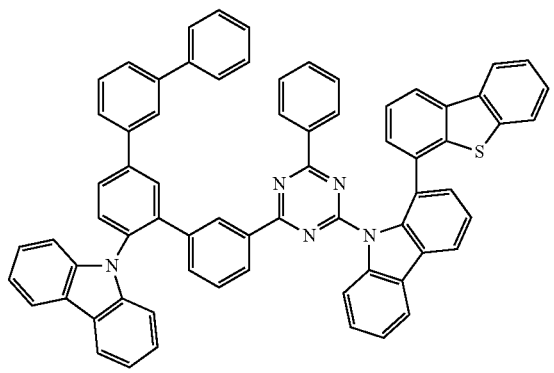
207

-continued
208
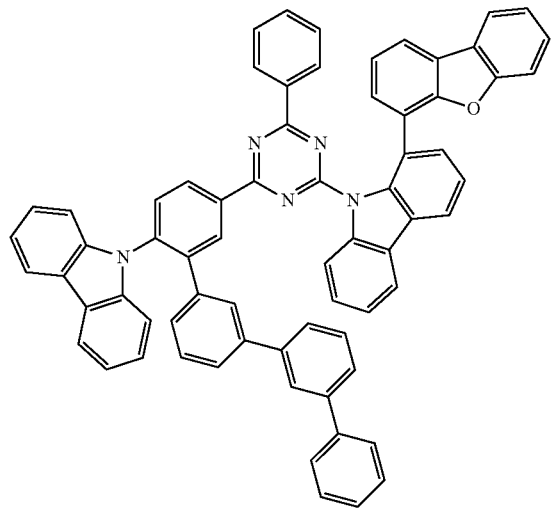
209
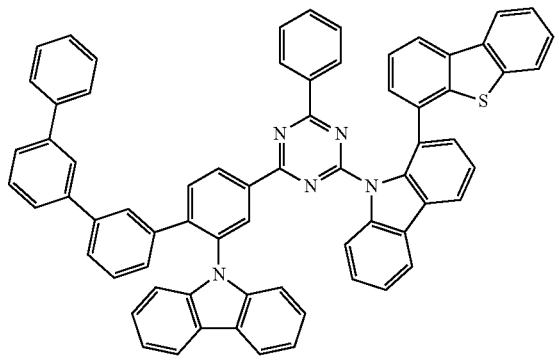
210
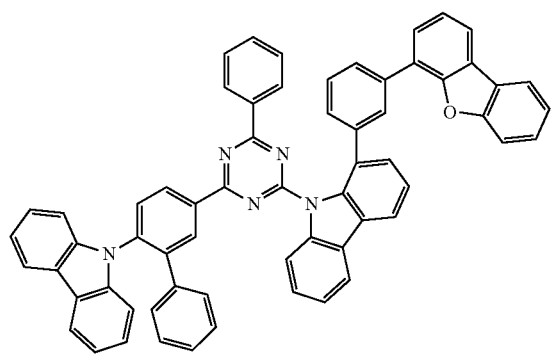
211
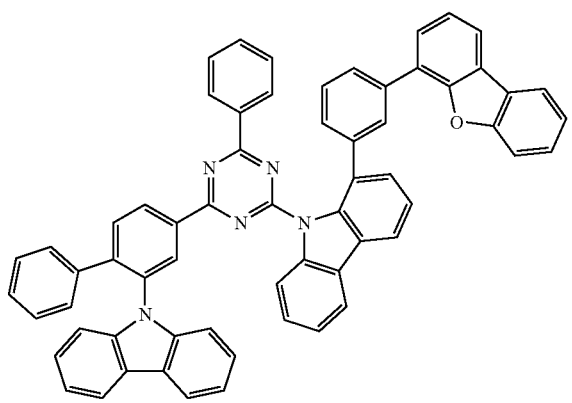
212
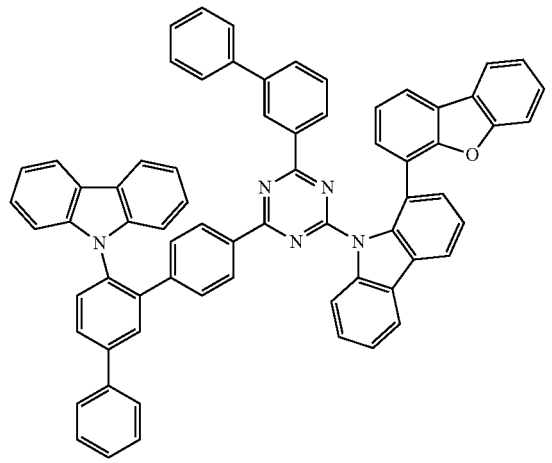
213
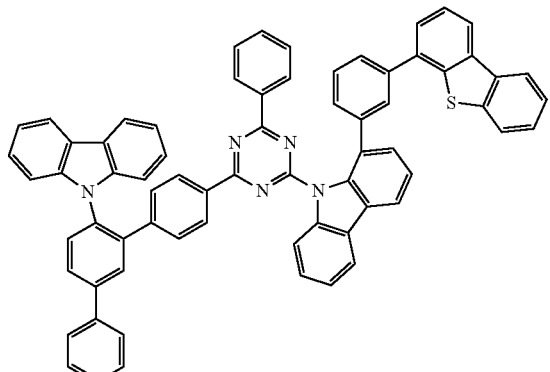

-continued
214
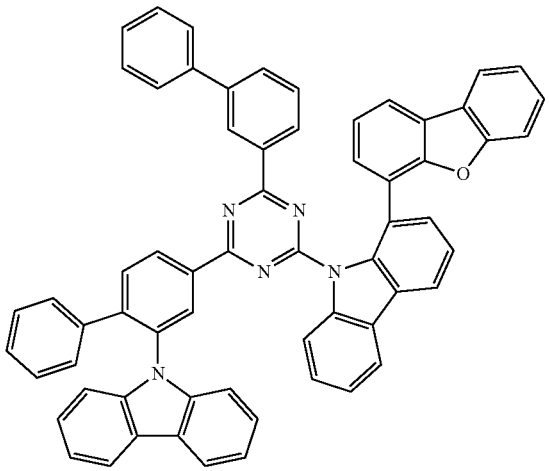
215
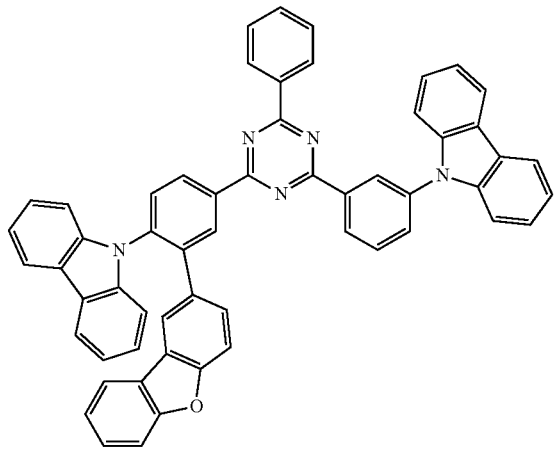
216
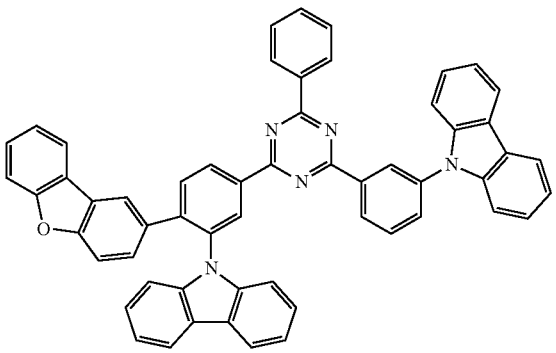
217
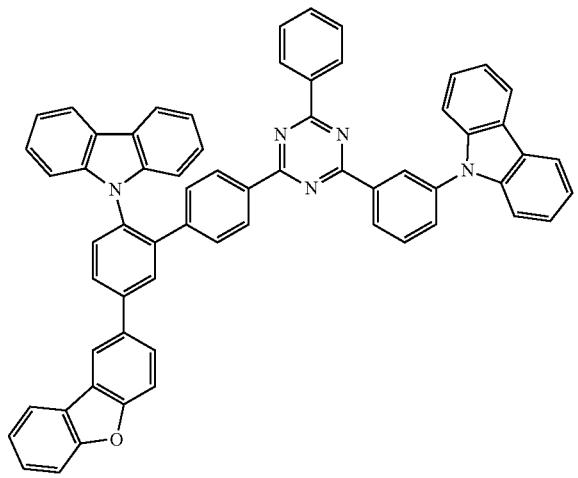
218
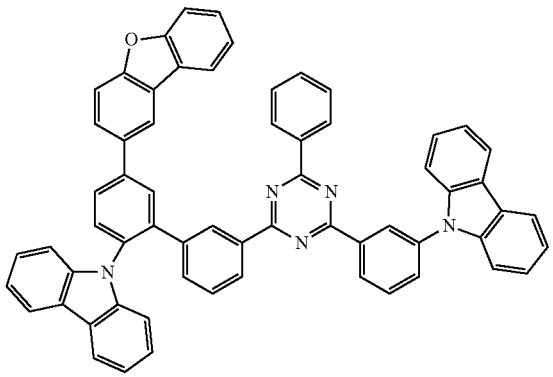
219
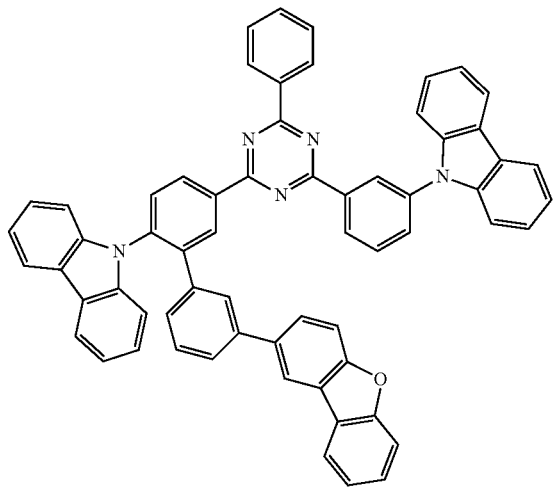

-continued
220
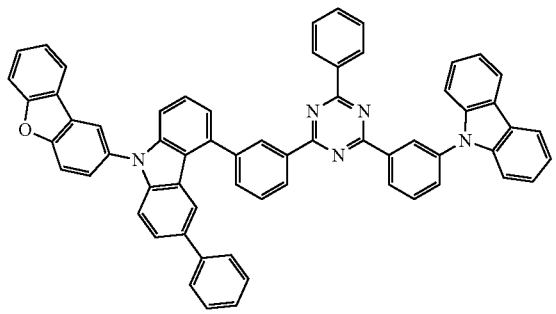
221
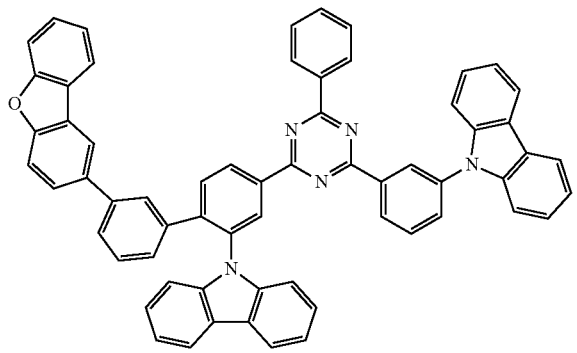
222
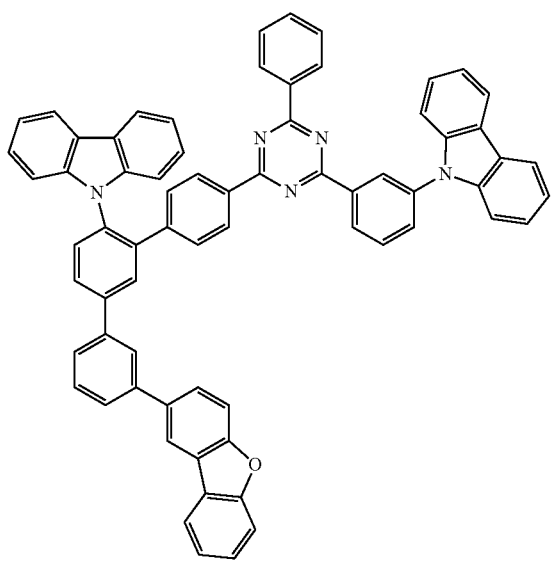
223
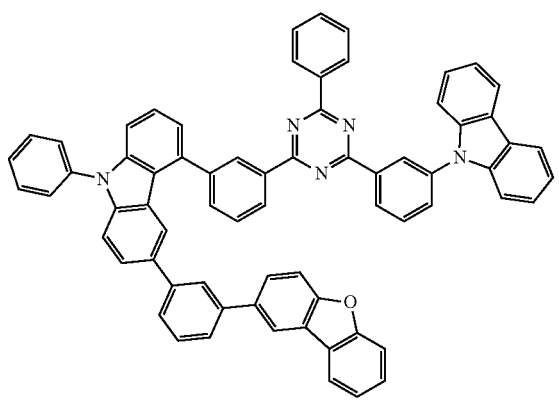
224
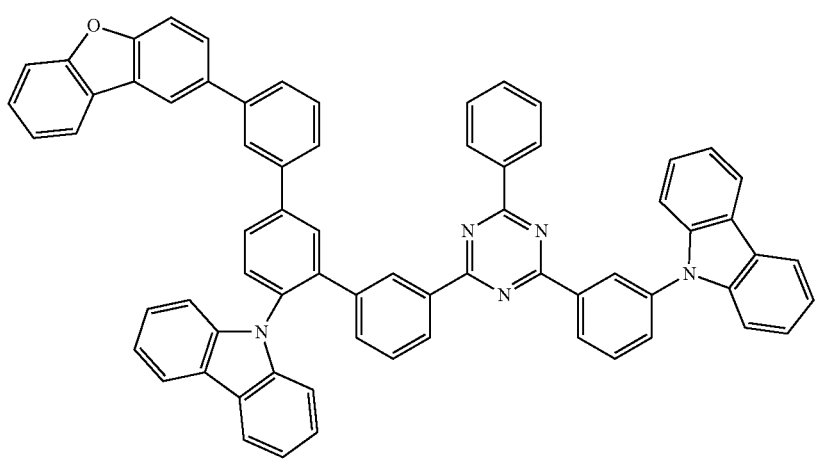

225
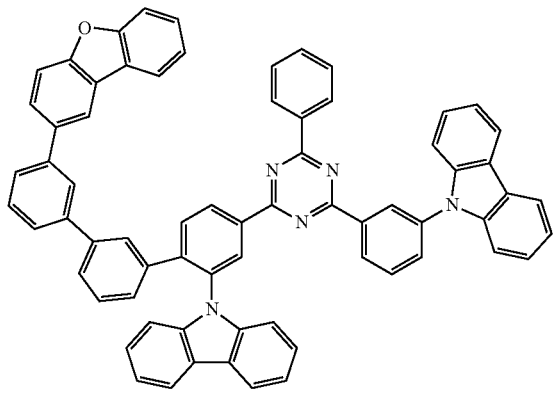
226
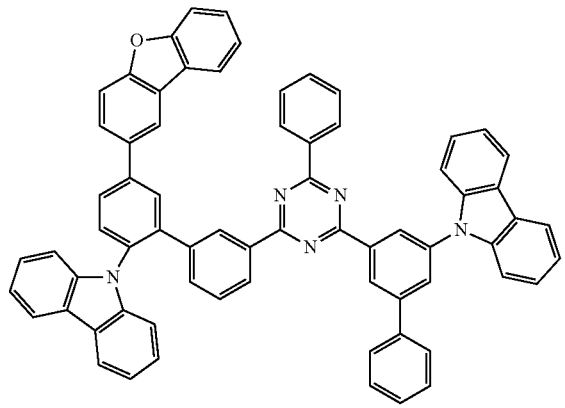
227
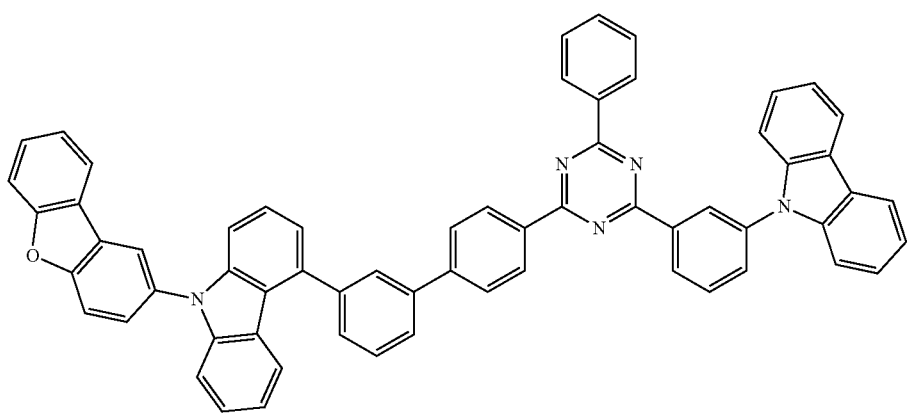
228
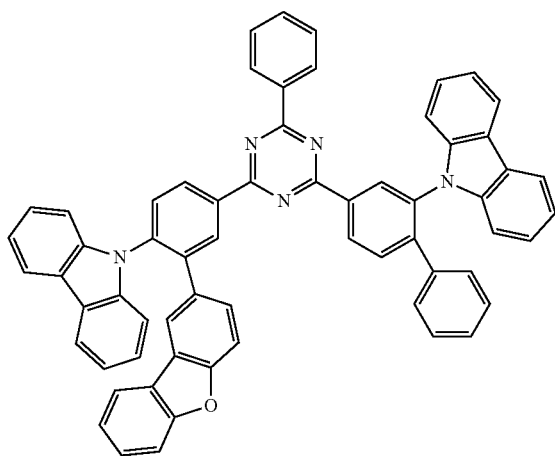
229
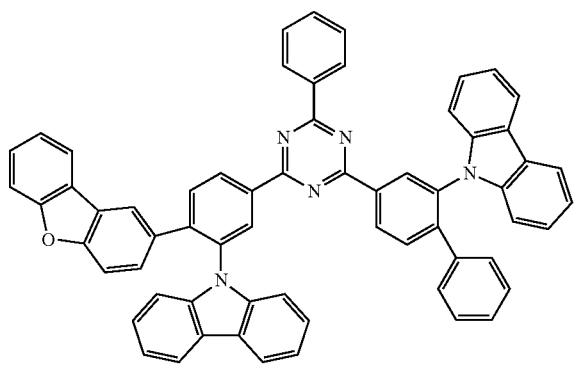

-continued
230
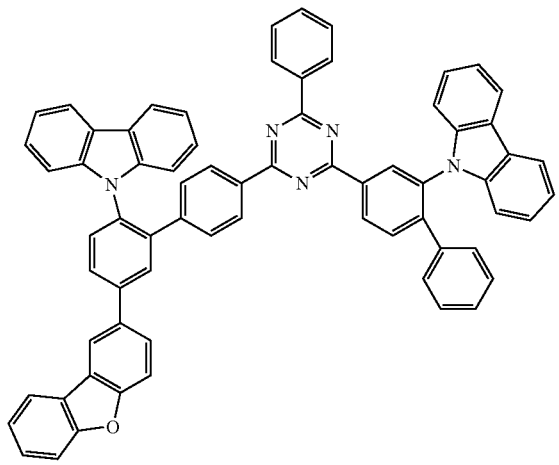
231
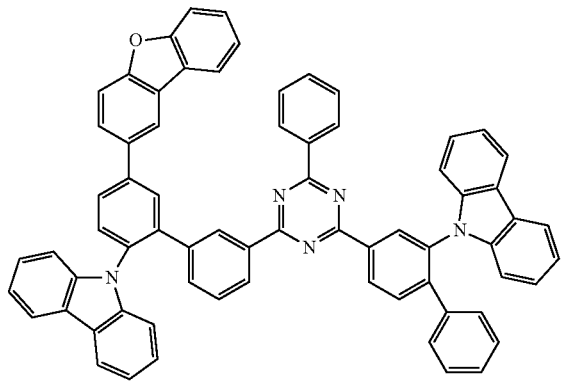
232
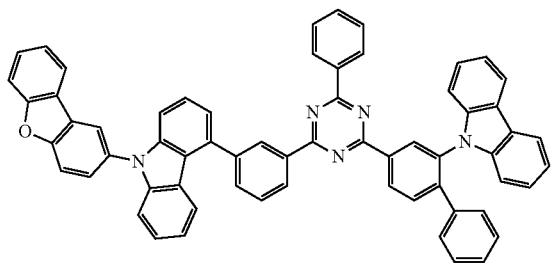
233
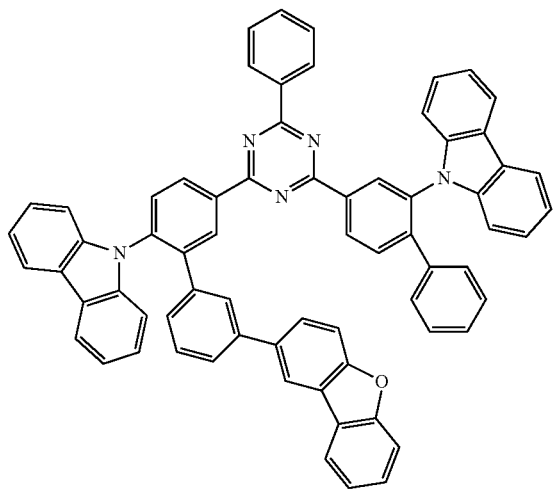
234
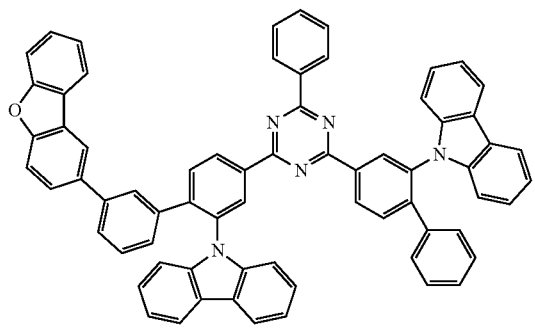
235
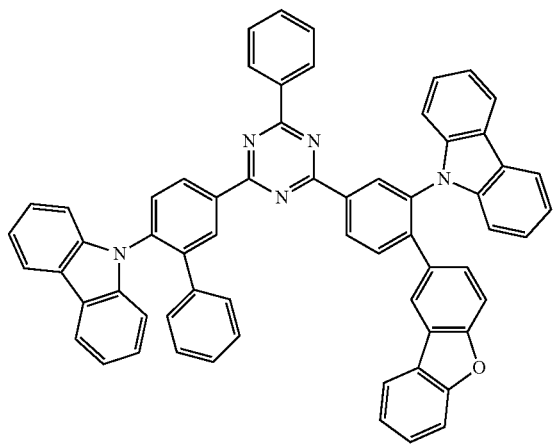

-continued
236
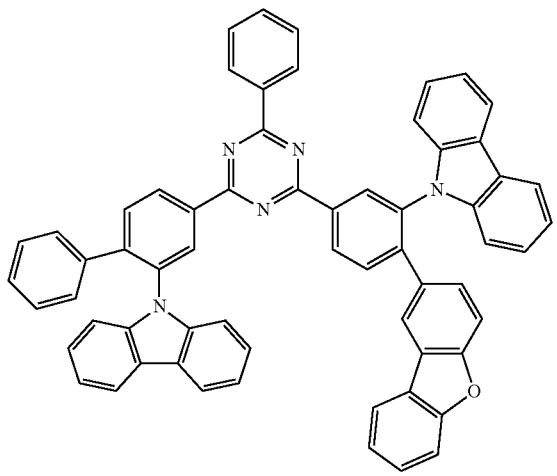
237
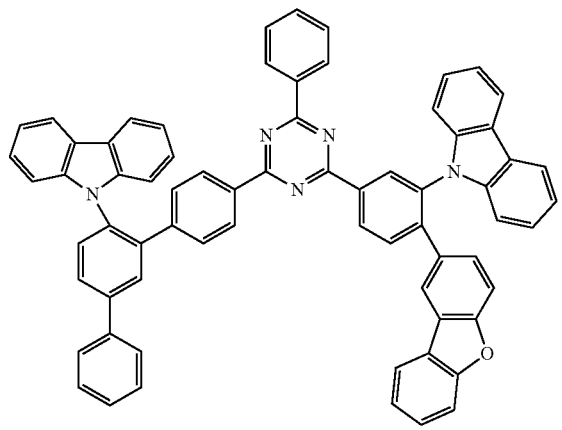
238
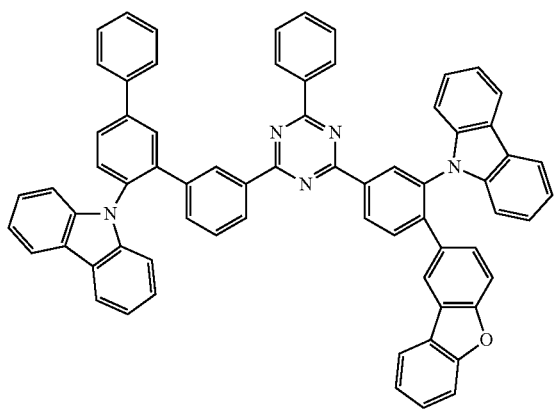
239
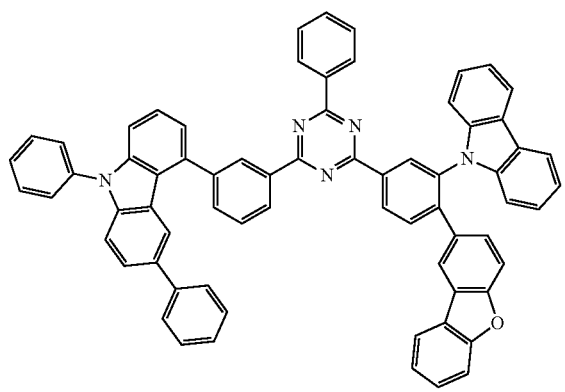
240
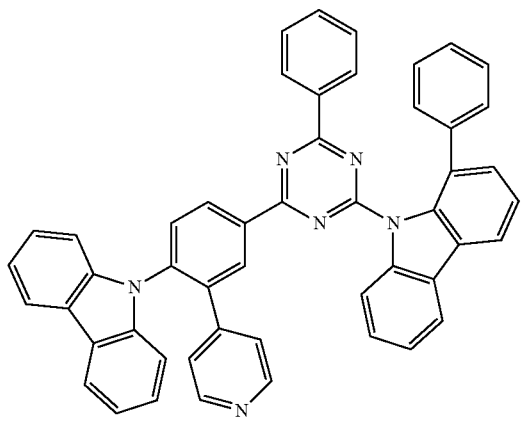
241
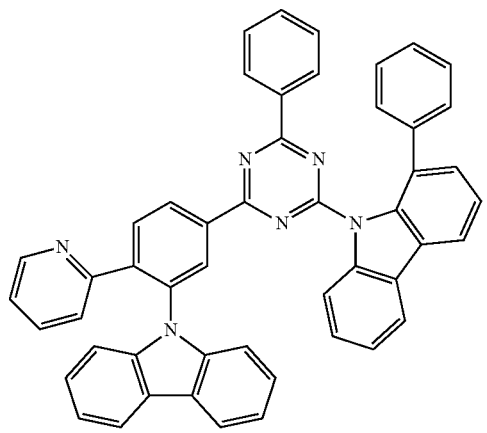

-continued
242
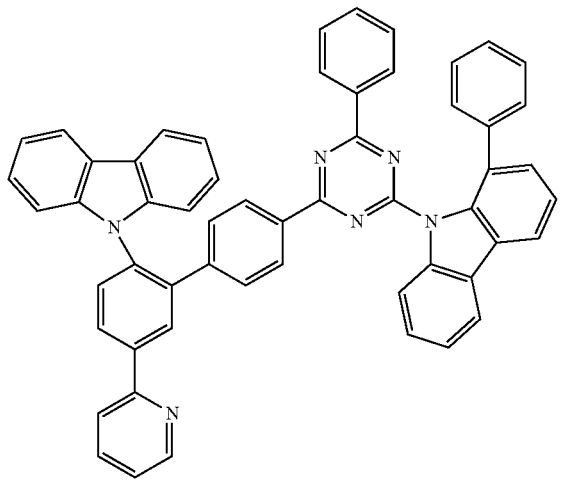
243
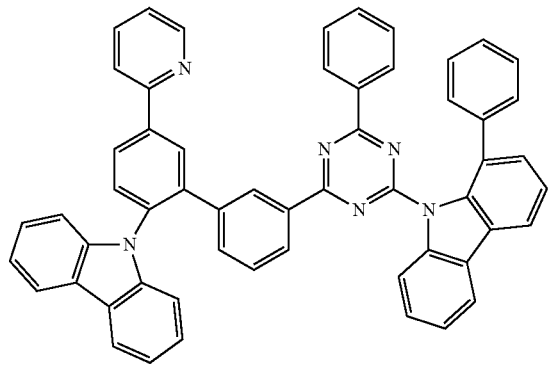
244
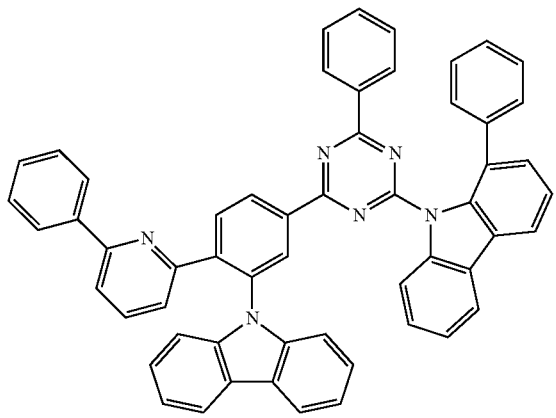
245
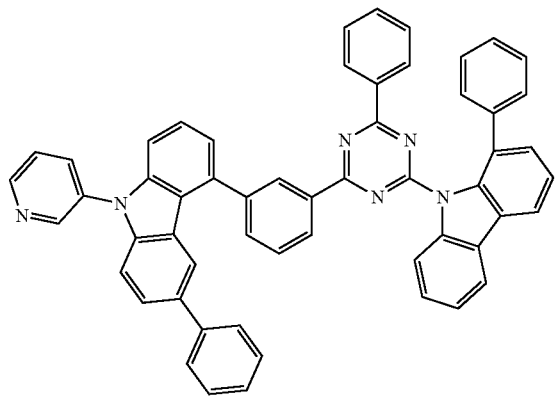
246
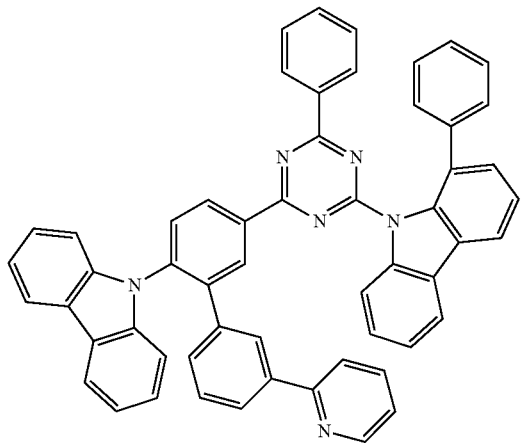
247
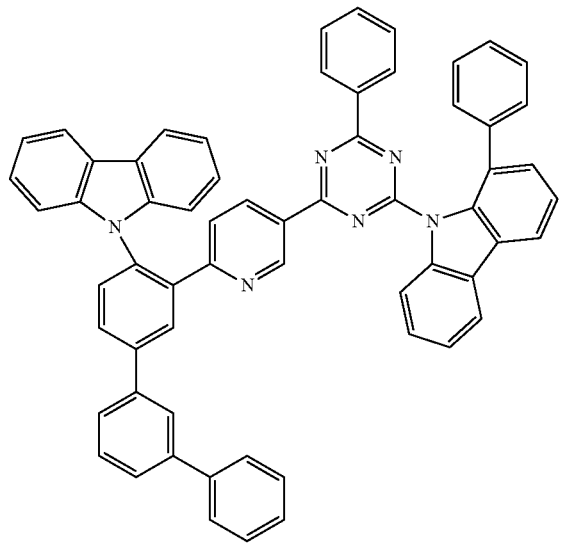

-continued
248
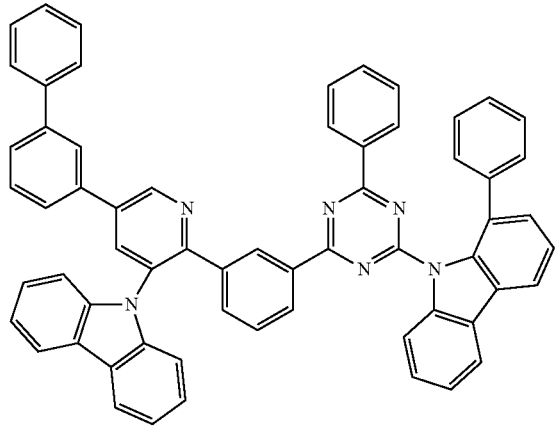
249
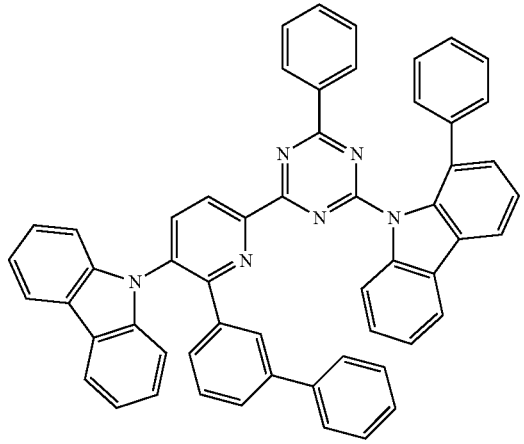
250
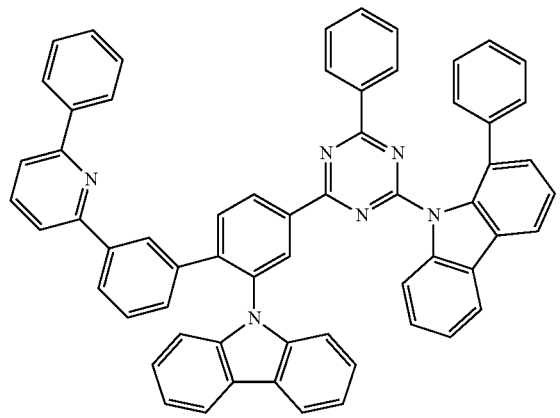
251
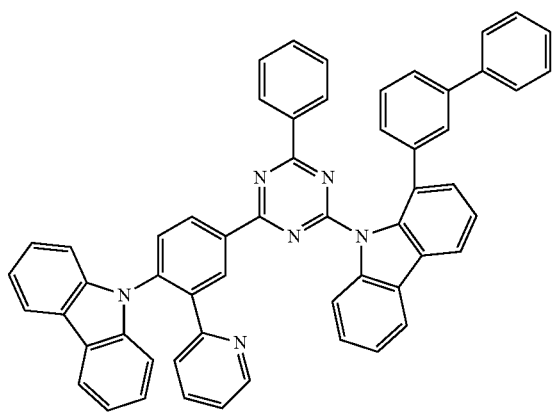
252
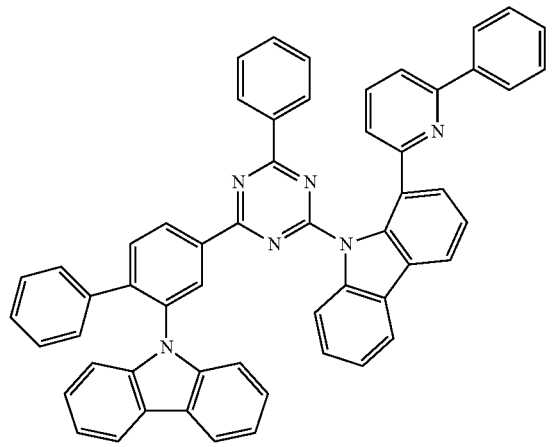
253
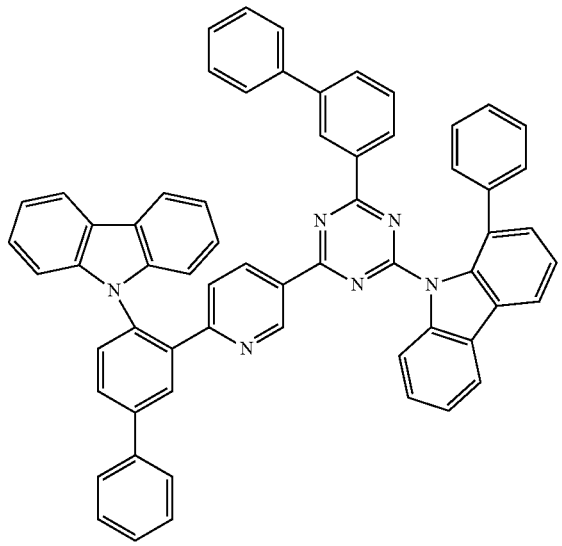

-continued
254
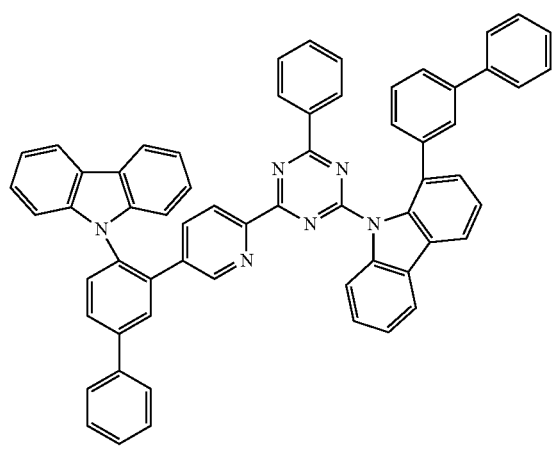
255
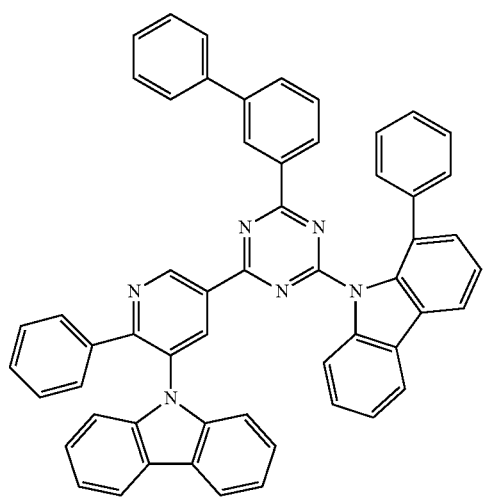
256
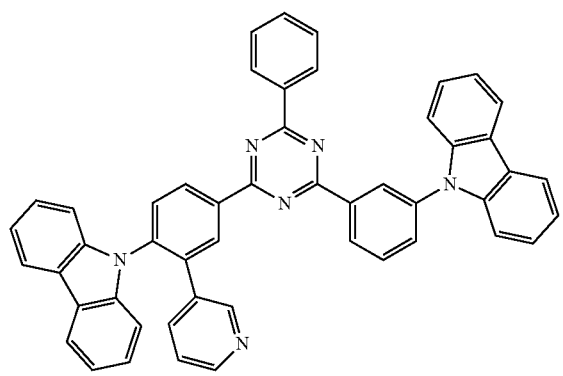
257
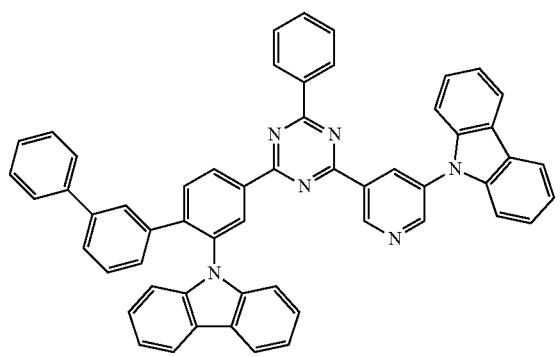
258
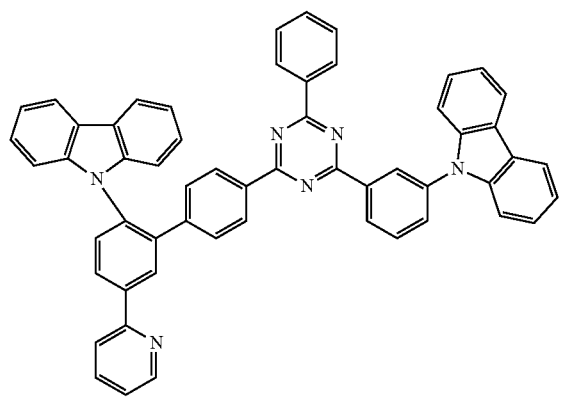
259
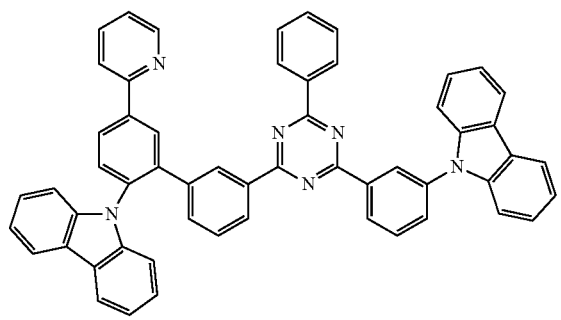

-continued
260
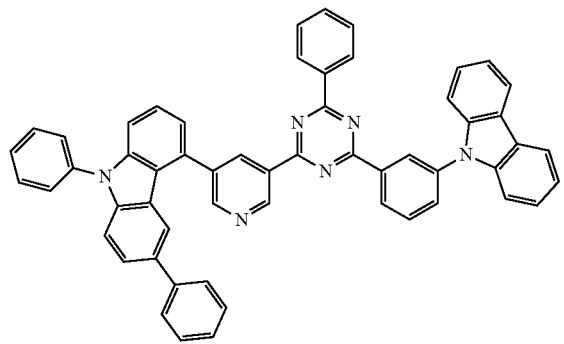
261
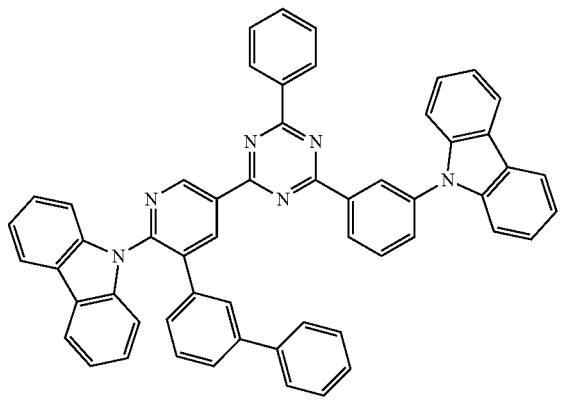
262
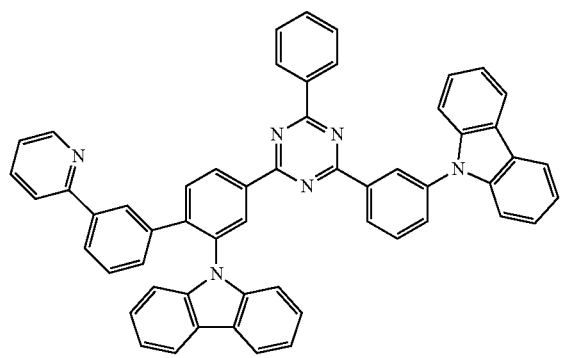
263
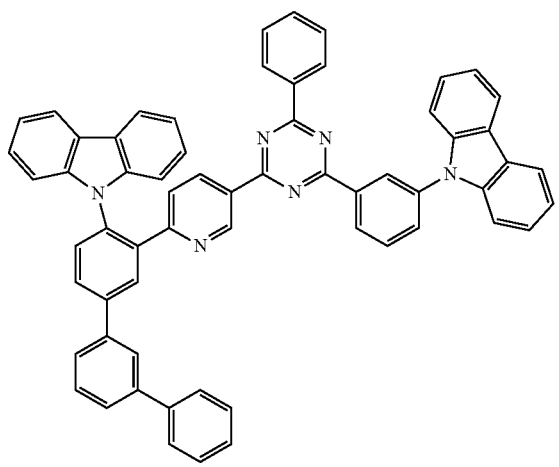
264
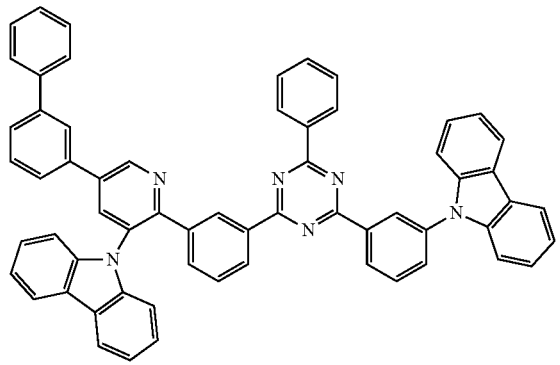
265
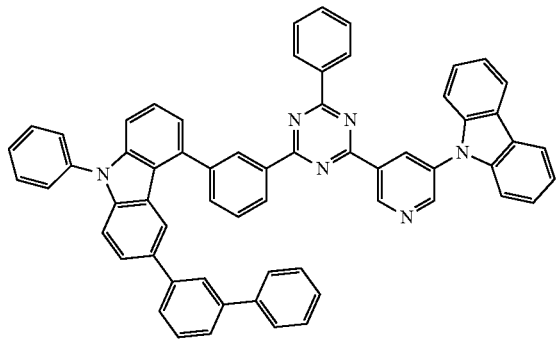

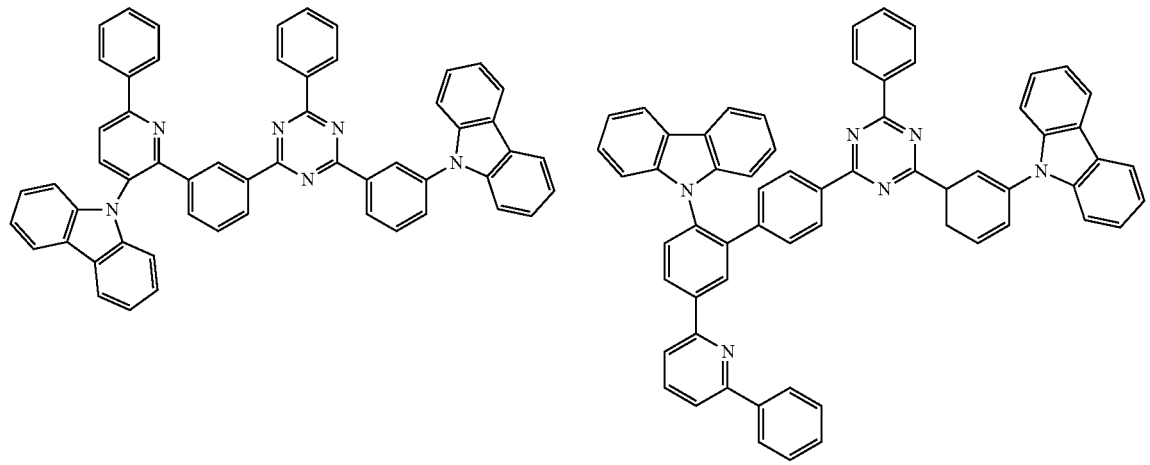
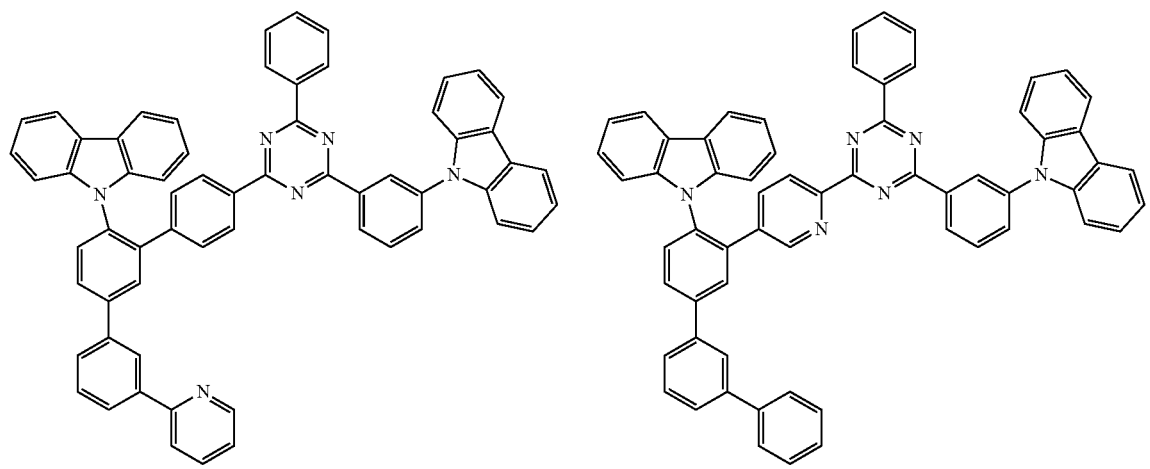
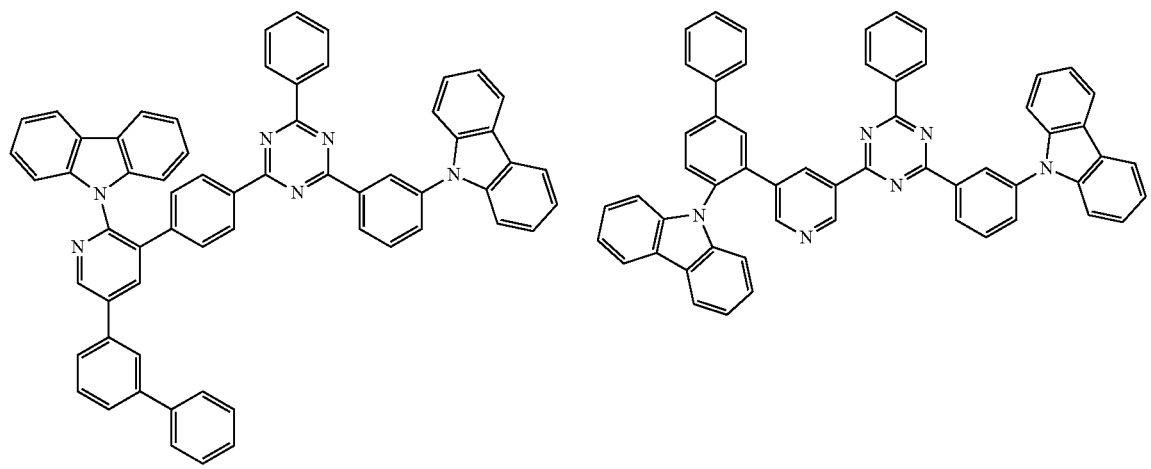

-continued
272
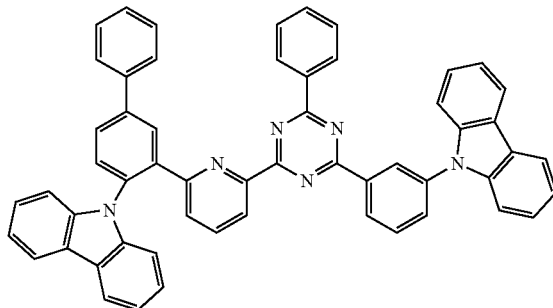
273
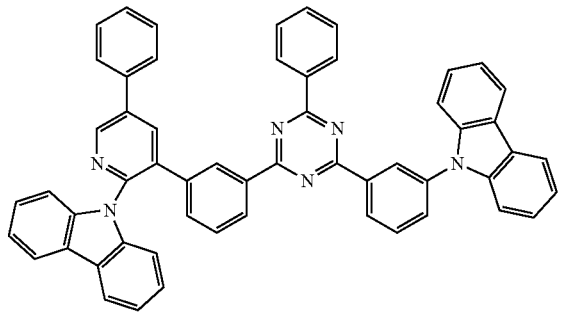
274
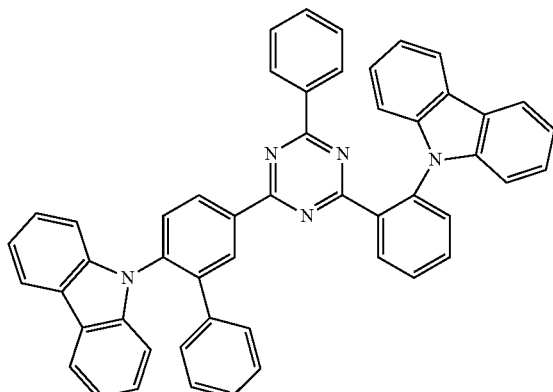
275
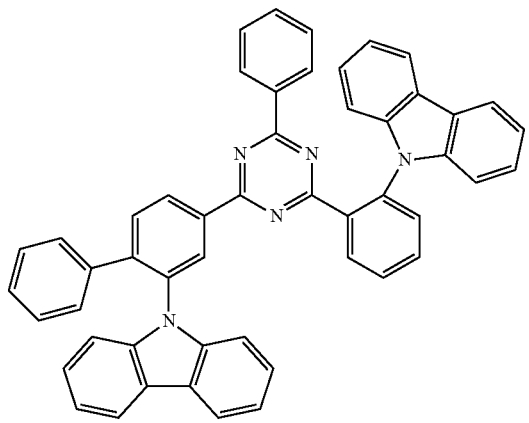
276
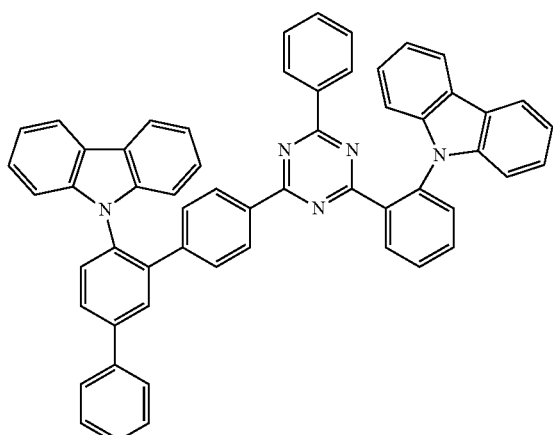
277
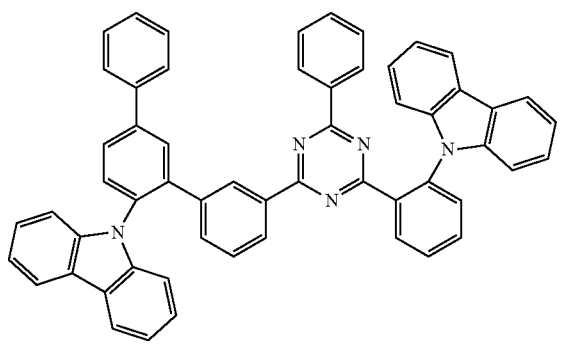
278
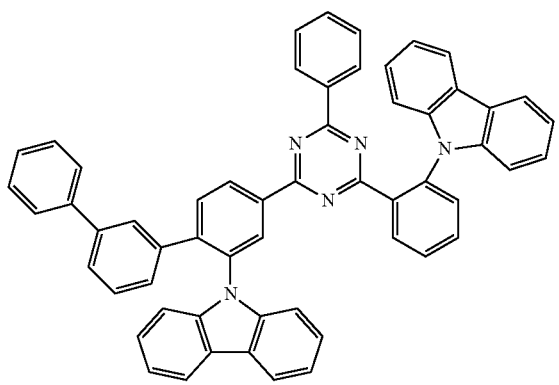
279
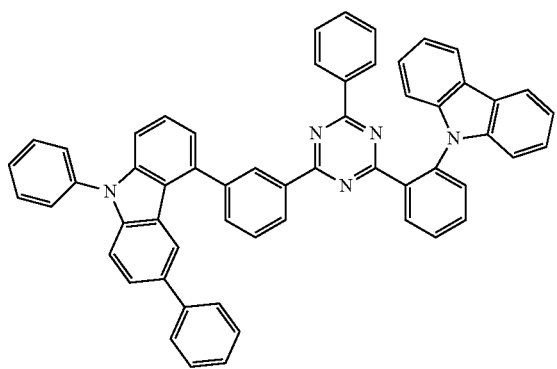

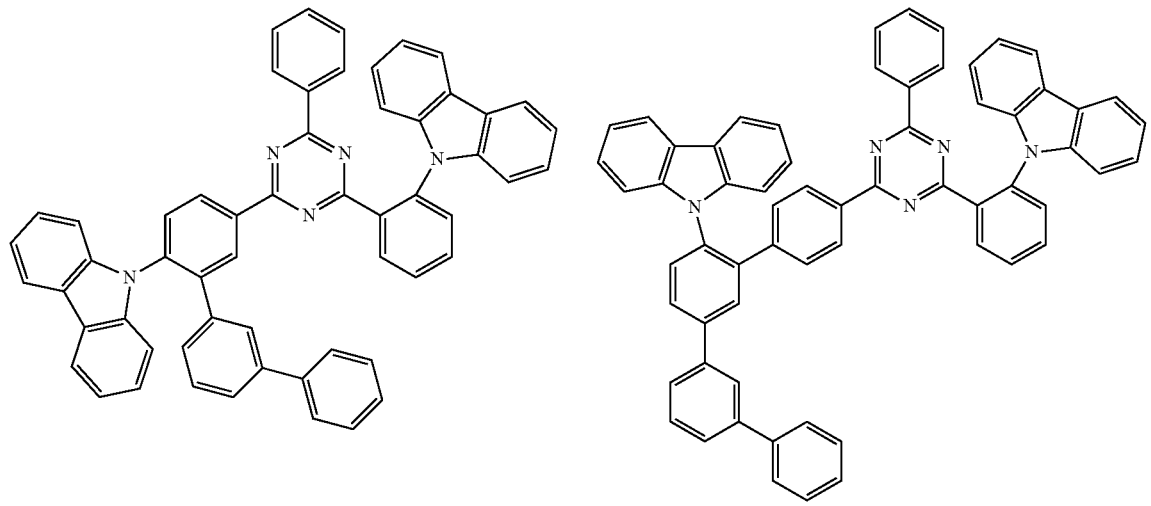
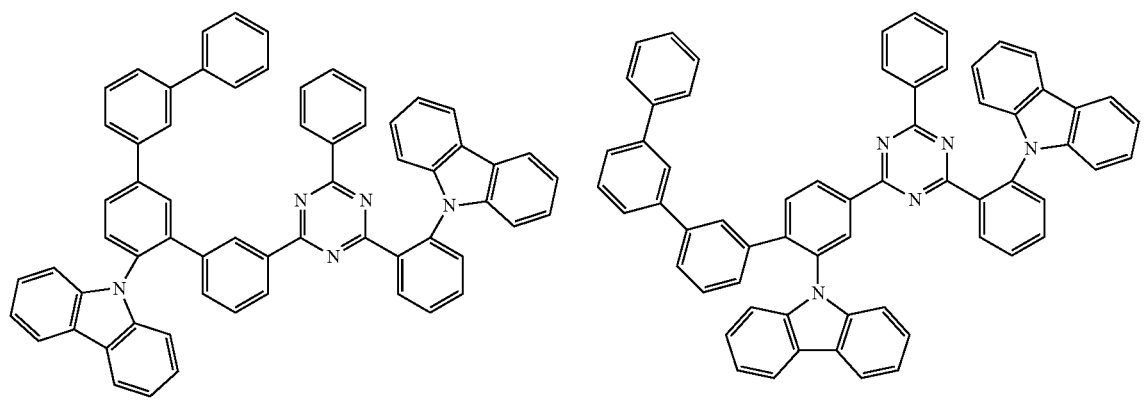
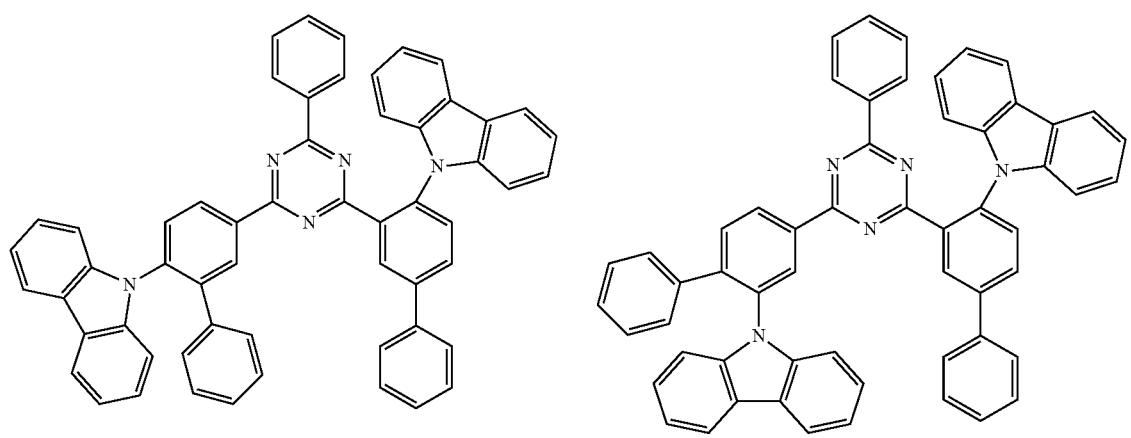

286
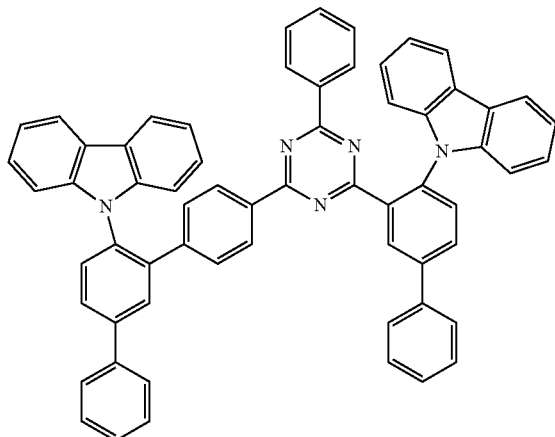
287
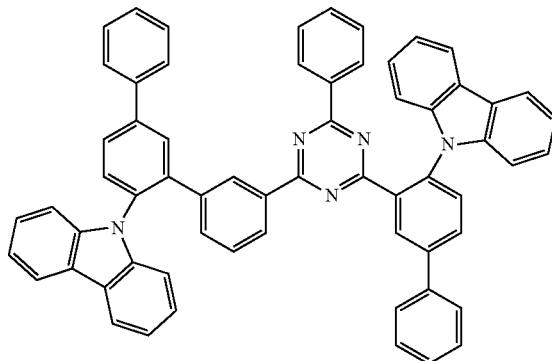
288
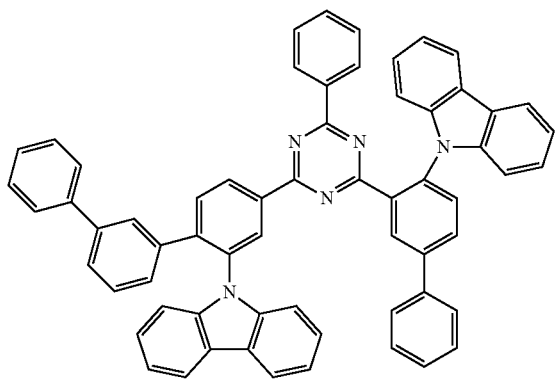
289
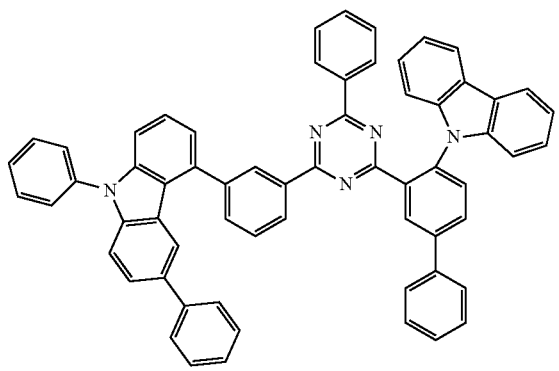
290
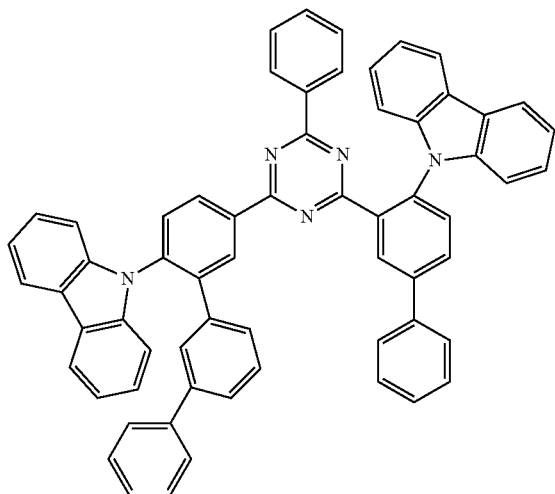
291
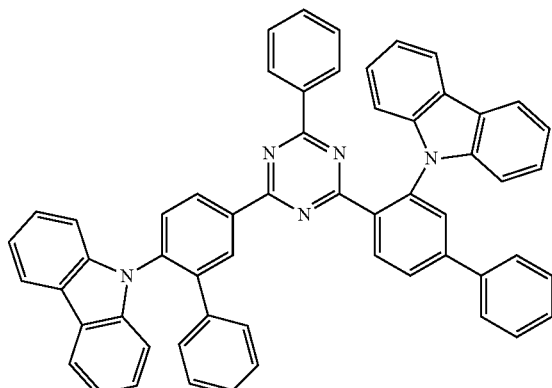

-continued
292
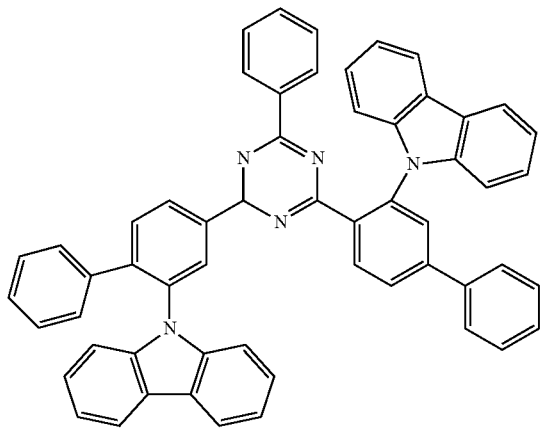
293
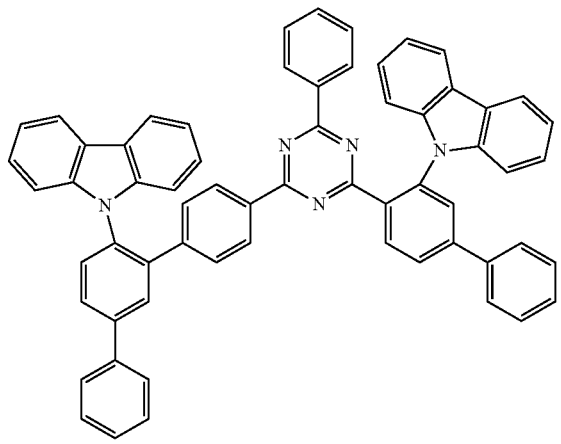
294
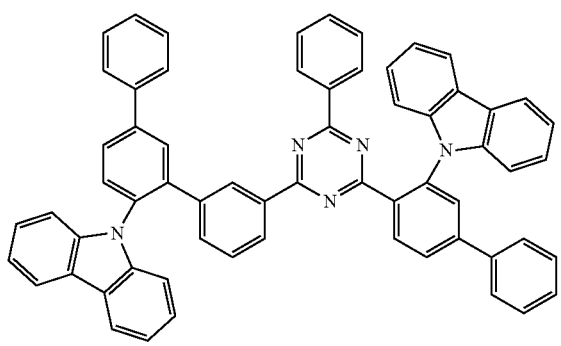
295
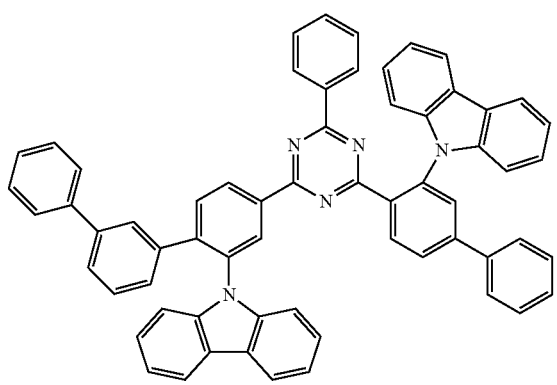
296
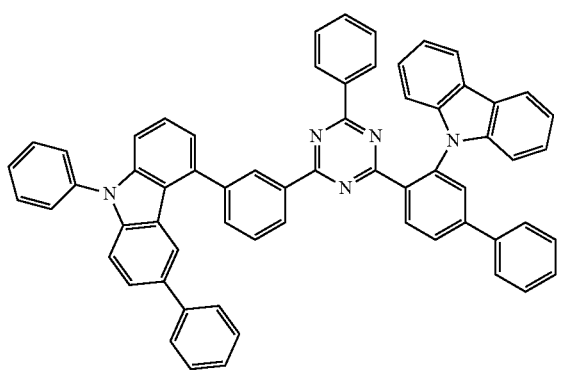
297
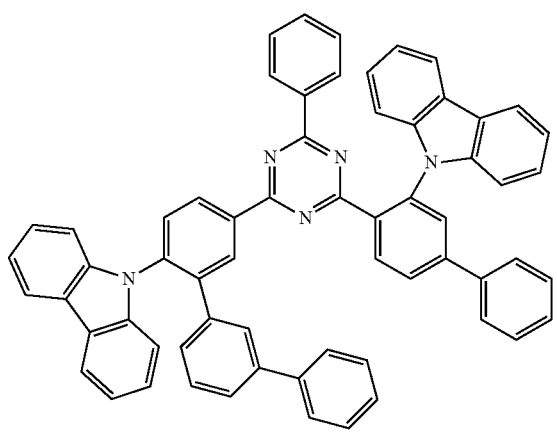

298
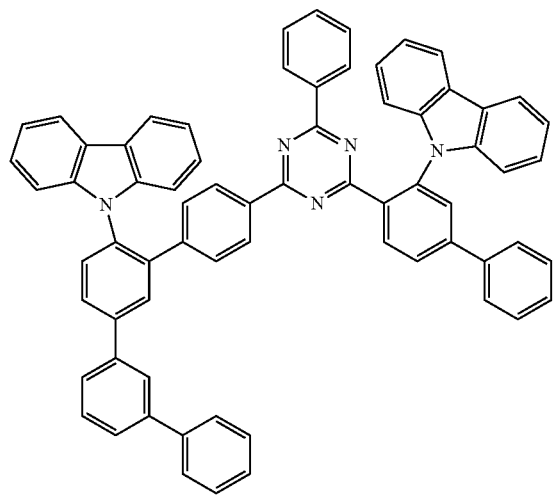
299
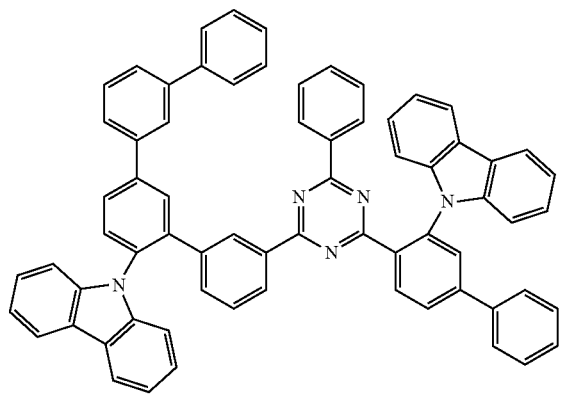
300
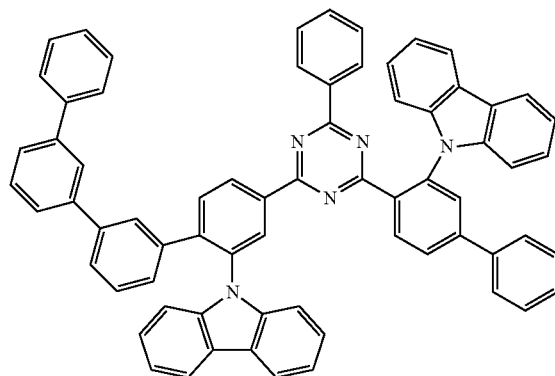
301
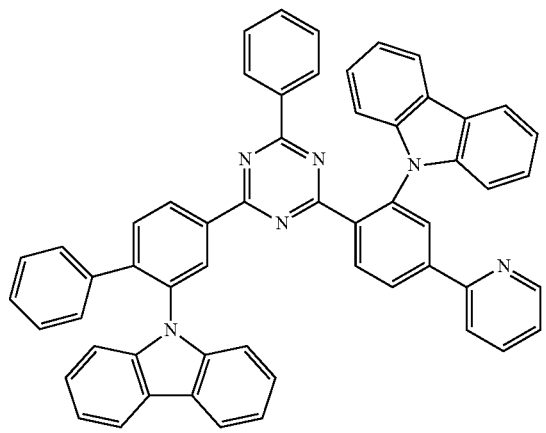
302
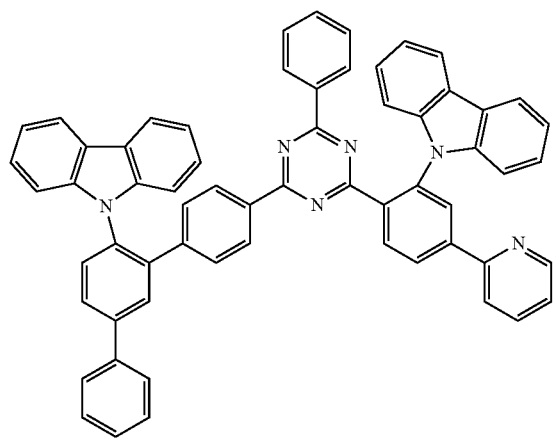
303
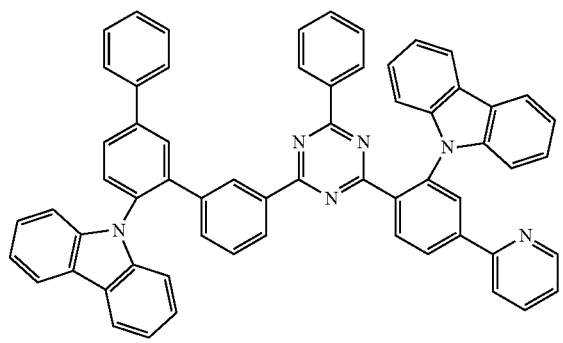

-continued
304
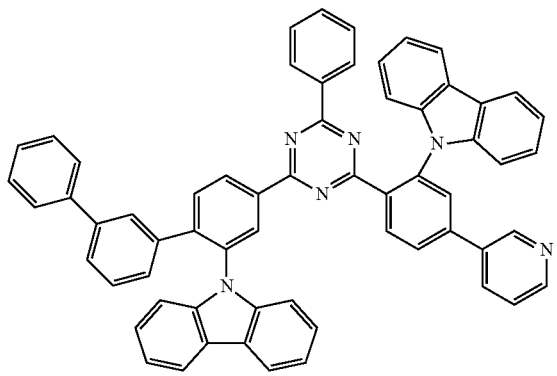
305
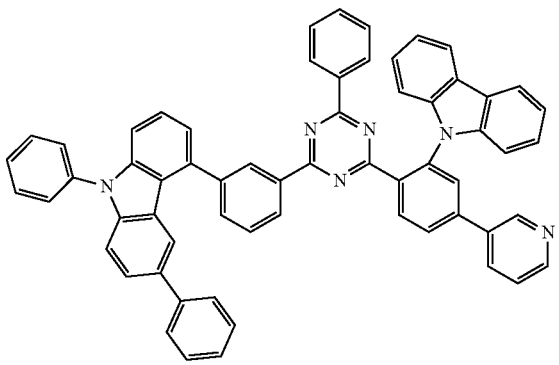
306
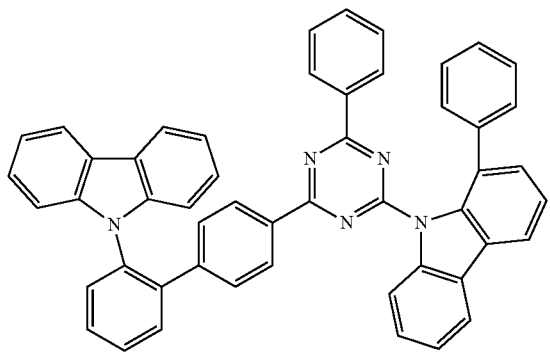
307
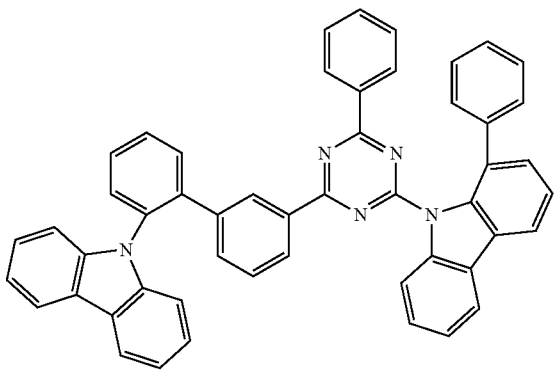
308
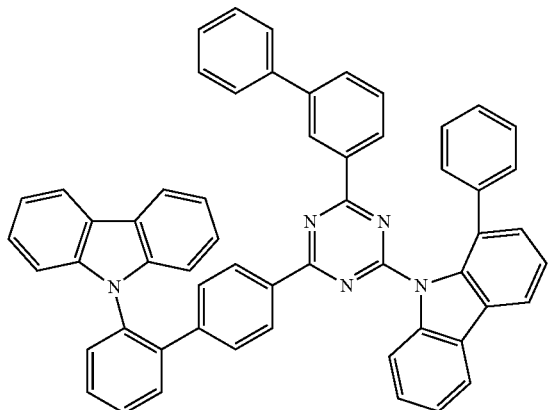
309
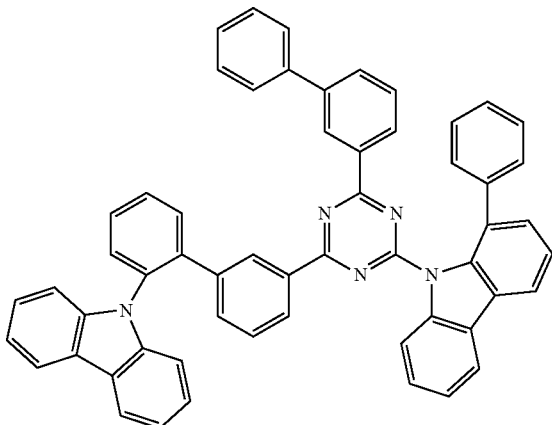
310
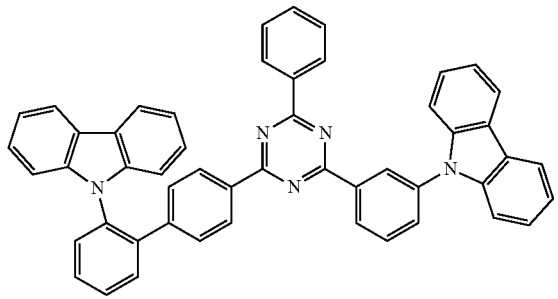
311
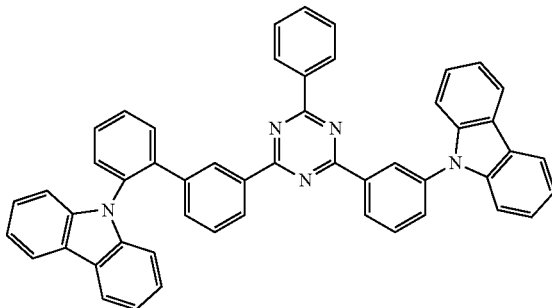

-continued
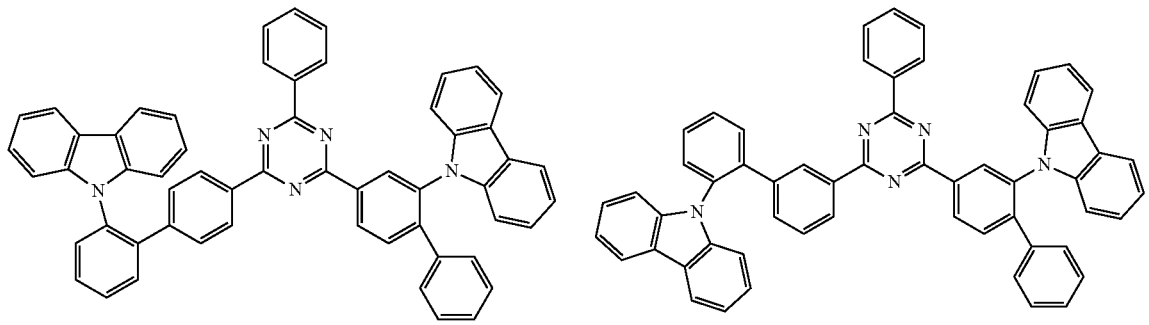
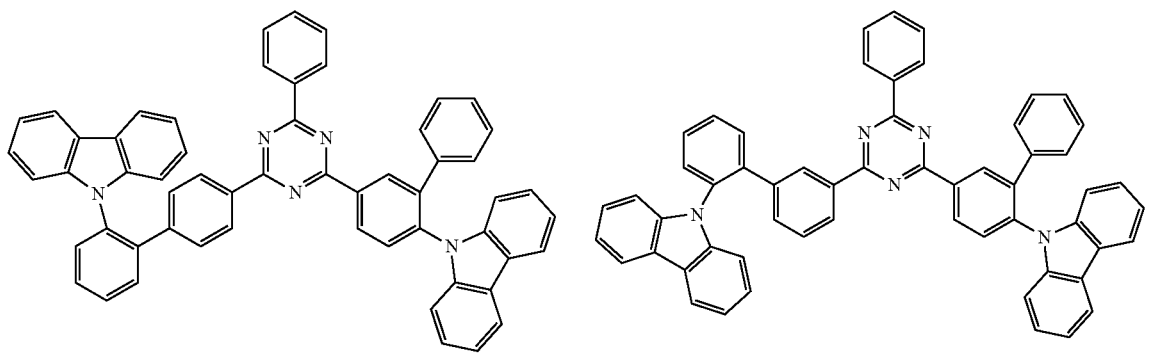
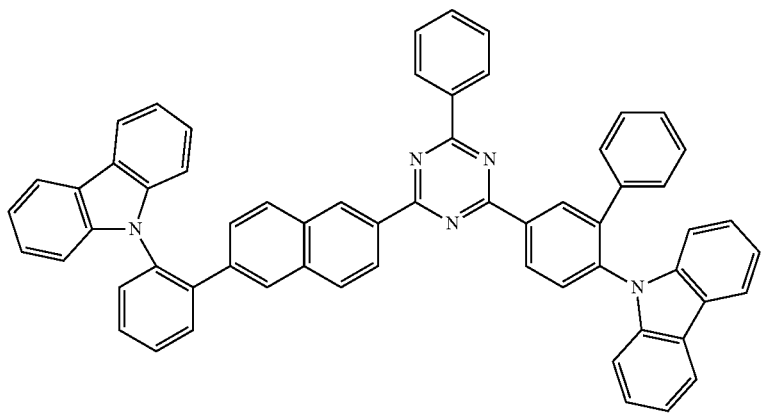
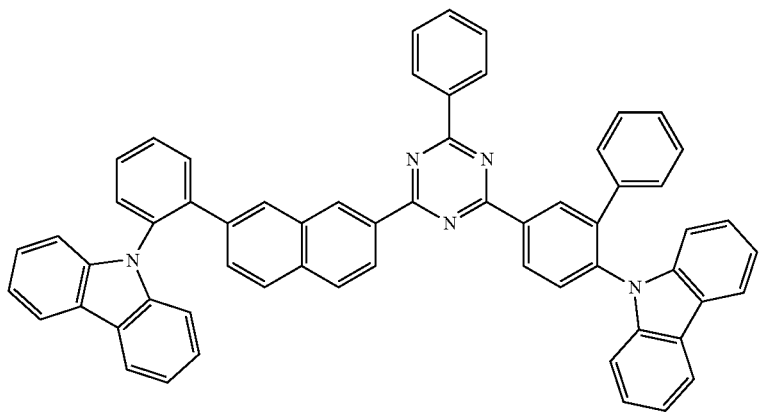

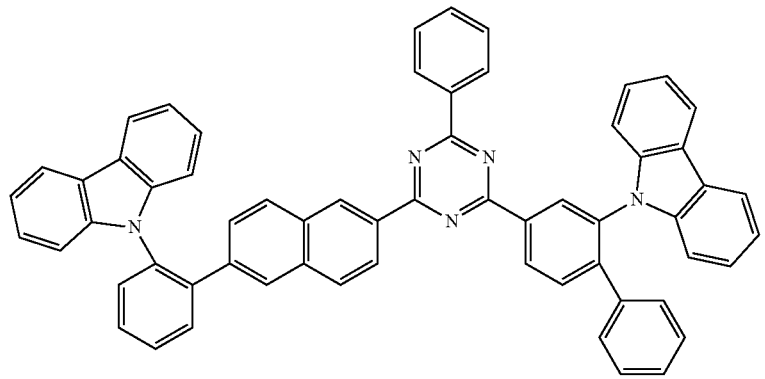
318
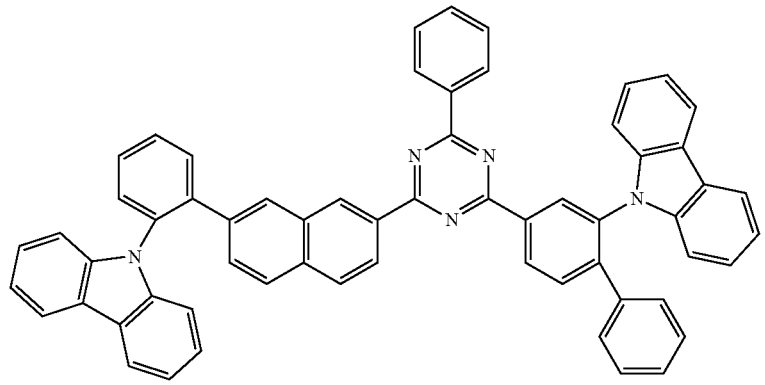
319
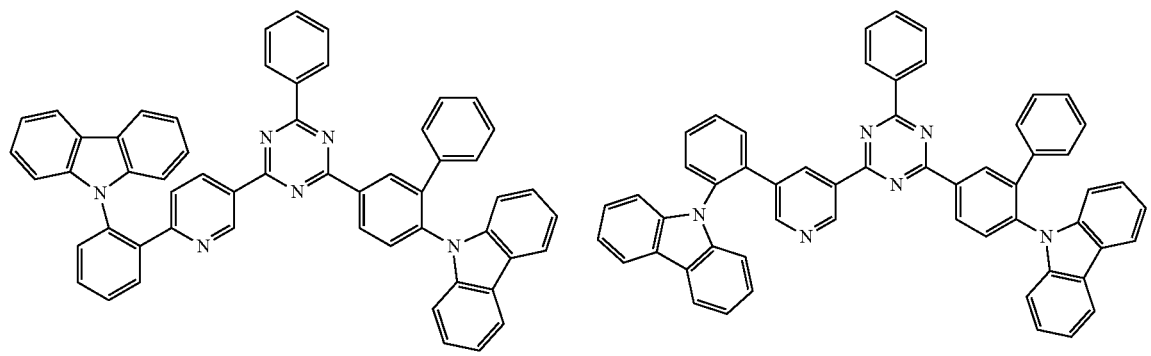
320 321
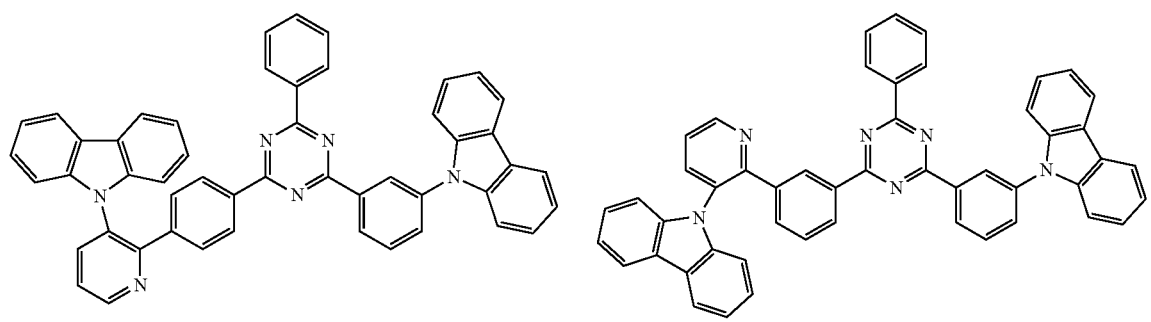
322 323

324
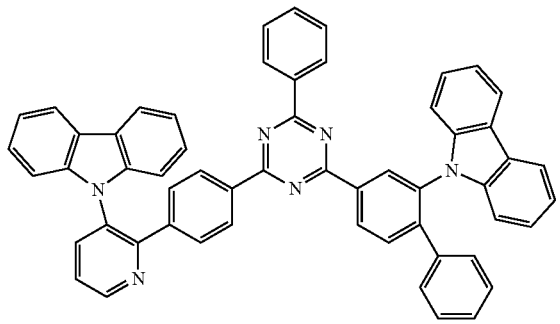
325
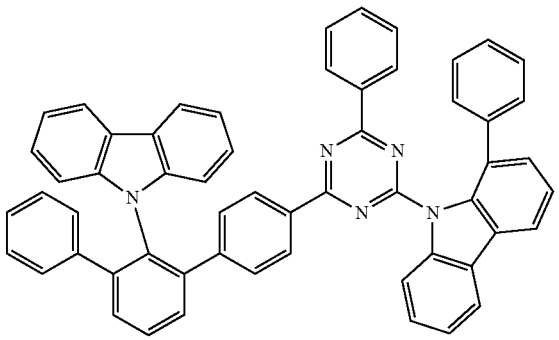
326
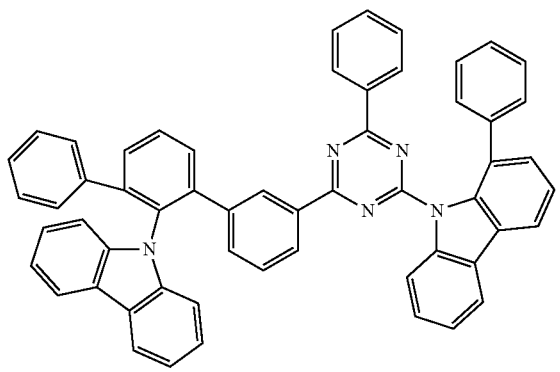
327
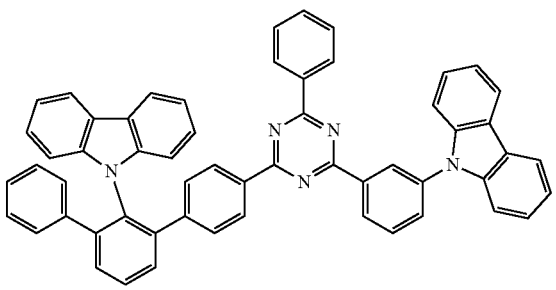
328
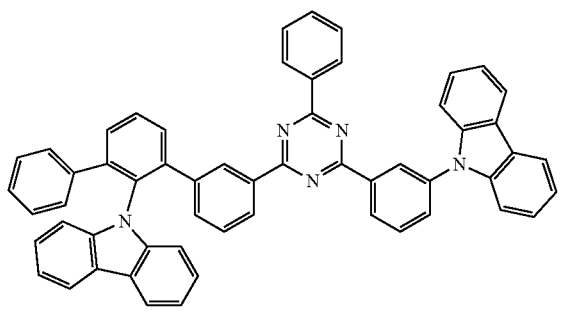
329
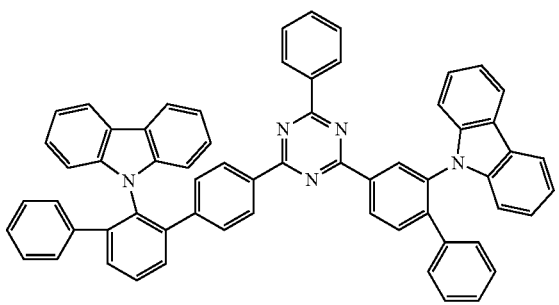
330
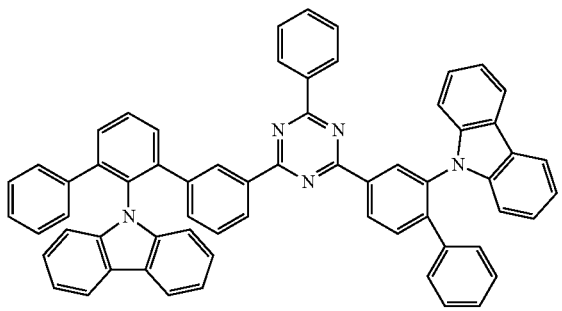
331
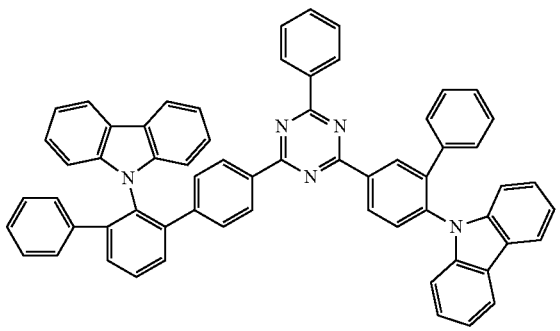

332
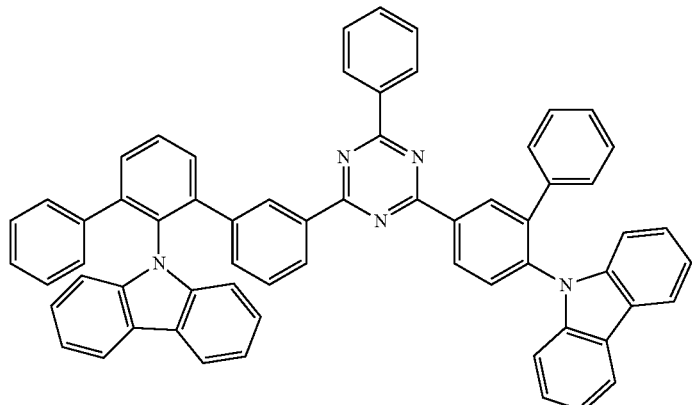
333
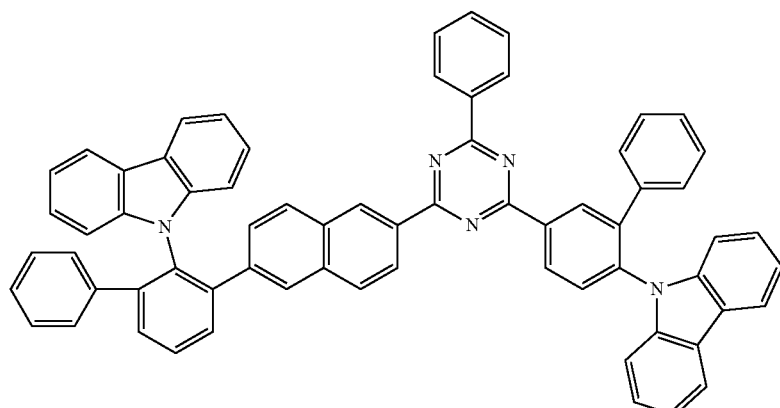
334
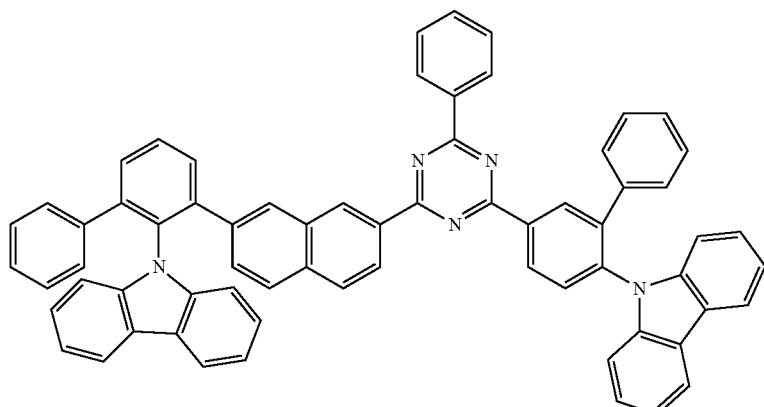
335
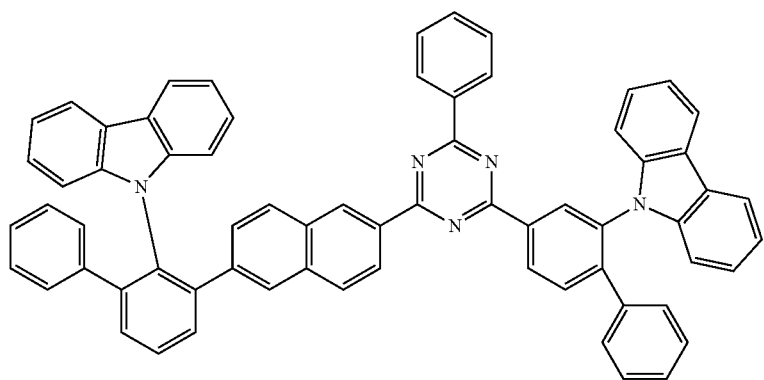

-continued
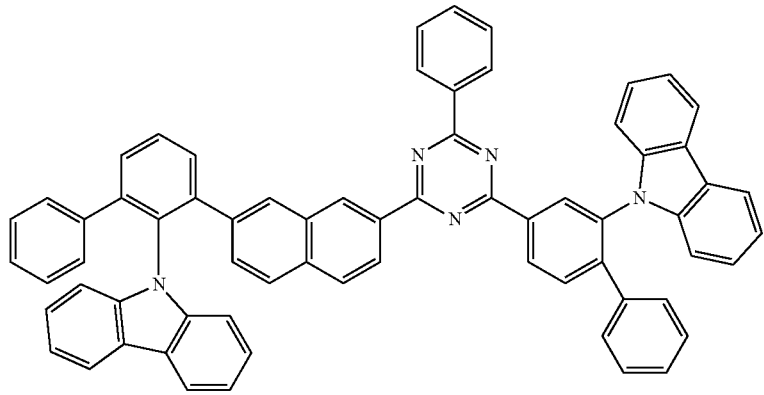
336
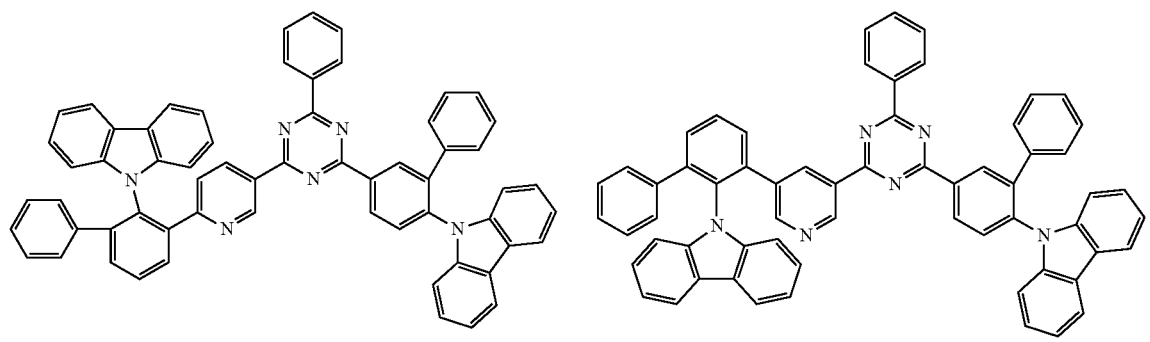
337 338
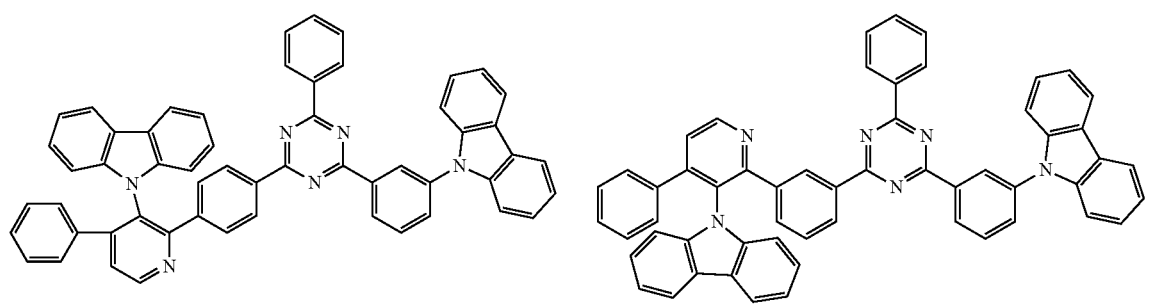
339 340
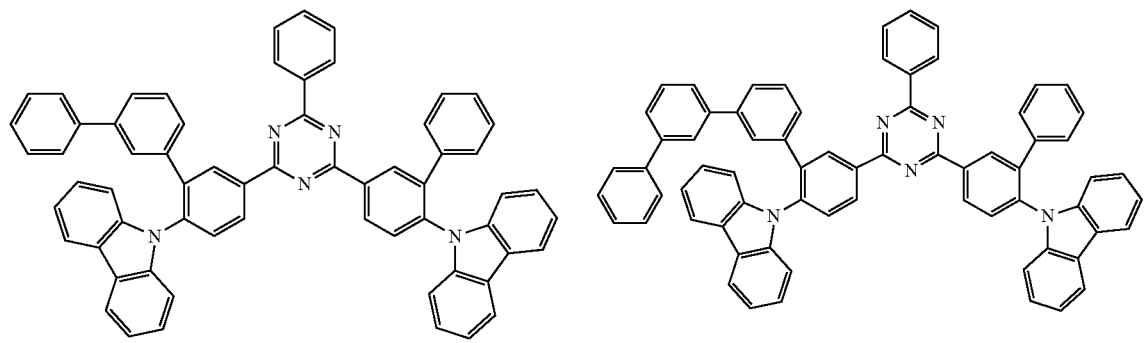
341 342

-continued
343
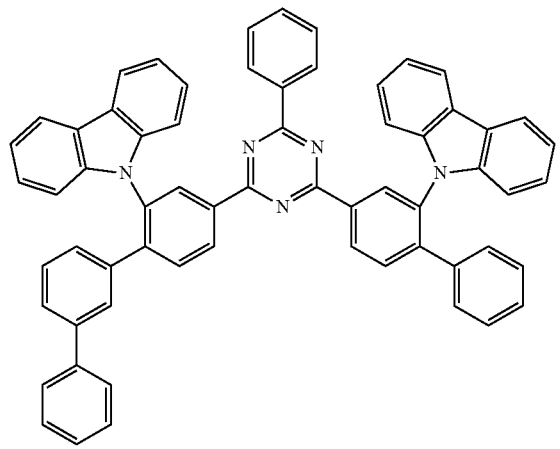
345
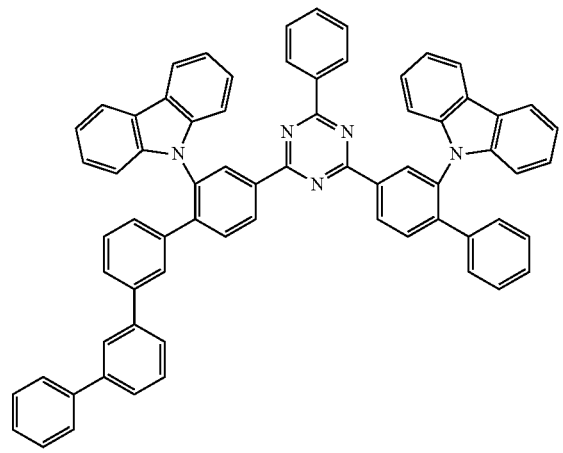
346
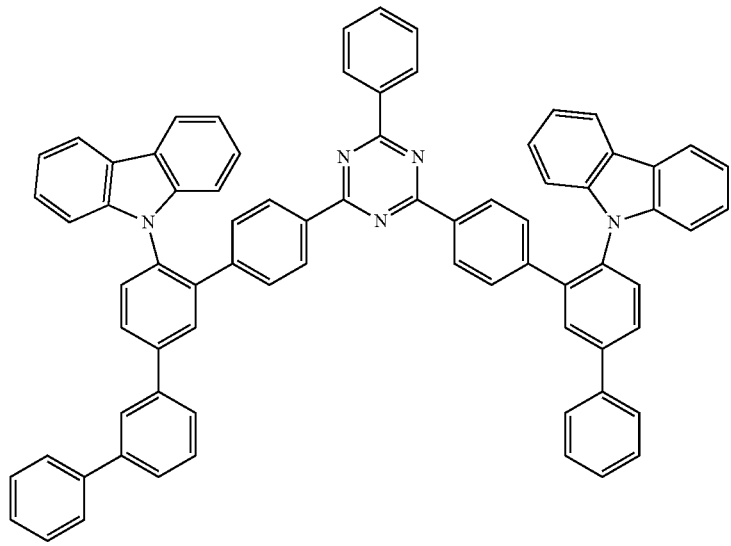
347
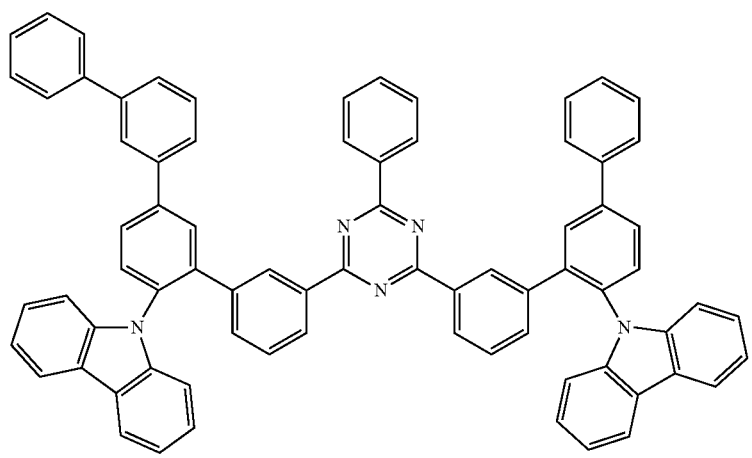

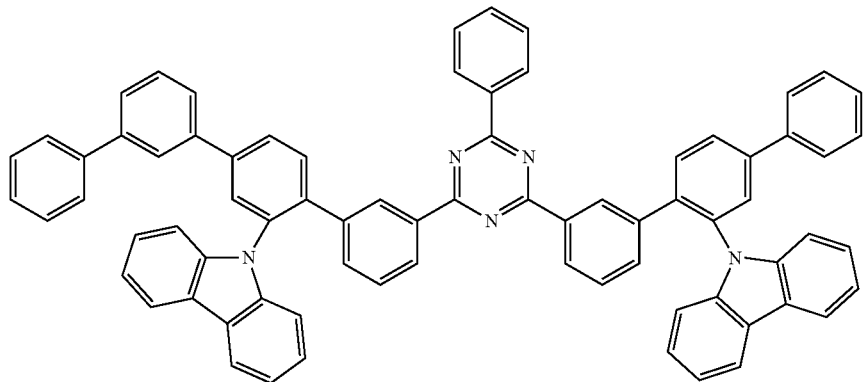
348
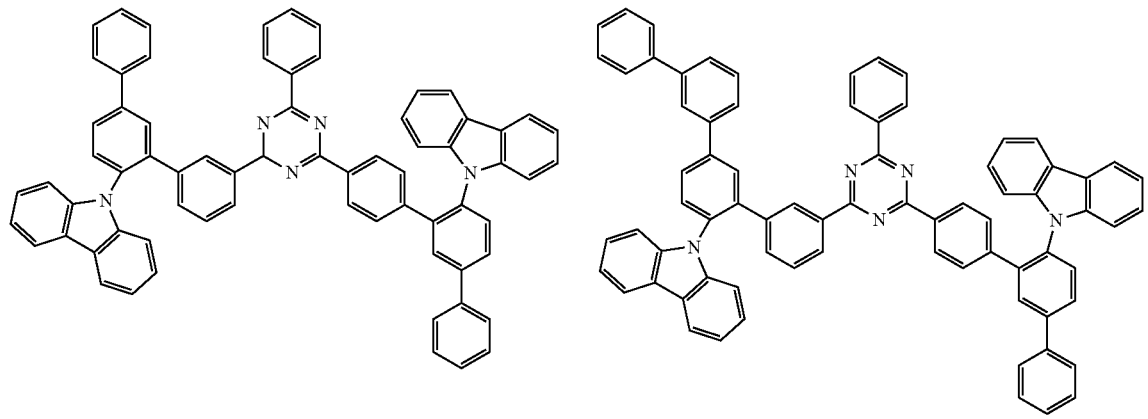
349
350
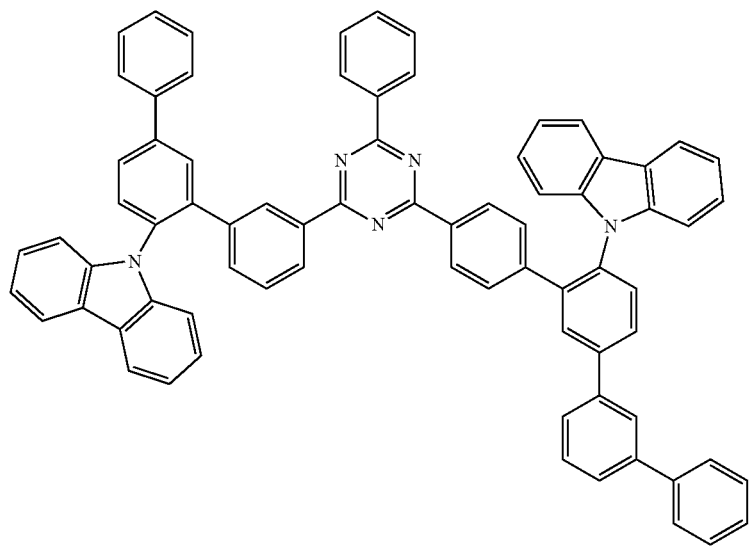
351

-continued
352
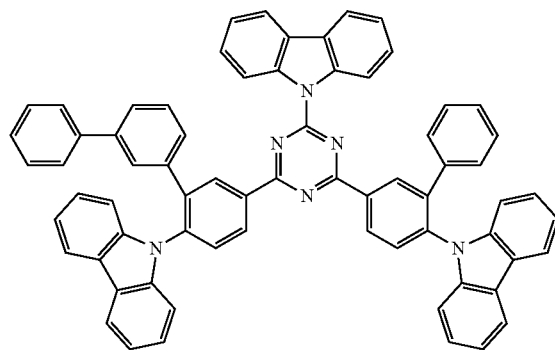
353
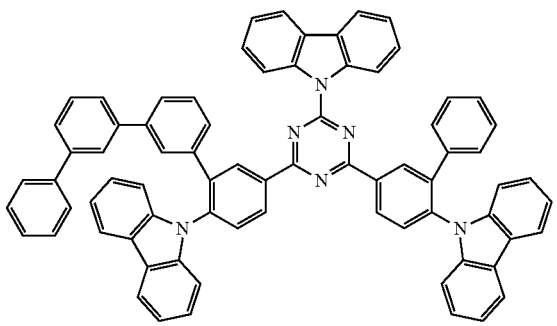
354
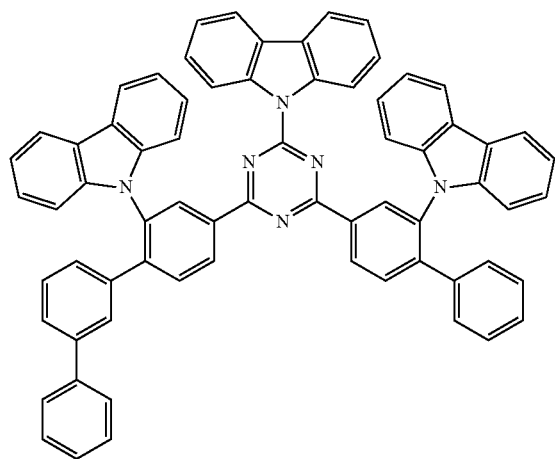
355
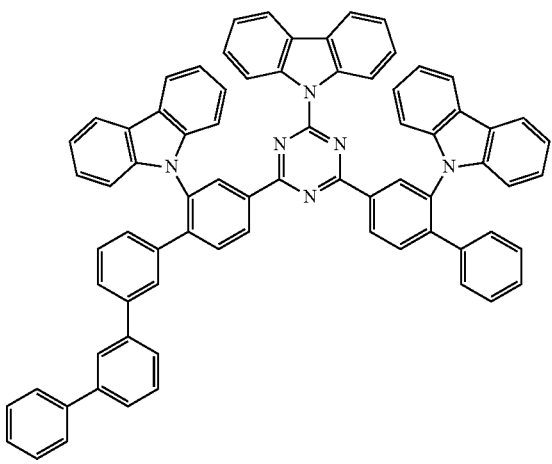
356
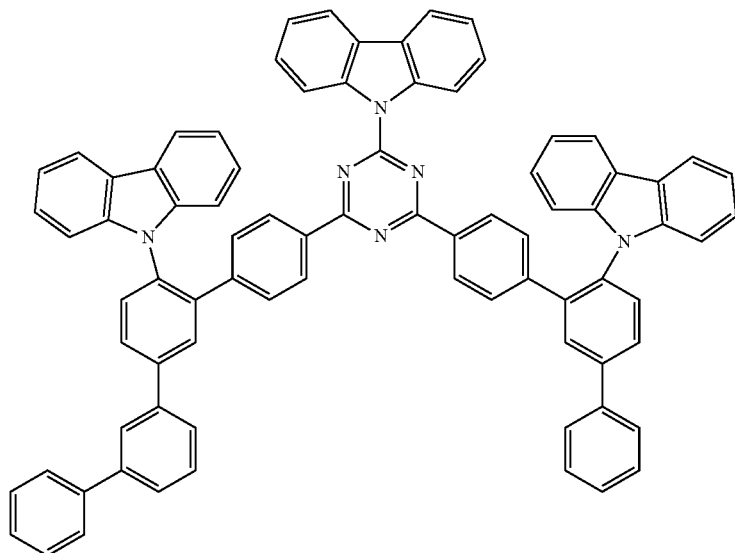

357
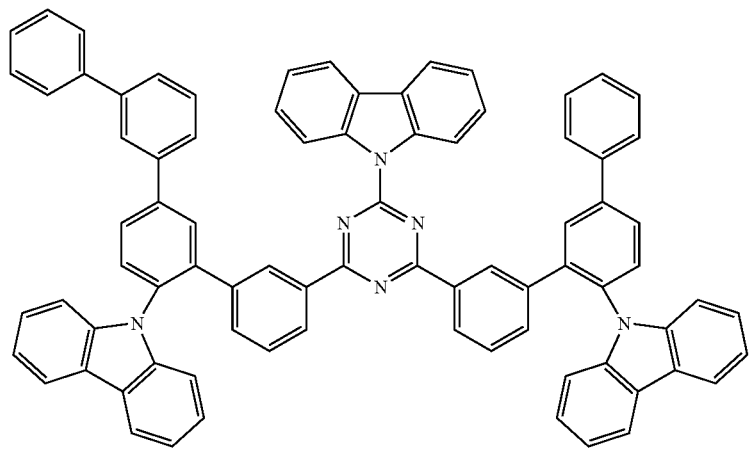
358
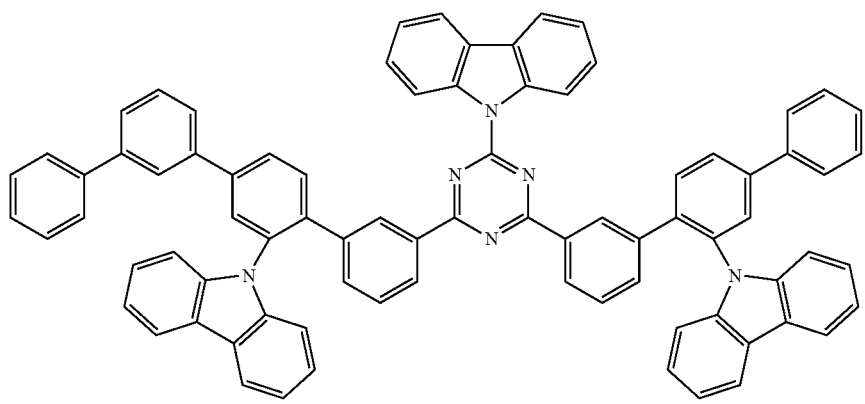
359  360
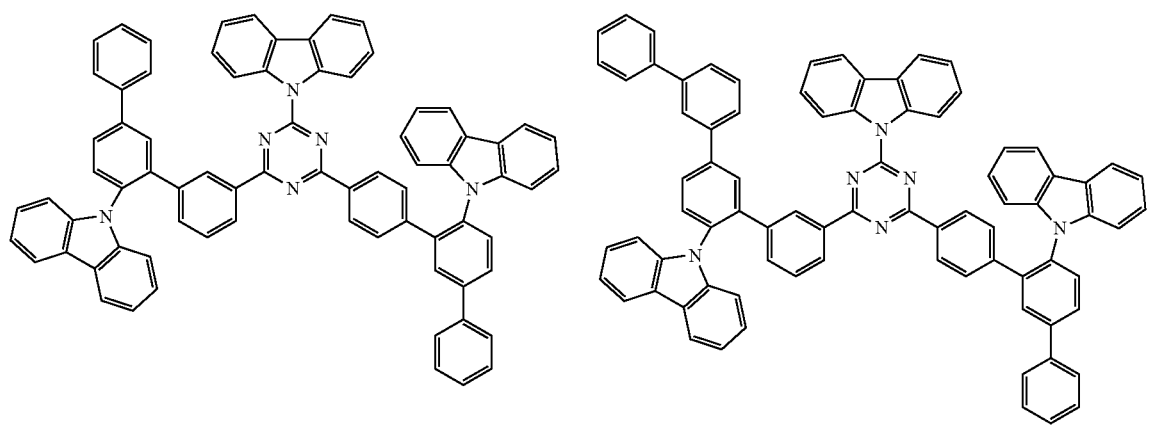

361
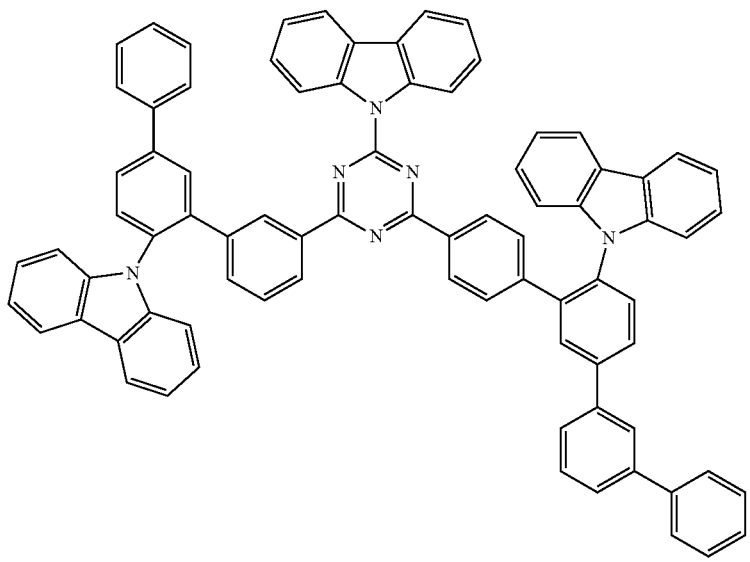
362 363
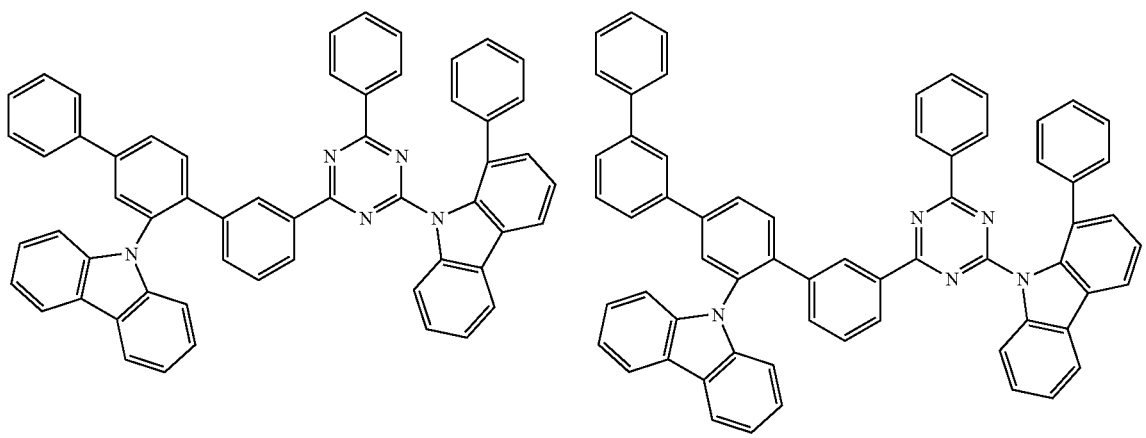
364 365
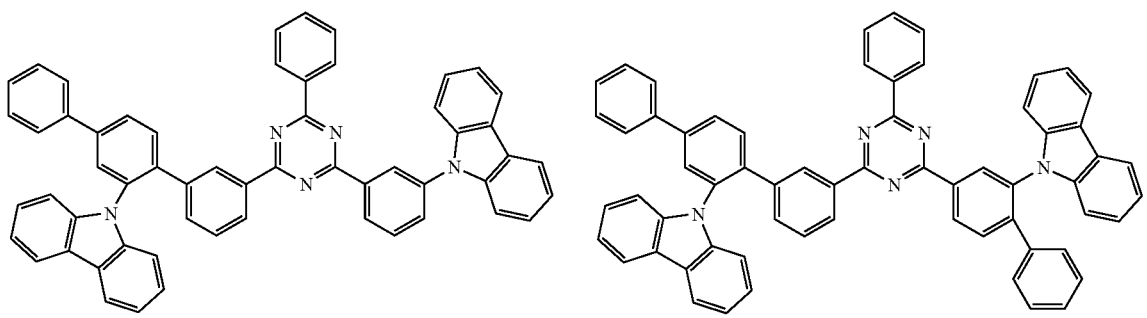

-continued
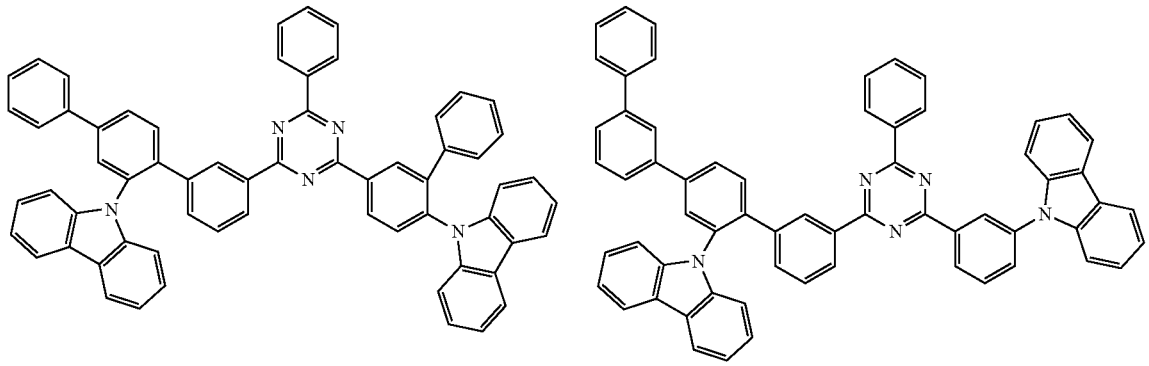
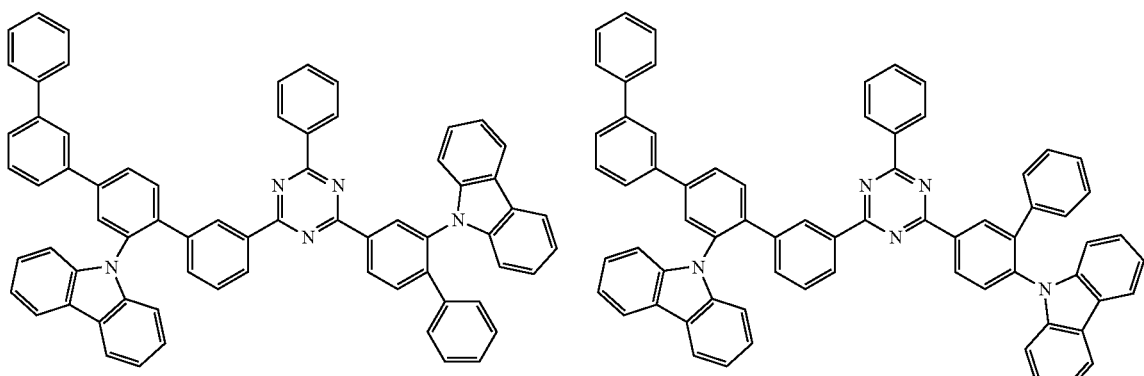
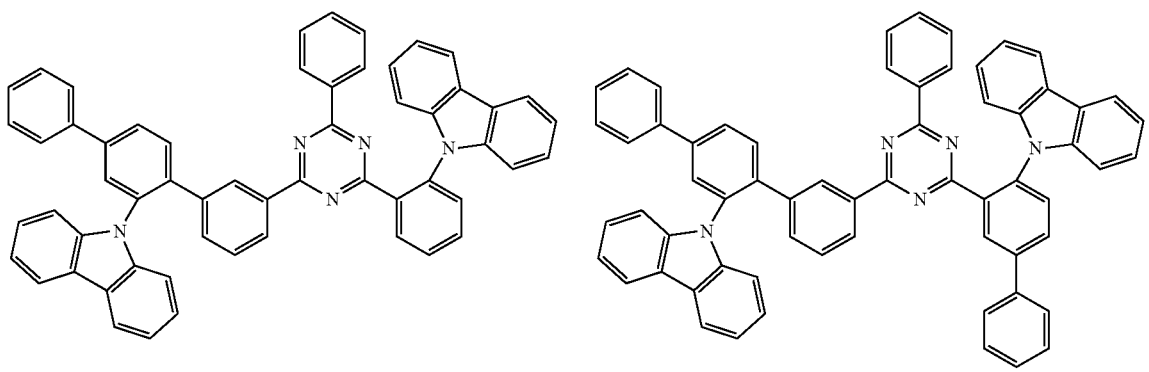
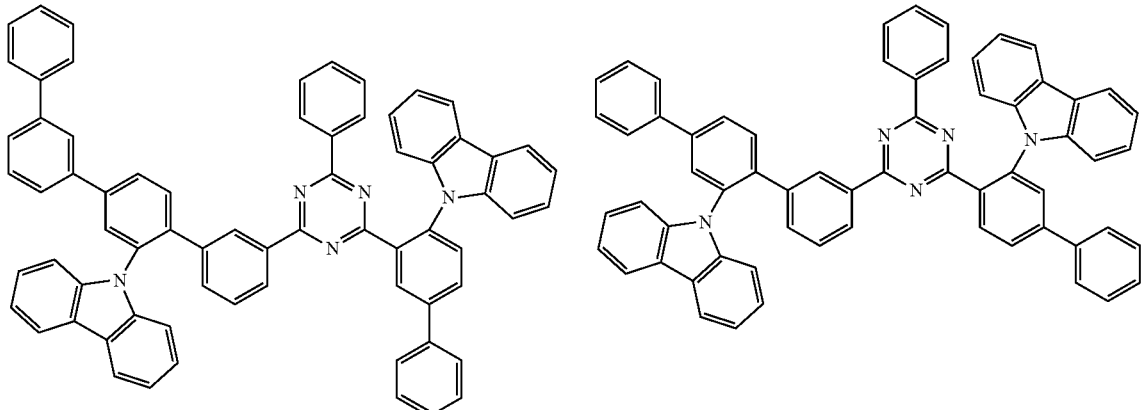

-continued
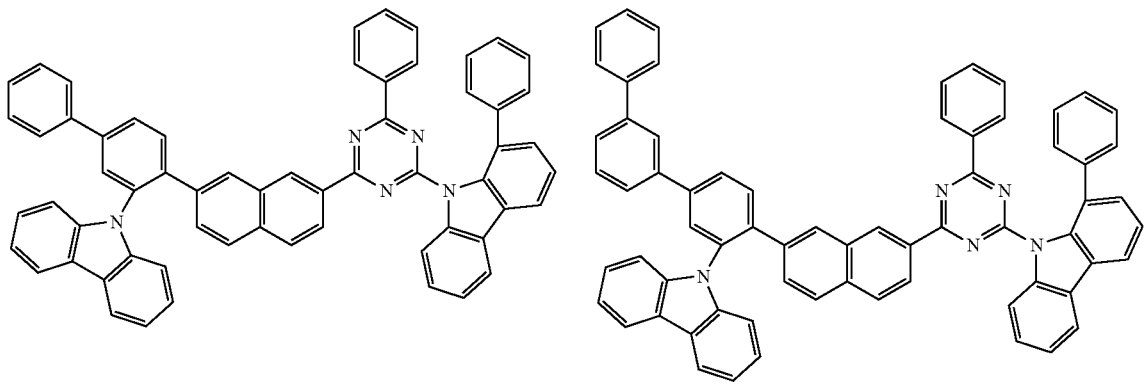
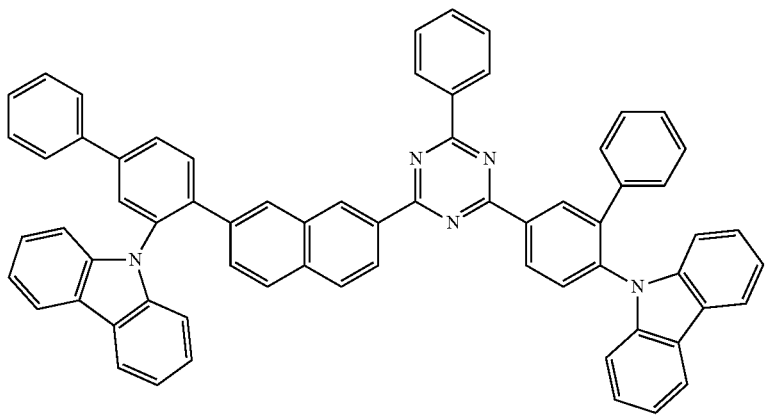
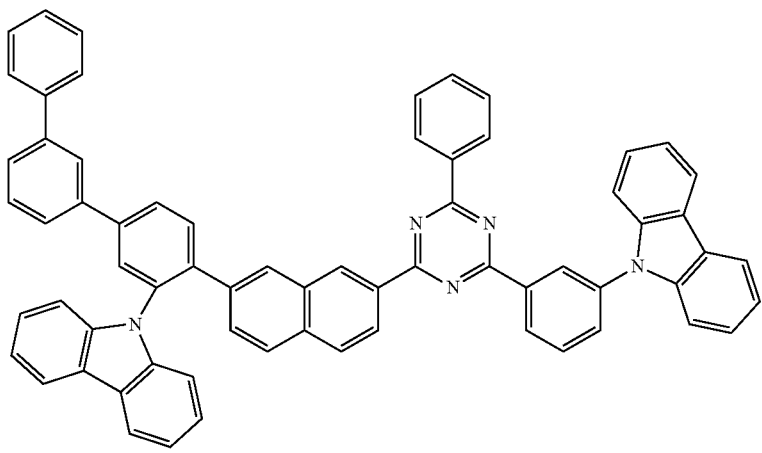
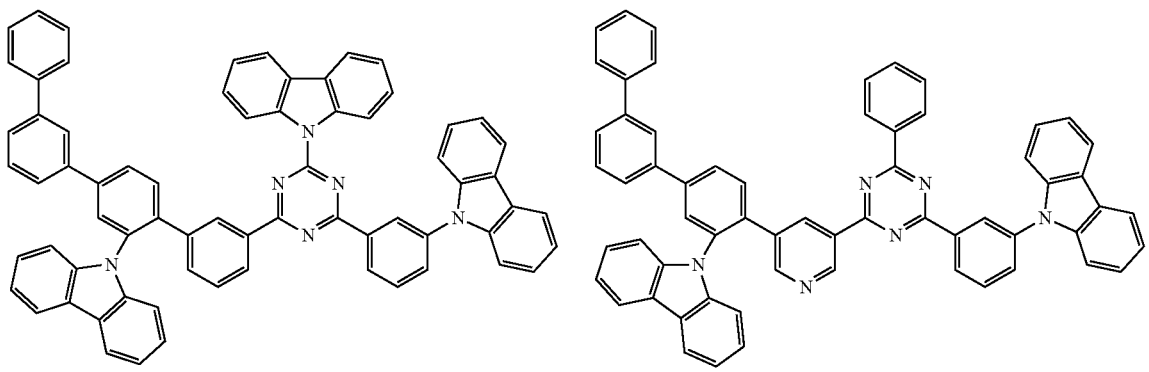

380
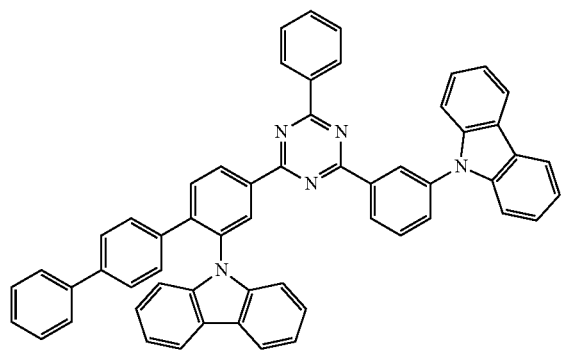
381
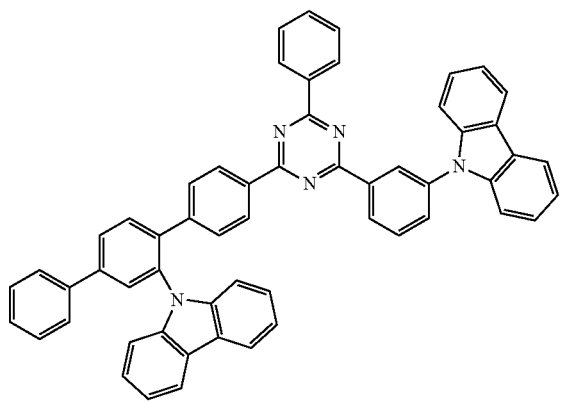
382
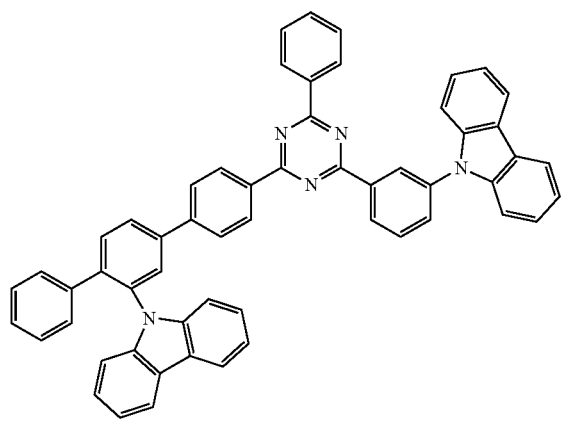
383
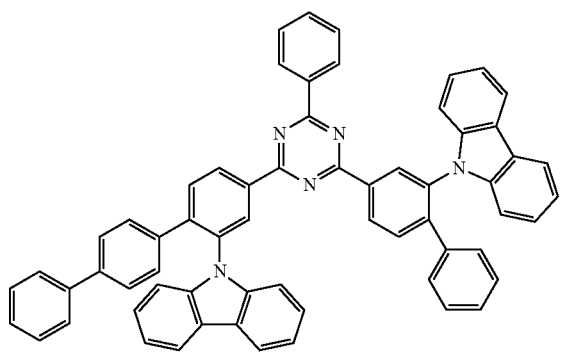
384
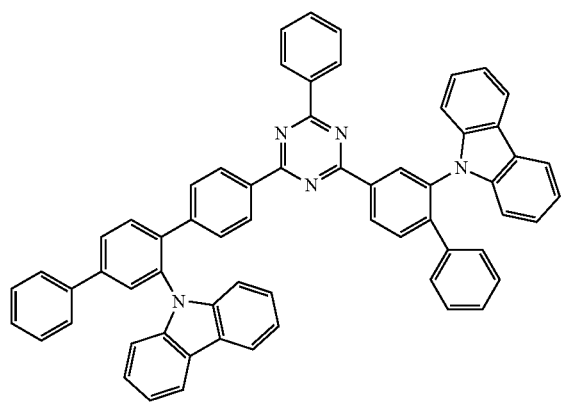
385
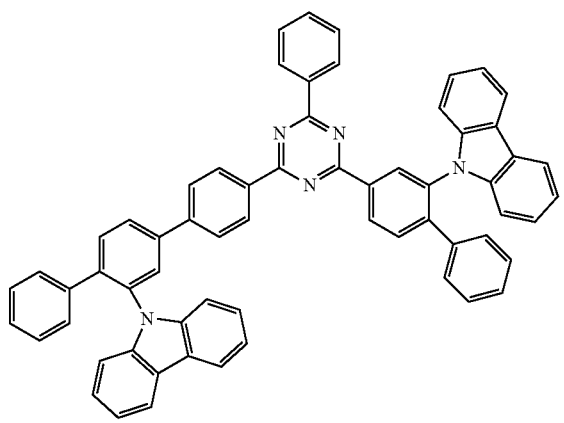

386
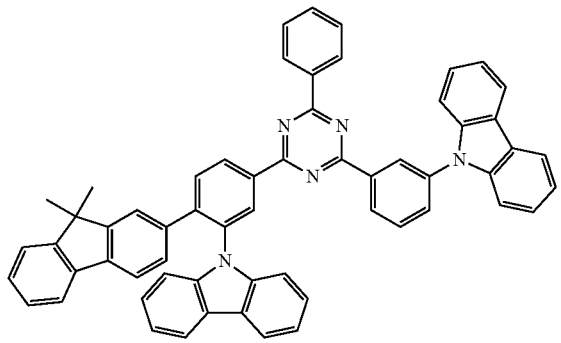
387
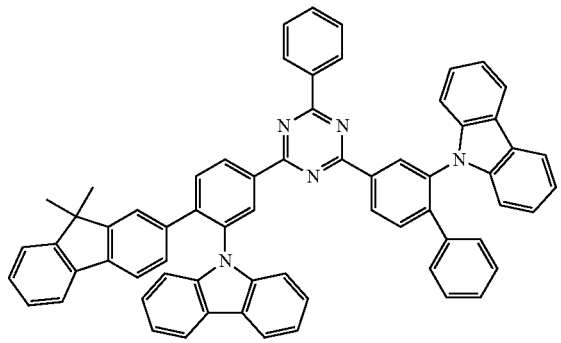
388
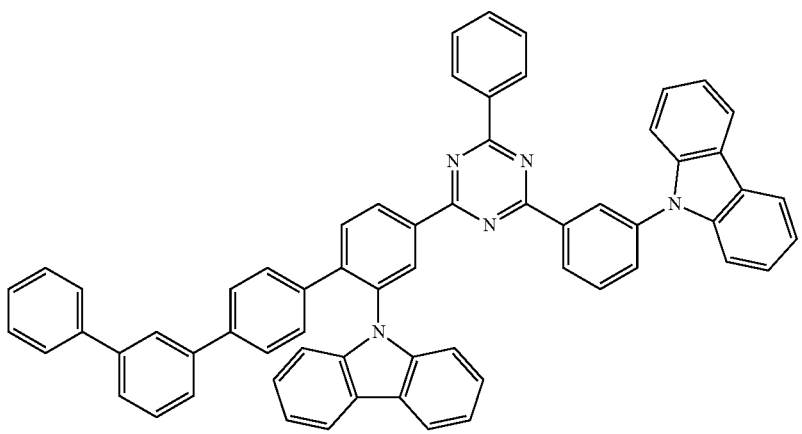
389
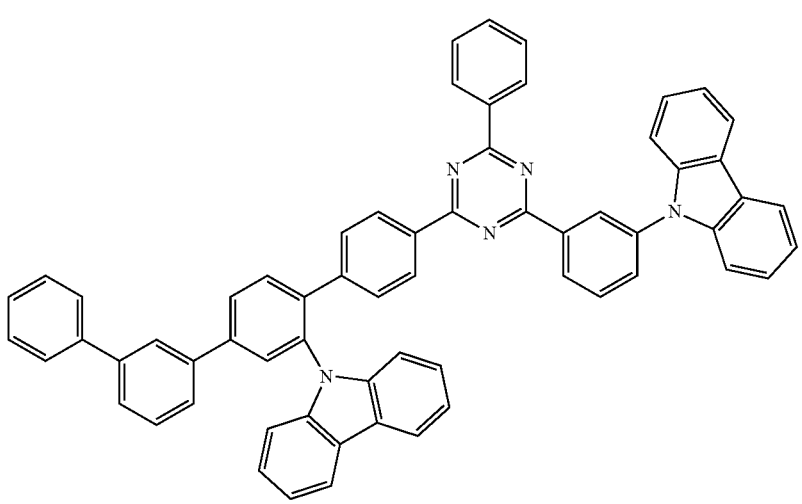

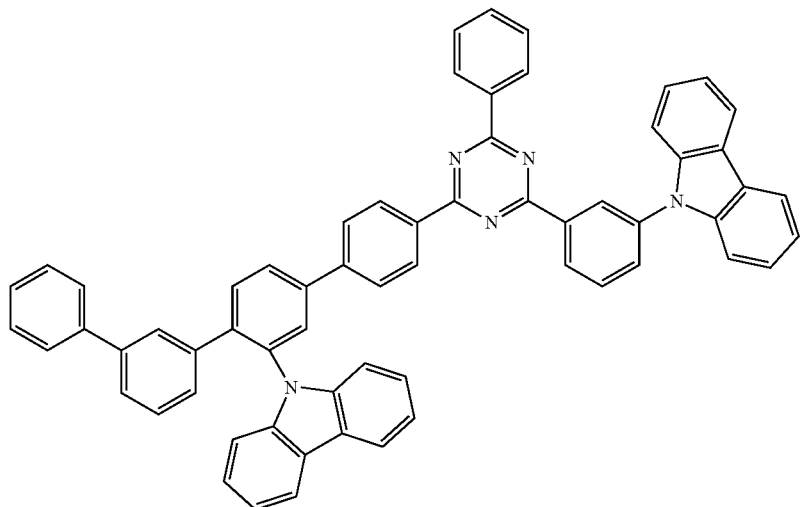
390
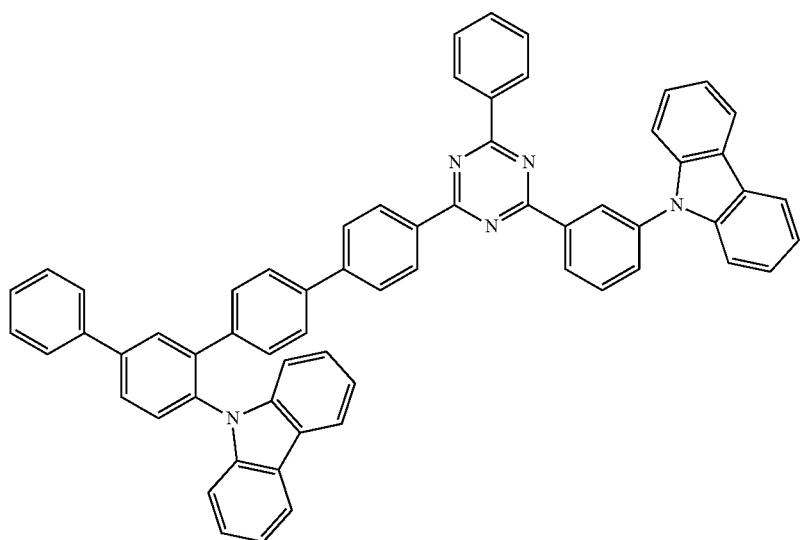
391
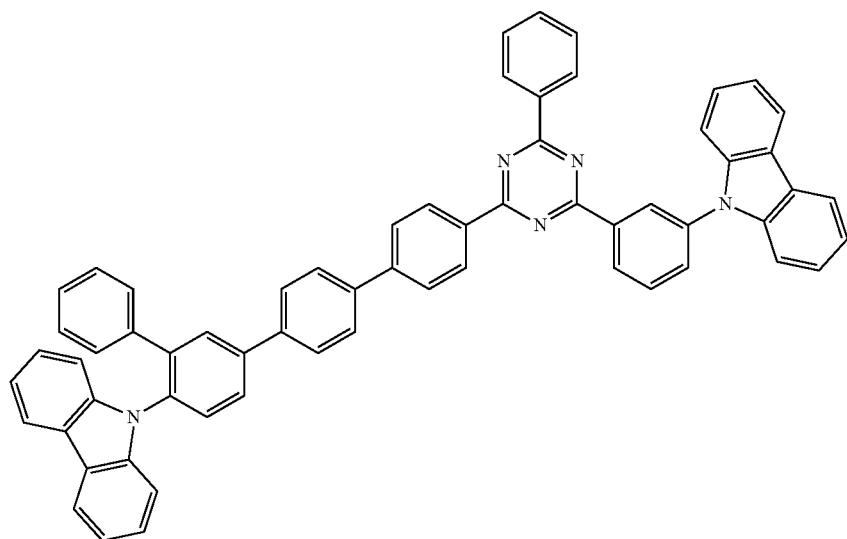
392

-continued
393
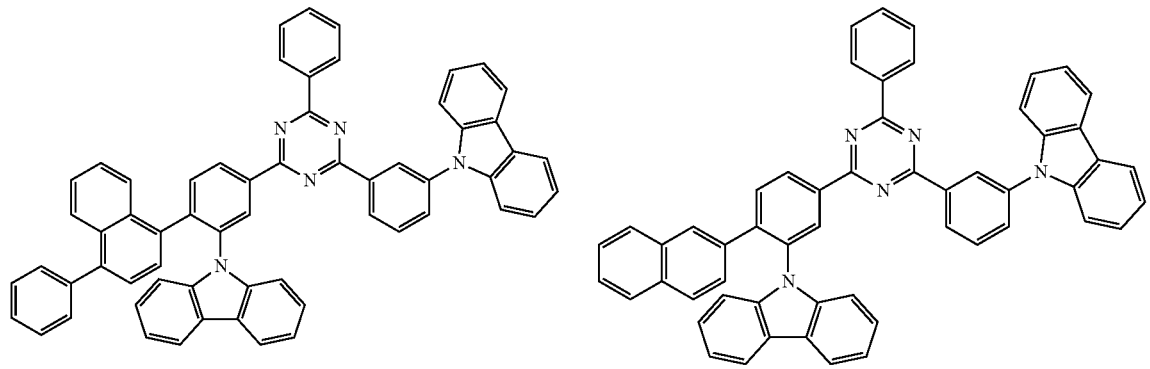
394
395
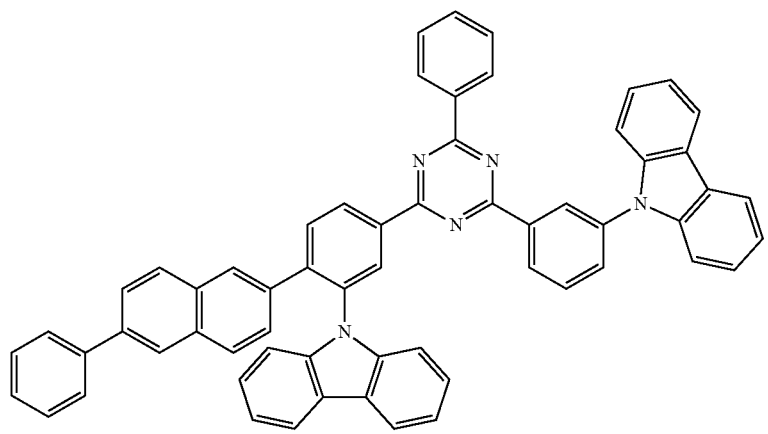
396
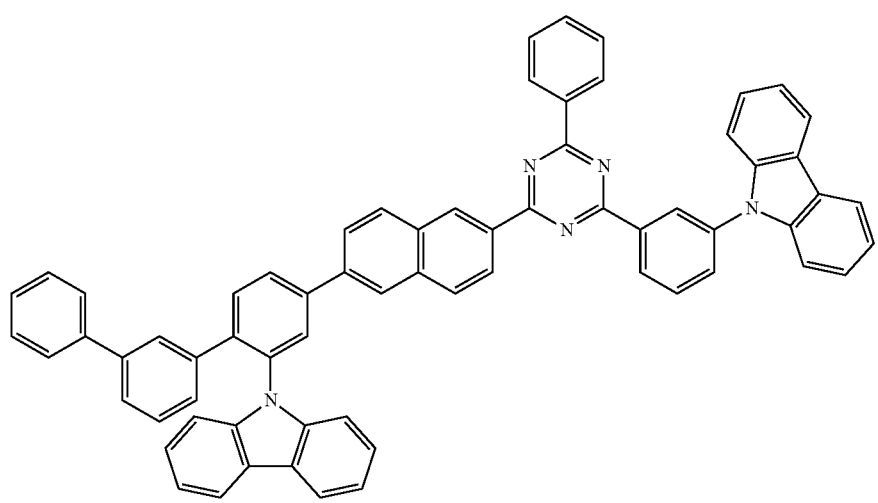

397
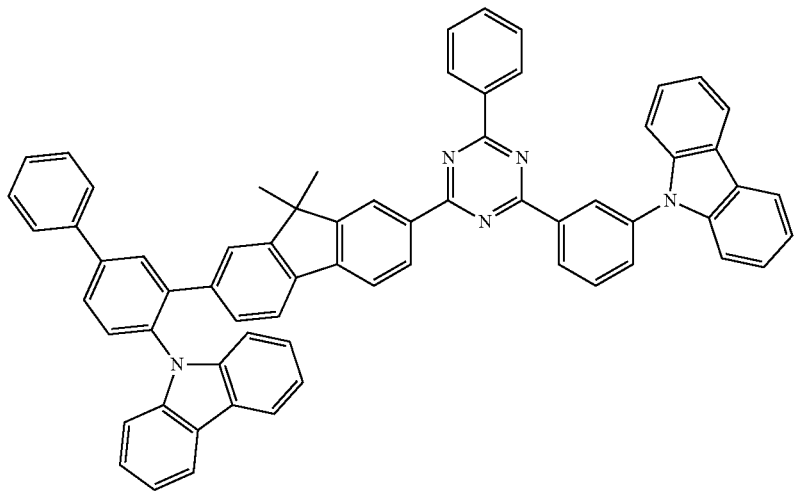
398
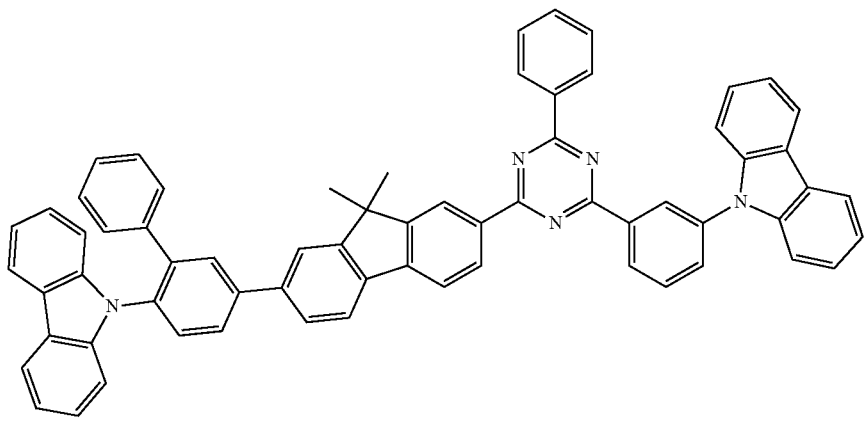
399
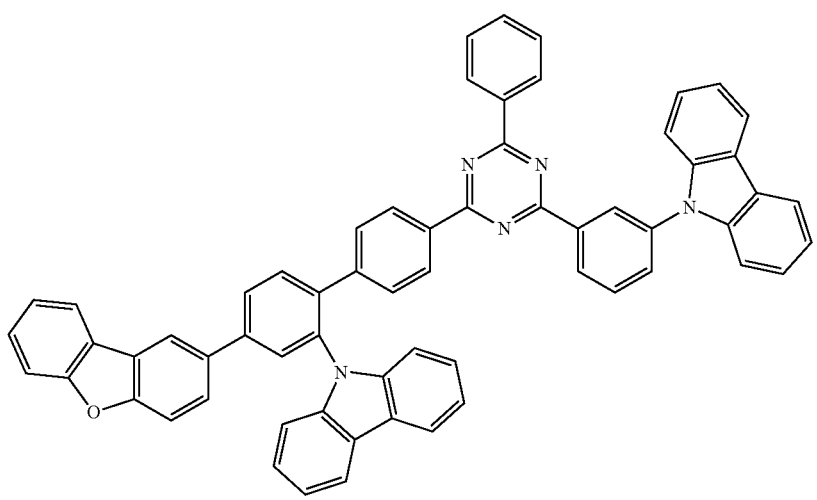

400
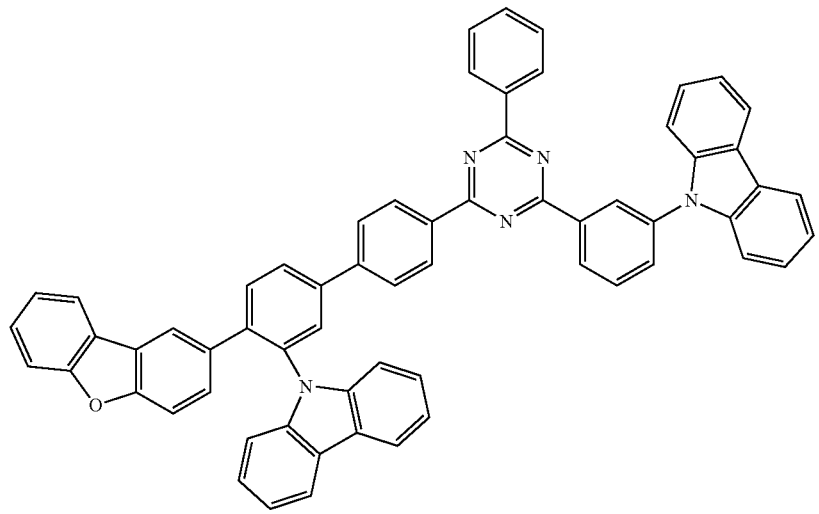
401
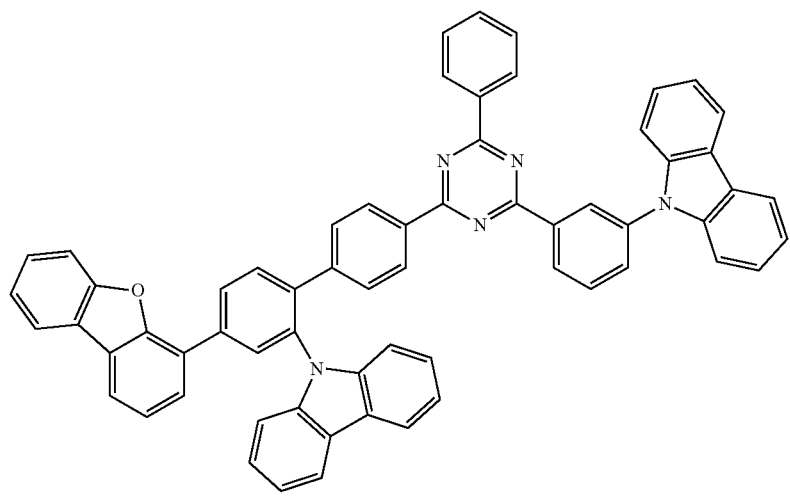
402
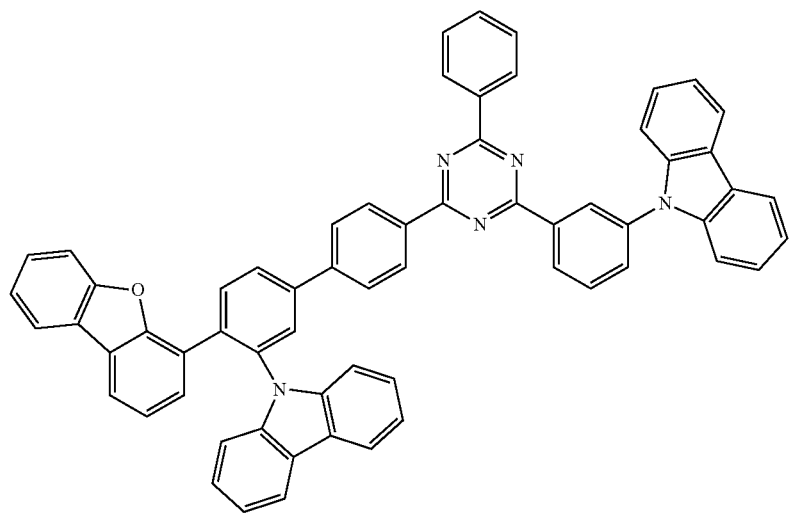

403
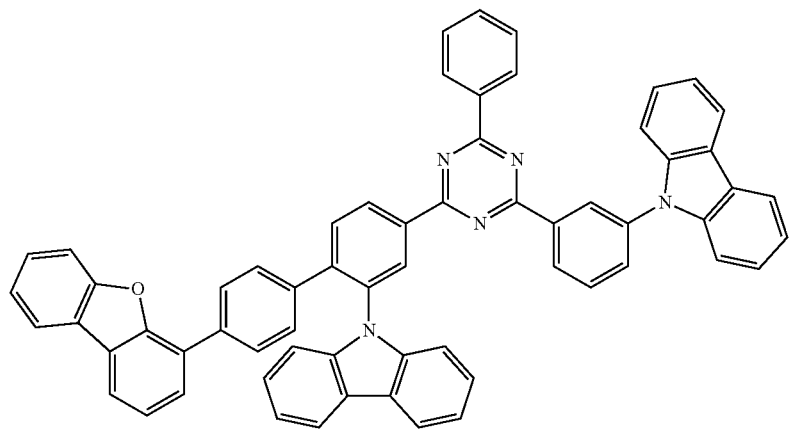
404 405
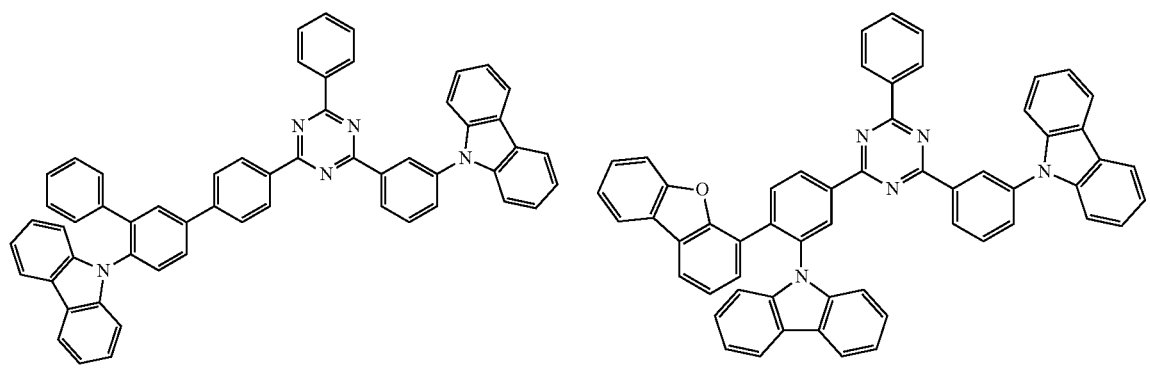
406 407
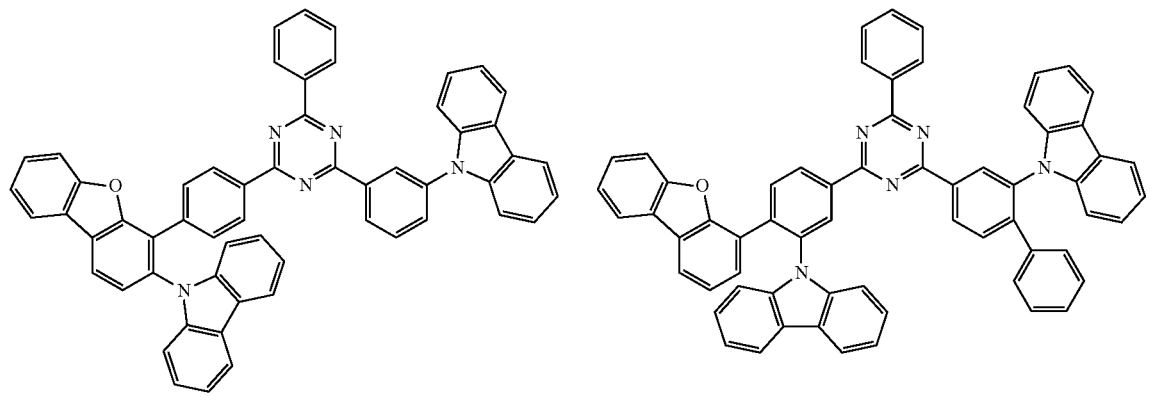
408 409
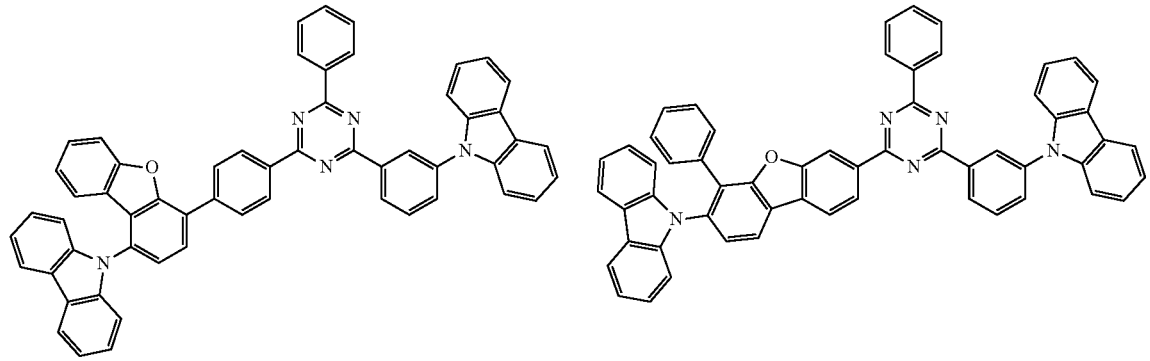

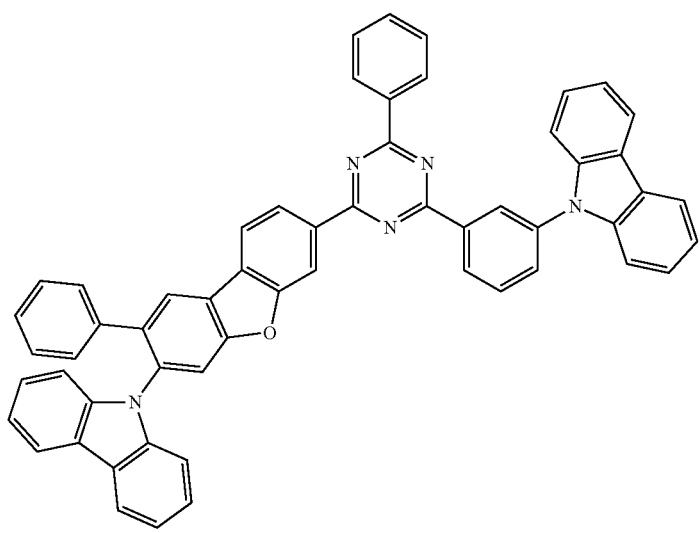
410
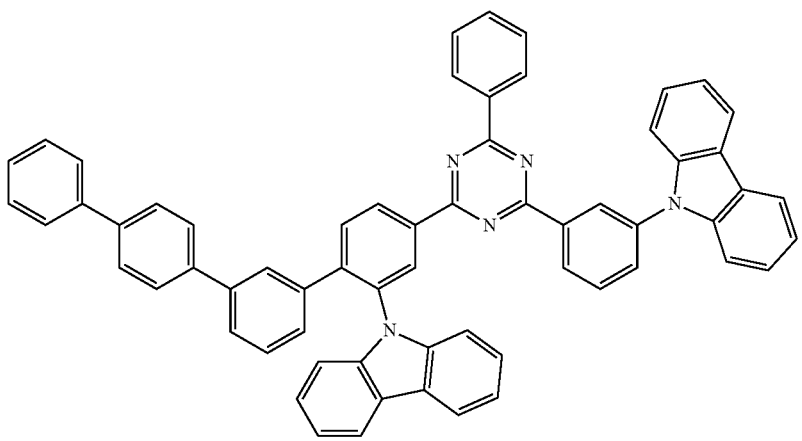
411
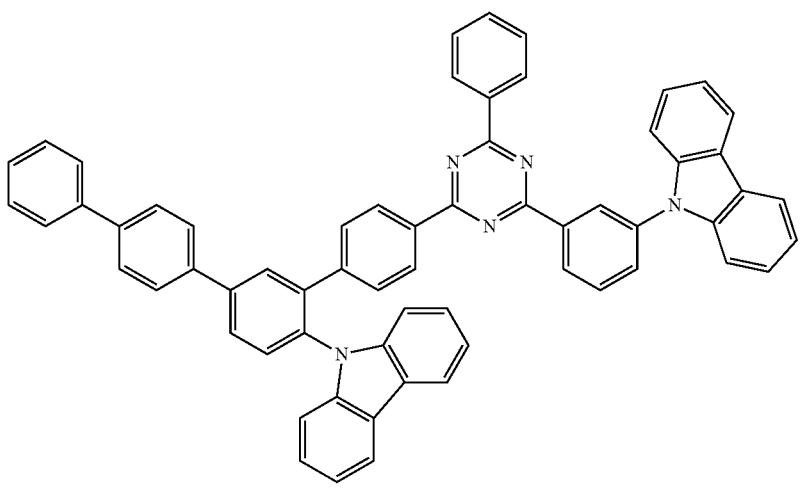
412

-continued
413
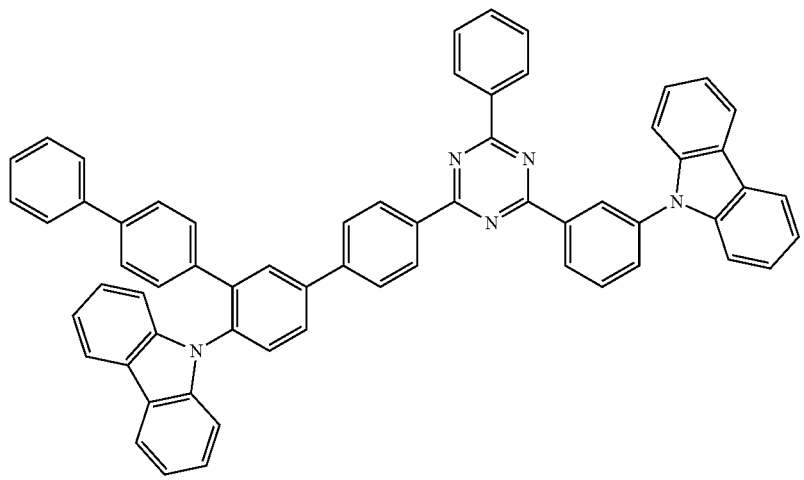
414
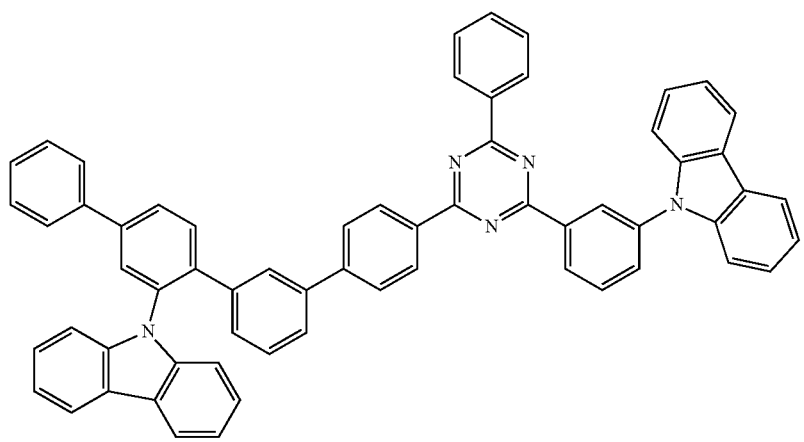
415
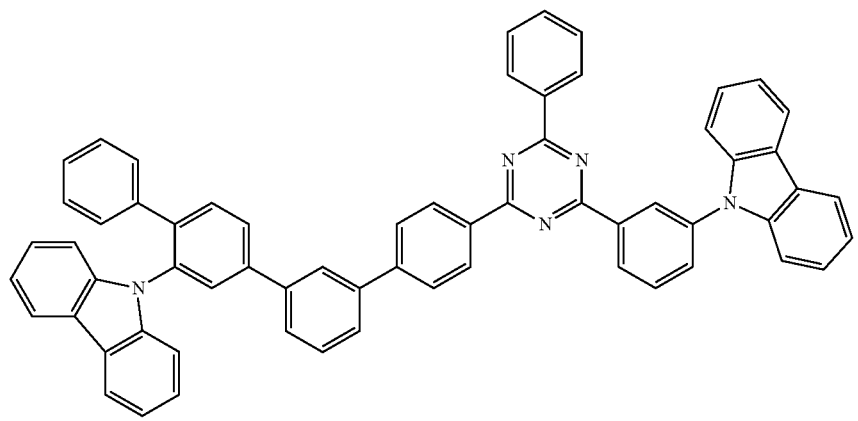

416
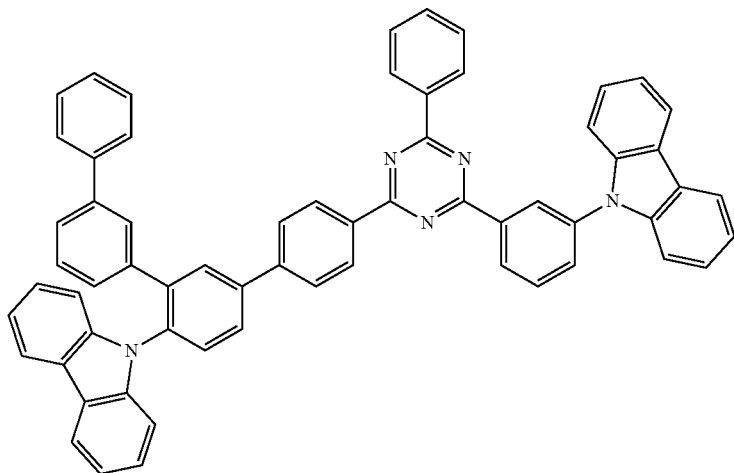
417
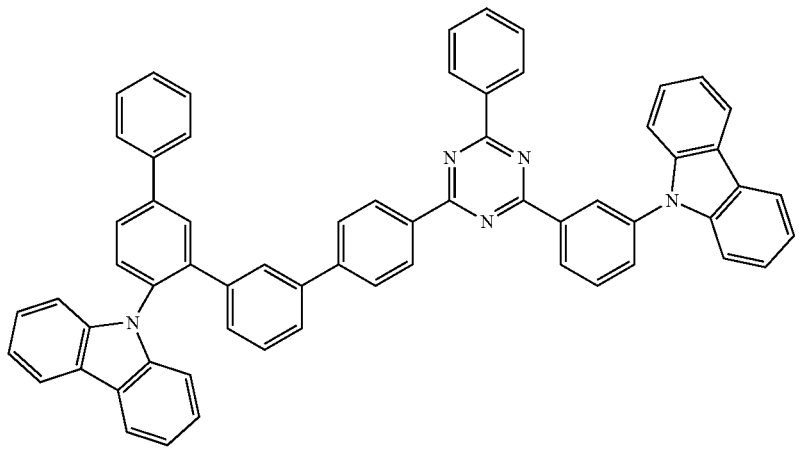
418
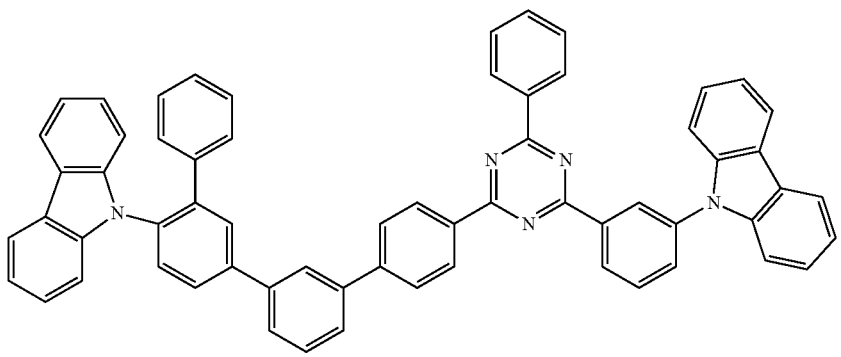
419 420
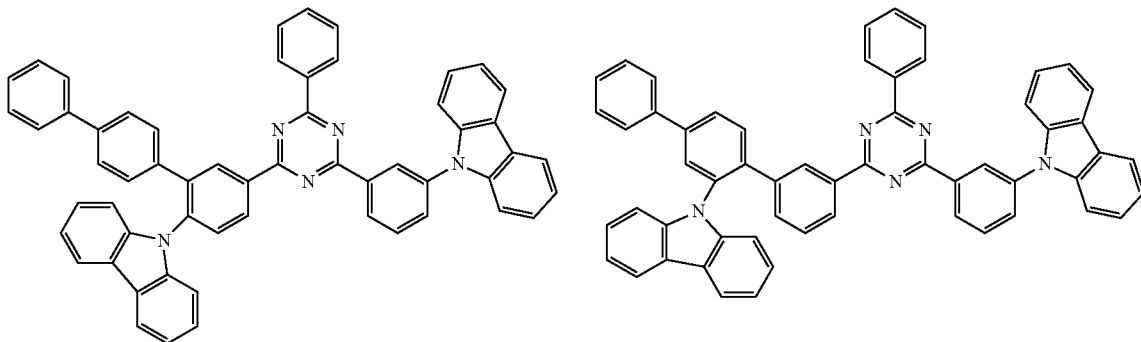

-continued
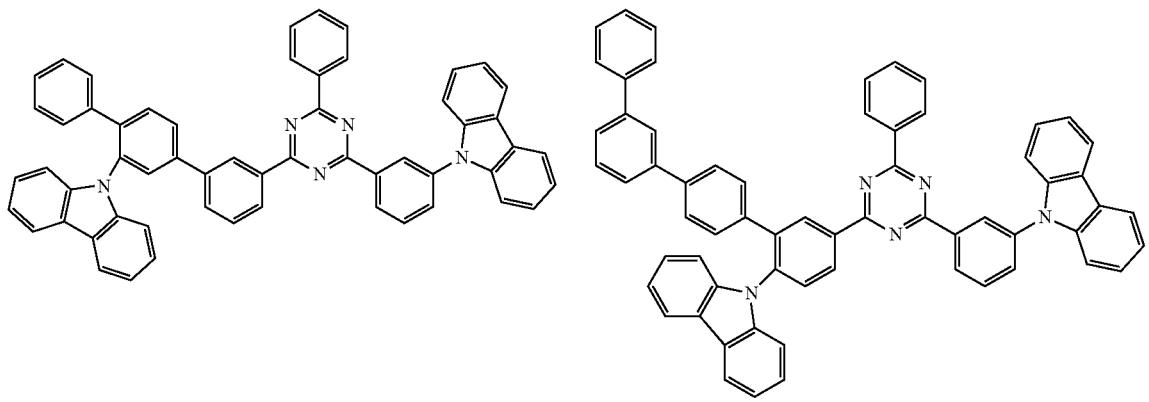
421 422
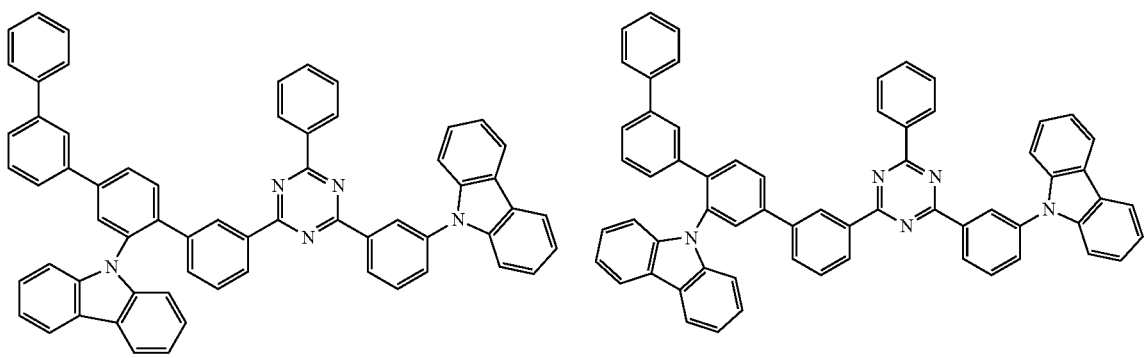
423 424
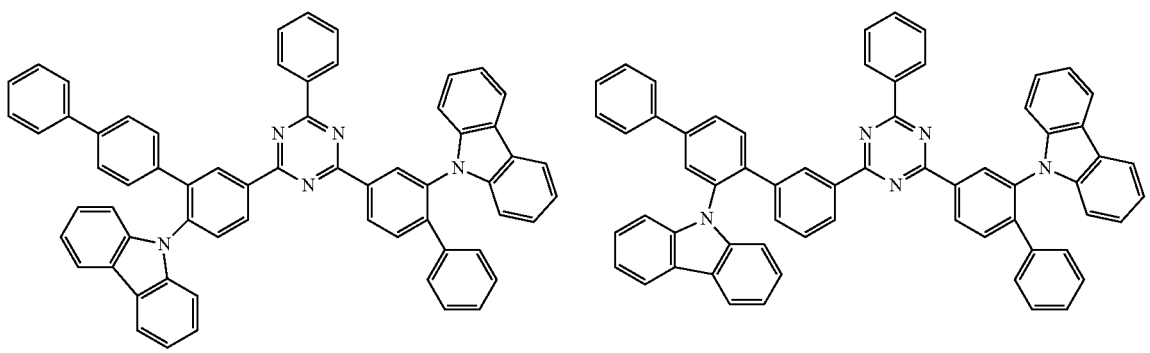
425 426
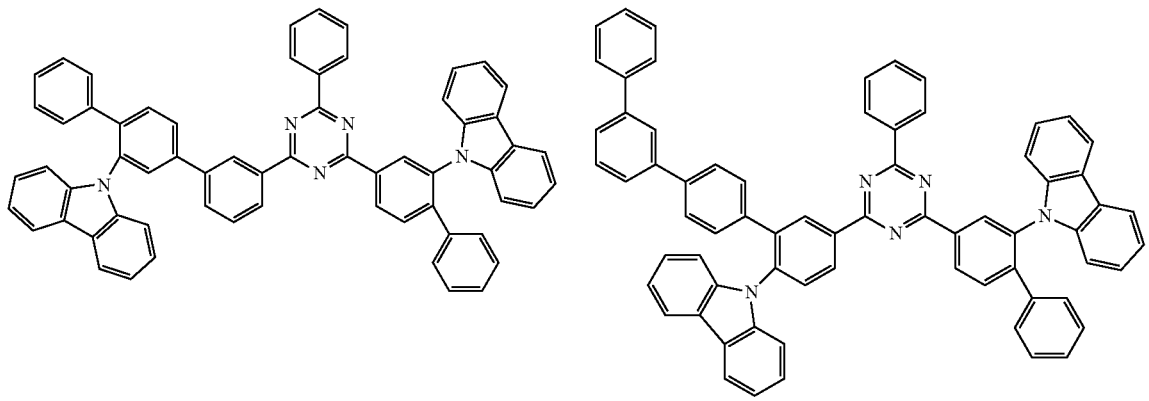
427 428

-continued
429
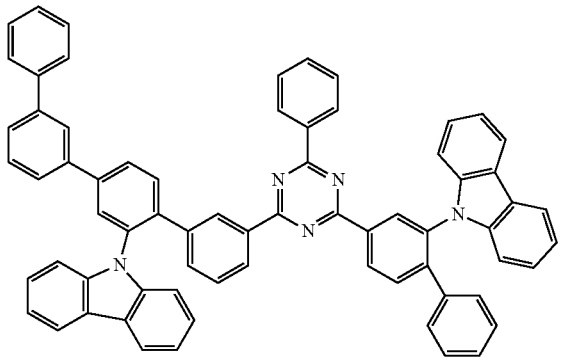
430
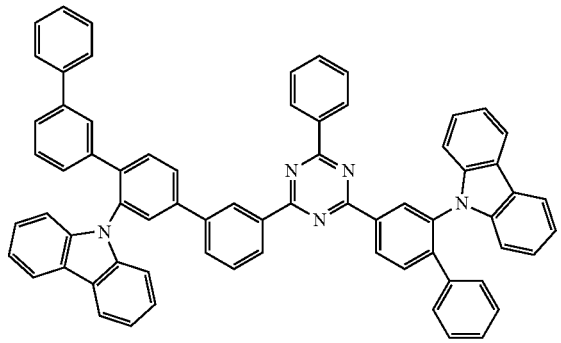
431
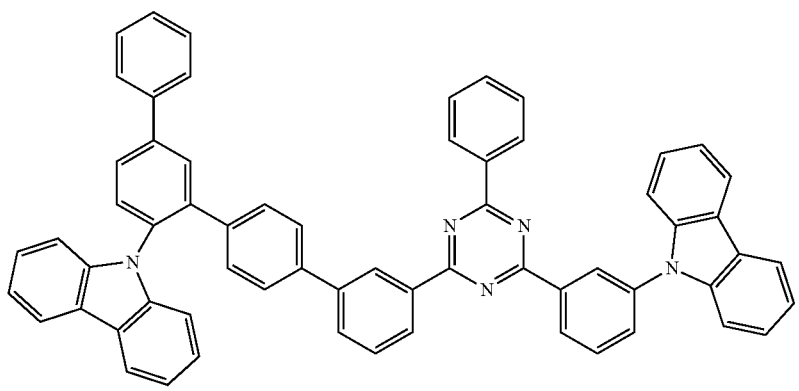
432
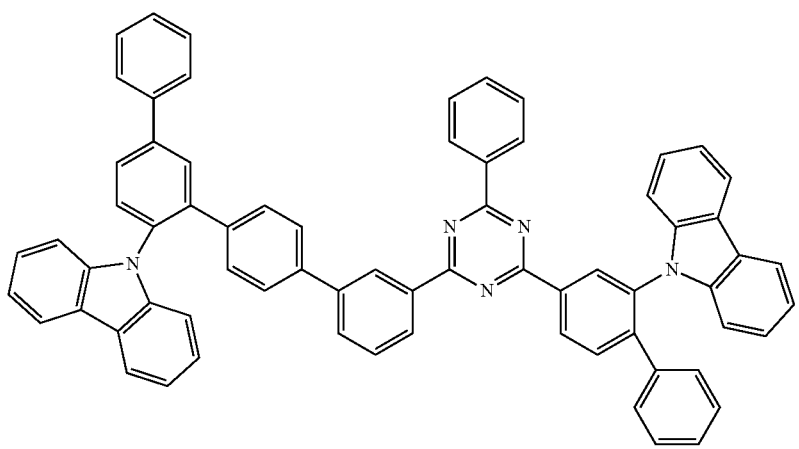

-continued
433
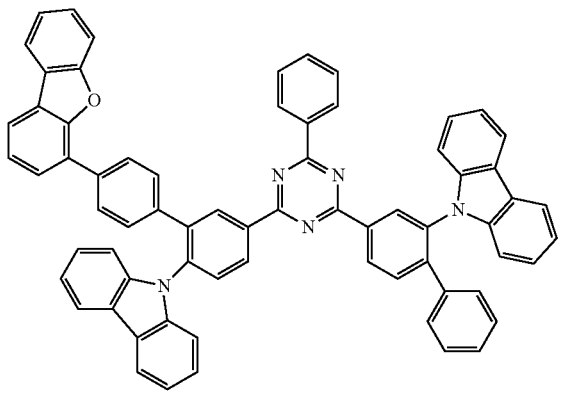
434
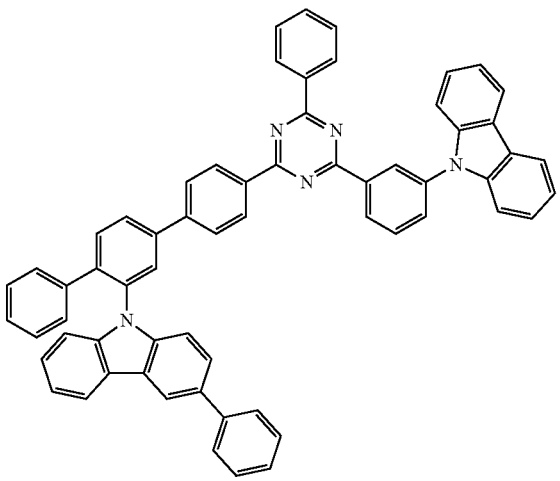
435
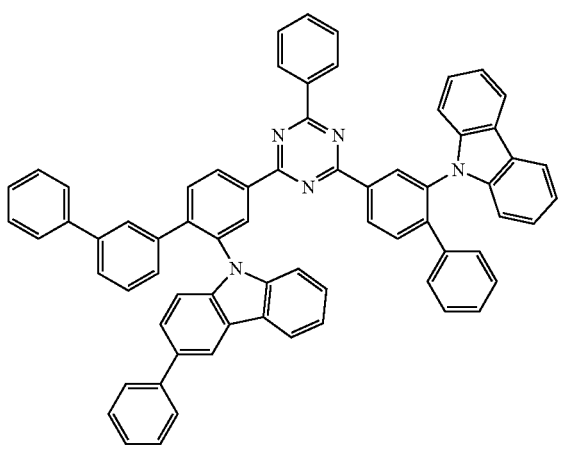
436
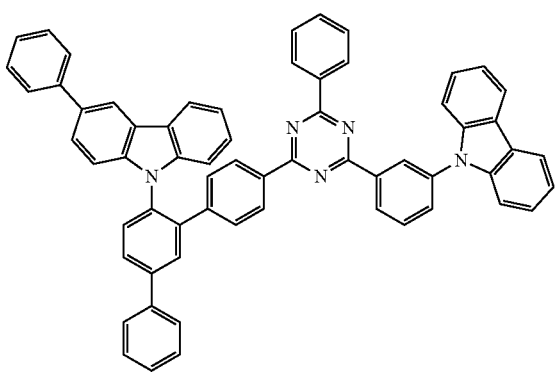
437
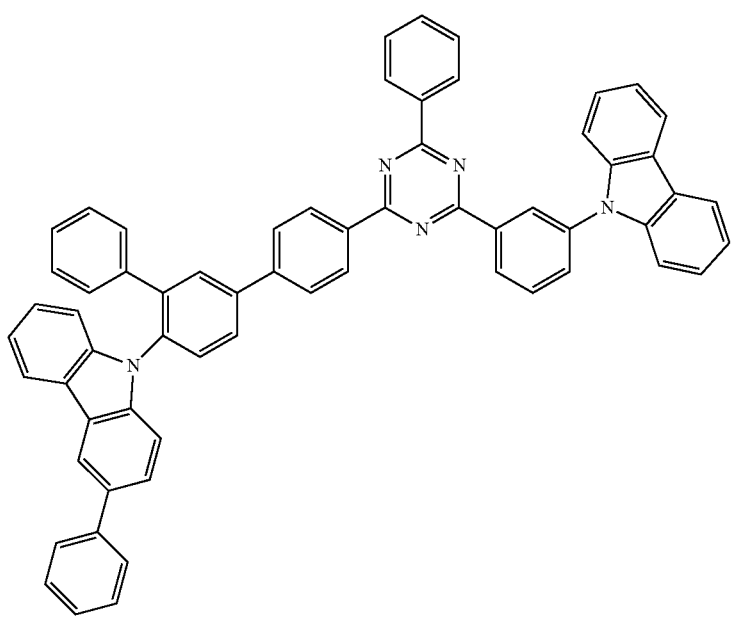

438
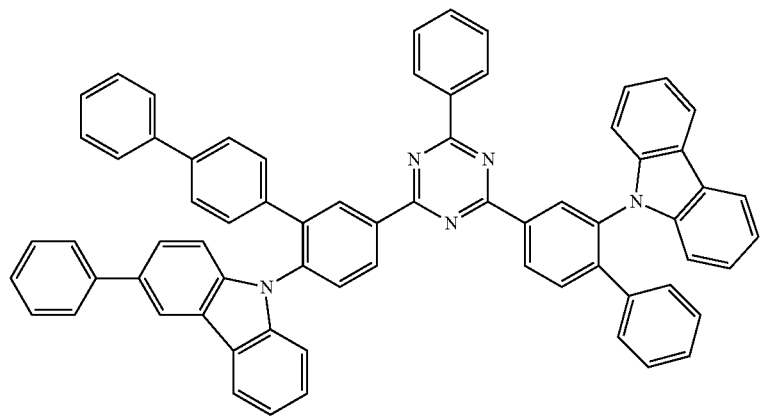
439
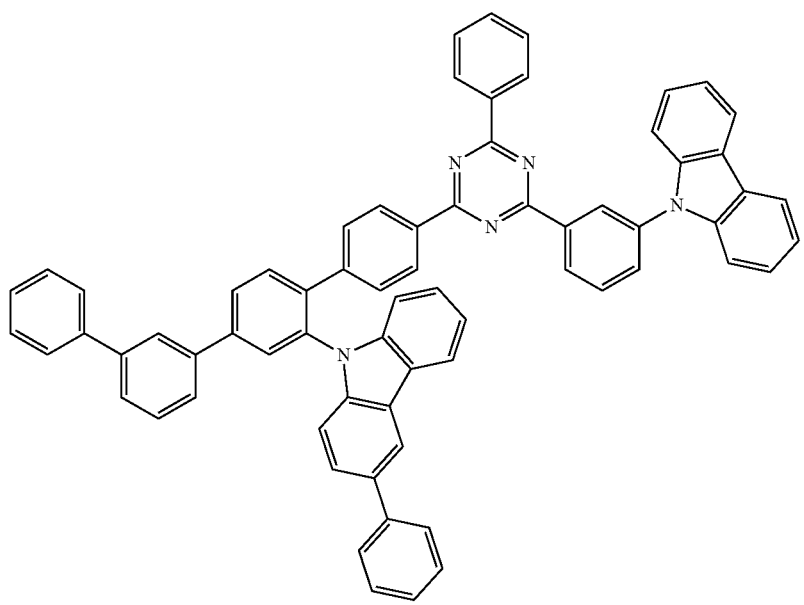
440
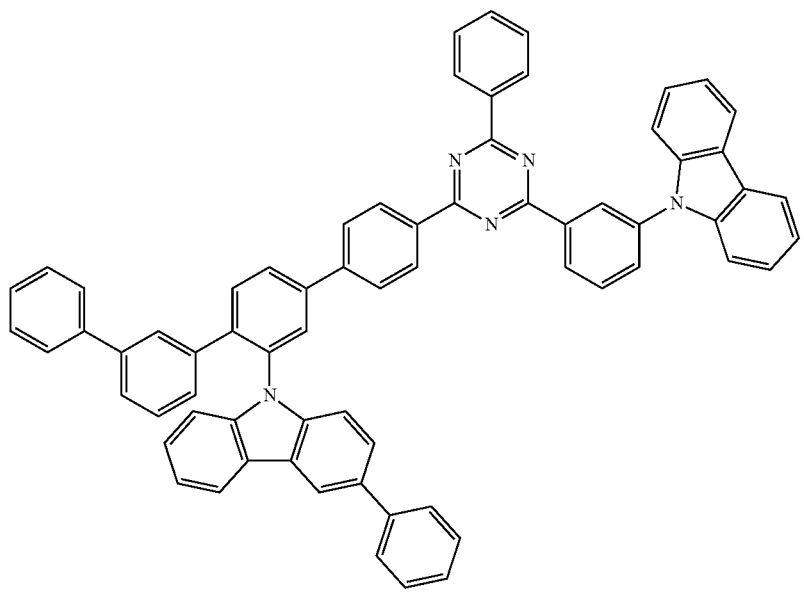

441
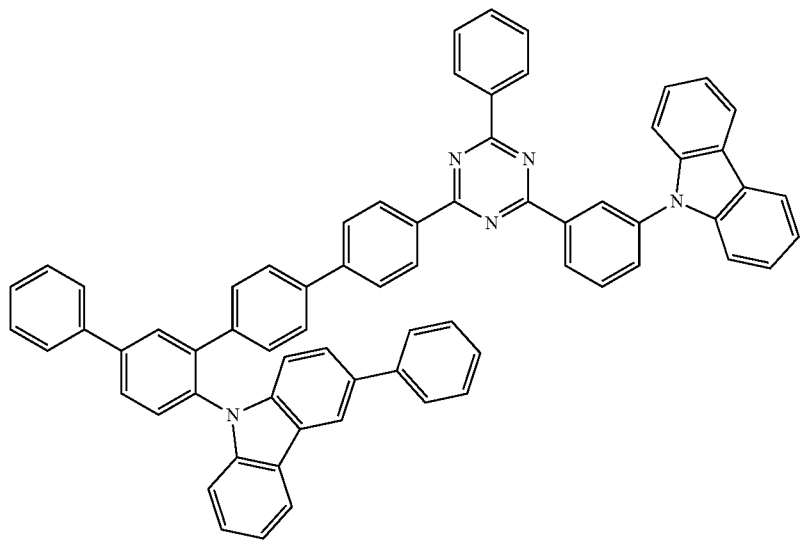
442
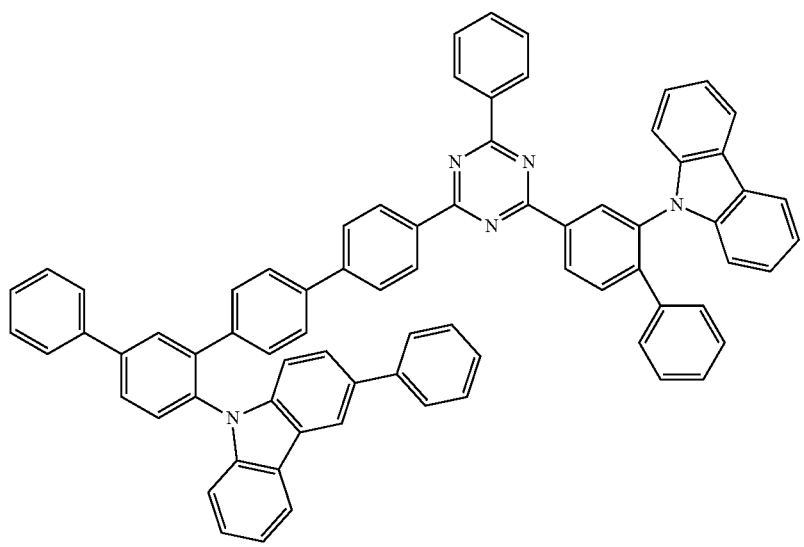
443 444
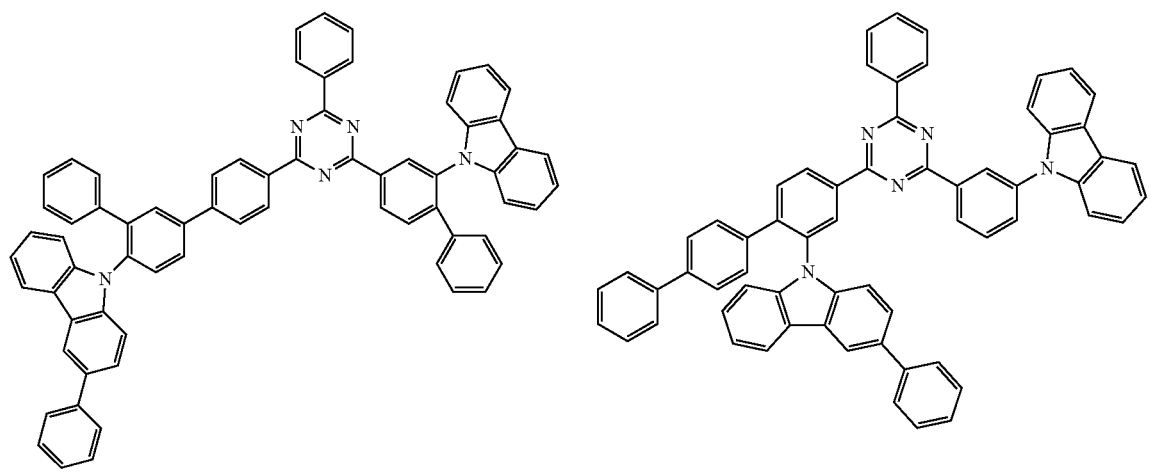

-continued
445
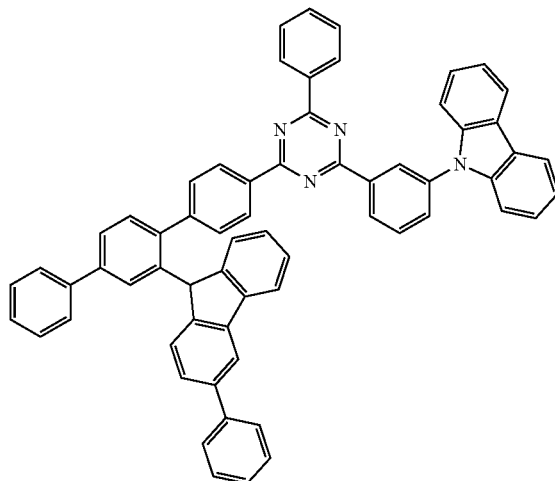
446
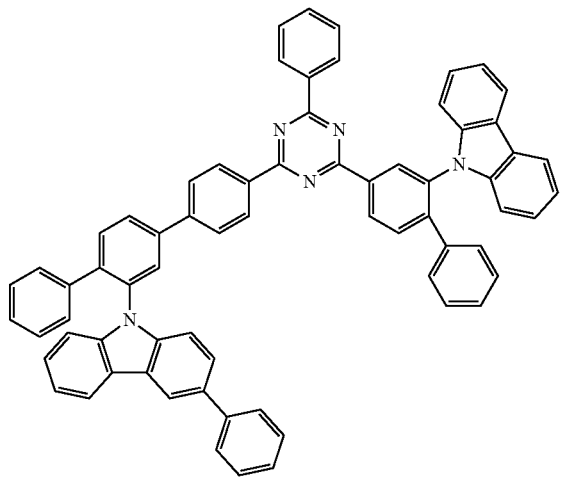
447
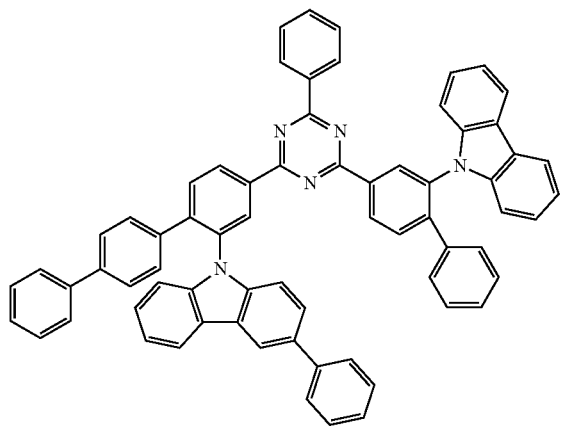
448
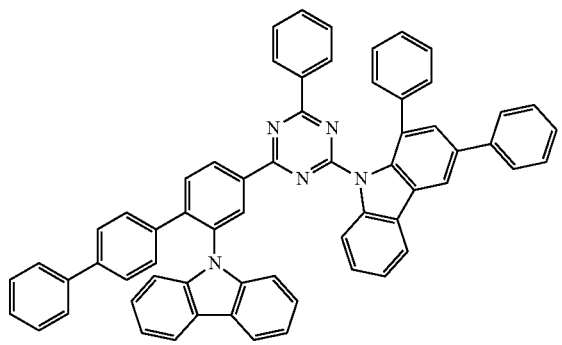
449
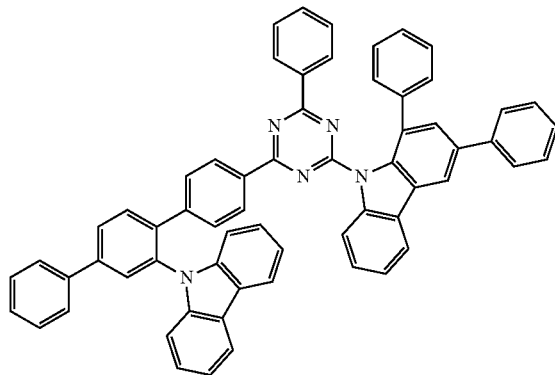
450
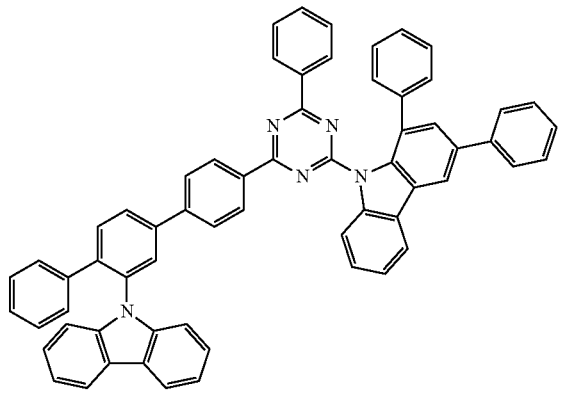

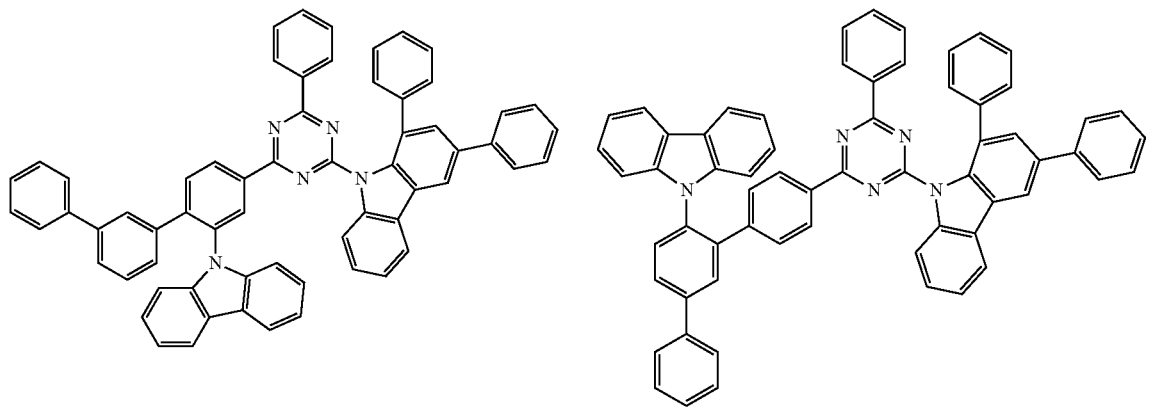
451 452
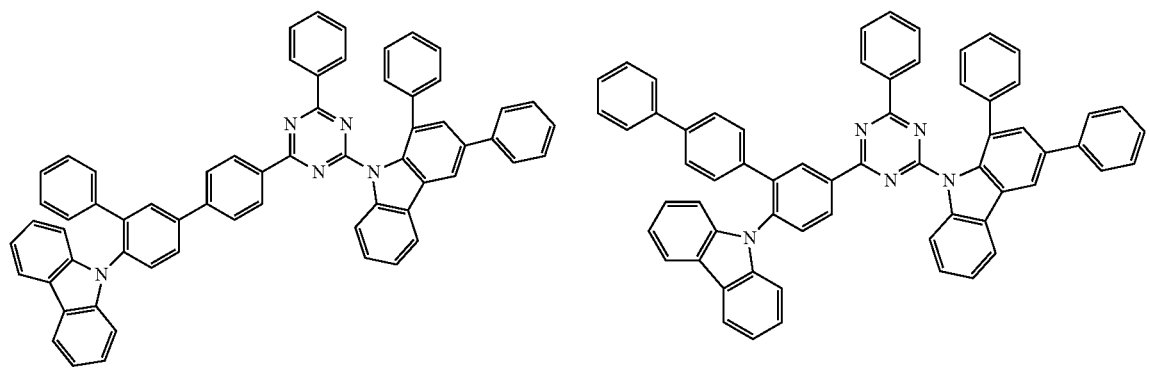
453 454
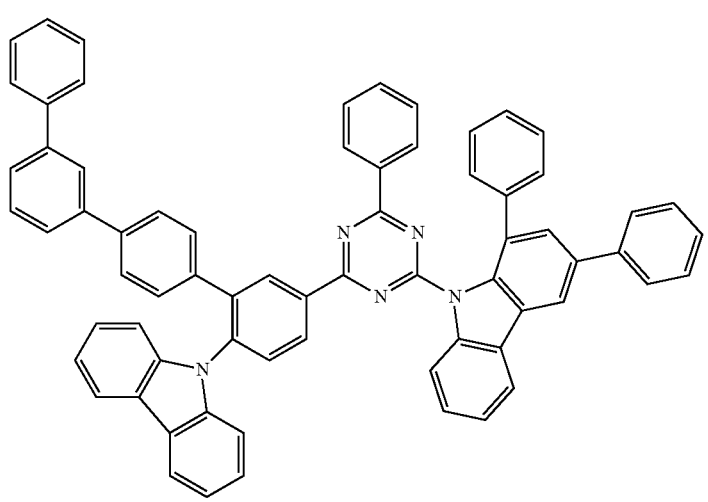
455

456
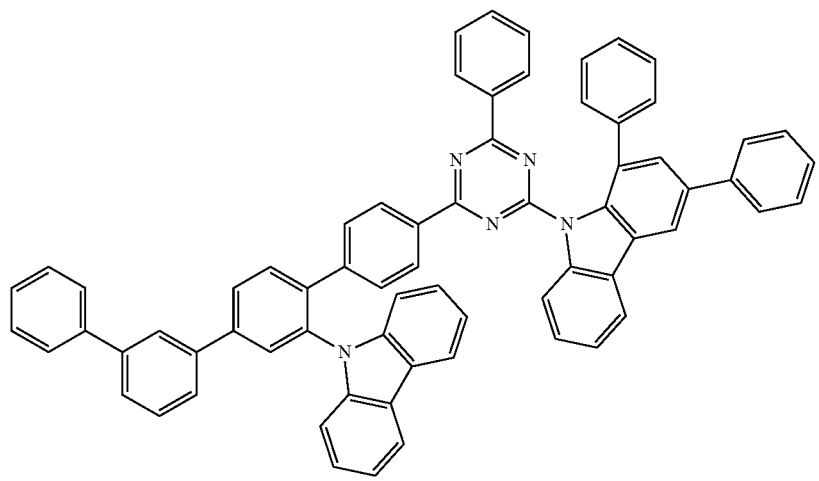
457
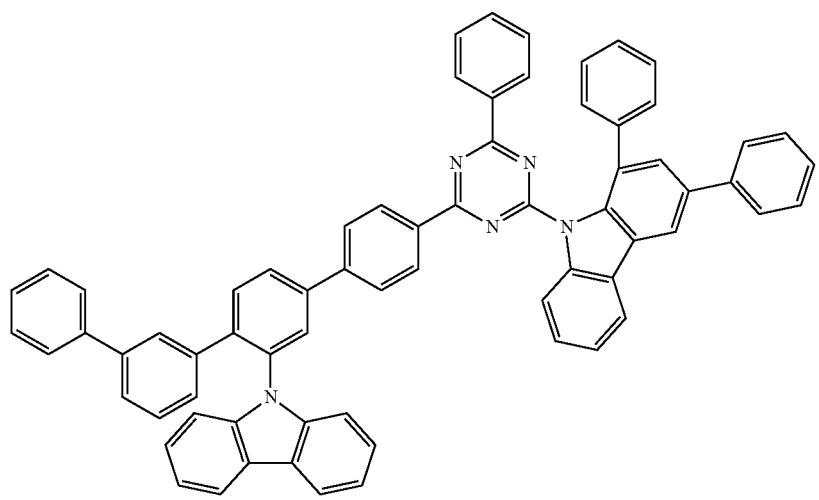
458
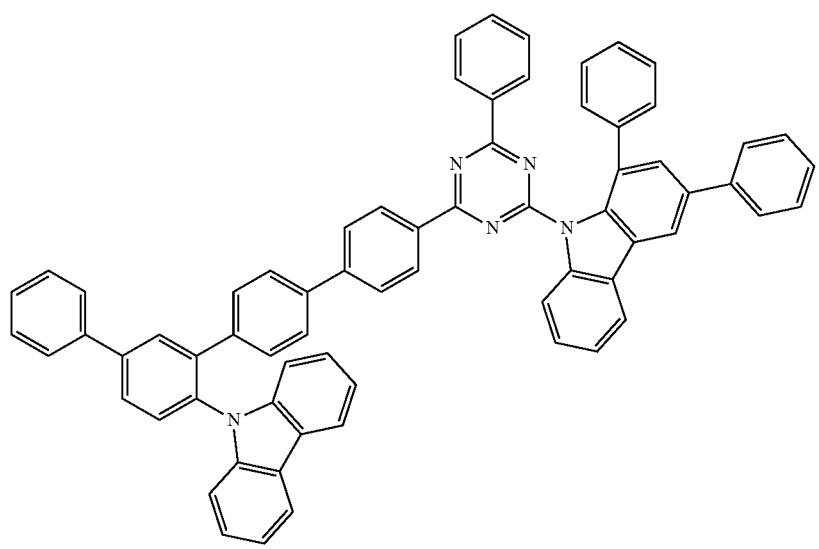

-continued
459
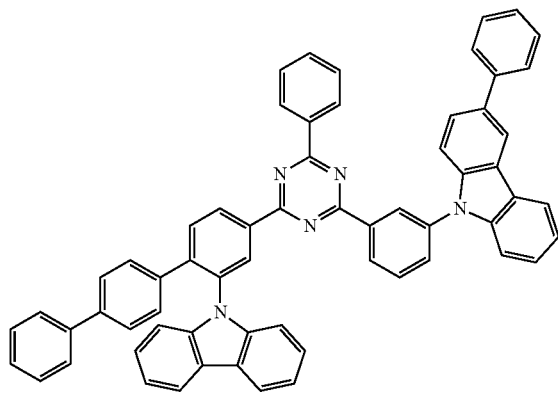
460
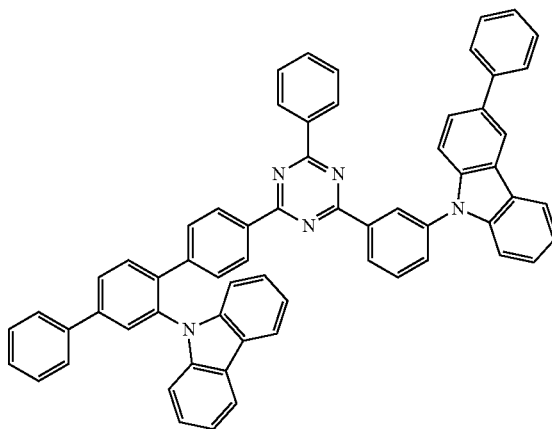
461
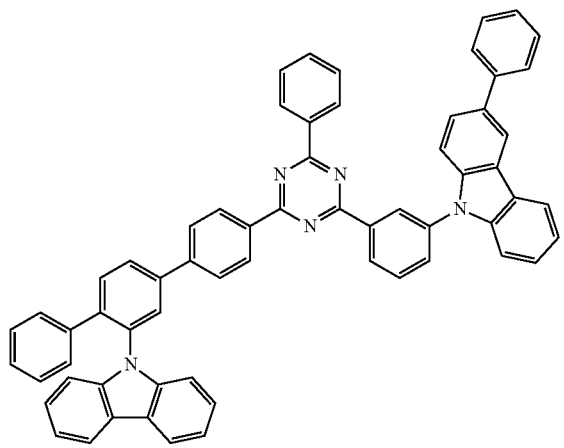
462
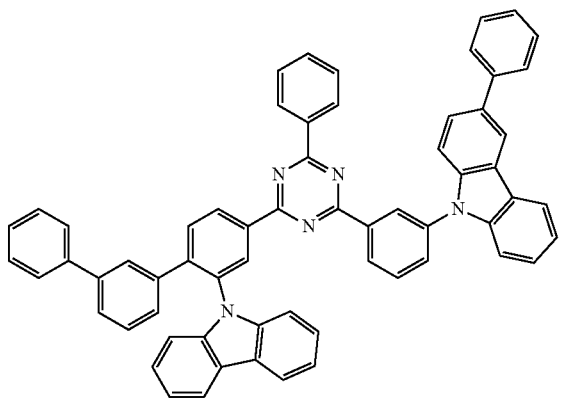
463
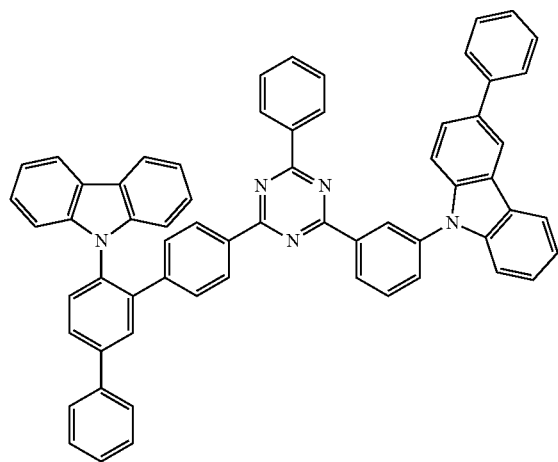
464
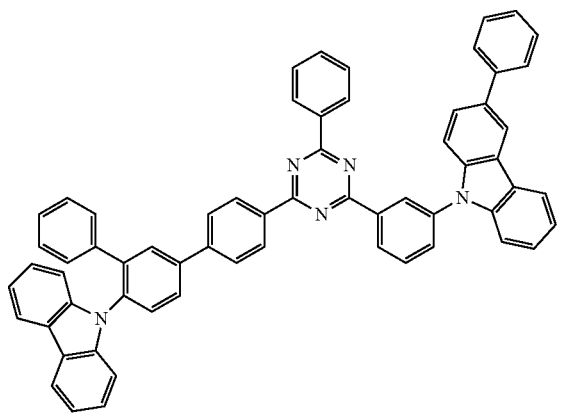

-continued
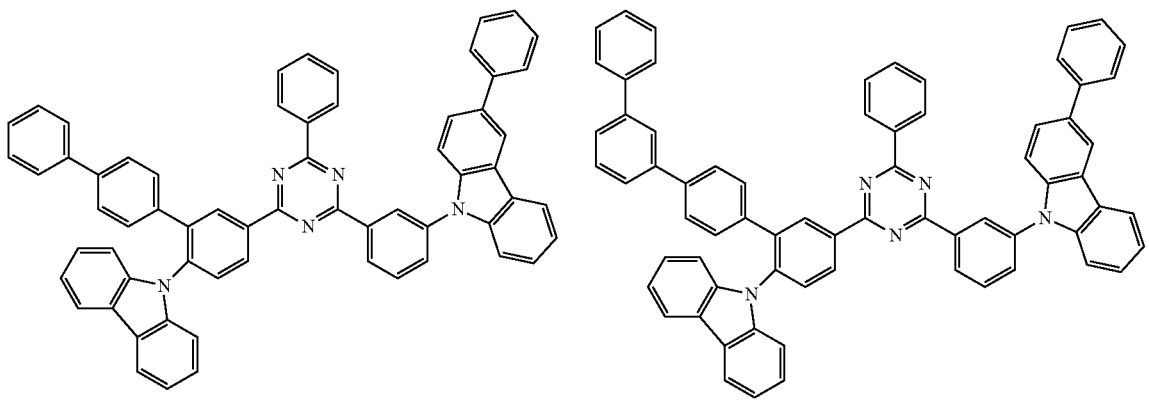
465
466
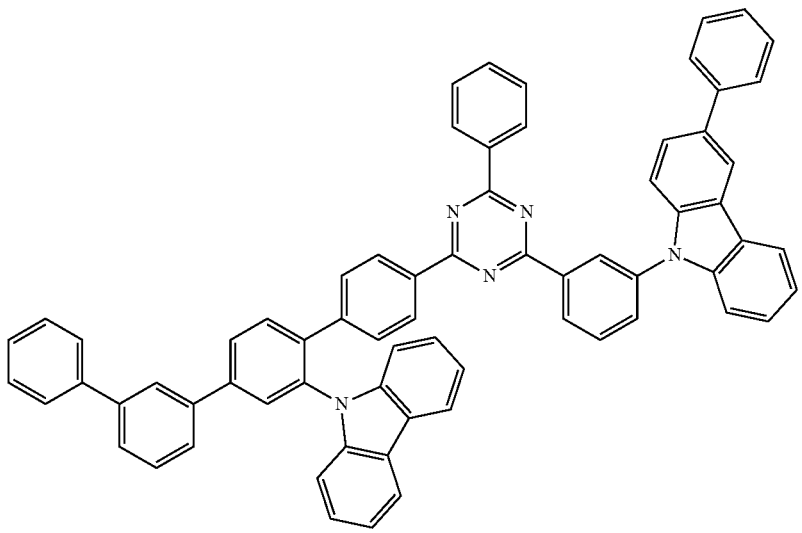
467
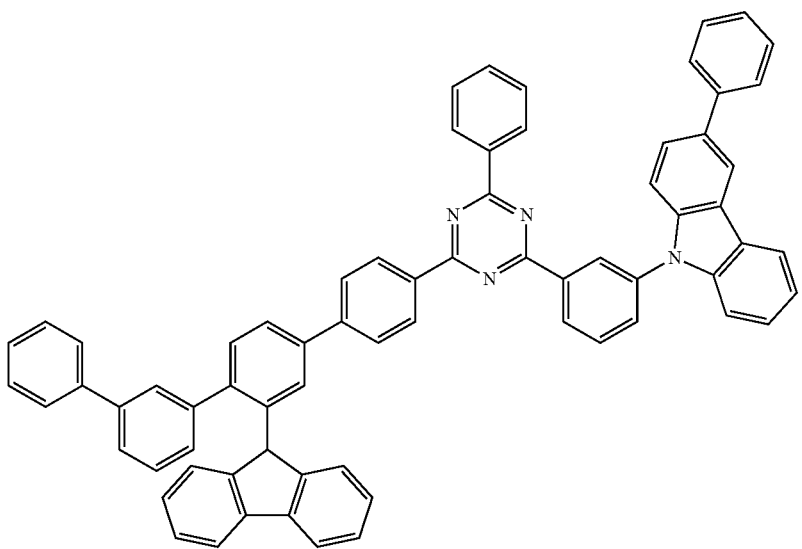
468

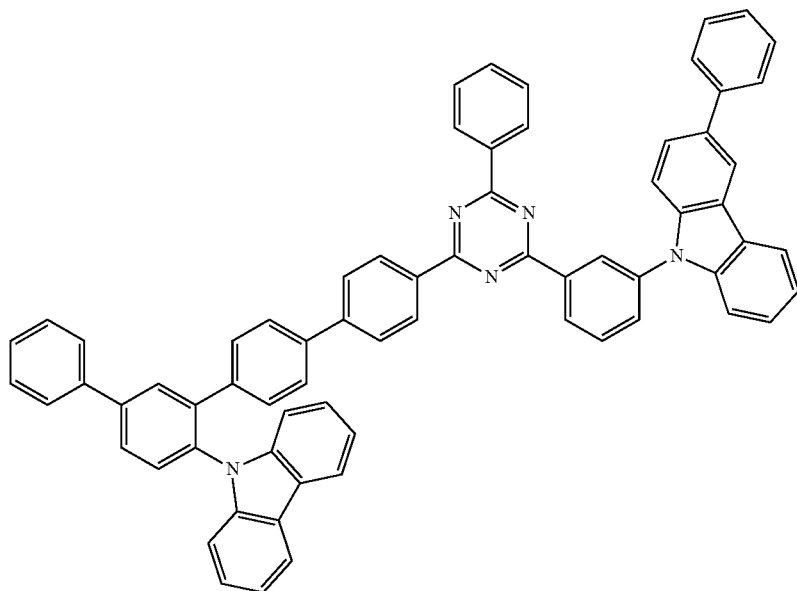
469
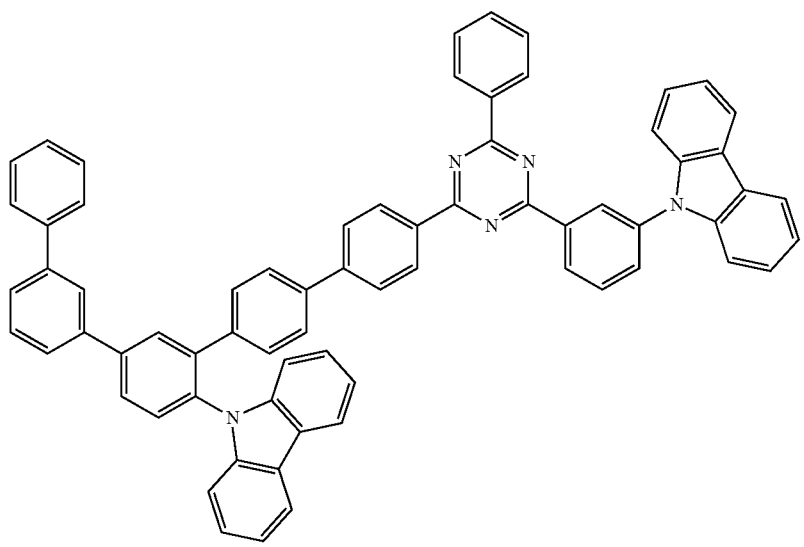
470

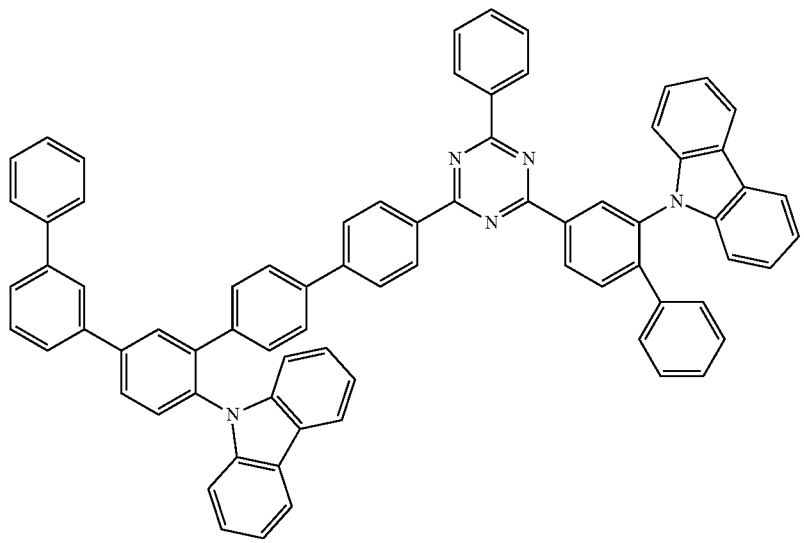
471
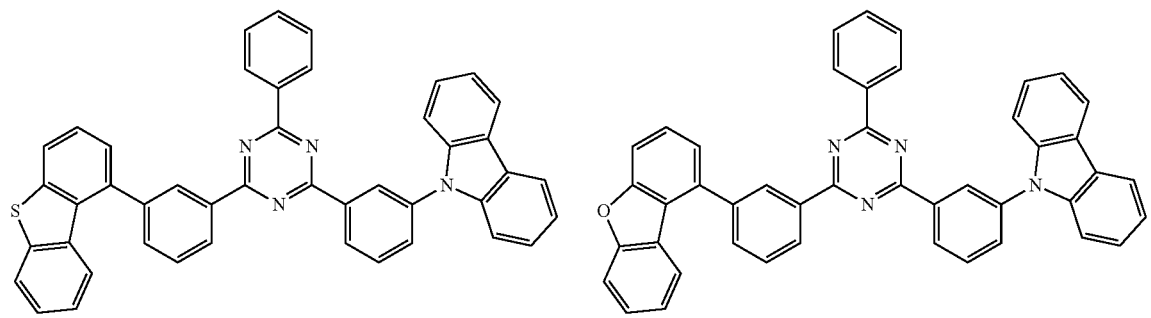
472 473
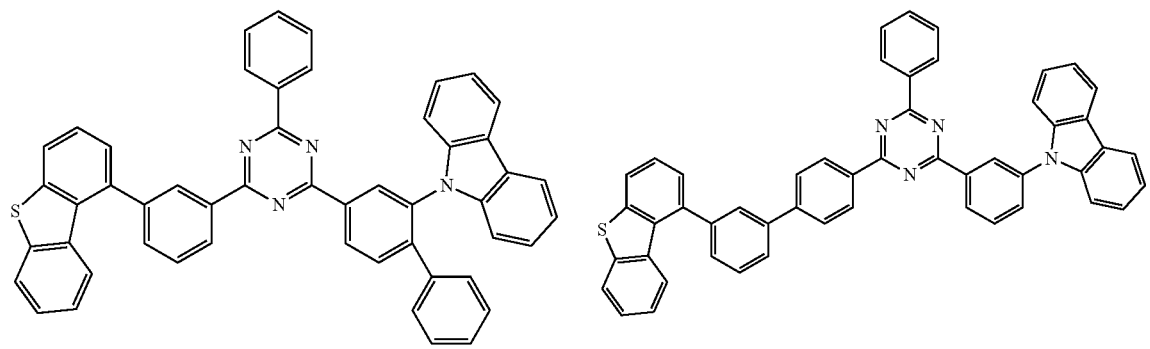
474 475
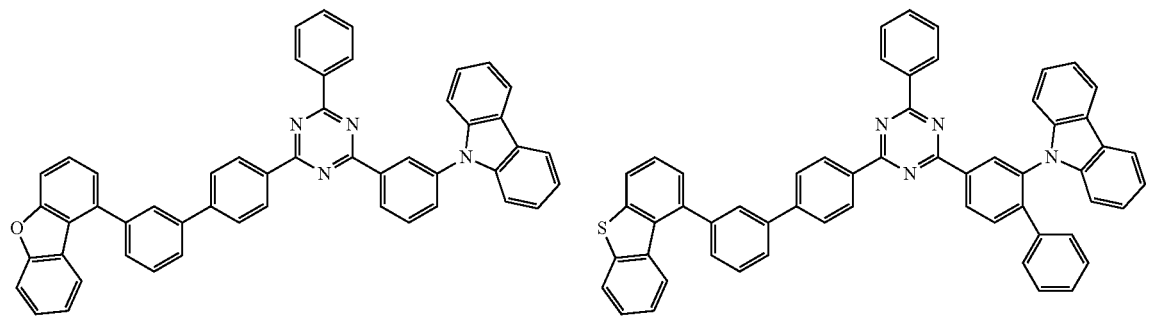
476 477

-continued
478
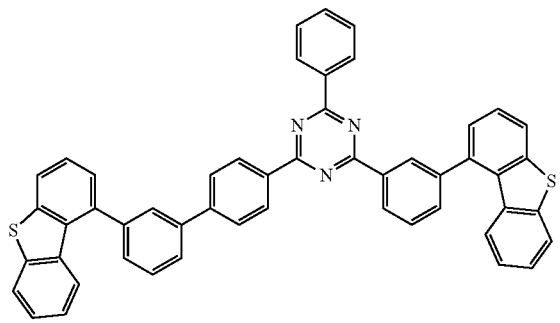
479
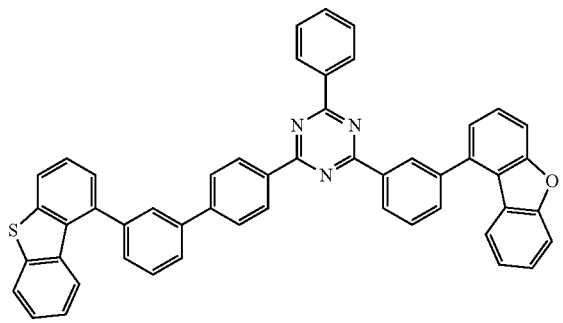
480
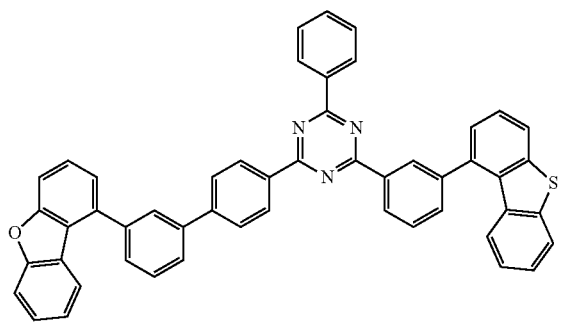
481
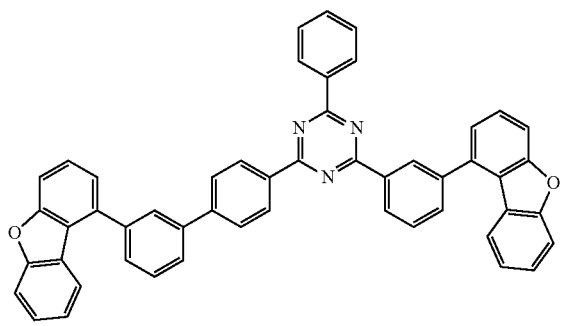
482
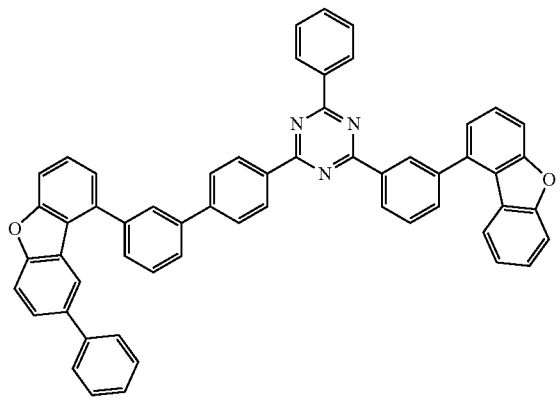
483
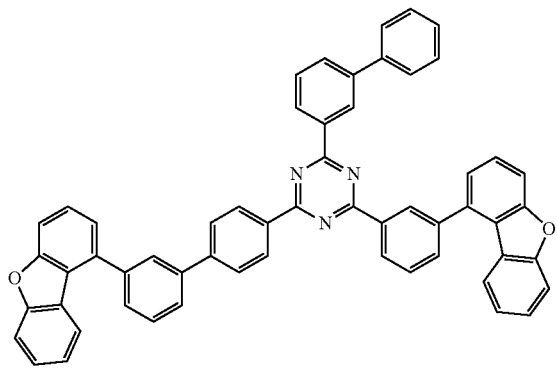
484
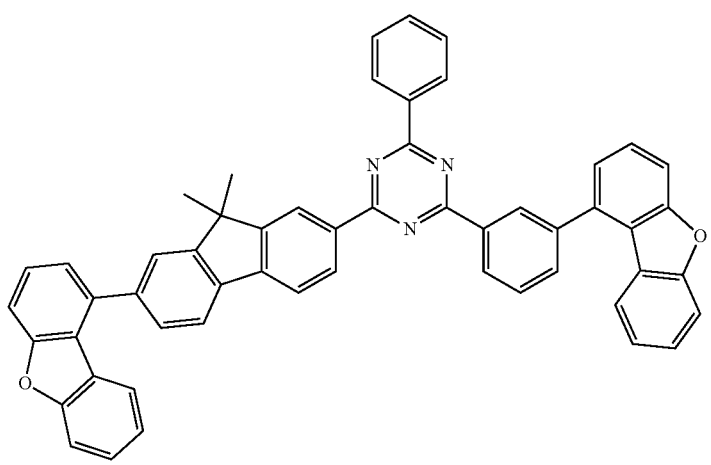

-continued
485
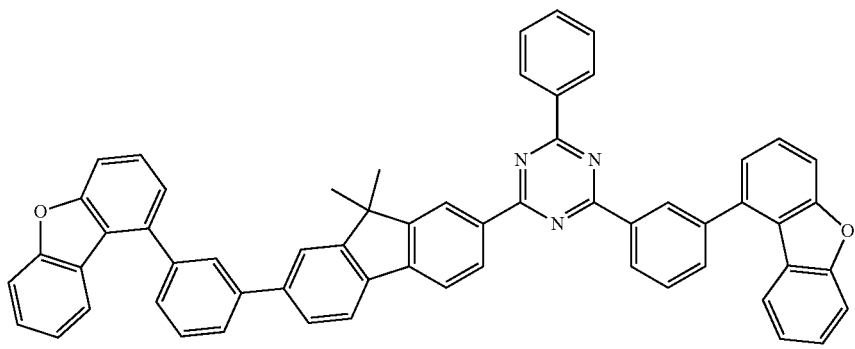
486
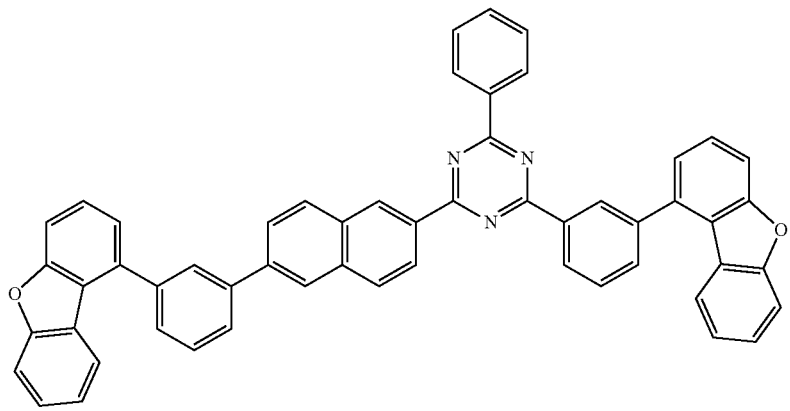
487 488
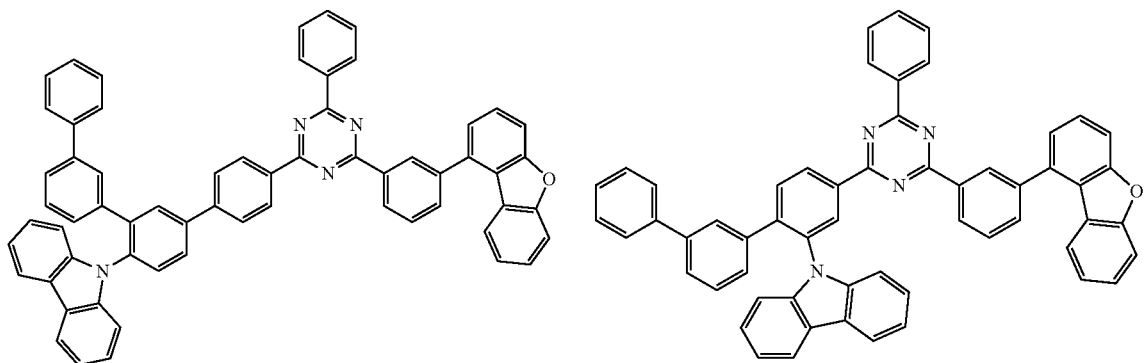
489
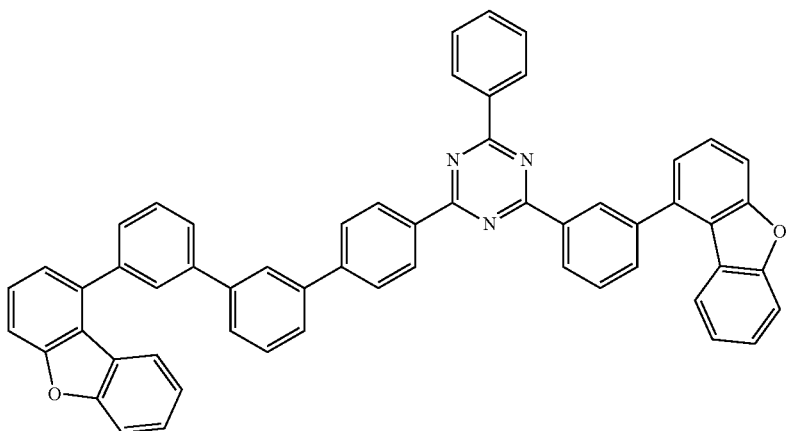

490
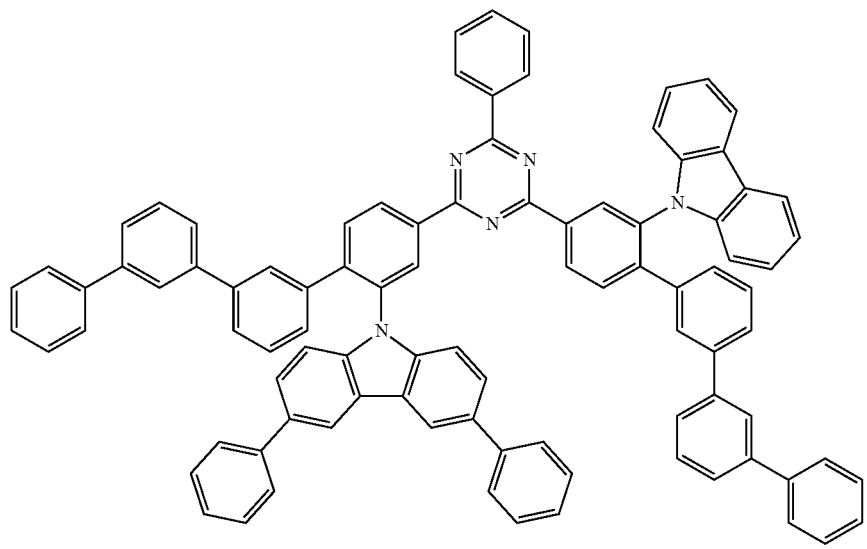
491
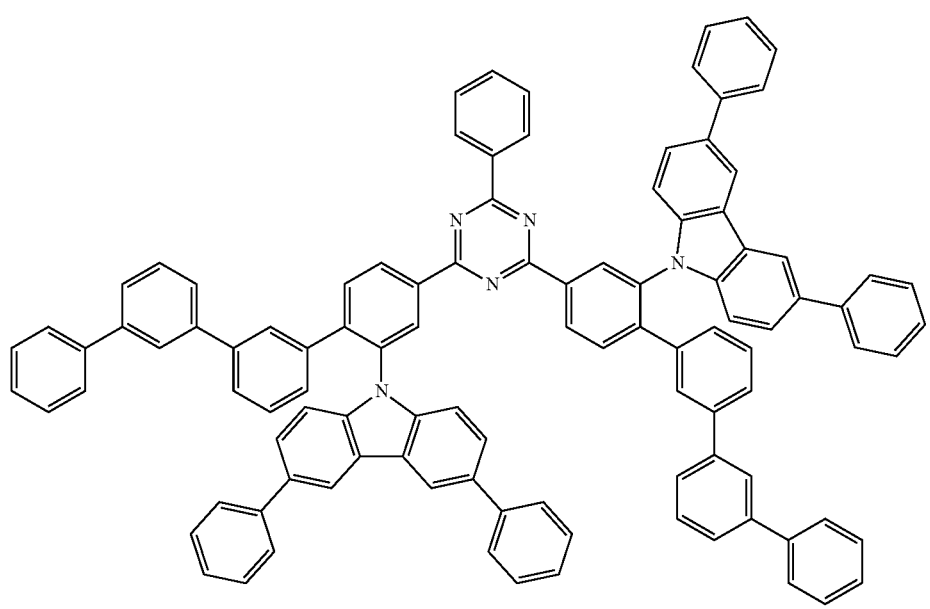
492
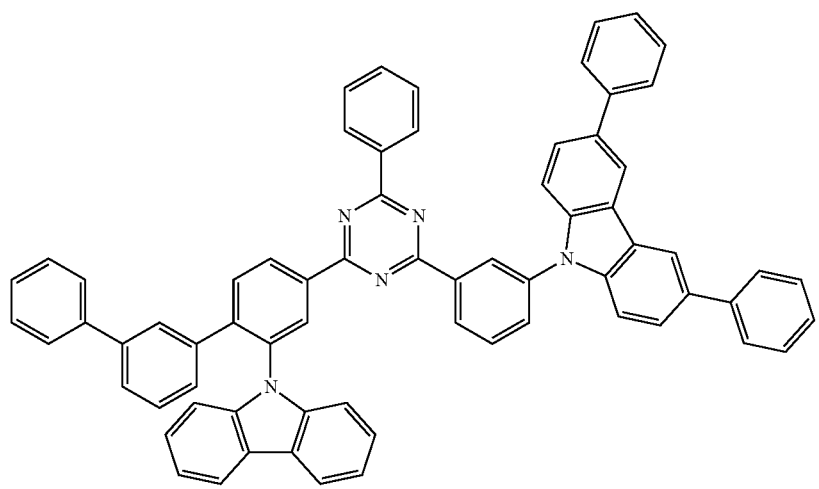

-continued
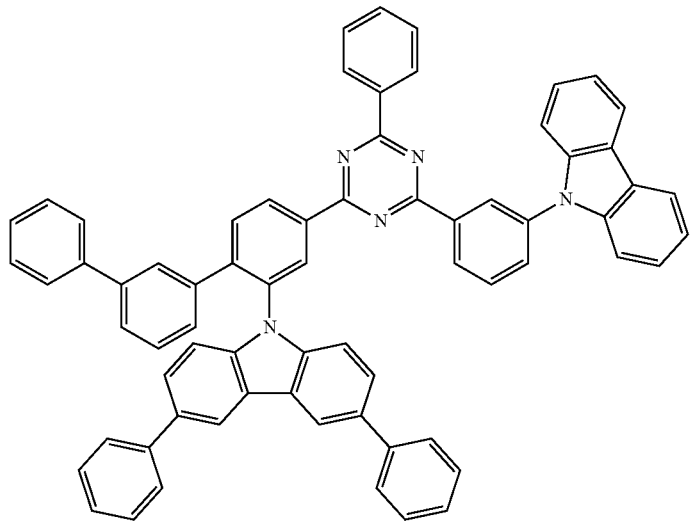
493
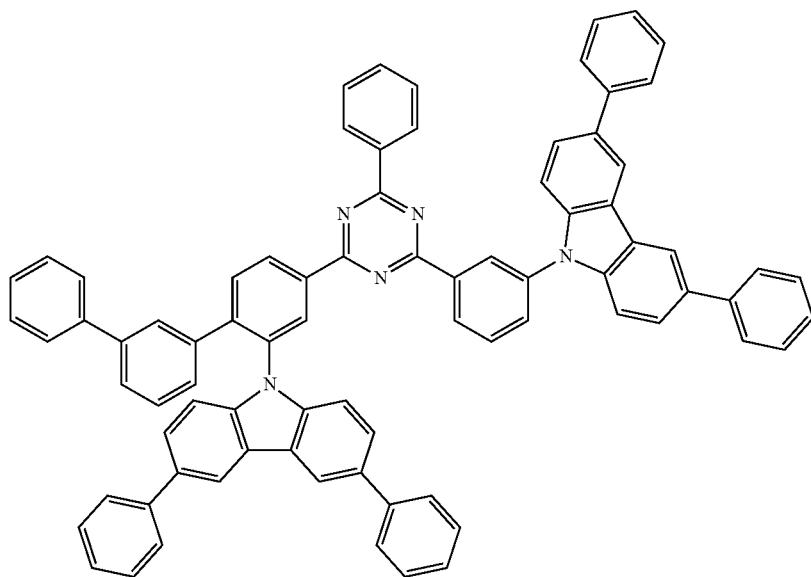
494
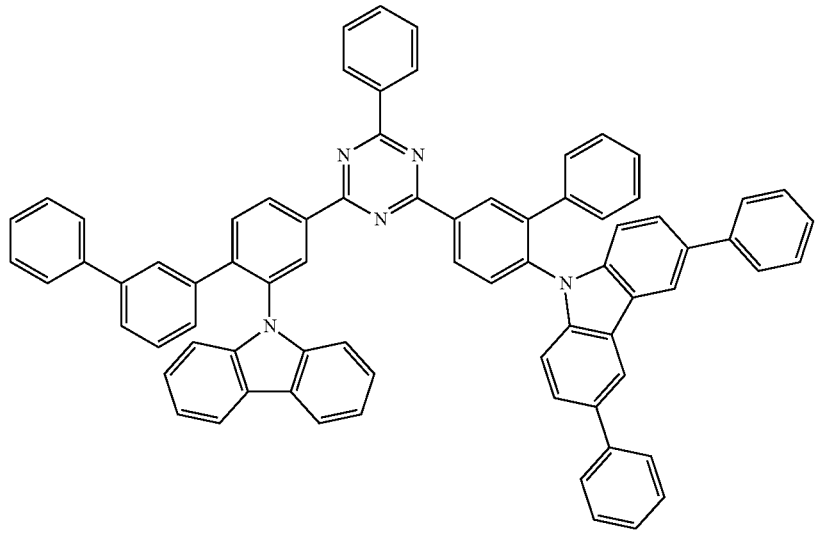
495

-continued
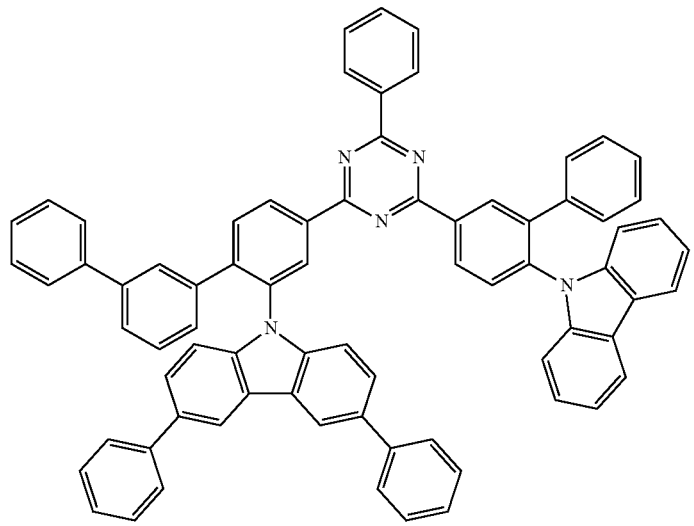
496
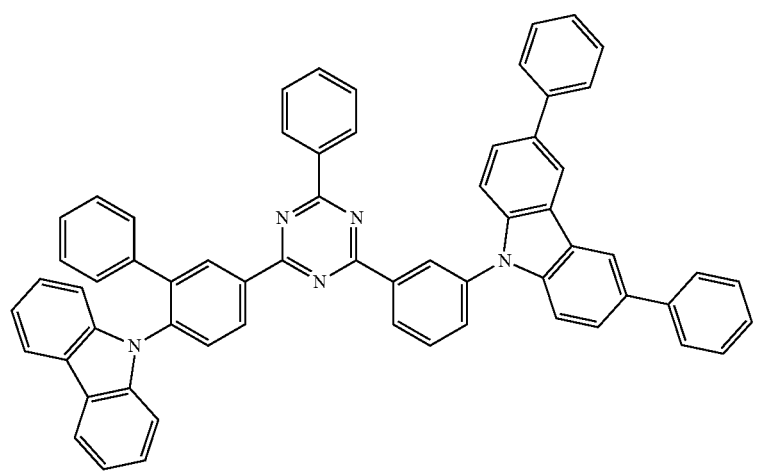
497
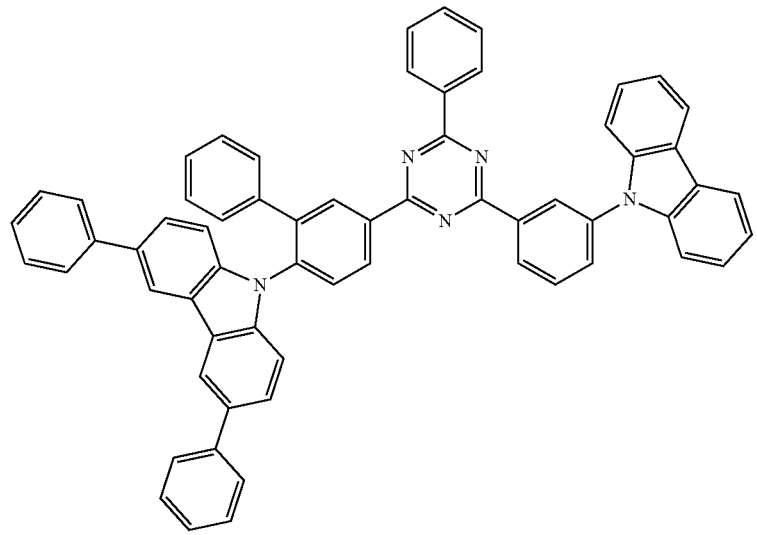
498

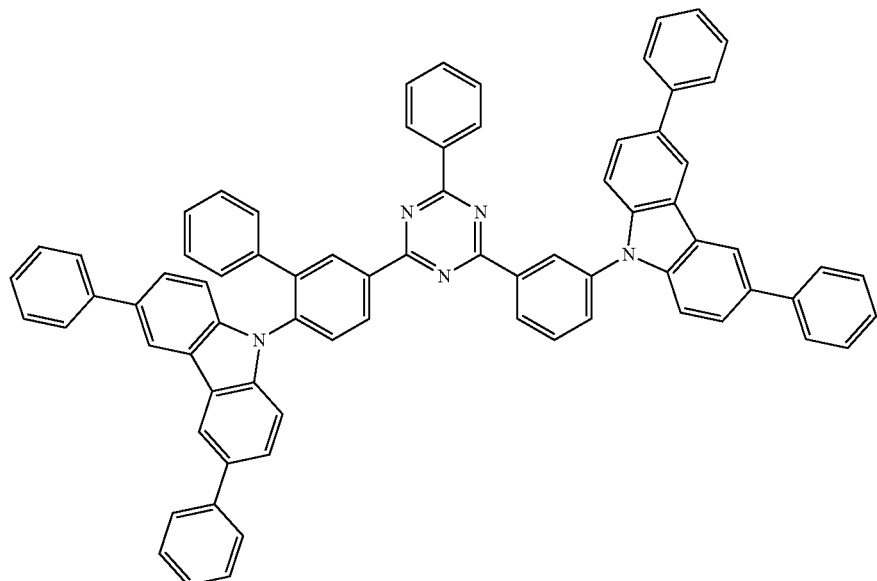
499
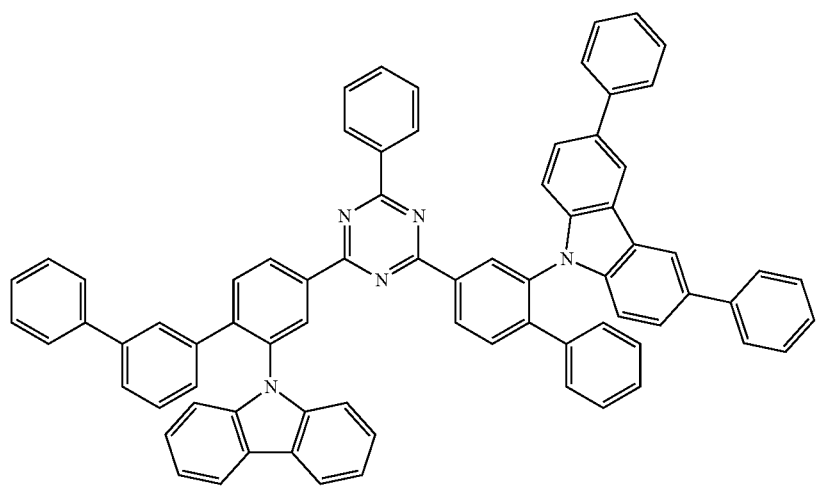
500
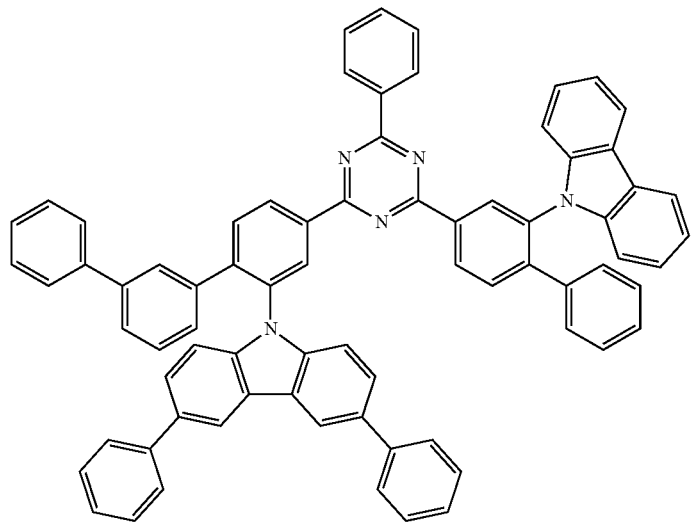
501

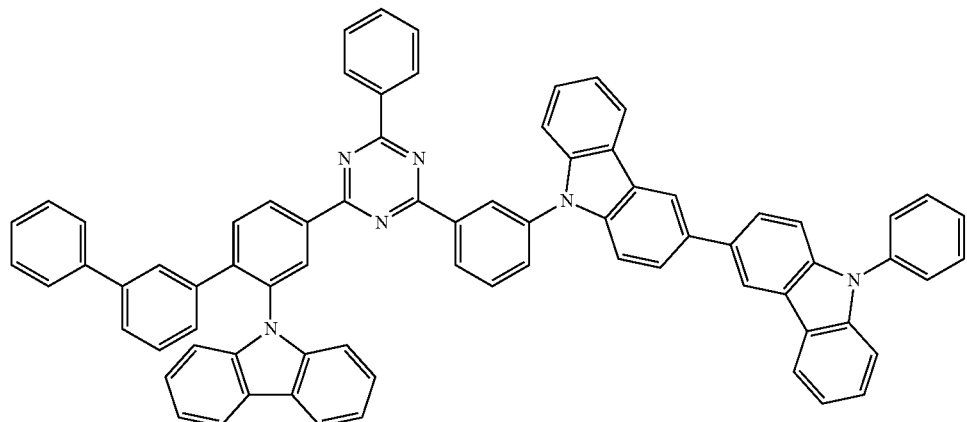
502
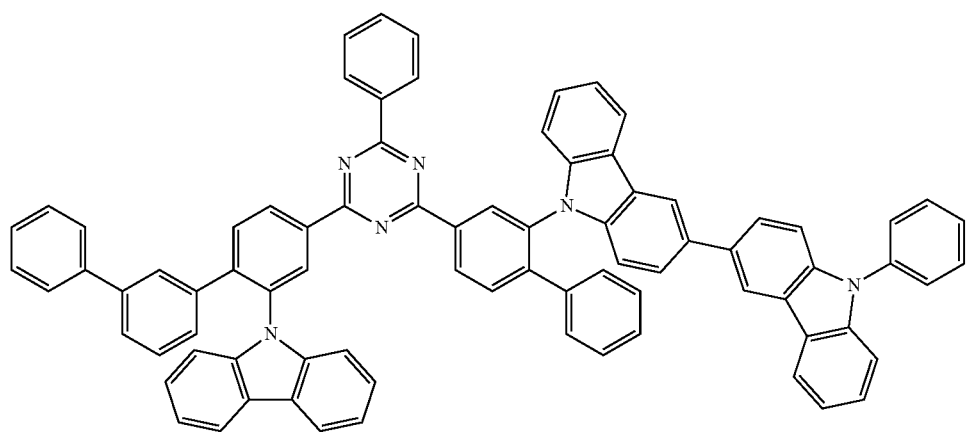
503
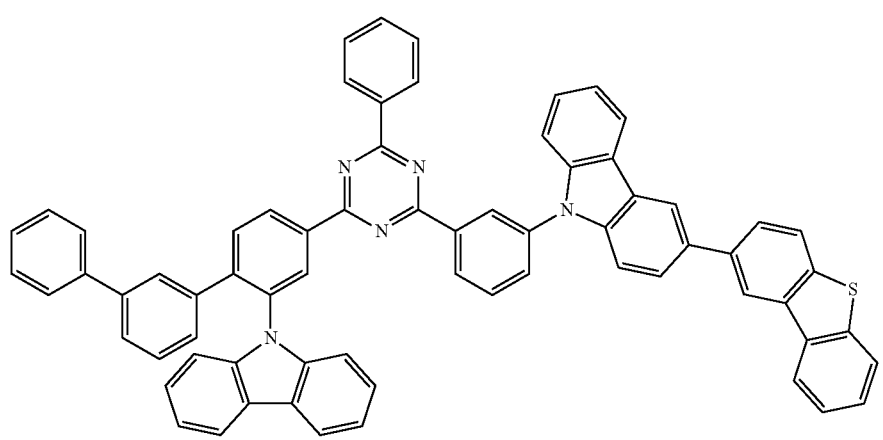
504

505
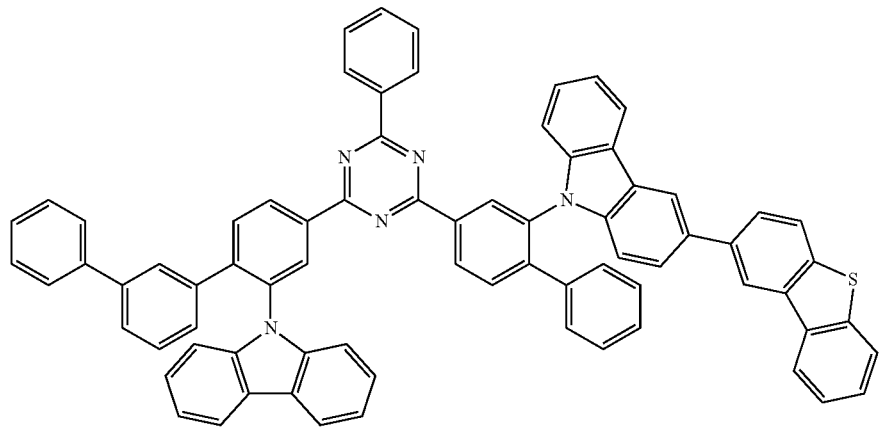
506
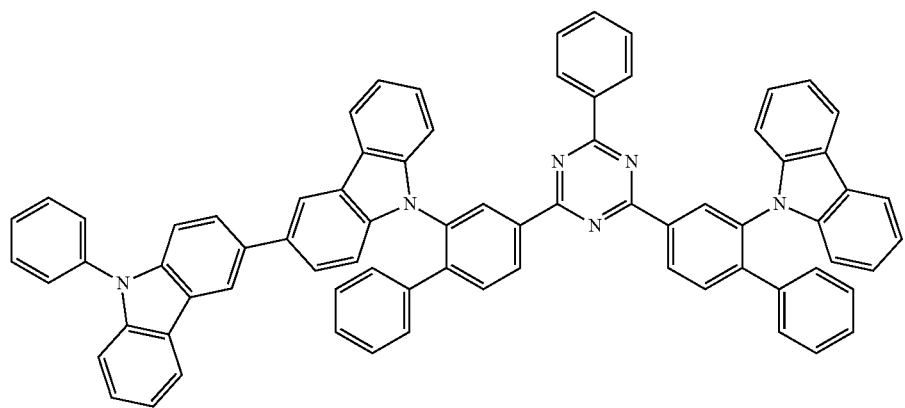
507
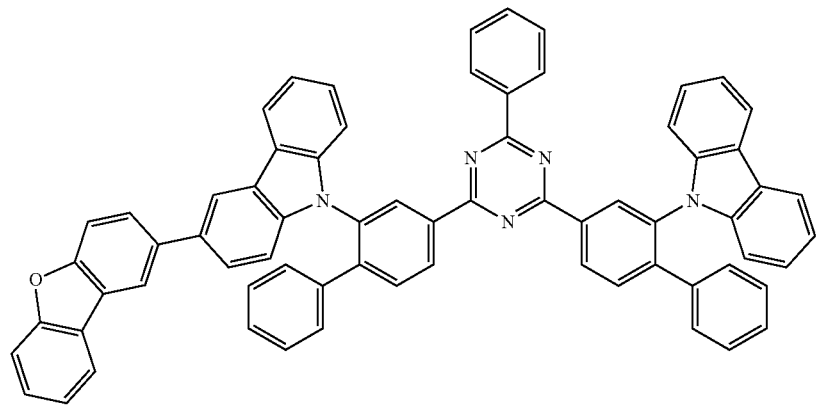

508

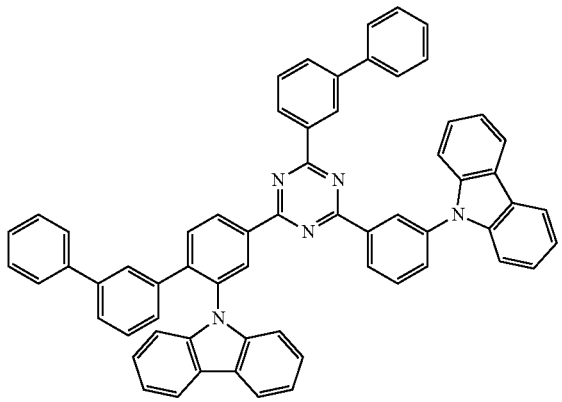

509

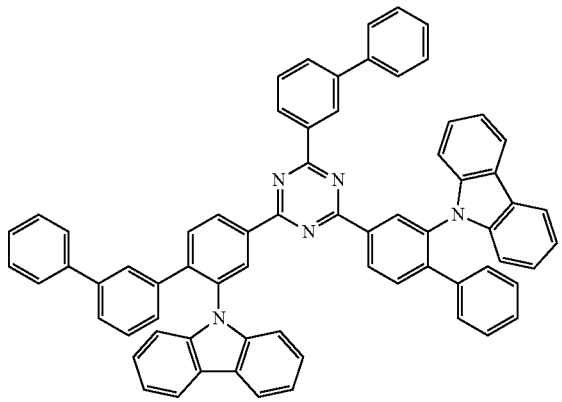

Since the heterocyclic compound represented by Formula 1 has high charge mobility and a high level of lowest exciton triplet energy, the heterocyclic compound represented by Formula 1 may have good electron transportability and excellent solubility in a solvent. When a layer is formed by a solution process with the heterocyclic compounds, the aggregation between the heterocyclic compounds is suppressed, thereby providing the layer having improved film-forming properties.

Therefore, even when the organic light-emitting device is manufactured by using solution coating, it is possible to maintain or improve the performance of the organic light-emitting device. Therefore, the organic light-emitting device may be manufactured without expensive vacuum deposition. In particular, it may be advantageous in manufacturing a large-area organic light-emitting device.

Since the heterocyclic compound represented by Formula 1 is substituted with two or more substituents having a large dihedral angle, as in Formulae 2-1 to 2-6, aggregation between molecules (homogeneous molecules or heterogeneous molecules) is suppressed to provide high solubility. A thin-film manufactured by a solution process also has thin-film characteristics (for example, charge mobility, density of state (DOS), or the like) similar to a deposited thin-film. The dihedral angle will be described below.

In addition, in the heterocyclic compound represented by Formula 1, since two or more carbazole-based substituents are linked to different positions in a triazine core, it is possible to prevent intermolecular pi-stacking with respect to a LUMO plane of the triazine core, it is possible to prevent quenching due to an aggregation site, and it is possible to implement a device having high efficiency and a long lifespan.

In addition, in the heterocyclic compound represented by Formula 1, since one or more of the substituents linked to the triazine core is included through an aryl-based linker, the triazine core and the aryl-based linker form the same plane due to a pi conjugation effect. Therefore, extended LUMO is formed, and stability for electron injection of a compound according to the present disclosure may be improved.

In addition, since the heterocyclic compound represented by Formula 1 is linked to the number 4 position of the substituent represented by Formula 2-1, the heterocyclic compound is twisted by steric repulsion caused by a hydrogen atom included in the number 5 position of the substituent, and thus has a large dihedral angle, and the substituent represented by Formula 2-1 functions as a substituent which suppresses pi-stacking with respect to the triazine core. Therefore, it is possible to implement a device which suppresses quenching caused by an aggregation site and has high efficiency and a long lifespan.

In addition, the heterocyclic compound represented by Formula 1 includes a carbazole-based substituent may have a large dihedral angle, as compared with a case where a dibenzofuranyl substituent is included, thereby obtaining a more excellent aggregation suppression effect between molecules.

In addition, in the heterocyclic compound represented by Formula 1, a carbazolyl group is not included in $Y_{11}$ to $Y_{14}$ or $Y_{21}$ to $Y_{24}$ in groups represented by Formulae 2-2 and 2-3, three carbazole moieties or fewer are included in the compound. Therefore, since hole transport capability is low and electron transport capability is high, the heterocyclic compound represented by Formula 1 may function as a material for forming an electron transporting host.

The heterocyclic compound represented by Formula 1 may be included in a pair of electrodes of an organic light-emitting device. For example, the heterocyclic compound represented by Formula 1 may be included in an emission layer, and may be suitable as a host.

The heterocyclic compound represented by Formula 1 may be synthesized by using a known organic synthesis method. A specific method of synthesizing the heterocyclic compound represented by Formula 1 can be understood by those of ordinary skill in the art by referring to Examples provided below.

Composition

Hereinafter, a composition according to an embodiment will be described in detail.

The composition may include at least one of the heterocyclic compound described above.

The heterocyclic compound has the deepest lowest unoccupied molecular orbital (LUMO) level among the compounds included in the composition. Therefore, the heterocyclic compound has high electron injection capability and/or electron transport capability.

Therefore, the electron injection capability and/or electron transport capability of the composition may be adjusted by adjusting the ratio that the heterocyclic compound occupies within the composition. Hence, it is possible to easily control the electron density profile according to the amount of the host and the thickness direction of the emission layer in the organic light-emitting device including the composition.

For example, the composition may further include a first compound represented by Formula 5:

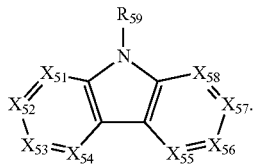

Formula 5

In Formula 5, $X_{51}$ may be N or $C(R_{51})$; $X_{52}$ may be N or $C(R_{52})$; $X_{53}$ may be N or $C(R_{53})$; $X_{54}$ may be N or $C(R_{54})$; $X_{55}$ may be N or $C(R_{55})$; $X_{56}$ may be N or $C(R_{56})$; $X_{57}$ may be N or $C(R_{57})$; and $X_{58}$ may be N or $C(R_{58})$, $R^{51}$ to $R^{58}$ may each independently be selected from hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and $R_{59}$ may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 5, two neighboring groups selected from $R_{51}$ to $R_{58}$ may optionally be linked to form a ring, but embodiments of the present disclosure are not limited thereto.

The first compound has the shallowest HOMO level, except for the light-emitting material (dopant) among the compounds included in the composition. Therefore, the first compound has high hole injection capability and/or hole transport capability.

Therefore, the hole injection capability and/or hole transport capability of the composition may be adjusted by adjusting the ratio that the first compound occupies within the composition. Hence, it is possible to easily control the hole density profile according to the amount of the host and the thickness direction of the emission layer in the organic light-emitting device including the composition.

While not wishing to be bound by theory, it is understood that when the composition includes the heterocyclic compound and the first compound, the composition may have excellent hole injection capability, hole transport capability, electron injection capability, and/or electron transport capability, and the composition may be used for the hole injection layer, the hole transport layer, the emission layer, the electron transport layer, and/or the electron injection layer of the organic light-emitting device. Accordingly, the control for holes and the control for electrons may be each independently performed. Therefore, work convenience may be increased in the process of optimizing the performance of the organic light-emitting device including the composition.

The composition may further include a light-emitting material.

The light-emitting material is not particularly limited as long as the light-emitting material has a light-emitting function. The light-emitting material may be a fluorescent dopant, a phosphorescent dopant, a quantum dot, or the like.

The fluorescent dopant is a compound capable of emitting light from singlet exciton. For example, the fluorescent dopant may be perylene and a derivative thereof, a rubrene and a derivative thereof, a coumarin and a derivative thereof, or a 4-dicyanomethylene-2-(p-dimethylaminostyryl)-6-methyl-4H-pyran (DCM) and a derivative thereof, but embodiments of the present disclosure are not limited thereto.

The phosphorescent dopant is a compound capable of emitting light from triplet exciton, and may be an organometallic compound. For example, the phosphorescent dopant may be an iridium complex, such as bis[2-(4,6-difluorophenyl)pyridinate]picolinate iridium(III) (FIrpic), bis(1-phenylisoquinoline)(acetylacetonate) iridium(II) $(Ir(piq)_2(acac))$, tris(2-phenylpyridine) iridium(III) $(Ir(ppy)_3)$, or tris (2-(3-p-xylyl)phenyl)pyridine iridium(III) (dopant), an osmium complex, a platinum complex, or the like, but embodiments of the present disclosure are not limited thereto.

The quantum dot may be a nanoparticle including group II-VI semiconductor, group III-V semiconductor, or group IV-IV semiconductor. For example, the quantum dot may be CdO, CdS, CdSe, CdTe, ZnO, ZnS, ZnSe, ZnTe, HgS, HgSe, HgTe, MgSe, MgS CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, GaN, GaP, GaAs, AlN, AlP, AlAs, InN, InP, InAs, InSb, GaNP, GaNAs, GaNSb, GaPAs, GaPSb, AlNP, AlNAs, AlNSb, AlPAs, AlPSb, InNP, InNAs, InPAs, InPSb, GaAlNP, SnS, SnSe, SnTe, PbS, PbSe, PbTe, SnSeS, SnSeTe, SnSTe, PbSeS, PbSeTe, PbSTe, SnPbS, SnPbSe, SnPbTe, or the like, but embodiments of the present disclosure are not limited thereto. In addition, the diameter of the quantum dot is not particularly limited, but may be in a range of about 1 nanometer (nm) to about 20 nm. The quantum dot may be a single core structure, or may be a core-shell structure.

The composition may further include a solvent.

The solvent is not particularly limited as long as the heterocyclic compound represented by Formula 1 and/or the first compound represented by Formula 5 is dissolved therein. For example, the solvent may be toluene, xylene, ethylbenzene, diethylbenzene, mesitylene, propylbenzene, cyclohexylbenzene, dimethoxybenzene, anisole, ethoxytoluene, phenoxytoluene, iso-propylbiphenyl, dimethylanisole, phenyl acetate, phenyl propionic acid, methyl benzoate, ethyl benzoate, or the like, but embodiments of the present disclosure are not limited thereto.

The concentration of the composition is not particularly limited, and may be appropriately controlled according to the purpose thereof.

The concentration of the heterocyclic compound represented by Formula 1 in the composition may be in a range of about 0.1 percent by weight (weight %) to about 10 weight %, for example, about 0.5 weight % to about 5 weight %, but embodiments of the present disclosure are not limited thereto. While not wishing to be bound by theory, it is understood that when the concentration of the heterocyclic compound represented by Formula 1 in the composition is within this range, coatability may be improved.

In an embodiment, in the case of the composition including the heterocyclic compound represented by Formula 1 and the first compound represented by Formula 5, the concentration of the heterocyclic compound may be in a range of about 0.1 weight % to about 10 weight %, for example, about 0.5 weight % to about 5 weight %, and the concentration of the first compound may be in a range of about 0.1 weight % to about 10 weight %, for example, about 0.5 weight % to about 5 weight %.

Therefore, the composition may be used as the material for the light-emitting device (for example, an organic light-emitting device, a quantum dot light-emitting device, or the like). For example, the composition may be used for the emission layer, the charge injection layer, and/or the charge transport layer of the light-emitting diode. For example, the composition may be used for the emission layer of the light-emitting device. In particular, the composition may be used to manufacture the light-emitting device by using solution process. At this time, the current efficiency and light-emitting lifespan of the light-emitting device may be maintained or improved.

Organic Light-Emitting Device

Hereinafter, an organic light-emitting device according to an embodiment will be described in detail with reference to the FIGURE. The FIGURE is a schematic view of an organic light-emitting device according to an embodiment.

An organic light-emitting device 100 according to an embodiment may include a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

The heterocyclic compound represented by Formula 1 may be included in, for example, an organic layer disposed between the first electrode 120 and the second electrode 180 (for example, the hole injection layer 130, the hole transport layer 140, the emission layer 150, the electron transport layer 160, or the electron injection layer 170). In an embodiment, the heterocyclic compound represented by Formula 1 may be included in the emission layer 150 as a host. Alternatively, the heterocyclic compound represented by Formula 1 may be included in another organic layer other than the emission layer 150. For example, the heterocyclic compound represented by Formula 1 may be included in the hole injection layer 130 and/or the hole transport layer 140 as a charge transport material.

The term "organic layer" as used herein refers to a single layer and/or a plurality of layers between the first electrode and the second electrode of the organic light-emitting device. The "organic layer" may include, in addition to an organic compound, an organometallic compound including metal.

The expression "(an organic layer) includes at least one organometallic compound" as used herein includes an embodiment in which "(an organic layer) includes identical heterocyclic compounds represented by Formula 1" and an embodiment in which "(an organic layer) includes two or more different heterocyclic compounds represented by Formula 1."

For example, the organic layer may include, as the heterocyclic compound, only Compound 1. In this embodiment, Compound 1 may be included in an emission layer of the organic light-emitting device. In one or more embodiments, the organic layer may include, as the heterocyclic compound, Compound 1 and Compound 2. In this embodiment, Compound 1 and Compound 2 may be included in an identical layer (for example, Compound 1 and Compound 2 may both be included in an emission layer).

The substrate 110 may be any substrate that is used in an organic light-emitting device according to the related art. The substrate 110 may be any substrate that is used in an organic light-emitting device according to the related art. For example, the substrate 110 may be a glass substrate, a silicon substrate, or a transparent plastic substrate, each having excellent mechanical strength, thermal stability, surface smoothness, ease of handling, and water resistance, but embodiments of the present disclosure are not limited thereto.

The first electrode 120 may be formed on the substrate 110. The first electrode 120 may be, for example, an anode, and may be formed of a material with a high work function to facilitate hole injection, such as an alloy or a conductive compound. The first electrode 120 may be a reflective electrode, a semi-transmissive electrode, or a transmissive electrode. The first electrode 120 may have a single-layered structure, or a multi-layered structure including two or more layers. For example, the first electrode 120 may be a transparent electrode formed of indium tin oxide (ITO), indium zinc oxide (IZO), tin oxide ($SnO_2$), or zinc oxide (ZnO), which has excellent transparency and conductivity. On the transparent first electrode 120, magnesium (Mg), aluminum (Al), aluminum-lithium (Al—Li), calcium (Ca), magnesium-indium (Mg—In), or magnesium-silver (Mg—Ag) may be disposed, so as to form a reflective electrode. In an embodiment, the first electrode 120 may have a three-layered structure of ITO/Ag/ITO, but embodiments of the present disclosure are not limited thereto.

The hole transport region may be disposed on the first electrode 120.

The hole transport region may include at least one selected from selected from a hole injection layer 130, a hole transport layer 140, an electron blocking layer (not shown), and a buffer layer (not shown).

The hole transport region may include only either a hole injection layer 130 or a hole transport layer 140. In an embodiment, the hole transport region may have a hole injection layer/hole transport layer structure or a hole injection layer/hole transport layer/electron blocking layer structure, wherein for each structure, constituting layers are sequentially stacked from the first electrode 120 in the stated order.

The hole injection layer 130 may include at least one selected from, for example, poly(ether ketone)-containing triphenylamine (TPAPEK), 4-iso-propyl-4'-methyldiphenyliodonium tetrakis(pentafluorophenyl) borate (PPBI), N,N'-diphenyl-N,N'-bis-[4-(phenyl-m-tolyl-amino)-phenyl]-biphenyl-4,4'-diamine (DNTPD), copper phthalocyanine, 4,4',4"-tris(3-methylphenylphenylamino) triphenylamine (m-MTDATA), N,N'-di(1-naphthyl)-N,N'-diphenylbenzidine (NPB), 4,4',4"-tris(diphenylamino) triphenylamine (TDATA), 4,4',4"-tris(N,N-2-naphthylphenylamino) triphenylamine (2-TNATA), polyanilineldodecylbenzene sulfonic acid (PANI/DBSA), poly(3,4-ethylenedioxythiophene)/poly(4-styrene sulfonate) (PEDOT/PSS), polyaniline/10-camphor sulfonic acid (PANI/CSA), and polyaniline/poly(4-styrene sulfonate) (PANI/PSS).

The hole injection layer 130 may have a thickness in a range of about 10 nm to about 1,000 nm, for example, about 10 nm to about 100 nm.

The hole transport layer 140 may include at least one selected from selected from, for example, a carbazole derivative, such as 1,1-bis[(di-4-tolylamino)phenyl]cyclohexane (TAPC), N-phenylcarbazole, and polyvinylcarbazole, N,N'-bis(3-methylphenyl)-N,N'-diphenyl-[1,1-biphenyl]-4,4'-diamine (TPD), 4,4',4"-tris(N-carbazolyl) triphenylamine (TCTA), N,N'-di(1-naphthyl)-N,N'-diphenylbenzidine (NPB), poly(9,9-dioctyl-fluorene-co-N-(4-butylphenyl)-diphenylamine (TFB), and amine-based polymer.

The hole transport layer 140 may have a thickness in a range of about 10 nm to about 1,000 nm, for example, about 10 nm to about 150 nm.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but embodiments of the present disclosure are not limited thereto. For example, non-limiting examples of the p-dopant are a quinone derivative, such as tetracyanoquinonedimethane (TCNQ) and 2,3,5,6-tetrafluoro-tetracyano-1,4-benzoquinonedimethane (F4-TCNQ), or the like; a metal oxide, such as a tungsten oxide and a molybdenum oxide; and a cyano group-containing compound, such as Compounds HT-D1 and HT-D2, but are not limited thereto.

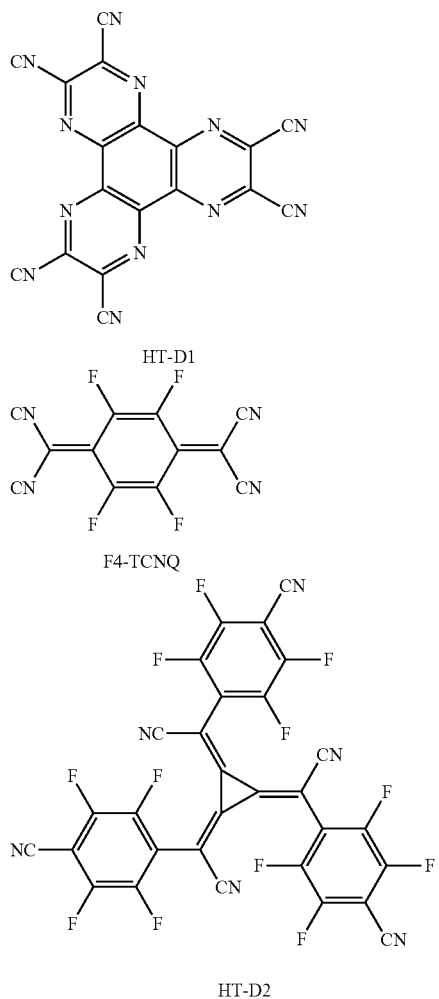

Meanwhile, when the hole transport region includes a buffer layer, a material for the buffer layer may be selected from materials for the hole transport region described above and materials for a host to be explained later, but embodiments of the present disclosure are not limited thereto.

In addition, when the hole transport region includes an electron blocking layer, a material for the electron blocking layer may be selected from materials for the hole transport region described above and materials for a host to be explained later, but embodiments of the present disclosure are not limited thereto. For example, when the hole transport region includes an electron blocking layer, a material for the electron blocking layer may be mCP.

The emission layer 150 may be formed on the hole transport region. The emission layer 150 is a layer that emits light by fluorescence or phosphorescence. The emission layer 150 may include a host and/or a dopant, and when included, the host may include the heterocyclic compound represented by Formula 1. In addition, the host and/or the dopant included in the emission layer 150 may be known materials.

For example, the host may include tris(8-quinolinato)aluminum ($Alq_3$), 4,4'-bis(carbazol-9-yl)biphenyl (CBP), poly(n-vinylcarbazole) (PVK), 9,10-di(naphthalene)anthracene (ADN), 4,4',4''-tris(N-carbazolyl)triphenylamine (TCTA), 1,3,5-tris(N-phenyl-benzimidazol-2-yl)benzene (TPBi), 3-tert-butyl-9,10-di(naphth-2-yl)anthracene (TBADN), distyrylarylene (DSA), and 4,4'-bis(9-carbazole)-2,2'-dimethyl-bipheny (dmCBP), but embodiments of the present disclosure are not limited thereto.

In an embodiment, the host may include a first compound represented by Formula 5, but embodiments of the present disclosure are not limited thereto:

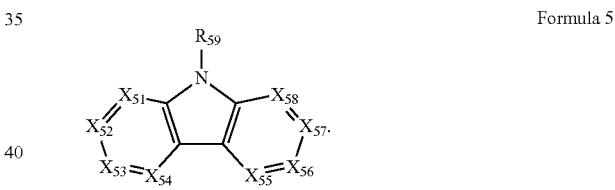

Formula 5

In Formula 5, $X_{51}$ may be N or $C(R_{51})$; $X_{52}$ may be N or $C(R_{52})$; $X_{53}$ may be N or $C(R_{53})$; $X_{54}$ may be N or $C(R_{54})$; $X_{55}$ may be N or $C(R_{56})$; $X_{56}$ may be N or $C(R_{56})$; $X_{57}$ may be N or $C(R_{57})$; and $X_{56}$ may be N or $C(R_{58})$, $R_{51}$ to $R_{58}$ may each independently be selected from hydrogen, deuterium, a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group, and $R_{59}$ may be selected from a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group.

In an embodiment, the first compound may be Compound H1, but embodiments of the present disclosure are not limited thereto:

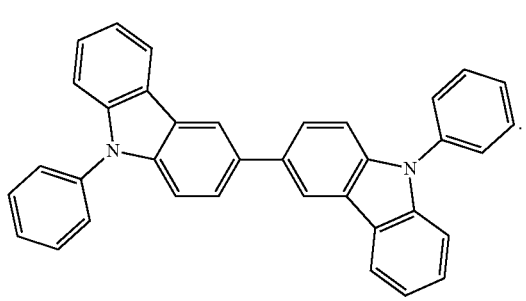

H-1

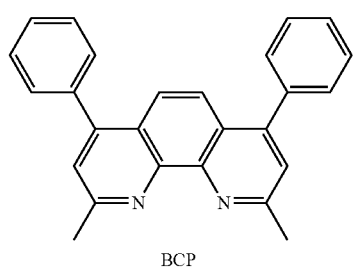

BCP

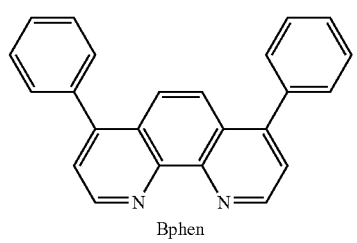

Bphen

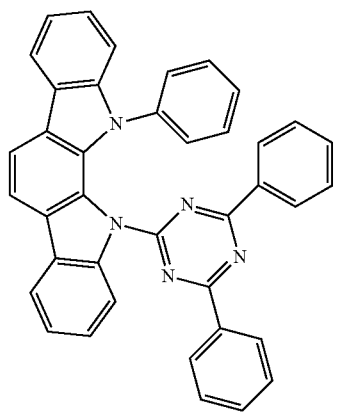

HB1

For example, the dopant may be a perylene and a derivative thereof, a rubrene and a derivative thereof, a coumarin and a derivative thereof, DCM and a derivative thereof, Flrpic, $Ir(piq)_2(acac)$, $Ir(ppy)_3$, tris(2-(3-p-xylyl)phenyl) pyridine iridium (III) (dopant) an osmium complex, a platinum complex, or the like, but embodiments of the present disclosure are not limited thereto.

When the emission layer includes a host and a dopant, an amount of the dopant may be about 0.01 parts by weight to about 15 parts by weight based on 100 parts by weight of the host material, but embodiments of the present disclosure are not limited thereto.

The emission layer 150 may have a thickness in a range of about 10 nm to about 60 nm.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The hole transport region may be disposed on the emission layer 150.

The electron transport region may include at least one selected from a hole blocking layer (not shown), an electron transport layer 160, and an electron injection layer 170.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

For example, the organic light-emitting device 100 may include, to prevent the excitons or holes from diffusing into the electron transport layer 160, a hole blocking layer disposed between the electron transport layer 160 and the emission layer 150. The hole blocking layer may include, for example, at least one selected from an oxadiazole derivative, a triazole derivative, BCP, BPhen, BAlq, and HB1, but embodiments of the present disclosure are not limited thereto.

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer 160 may include a tris (8~quinolinato) aluminum ($Alq_3$), BAlq, a compound including a pyridine ring, such as 1,3,5-tri[(3-pyridyl)-phen-3-yl]benzene, a compound including a triazine ring, such as 2,4,6-tris(3'-(pyridin-3-yl)biphenyl-3-yl)-1,3,5-triazine, a compound including an imidazole ring, such as 2-(4-(N-phenylbenzimnidazolyl-1-yl-phenyl)-9,10-dinaphthylanthracene, a compound including a triazole ring, such as TAZ and NTAZ, 1,3,5-tris(N-phenyl-benzimidazol-2-yl)benzene (TPBi), BCP, or BPhen:

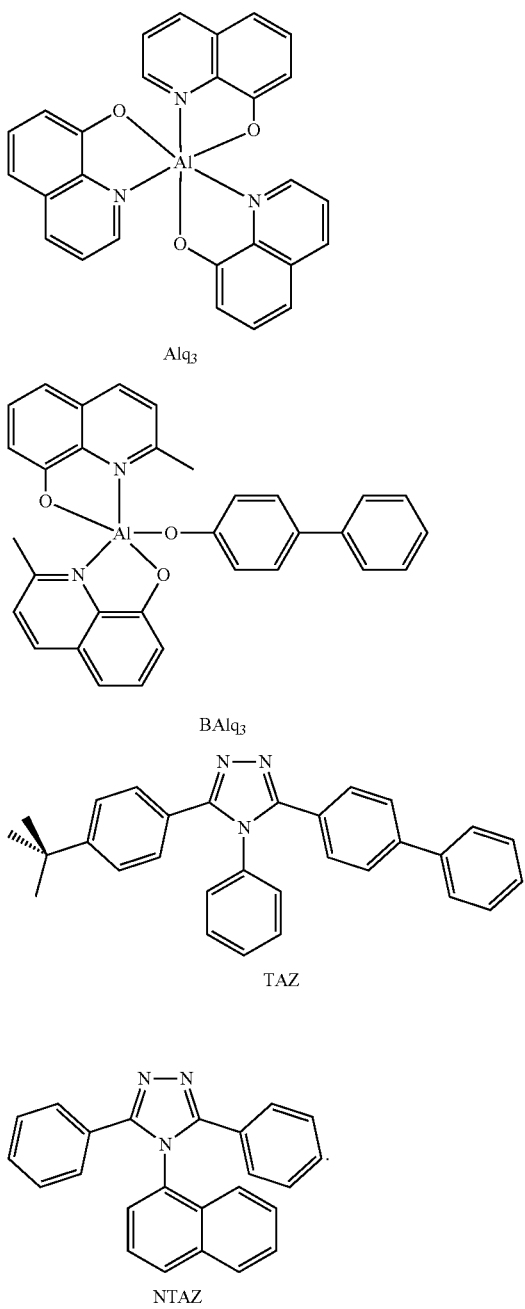

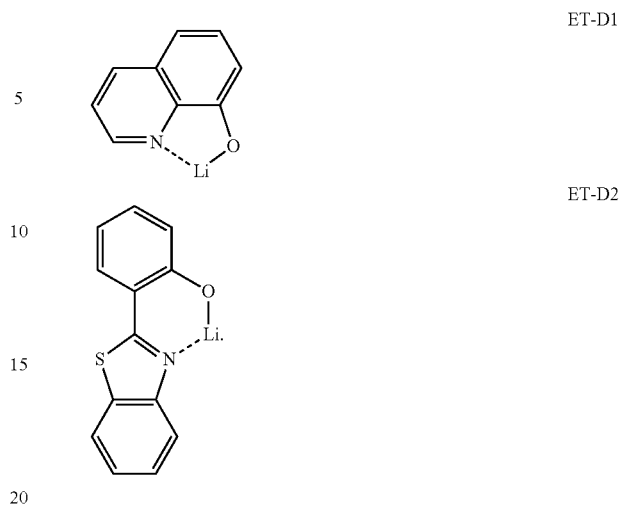

In one or more embodiments, the electron transport layer 160 may include a commercial product, such as KLET-01, KLET-02, KLET-03, KLET-10, or KLET-M1 (these products are available from Chemipro Kasei).

Also, the electron transport layer 160 may further include, in addition to the materials described above, a metal-containing material.

The metal-containing material may include a Li complex. The Li complex may include, for example, Compound ET-D1 (lithium 8-hydroxyquinolate, LiQ) or ET-D2:

The electron transport layer 160 may be formed to a thickness, for example, in a range of about 15 nm to about 50 nm.

The electron injection layer 170 may be formed on the electron transport layer 160.

The electron injection layer 170 may include, for example, an lithium compound, such as (8-hydroxyquinolinato)lithium (LiQ) and lithium fluoride (LiF), sodium chloride (NaCl), cesium fluoride (CsF), lithium oxide ($Li_2O$), or barium oxide (BaO).

The electron injection layer 170 may be formed to a thickness in a range of about 0.3 nm to about 9 nm.

The first electrode 180 may be formed on the substrate 170. The second electrode 180 may be formed on the electron injection layer 170. The second electrode 180 may be a cathode and may be formed by using a material having a low work function among a metal, an alloy, an electrically conductive compound, and any combination thereof. For example, the second electrode 180 may be formed as a reflective electrode by using a metal such as lithium (Li), magnesium (Mg), aluminum (Al), and calcium (Ca), or an alloy such as aluminum-lithium (Al—Li), magnesium-indium (Mg—In), and magnesium-silver (Mg—Ag). Alternatively, the second electrode 180 may be formed as a transparent electrode by using the metal or the alloy thin-film having a thickness of 20 nm or less, or a transparent conductive film such as indium tin oxide ($In_2O_3$—$SnO_2$) and indium zinc oxide ($In_2O_3$—ZnO).

In addition, the stacked structure of the organic light-emitting device 100 according to the embodiment is not limited to the above-described stacked structure. The organic light-emitting device 100 according to the embodiment may be formed in other known stacked structures. For example, in the organic light-emitting device 100, at least one selected from the hole injection layer 130, the hole transport layer 140, the electron transport layer 160, and the electron injection layer 170 may be omitted. The organic light-emitting device 100 may further include another layer. In addition, each layer of the organic light-emitting device 100 may be a single layer or a multi-layer.

A method of manufacturing each layer of the organic light-emitting device 100 according to the embodiment is not particularly limited. For example, each layer of the organic light-emitting device 100 according to the embodiment may be manufactured by using various methods, such as vacuum deposition, solution process, and Langmuir-Blodgett (LB) deposition.

The solution process may include spin coating, casting, micro gravure coating, gravure coating, bar coating, roll coating, wire bar coating, dip coating, spry coating, screen printing, flexographic printing, offset printing, and ink-jet printing.

Examples of the solvent used in the solution process may include toluene, xylene, diethyl ether, chloroform, ethyl acetate, dichloromethane, tetrahydrofuran, acetone, acetonitrile, N,N-dimethylformamide, dimethylsulfoxide, anisole, hexamethylphosphoric acid triamide, 1,2-dichloroethane, 1,1,2-trichloroethane, chlorobenzene, o-dichlorobenzene, dioxane, cyclohexane, n-pentane, n-hexane, n-heptane, n-octane, n-nonane, n-decane, methyl ethyl ketone, cyclohexanone, butyl acetate, ethyl cellosolve acetate, ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, 1,2-hexanediol, methanol, ethanol, propanol, iso-propanol, cyclohexanal, and N-methyl-2-pyrrolidone, but the solvent is not limited as long as the solvent can dissolve the material used to form each layer.

Considering the coatability, the concentration of the composition used in the solution process may be in a range from about 0.1 weight % to about 10 weight %, for example, in a range from about 0.5 weight % to about 5 weight %, but embodiments of the present disclosure are not limited thereto.

The compound used in the vacuum deposition may be different according to the structure and thermal characteristics of the target layer, but may be selected from, for example, a deposition temperature of about 100° C. to about 500° C., a vacuum degree of about $10^{-8}$ torr to about $10^{-3}$ torr, a deposition rate of about 0.01 Angstroms per second (Å/sec) to about 100 Å/sec.

In an embodiment, the first electrode 120 may be an anode, and the second electrode 180 may be a cathode.

For example, the first electrode 120 may be an anode; the second electrode 180 may be a cathode; the organic layer may include the emission layer 150 between the first electrode 120 and the second electrode 180; the organic layer may further include a hole transport region disposed between the first electrode 120 and the emission layer 150 and an electron transport region disposed between the emission layer 150 and the second electrode 180; the hole transport region may include at least one selected from a hole injection layer 130, a hole transport layer 140, a buffer layer, and an electron blocking layer; and the electron transport region may include at least one selected from a hole blocking layer, an electron transport layer 160, and an electron injection layer 170.

In one or more embodiments, the first electrode 120 may be a cathode, and the second electrode 180 may be an anode.

Hereinbefore, the organic light-emitting device has been described with reference to the FIGURE, but embodiments of the present disclosure are not limited thereto.

Description of Substituents

The expression "X and Y may each independently be" as used herein refers to a case where X and Y may be identical to each other, or a case where X and Y may be different from each other.

The term "substituted" as used herein refers to a case where hydrogen of a substituent such as $R_1$ may be further substituted with other substituents.

The term "$C_1$-$C_{24}$ alkyl group" as used herein refers to a linear or branched aliphatic saturated hydrocarbon monovalent group having 1 to 24 carbon atoms, and examples thereof include a methyl group, an ethyl group, an n-propyl group, an iso-propyl group, an n-butyl group, an iso-butyl group, a sec-butyl group, a tert-butyl group, an n-pentyl group, an iso-pentyl group, a tert-pentyl group, a neopentyl group, a 1,2-dimethylpropyl group, an n-hexyl group, an iso-hexyl group, a 1,3-dimethylbutyl group, a 1-iso-propylpropyl group, a 1,2-dimethylbutyl group, an n-heptyl group, a 1,4-dimethylpentyl group, 3-ethylpentyl group, a 2-methyl-1-iso-propylpropyl group, a 1-ethyl-3-methylbutyl group, an n-octyl group, a 2-ethylhexyl group, a 3-methyl-1-iso-propylbutyl group, a 2-methyl-1-iso-propyl group, a 1-tert-butyl-2-methylpropyl group, an n-nonyl group, a 3,5,5-trimethyldecyl group, an n-decyl group, an iso-decyl group, an n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, and an n-tetracosyl group.

The term "$C_1$-$C_{24}$ alkylene group" as used herein refers to a divalent group having the same structure as the $C_1$-$C_{24}$ alkyl group.

The term "$C_1$-$C_{24}$ alkoxy group" as used herein refers to a monovalent group represented by —$OA_{101}$ (wherein $A_{101}$ is the $C_1$-$C_{24}$ alkyl group), and examples thereof include a methoxy group, an ethoxy group, a propoxy group, an iso-propoxy group, an n-butoxy group, an iso-butoxy group, a sec-butoxy group, a tert-butoxy group, an n-pentoxy group, an iso-pentoxy group, a tert-pentoxy group, a neopentoxy group, an n-hexyloxy group, an iso-hexyloxy group, a heptyloxy group, an octyloxy group, a nonyloxy group, a decyloxy group, an undeoxy group, a dodecyloxy group, a tridecyloxy group, a tetradecyloxy group, a pentadecyloxy group, a hexadecyloxy group, a heptadecyloxy group, an octadecyloxy group, a 2-ethylhexyloxy group, and a 3-ethylpentyloxy group.

The term "$C_1$-$C_{24}$ alkylthio group" as used herein refers to a monovalent group represented by —$SA_{102}$ (wherein $A_{102}$ is the $C_1$-$C_{24}$ alkyl group).

The term "$C_3$-$C_{30}$ cycloalkyl group" as used herein refers to a monovalent saturated hydrocarbon monocyclic group having 3 to 30 carbon atoms involved in the ring formation, and examples thereof include a cyclopropyl group, a cyclobutyl group, a cyclopentyl group, a cyclohexyl group, and a cycloheptyl group. The term "$C_3$-$C_{30}$ cycloalkylene group" as used herein refers to a divalent group having the same structure as the $C_3$-$C_{30}$ cycloalkyl group.

The term "$C_5$-$C_{30}$ aryl group" as used herein refers to a monovalent group having a carbocyclic aromatic system having 6 to 30 carbon atoms involved in the ring formation (that is, when substituted with a substituent, the atom not included in the substituent is not counted as the carbon involved in the ring formation), and the term "$C_6$-$C_{30}$ arylene group" as used herein refers to a divalent group having a carbocyclic aromatic system having 6 to 30 carbon atoms. Non-limiting examples of the $C_6$-$C_{30}$ aryl group include a phenyl group, a naphthyl group, an anthracenyl group, a phenanthrenyl group, a pyrenyl group, and a chrysenyl group. When the $C_6$-$C_{30}$ aryl group and the $C_6$-$C_{30}$ arylene group each include two or more rings, the rings may be fused to each other.

The term "$C_6$-$C_{30}$ aryloxy group" as used herein refers to a group represented by —$OA_{103}$ (wherein $A_{103}$ is the $C_6$-$C_{30}$ aryl group). Examples thereof include a 1-naphthyloxy group, a 2-naphthyloxy group, and a 2-azulenyloxy group.

The term "$C_6$-$C_{30}$ arylthio group" as used herein refers to a group represented by —$SA_{104}$ (wherein $A_{104}$ is the $C_6$-$C_{30}$ aryl group).

The term "$C_1$-$C_{30}$ heteroaryl group" as used herein refers to a monovalent group having a heterocyclic aromatic system that has at least one heteroatom selected from N, O, Si, P, and S as a ring-forming atom, and 1 to 30 carbon atoms. The term "$C_1$-$C_{30}$ heteroarylene group" as used herein refers to a divalent group having a heterocyclic aromatic system that has at least one heteroatom selected from N, O, Si, P, and S as a ring-forming atom, and 1 to 30 carbon atoms. Non-limiting examples of the $C_1$-$C_{30}$ heteroaryl group include a pyridinyl group, a pyrimidinyl group, a pyrazinyl group, a pyridazinyl group, a triazinyl group, a quinolinyl group, and an isoquinolinyl group. When the $C_5$-$C_{50}$ heteroaryl group and the $C_5$-$C_{30}$ heteroarylene group each include two or more rings, the two or more rings may be fused to each other.

The term "$C_6$-$C_{30}$ heteroaryloxy group" as used herein refers to a group represented by —$SA_{102}$ (wherein $A_{102}$ is the $C_6$-$C_{30}$ heteroaryl group). Examples thereof include a 2-furanyloxy group, a 2-thienyloxy group, a 2-indolyloxy group, a 3-indolyloxy group, a 2-benzofuryloxy group, and a 2-benzothienyloxy group.

The term "$C_6$-$C_{30}$ heteroarylthio group" as used herein refers to a group represented by —$SA_{106}$ (wherein $A_{106}$ is the $C_1$-$C_{30}$ heteroaryl group).

The term "$C_7$-$C_{30}$ arylalkyl group" as used herein refers to an aryl group substituted with an alkyl group, and is a monovalent group in which the sum of carbon atoms in the alkyl group and the aryl group that constitute the $C_7$-$C_{30}$ arylalkyl group is in a range of 7 to 30. Examples of the $C_7$-$C_{30}$ aryl alkyl group include a benzyl group, a phenylethyl group, a phenylpropyl group, and a naphthylmethyl group.

The term "$C_5$-$C_{30}$ arylthio group" as used herein refers to a group represented by -$QA_{105}$ (wherein $A_{105}$ is the $C_7$-$C_{30}$ arylalkyl group).

The term "$C_6$-$C_{30}$ arylalkylthio group" as used herein refers to a group represented by —$SA_{106}$ (wherein $A_{106}$ is the $C_7$-$C_{30}$ arylalkyl group).

The term "$C_6$-$C_{30}$ arylalkenyl group" as used herein refers to an aryl group substituted with an alkenyl group, and is a monovalent group in which the sum of carbon atoms in the alkenyl group and the aryl group that constitute the $C_8$-$C_{30}$ arylalkenyl group is in a range of 8 to 30.

The term "$C_8$-$C_{30}$ arylalkynyl group" as used herein refers to an aryl group substituted with an alkynyl group, and is a monovalent group in which the sum of carbon atoms in the alkynyl group and the aryl group that constitute the $C_8$-$C_{30}$ arylalkynyl group is in a range of 8 to 30.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The term "$C_5$-$C_{30}$ carbocyclic group" as used herein refers to a monocyclic group or a polycyclic group, and, according to its chemical structure, a monovalent, divalent, trivalent, tetravalent, pentavalent, or hexavalent group.

The term "$C_1$-$C_{30}$ heterocyclic group" as used herein refers to a saturated or unsaturated cyclic group having, as a ring-forming atom, at least one heteroatom selected from N, O, Si, P, and S other than 1 to 30 carbon atoms. The term "$C_1$-$C_{30}$ heterocyclic group" as used herein refers to a monocyclic group or a polycyclic group, and, according to its chemical structure, a monovalent, divalent, trivalent, tetravalent, pentavalent, or hexavalent group.

At least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —CD2H, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —Si$(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{10}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_5$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{37})$, —$B(Q_{36})(Q_{37})$, and —$P(=O)(Q_{38})(Q_{39})$, and Q1 to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

Others

The expression "A to B" as used herein refers to a range from A to B, including A and B.

While the embodiments of the present disclosure have been described with reference to the accompanying drawings, it is understood that the present disclosure is not limited to these embodiments. It is apparent to those of ordinary skill in the art that various modifications or changes may be made thereto without departing from the spirit and scope of the appended claims. It is understood that various modifications or changes fall within the technical scope of the present disclosure.

Hereinafter, a heterocyclic compound represented by Formula 1 and an organic light-emitting device including the same will be described in detail with reference to Examples and Comparative Examples. Examples provided below are merely an example, and the heterocyclic compound and the organic light-emitting device, according to embodiments, are not limited to Examples provided below.

The wording "'B' was used instead of 'A'" used in describing Synthesis Examples means that a molar equivalent of 'A' was identical to a molar equivalent of 'B'.

In addition, "%" is weight % unless specified otherwise.

Analysis of Dihedral Angle

Hereinafter, a dihedral angle of the compound represented by Formula 1 was analyzed. First, referring to Formula 100, a single bond is represented by A-B, and a lower structure in which LUMO is distributed is linked to form a plane including "X-A-B", Meanwhile, a substituent forms a plane including "A-B—Y". An angle between the two planes (the plane including "X-A-B" and the plane including "A-B—Y") was defined as a dihedral angle. In an embodiment, an angle between a triazine ring plane and an $Ar_1$ plane in Formula 1 was defined as "dihedral angle I", and an angle between a triazine ring and an $Ar_2$ plane was defined as "dihedral angle II". In addition, the actual compound was identified by a known method (for example, solid NMR analysis using compounds or the like in which an element of a dihedral angle region was labeled with an isotope).

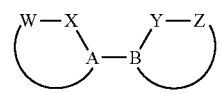

Formula 100

The dihedral angle was calculated by using quantum chemical calculation software (Gaussian 09, Revision D.01). In the first stage, a molecular structure was drawn by using molecule rendering software (Marvin sketch17.5.0, ChemAxon), conformation was calculated, and a conformation structure having an energy minimum value was used as an initial structure.

In the second stage, a dihedral angle was calculated in the initial structure obtained in the first stage by using quantum chemical calculation software (Gaussian 09, Revision D.01, Gaussian). In this case, the optimization of a molecular structure was performed so as to improve the accuracy of simulation for an actual molecular structure. A dihedral angle of each of W—X-A-B and A~B—Y—Z in Formula 100 was limitedly designated so as not to change in the initial structure, and the other regions were set to change. In this manner, the optimization of the molecular structure was performed by using B3LYP/6-31G* as a keyword.

In the third stage, B3LYP/6-31+G** was used as a keyword using the optimized molecular structure to calculate energy calculation (total energy value of the molecule, molecular orbital energy level, or the like) and the molecular orbital distribution. In the calculation result, a part corresponding to X-A-B—Y was selected with respect to a compound capable of knowing a LUMO distribution, and an absolute value of a dihedral angle on an included angle side. The dihedral angle of the optimized structure was represented by $DA_0$, and results thereof are shown in Table 1.

Calculation of Rotational Barrier Energy

Rotational barrier energy of the dihedral angle was calculated by using the optimized structure obtained in the second stage among the methods used in the analysis of dihedral angle. In the calculation of the rotational barrier energy, the dihedral angle of each of W—X-A-B and A-B—Y—Z in Formula 100 was limitedly designated so as not to change in the initial structure, and the other regions were set to change. The dihedral angle of a target portion was changed by 5° per step. At this time, the optimization of the molecular structure was performed so as to improve the accuracy of simulation for the actual molecular structure. B3LYP/6-31G* was used as a keyword for optimizing the molecular structure.

Then, energy calculation (total energy value of the molecule, molecular orbital energy level, or the like) using B3LYP/6-31+G** as a keyword was performed. This process was performed on the dihedral angel of 0° to 360°. When the dihedral angel was x axis and the total energy value of the molecule obtained at this time was y axis, the rotational barrier energy of the target dihedral angle was obtained. In this result, a minimum value of a dihedral angle capable of reaching thermal energy (298 Kelvins (K)=25 millielectron volts (meV)=2.5 kilojoules per mole, kJ/mol) at room temperature was obtained. The dihedral angle of this calculation is represented by $DA_Et$, and results thereof are shown in Table 1.

TABLE 1

| Compound | I | | II | | A | B | C |
|---|---|---|---|---|---|---|---|
| | $DA_0$ | $DA_{rt}$ | $DA_0$ | $DA_{rt}$ | $DA_0$ | $DA_0$ | $DA_0$ |
| Compound 1 | 67.8 | 52 | 47.1 | 32 | 3.2 | — | 5.4 |
| Compound 2 | 70.9 | 52 | 46.2 | 32 | 2.7 | — | 4.6 |
| Compound 3 | 69.4 | 52 | 49.1 | 32 | 4.6 | — | 4.6 |
| Compound 4 | 75.6 | 52 | 52.1 | 32 | 6.8 | — | 3.3 |
| Compound 5 | 70.9 | 52 | 46.2 | 32 | 7.0 | — | 5.9 |
| Compound 6 | 59.1 | 40 | 46.6 | 32 | 9.0 | — | 5.3 |
| Comparative Example Compound C1 | 69.3 | 52 | 70.0 | 52 | 8.4 | 6.7 | 0.5 |
| Comparative Example Compound C2 | 54.9 | 36 | 38.7 | 27 | 3.4 | 0 | 3.0 |
| Comparative Example Compound C3 | 38.7 | 27 | 38.7 | 27 | — | — | 3.0 |
| Comparative Example Compound C4 | 58.5 | 36 | 56.8 | 36 | 7.7 | 1.8 | 0.4 |
| Comparative Example Compound C5 | 71.8 | 52 | 53.5 | 36 | 0.5 | 1.9 | 1.1 |
| Comparative Example Compound C6 | 51.3 | 36 | 40.9 | 27 | 3.3 | — | 1.7 |
| Comparative Example Compound C7 | 36 | 21 | 41.7 | 31 | 3.3 | — | 2.2 |
| Comparative Example Compound C8 | 58.6 | 55 | 10.8 | 25 | 1.5 | — | 1.5 |

TABLE 1-continued

| Compound | I | | II | | A | B | C |
|---|---|---|---|---|---|---|---|
| | $DA_0$ | $DA_{rt}$ | $DA_0$ | $DA_{rt}$ | $DA_0$ | $DA_0$ | $DA_0$ |

Compound 1

Compound 2

Compound 3

TABLE 1-continued
| Compound | I | | II | | A | B | C |
|---|---|---|---|---|---|---|---|
| | $DA_0$ | $DA_{rt}$ | $DA_0$ | $DA_{rt}$ | $DA_0$ | $DA_0$ | $DA_0$ |
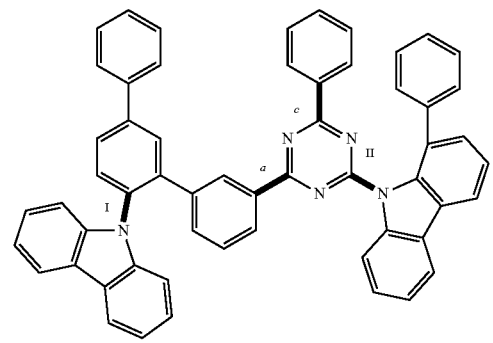
Compound 4
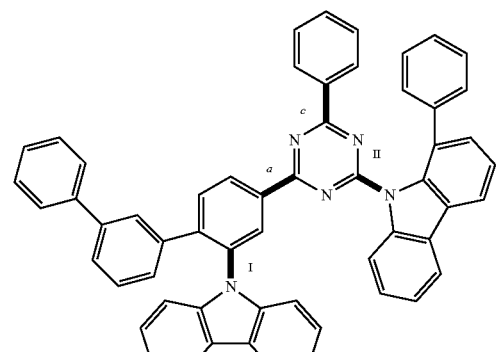
Compound 5
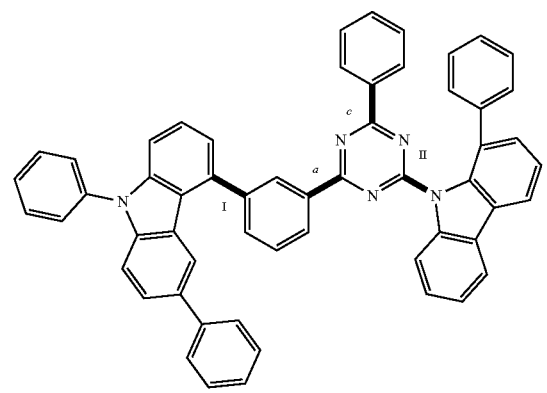
Compound 6
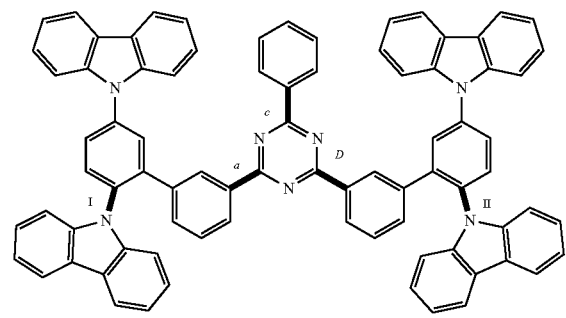
C1
TABLE 1-continued
| Compound | I | | II | | A | B | C |
|---|---|---|---|---|---|---|---|
| | $DA_0$ | $DA_{rt}$ | $DA_0$ | $DA_{rt}$ | $DA_0$ | $DA_0$ | $DA_0$ |
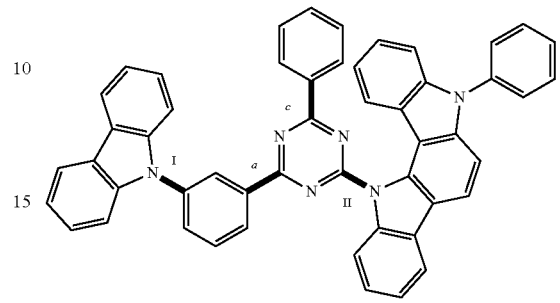
C2
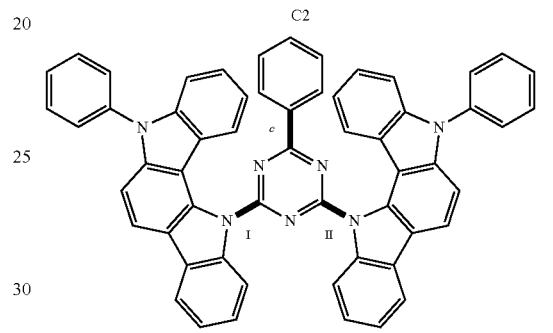
C3
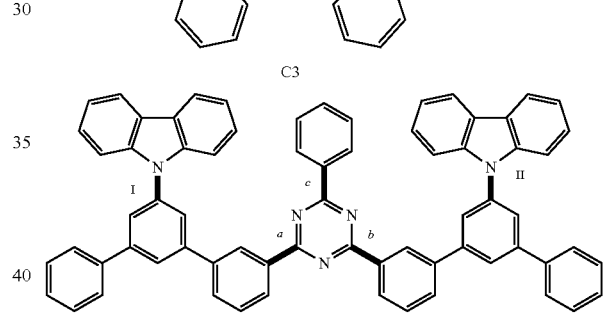
C4
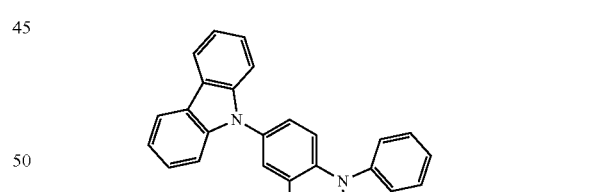
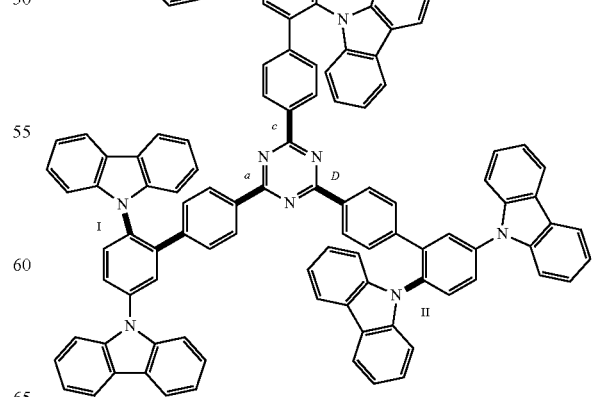
C5

TABLE 1-continued

| Compound | I | | II | | A | B | C |
|---|---|---|---|---|---|---|---|
| | $DA_0$ | $DA_{rt}$ | $DA_0$ | $DA_{rt}$ | $DA_0$ | $DA_0$ | $DA_0$ |

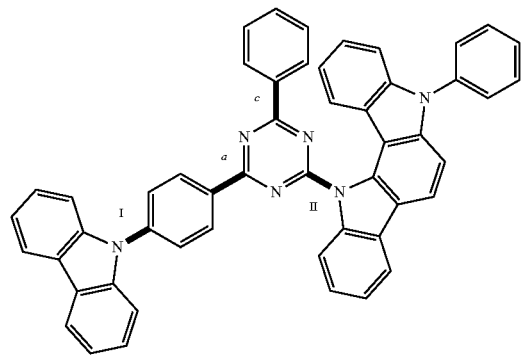 [SMILES: c1ccc(-c2nc(-c3ccc(-n4c5ccccc5c5ccccc54)cc3)nc(-n3c4ccccc4c4ccc5c(c6ccccc6n5-c5ccccc5)c43)n2)cc1]

C6

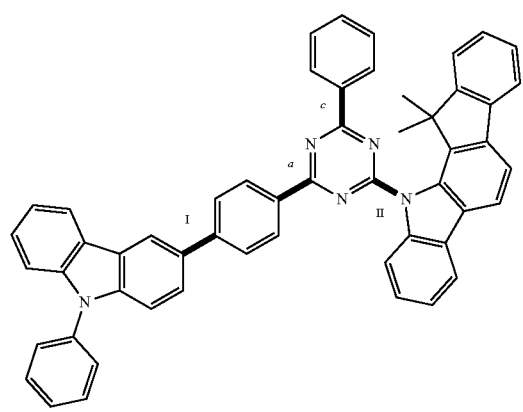

C7

TABLE 1-continued

| Compound | I | | II | | A | B | C |
|---|---|---|---|---|---|---|---|
| | $DA_0$ | $DA_{rt}$ | $DA_0$ | $DA_{rt}$ | $DA_0$ | $DA_0$ | $DA_0$ |

C8

Referring to Table 1, in the compound represented by Formula 1 according to the present disclosure, a substituent $Ar_1$ linked to the LUMO region has large $DA_0$ of 50° or more and large $DA_{rt}$ of 40° or more, and a substituent $Ar_2$ linked to the LUMO region has large $DA_0$ of 30° or more and large $DA_{rt}$ of 20° or more.

Referring to Table 1, the compound according to the present disclosure has a large dihedral angel $DA_0$ of the most stable structures of the $Ar_1$ plane and the $Ar_2$ plane with respect to the LUMO region and a large minimum value $DA_{rt}$ of the dihedral angle capable of reaching thermal energy at room temperature, as compared with Comparative Example Compounds. Therefore, the compound according to the present disclosure may stereoscopically suppress interaction between homogeneous molecules or heterogeneous molecules existing around the triazine ring plane in which LUMO is distributed. Therefore, even when an organic light-emitting device is manufactured by a coating process, it is expected that deterioration of thin-film characteristics caused by aggregation will be prevented.

Molecular Weight and Molecular Weight Ratio

The molecular weight of each compound was calculated by using molecular structure drawing software (ChemSioDraw Ultra, CamvridgeSoft). The HOMO distribution was obtained by the molecular orbital calculation using the above-described quantum chemical calculation software, and HOMO was visualized to confirm the molecular structure in which HOMO was distributed (gray scale region in Table 2). The molecular structure drawing software calculated molecular weight ratios based on the molecular weight of the corresponding structure. Results thereof are shown in Table 2.

TABLE 2
| Compound | Molecular Structure Molecular Weight (Mw) | HOMO energy, HOMO phore Mw, and Mw/Mw ratio | LUMO energy |
|---|---|---|---|
| Compound 1 | 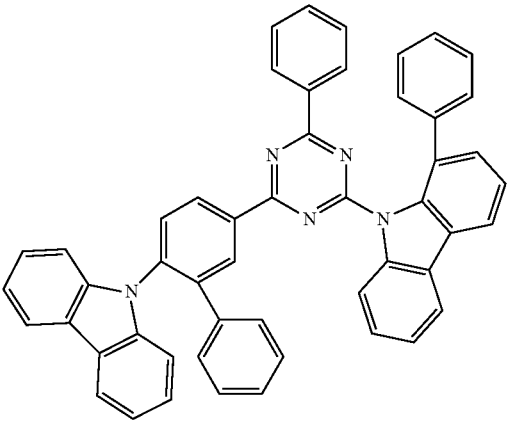<br>1 | −5.68 eV, 241.29, 33.7% | −2.35 eV |
| Compound 2 | 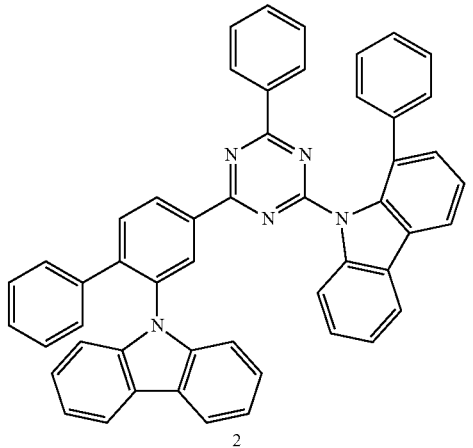<br>2 | −5.67 eV, 241.29, 33.7% | −2.37 eV |
| Compound 3 | 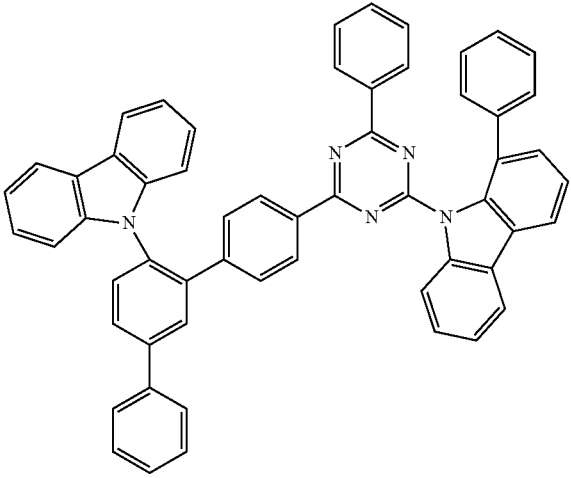<br>3 | −5.69 eV, 241.29, 30.5% | −2.26 eV |

TABLE 2-continued

| Compound | Molecular Structure Molecular Weight (Mw) | HOMO energy, HOMO phore Mw, and Mw/Mw ratio | LUMO energy |
|---|---|---|---|
| Compound 4 | 4 | −5.62 eV, 241.29, 30.5% | −2.17 eV |
| Compound 5 | 5 | −5.70 eV, 241.29, 30.5% | −2.37 eV |
| Compound 6 | 6 | −5.35 eV, 318.40, 40.2% | −2.13 eV |

TABLE 2-continued

| Compound | Molecular Structure<br>Molecular Weight (Mw) | HOMO energy,<br>HOMO phore Mw,<br>and Mw/Mw ratio | LUMO energy |
|---|---|---|---|
| Comparative Example Compound C1 | C1 | −5.61 eV, 815.00, 72.6% | −2.26 eV |
| Comparative Example Compound C5 | C5 | −5.68 eV, 815.00, 53.3% | −2.37 eV |
| Comparative Example Compound C6 | C6 | −5.45 eV, 331.40, 45.5% | −2.29 eV |

Referring to Table 1 (dihedral angle) and Table 2 (HOMO/LUMO drawing), it is confirmed that, in the compound represented by Formula 1 according to the present disclosure, at least two of substituents directly linked to a triazine ring are linked at a small dihedral angle of 15° or less, and thus, LUMO is distributed to expand in two or more directions of the substituent in the triazine ring.

Referring to Table 2, it is confirmed that the compound according to the present disclosure has a small molecular weight ratio of a HOMO region, as compared with Comparative Example Compounds. That is, it is confirmed that the compound according to the present disclosure has a low HOMO molecular weight ratio, suppresses hole transport capability, and has excellent electron transport capability derived from the LUMO region. Therefore, it is expected that the compound according to the present disclosure will be used as an emission layer, an electron transport layer, an electron injection layer, a hole blocking layer, and the like of an organic light-emitting device.

Measurement of Solubility 50 milligrams (mg) of a solid sample was added to a colorless sample bottle, 500 mg of a solvent was added thereto, ultrasonic waves were irradiated for 5 minutes at room temperature, and the presence or absence of the solid sample was checked visually. When the solid sample was dissolved, at this time, without any remaining solid sample, the solubility was 10 weight % or more. When the solid sample remained, a solvent was slightly added thereto and ultrasonic wave irradiation was repeated, so that the solid sample was completely dissolved. The solubility was calculated through the amount of the solvent when the solid sample was dissolved.

TABLE 3

| Compound | solubility in methyl benzoate |
|---|---|
| Compound 1 | 5 wt % |
| Compound 3 | 4 wt % |
| Compound 4 | 6 wt % |
| Compound 5 | 4 wt % |
| Compound 6 | 6 wt % |
| Compound 130 | 2 wt % |
| Compound 341 | 4 wt % |
| Compound C1 | 1 wt % |
| Compound C4 | 0.5 wt % |
| Compound C5 | 0.2 wt % |
| Compound C6 | 0.2 wt % |

Referring to Table 3, it is confirmed that Comparative Example Compounds C1, C4, C5, and C6 do not satisfy the characteristics of the present disclosure, that is, the dihedral angle condition or the condition in which the number of carbazole moieties is three or less has low solubility, and the compound satisfying the conditions according to the present disclosure has high solubility. In addition, referring to Tables 2 and 3, it is confirmed that the compound in which three substituents linked to the triazine ring are different from each other has high solubility, as compared with the compound in which two or more of the substituents linked to the triazine ring are same. Therefore, the compound in which three substituents linked to the triazine ring have different structures is suitable for, in particular, the manufacture of an organic light-emitting device by using a coating process among the embodiments of the present disclosure.

Evaluation of Photochemical Stability

Photochemical stability was evaluated in the following conditions.

Manufacture of Sample to be Measured

In a glove box of a nitrogen atmosphere in which a moisture concentration was 1 part per million (ppm) or less and an oxygen concentration was 1 ppm or less, a thin-film having a film thickness of 50 nm was formed on a quartz substrate in a methyl benzoate solution of an evaluation host material:a green phosphorescence material TEG=100 weight %:5 weight %, and solid ink having a concentration of 4 weight % by a coating process at a solid ratio. The thin-film was processed at a vacuum degree of $1E^{-3}$ Pa at a temperature of 120° C. for 15 minutes. The thin-film was transferred to a vacuum deposition apparatus, and a round aluminum thin-film having a diameter of 2 millimeters (mm) and a film thickness of 100 nm was formed by using a metal mask by vacuum deposition. This was used as a sealing measurement sample by using a dried glass sealing tube and an ultrasonic curable resin.

Measurement System

A measurement system includes the following two parts.
1. PL intensity measurement system
2. UV irradiation deterioration meter 1. PL Intensity Measurement System A high-power UV-Vis optical fiber light source unit (L10290 manufactured by Hamamatsu Photonics Co., Ltd.) and an ultraviolet-transmission visible-absorption filter (S76-U340 manufactured by Misumi Co., Ltd.) were used, and light from which light having a wavelength of 250 nm or less and light having a wavelength of 400 nm or more were removed was used as an excitation light source. An optical receiver used a small fiber optical spectrometer (USB2000+UV-VIS manufactured by Ocean Photonics). Upon measurement, a sample substrate was installed such that the excitation light was exactly incident on a sample film measurement region coated with aluminum at an angle of 20° or more from the front of the quartz substrate side. Due to the excitation light, the sample film measurement region radiated light emission in the semispherical direction of the quartz substrate. The optical receiver was provided at a position where it is possible to capture this luminescence and avoid specular reflection of the excitation light by the quartz substrate. In order to make the intensity of the excitation light irradiated on the sample constant every time of measurement, the intensity of the excitation light and the geometrical arrangement of the optical system were kept constant.

2. UV Irradiation Deterioration Meter

UV-LED (manufactured by CCS) having a maximum emission wavelength of 365 nm as a light source, and light in which intensity in an irradiation spherical surface was made uniform through a synthetic quartz light pipe having a diameter of 2 mm and a length of 75 mm (#65-829 manufactured by Edmund Optics) was used as excitation light. The excitation light flux intensity was controlled by using a digital power source (PD3-10024-8-PI manufactured by CCS Corporation) and an optical power meter (8230E manufactured by ADCMT). The quartz substrate side of the excitation light sphere and the sample film was aligned and then closely contacted. By exciting the excitation light to the sample film on the quartz substrate side for a certain period of time, the sample film was optically loaded and deteriorated.

Photochemical Deterioration Test at Excitation Light Flux Intensity of 10 mW

First stage: The PL intensity of the sample thin-film before deterioration was measured by using the PL light intensity measurement system described in the above 1. Second stage: After the excitation light irradiation was performed for deterioration of the excitation light flux intensity at 10 milliwatts (mW) for 5 minutes by using the UV irradiation deterioration meter described in the above 2, the PL intensity of the sample thin-film loaded for 5 minutes was measured by using the PL intensity measurement system described in the above 1. Then, the same operation as in the second stage was repeated to measure the PL intensity of the sample thin-film with respect to the time when the excitation light load was applied.

Photochemical Deterioration Test at Excitation Light Flux Intensity of 20 mW

The same measurement as in the above-described deterioration test of 10 mW was performed except that the excitation light intensity was changed to 20 mW.

Photochemical Deterioration Test at Excitation Light Flux Intensity of 50 mW

The same measurement as in the above-described deterioration test of 10 mW was performed except that the excitation light intensity was changed to 50 mW.

Photochemical Deterioration Test Analysis

First, based on decay data of the luminescence intensity obtained in the photochemical deterioration tests in which the excitation light flux intensity was variously changed, the following relationship was applied to adjust the acceleration coefficient "a" to obtain a decay curve independent of the excitation light flux intensity.

Vertical axis: $R_{I(t)} = I_{(t)}/I_0$

Horizontal axis: $X_c = E^a \times t$ $R_{I(t)}$: PL intensity ratio of sample film to initial luminance at excitation light irradiation time t t: Excitation light irradiation time $I_{(t)}$: Light emission intensity of sample film at excitation light irradiation time t $I_0$: Light emission intensity of sample film before excitation light irradiation $X_c$: Corrected excitation light integrating intensity E: Excitation light flux intensity a: Accumulation coefficient The corrected excitation light integrating intensity $X_c 90$ required for $R_{I(t)}$ to reach 0.9 (light emission intensity was lowered by 10%) in a "decay curve that does not depend on the excitation light flux intensity" obtained by this analysis was used as photochemical stability in this example. As the value of $X_c 90$ is higher, higher energy is required to lower the light emission intensity, and means difficulty of deterioration. Table 4 below shows the Xc90 results as relative values.

TABLE 4

| Compound | photochemical stability(Xc90) |
|---|---|
| Compound 3 | 290 |
| Compound 4 | 410 |
| Compound 306 | 100 |
| Compound 307 | 140 |

Referring to Table 4, it is confirmed that, in Compound in which Ar1 corresponds to Formula 2-1 or 2-2, Compound Y3 or Y13 that is a phenyl group has a large $X_c 90$ and high photochemical stability. Therefore, when a compound in which $Y_2$ or $Y_3$ is $C(R_{13})$, or $Y_{12}$ or $Y_{13}$ is $C(R_{15})$, and $R_{13}$ or $R_{15}$ is an aromatic hydrocarbon ring group or an aromatic heteroring group in Formulae 2-1 and 2-2 is applied to an organic light-emitting device (in particular, an emission layer), it can be confirmed that the effect of a long lifespan will be expected.

Evaluation Method of Organic Light-Emitting Device

Evaluation of Current Efficiency and Durability (Emission Lifespan)

For Examples and Comparative Examples, the current efficiency and durability (emission lifespan) were evaluated under the following conditions. First, the voltage and current applied to the organic light-emitting device were measured by using a DC constant voltage power source (source meter manufactured by KEYENCE), and the luminance of the organic light-emitting device was measured by using a luminance measurement device (Topcon SR-3).

The current efficiency (candelas per ampere, cd/A) was calculated by calculating the current value (current density) per unit area in the size and the current value of the organic light-emitting device and dividing the luminance (candelas per square meter, $cd/m^2$) by the current density (amperes per square meter, $A/m^2$). In addition, the current efficiency indicates efficiency (conversion efficiency) of converting the current into light emission energy. As the current efficiency is higher, the performance of the organic light-emitting device is higher.

In the durability (emission lifespan), "$LT_{80}(h)$" indicates the time (hours, hr) that lapsed when light emitting luminance decreasing with the lapse of the continuous operation time in the current value at which initial luminance in each organic light-emitting device was 6,000 $cd/m^2$ was 80% of initial luminance.

EXAMPLES

Synthesis Example 1: Synthesis of Compound 1

(1) Synthesis of Intermediate 1-1

Intermediate 1-1 was synthesized according to the Reaction Scheme:

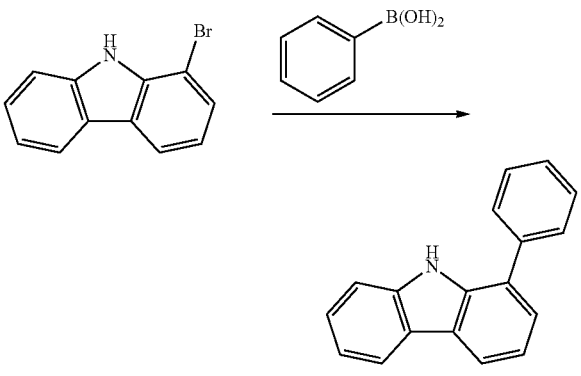

Intermediate 1-1

1-Bromocarbazole (307 millimoles, mmol, 75.6 grams, g), phenylboronic acid (338 mmol, 41.2 g), 2 molar (M) aqueous solution (230 milliliters, ml) of potassium carbonate (461 mmol, 63.7 g), and 1,4-dioxane (614 ml) were added to a three-necked flask, the flask was flushed with nitrogen, palladium acetate(II) (9.2 mmol, 2.07 g), tri(o-tolyl)phosphine [P(o-tolyl)$_3$] (13.8 mmol, 4.20 g) was added thereto, and the reaction mixture was heated under stirring at a temperature of 80° C. for 8 hours. The reaction mixture was cooled to room temperature, diluted with toluene (1 liter, L), filtered by using celite, and washed twice with water by using a separatory funnel. The reaction mixture was dried by using anhydrous magnesium sulfate, filtered through a silica gel pad, and then, concentrated. The precipitated solid was dispersed in hexane (300 ml), and refluxed for 2 hours in a nitrogen atmosphere. The reaction mixture was cooled to room temperature, and an object was collected by filtering to obtain Intermediate 1-1. The amount of Intermediate 1-1 obtained was 58.9 g and the yield of Intermediate 1-1 was 79%.

Then, Intermediate 1-2 was synthesized according to the following Reaction Scheme.

(2) Synthesis of Intermediate 1-2

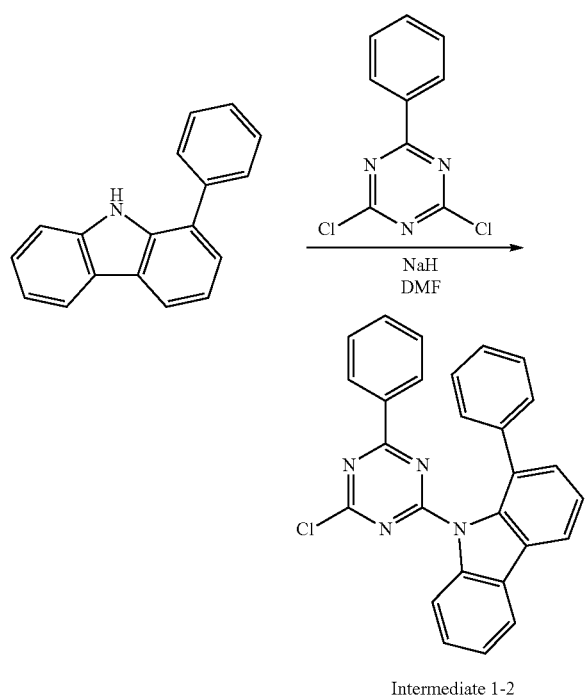

Intermediate 1-2

Intermediate 1-1 (224.4 mmol, 54.5 g) and dimethylformamide (440 ml) were added to a three-necked flask, the flask was flushed with nitrogen, and the reaction mixture was cooled to 0° C. Sodium hydride (6% paraffin dispersion) (235.6 mmol, 9.12 g) was added thereto stepwise, while observing the amount of hydrogen gas generated, and then heated under stirring at a temperature of 0° C. for 1 hour. 2-phenyl-4,6-dichlorotriazine (246.8 mmol, 55.8 g) was added thereto, the reaction mixture was stirred at a temperature of 0° C. for 30 minutes, and then, at room temperature for 1 hour. Then, the reaction mixture was stirred at a temperature of 80° C. for 4 hours. The reaction mixture was cooled to room temperature, diluted with toluene (500 ml), and quenched with a small amount of water. The reaction mixture was filtered by using celite and washed three times with water by using a separatory funnel. The reaction mixture was dried by using anhydrous magnesium sulfate, filtered through a silica gel pad, and then, concentrated. The resultant obtained therefrom was separated by silica gel column chromatography (developing agent hexane:ethyl acetate=7:3) to obtain Intermediate 1-2. The amount of Intermediate 1-2 obtained was 56.2 g, and the yield of Intermediate 1-2 was 58%.

Then, Intermediate 1-3 was synthesized according to the following Reaction Scheme.

(3) Synthesis of Intermediate 1-3

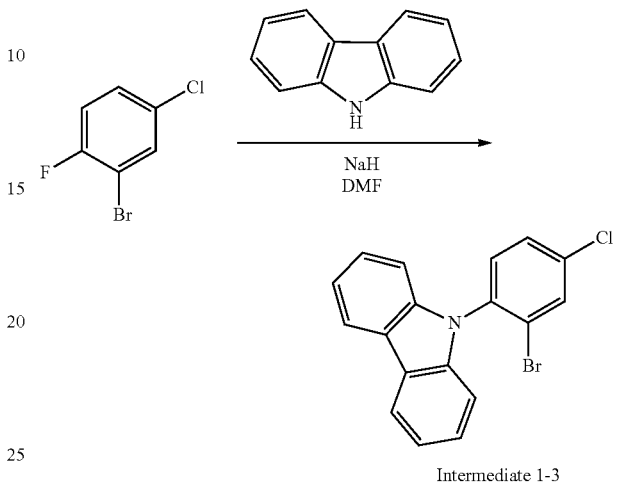

Intermediate 1-3

Carbazole (800 mmol, 133.8 g), 2-bromo-4-chloro-1-fluorobenzene (840 mmol 175.9 g), and dimethylformamide (160 ml) were added to a three-necked flask, and the flask was flushed with nitrogen. Sodium hydride (62% paraffin dispersion) (800 mmol, 31.0 g) was added thereto stepwise five or more times, while observing the amount of hydrogen gas generated, and the reaction mixture was slowly heated while observing the amount of hydrogen gas generated. The reaction mixture was then heated under stirring at a temperature of 150° C. for 20 hours. The reaction mixture was cooled to room temperature, diluted with toluene (1 L), and quenched with a small amount of water in a nitrogen atmosphere. The reaction mixture was filtered by using celite and washed three times with water by using a separatory funnel. The reaction mixture was dried by using anhydrous magnesium sulfate, filtered through a silica gel pad, and then, concentrated. The resultant obtained therefrom was recrystallized in a mixed solvent of ethanol:methanol=1:1 to obtain Intermediate 1-3. The amount of Intermediate 1-3 obtained was 156.1 g and the yield of Intermediate 1-3 was 55%.

Then, Intermediate 1-4 was synthesized according to the following Reaction Scheme.

(4) Synthesis of Intermediate 1-4

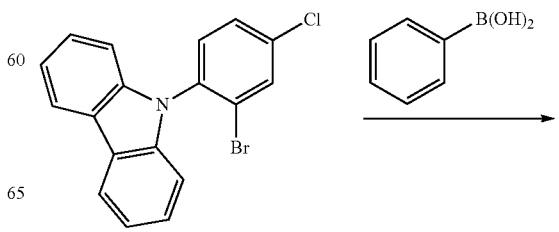

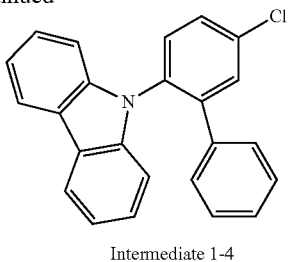

Intermediate 1-4

Intermediate 1-3 (435 mmol, 155.1 g), phenylboronic acid (478.5 mmol, 58.3 g), 2 M aqueous solution (435 ml) of potassium carbonate (652.5 mmol, 90.2 g), toluene (870 ml), and ethanol (218 ml) were added to a three-necked flask, and the flask was flushed with nitrogen. Tetrakis(triphenylphosphine)palladium(0) (Pd(PPh$_3$)$_4$) (21.8 mmol, 25.1 g) was added thereto, and the reaction mixture was heated under stirring at a temperature of 80° C. for 8 hours. The reaction mixture was cooled, diluted with toluene (1 L), filtered by using celite, and washed twice with water by using a separatory funnel. The reaction mixture was dried by using anhydrous magnesium sulfate, filtered through a silica gel pad, and then, concentrated. The precipitated solid was purified by silica gel column chromatography (developing solvent hexane:toluene=7:3) and recrystallized in ethanol to obtain Intermediate 1-4. The amount of Intermediate 1-4 obtained was 109.3 g and the yield of Intermediate 1-4 was 71%.

Then, Intermediate 1-5 was synthesized according to the following Reaction Scheme.

(5) Synthesis of Intermediate 1-5

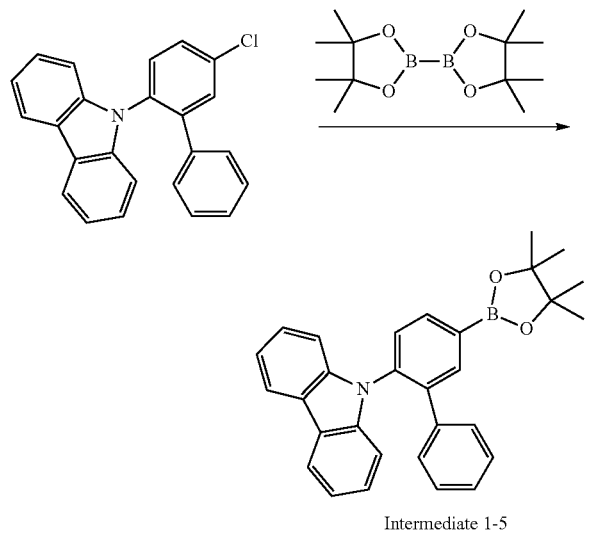

Intermediate 1-5

Intermediate 1-4 (305 mmol, 107.9 g), bis(pinacolato) diboron (335.5 mmol, 85.2 g), potassium acetate (610 mmol, 59.9 g), 1,4-dioxane (610 ml) were added to a three-necked flask, and the flask was flushed with nitrogen. Bis(dibenzylideneacetone)palladium(0) (15.25 mmol, 8.76 g) and tricyclohexylphosphonium tetrafluoroborate (12.2 mmol, 4.49 g) were added thereto, and the reaction mixture was heated under stirring at a temperature of 80° C. for 8 hours. The reaction mixture were cooled to room temperature, diluted with toluene (1 L), filtered by using celite, and washed twice with water by using a separatory funnel. The reaction mixture was dried by using anhydrous magnesium sulfate, filtered through a silica gel pad, and then, concentrated. The reaction mixture was dispersed in hexane (300 ml), sonicated for 30 minutes, filtered, and the vacuum-dried (50° C., 6 hours) to obtain Intermediate 1-5. The amount of Intermediate 1-5 obtained was 112.7 g and the yield of Intermediate 1-5 was 83%.

Then, Compound 1 was synthesized according to the following Reaction Scheme.

(6) Synthesis of Compound 1

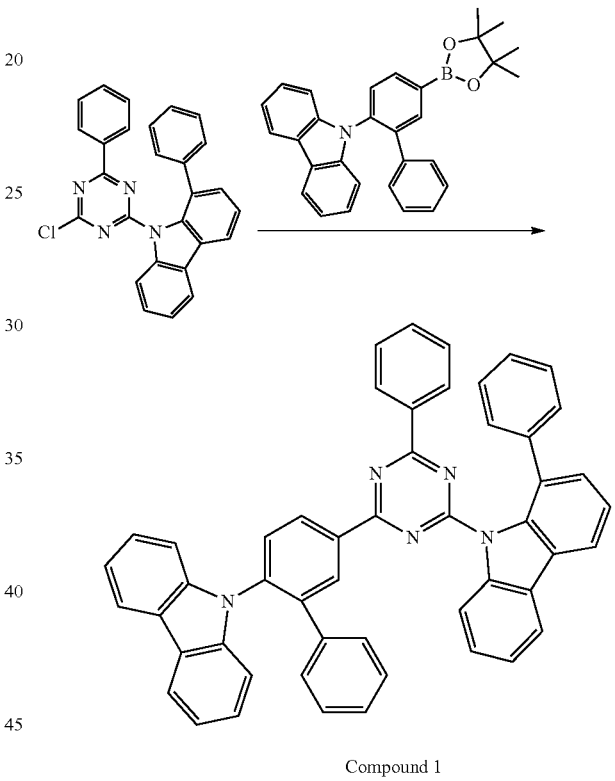

Compound 1

Intermediate 1-2 (10 mmol, 4.33 g), Intermediate 1-5 (11 mmol, 4.90 g), 1 M aqueous solution (15 ml) of potassium carbonate (15 mmol, 2.07 g), toluene (100 ml), and ethanol (20 ml) were added to a three-necked flask, and flask was flushed with nitrogen. Tetrakis(triphenylphosphine) palladium(0) (Pd(PPh$_3$)$_4$ (0.5 mmol, 0.58 g) was added thereto, and the reaction mixture was heated under stirring at a temperature of 80° C. for 8 hours. The reaction mixture was cooled to room temperature, diluted with toluene (200 ml), filtered by using celite, and washed twice with water by using a separatory funnel. The reaction mixture was dried by using an anhydrous magnesium sulfate, filtered through a silica gel pad, and then, concentrated. The reaction mixture was purified by silica gel column chromatography (developing solvent hexane:toluene=6:4) and recrystallized in a mixed solvent of ethyl acetate:ethanol=2:8 to obtain Compound 1. The amount of Compound 1 obtained was 5.30 g and the yield of Compound 1 was 74%.

Synthesis Example 2: Synthesis of Compound 3

(1) Synthesis of Intermediate 3-1

Intermediate 3-1 was synthesized according to the following Reaction Scheme:

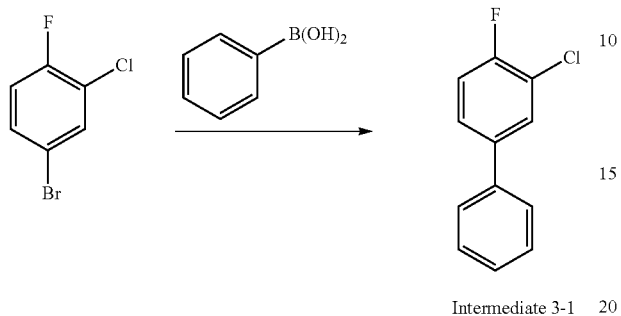

Intermediate 3-1

4-Bromo-2-chloro-I-fluorobenzene (720 mmol, 150.8 g), phenylboronic acid (792 mmol, 96.6 g), 2 M aqueous solution (360 ml) of potassium carbonate (1,080 mmol, 149.3 g), toluene (720 mi), and ethanol (144 ml) were added to a three-necked flask, and the flask was flushed with nitrogen. Tetrakis(triphenylphosphine) palladium(0) (Pd(PPh$_3$)$_4$ (21.6 mmol, 21.6 g) was added thereto, and the reaction mixture was heated under stirring at a temperature 80° C. for 8 hours. The reaction mixture was cooled to room temperature, diluted with toluene (1 L), filtered by using celite, and washed twice with water by using a separatory funnel. The reaction mixture was dried by using anhydrous magnesium sulfate, filtered through a silica gel pad, and then, concentrated. The precipitated solid was purified by silica gel column chromatography (developing solvent hexane:toluene=7:3) and recrystallized in methanol to obtain Intermediate 3-1. The amount of Intermediate 3-1 obtained was 101.2 g and the yield of Intermediate 3-1 was 68%.

Then, Intermediate 3-2 was synthesized according to the following Reaction Scheme.

(2) Synthesis of Intermediate 3-2

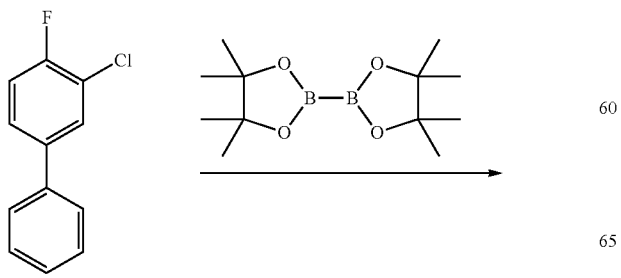

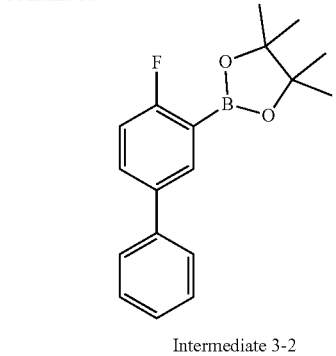

Intermediate 3-2

Intermediate 3-1 (488 mmol, 100.8 g), bis(pinacolato)diboron (536.8 mmol, 136.3 g), potassium acetate (976 mmol, 95.8 g), and 1,4-dioxane (976 ml) were added to a three-necked flask, and the flask was flushed with nitrogen. Bis(dibenzylideneacetone)palladium(0) (24.4 mmol, 14.0 g) and tricyclohexylphosphonium tetrafluoroborate (19.5 mmol, 7.2 g) were added thereto, and the reaction mixture was heated under stirring at a temperature of 80° C. for 8 hours. The reaction mixture was cooled to room temperature, diluted with toluene (1 L), filtered by using celite, and washed twice with water by using a separatory funnel. The reaction mixture was dried by using anhydrous magnesium sulfate, filtered through a silica gel pad, and then, concentrated. The reaction mixture was dispersed in hexane (300 ml), sonicated for 30 minutes, filtered, and vacuum-dried (50° C., 6 hours) to obtain Intermediate 3-2. The amount of Intermediate 3-2 obtained was 116.4 g and the yield of Intermediate 3-2 was 80%.

Then, Intermediate 3-3 was synthesized according to the following Reaction Scheme.

(3) Synthesis of Intermediate 3-3

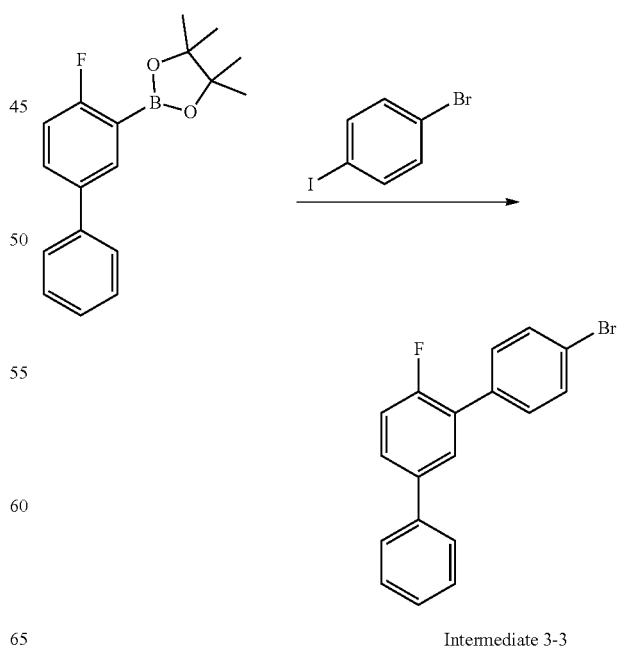

Intermediate 3-3

Intermediate 3-2 (388 mmol, 115.7 g), 1-bromo-4-iodine benzene (426.8 mmol, 120.7 g), 2 M aqueous solution (291 ml) of potassium carbonate (582 mmol, 80.4 g), toluene (776 ml), and ethanol (194 ml) were added to a three-necked flask, and the flask was flushed with nitrogen. Tetrakis (triphenylphosphine)palladium(0) (Pd(PPh$_3$)$_4$) (19.4 mmol, 22.4 g) was added thereto, and the reaction mixture was heated under stirring at a temperature of 70° C. for 8 hours. The reaction mixture was cooled to room temperature, diluted with toluene (1 L), filtered by using celite, and washed twice with water by using a separatory funnel. The reaction mixture was dried by using anhydrous magnesium sulfate, filtered through a silica gel pad, and then, concentrated. The precipitated solid was purified by silica gel column chromatography (developing solvent hexane:toluene=7:3) and recrystallized in methanol to obtain Intermediate 3-3. The amount of Intermediate 3-3 obtained was 90.1 g and the yield of Intermediate 3-3 was 71%.

Then, Intermediate 3-4 was synthesized according to the following Reaction Scheme.

(4) Synthesis of Intermediate 3-4

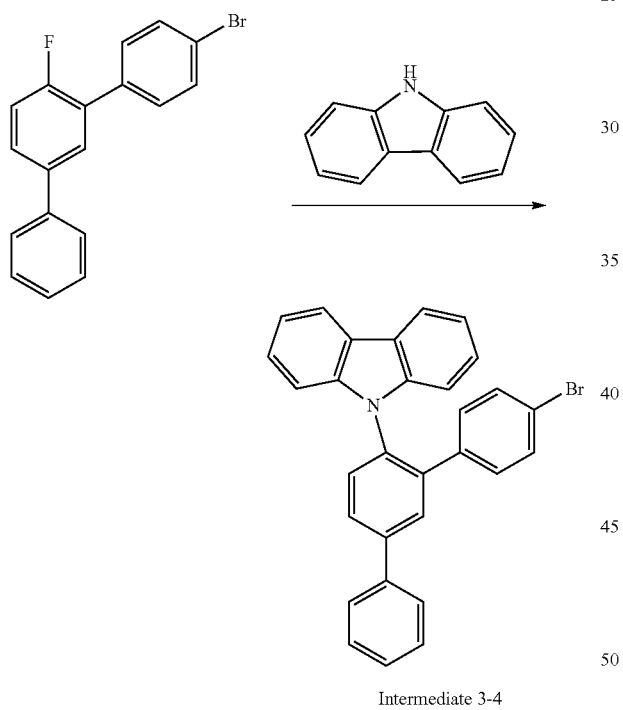

Intermediate 3-4

Carbazole (409.5 mmol, 68.5 g), Intermediate 3-3 (273 mmol, 89.3 g), and dimethylformamide (137 ml) were added to a three-necked flask, and the flask was flushed with nitrogen. Sodium hydride (62% paraffin dispersion) (327.6 mmol, 12.7 g) was added thereto stepwise five or more times, while observing the amount of hydrogen gas generated, and the reaction mixture was slowly heated, while observing the amount of hydrogen gas generated, and then heated under stirring at a temperature of 150° C. for 20 hours. The reaction mixture was cooled to room temperature, diluted with toluene (1 L), and quenched with a small amount of water in a nitrogen atmosphere. The reaction mixture was filtered by using celite and washed three times with water by using a separatory funnel. The reaction mixture was dried by using anhydrous magnesium sulfate, filtered through a silica gel pad, and then, concentrated. The resultant obtained therefrom was recrystallized in a mixed solvent of ethanol:methanol=1:1 to obtain Intermediate 3-4. The amount of Intermediate 3-4 obtained was 110.1 g and the yield of Intermediate 3-4 was 85%.

Then, Intermediate 3-5 was synthesized according to the following Reaction Scheme.

(5) Synthesis of Intermediate 1-5

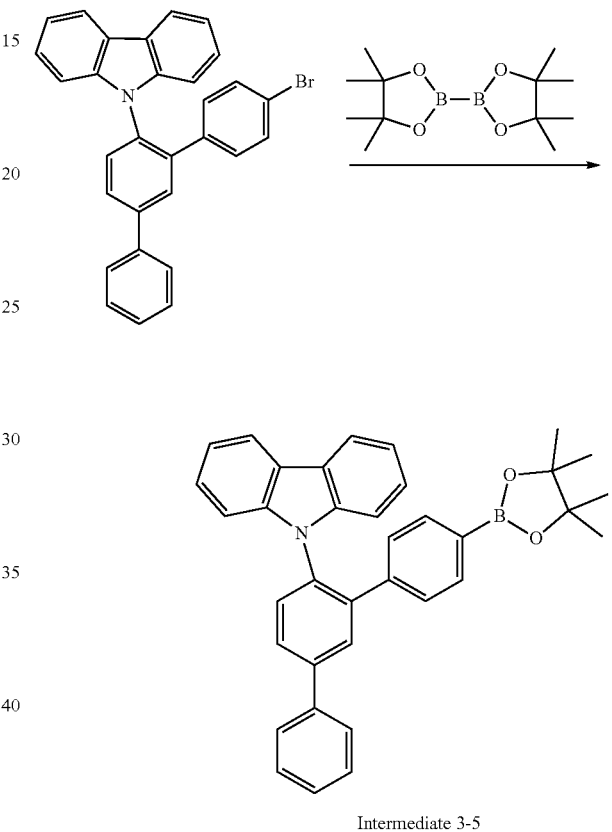

Intermediate 3-5

Intermediate 3-4 (230 mmol, 109.1 g), bis(pinacolato) diboron (253 mmol, 64.2 g), potassium acetate (460 mmol, 45.1 g), and 1,4-dioxane (460 ml) were added to a three-necked flask, and the flask was flushed with nitrogen, Bis(dibenzylideneacetone)palladium(0) (11.5 mmol, 6.61 g) and tricyclohexylphosphonium tetrafluoroborate (9.2 mmol, 9.6 g) were added thereto, and the reaction mixture was heated under stirring at a temperature of 80° C. for 8 hours. The reaction mixture was cooled to room temperature, diluted with toluene (1 L), filtered by using celite, and washed twice with water by using a separatory funnel. The reaction mixture was dried by using anhydrous magnesium sulfate, filtered through a silica gel pad, and then, concentrated. The reaction mixture was dispersed in hexane (300 ml), sonicated for 30 minutes, filtered, and vacuum-dried (50° C., 6 hours) to obtain Intermediate 3-5. The amount of Intermediate 3-5 obtained was 100.7 g and the yield of Intermediate 3-5 was 84%.

Then, Intermediate 3-6 was synthesized according to the following Reaction Scheme.

(5) Synthesis of Intermediate 3-6

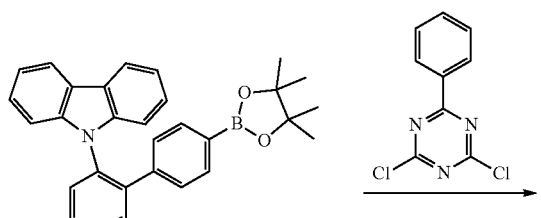

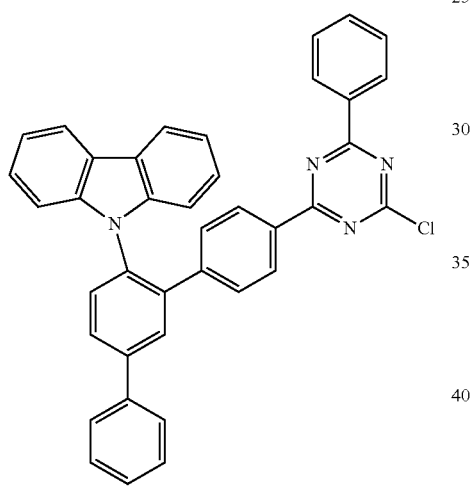

Intermediate 3-6

Intermediate 3-5 (190 mmol, 99.1 g), 2,4-dichloro-6-phenyl-1,3,5-triazine (380 mmol, 85.9 g), 2 M aqueous solution (190 ml) of potassium carbonate (380 mmol, 52.5 g), and tetrahydrofuran (950 ml) were added to a three-necked flask, and the flask was flushed with nitrogen. The reaction mixture was heated under stirring at a temperature of 70° C. for 30 minutes, and a sample was dissolved therein and cooled to room temperature. 2 M aqueous solution (190 ml) of potassium carbonate (380 mmol, 52.5 g), tri(o-tolyl)phosphine (15.2 mmol, 4.6 g), and palladium acetate (9.5 mmol, 2.1 g) were added thereto, and the reaction mixture was heated under stirring at a temperature of 50° C. for 2 hours. The reaction mixture was cooled to room temperature, diluted with toluene (1.5 L), filtered by using celite, and washed twice with water by using a separatory funnel. The reaction mixture was dried by using anhydrous magnesium sulfate, filtered through a silica gel pad, and then, concentrated. The reaction mixture was recrystallized twice by using ethyl acetate:hexane=3:7 to obtain Intermediate 3-6. The amount of Intermediate 3-6 obtained was 72.3 g and the yield of Intermediate 3-6 was 65%.

Then, Compound 3 was synthesized according to the following Reaction Scheme.

(7) Synthesis of Compound 3

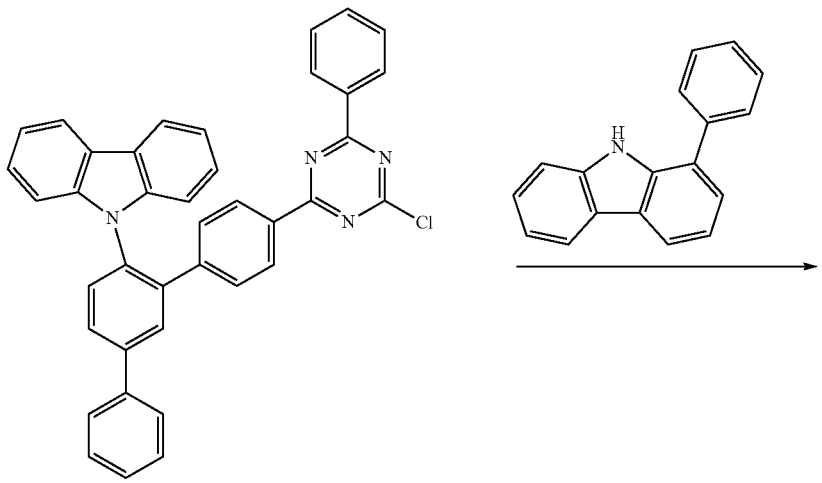

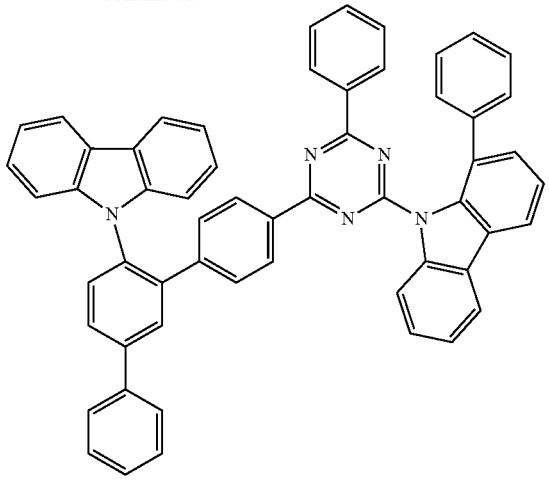

Compound 3

Intermediate 3-6 (15 mmol, 8.78 g), 1-phenylcarbazole (22.5 mmol, 5.47 g), and dimethylformamide (30 ml) were added to a three-necked flask, and the flask was flushed with nitrogen, Sodium hydride (62% paraffin dispersion) (22.5 mmol, 0.87 g) was added thereto stepwise, while observing the amount of hydrogen gas generated, and the reaction mixture was slowly heated, while observing the amount of hydrogen gas generated, and then heated under stirring at a temperature of 120° C. for 8 hours. The reaction mixture was cooled to room temperature and diluted with methanol (200 ml) and quenched. The precipitated solid was sonicated for 10 minutes, filtered, and vacuum-dried (50° C., 6 hours). The solid was heated and dissolved in toluene (200 ml), filtered through a silica gel pad, and then, concentrated. The resultant obtained therefrom was recrystallized twice in ethyl acetate to obtain Compound 3. The amount of Compound 3 obtained was 8.32 g and the yield of Compound 3 was 70%.

Synthesis Example 3: Synthesis of Compound 5

(1) Synthesis of Intermediate 5-1

Intermediate 5-1 was synthesized according to the Reaction Scheme:

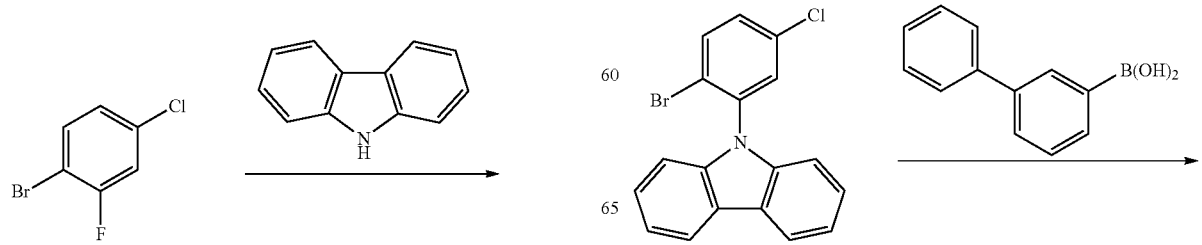

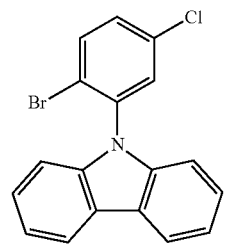

Intermediate 5-1

Intermediate 5-1 was synthesized in the same manner as in Synthesis of intermediate 1-3, except that a reagent was changed to a reagent shown in the above Reaction Scheme. The amount of Intermediate 5-1 obtained was 214.0 g and the yield of Intermediate 5-1 was 75%.

Then, Intermediate 5-2 was synthesized according to the following Reaction Scheme.

(2) Synthesis of Intermediate 5-2

-continued

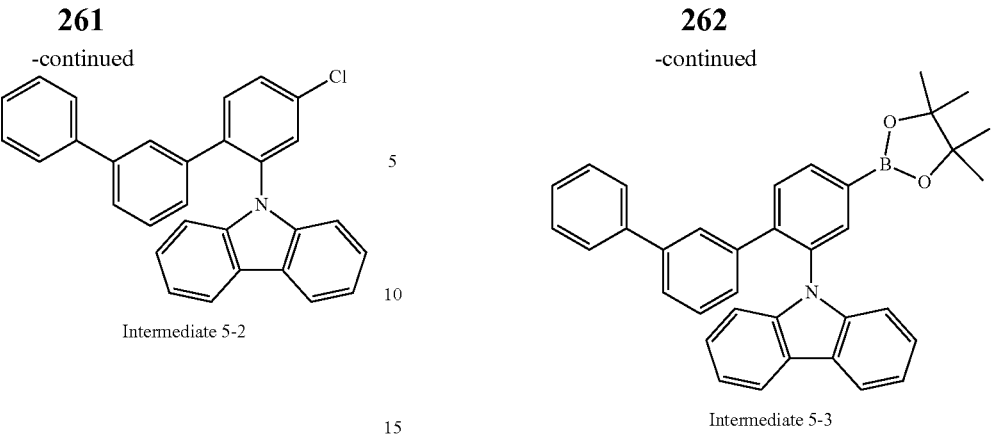

Intermediate 5-2

Intermediate 5-2 was synthesized in the same manner as in Synthesis of Intermediate 1-4, except that phenylboronic acid was changed to 3-biphenylboronic acid) (660 mmol, 130.7 g), The amount of Intermediate 5-2 obtained was 221.9 g and the yield of Intermediate 5-2 was 86%.

Then, Intermediate 5-3 was synthesized according to the following Reaction Scheme.

(3) Synthesis of Intermediate 5-3

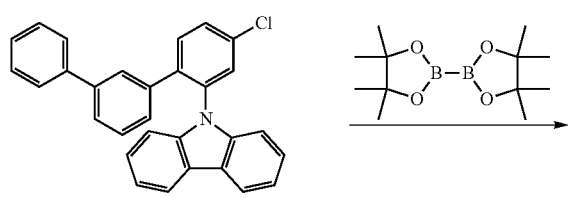

Intermediate 5-3

Intermediate 5-3 was synthesized in the same manner as in Synthesis of Intermediate 1-5, except that Intermediate 1-4 was changed to Intermediate 5-2. The amount of Intermediate 5-3 obtained was 126.7 g and the yield of Intermediate 5-3 was 81%.

Then, Compound 5 was synthesized according to the following Reaction Scheme.

(4) Synthesis of Compound 5

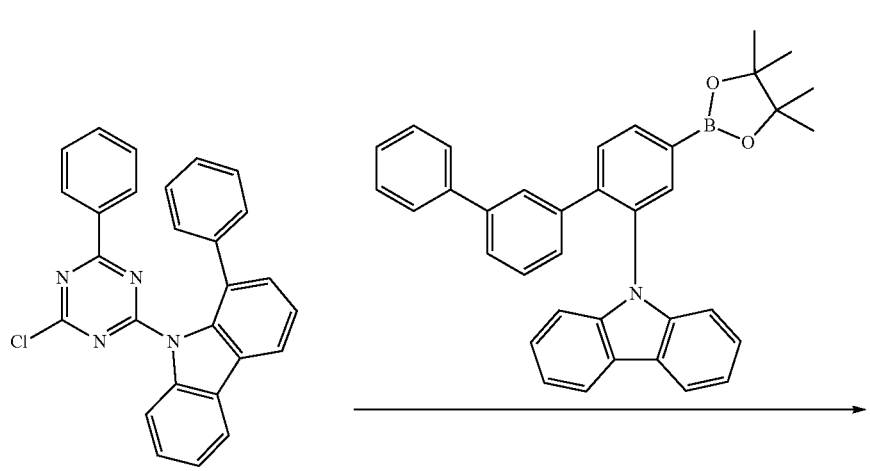

-continued

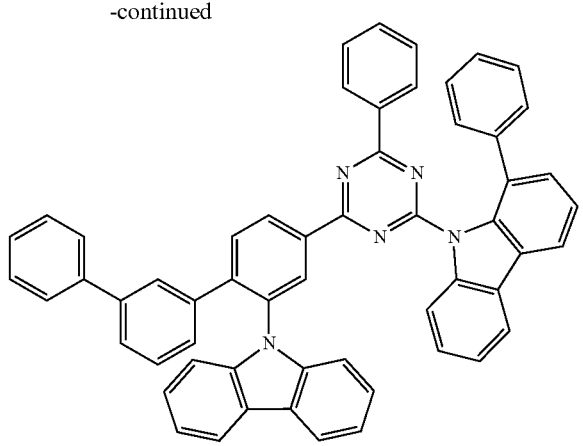

Compound 5

Compound 5 was synthesized in the same manner as in Synthesis of Compound 1, except that Intermediate 1-5 was changed to Intermediate 5-3. The amount of Compound 5 obtained was 6.57 g and the yield of Compound 5 was 83%.

Compounds shown in Table 5 other than Compounds 1, 3, and 5 were synthesized by combining the same methods or methods known to those of ordinary skill in the art.

TABLE 5

| Compound number | Molecular structure |
|---|---|
| 1 | 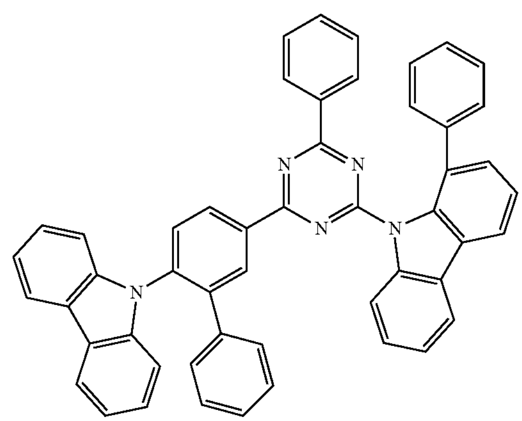 [SMILES: c1ccc(-c2nc(-c3ccc(-n4c5ccccc5c5ccccc54)c(-c4ccccc4)c3)nc(-n3c4ccccc4c4cccc(-c5ccccc5)c43)n2)cc1] |
| 3 | 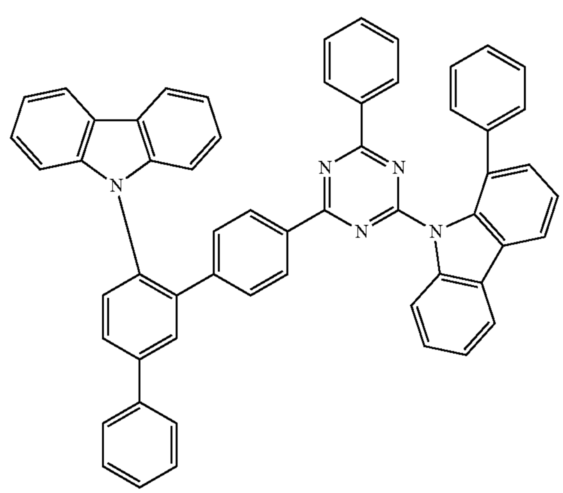 [SMILES: c1ccc(-c2ccc(-n3c4ccccc4c4ccccc43)c(-c3ccc(-c4nc(-c5ccccc5)nc(-n5c6ccccc6c6cccc(-c7ccccc7)c65)n4)cc3)c2)cc1] |

TABLE 5-continued
| Compound number | Molecular structure |
| --- | --- |
| 4 | 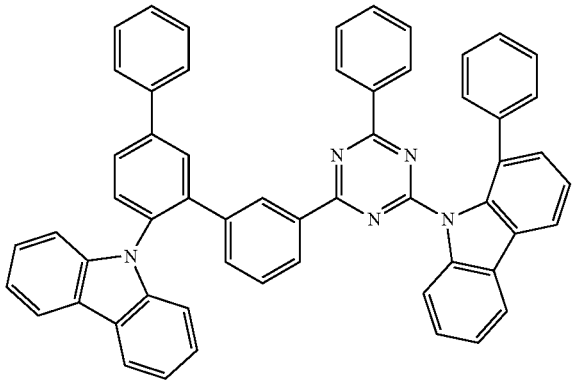 [SMILES: c1ccc(-c2ccc(-n3c4ccccc4c4ccccc43)c(-c3cccc(-c4nc(-c5ccccc5)nc(-n5c6ccccc6c6cccc(-c7ccccc7)c65)n4)c3)c2)cc1] |
| 5 | 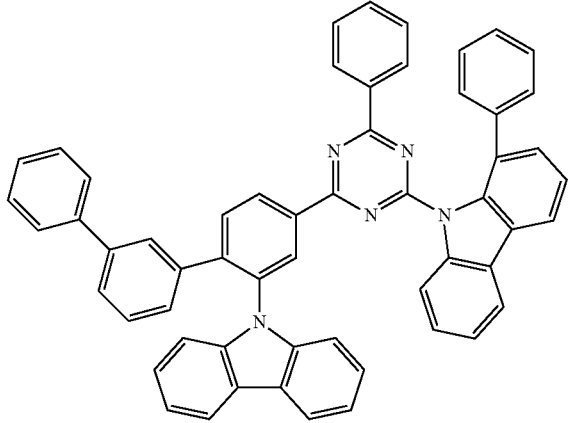 [SMILES: c1ccc(-c2cccc(-c3ccc(-c4nc(-c5ccccc5)nc(-n5c6ccccc6c6cccc(-c7ccccc7)c65)n4)cc3-n3c4ccccc4c4ccccc43)c2)cc1] |
| 6 | 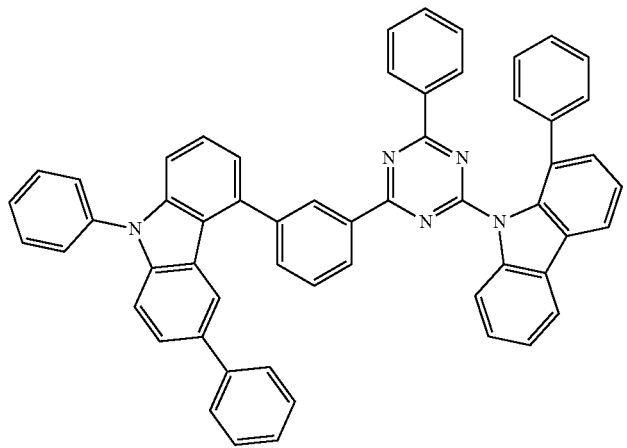 [SMILES: c1ccc(-c2ccc3c(c2)c2c(-c4cccc(-c5nc(-c6ccccc6)nc(-n6c7ccccc7c7cccc(-c8ccccc8)c76)n5)c4)cccc2n3-c2ccccc2)cc1] |

TABLE 5-continued
| Compound number | Molecular structure |
|---|---|
| 8 | 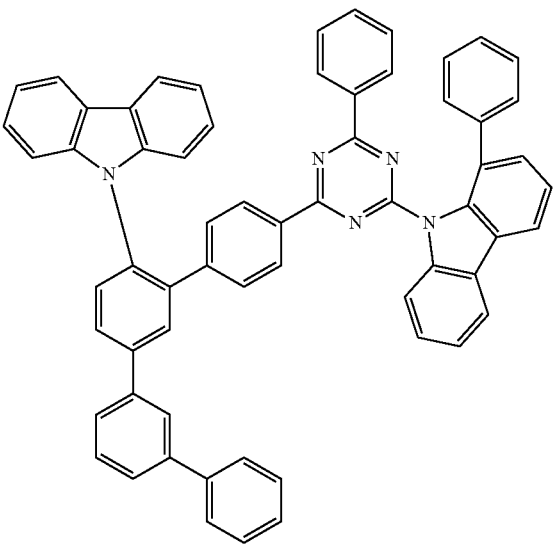 [SMILES: c1ccc(-c2cccc(-c3ccc(-n4c5ccccc5c5ccccc54)c(-c4ccc(-c5nc(-c6ccccc6)nc(-n6c7ccccc7c7cccc(-c8ccccc8)c76)n5)cc4)c3)c2)cc1] |
| 9 | 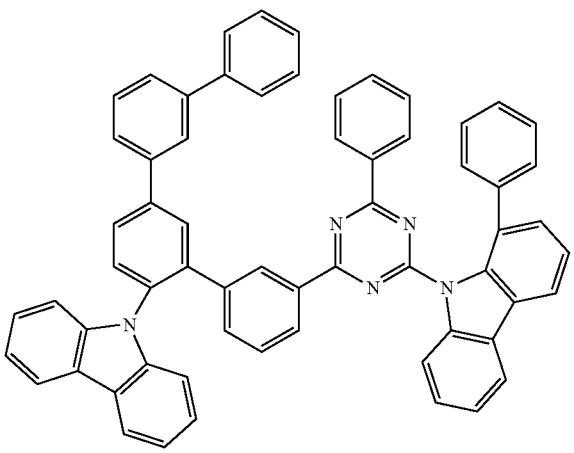 [SMILES: c1ccc(-c2cccc(-c3ccc(-n4c5ccccc5c5ccccc54)c(-c4cccc(-c5nc(-c6ccccc6)nc(-n6c7ccccc7c7cccc(-c8ccccc8)c76)n5)c4)c3)c2)cc1] |
| 48 | 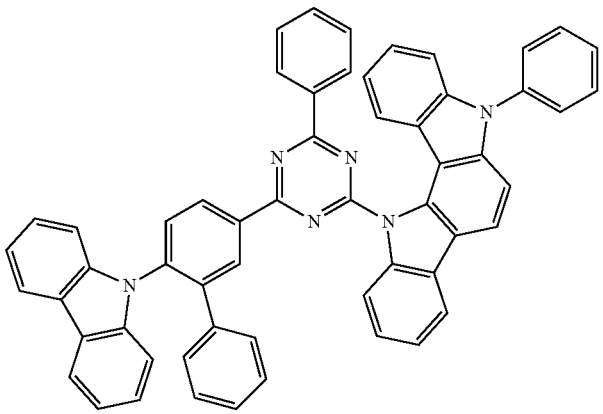 [SMILES: c1ccc(-c2nc(-c3ccc(-n4c5ccccc5c5ccccc54)c(-c4ccccc4)c3)nc(-n3c4ccccc4c4ccc5c(c6ccccc6n5-c5ccccc5)c43)n2)cc1] |

TABLE 5-continued
| Compound number | Molecular structure |
| --- | --- |
| 64 | 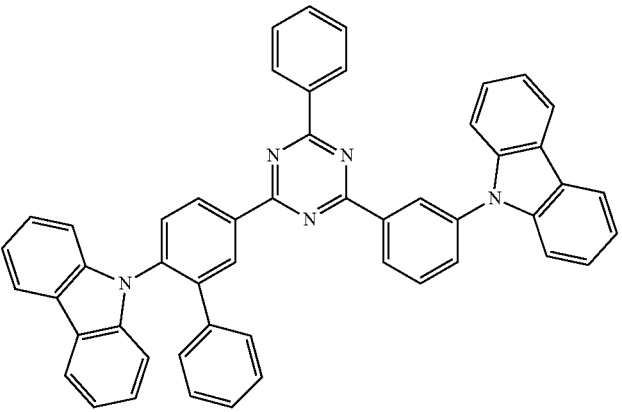 [SMILES: c1ccc(-c2nc(-c3cccc(-n4c5ccccc5c5ccccc54)c3)nc(-c3ccc(-n4c5ccccc5c5ccccc54)c(-c4ccccc4)c3)n2)cc1] |
| 65 | 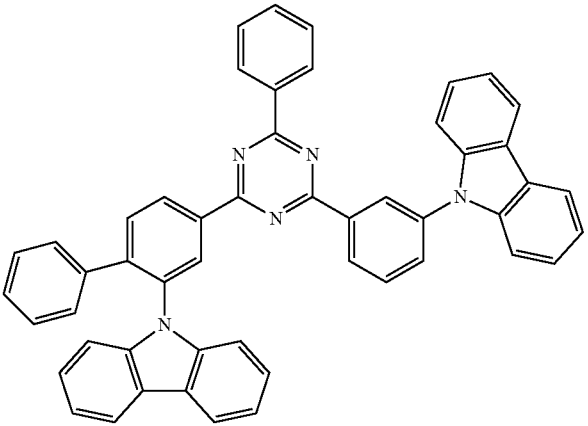 [SMILES: c1ccc(-c2nc(-c3cccc(-n4c5ccccc5c5ccccc54)c3)nc(-c3ccc(-c4ccccc4)c(-n4c5ccccc5c5ccccc54)c3)n2)cc1] |
| 70 | 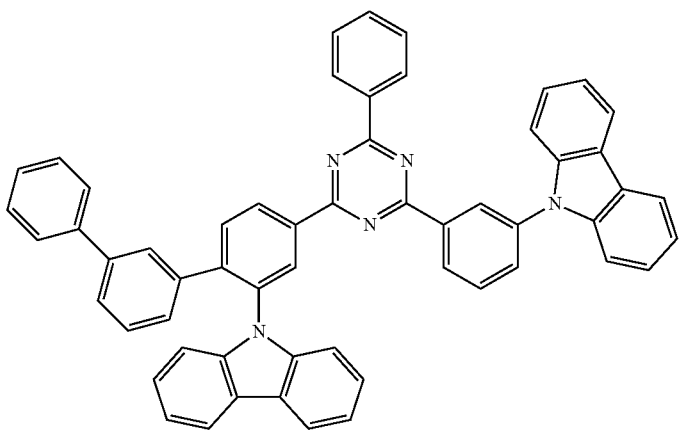 [SMILES: c1ccc(-c2cccc(-c3ccc(-c4nc(-c5ccccc5)nc(-c5cccc(-n6c7ccccc7c7ccccc76)c5)n4)cc3-n3c4ccccc4c4ccccc43)c2)cc1] |

TABLE 5-continued

| Compound number | Molecular structure |
|---|---|
| 71 | 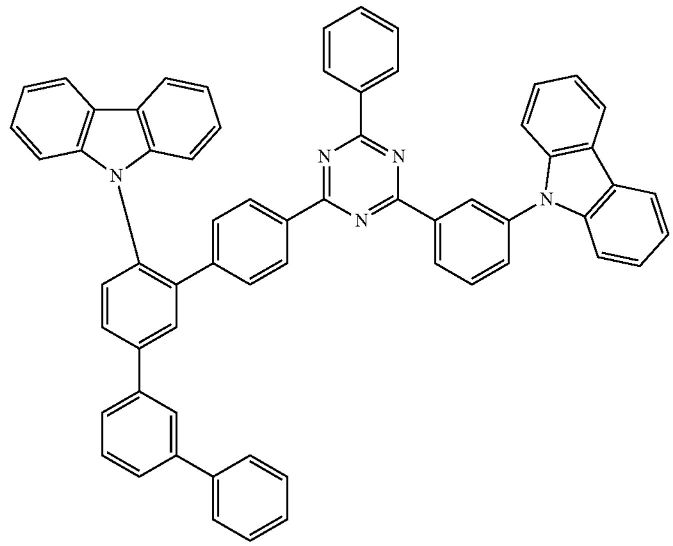 [SMILES: c1ccc(-c2cccc(-c3ccc(-n4c5ccccc5c5ccccc54)c(-c4ccc(-c5nc(-c6ccccc6)nc(-c6cccc(-n7c8ccccc8c8ccccc87)c6)n5)cc4)c3)c2)cc1] |
| 81 | 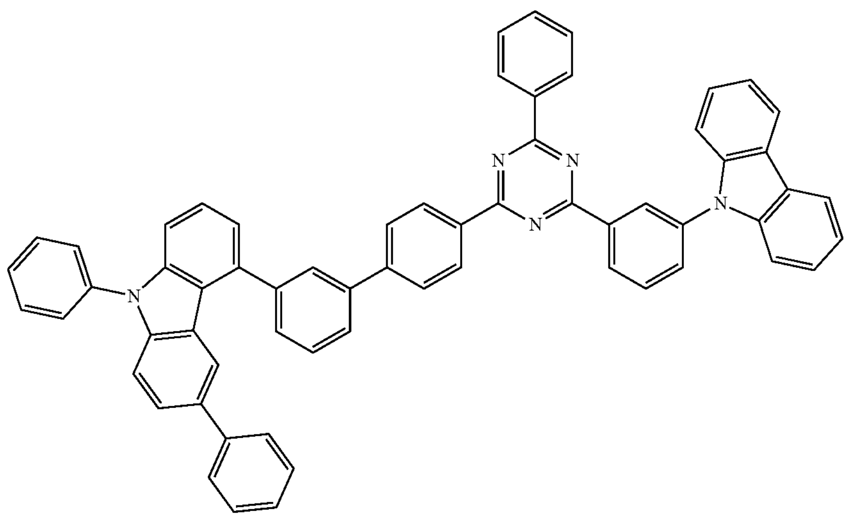 [SMILES: c1ccc(-c2ccc3c(c2)c2c(-c4cccc(-c5ccc(-c6nc(-c7ccccc7)nc(-c7cccc(-n8c9ccccc9c9ccccc98)c7)n6)cc5)c4)cccc2n3-c2ccccc2)cc1] |
| 89 | 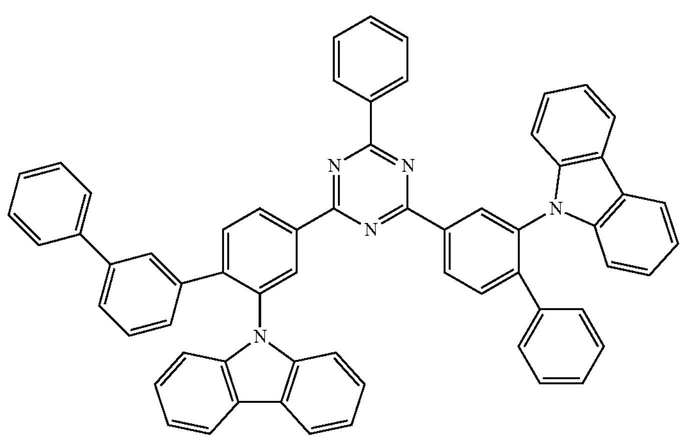 [SMILES: c1ccc(-c2cccc(-c3ccc(-c4nc(-c5ccccc5)nc(-c5ccc(-c6ccccc6)c(-n6c7ccccc7c7ccccc76)c5)n4)cc3-n3c4ccccc4c4ccccc43)c2)cc1] |

TABLE 5-continued

| Compound number | Molecular structure |
|---|---|
| 106 | 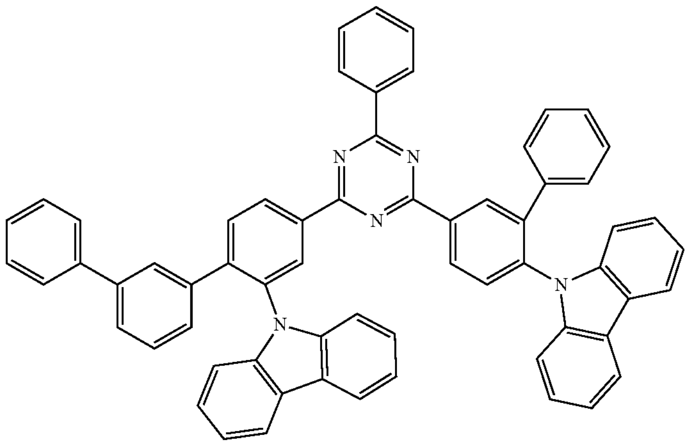 [SMILES: c1ccc(-c2cccc(-c3ccc(-c4nc(-c5ccccc5)nc(-c5ccc(-n6c7ccccc7c7ccccc76)c(-c6ccccc6)c5)n4)cc3-n3c4ccccc4c4ccccc43)c2)cc1] |
| 130 | 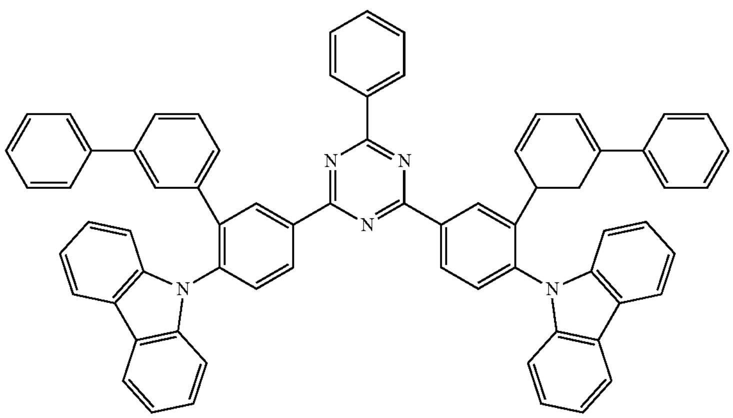 [SMILES: C1=CC(c2cc(-c3nc(-c4ccccc4)nc(-c4ccc(-n5c6ccccc6c6ccccc65)c(-c5cccc(-c6ccccc6)c5)c4)n3)ccc2-n2c3ccccc3c3ccccc32)CC(c2ccccc2)=C1] |
| 133 | 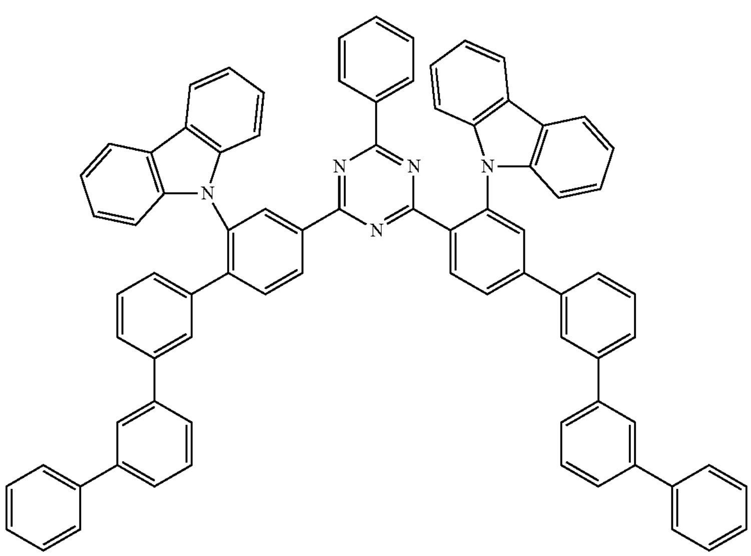 [SMILES: c1ccc(-c2cccc(-c3cccc(-c4ccc(-c5nc(-c6ccccc6)nc(-c6ccc(-c7cccc(-c8cccc(-c9ccccc9)c8)c7)c(-n7c8ccccc8c8ccccc87)c6)n5)c(-n5c6ccccc6c6ccccc65)c4)c3)c2)cc1] |

TABLE 5-continued
| Compound number | Molecular structure |
| --- | --- |
| 216 | 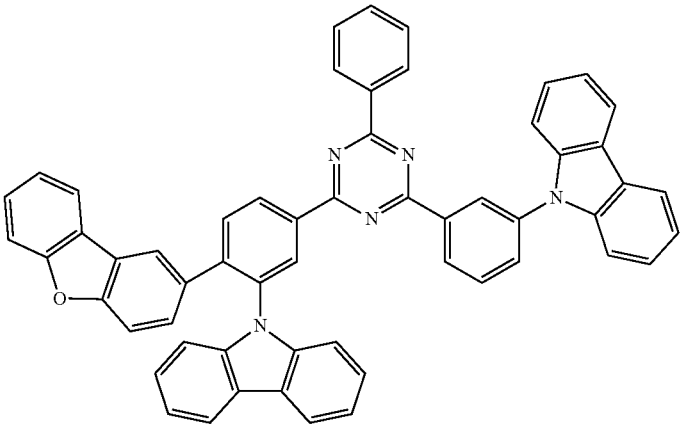 [SMILES: c1ccc(-c2nc(-c3cccc(-n4c5ccccc5c5ccccc54)c3)nc(-c3ccc(-c4ccc5oc6ccccc6c5c4)c(-n4c5ccccc5c5ccccc54)c3)n2)cc1] |
| 306 | 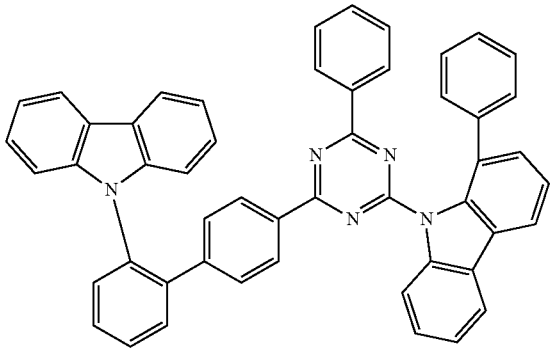 [SMILES: c1ccc(-c2nc(-c3ccc(-c4ccccc4-n4c5ccccc5c5ccccc54)cc3)nc(-n3c4ccccc4c4cccc(-c5ccccc5)c43)n2)cc1] |
| 307 | 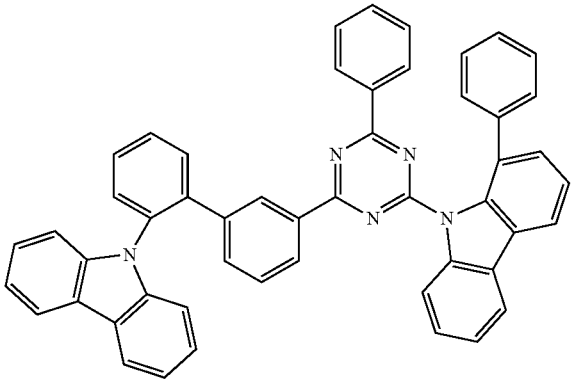 [SMILES: c1ccc(-c2nc(-c3cccc(-c4ccccc4-n4c5ccccc5c5ccccc54)c3)nc(-n3c4ccccc4c4cccc(-c5ccccc5)c43)n2)cc1] |
| 341 | 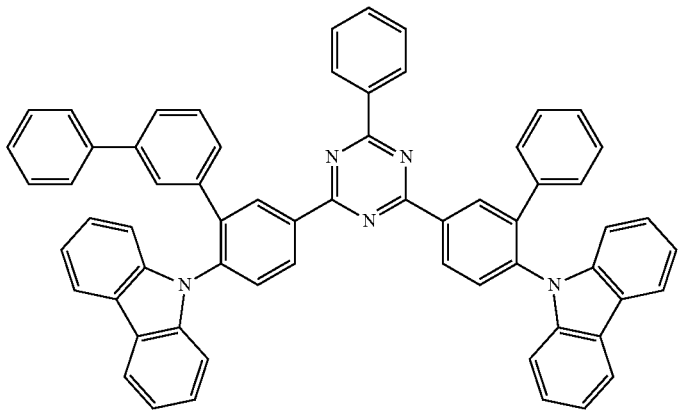 [SMILES: c1ccc(-c2cccc(-c3cc(-c4nc(-c5ccccc5)nc(-c5ccc(-n6c7ccccc7c7ccccc76)c(-c6ccccc6)c5)n4)ccc3-n3c4ccccc4c4ccccc43)c2)cc1] |

TABLE 5-continued
| Compound number | Molecular structure |
|---|---|
| 386 | 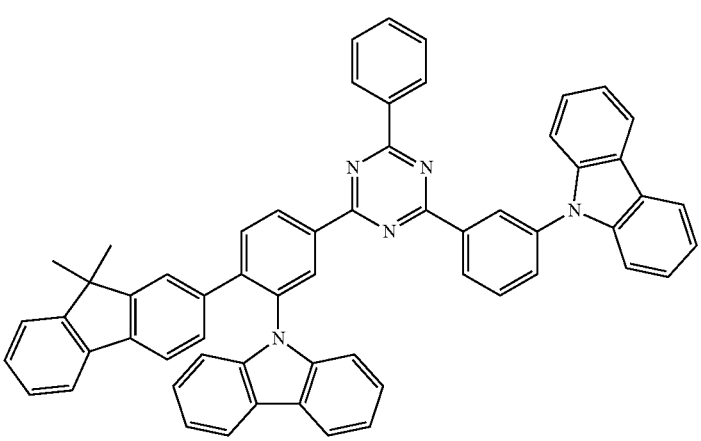 [SMILES: CC1(C)c2ccccc2-c2ccc(-c3ccc(-c4nc(-c5ccccc5)nc(-c5cccc(-n6c7ccccc7c7ccccc76)c5)n4)cc3-n3c4ccccc4c4ccccc43)cc21] |
| 388 | 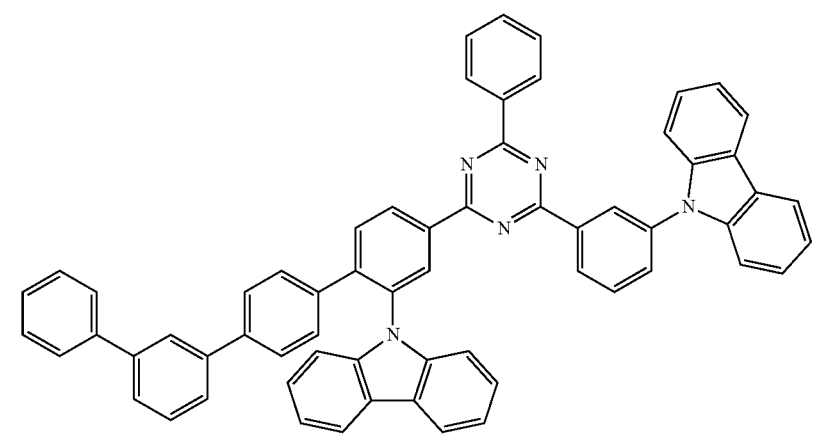 [SMILES: c1ccc(-c2cccc(-c3ccc(-c4ccc(-c5nc(-c6ccccc6)nc(-c6cccc(-n7c8ccccc8c8ccccc87)c6)n5)cc4-n4c5ccccc5c5ccccc54)cc3)c2)cc1] |
| 390 | 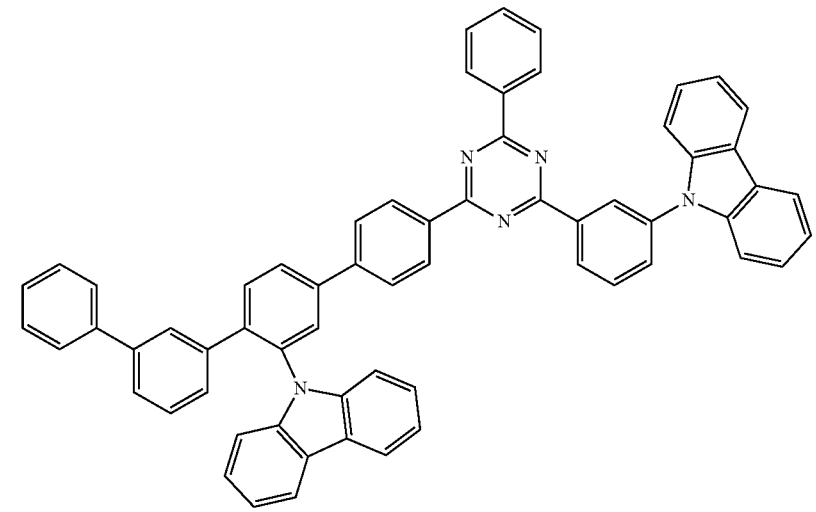 [SMILES: c1ccc(-c2cccc(-c3ccc(-c4ccc(-c5nc(-c6ccccc6)nc(-c6cccc(-n7c8ccccc8c8ccccc87)c6)n5)cc4)cc3-n3c4ccccc4c4ccccc43)c2)cc1] |

TABLE 5-continued

| Compound number | Molecular structure |
|---|---|
| 404 | 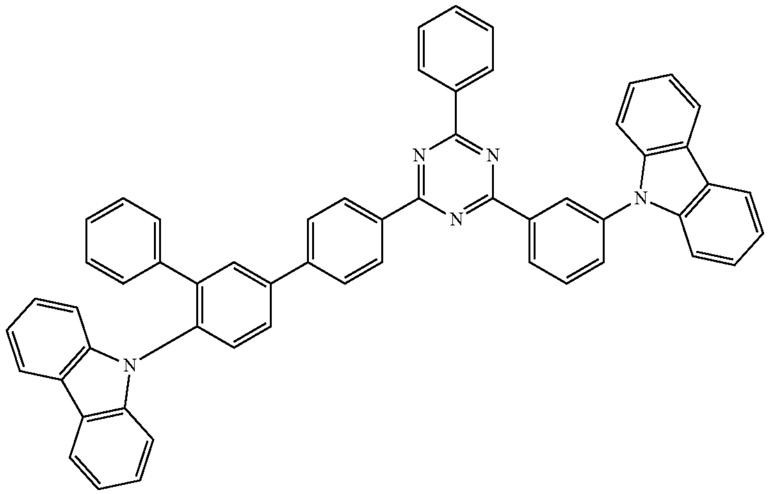 [SMILES: c1ccc(-c2nc(-c3ccc(-c4ccc(-n5c6ccccc6c6ccccc65)c(-c5ccccc5)c4)cc3)nc(-c3cccc(-n4c5ccccc5c5ccccc54)c3)n2)cc1] |
| 405 | 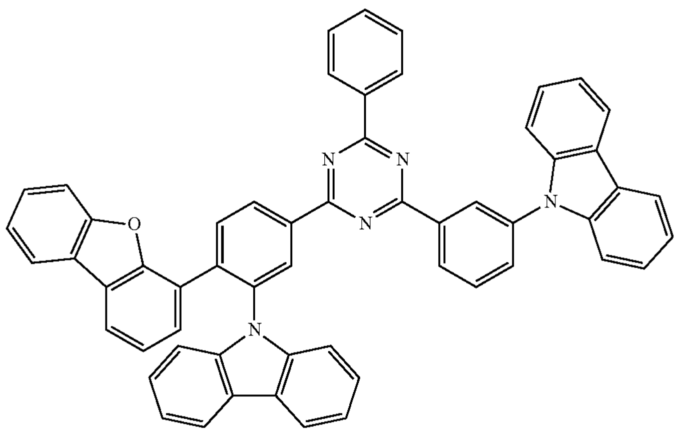 [SMILES: c1ccc(-c2nc(-c3cccc(-n4c5ccccc5c5ccccc54)c3)nc(-c3ccc(-c4cccc5c4oc4ccccc45)c(-n4c5ccccc5c5ccccc54)c3)n2)cc1] |
| 418 | 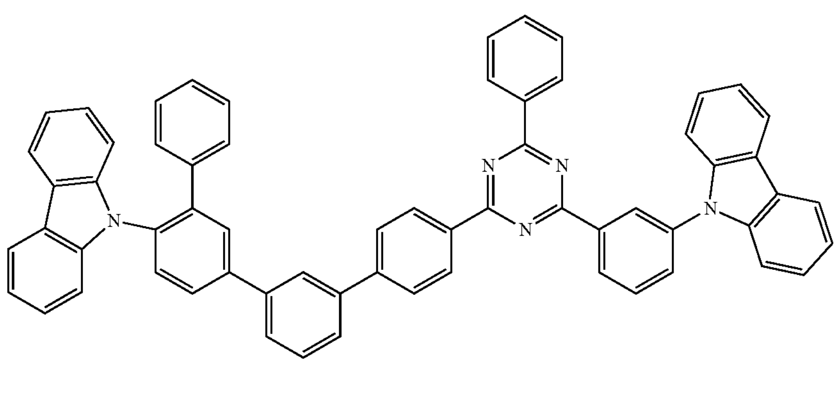 [SMILES: c1ccc(-c2nc(-c3ccc(-c4cccc(-c5ccc(-n6c7ccccc7c7ccccc76)c(-c6ccccc6)c5)c4)cc3)nc(-c3cccc(-n4c5ccccc5c5ccccc54)c3)n2)cc1] |

TABLE 5-continued
| Compound number | Molecular structure |
|---|---|
| 421 | 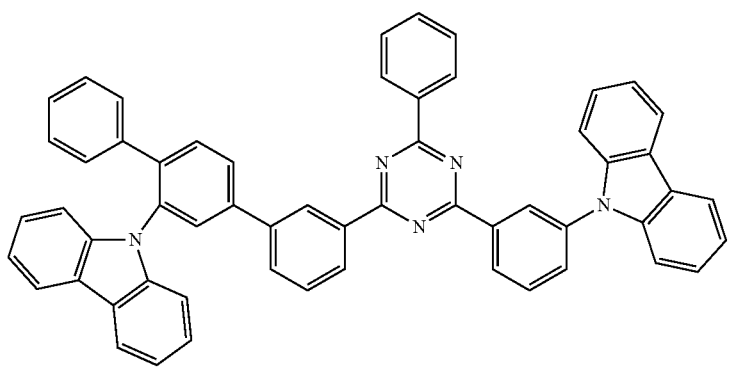 [SMILES: c1ccc(-c2nc(-c3cccc(-c4ccc(-c5ccccc5)c(-n5c6ccccc6c6ccccc65)c4)c3)nc(-c3cccc(-n4c5ccccc5c5ccccc54)c3)n2)cc1] |
| 470 | 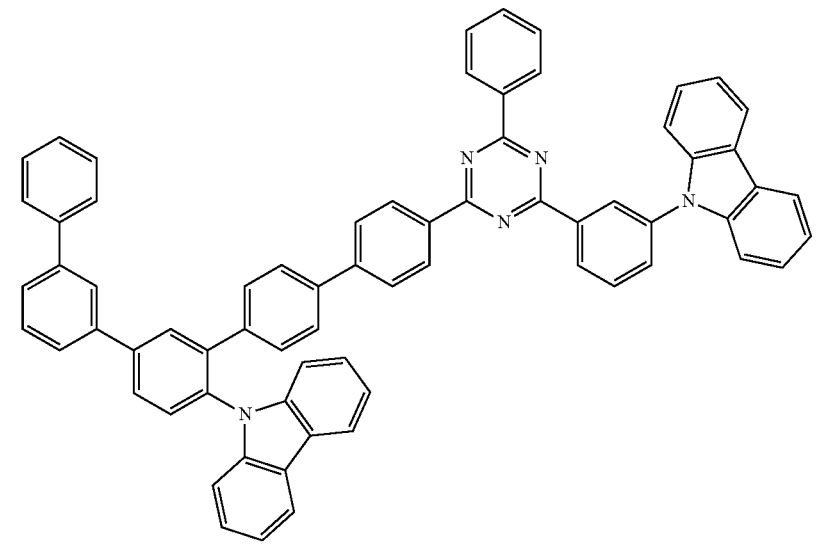 [SMILES: c1ccc(-c2cccc(-c3ccc(-n4c5ccccc5c5ccccc54)c(-c4ccc(-c5ccc(-c6nc(-c7ccccc7)nc(-c7cccc(-n8c9ccccc9c9ccccc98)c7)n6)cc5)cc4)c3)c2)cc1] |
| 492 | 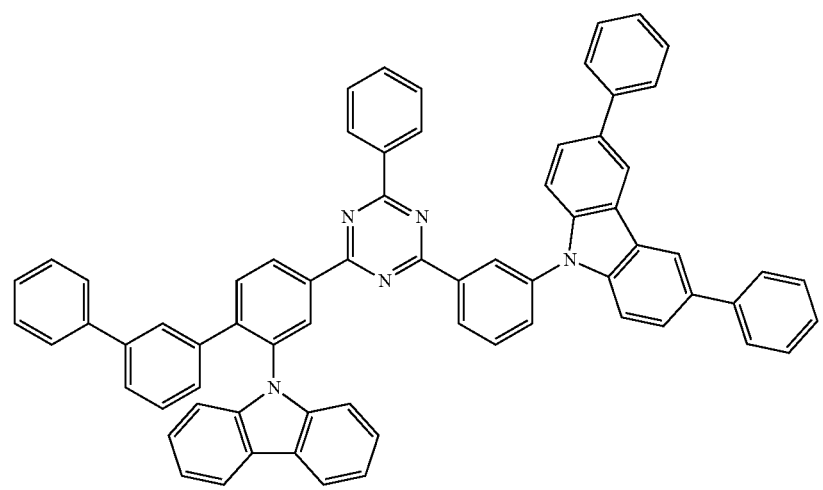 [SMILES: c1ccc(-c2cccc(-c3ccc(-c4nc(-c5ccccc5)nc(-c5cccc(-n6c7ccc(-c8ccccc8)cc7c7cc(-c8ccccc8)ccc76)c5)n4)cc3-n3c4ccccc4c4ccccc43)c2)cc1] |

TABLE 5-continued

| Compound number | Molecular structure |
|---|---|
| 508 | 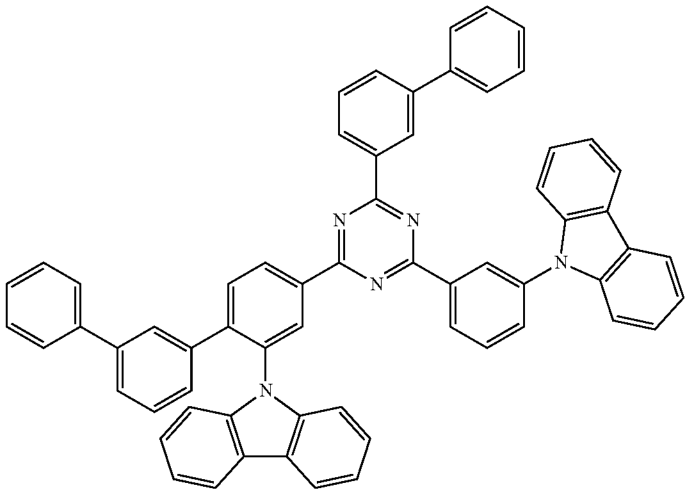 [SMILES: c1ccc(-c2cccc(-c3nc(-c4cccc(-n5c6ccccc6c6ccccc65)c4)nc(-c4ccc(-c5cccc(-c6ccccc6)c5)c(-n5c6ccccc6c6ccccc65)c4)n3)c2)cc1] |

Example 1

As a first electrode, poly(3,4-ethylene dioxythiophene)/poly(4-styrene sulfonate) (PEDOT/PSS) (Sigma-Aldrich) was coated on a glass substrate, on which a 150-nm ITO (anode) having a stripe shape, to a dry film thickness of 30 nm by spin coating to form a hole injection layer.

Then, 1 weight % of a solution, in which poly(9,9-dioctyl-fluorene-co-N-(4-butylphenyl)-diphenylamine) (TFB) was dissolved in xylene, was coated on the hole injection layer to a dry film thickness of 30 nm by spin coating and heated at a temperature of 230° C. for 1 hour to form a hole transport layer.

Then, a toluene solution containing H-1 as a material for forming a hole transporting host, Compound 1 synthesized in Synthesis Example 1 as a material for forming an electron transporting host, and tris(2-(3-p-xylyl)phenyl)pyridine iridium (TEG) was coated on the hole transport layer to a dry film thickness of 50 nm by spin coating and heated at a temperature of 120° C. for 1 hour to form an emission layer. At this time, H-1, Compound 1, and TEG were 25 weight %, 70 weight %, and 5 weight % based on the total weight of the emission layer, respectively.

Then, the substrate on which up to the emission layer was formed was provided to a vacuum deposition apparatus. (8-hydroxyquinolinolato)lithium (LiQ) and KLET-03 (Chemipro Kasei) were co-deposited on the emission layer to form an electron transport layer having a thickness of 30 nm.

Then, lithium fluoride (LiF) was deposited on the electron transport layer by a vacuum deposition apparatus to form an electron injection layer having a thickness of 1 nm.

Then, aluminum (Al) was deposited on the electron injection layer by a vacuum deposition apparatus to form a second electrode (cathode) having a thickness of 100 nm, thereby completing the manufacture of an organic light-emitting device.

The organic light-emitting device was sealed by using a glass sealing tube containing a drying agent and an ultraviolet curable resin in a glove box in a nitrogen atmosphere, in which moisture and oxygen concentrations were 1 ppm or less and was then evaluated. The results thereof are shown in Table 6.

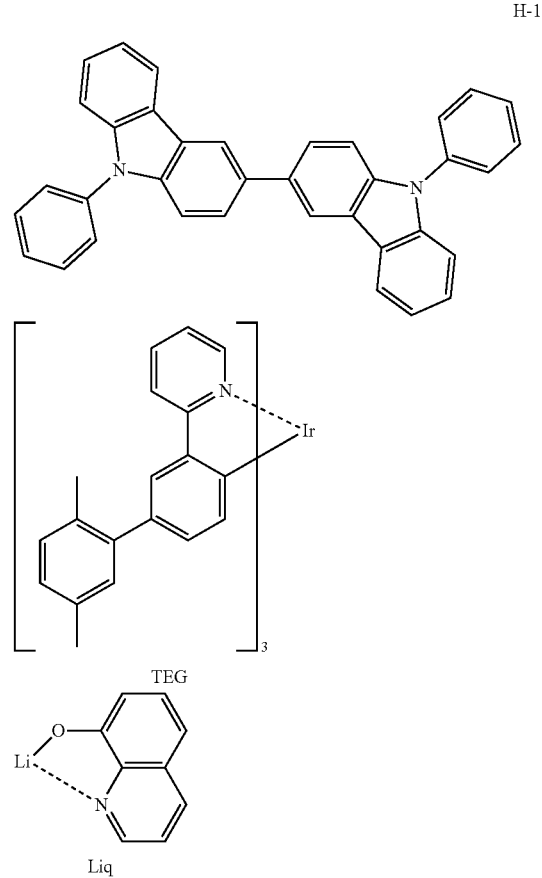

Examples 2 to 27

Organic light-emitting devices were manufactured in the same manner as in Example 1, except that Compounds 3, 4, 5, 6, 8, 9, 48, 64, 65, 70, 71, 81, 89, 106, 133, 216, 386, 388, 390, 404, 405, 418, 421, 470, 492, and 508 were each used instead of Compound 1 as a material for forming an electron transporting host. The results thereof are shown in Table 6.

Comparative Example 1

An organic light-emitting device was manufactured in the same manner as in Example 1, except that Comparative Example Compound C1 was used instead of Compound 1 as a material for forming an electron transporting host. The evaluation results thereof are shown in Table 6.

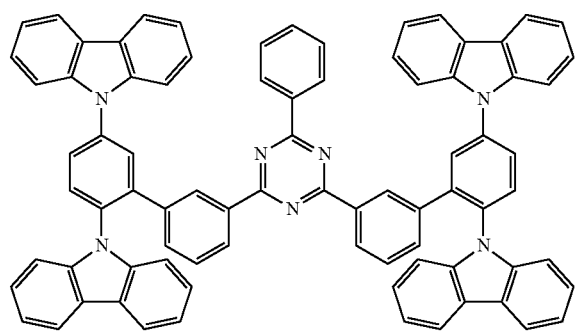

Comparative Example 2

An organic light-emitting device was manufactured in the same manner as in Example 1, except that Comparative Example Compound C2 was used instead of Compound 1 as a material for forming an electron transporting host. The evaluation results thereof are shown in Table 6.

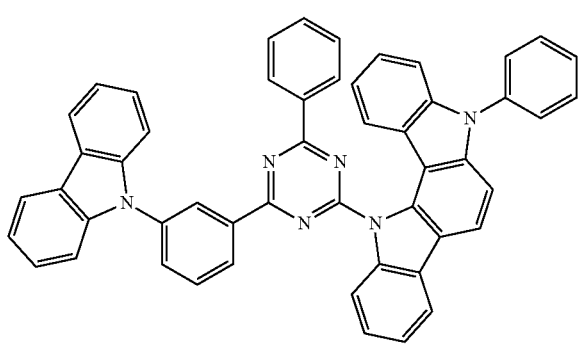

Comparative Example 3

An organic light-emitting device was manufactured in the same manner as in Example 1, except that Comparative Example Compound C3 was used instead of Compound 1 as a material for forming an electron transporting host. The evaluation results thereof are shown in Table 6.

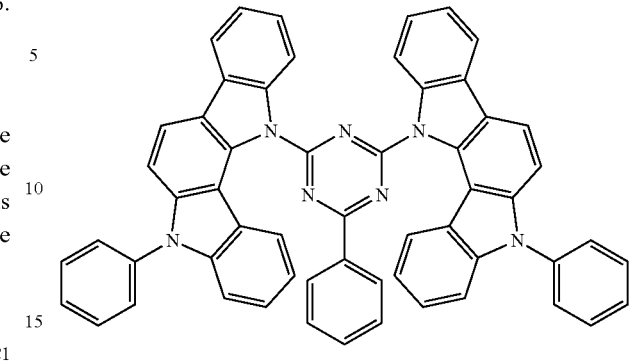

Comparative Example 4

An organic light-emitting device was manufactured in the same manner as in Example 1, except that Comparative Example Compound C6 was used instead of Compound 1 as a material for forming an electron transporting host. The evaluation results thereof are shown in Table 6.

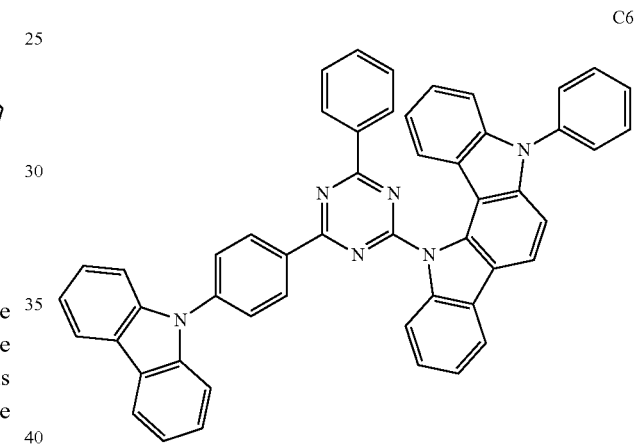

Comparative Example 5

An organic light-emitting device was manufactured in the same manner as in Example 1, except that Comparative Example Compound C7 was used instead of Compound 1 as a material for forming an electron transporting host. The evaluation results thereof are shown in Table 6.

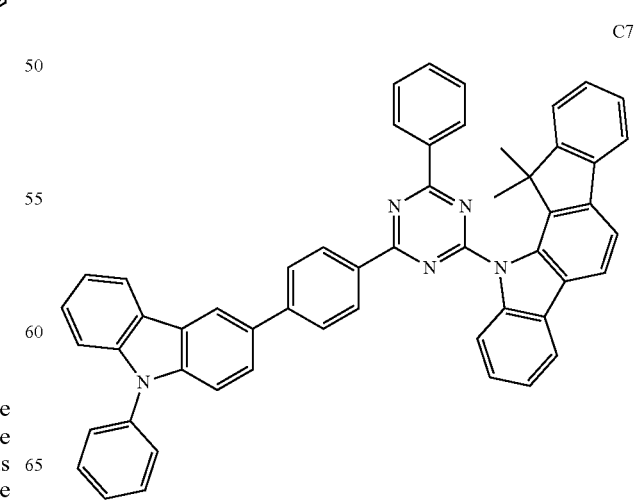

Comparative Example 6

An organic light-emitting device was manufactured in the same manner as in Example 1, except that Comparative Example Compound C9 was used instead of Compound 1 as a material for forming an electron transporting host. The evaluation results thereof are shown in Table 6.

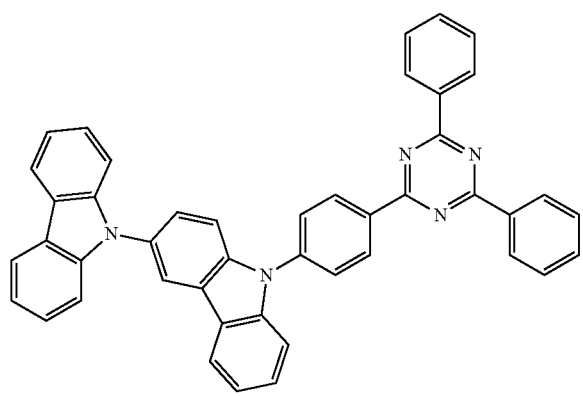

C9

Comparative Example 7

An organic light-emitting device was manufactured in the same manner as in Example 1, except that Comparative Example Compound C10 was used instead of Compound 1 as a material for forming an electron transporting host. The evaluation results thereof are shown in Table 6.

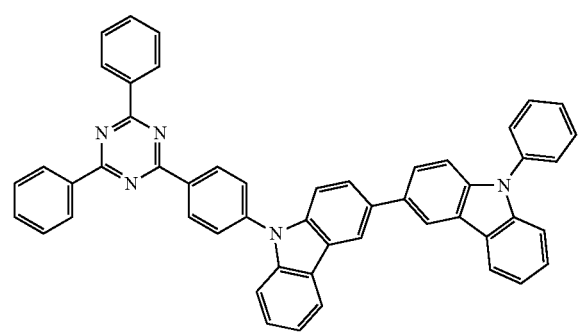

C10

TABLE 6

| | Material for forming electron transporting host | Current efficiency | Emission lifespan |
| --- | --- | --- | --- |
| Example 1 | Compound 1 | 131 | 190 |
| Example 2 | Compound 3 | 148 | 205 |
| Example 3 | Compound 4 | 144 | 245 |
| Example 4 | Compound 5 | 137 | 195 |
| Example 5 | Compound 6 | 122 | 140 |
| Example 6 | Compound 8 | 140 | 200 |
| Example 7 | Compound 9 | 139 | 185 |
| Example 8 | Compound 48 | 130 | 230 |
| Example 9 | Compound 64 | 136 | 255 |
| Example 10 | Compound 65 | 138 | 285 |
| Example 11 | Compound 70 | 149 | 300 |
| Example 12 | Compound 71 | 148 | 175 |
| Example 13 | Compound 81 | 128 | 240 |
| Example 14 | Compound 89 | 152 | 285 |
| Example 15 | Compound 106 | 151 | 315 |
| Example 16 | Compound 133 | 144 | 225 |
| Example 17 | Compound 216 | 146 | 290 |
| Example 18 | Compound 386 | 140 | 260 |
| Example 19 | Compound 388 | 143 | 255 |
| Example 20 | Compound 390 | 151 | 295 |
| Example 21 | Compound 404 | 148 | 310 |
| Example 22 | Compound 405 | 132 | 270 |
| Example 23 | Compound 418 | 146 | 290 |
| Example 24 | Compound 421 | 137 | 285 |
| Example 25 | Compound 470 | 142 | 210 |
| Example 26 | Compound 492 | 141 | 255 |
| Example 27 | Compound 508 | 145 | 310 |
| Comparative Example 1 | Comparative Example Compound C1 | 100 | 100 |
| Comparative Example 2 | Comparative Example Compound C2 | 94 | 115 |
| Comparative Example 3 | Comparative Example Compound C3 | 69 | 90 |
| Comparative Example 4 | Comparative Example Compound C6 | 107 | 120 |
| Comparative Example 5 | Comparative Example Compound C7 | 53 | 30 |
| Comparative Example 6 | Comparative Example Compound C9 | 113 | 70 |
| Comparative Example 7 | Comparative Example Compound C10 | 76 | 85 |

Referring to Table 6, it is confirmed that Examples 1 to 27 using the compound of the present disclosure as a host material exhibit excellent current efficiency, as compared with those of Comparative Examples 1 to 7, and also exhibit improved emission lifespan. In addition, Examples 1 to 27 exhibit characteristics in which a film is in a uniform and defect-free state after heating at a temperature of 125° C., and further exhibit excellent film formation characteristics. Therefore, it is confirmed that Compound according to the present disclosure is suitable for use as a material for an organic light-emitting device for a coating process.

Since the heterocyclic compound has improved electric characteristics and/or thermal stability, the organic light-emitting device including the heterocyclic compound may have improved current efficiency and lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present description as defined by the following claims.

What is claimed is:
1. A heterocyclic compound represented by Formula 1:
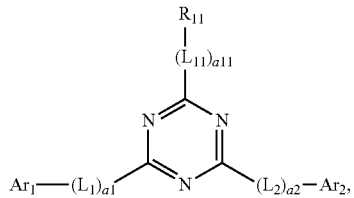
Formula 1
Ar₁ is selected from groups represented by Formulae 2-1(2) to 2-1(6), 2-2(1) to 2-2(18), and 2-3(1) to 2-3(13), and
Ar₂ is selected from groups represented by Formulae 2-1(1) to 2-1(6), 2-2(1) to 2-2(18), 2-3(1) to 2-3(13), and 2-6(1) to 2-6(11):
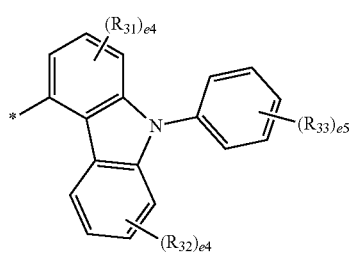
2-1(1)
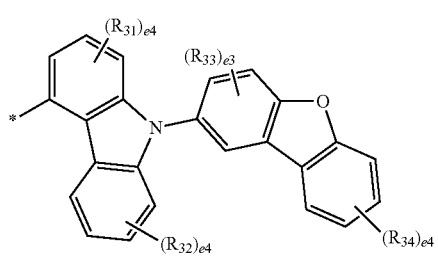
2-1(2)
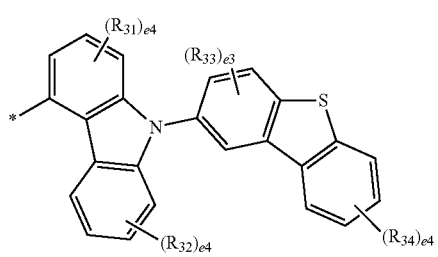
2-1(3)
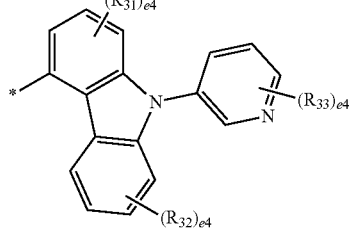
2-1(4)
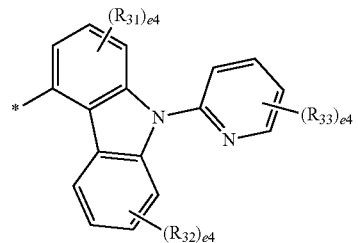
2-1(5)
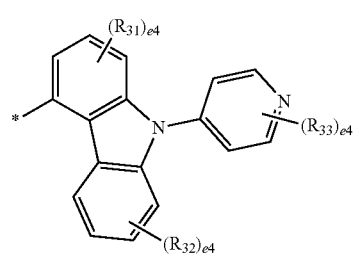
2-1(6)
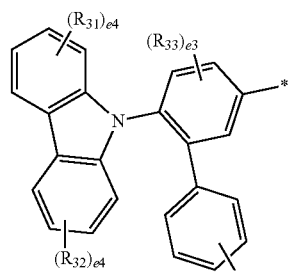
2-2(1)
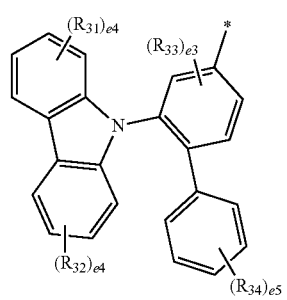
2-2(2)
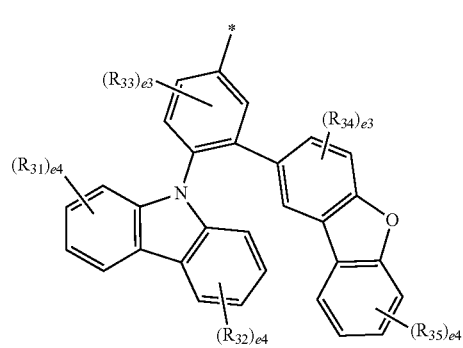
2-2(3)

2-2(4) 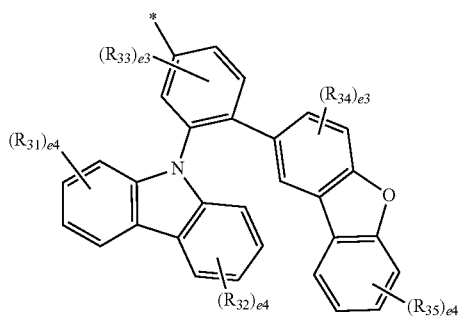
2-2(5) 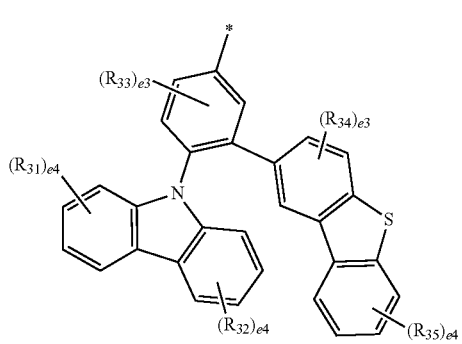
2-2(6) 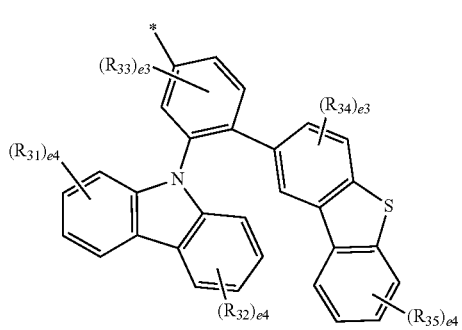
2-2(7) 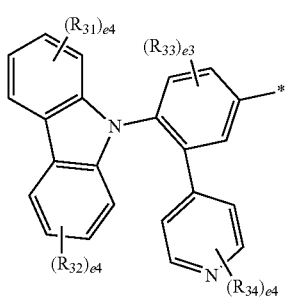
2-2(8) 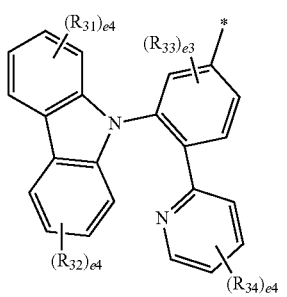
2-2(9) 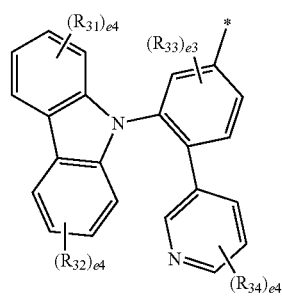
2-2(10) 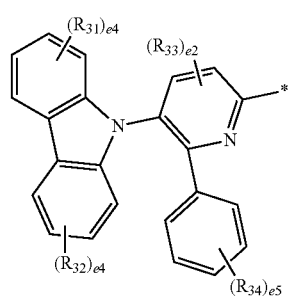
2-2(11) 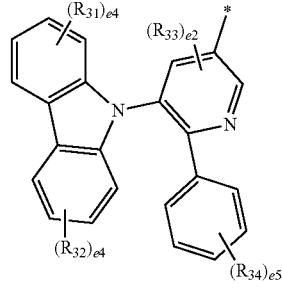
2-2(12) 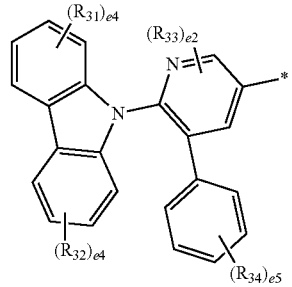
2-2(13)

-continued
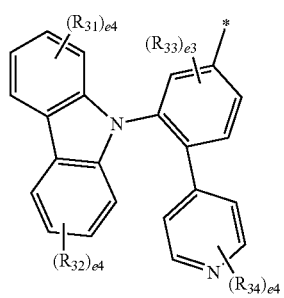
2-2(14)
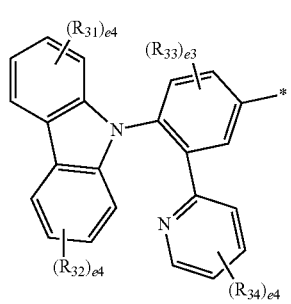
2-2(15)
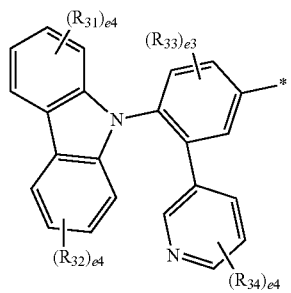
2-2(16)
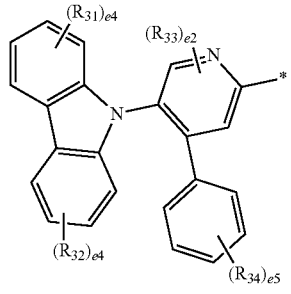
2-2(17)
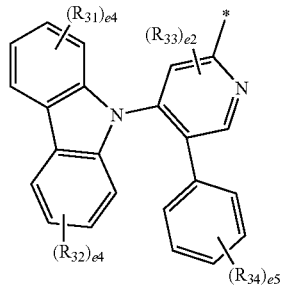
2-2(18)
-continued
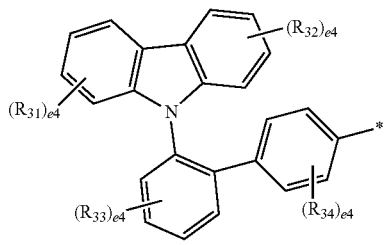
2-3(1)
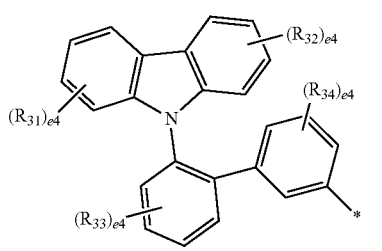
2-3(2)
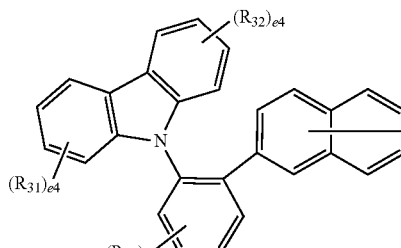
2-3(3)
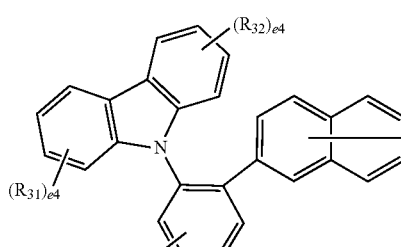
2-3(4)
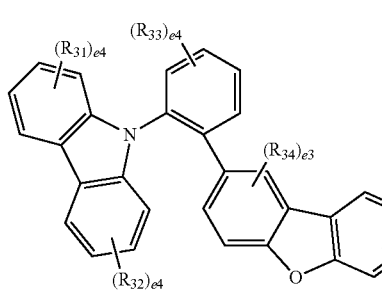
2-3(5)
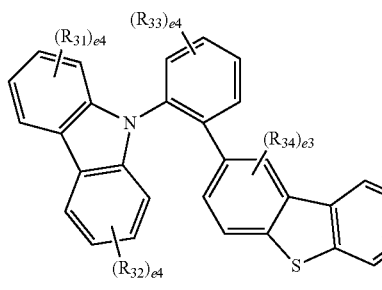
2-3(6)

-continued
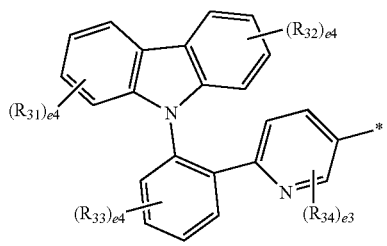
2-3(7)
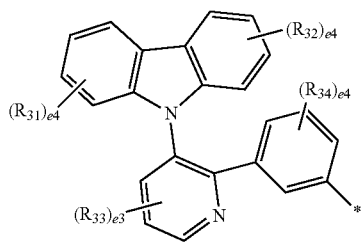
2-3(8)
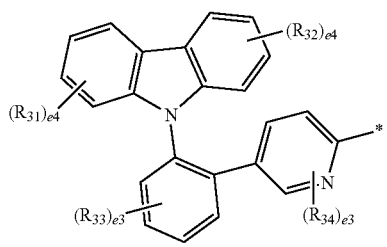
2-3(9)
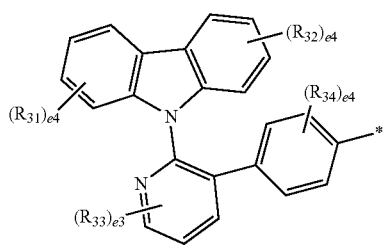
2-3(10)
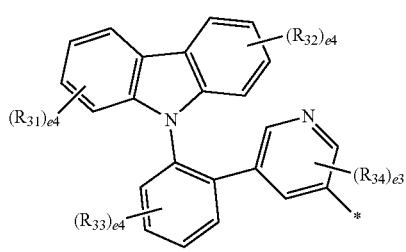
2-3(11)
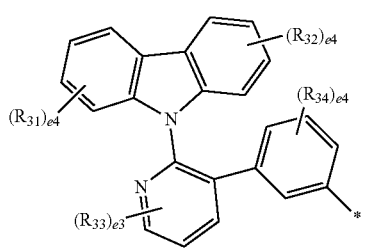
2-3(12)
-continued
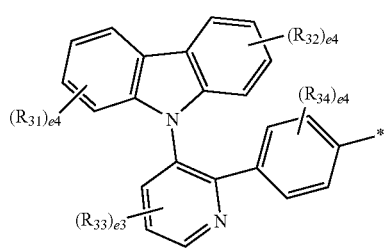
2-3(13)
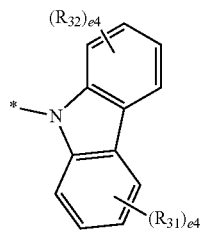
2-6(1)
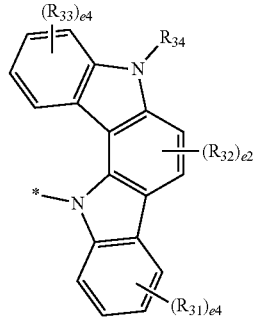
2-6(2)
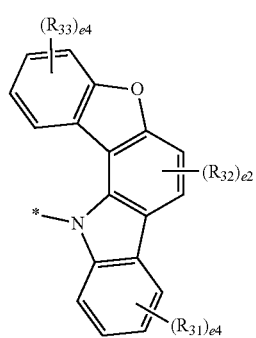
2-6(3)
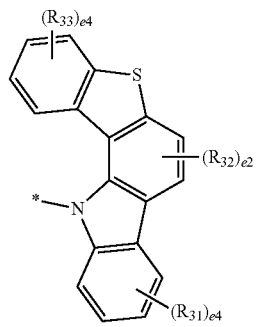
2-6(4)

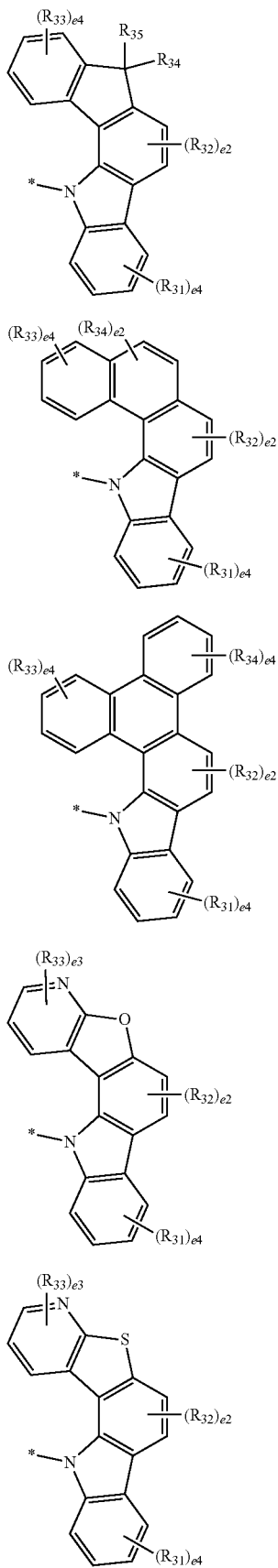
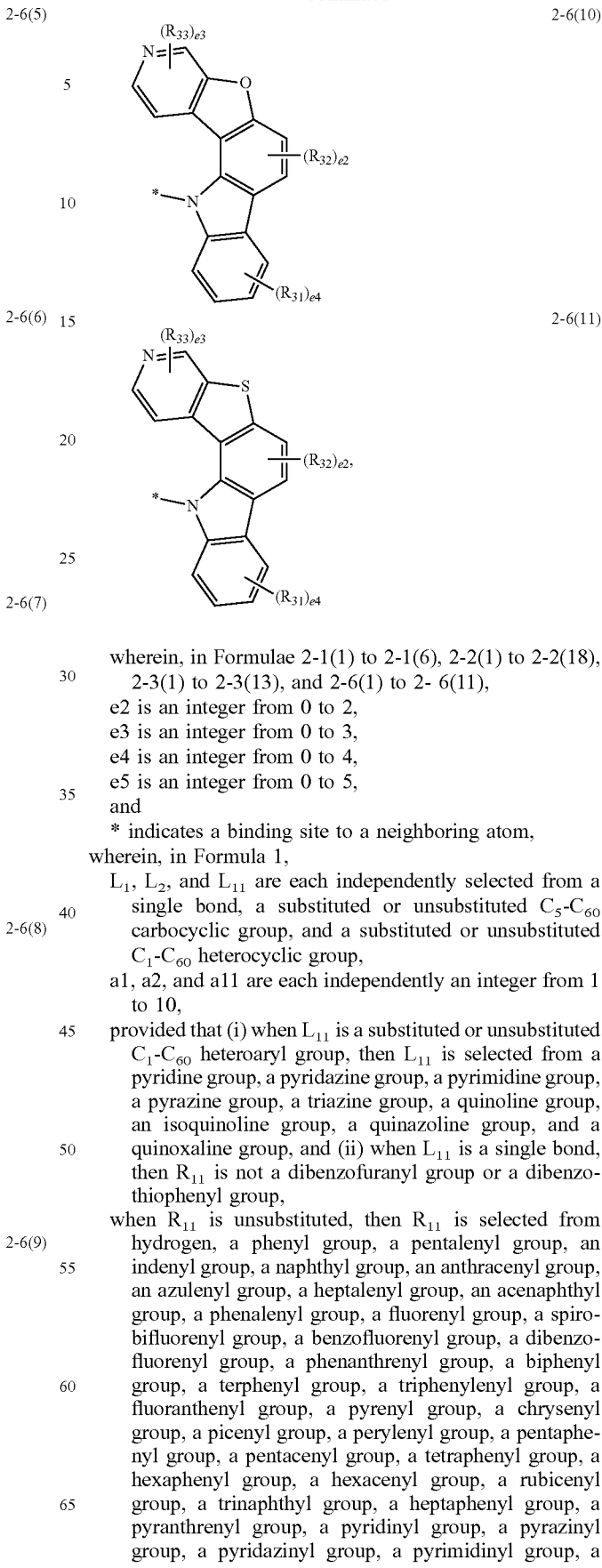

wherein, in Formulae 2-1(1) to 2-1(6), 2-2(1) to 2-2(18), 2-3(1) to 2-3(13), and 2-6(1) to 2-6(11),
e2 is an integer from 0 to 2,
e3 is an integer from 0 to 3,
e4 is an integer from 0 to 4,
e5 is an integer from 0 to 5,
and
* indicates a binding site to a neighboring atom,
wherein, in Formula 1,
$L_1$, $L_2$, and $L_{11}$ are each independently selected from a single bond, a substituted or unsubstituted $C_5$-$C_{60}$ carbocyclic group, and a substituted or unsubstituted $C_1$-$C_{60}$ heterocyclic group,
a1, a2, and a11 are each independently an integer from 1 to 10,
provided that (i) when $L_{11}$ is a substituted or unsubstituted $C_1$-$C_{60}$ heteroaryl group, then $L_{11}$ is selected from a pyridine group, a pyridazine group, a pyrimidine group, a pyrazine group, a triazine group, a quinoline group, an isoquinoline group, a quinazoline group, and a quinoxaline group, and (ii) when $L_{11}$ is a single bond, then $R_{11}$ is not a dibenzofuranyl group or a dibenzothiophenyl group,
when $R_{11}$ is unsubstituted, then $R_{11}$ is selected from hydrogen, a phenyl group, a pentalenyl group, an indenyl group, a naphthyl group, an anthracenyl group, an azulenyl group, a heptalenyl group, an acenaphthyl group, a phenalenyl group, a fluorenyl group, a spirobifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group; and when $R_{11}$ is substituted, then $R_{11}$ is selected from a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group, in Formulae 2-1(1) to 2-1(6), 2-2(1) to 2-2(18), and 2-3(1) to 2-3(13), $R_{31}$ to $R_{35}$ are each independently selected from hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —N($Q_1$)($Q_2$), any neighboring groups selected from $R_{31}$ to $R_{35}$ are optionally linked to form a substituted or unsubstituted $C_5$-$C_{30}$ carbocyclic group or a substituted or unsubstituted $C_2$-$C_{30}$ heterocyclic group, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the unsubstituted $C_7$-$C_{60}$ alkylaryl group, the substituted $C_6$-$C_{60}$ aryloxy group, the substituted $C_6$-$C_{60}$ arylthio group, the substituted $C_1$-$C_{60}$ heteroaryl group, the substituted $C_2$-$C_{60}$ alkylheteroaryl group, the substituted $C_1$-$C_{60}$ heteroaryloxy group, the substituted $C_1$-$C_{60}$ heteroarylthio group, the substituted monovalent non-aromatic condensed polycyclic group, the substituted monovalent non-aromatic condensed heteropolycyclic group, the substituted C5-C30 carbocyclic group, and the substituted $C_2$-$C_{30}$ heterocyclic group is selected from:
deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, and —$C(=O)(Q_{11})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, and —$C(=O)(Q_{21})$; and —$Si(Q_{31})(Q_{32})(Q_{33})$, —$N(Q_{31})(Q_{32})$, and —$C(=O)(Q_{31})$, $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenyl pyridinyl group, a phenyl pyrimidinyl group, a phenyl triazinyl group, a diphenyl pyridinyl group, a diphenyl pyrimidinyl group, a diphenyl triazinyl group, a pyridinyl phenyl group, a dipyridinyl phenyl group, a pyrimidinyl phenyl group, a dipyrimidinyl phenyl group, a triazinyl phenyl group, a ditriazinyl phenyl group, a fluorenyl group, a spiro-bifluorenyl group, a dimethylfluorenyl group, a diphenyl fluorenyl group, a carbazolyl group, a phenylcarbazolyl group, a biphenylcarbazolyl group, a dibenzofuranyl group, a phenyl dibenzofuranyl group, a diphenyl dibenzofuranyl group, a dibenzothiophenyl group, a phenyl dibenzothiophenyl group, and a diphenyl dibenzothiophenyl group, and

* indicates a binding site to a neighboring atom.

2. The heterocyclic compound of claim 1, wherein
$L_1$, $L_2$, and $L_{11}$ are each independently selected from:
a single bond, a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group; and a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group, each substituted with at least one selected from deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonyl group, and a thioxanthonyl group.

3. The heterocyclic compound of claim 1, wherein a1, a2, and a11 are each independently 1 or 2.

4. The heterocyclic compound of claim 1, wherein,
when $Ar_2$ is a group represented by Formula 2-1(1), $L_2$ is respectively linked to the group represented by Formula 2-1(1), is selected from:
a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group; and
a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group, each substituted with at least one selected from deuterium, a cyano group, a phenyl group, a naphthyl group, and a pyridinyl group.

5. The heterocyclic compound of claim 1, wherein,
when $Ar_2$ is a group represented by Formula 2-1(1), $L_2$ is respectively linked to the group represented by Formula 2-1(1), $L_2$ is selected from groups represented by Formulae 3-1 to 3-5:

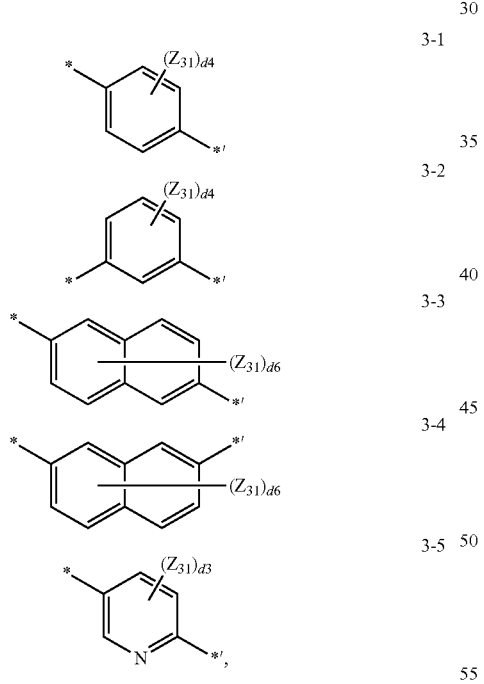

wherein $Z_{31}$ is selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzosilolyl group, and —Si($Q_{31}$)($Q_{32}$)($Q_{33}$), d3 is an integer from 0 to 3,
d4 is an integer from 0 to 4,
d6 is an integer from 0 to 6, and
* and *' each indicate a binding site to a neighboring atom.

6. The heterocyclic compound of claim 1, wherein $R_{31}$ to $R_{35}$ are independently hydrogen or deuterium.

7. The heterocyclic compound of claim 1, wherein, when $Ar_2$ is a group represented by Formula 2-1(1), $R_{31}$ and $R_{32}$ are each independently selected from: hydrogen, a phenyl group, a naphthyl group, a pyridinyl group, a pyrazinyl group, a pyrimidinyl group, and a pyridazinyl group; and a phenyl group, a naphthyl group, a pyridinyl group, a pyrazinyl group, a pyrimidinyl group, and a pyridazinyl group, each substituted with at least one selected from deuterium, —F, —Cl, —Br, —I, a cyano group, a phenyl group, a naphthyl group, a pyridinyl group, a pyrazinyl group, a pyrimidinyl group, and a pyridazinyl group.

8. The heterocyclic compound of claim 1, wherein,
when $Ar_2$ is a group represented by Formula 2-6(1) and $L_2$ is a single bond, $X_1$, $R_{31}$ and $R_{32}$ are each independently a substituted or unsubstituted $C_6$-$C_{60}$ aryl group or a substituted or unsubstituted $C_1$-$C_{60}$ heteroaryl group.

9. The heterocyclic compound of claim 1, wherein $R_{31}$ to $R_{35}$ are each independently selected from:
hydrogen, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group; and hydrogen or a phenyl group, a pentalenyl group, an indenyl group, a naphthyl group, an anthracenyl group, an azulenyl group, a heptalenyl group, an acenaphthyl group, a phenalenyl group, a fluorenyl group, a spirobifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spirobifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, and an imidazopyrimidinyl group.

10. The heterocyclic compound of claim 1, wherein the heterocyclic compound comprises three carbazole moieties or fewer.

11. A heterocyclic compound, wherein the heterocyclic compound is selected from Compounds 1 to 509:

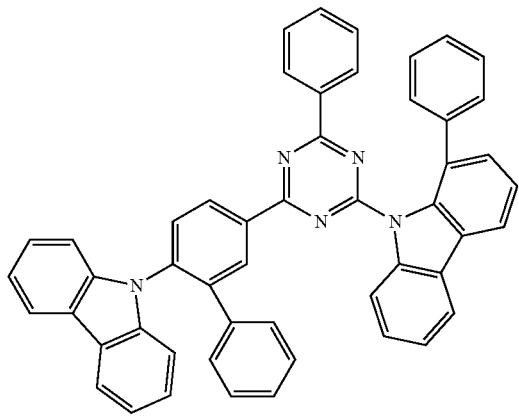

1

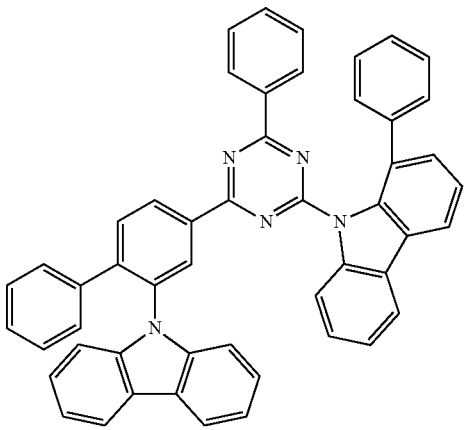

2

-continued
3
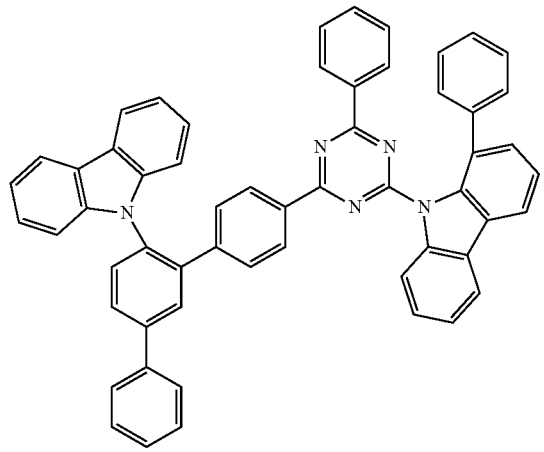
4
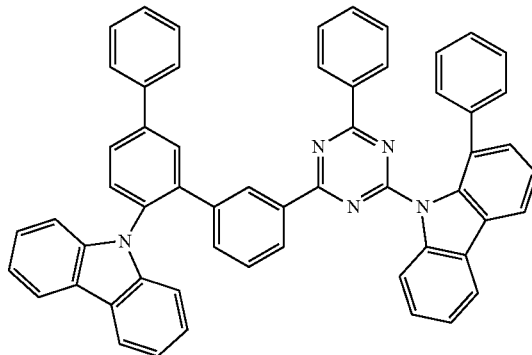
5
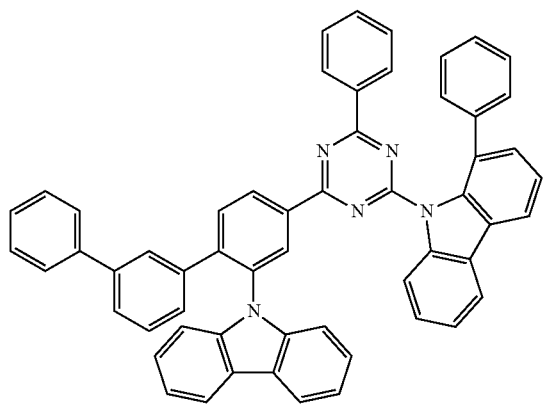
6
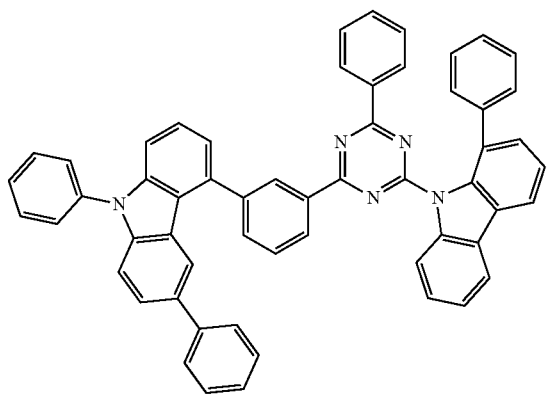
7
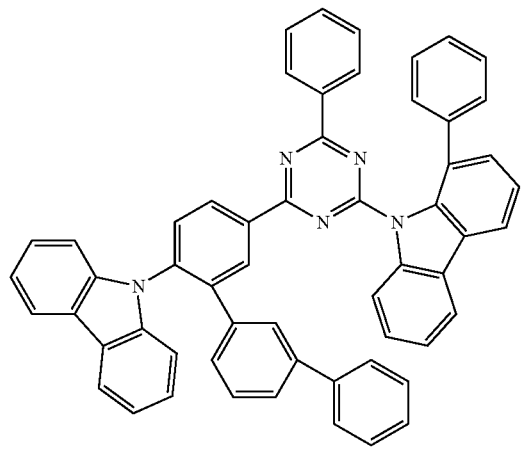
8
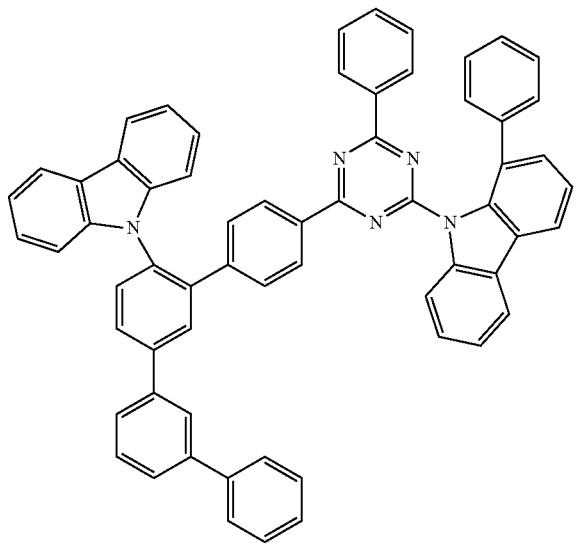

-continued
9
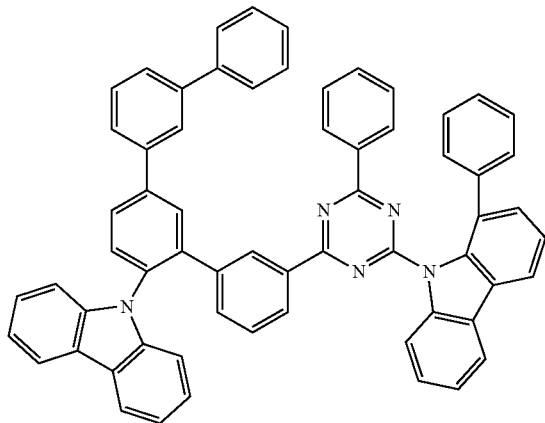
10
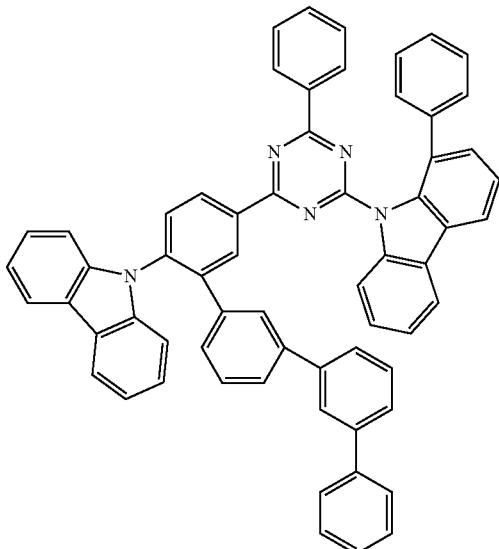
11
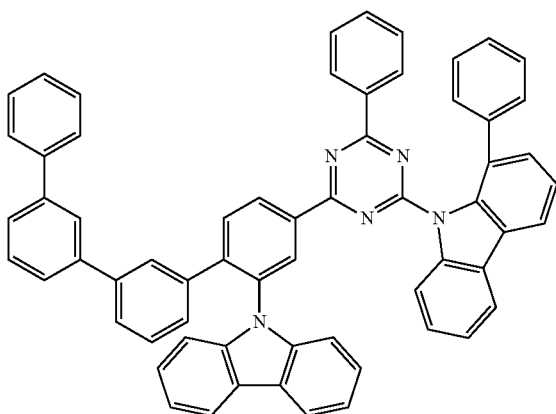
12
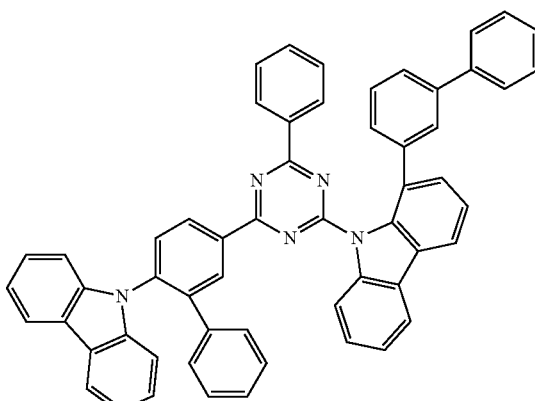
13
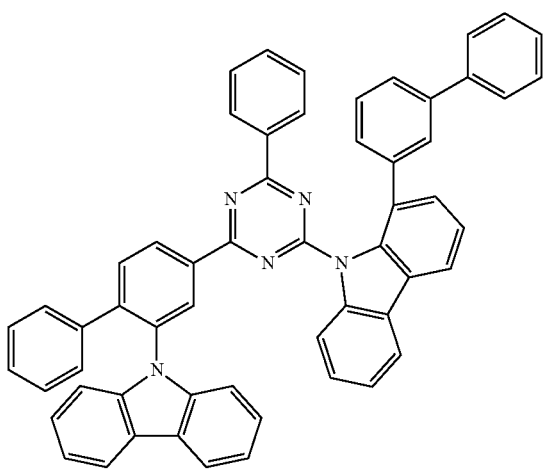
14
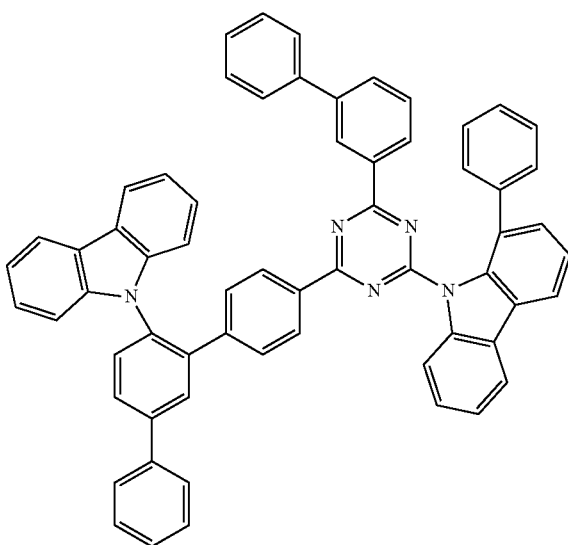

-continued
15
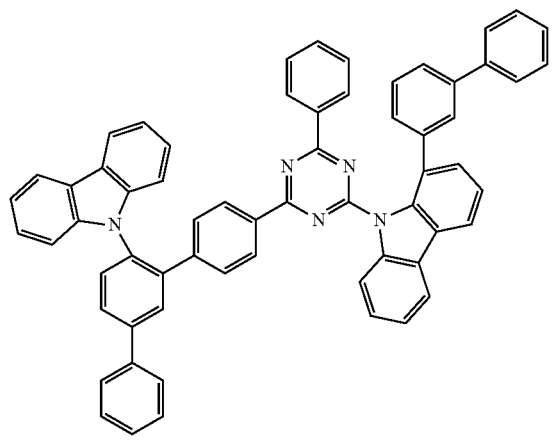
16
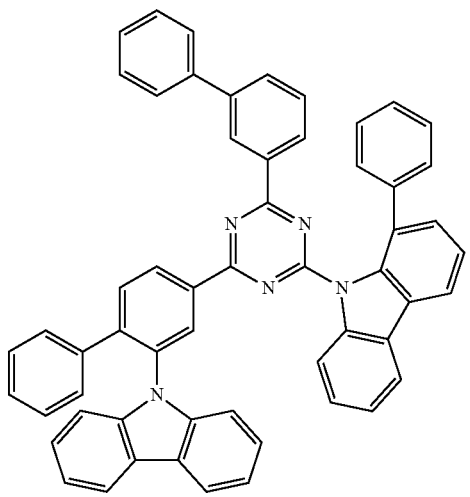
17
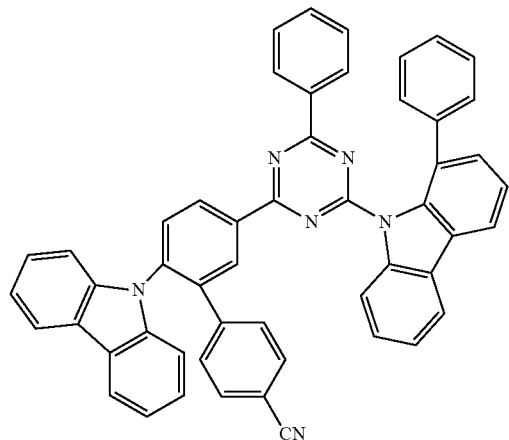
18
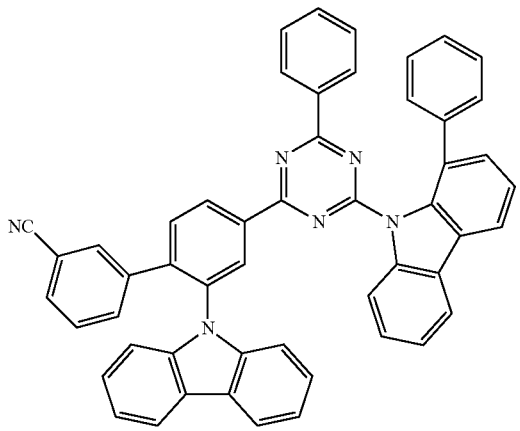
19
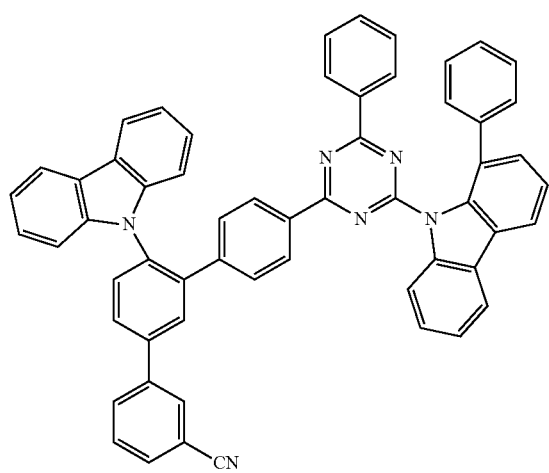
20
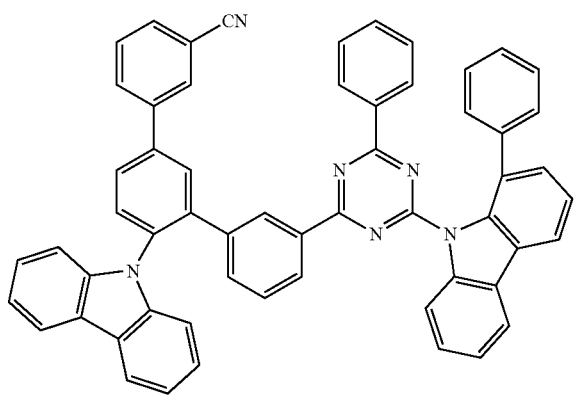

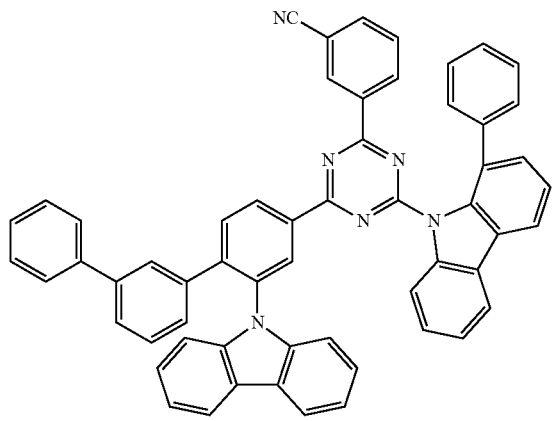
21
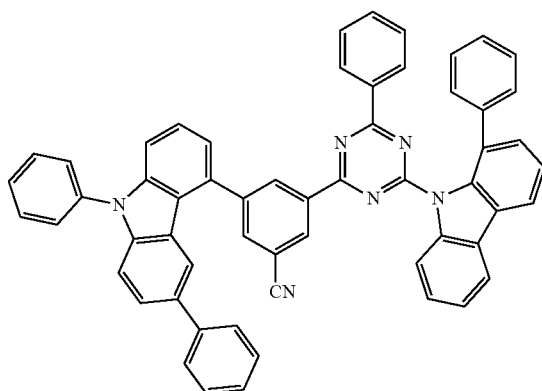
22
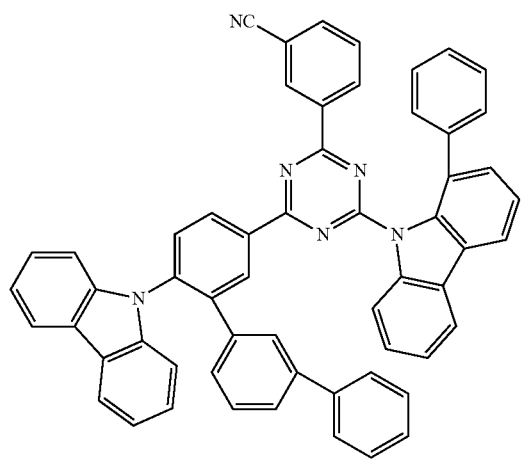
23
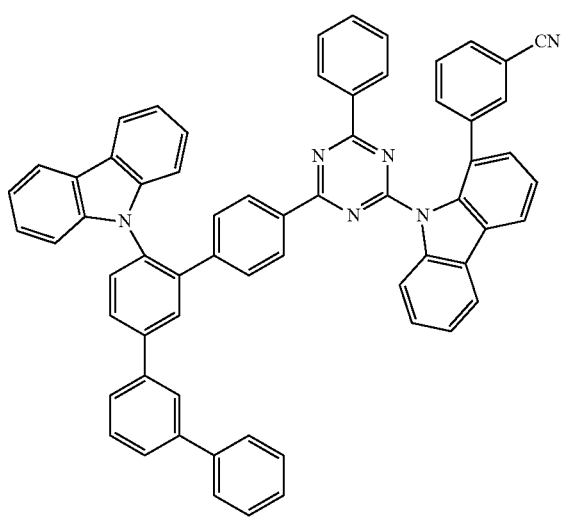
24
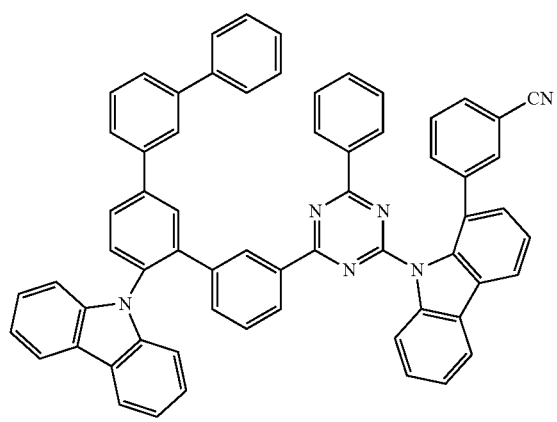
25
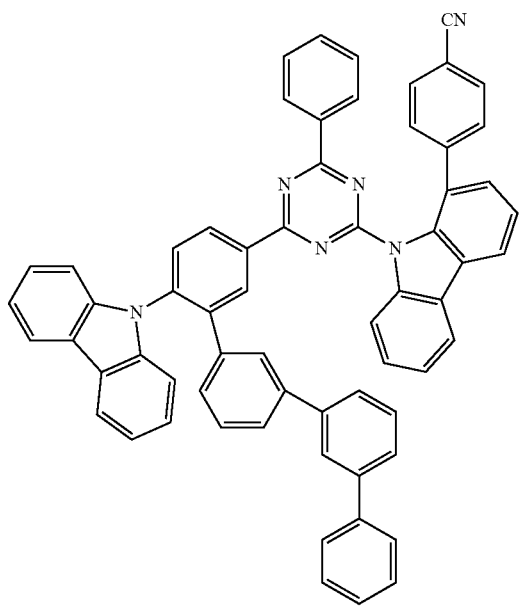
26

-continued
27
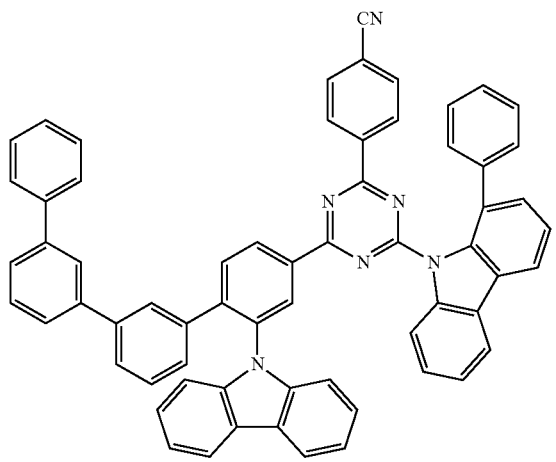
28
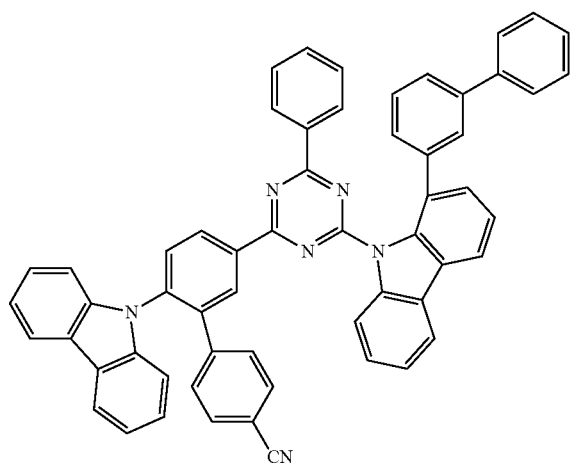
29
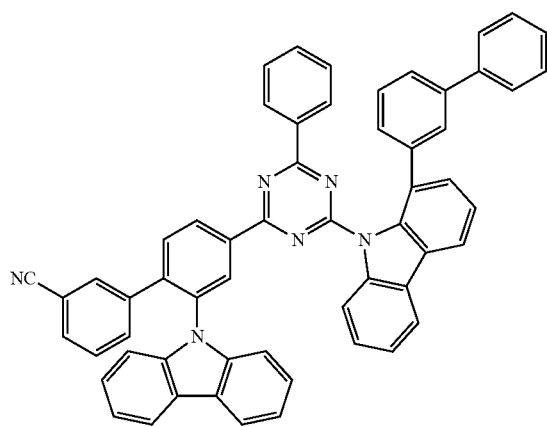
30
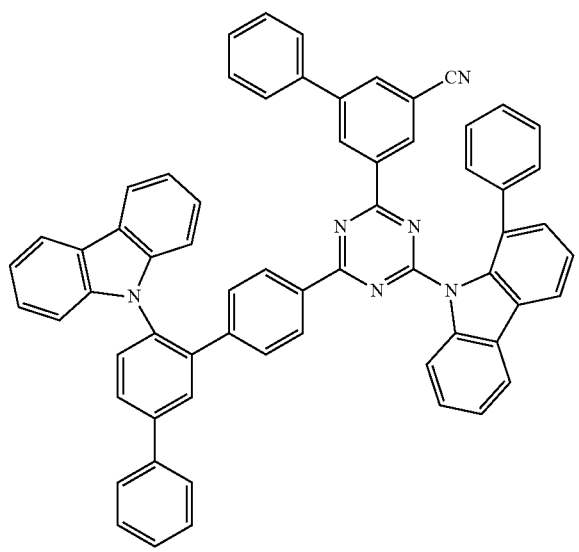
31
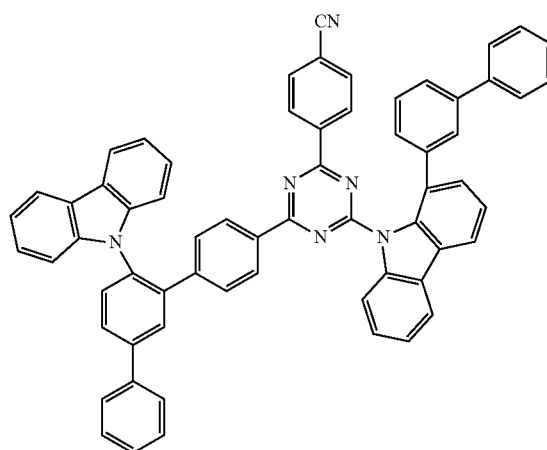
32
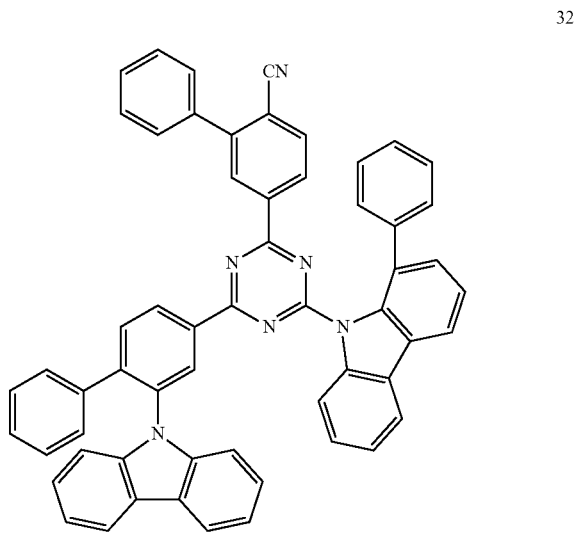

-continued
33
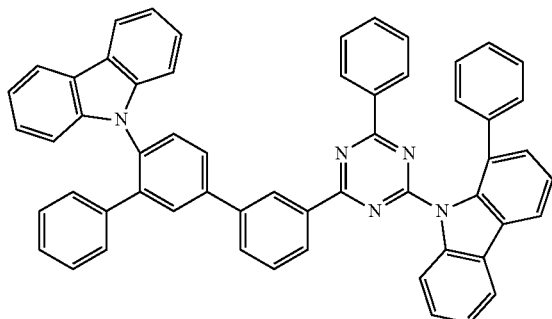
34
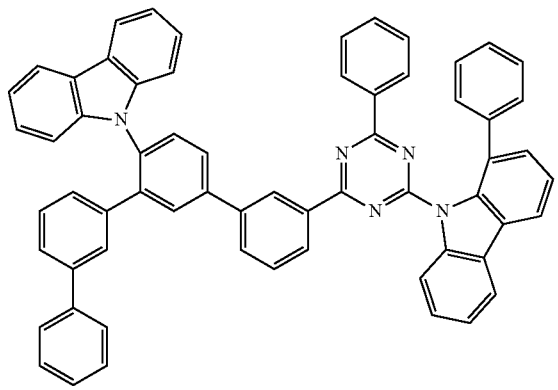
35
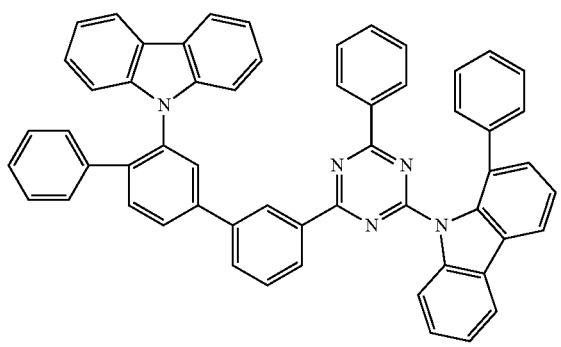
36
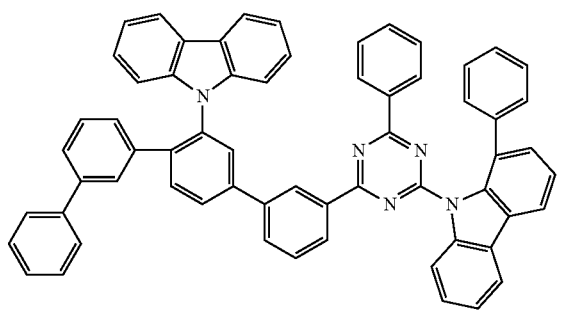
37
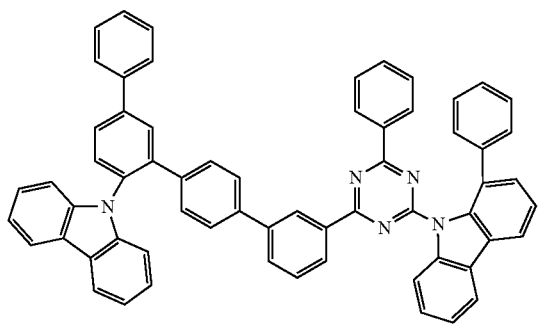
38
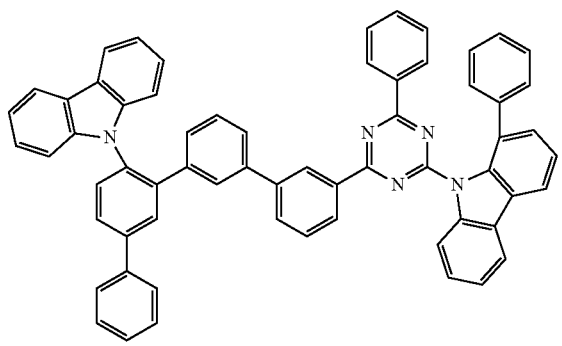
39
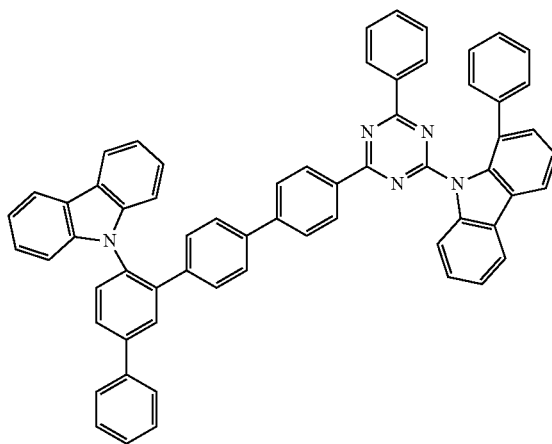
40
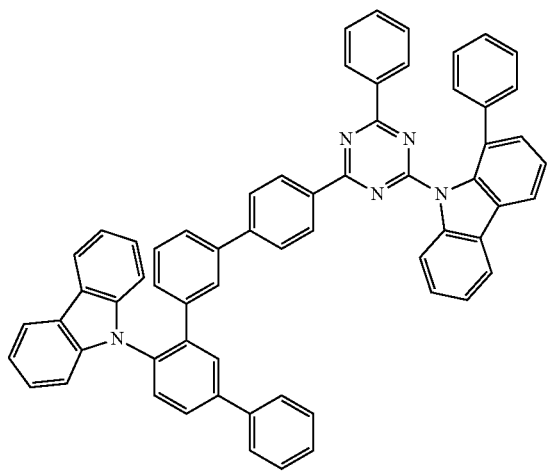

41
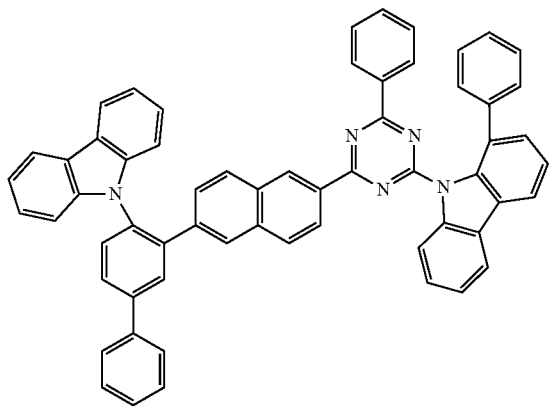
42
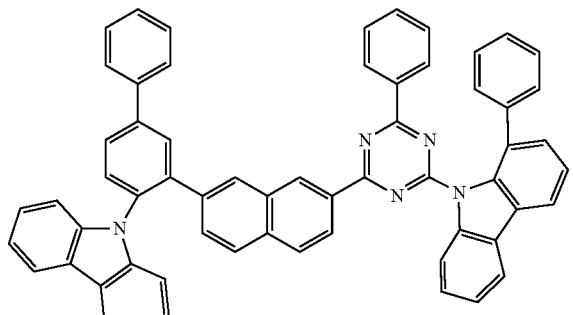
43
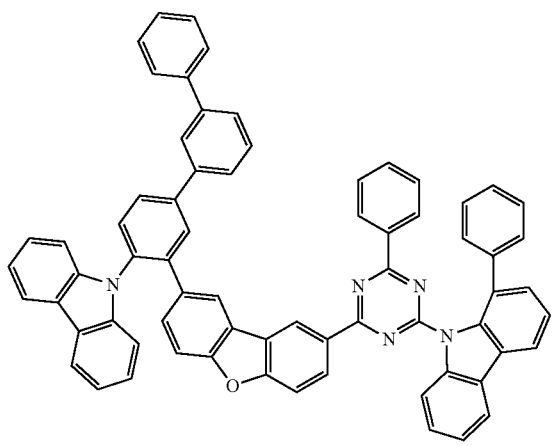
44
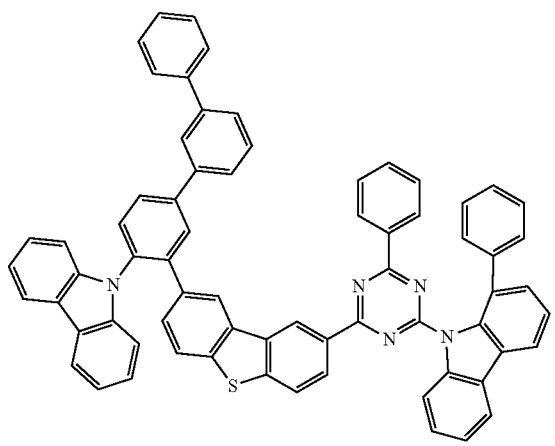
45
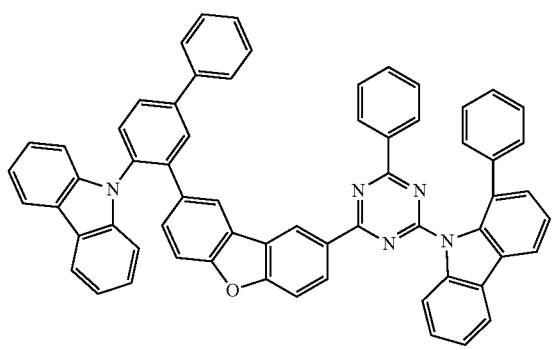
46
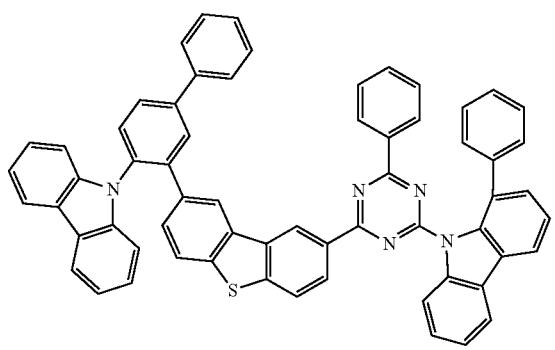

-continued
47
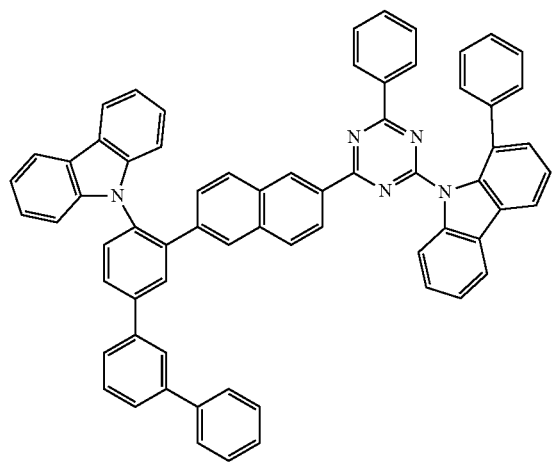
48
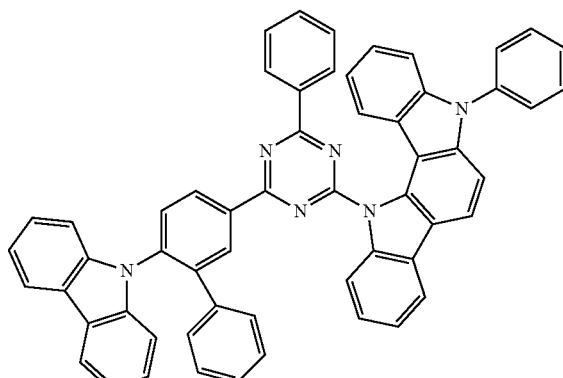
49
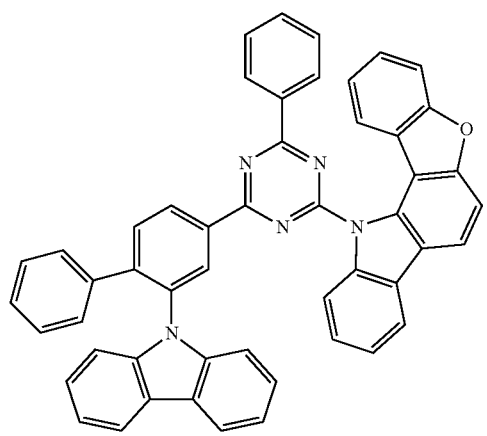
50
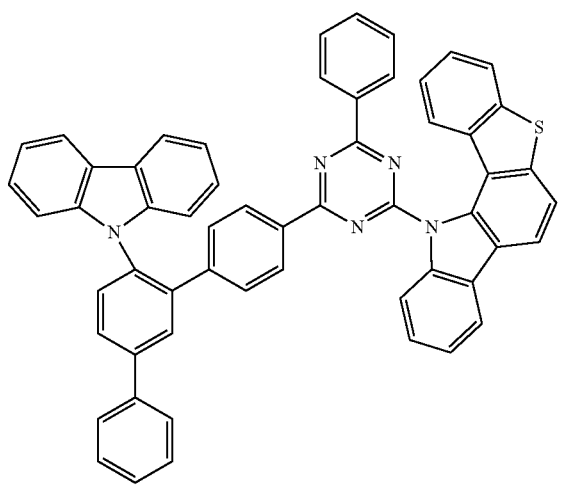
51
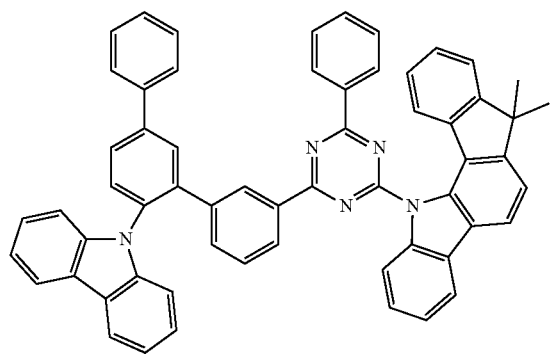
52
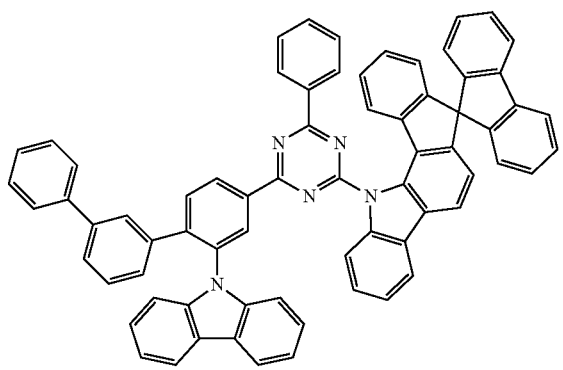

-continued
53
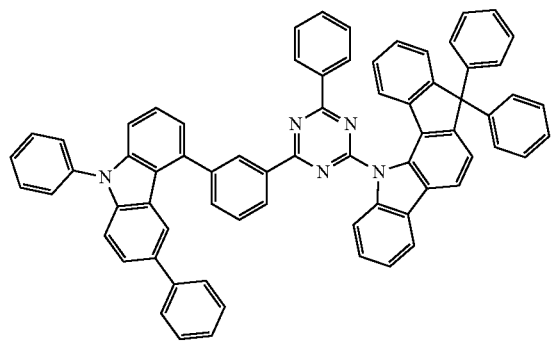
54
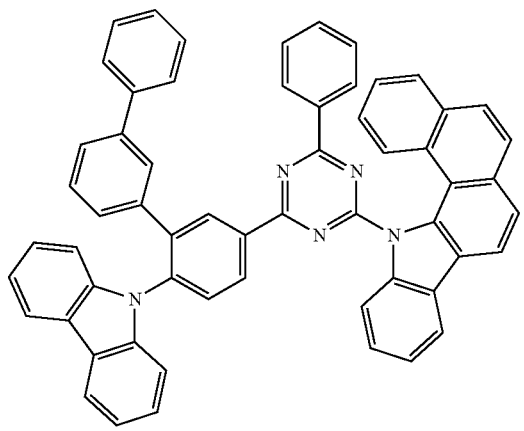
55
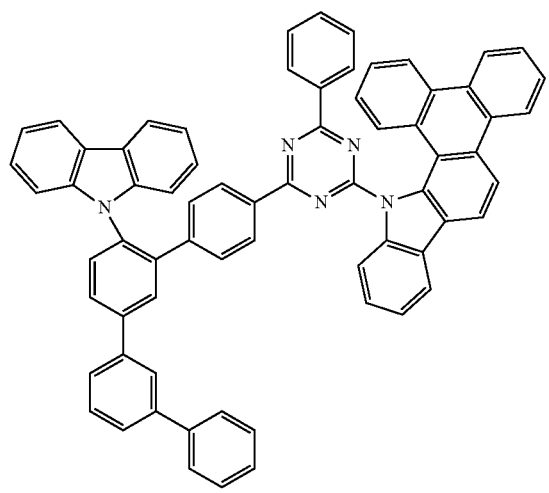
56
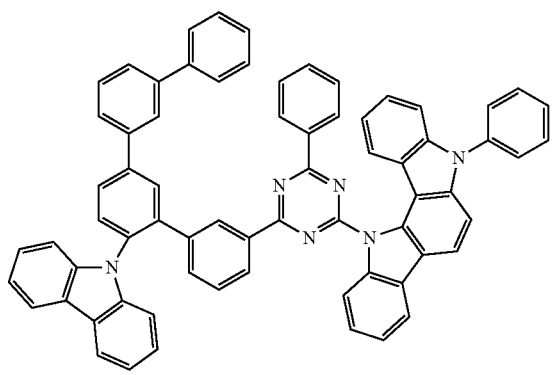
57
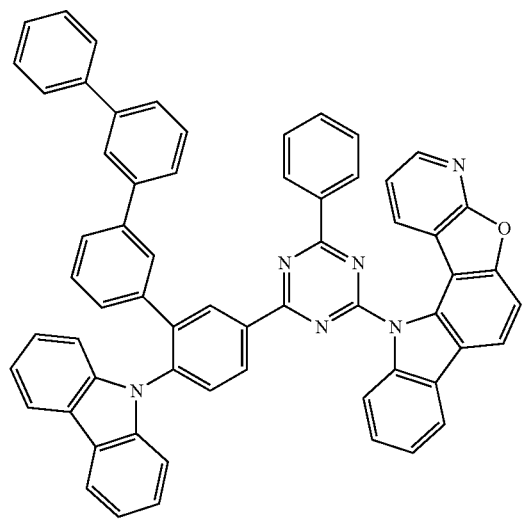
58
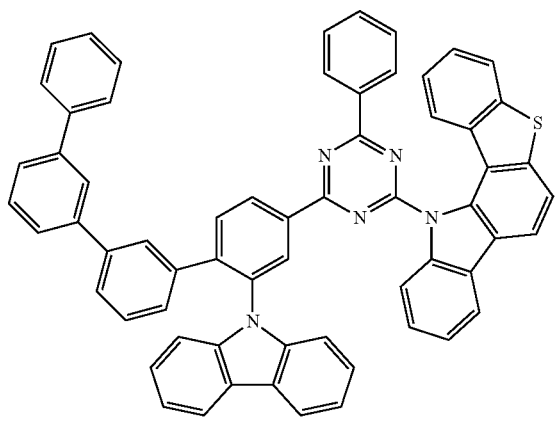

-continued
59
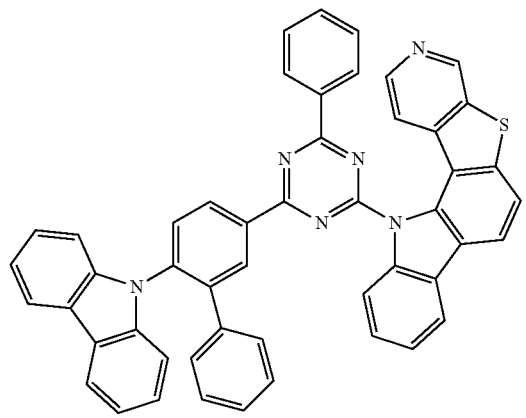
60
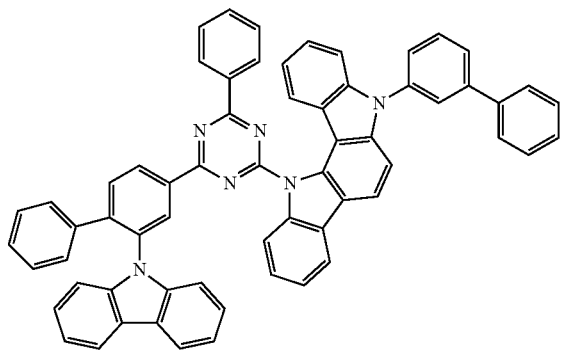
61
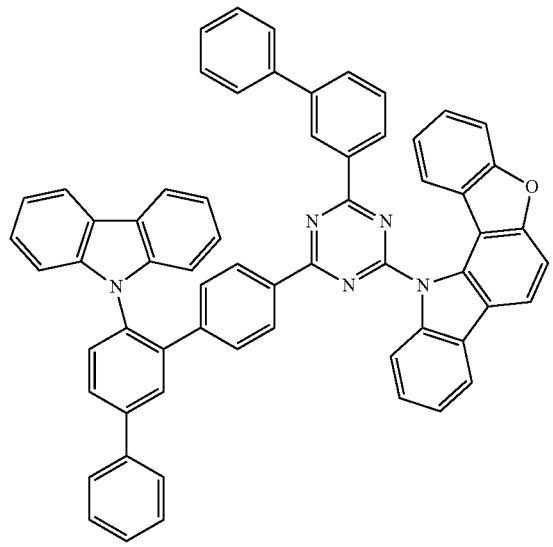
62
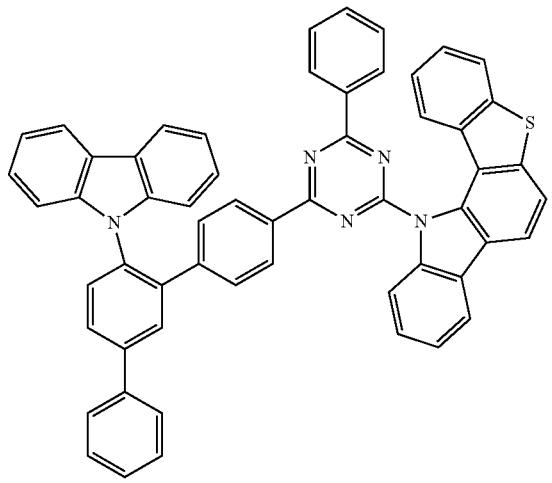
63
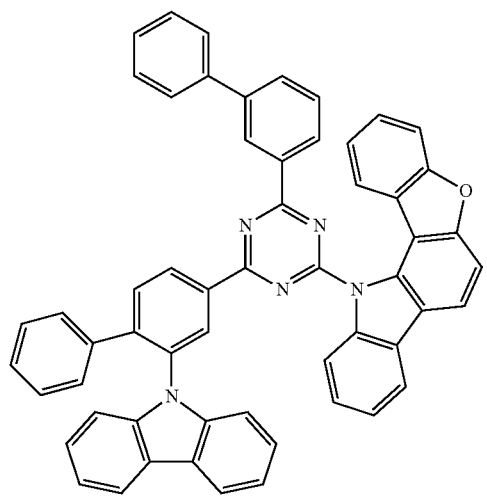
64
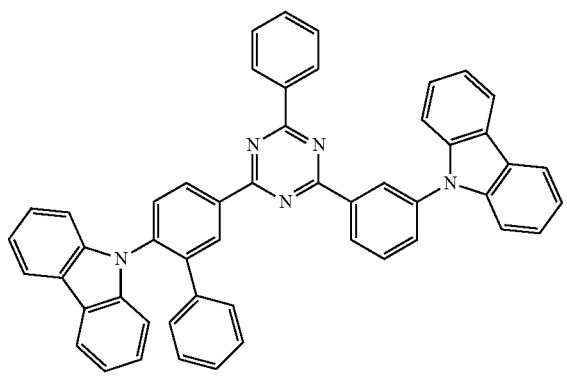

327
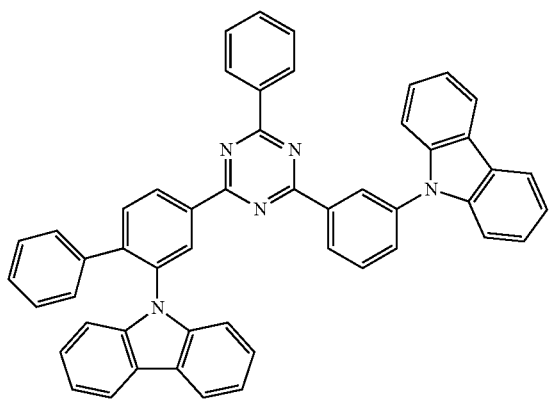
328
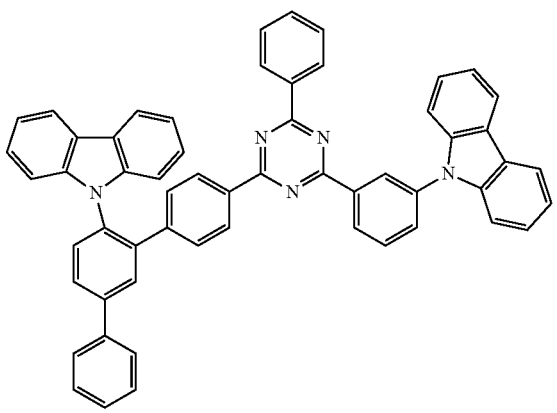
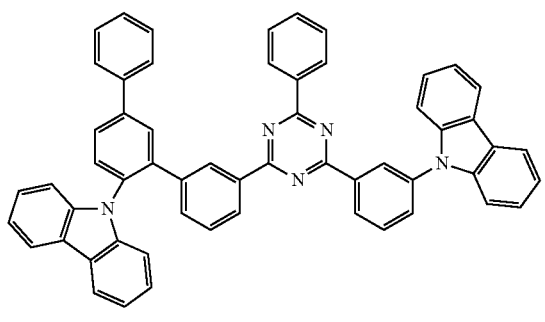
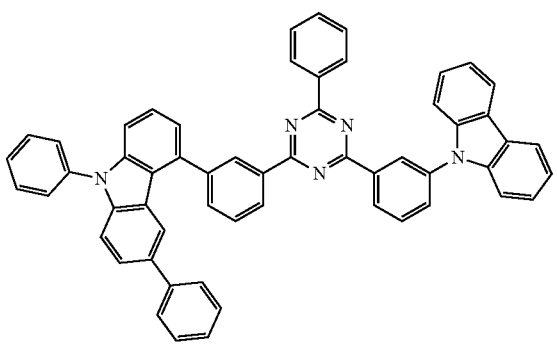
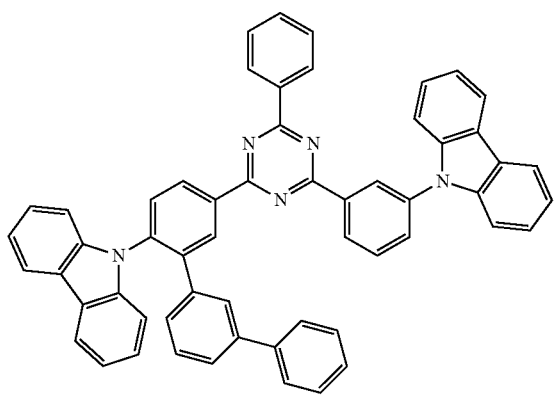
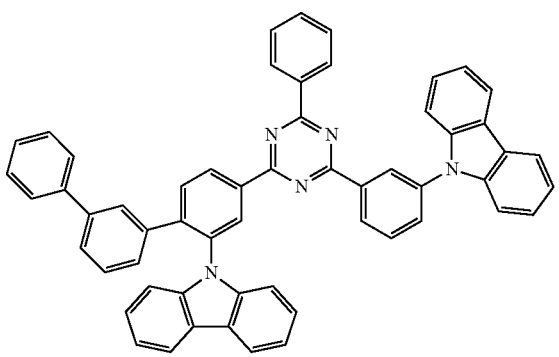

-continued
71
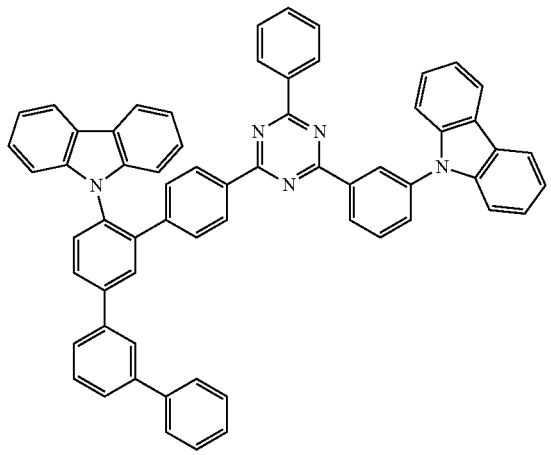
72
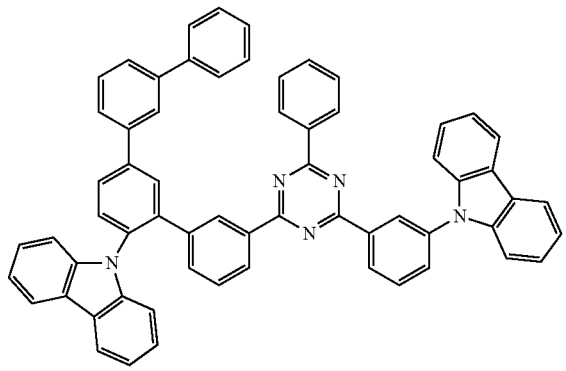
73
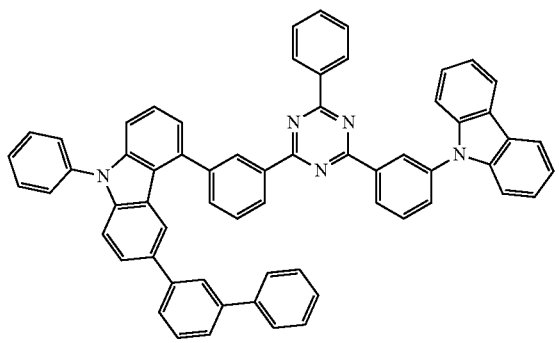
74
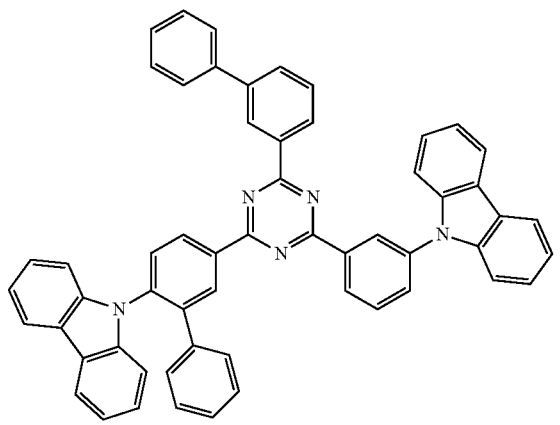
75
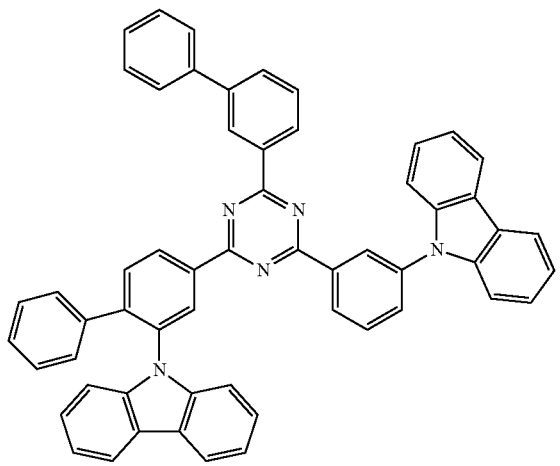
76
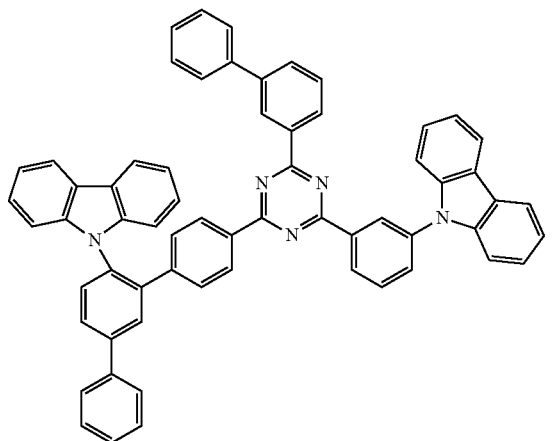

77
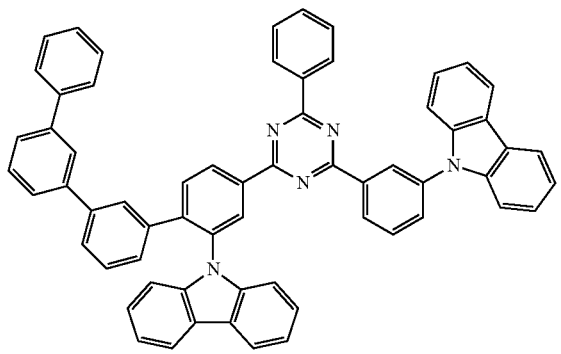
78
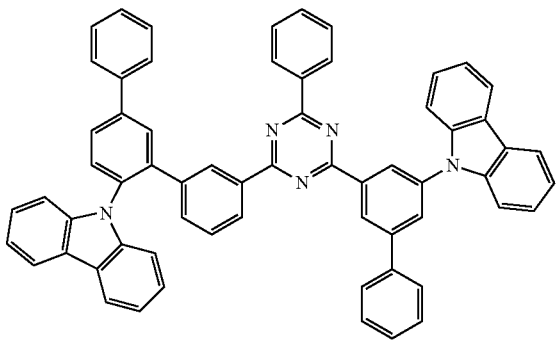
79
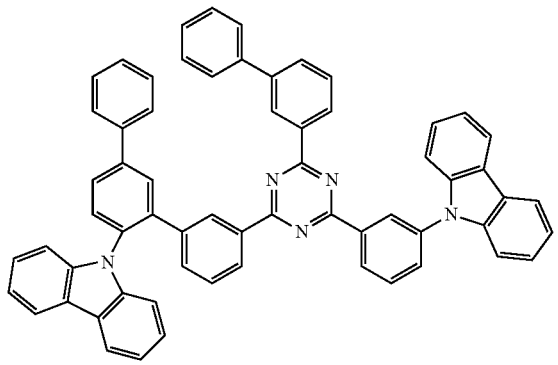
80
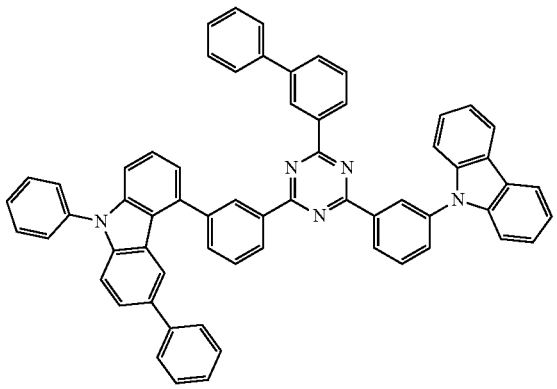
81
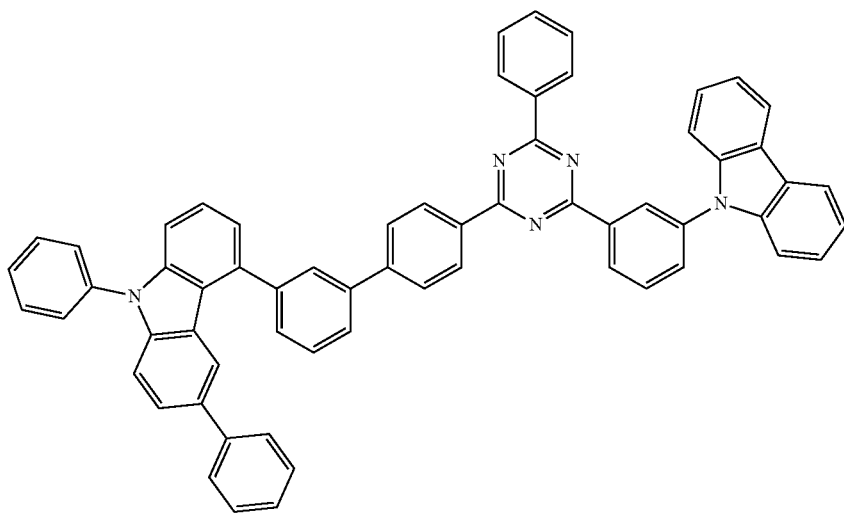

-continued
82
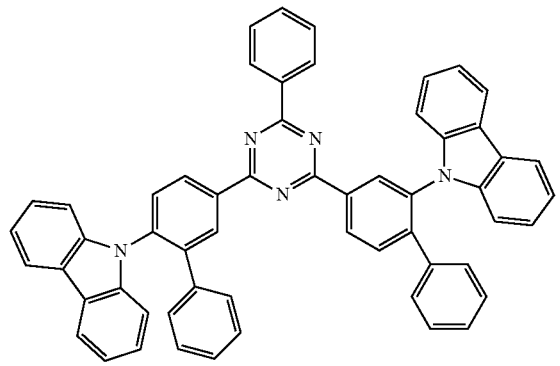
83
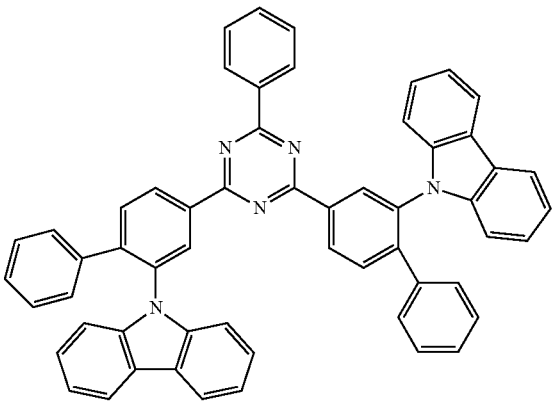
84
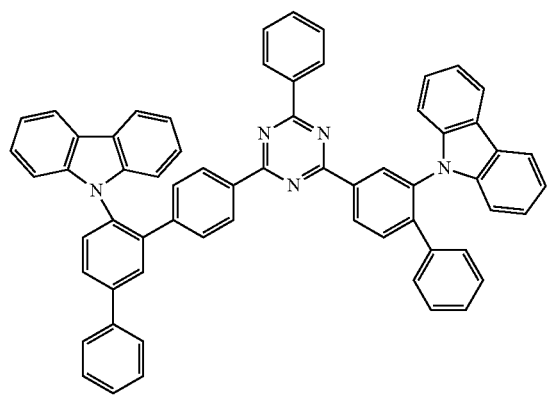
85
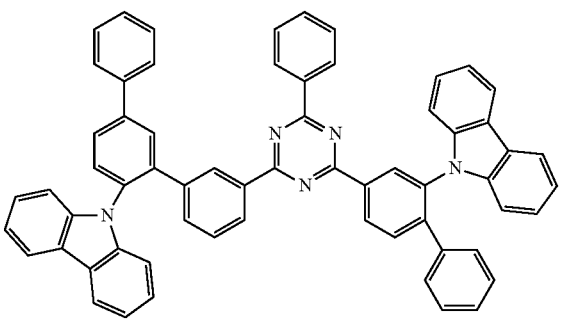
86
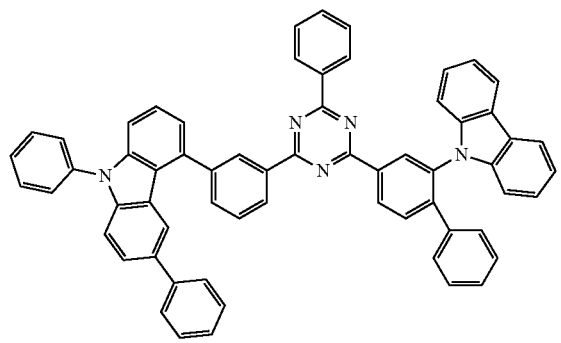
87
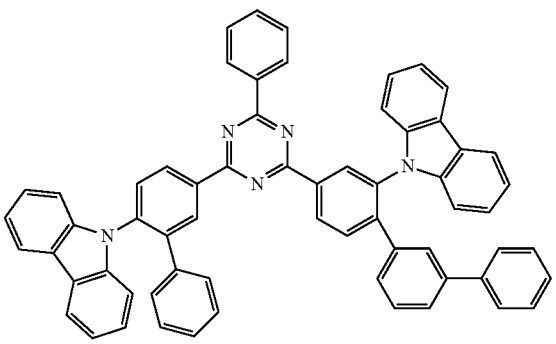
88
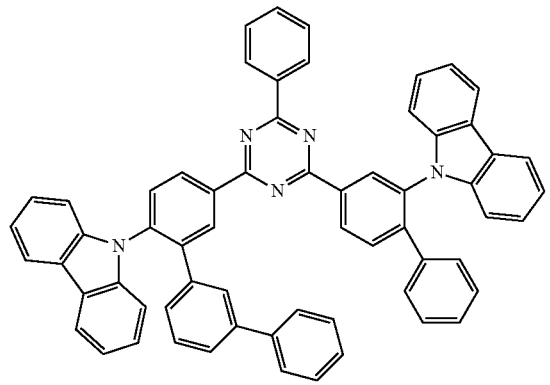
89
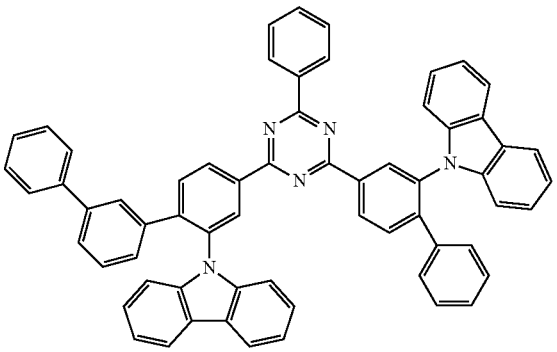

90
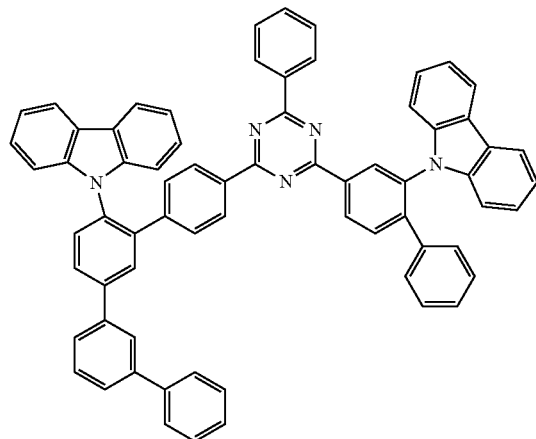
91
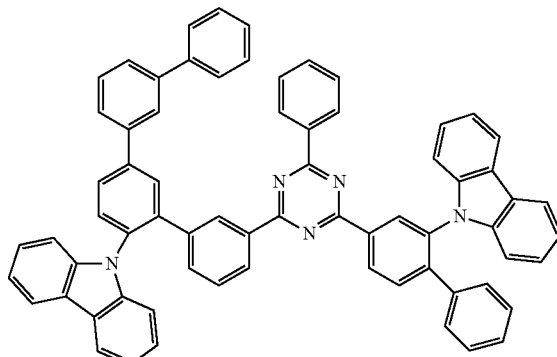
92
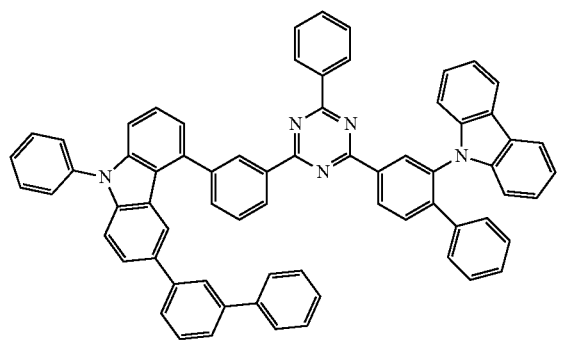
93
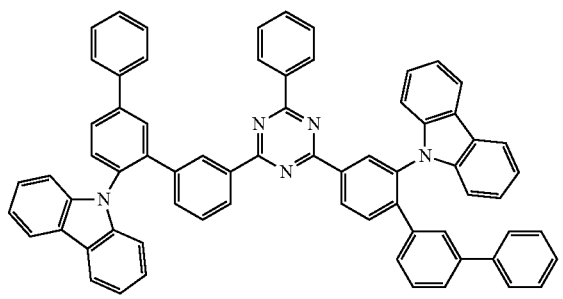
94
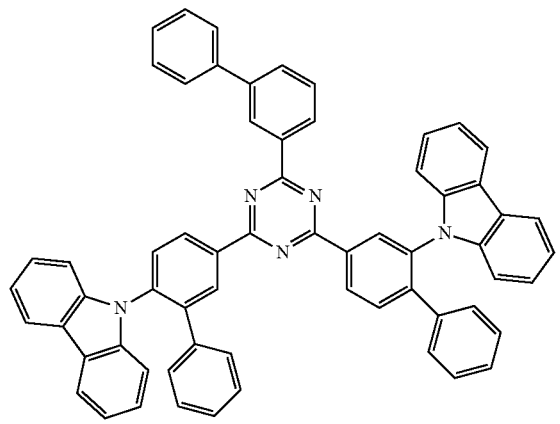
95
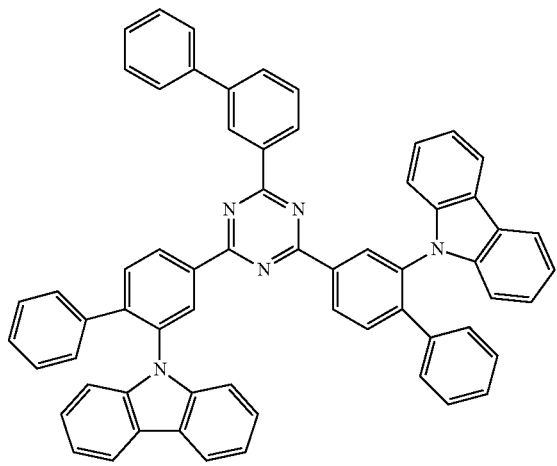

96
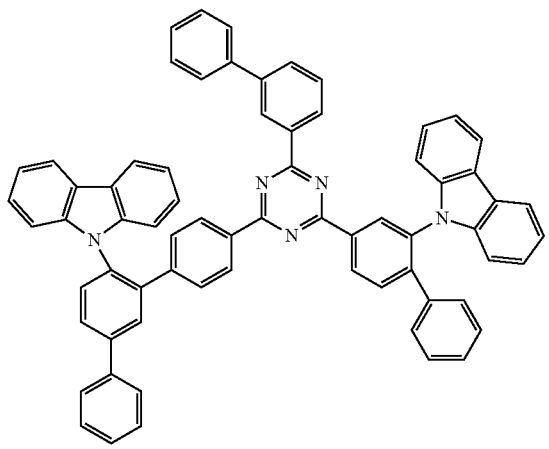
97
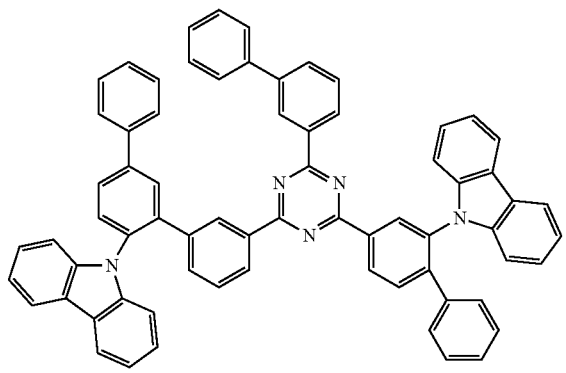
98
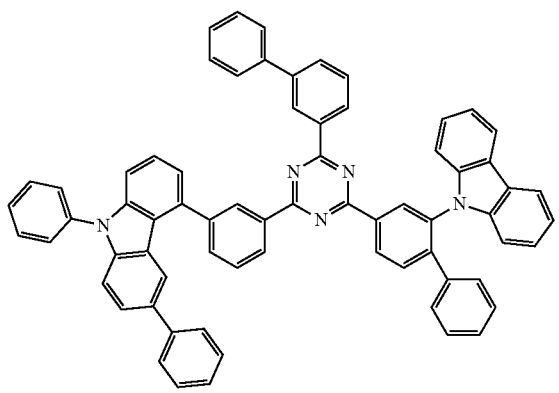
99
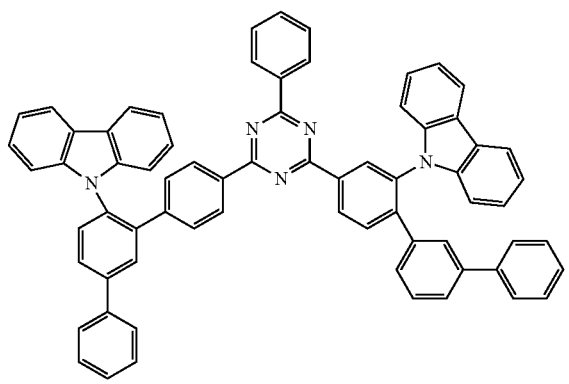
100
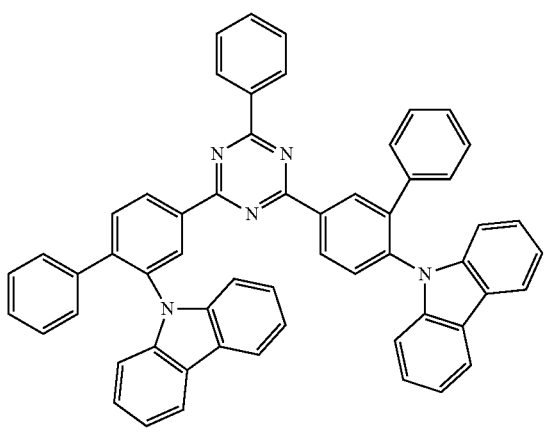
101
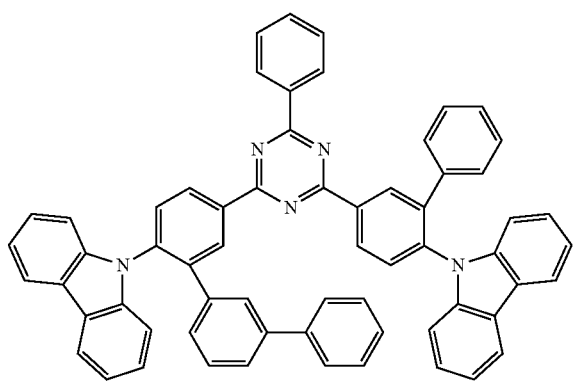

-continued
102
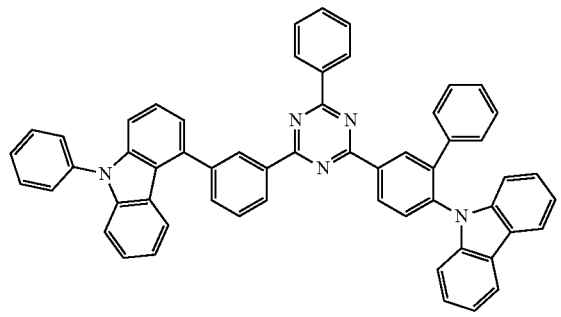
103
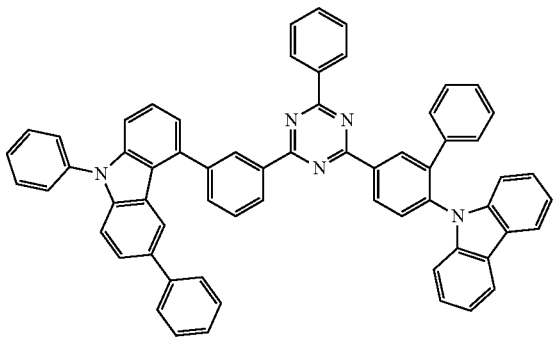
104
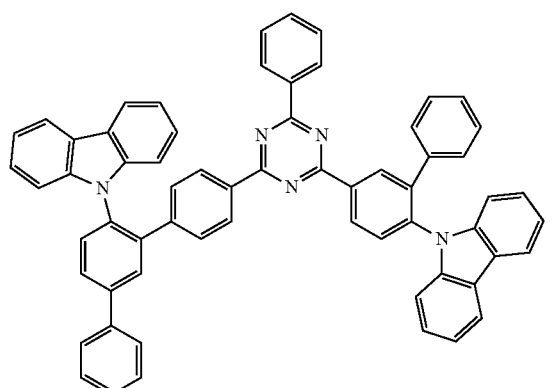
105
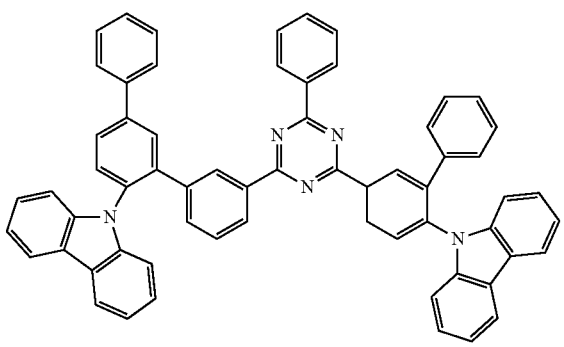
106
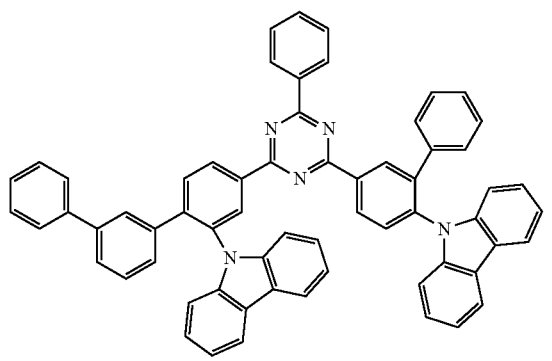
107
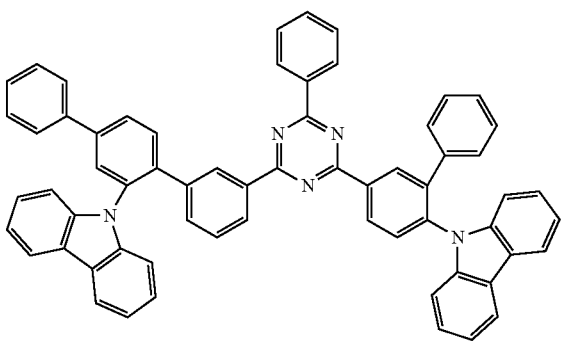
108
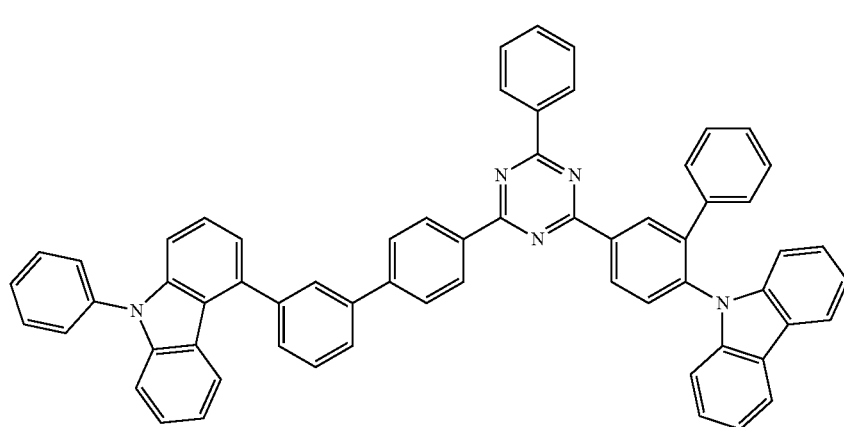

-continued
109
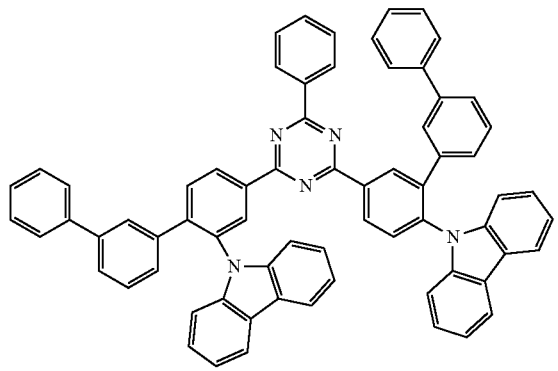
110
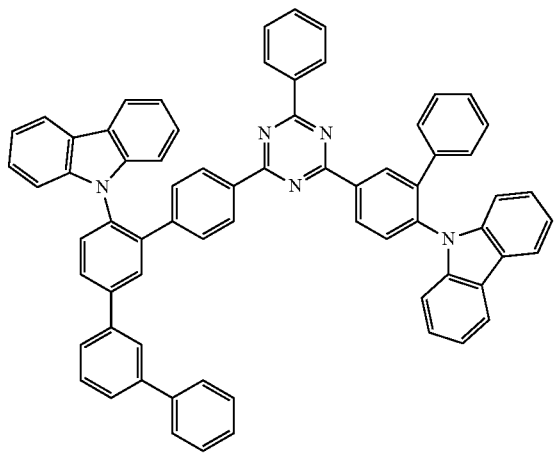
111
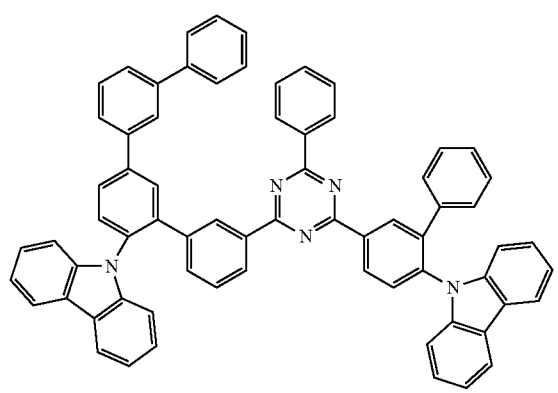
112
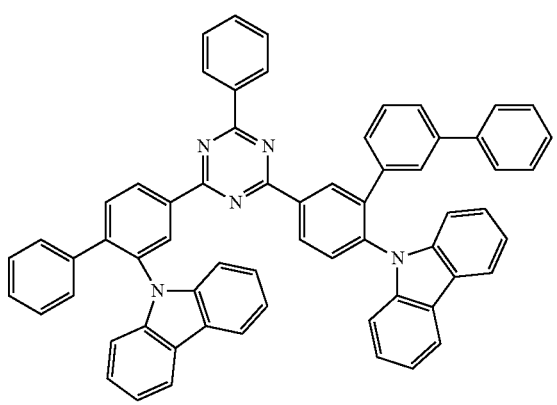
113
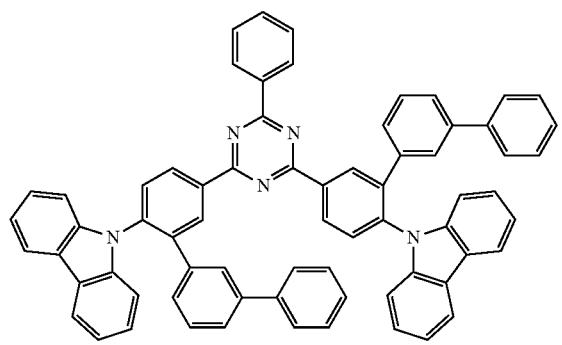
114
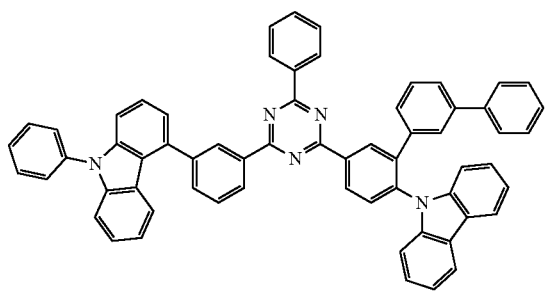
115
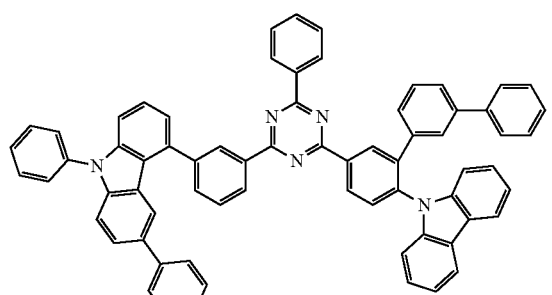
116
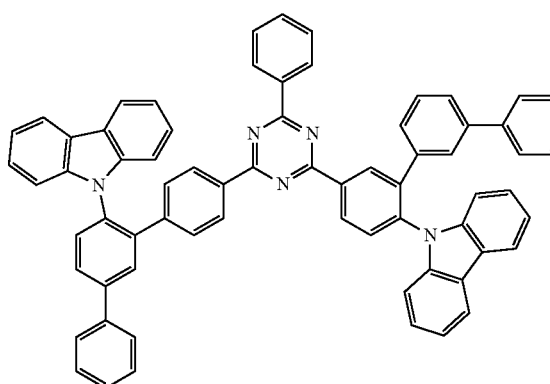

117
118
-continued
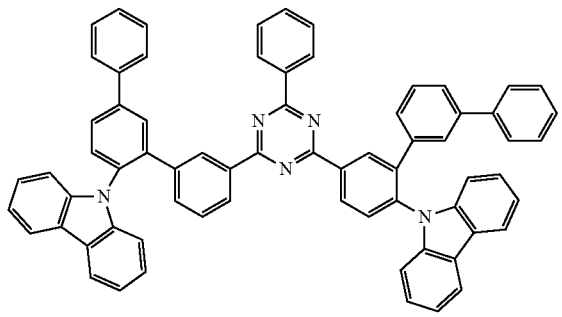
117
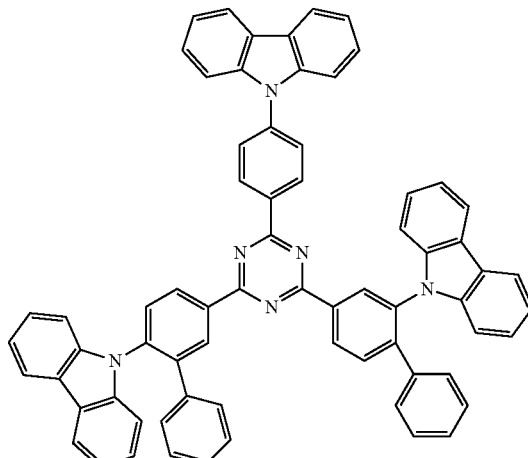
118
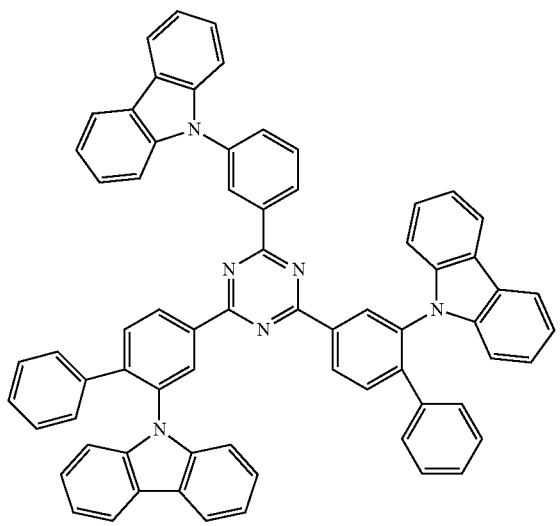
119
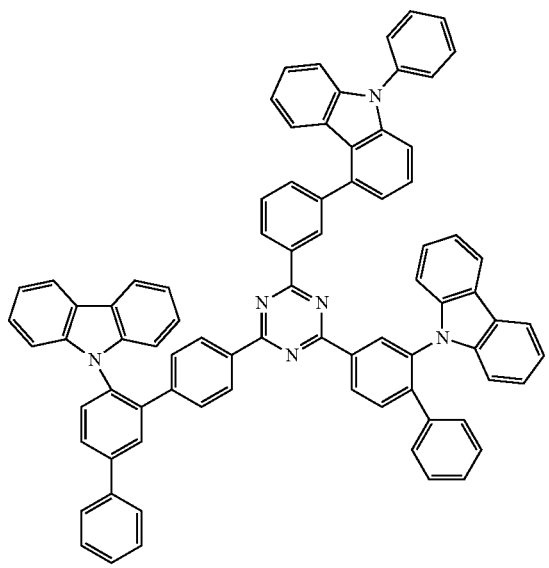
120
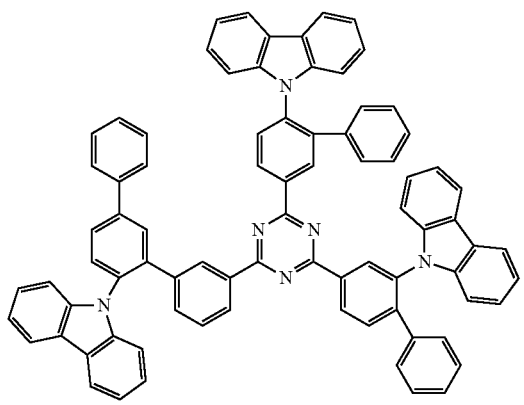
121
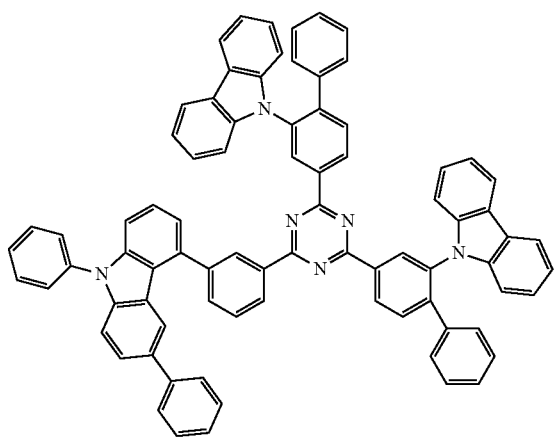
122

123
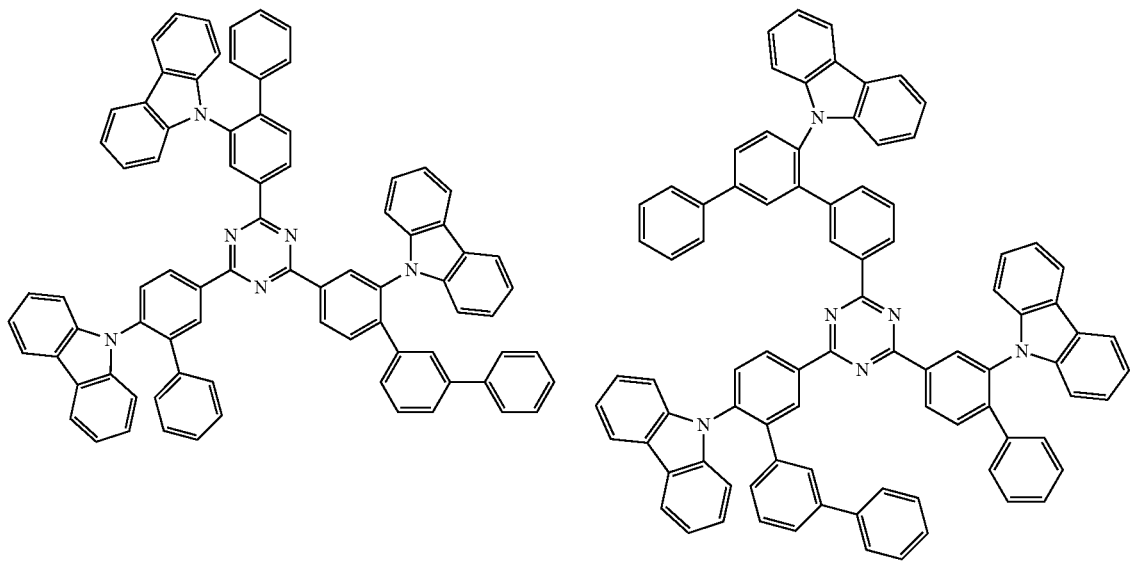
124
125
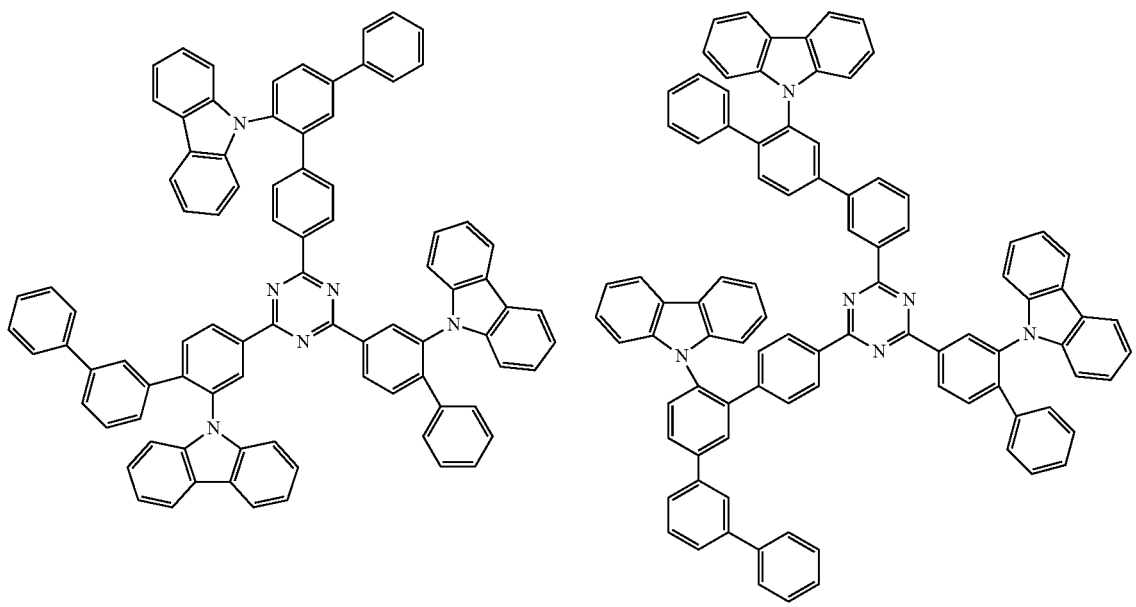
126

-continued
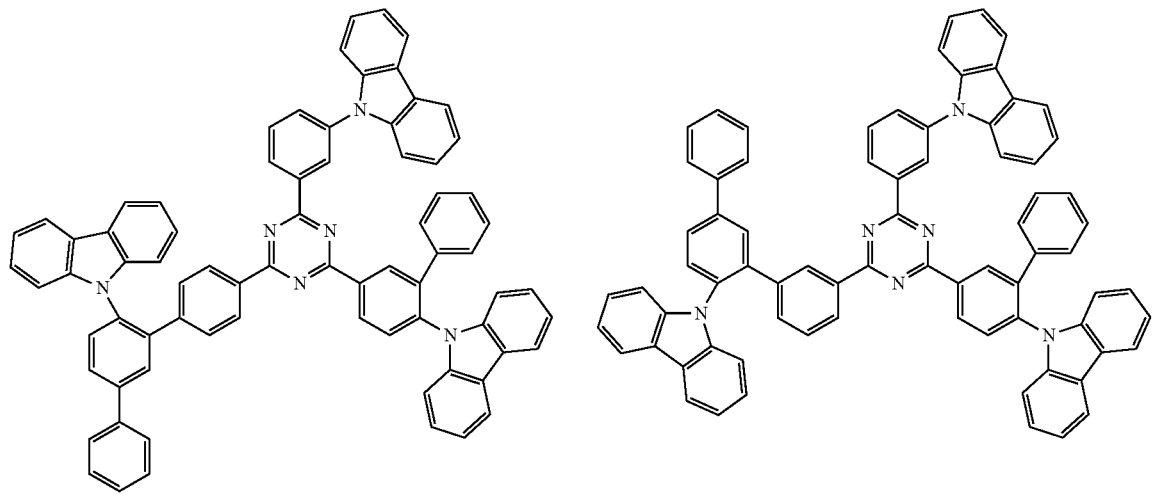
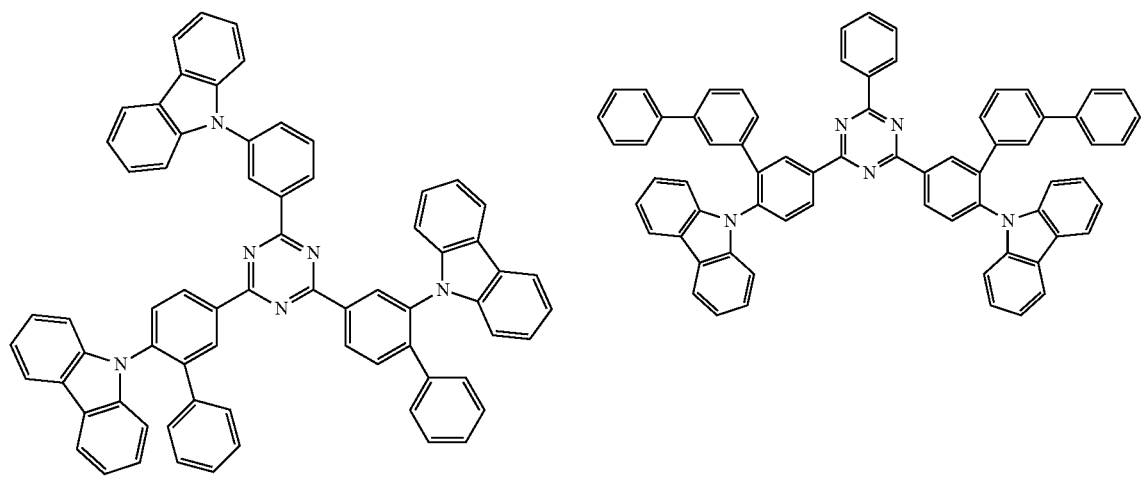
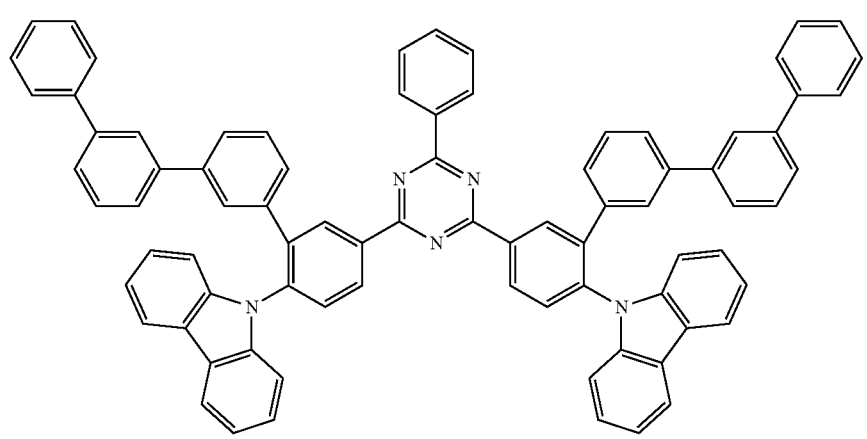

132
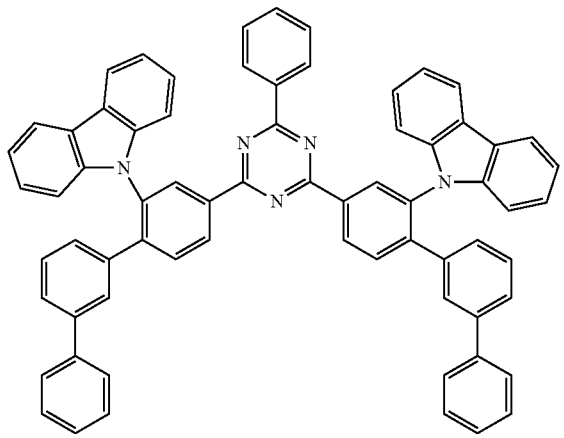
133
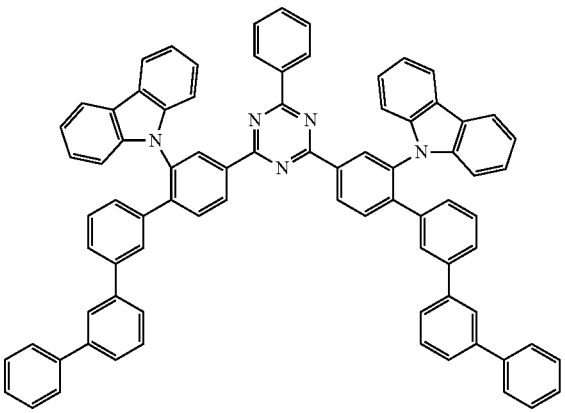
134
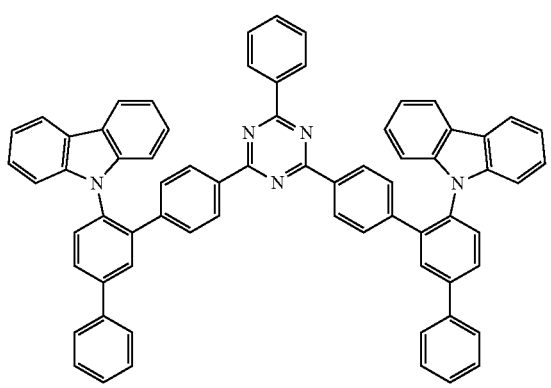
135
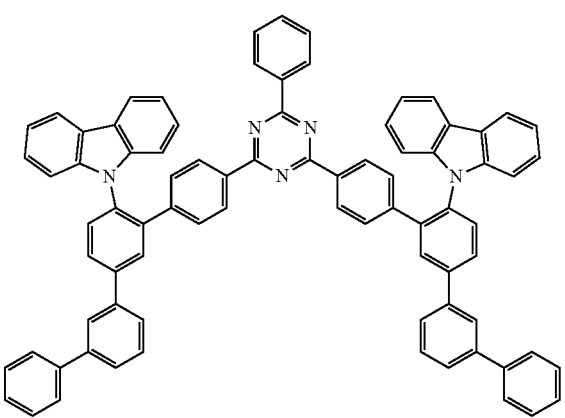
136
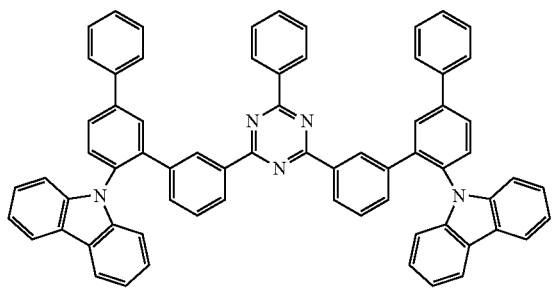
137
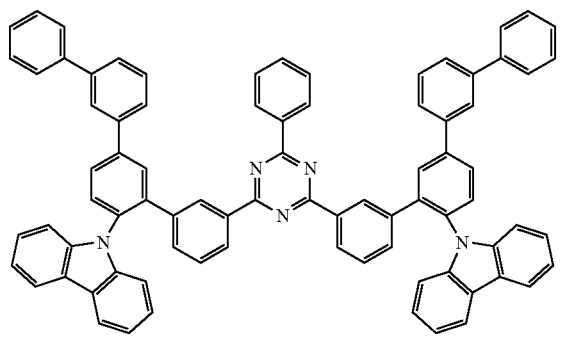
138
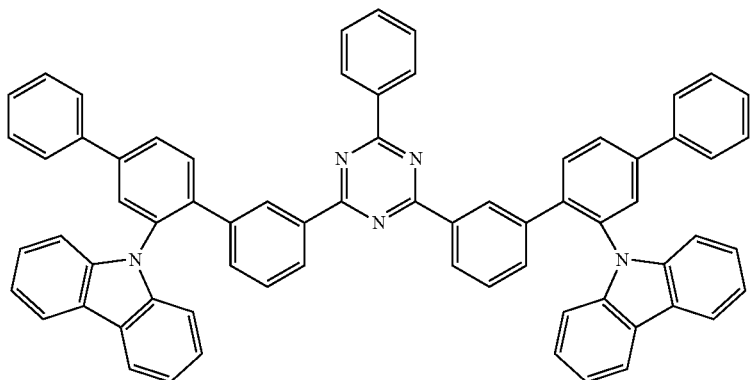

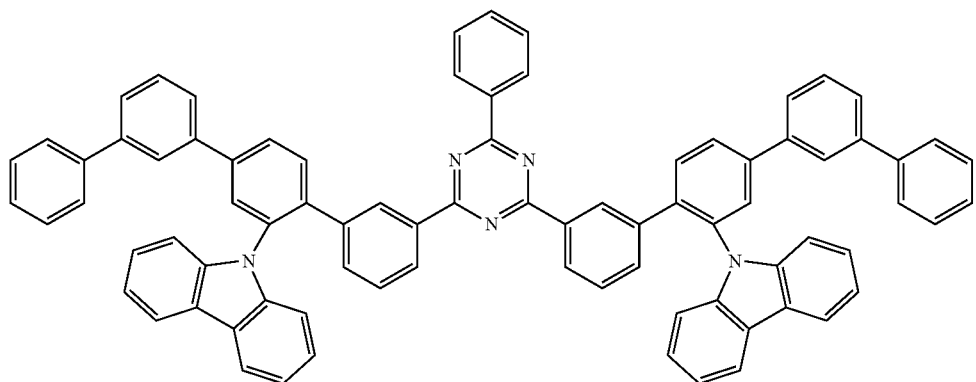
139
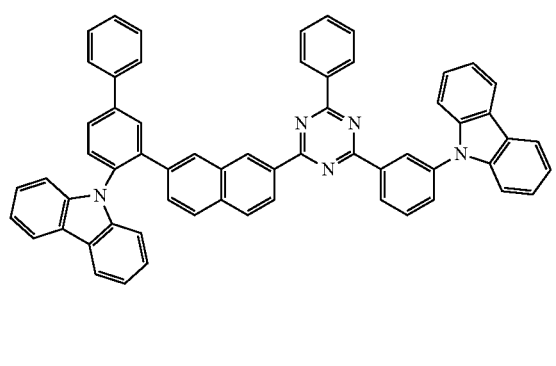
140
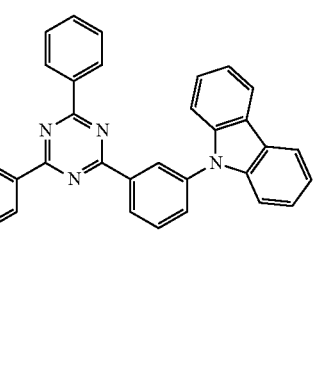
141
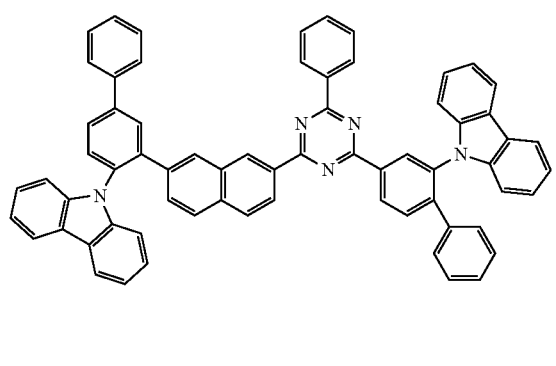
142
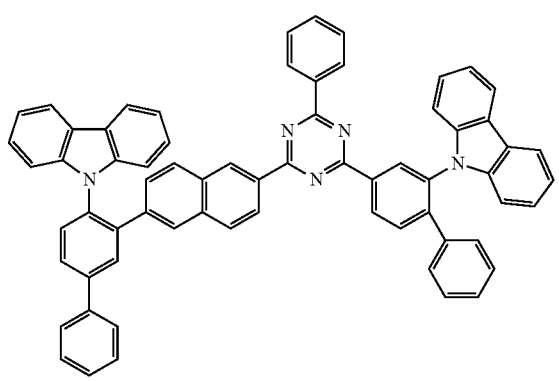
143
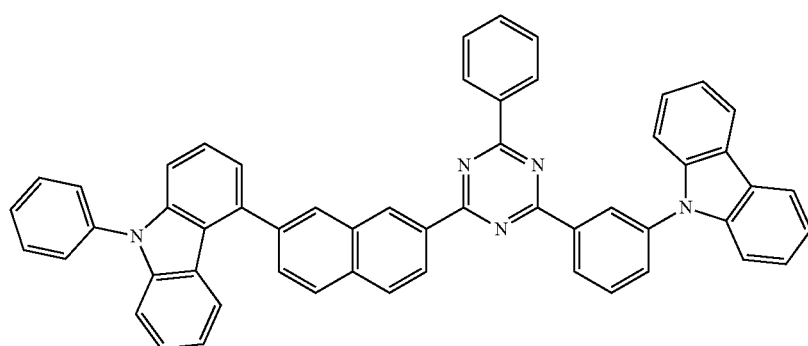
144

145
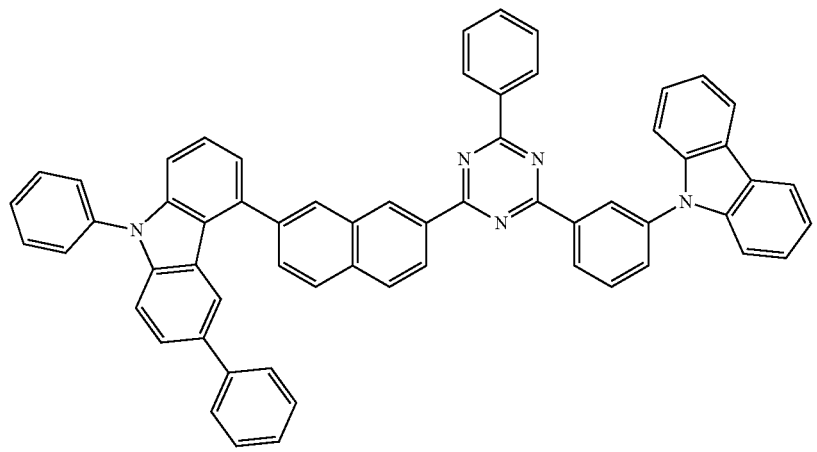
146
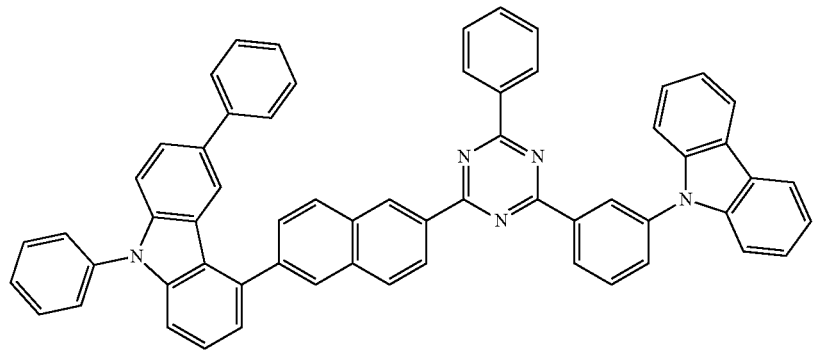
147
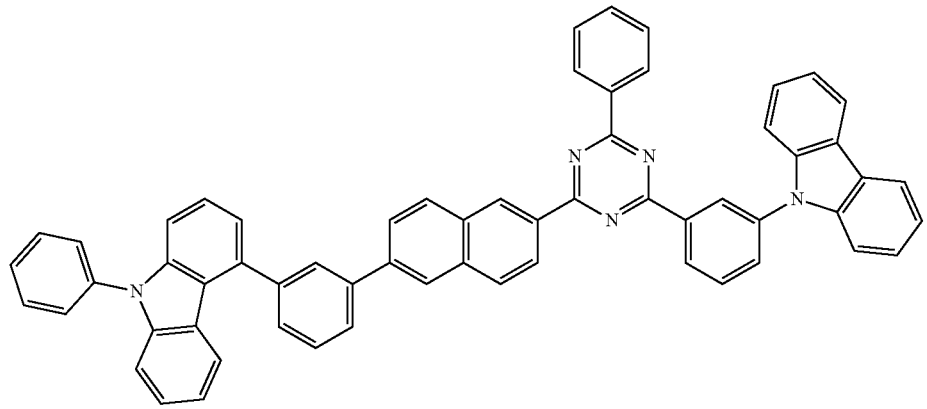
148 149
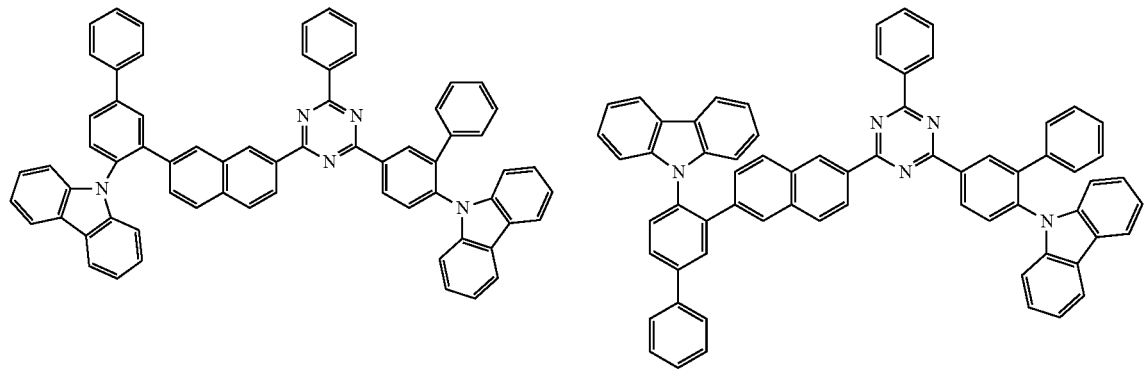

150
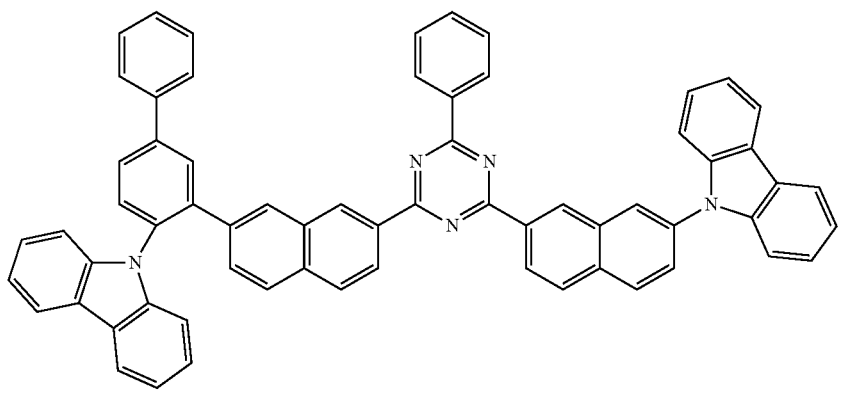
151
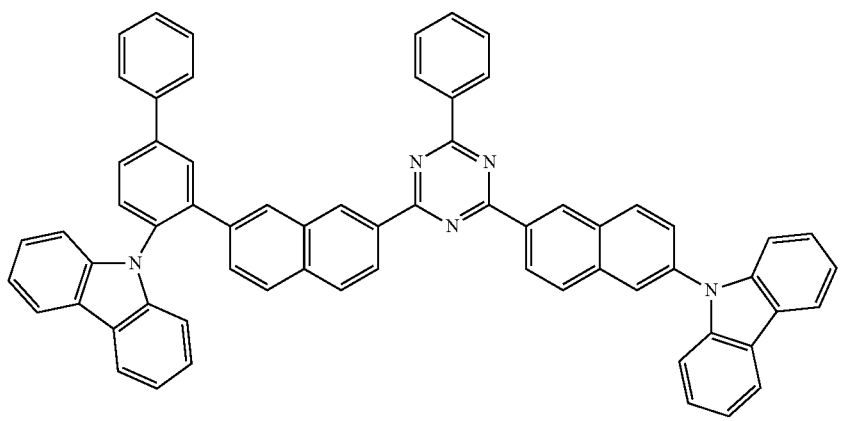
152 153
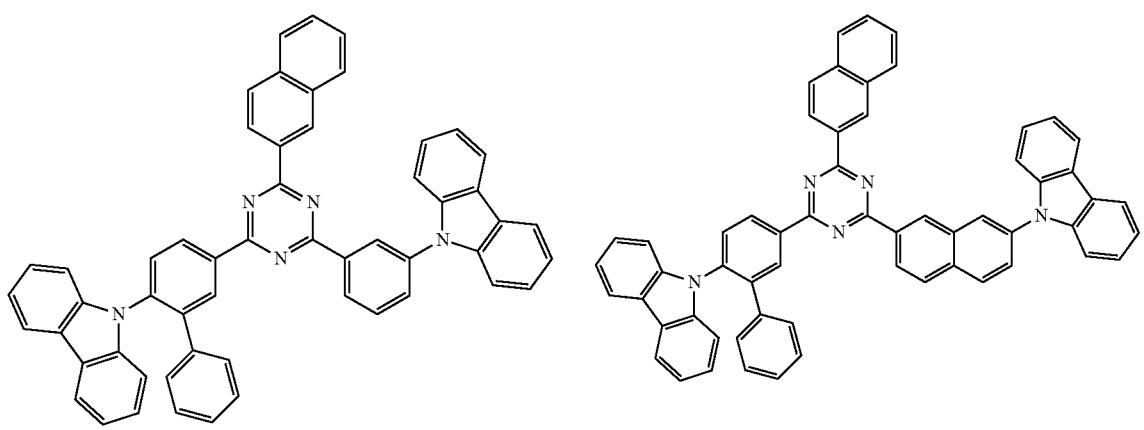

154
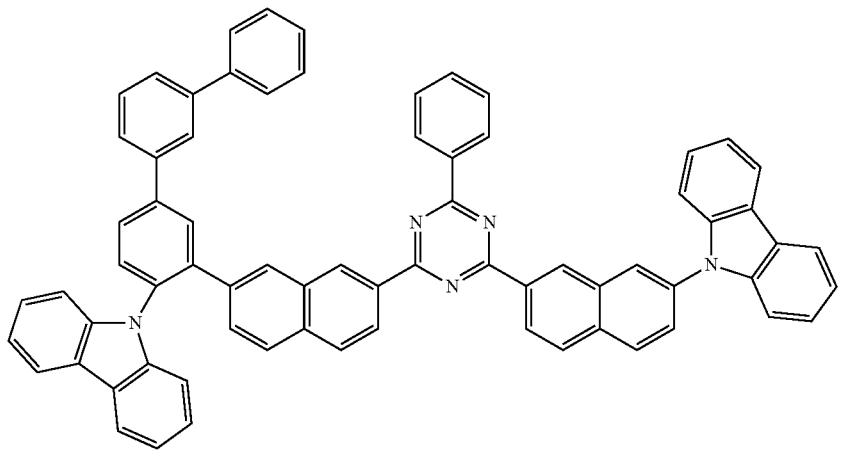
155
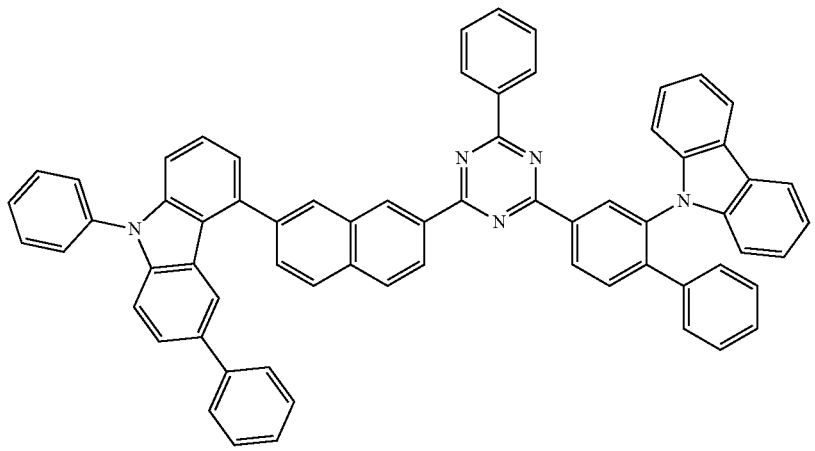
156
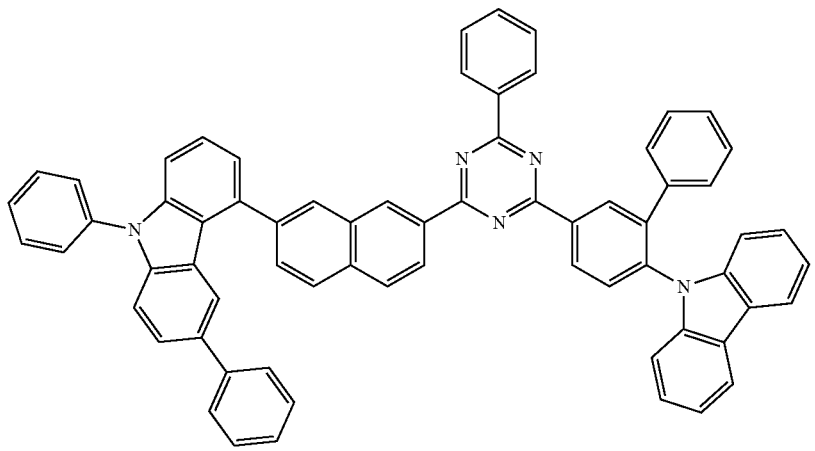

157
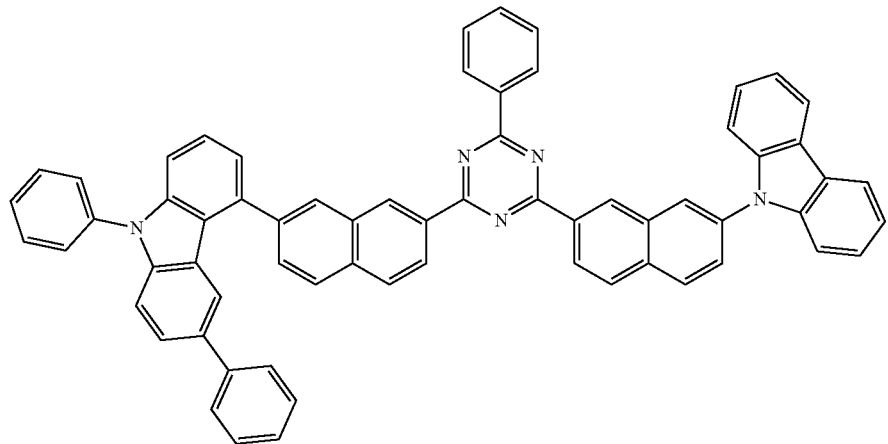
158
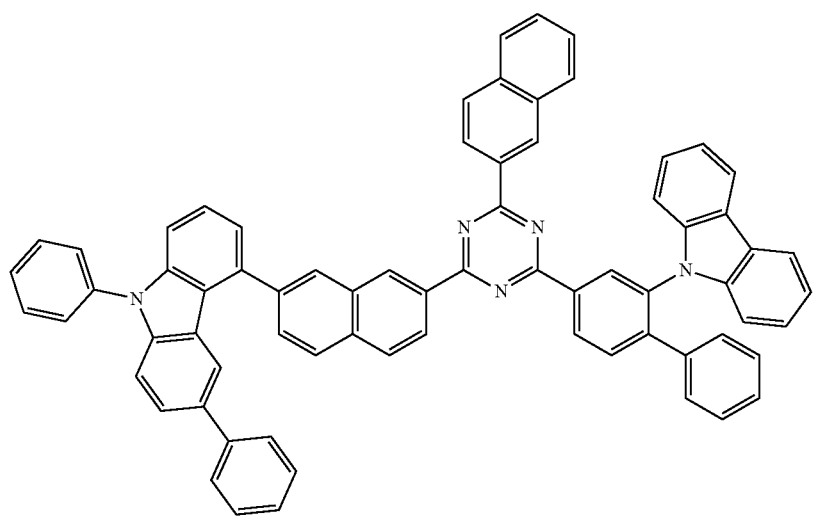
159
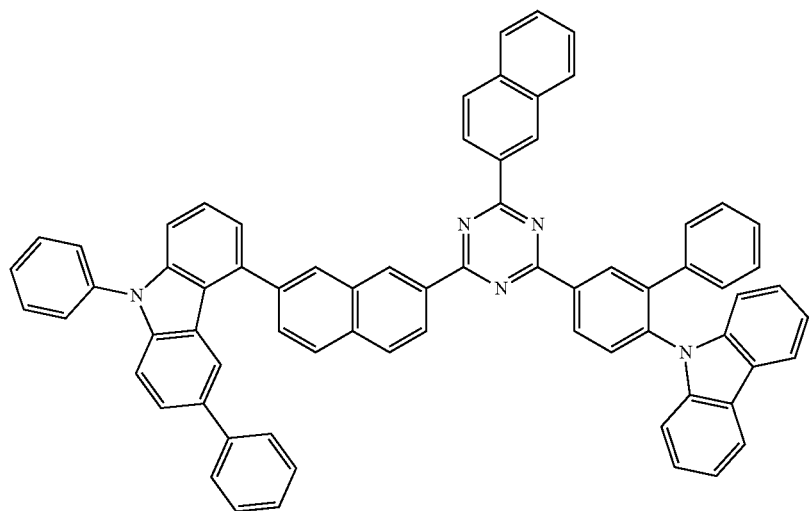

-continued
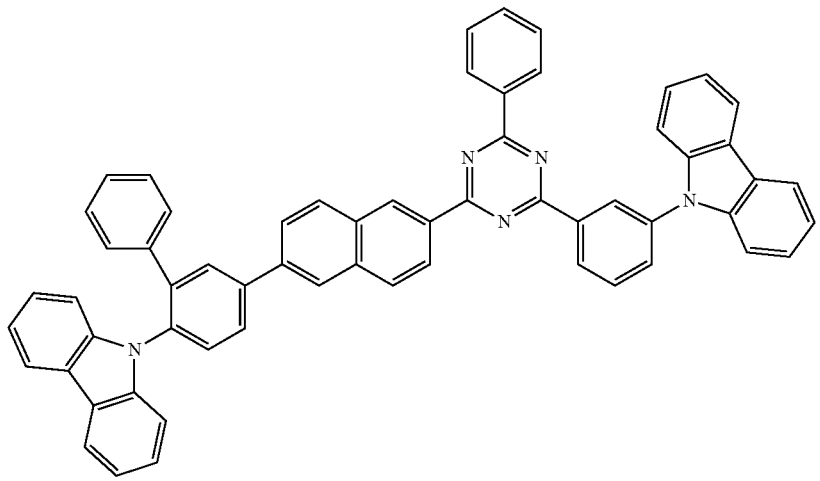
160
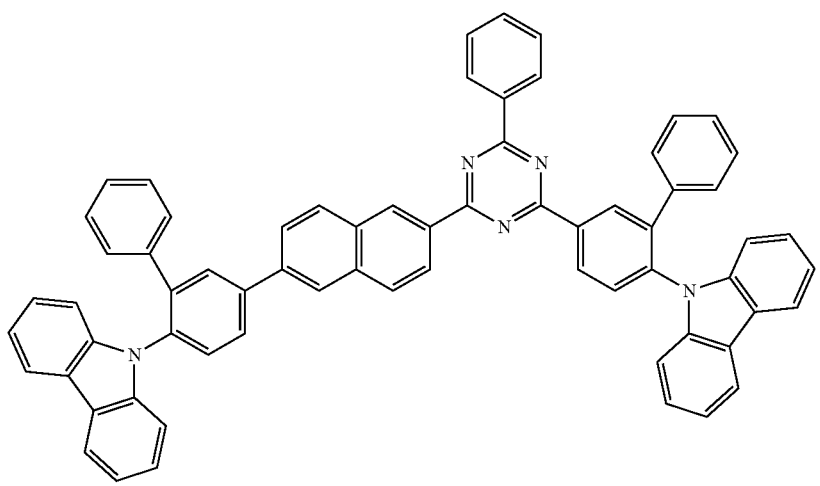
161
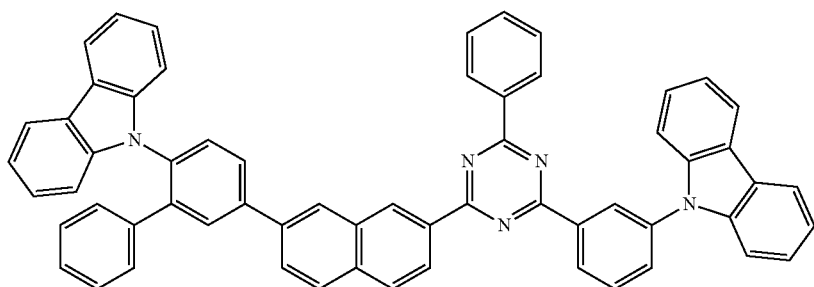
162

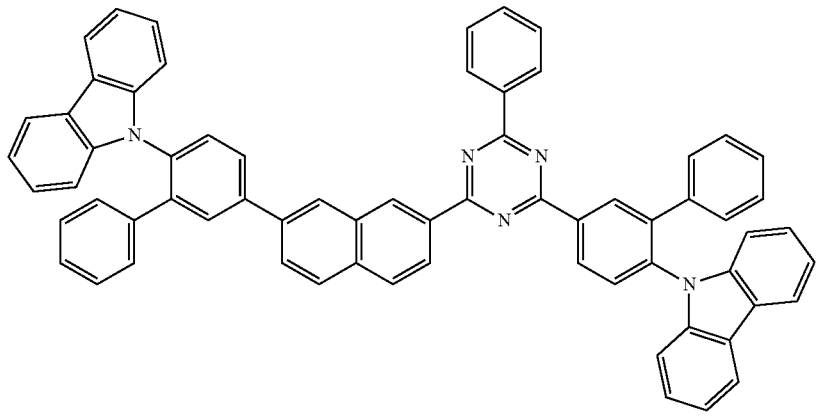
163
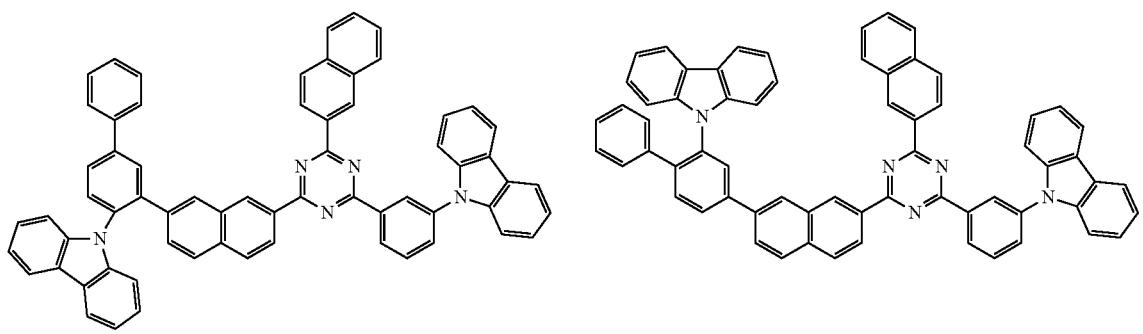
164 165
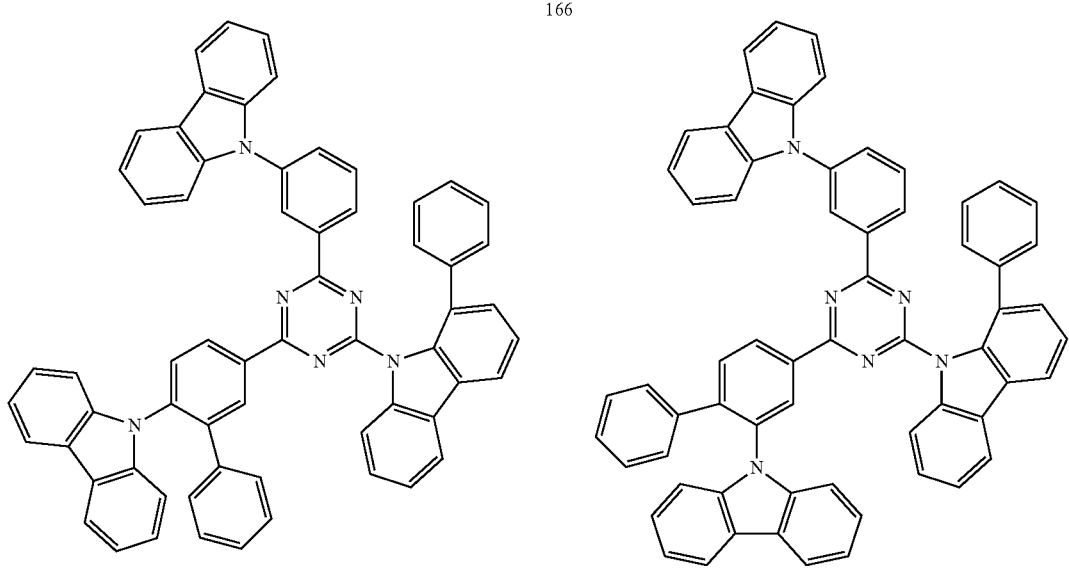
166 167

168
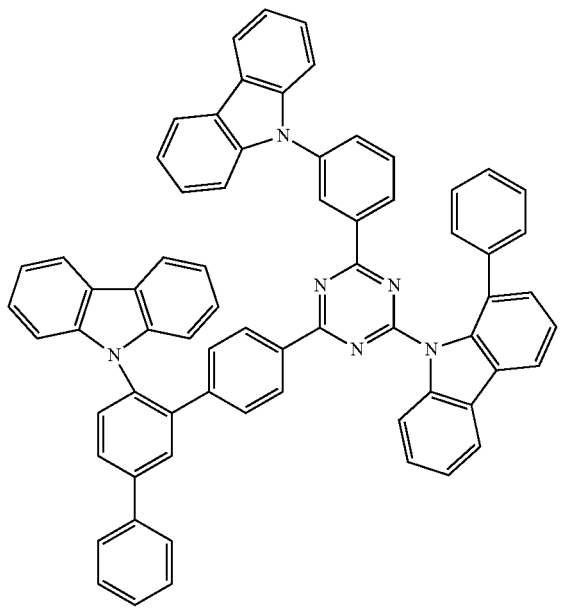
169
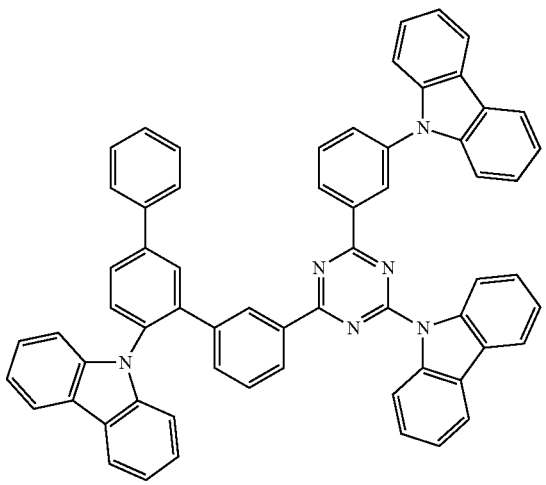
170
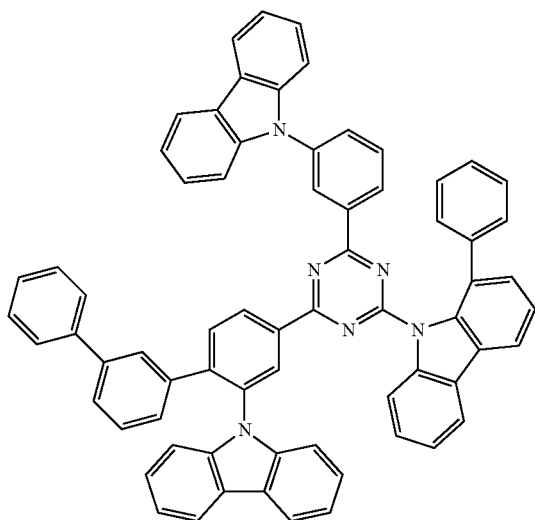
171
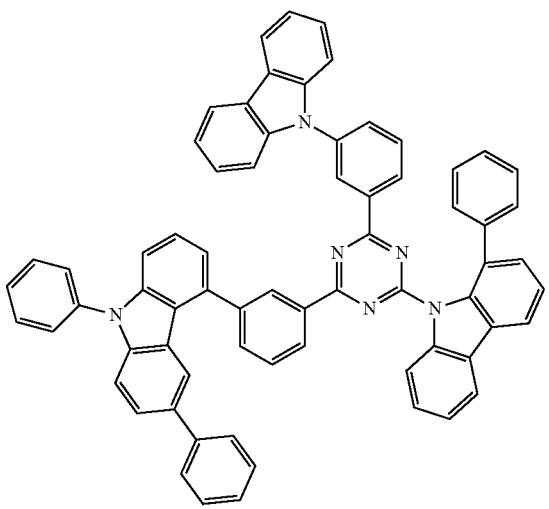

-continued
172
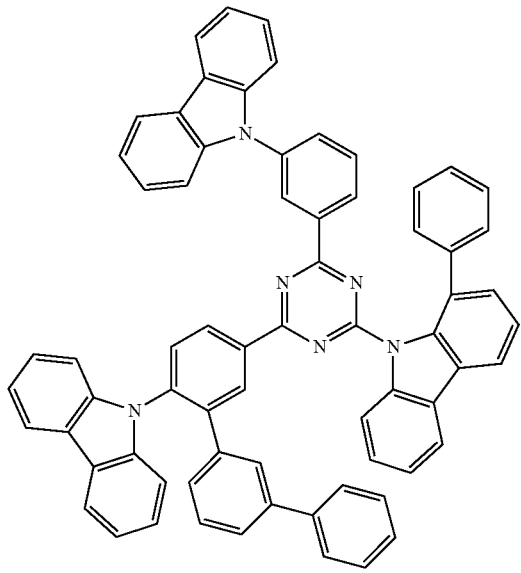
173
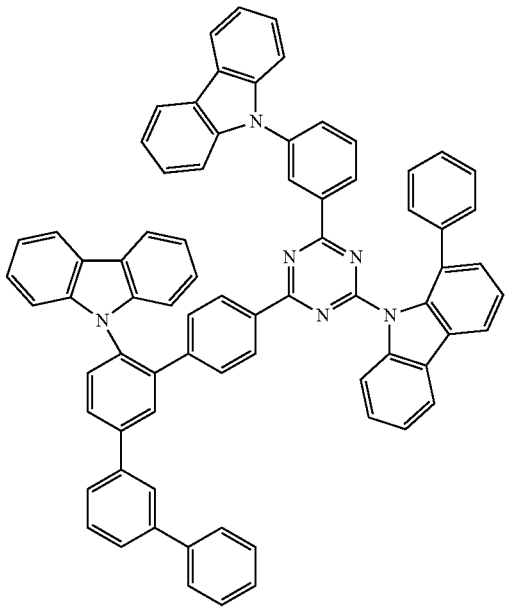
174
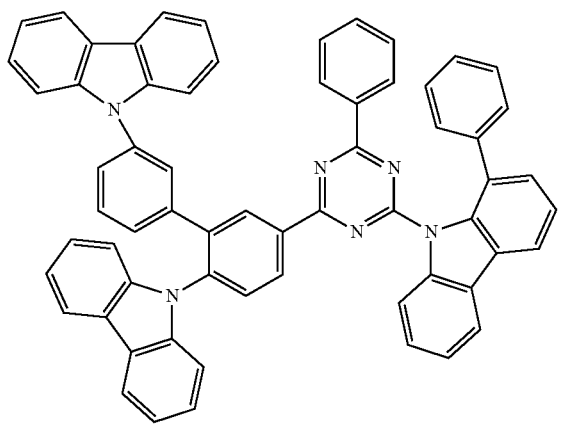
175
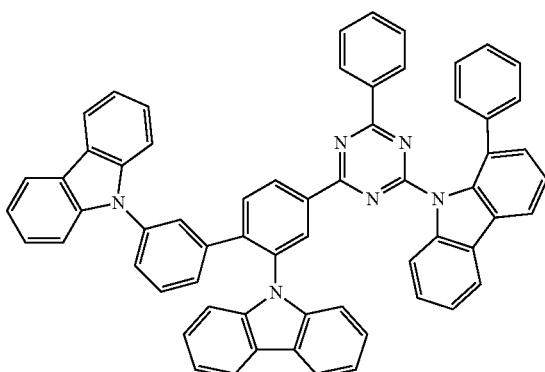
176
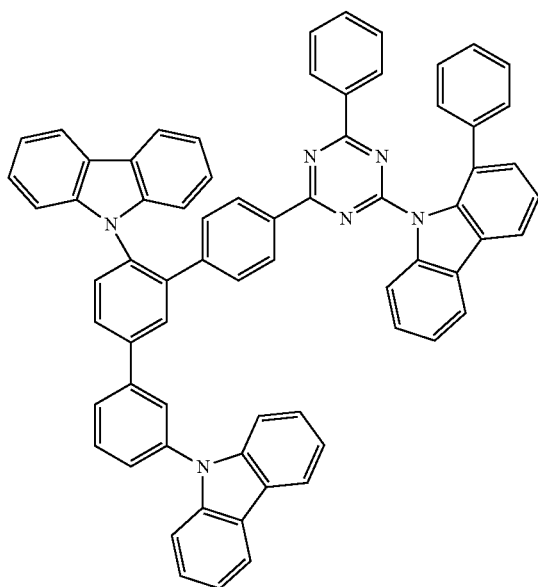
177
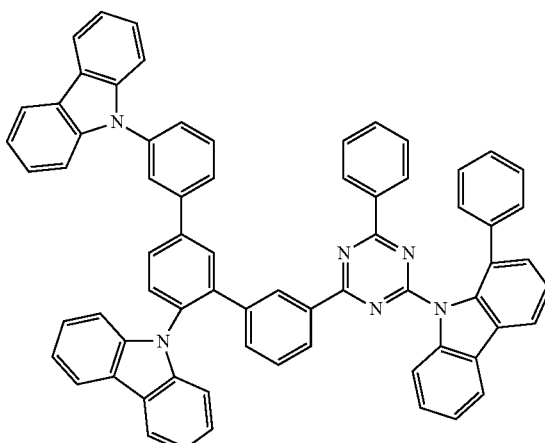

-continued
178
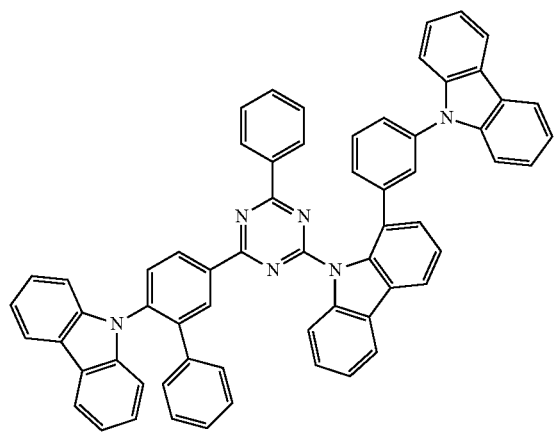
179
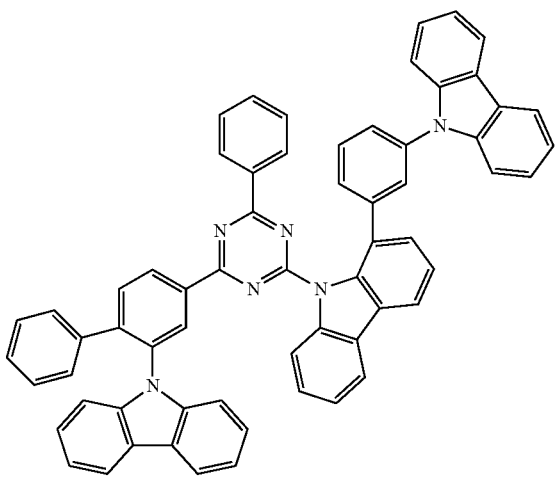
180
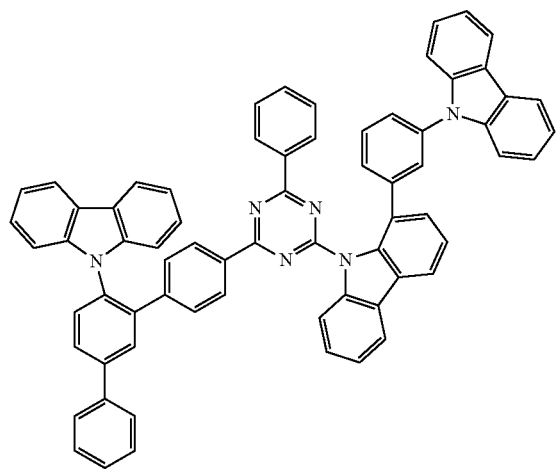
181
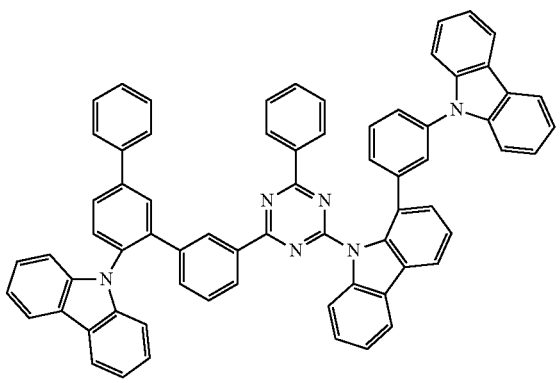
182
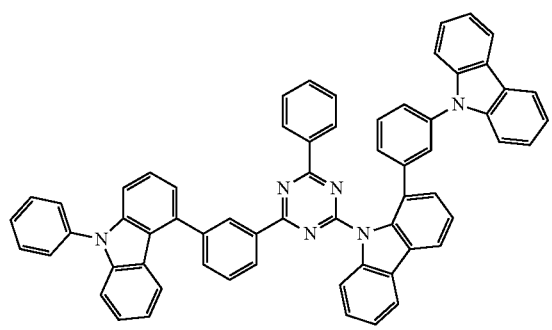
183
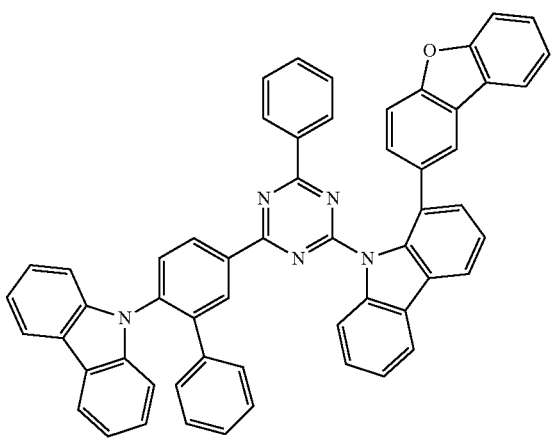

-continued
184
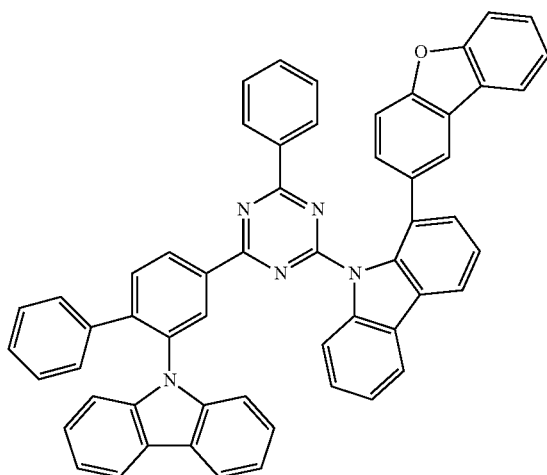
185
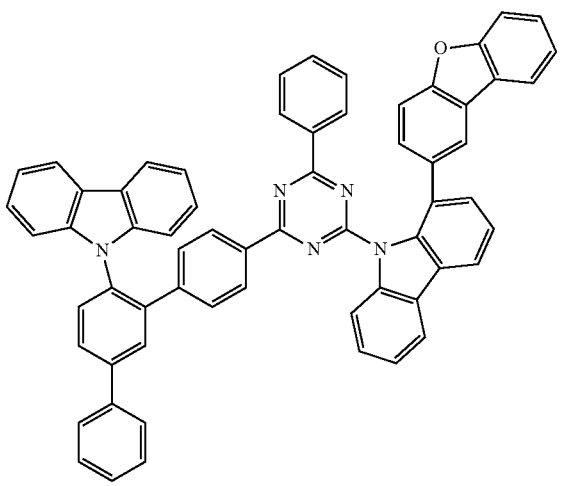
186
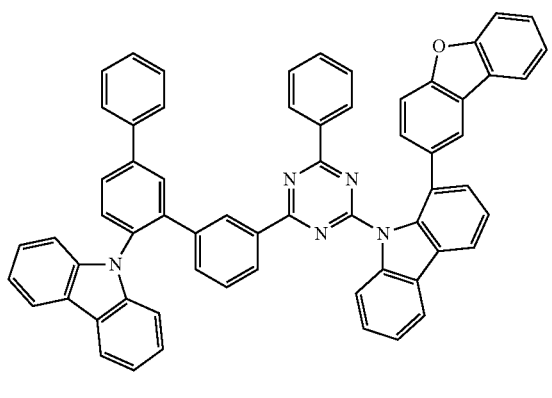
187
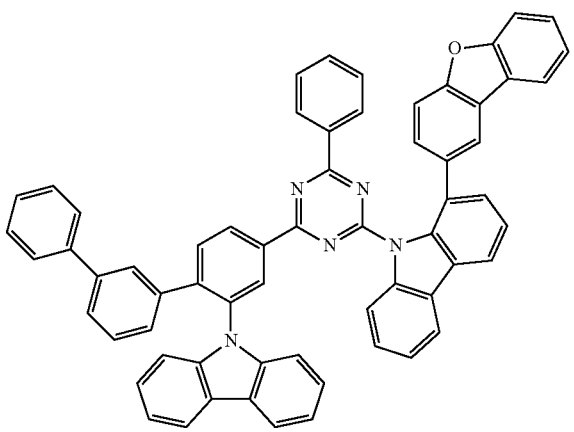
188
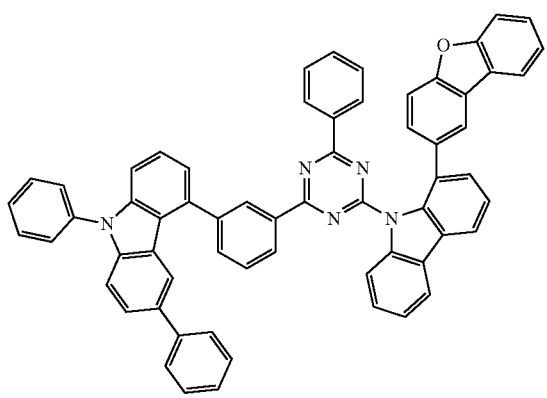
189
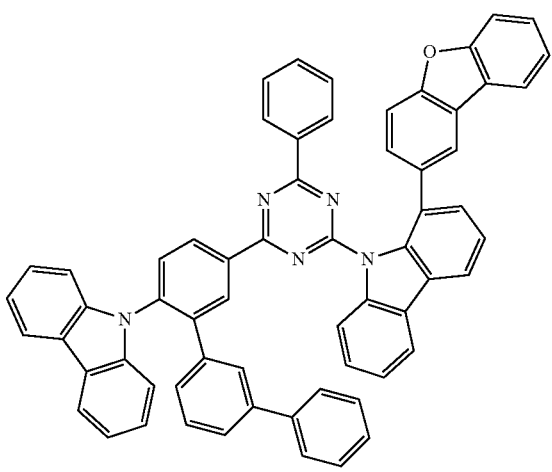

190
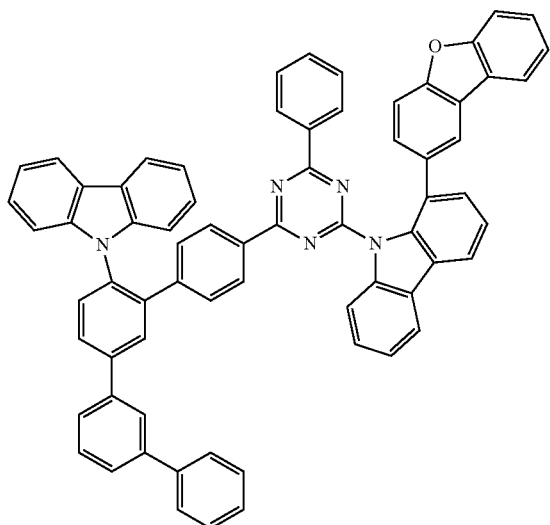
191
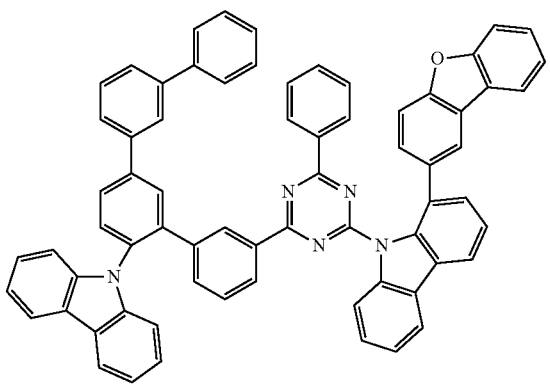
192
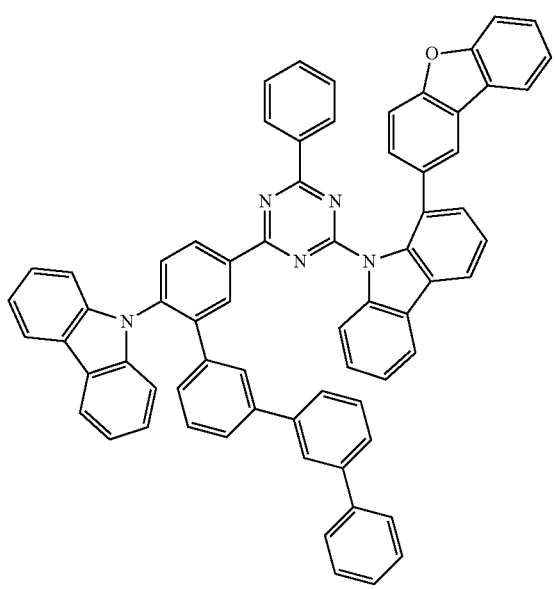
193
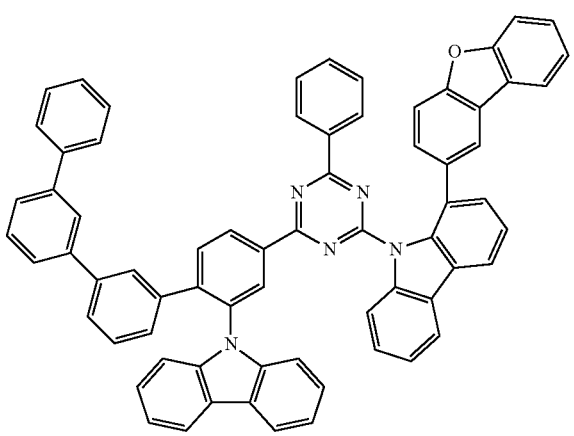
194
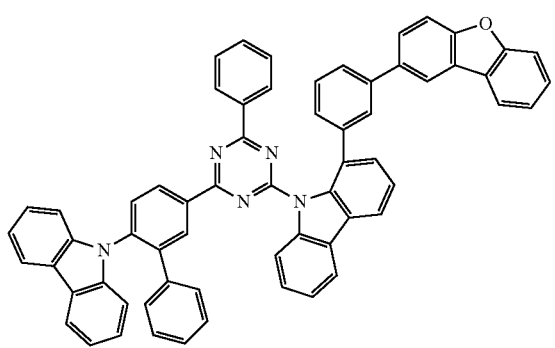
195
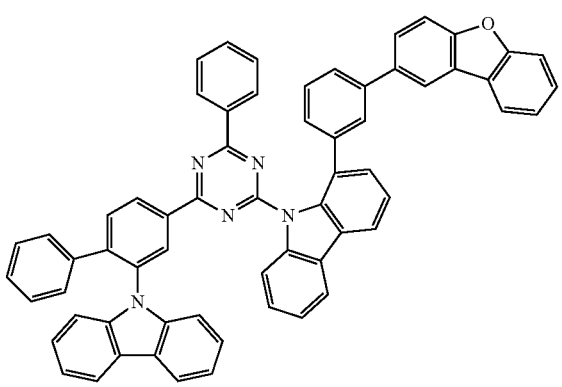

-continued
196
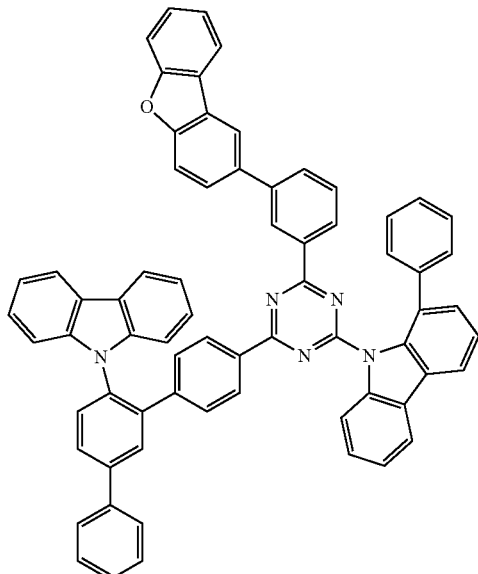
197
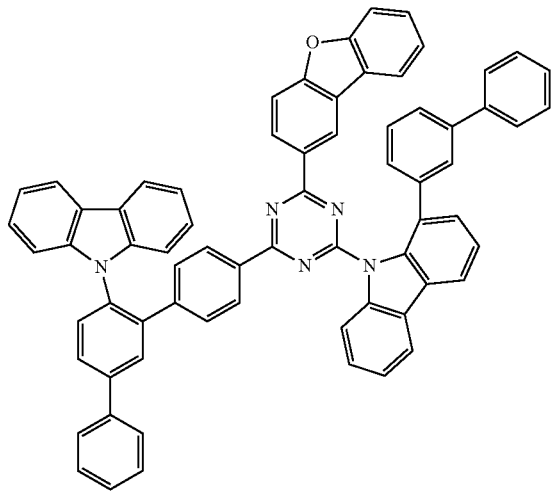
198
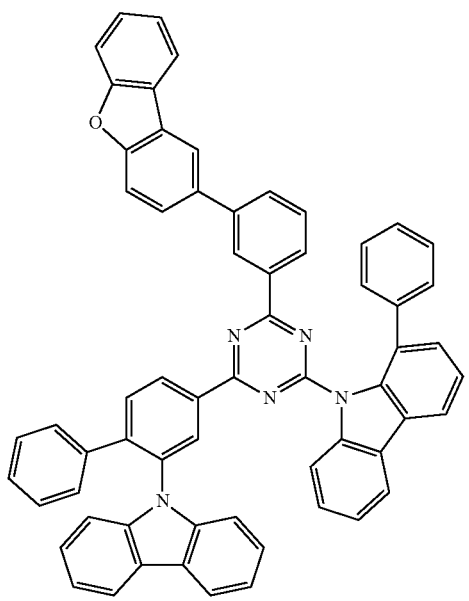
199
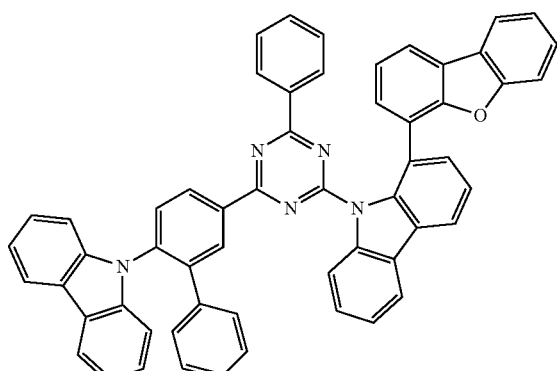
200
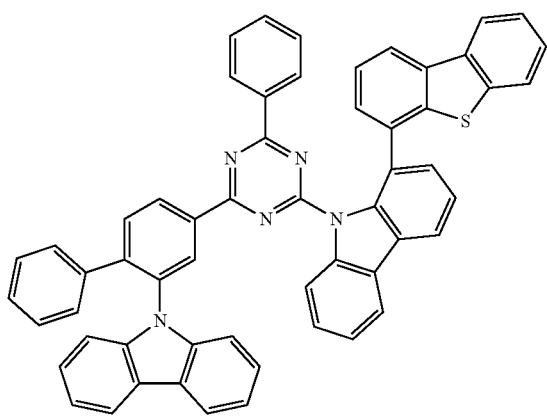
201
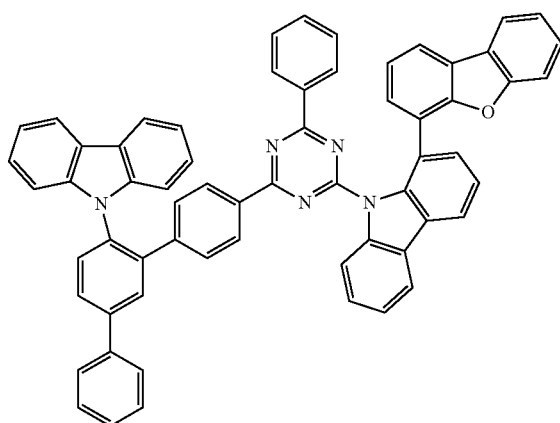

-continued
377
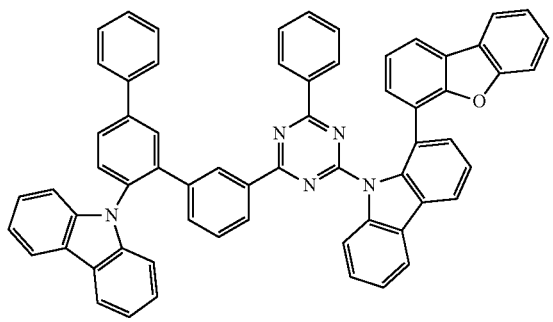
202
378
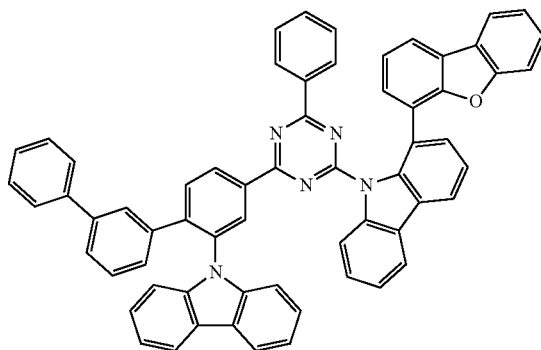
203
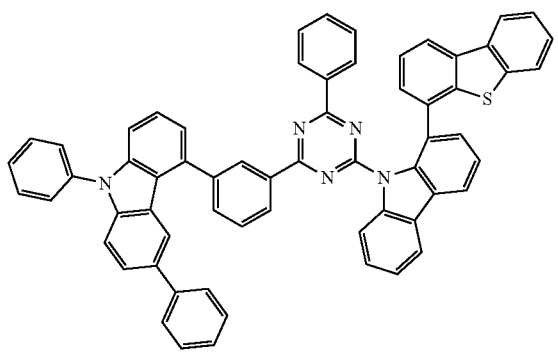
204
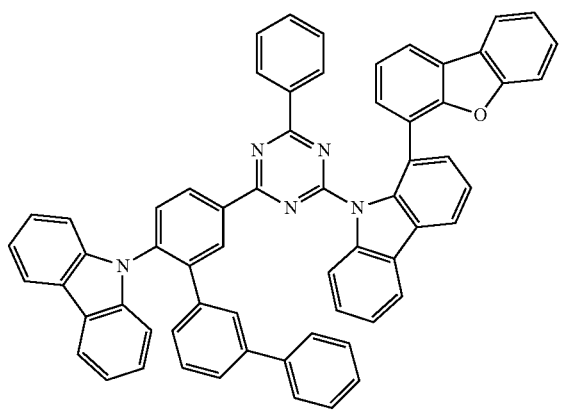
205
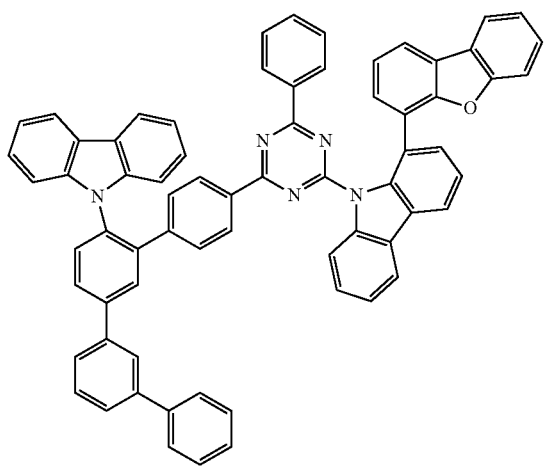
206
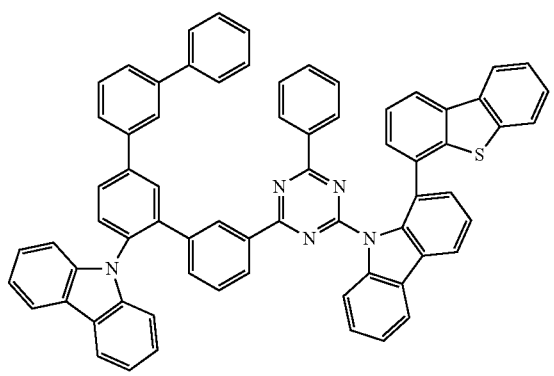
207

208
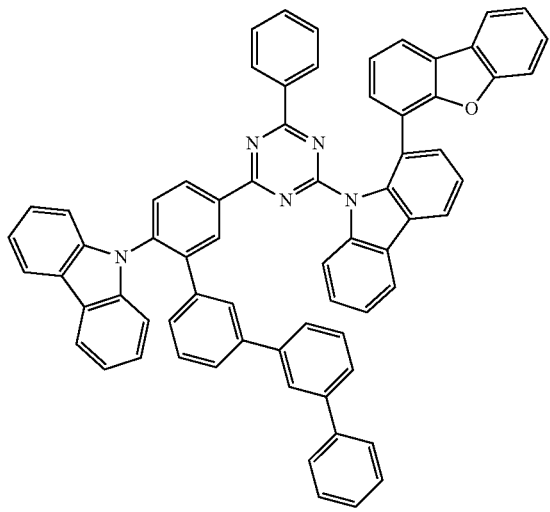
209
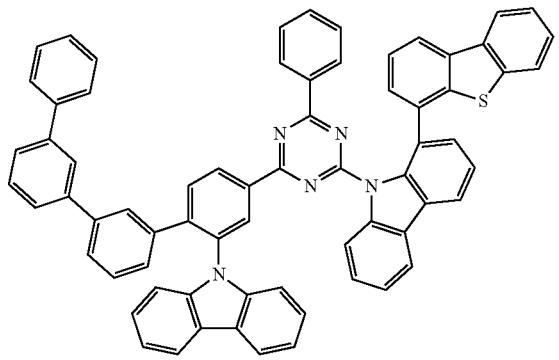
210
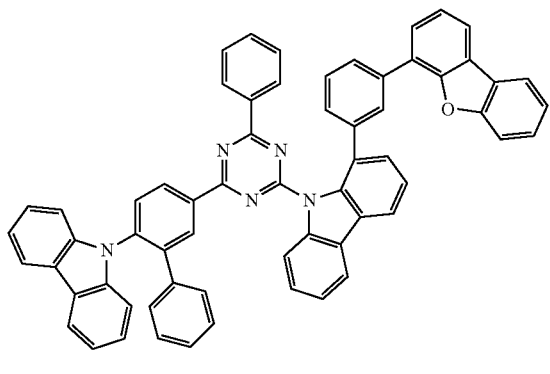
211
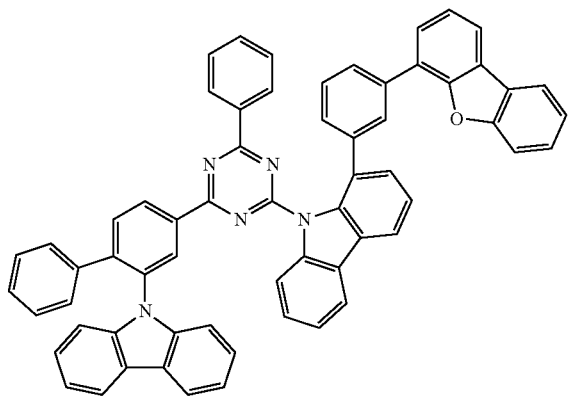
212
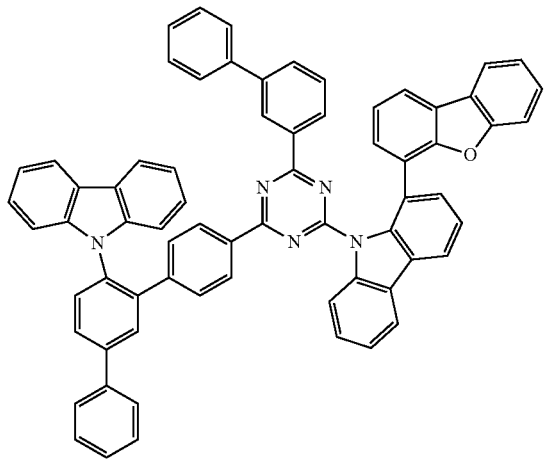
213
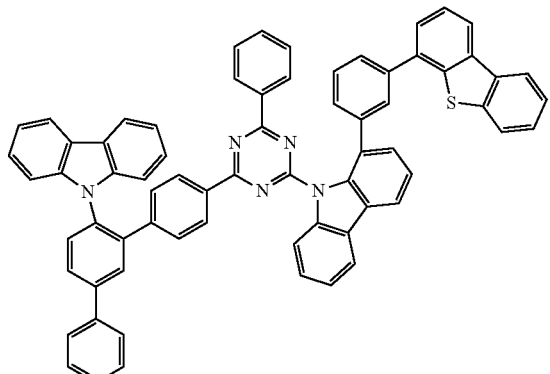

214
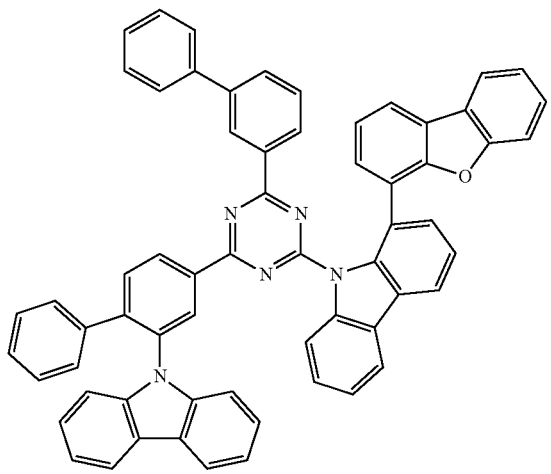
215
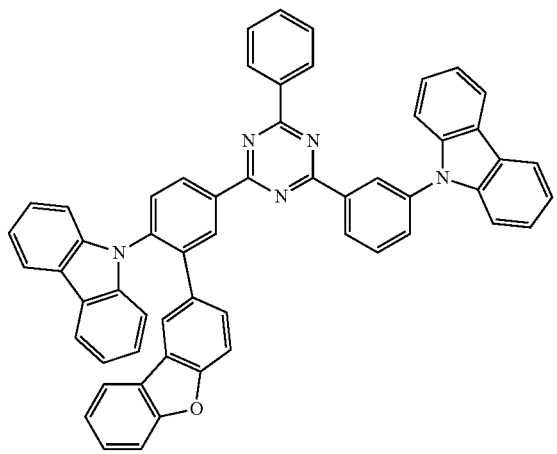
216
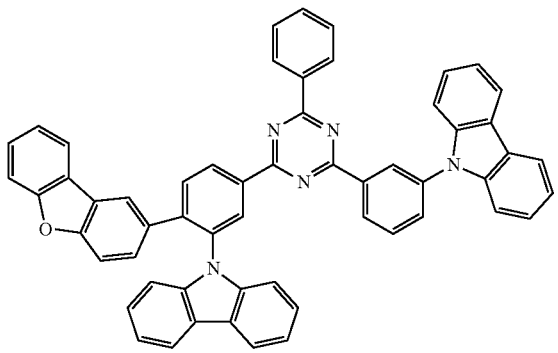
217
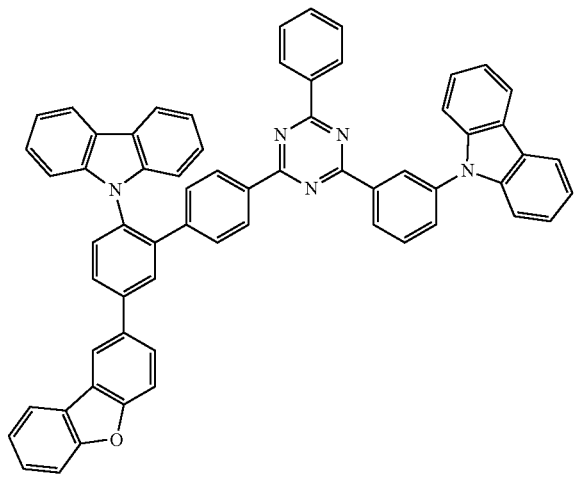
218
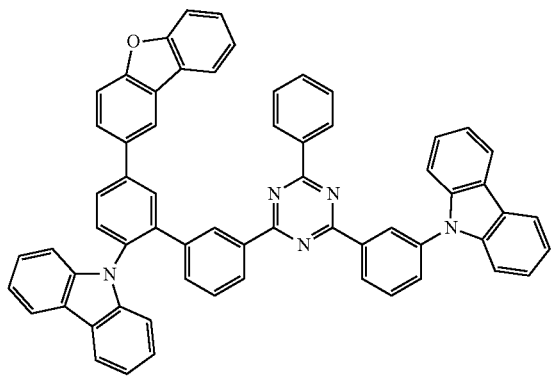
219
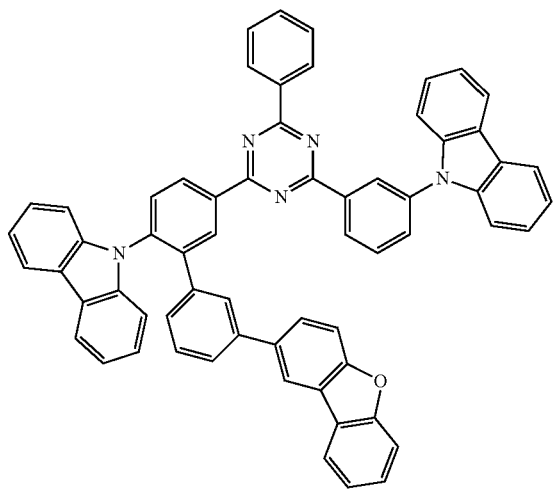

-continued
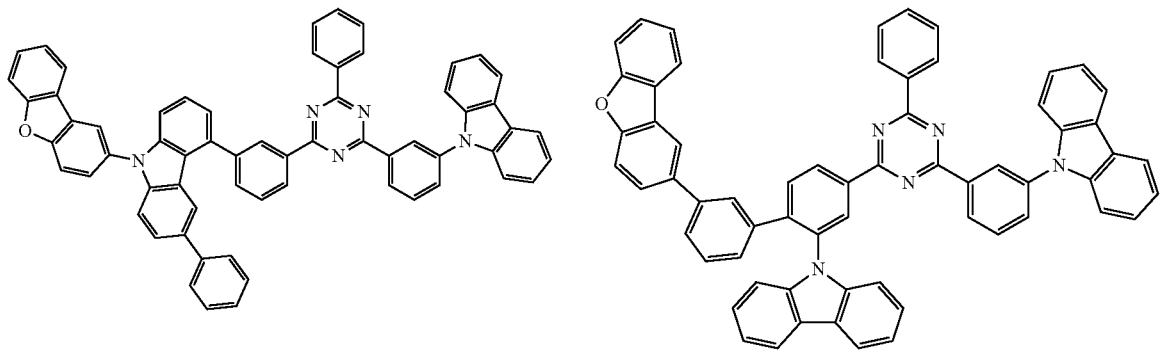
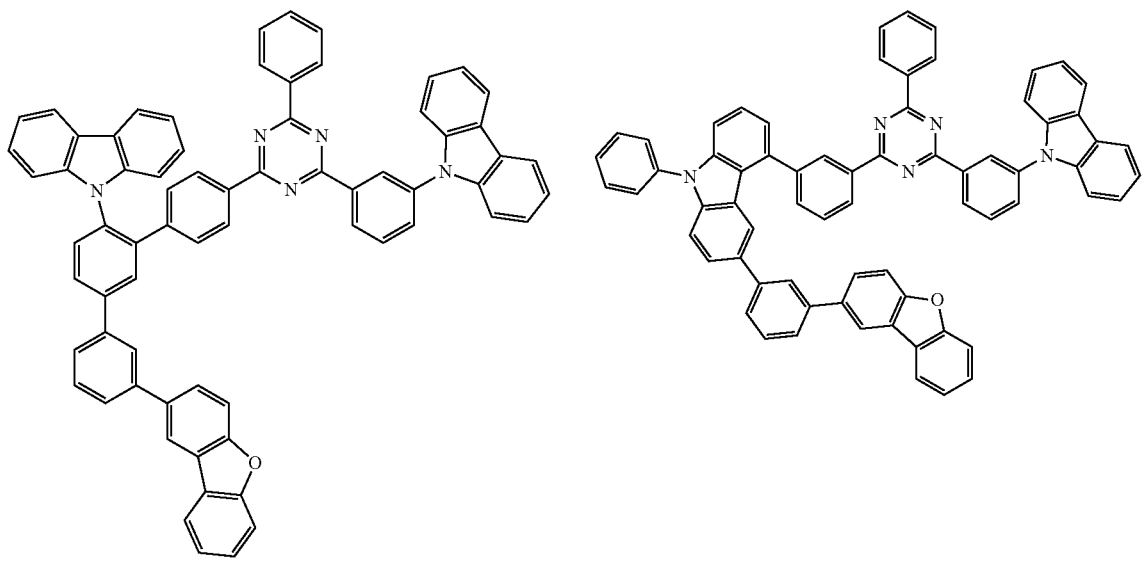
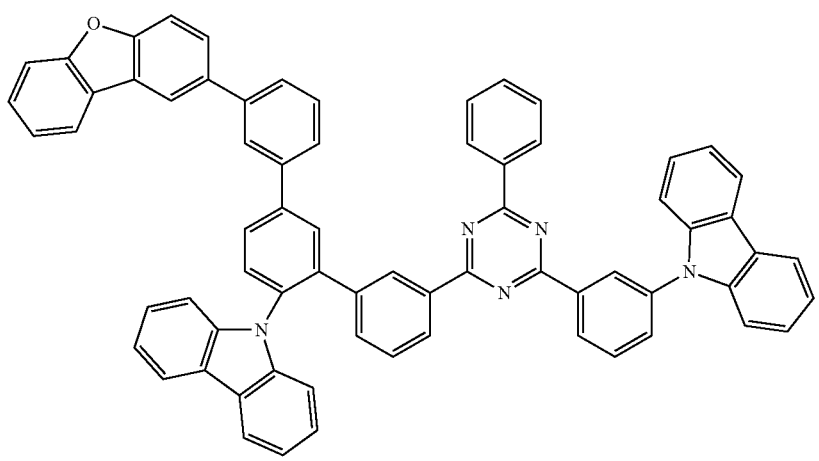

-continued
225
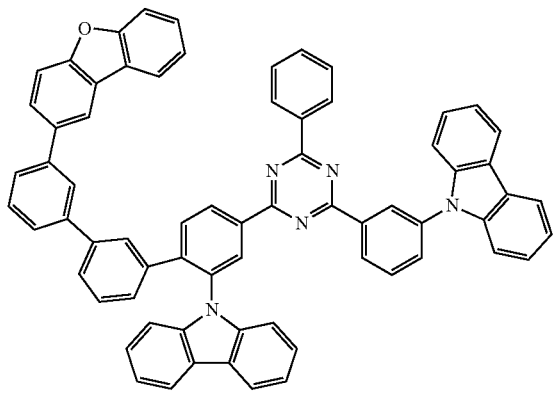
226
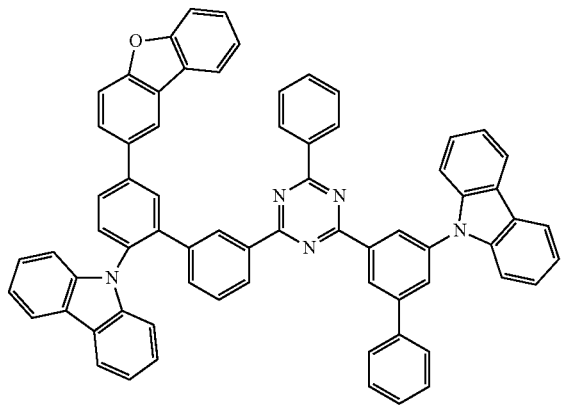
227
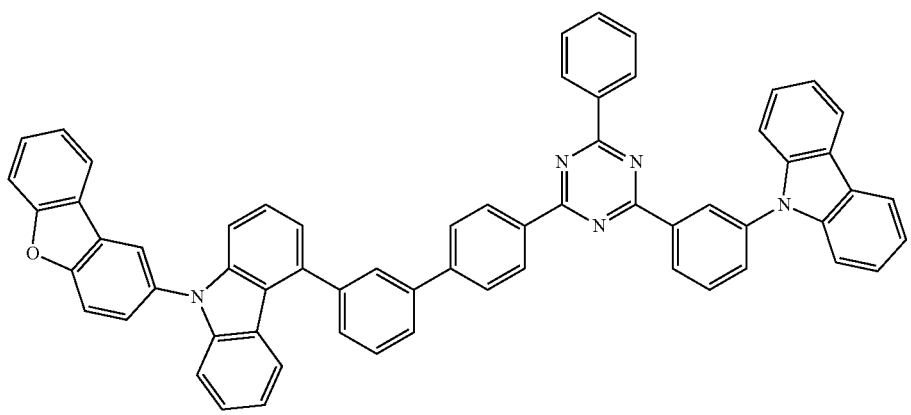
228
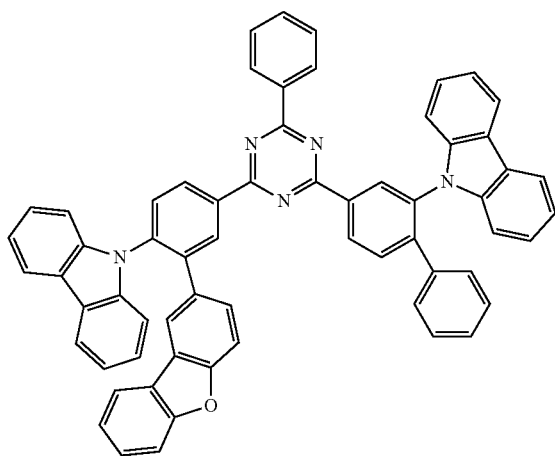
229
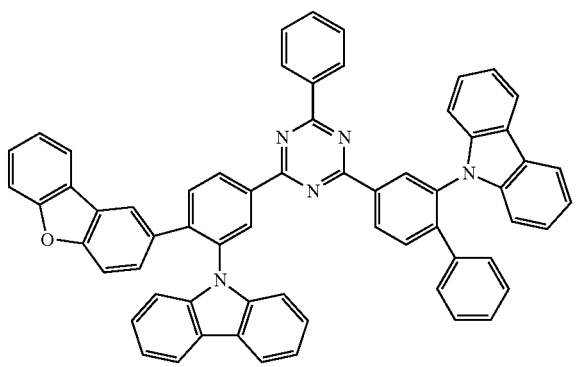

-continued
230
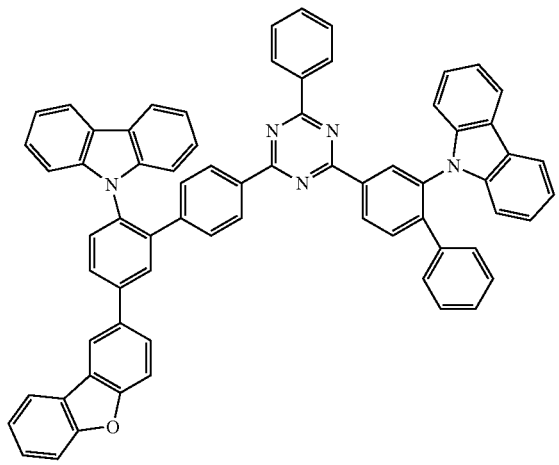
231
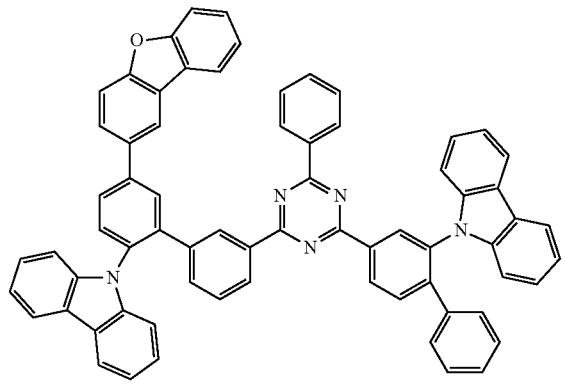
232
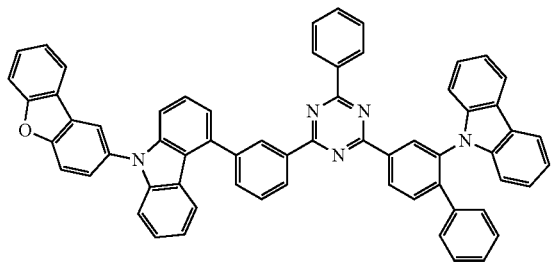
233
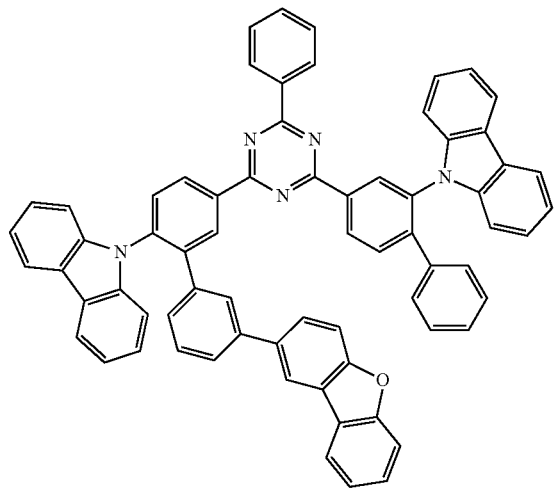
234
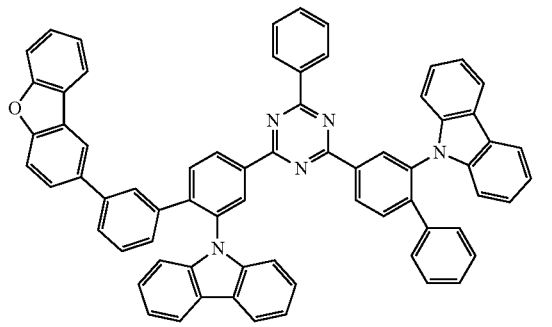
235
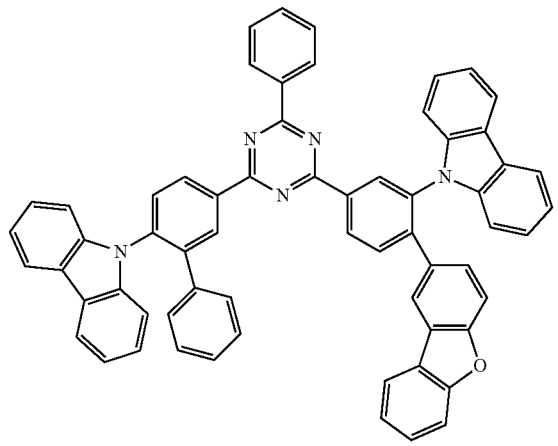

-continued
236
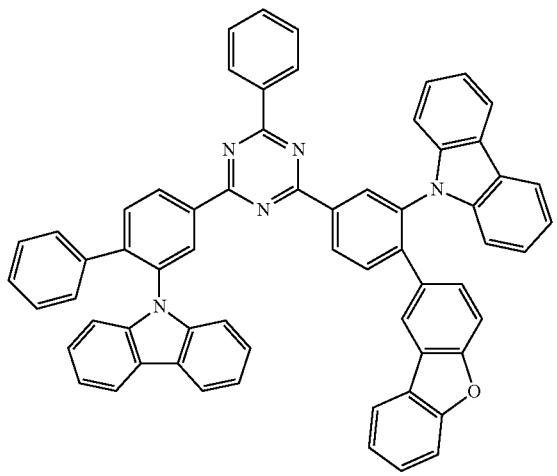
237
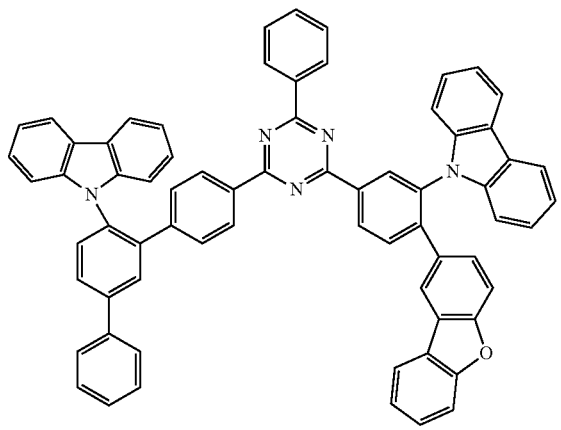
238
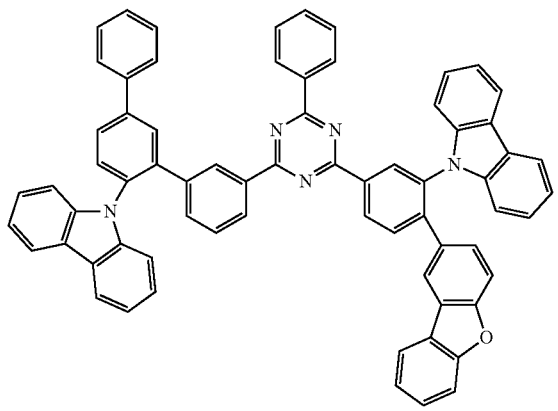
239
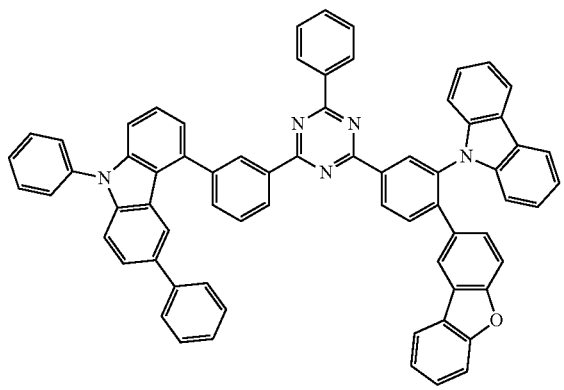
240
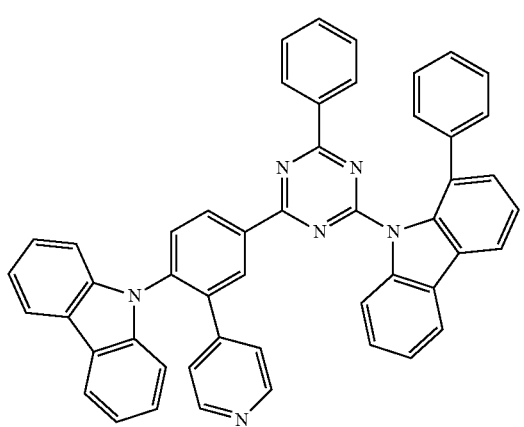
241
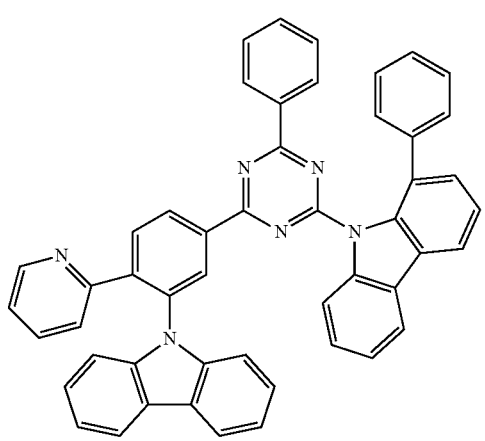

-continued
242
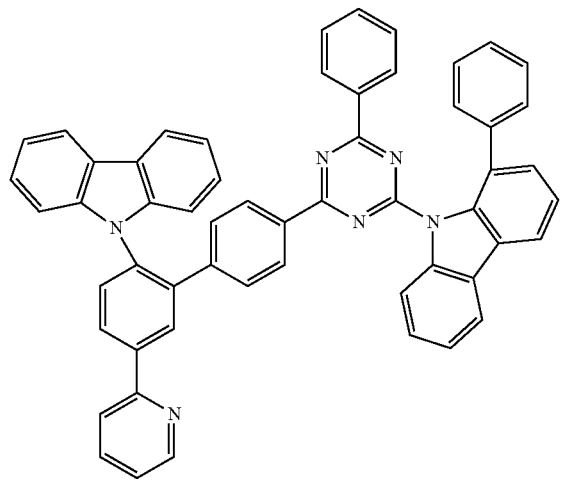
243
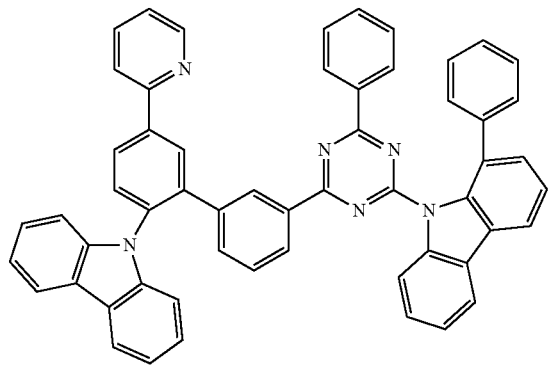
244
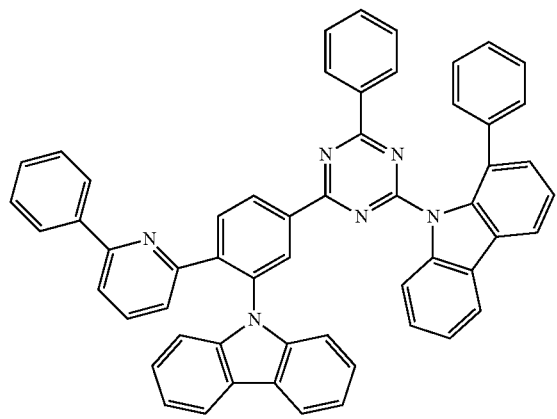
245
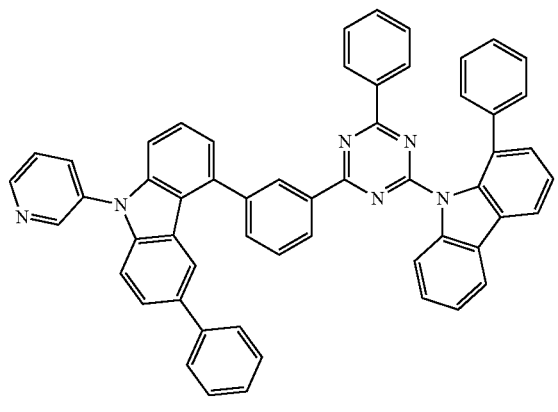
246
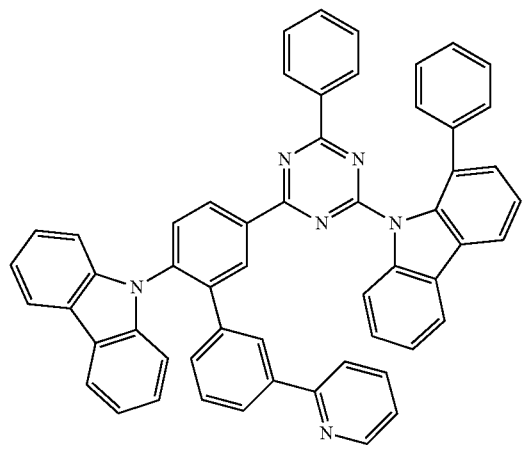
247
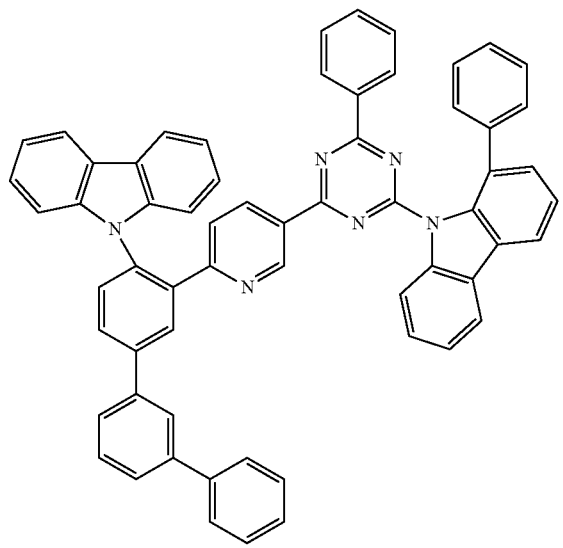

393
394
-continued
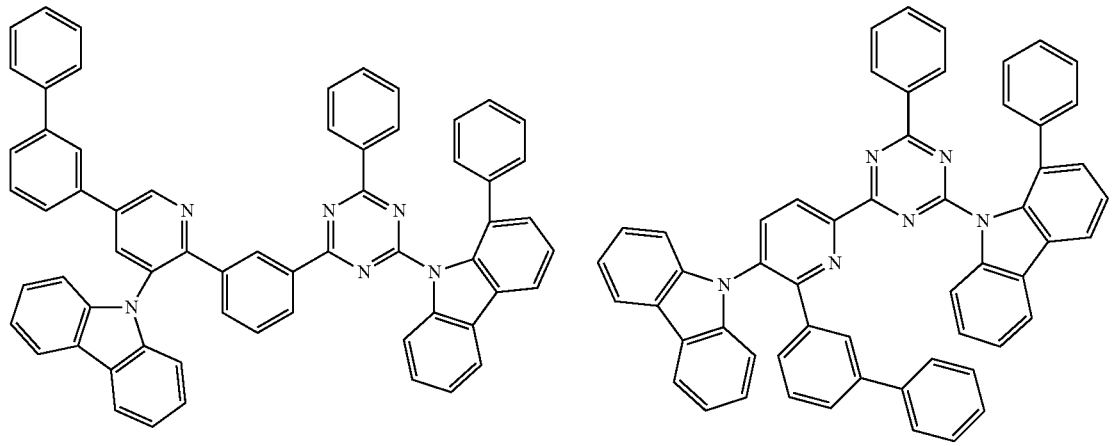
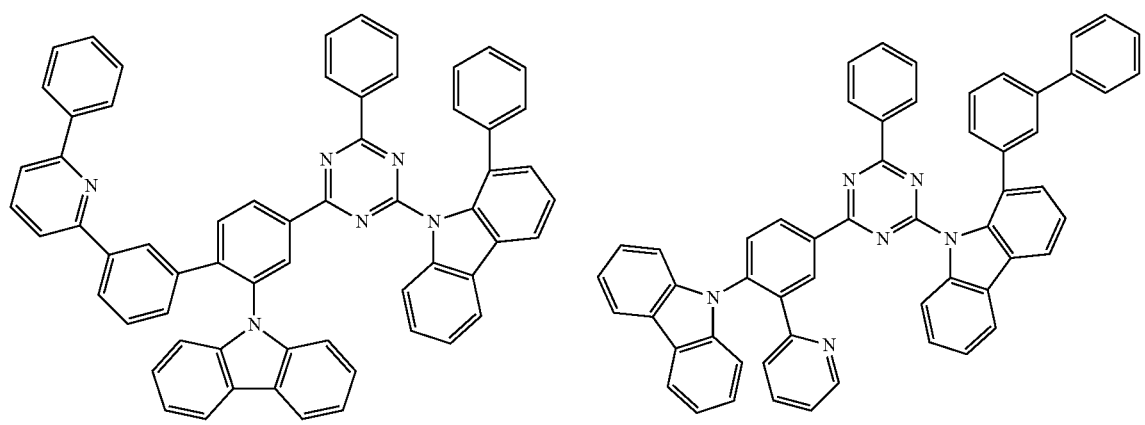
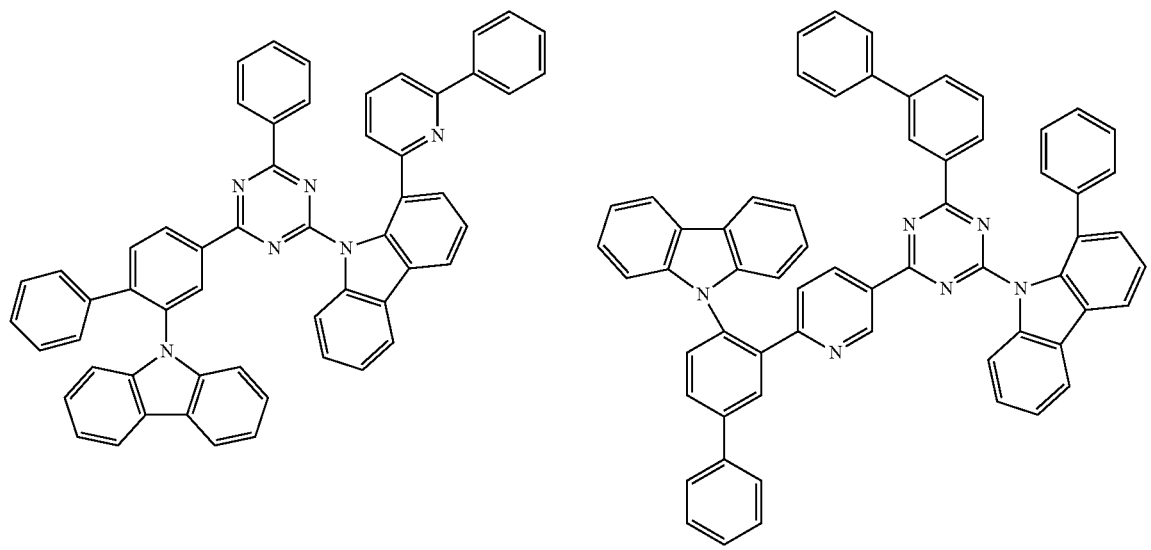

-continued
254
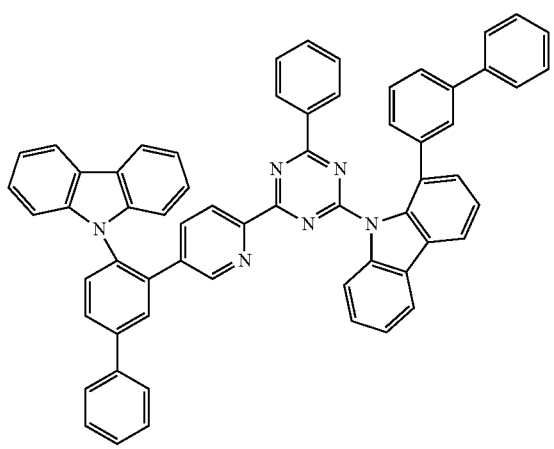
255
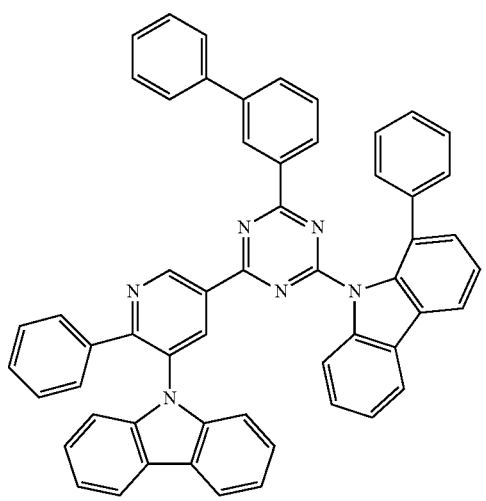
256
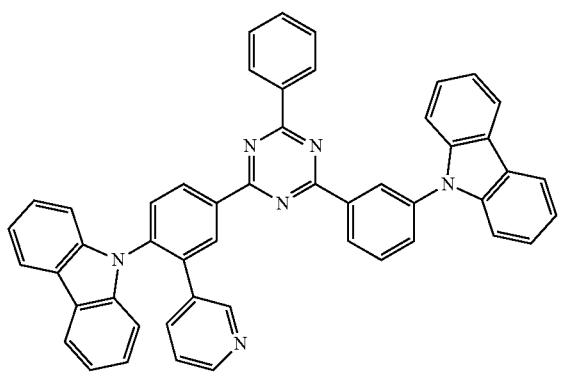
257
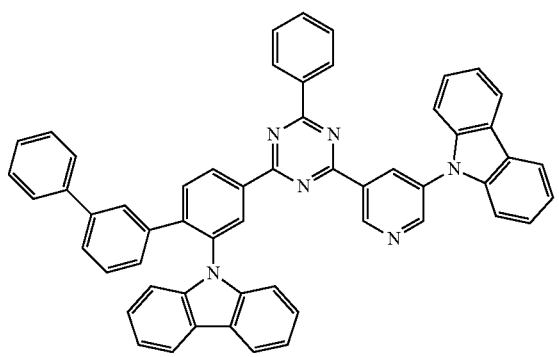
258
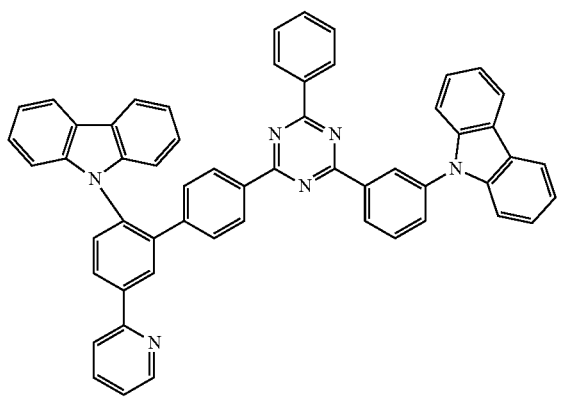
259
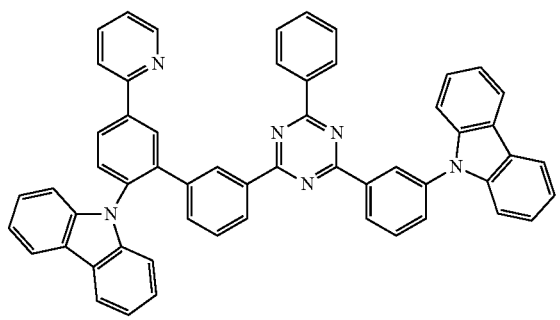

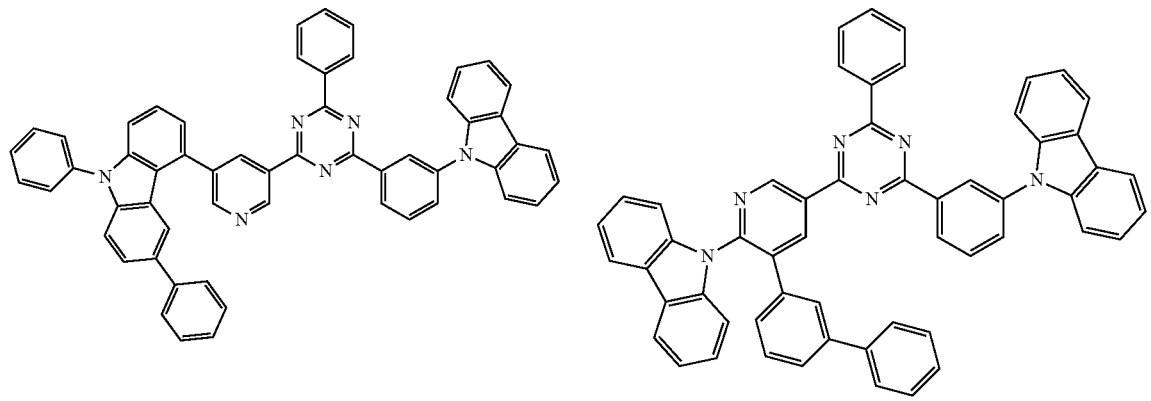
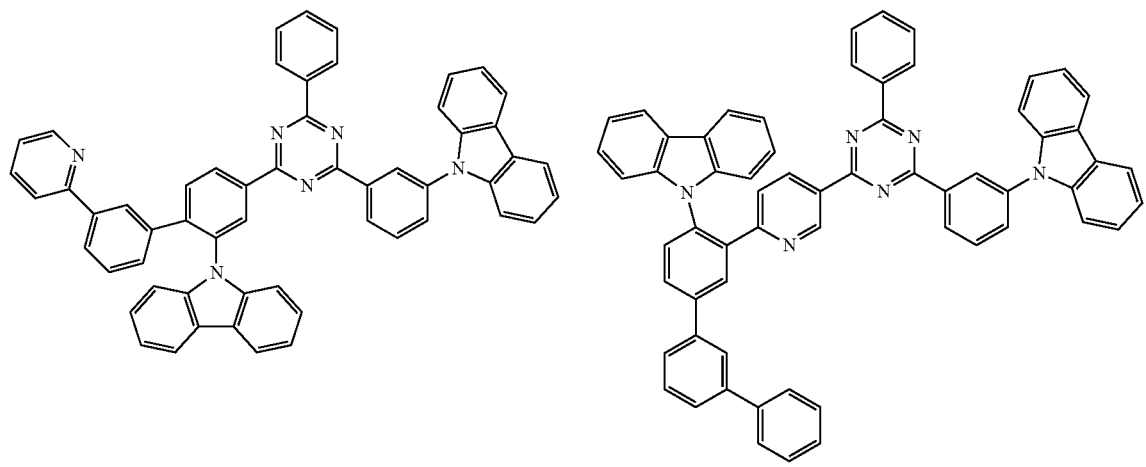
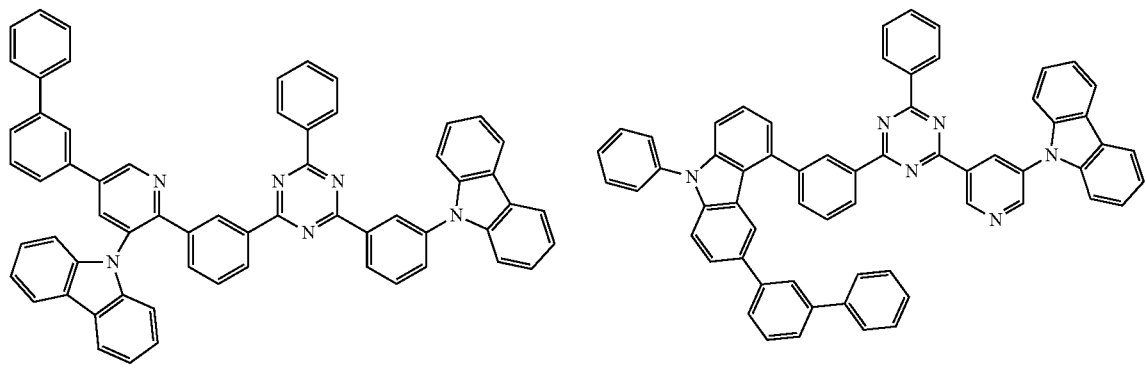

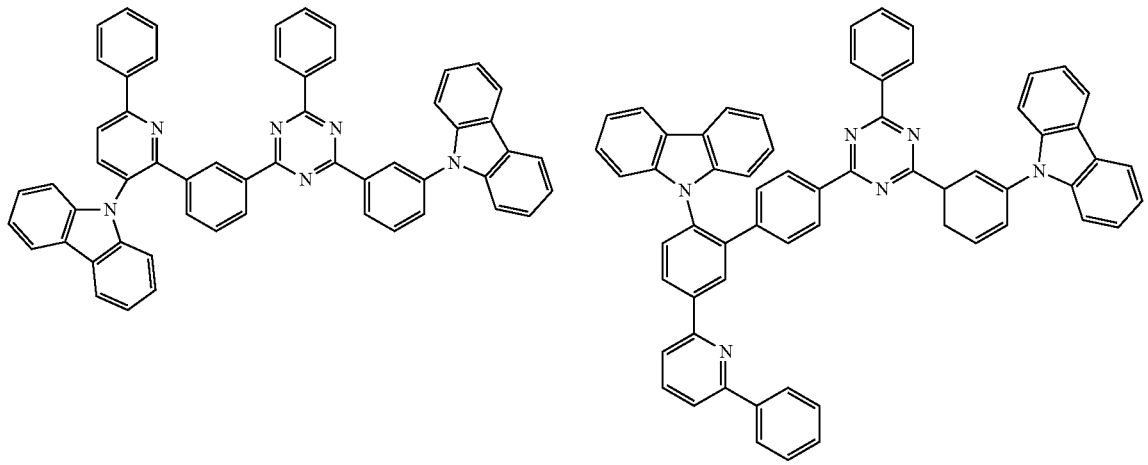
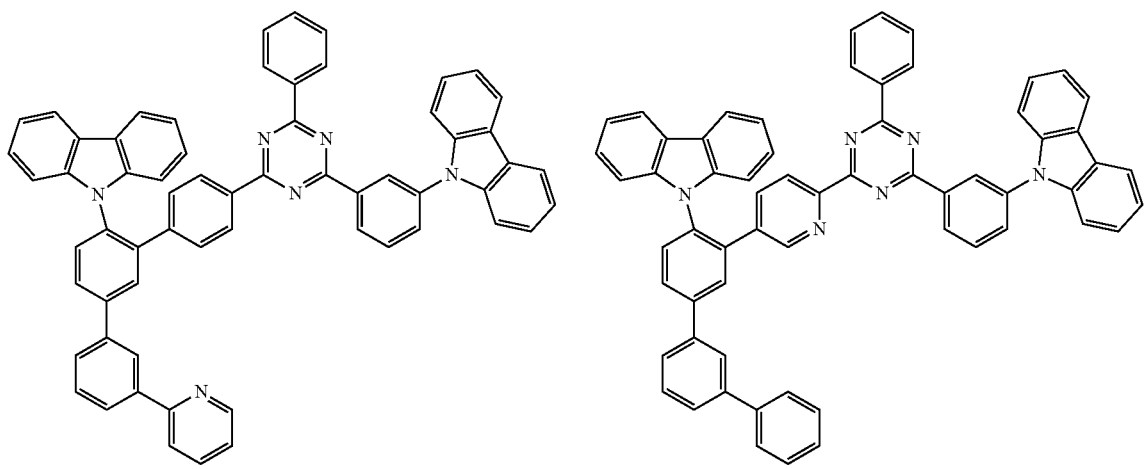
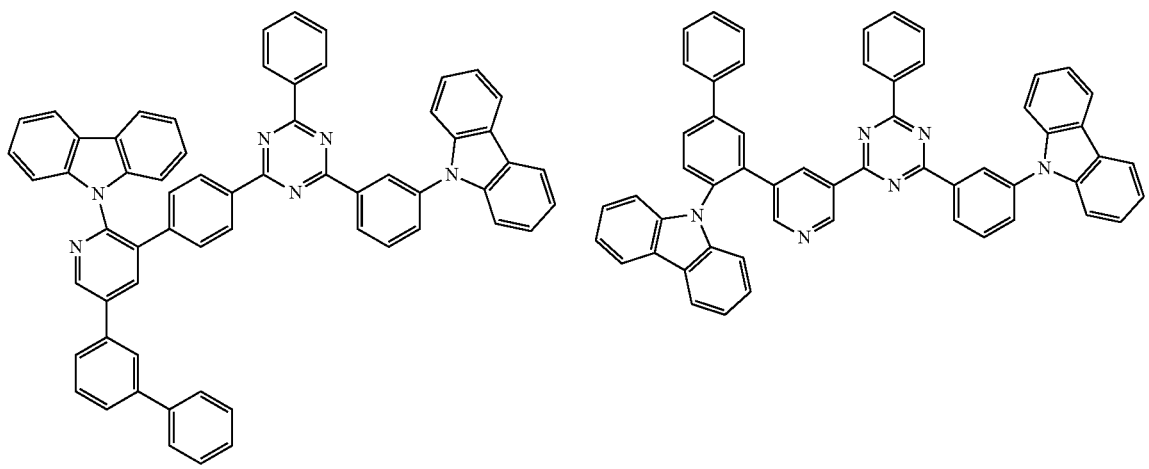

-continued
272
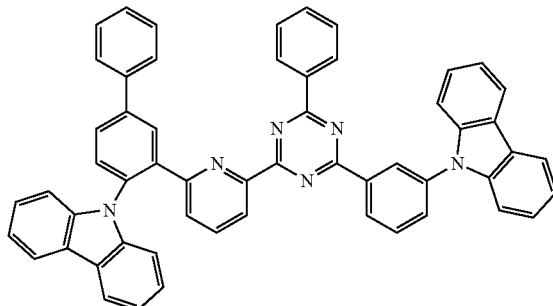
273
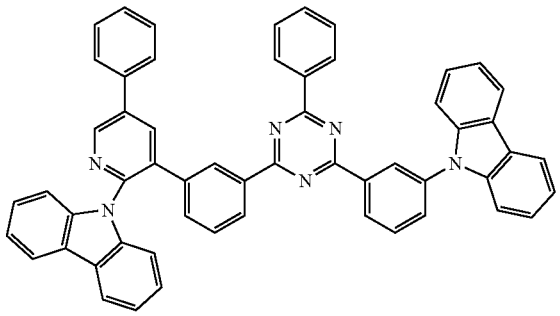
274
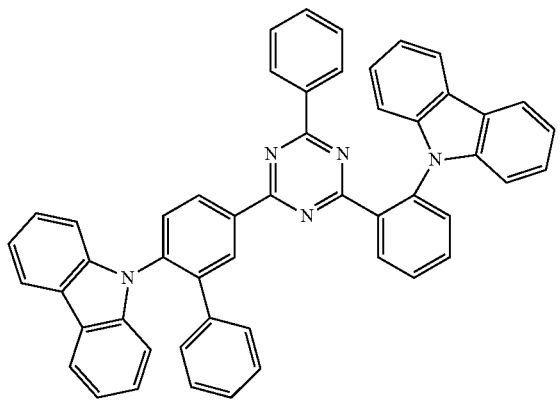
275
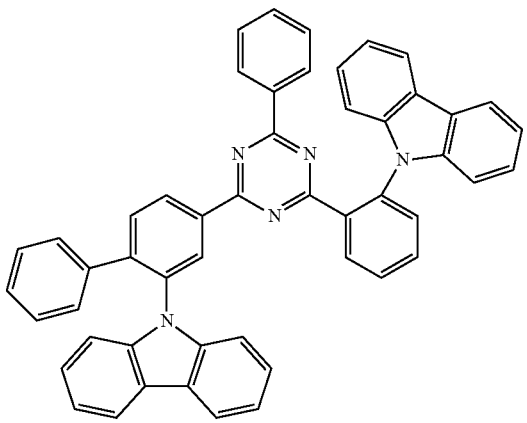
276
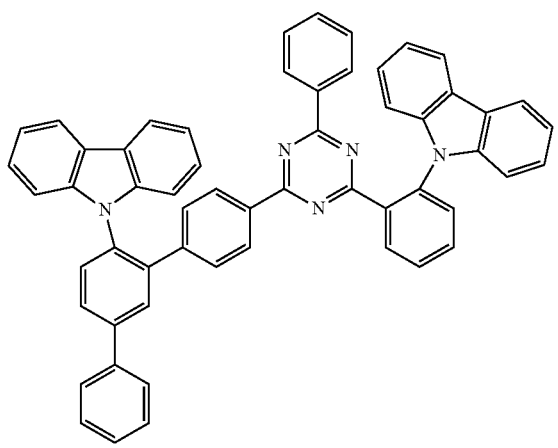
277
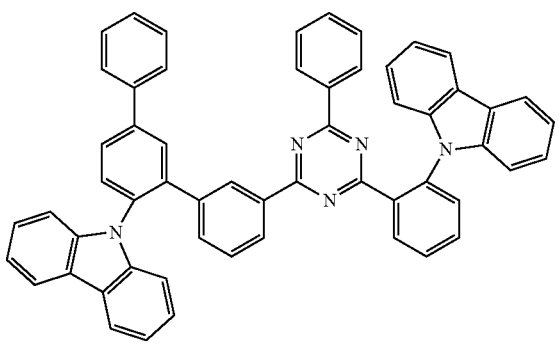
278
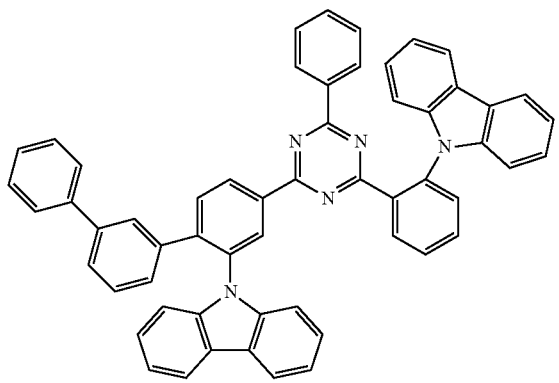
279
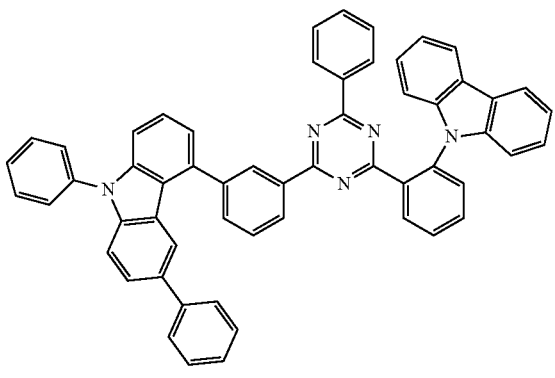

-continued
280 281
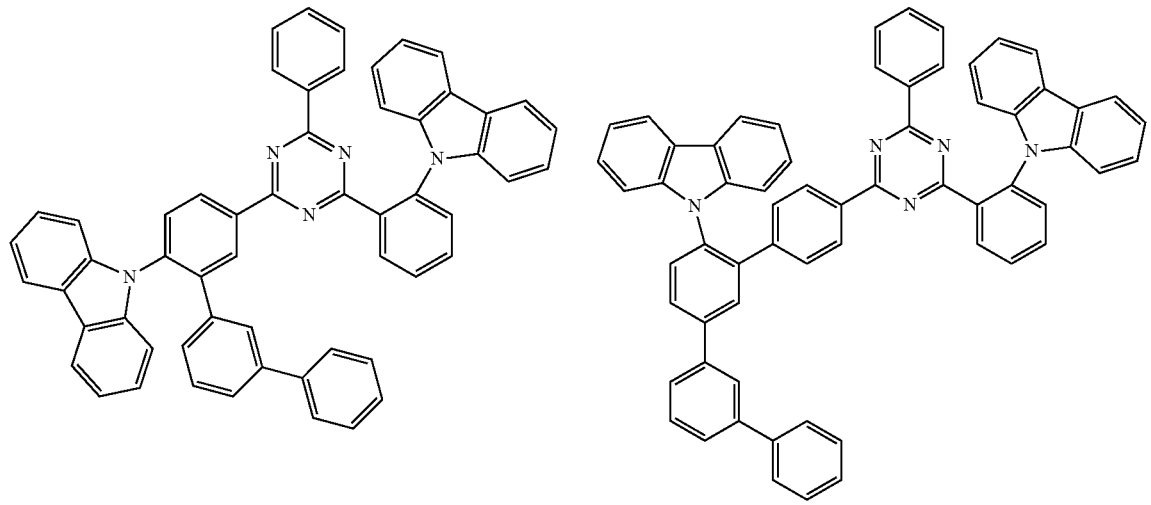
282 283
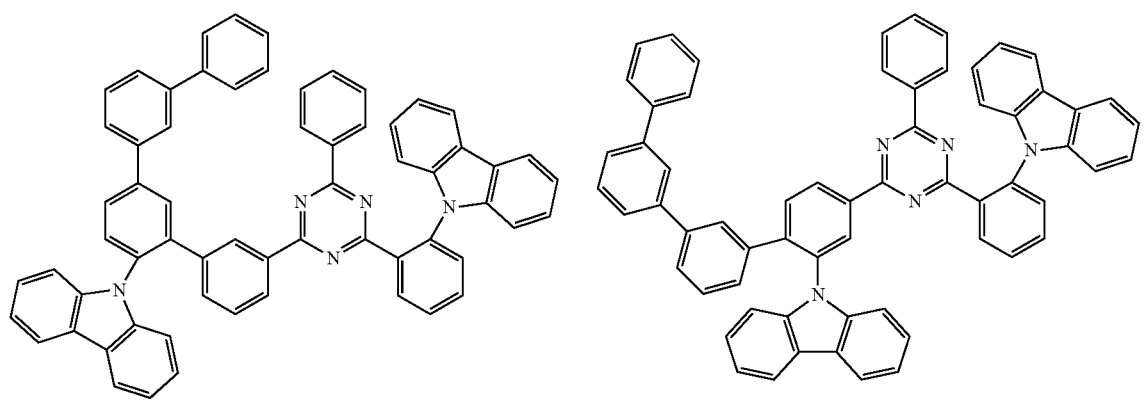
284 285
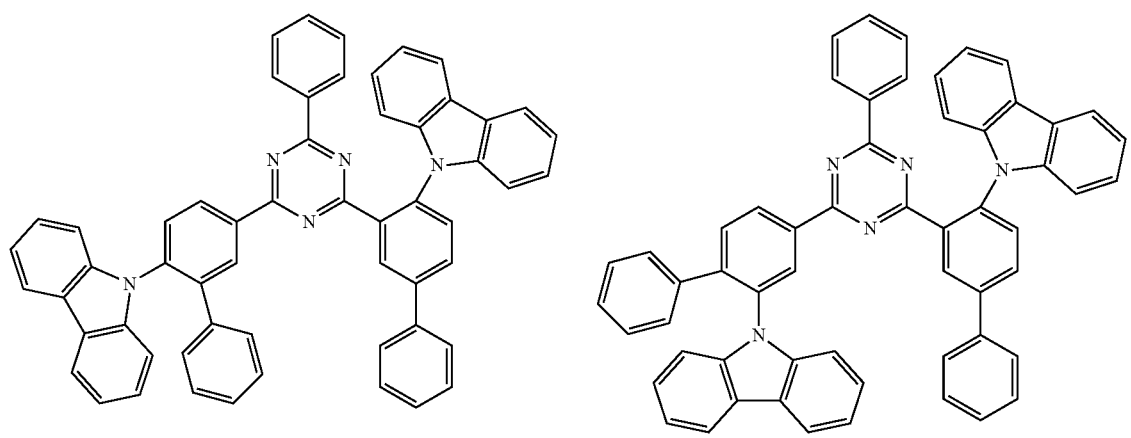

-continued
286
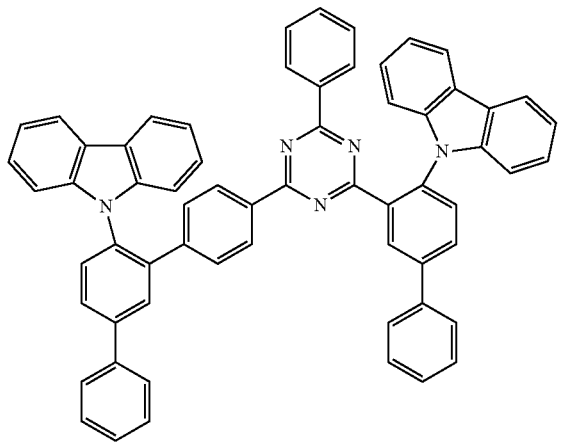
287
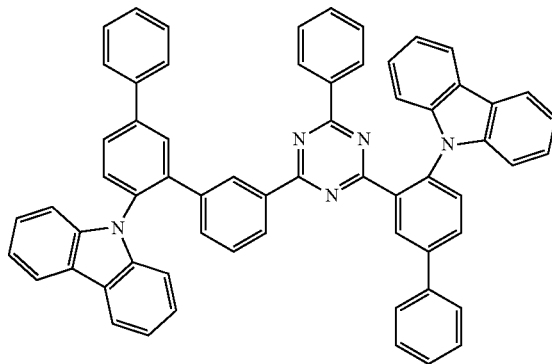
288
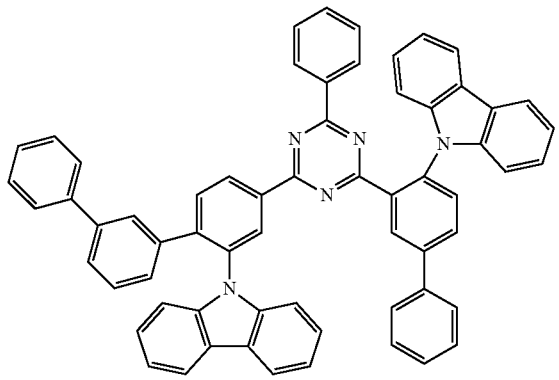
289
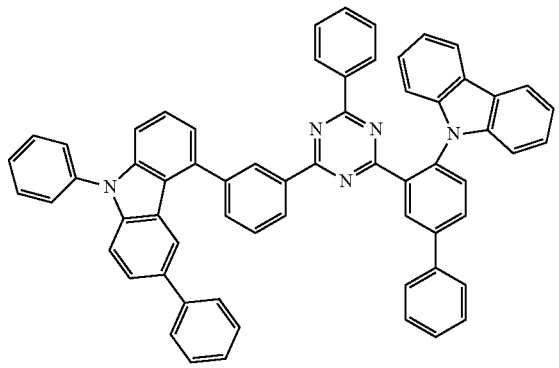
290
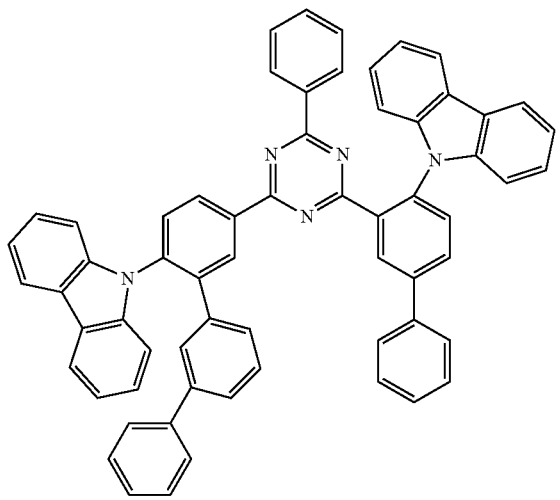
291
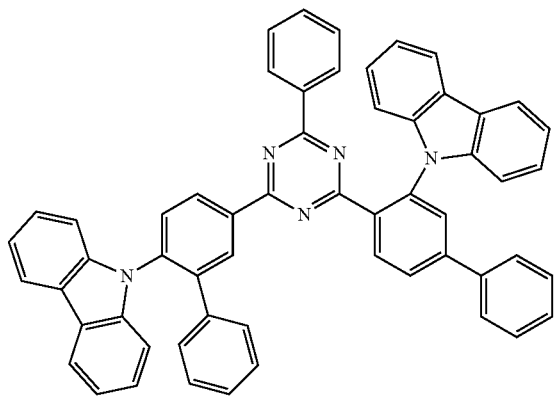

-continued
407
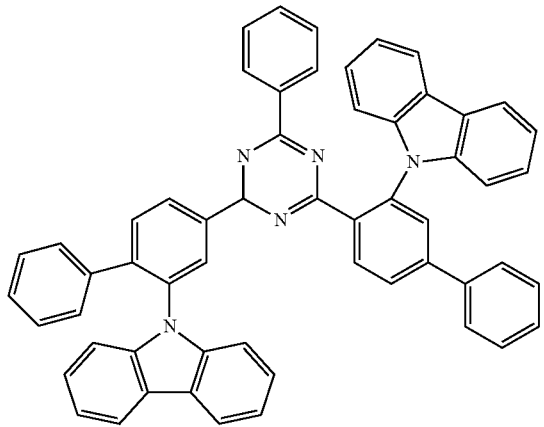
292
408
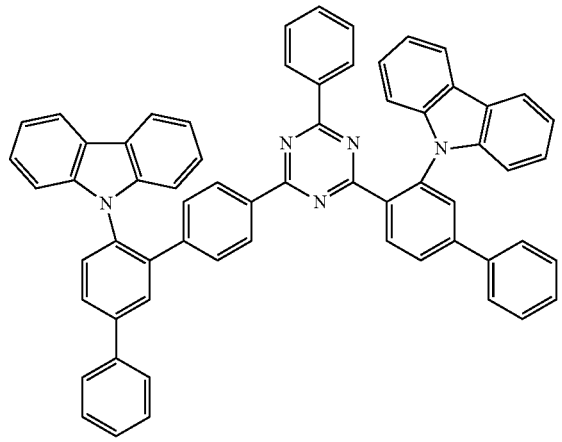
293
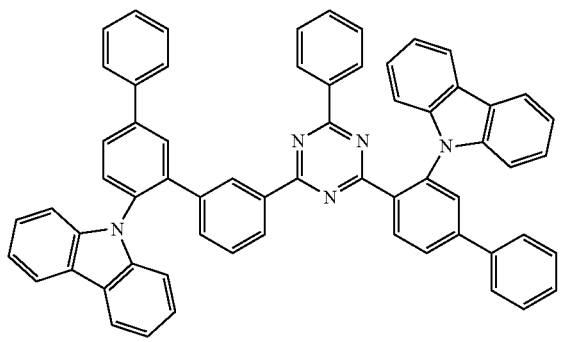
294
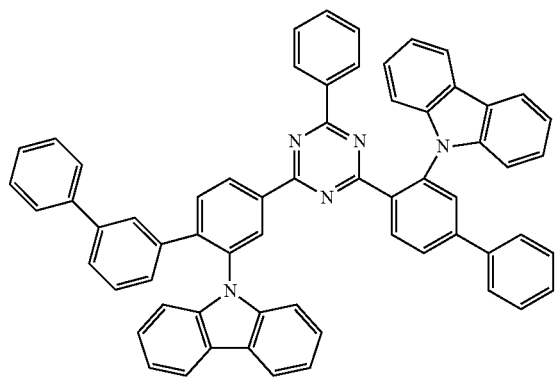
295
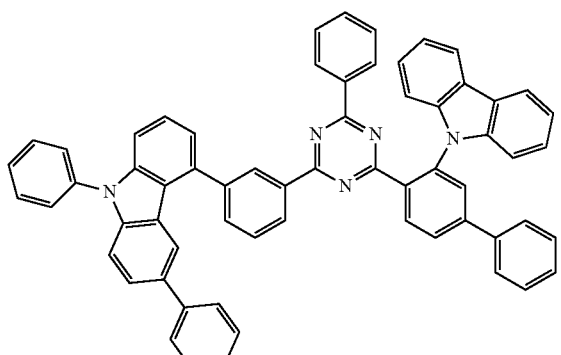
296
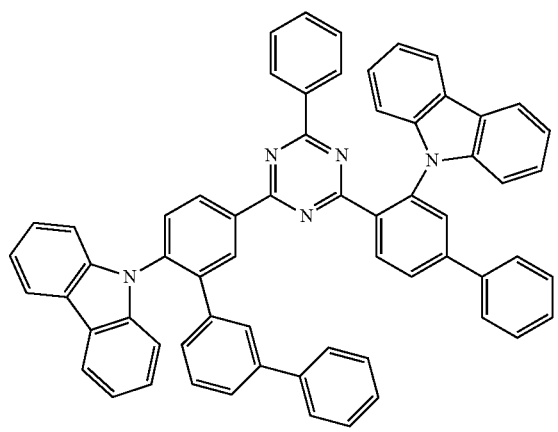
297

-continued
298
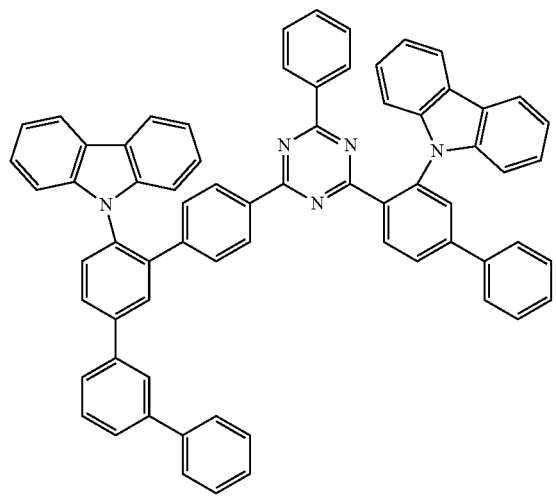
299
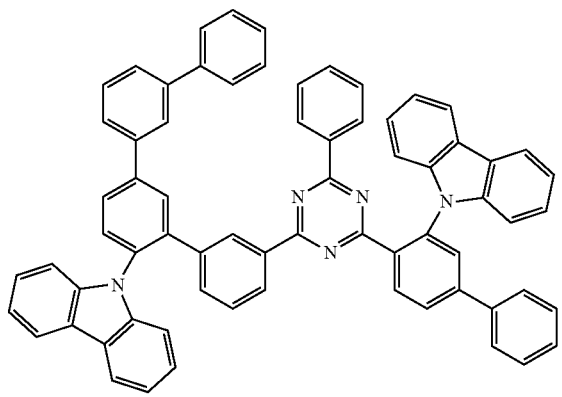
300
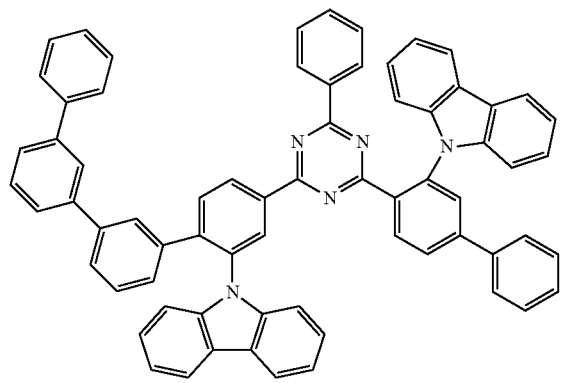
301
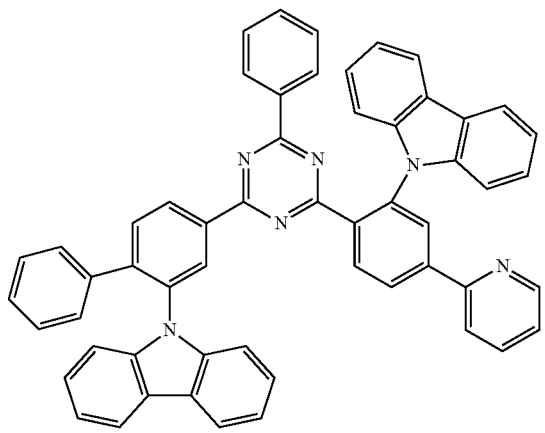
302
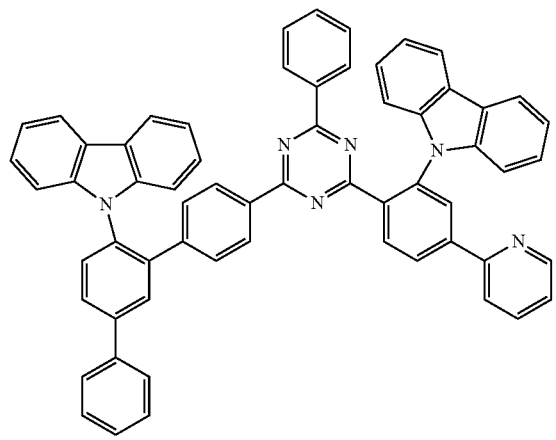
303
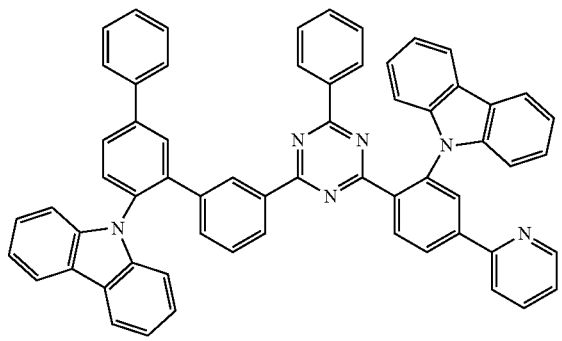

411 412
-continued
304
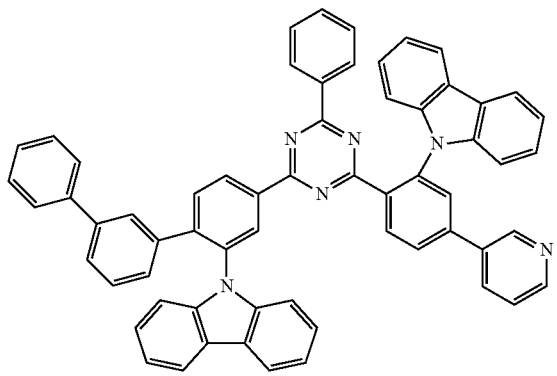
305
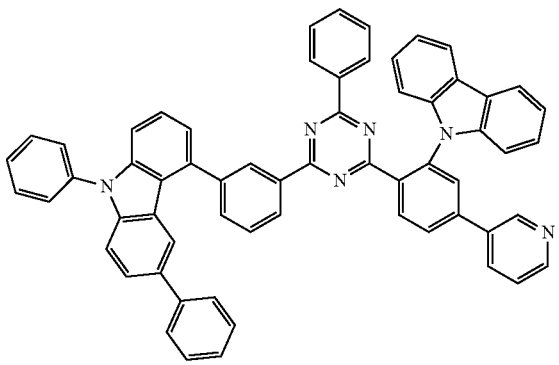
306
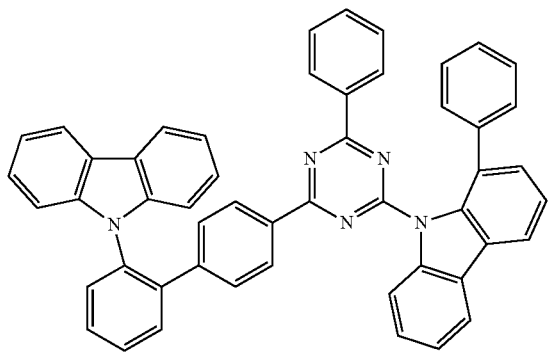
307
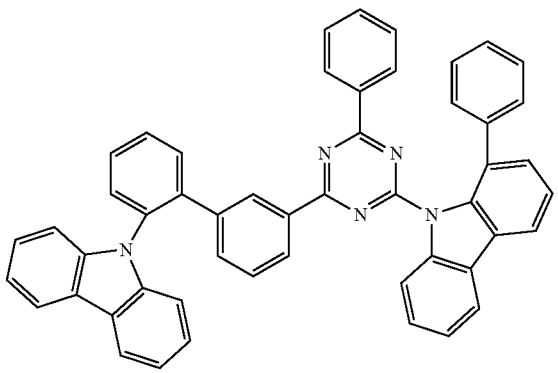
308
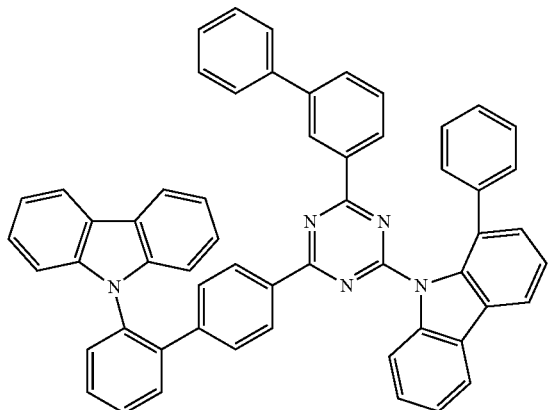
309
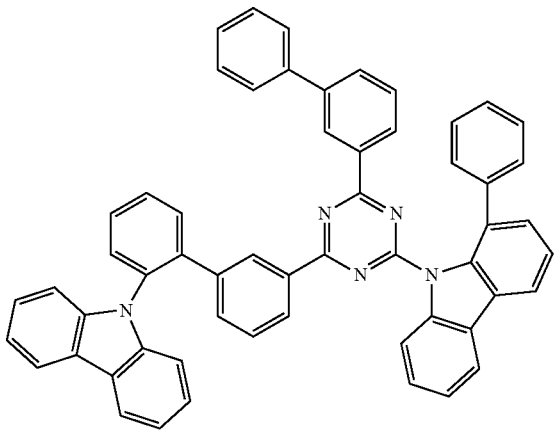
310
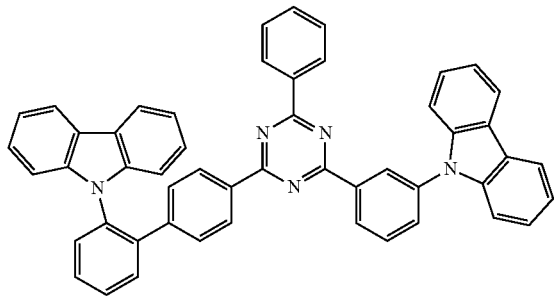
311
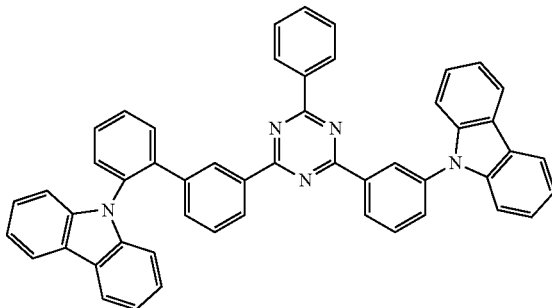

413 414
-continued
312
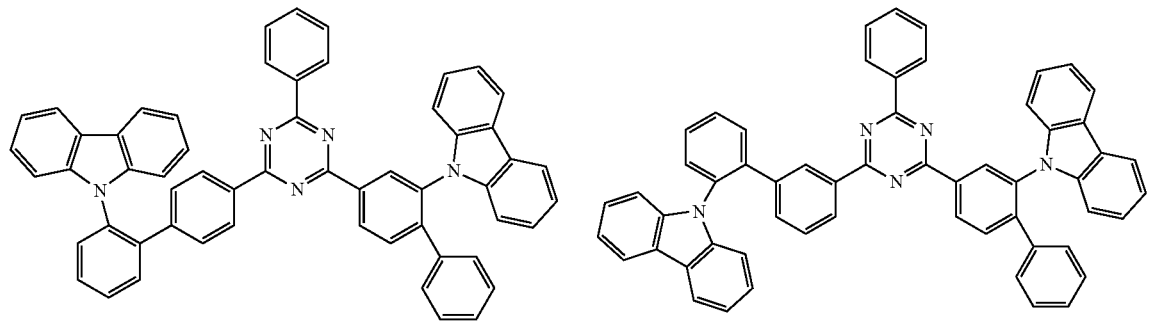
313
314
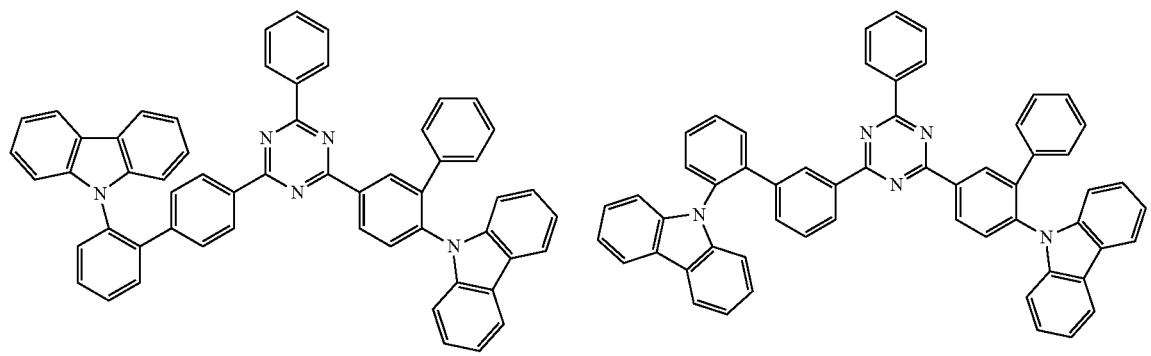
315
316
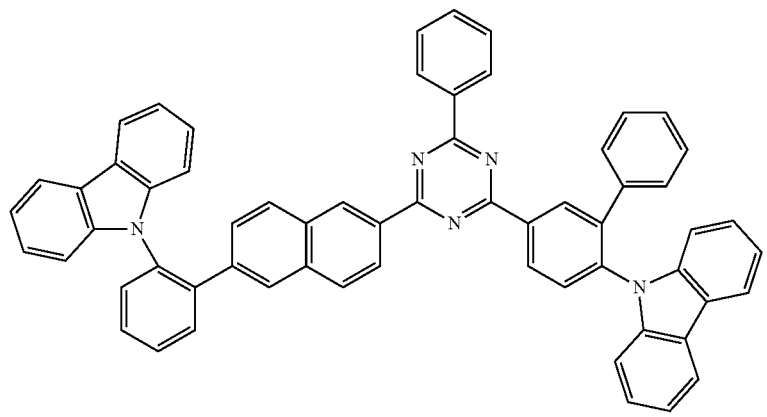
317
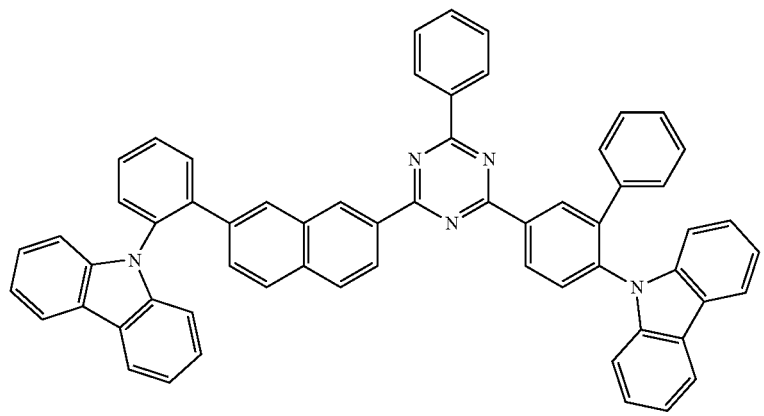

318
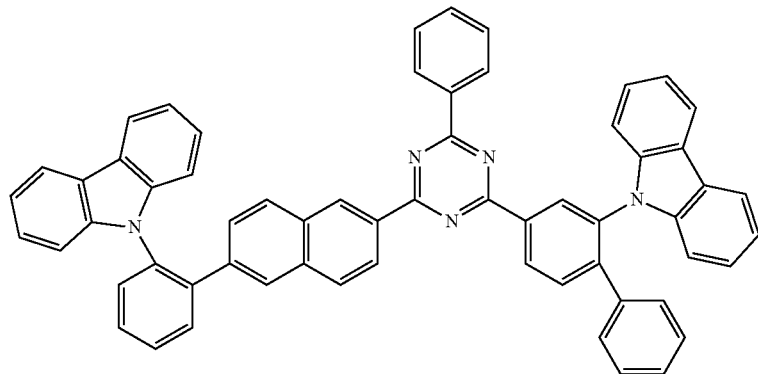
319
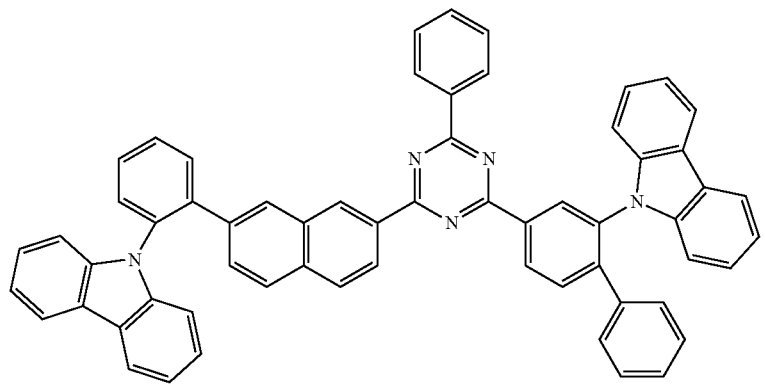
320 321
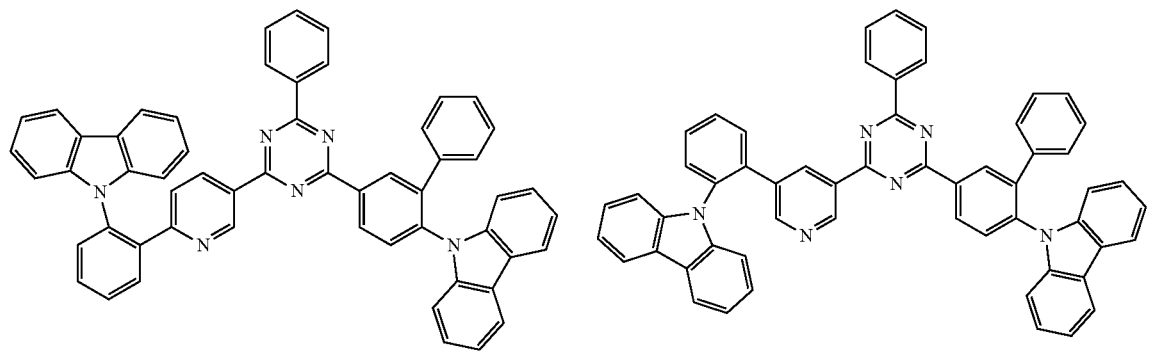
322 323
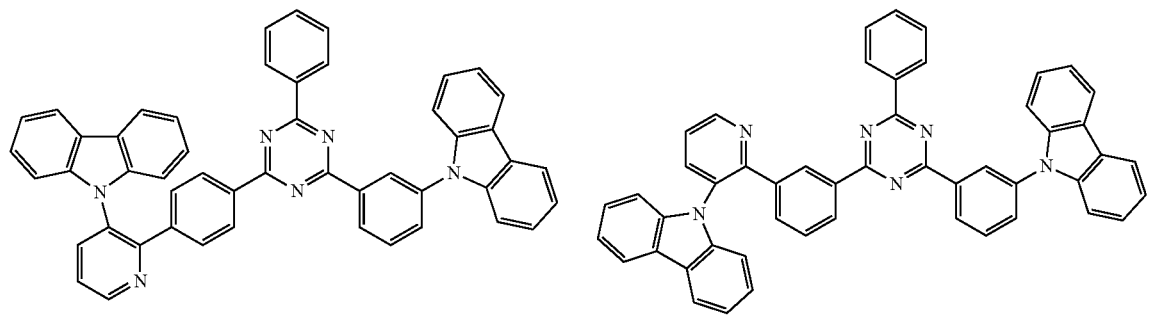

324
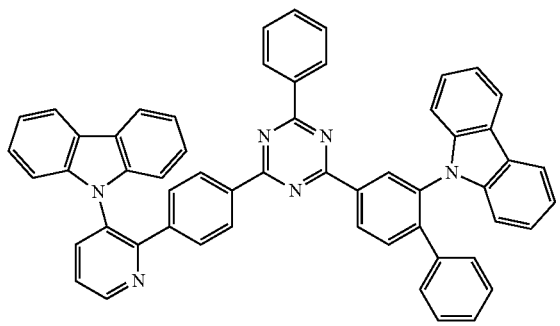
325
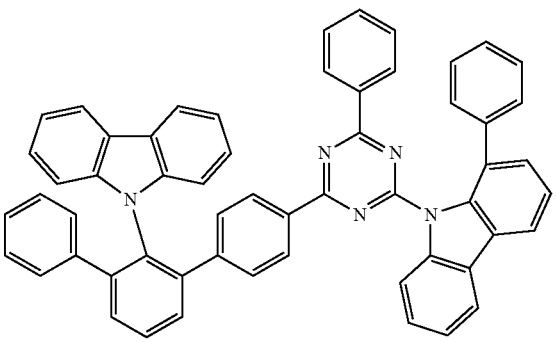
326
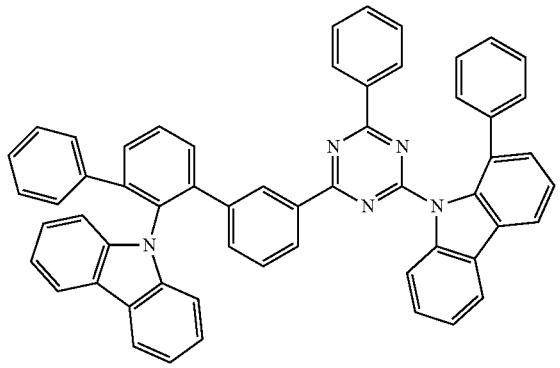
327
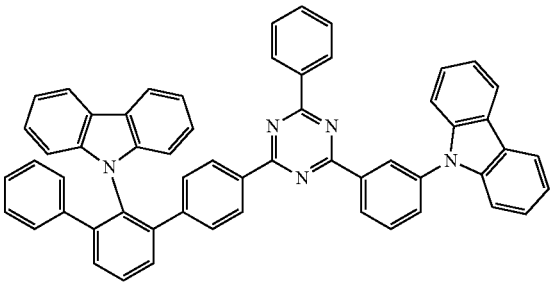
328
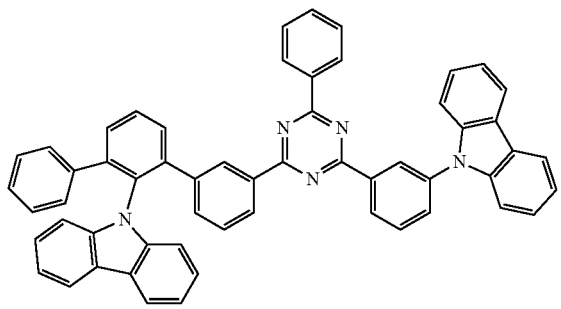
329
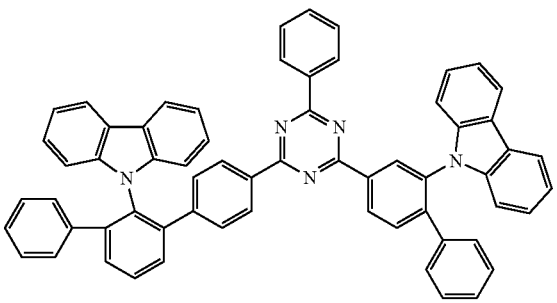
330
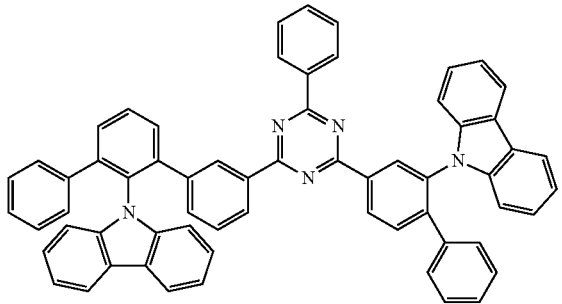
331
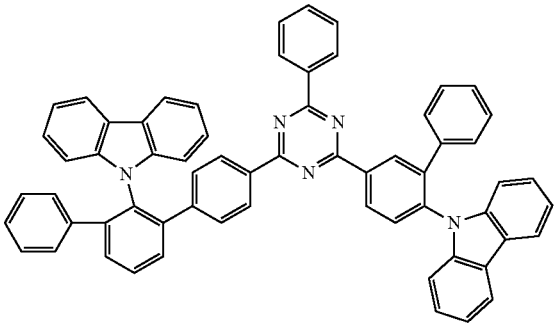

-continued
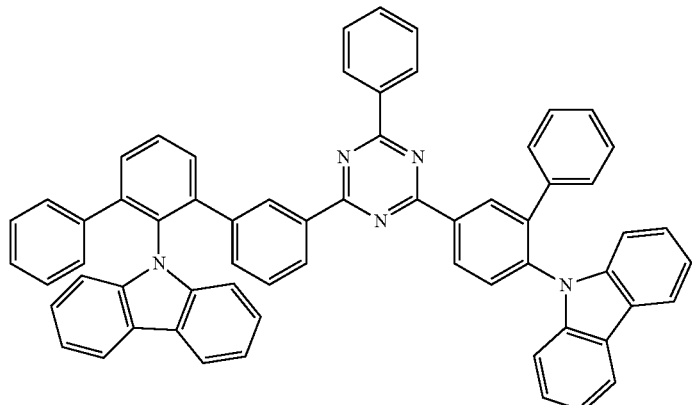
332
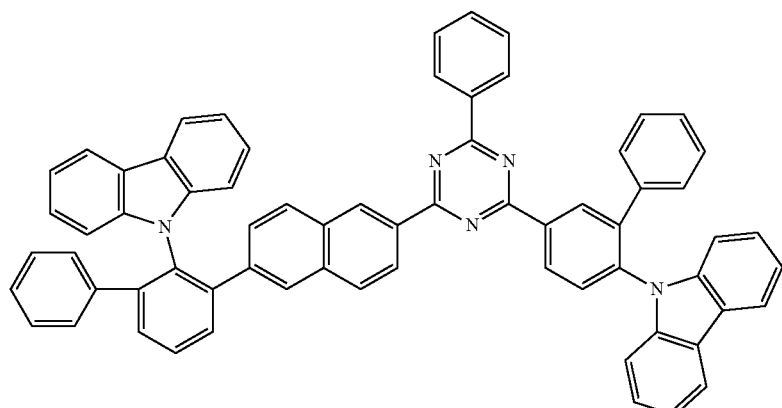
333
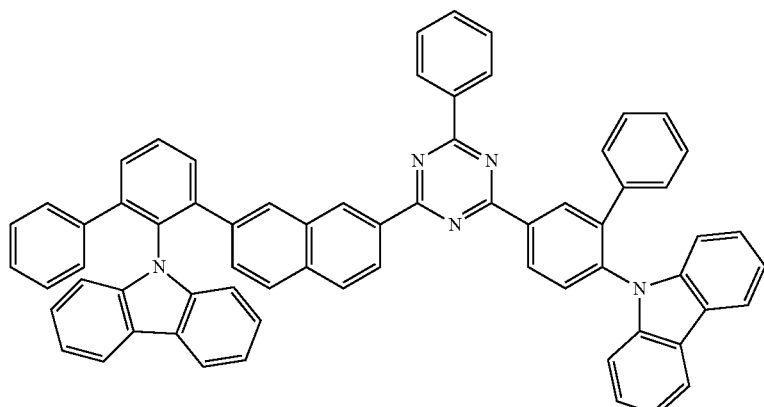
334
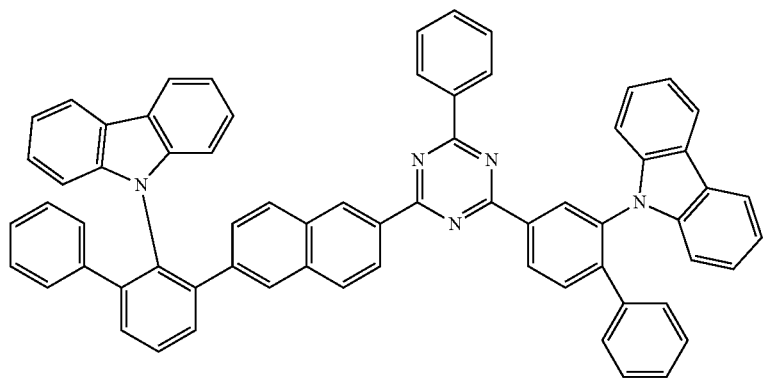
335

-continued
336
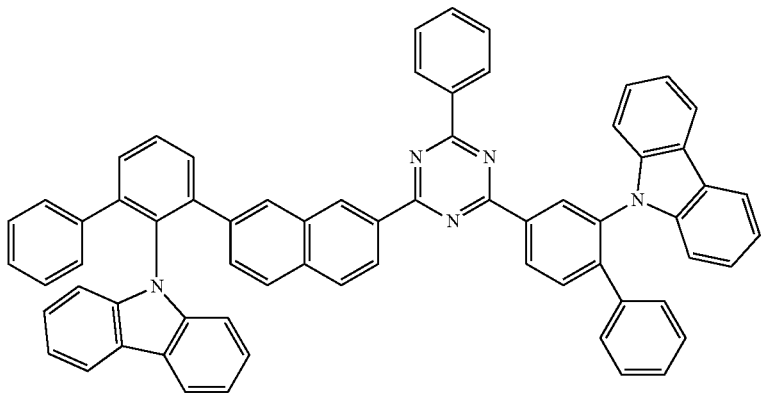
337 338
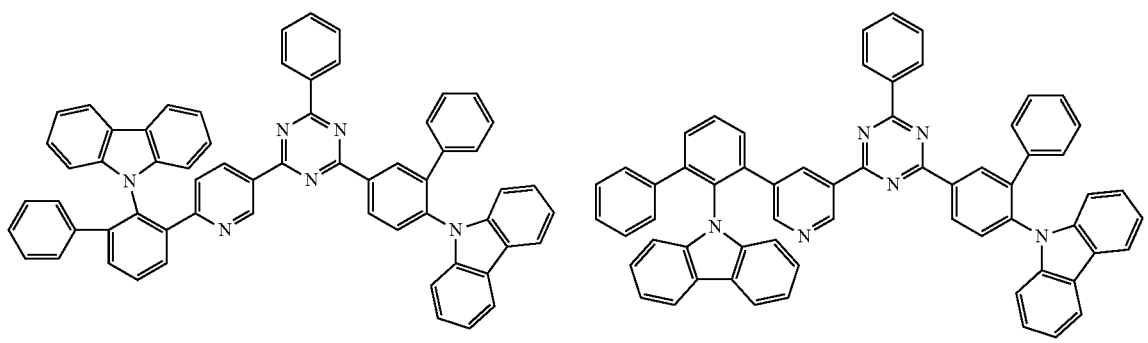
339 340
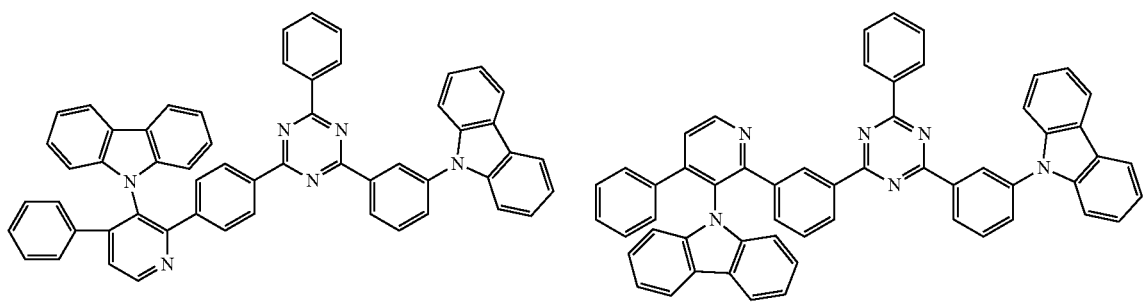
341 342
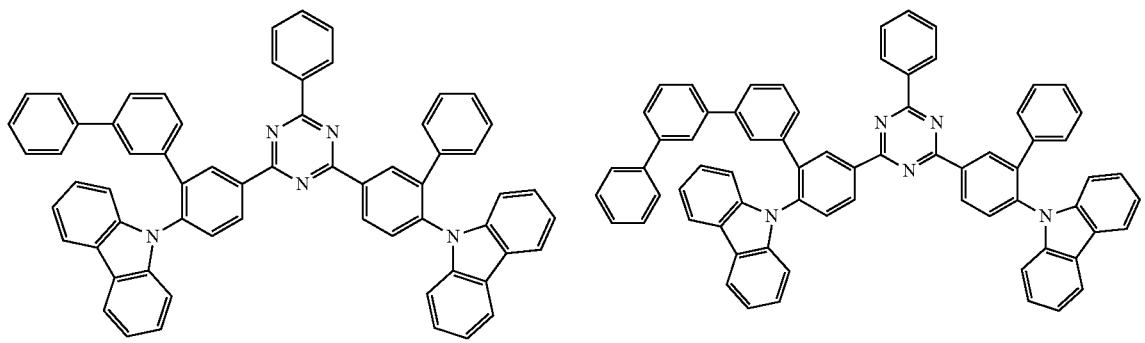

343
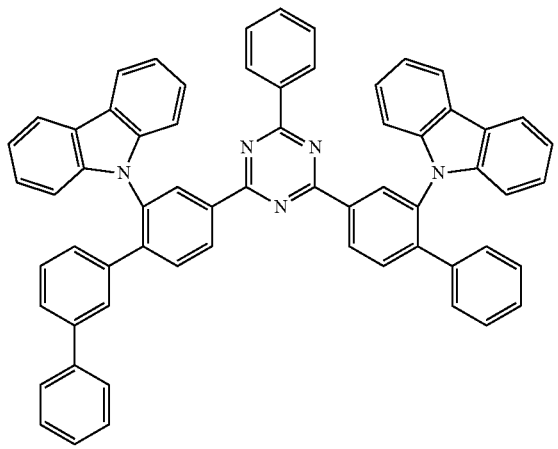
345
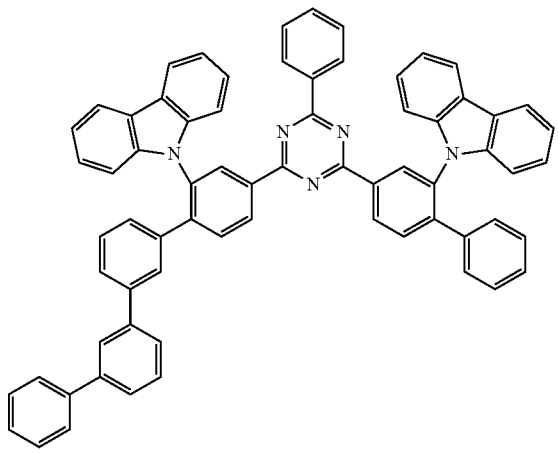
346
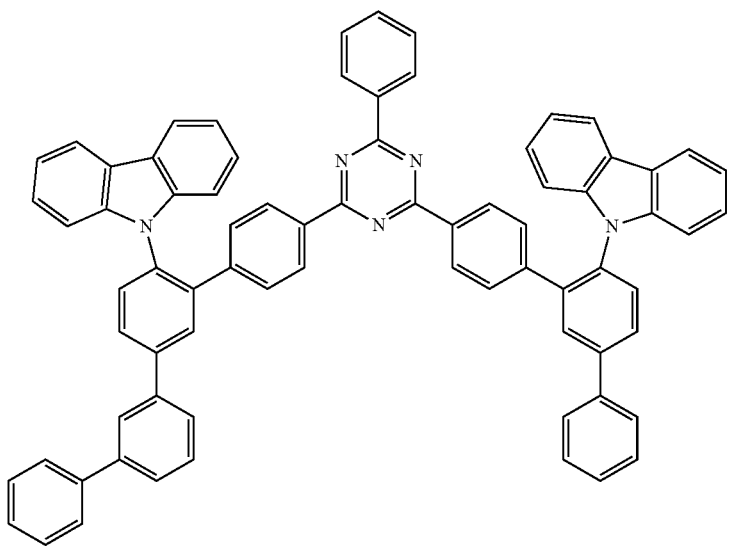
347
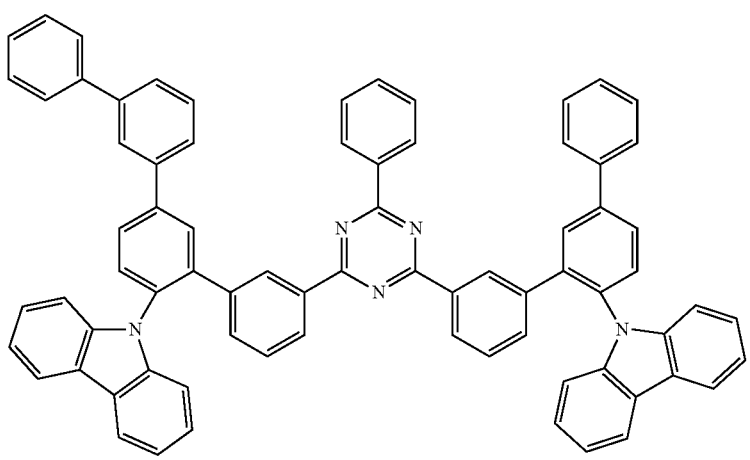

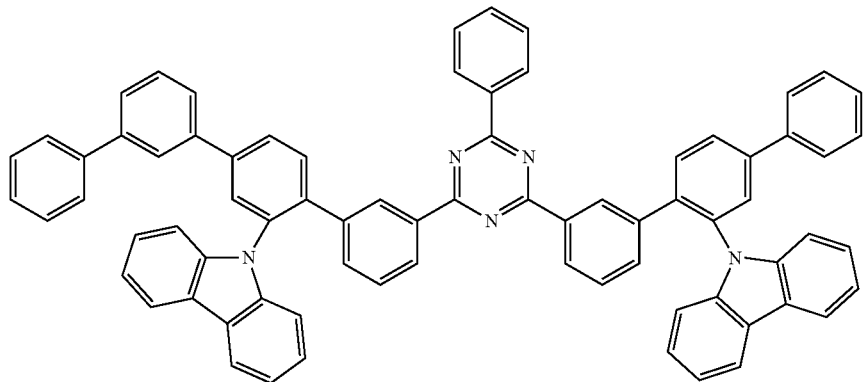
348
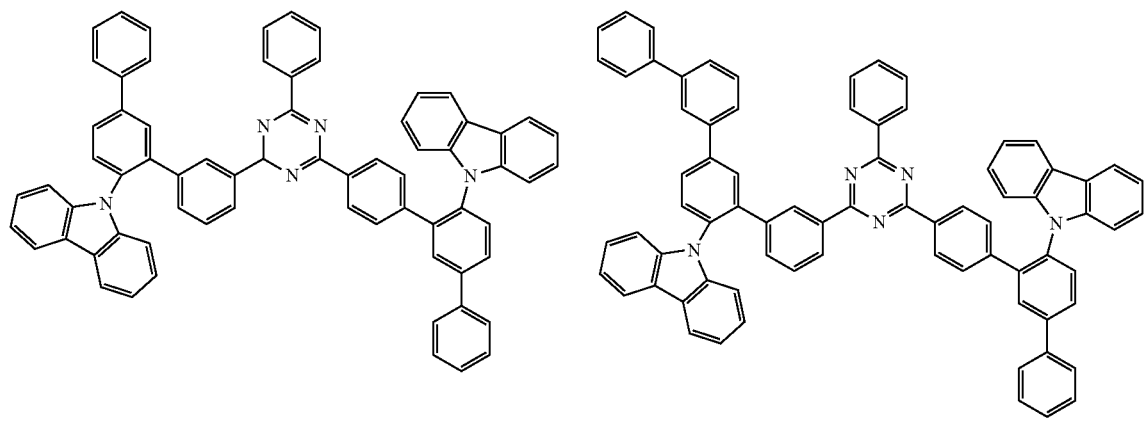
349
350
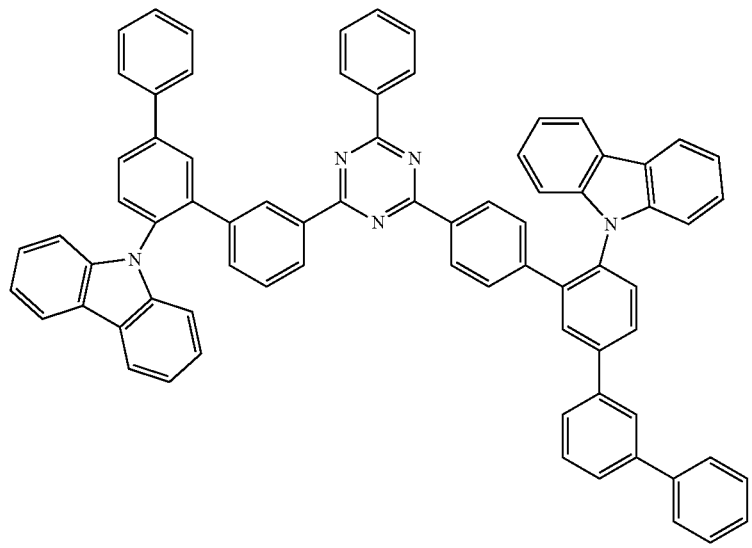
351

-continued
352
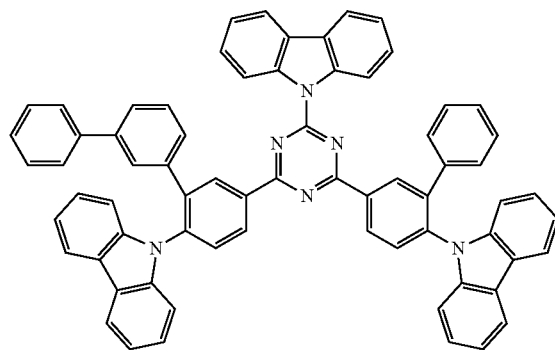
353
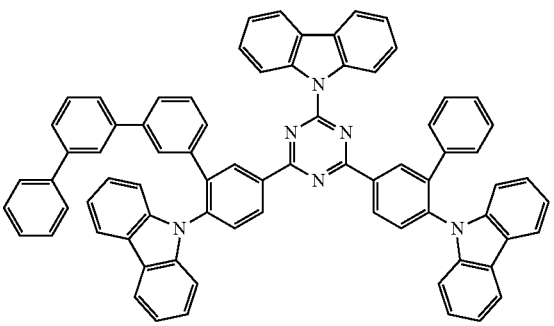
354
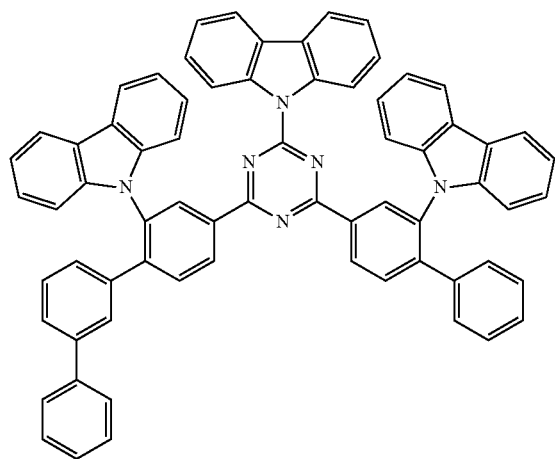
355
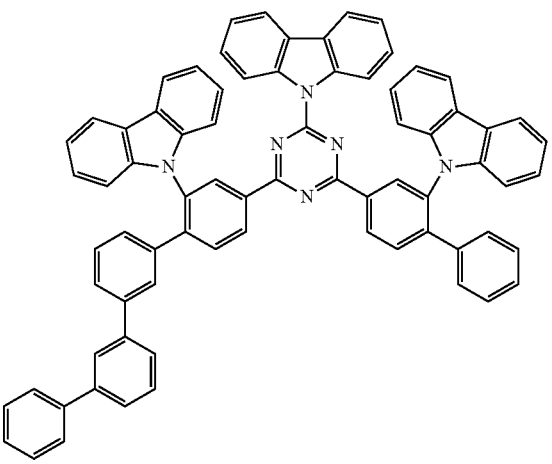
356
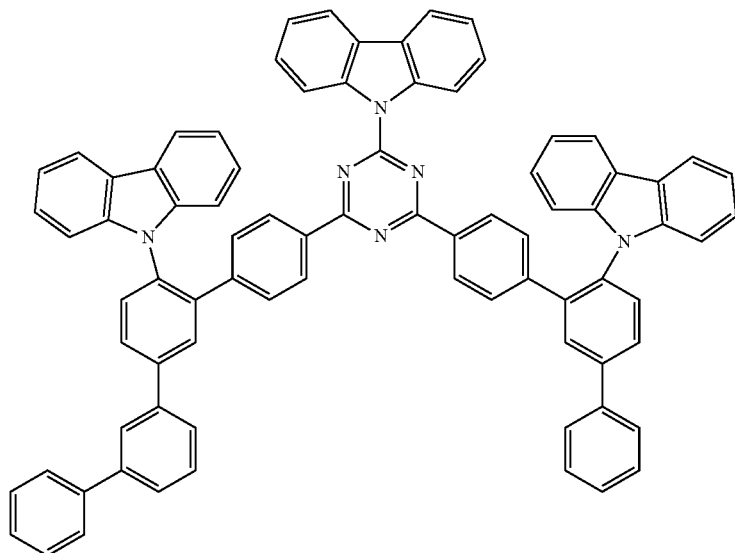

357
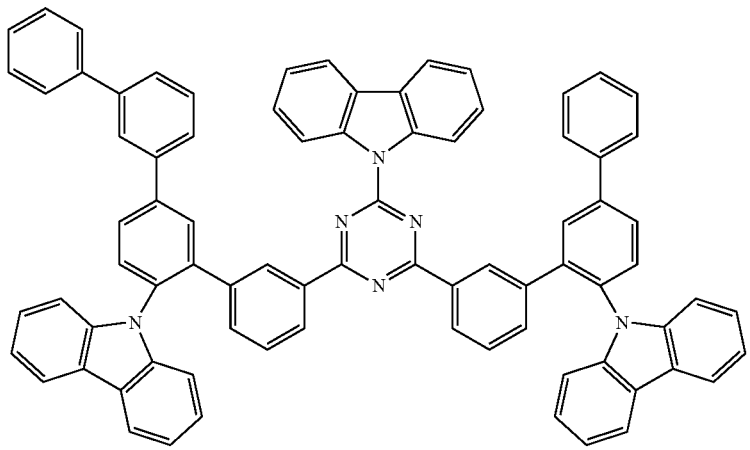
358
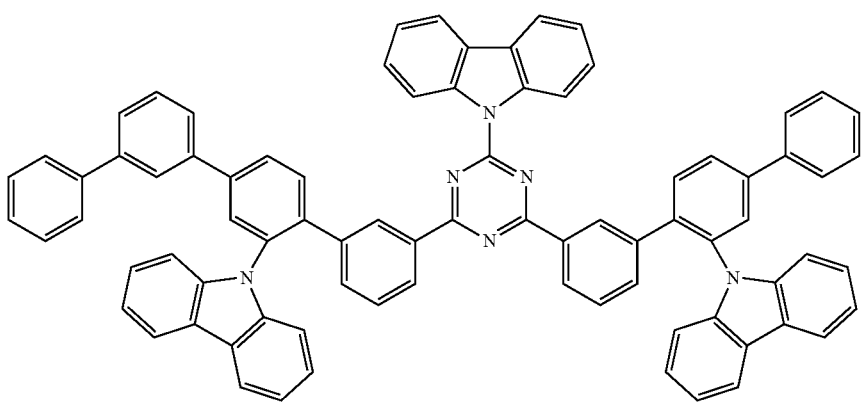
359 360
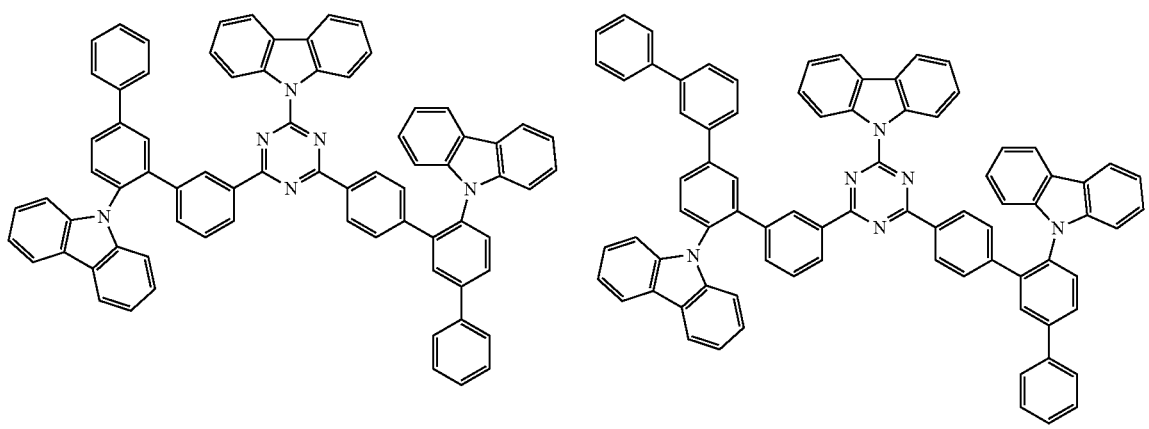

-continued
361
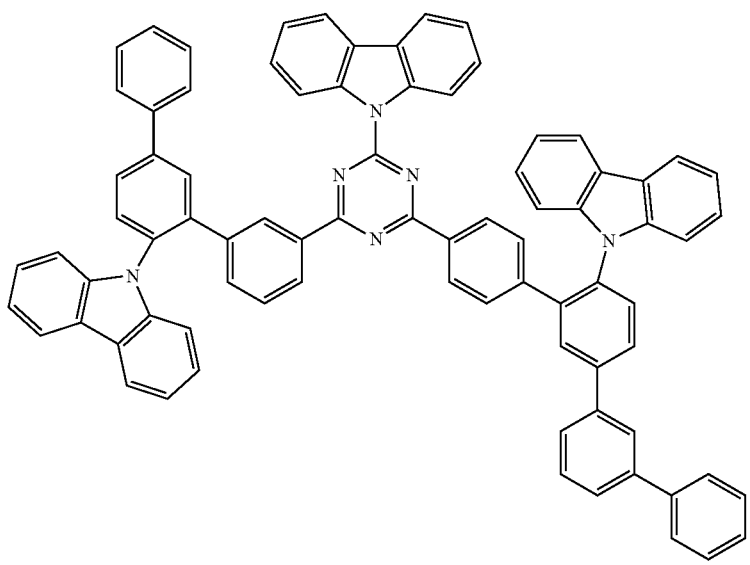
362
363
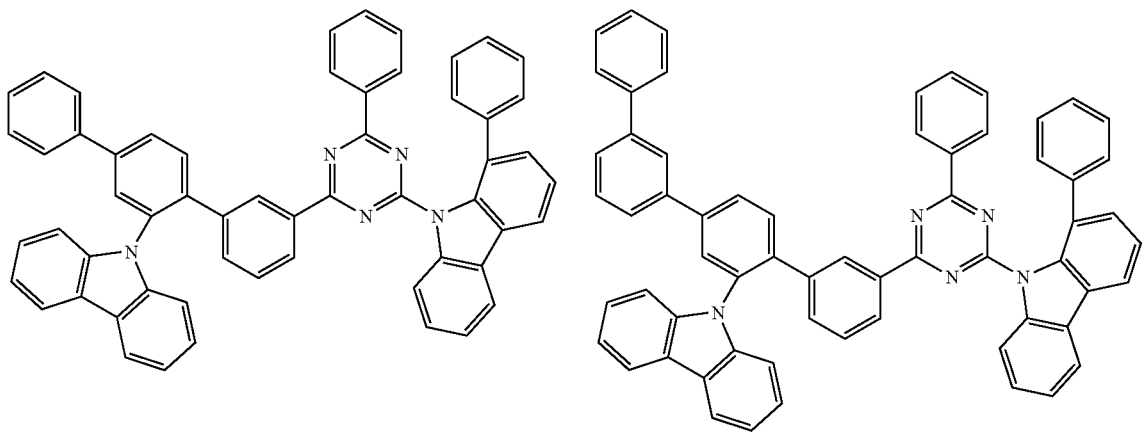
364
365
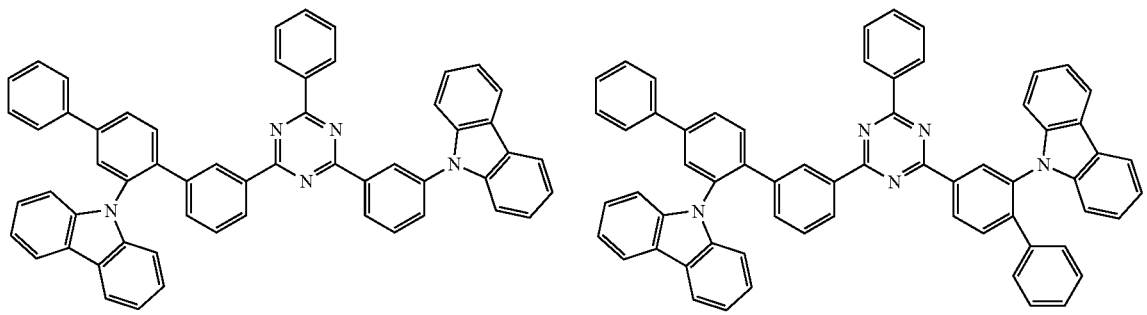

-continued
366 367
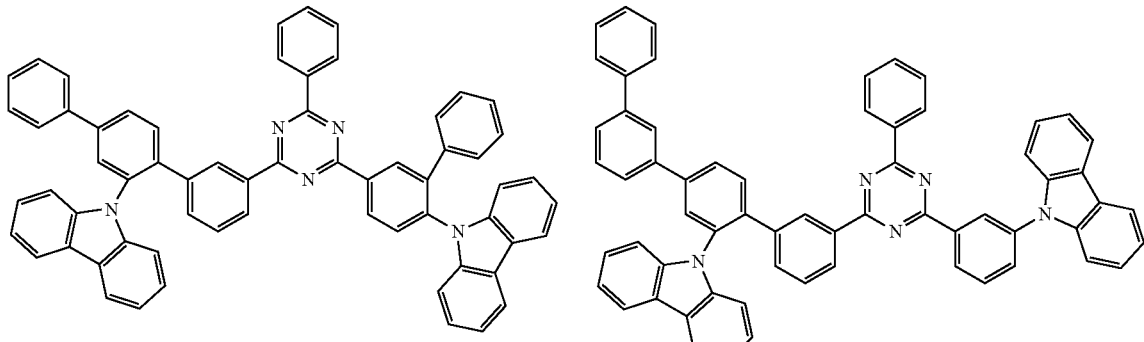
368 369
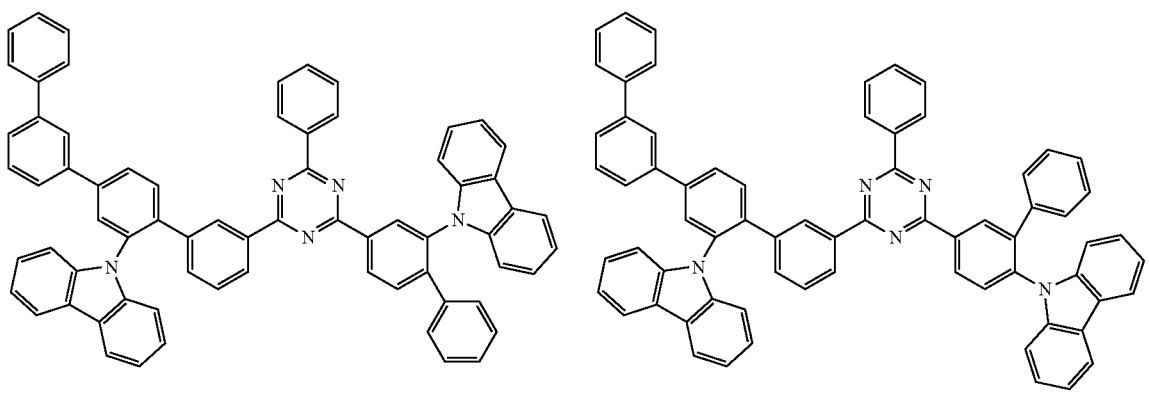
370 371
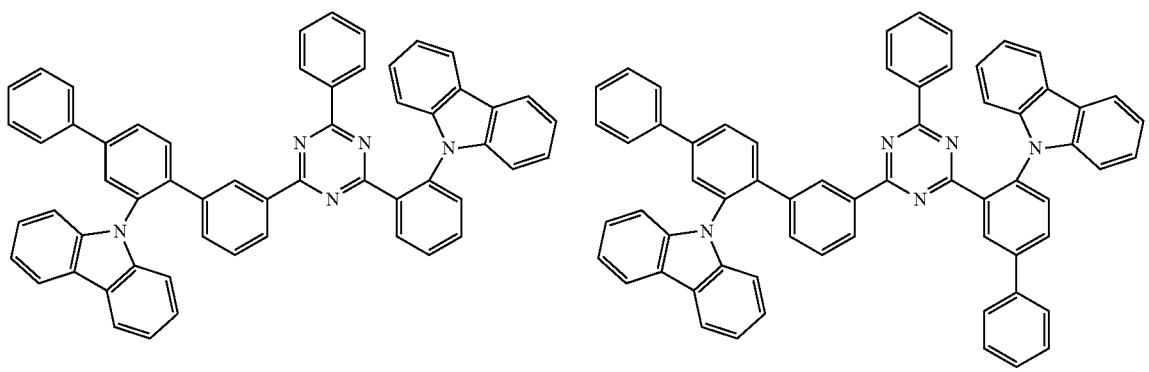
372 373
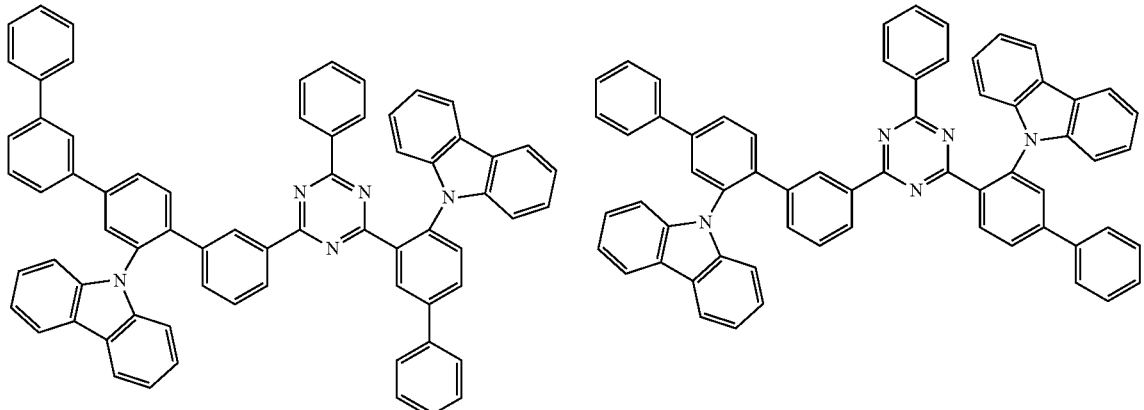

-continued
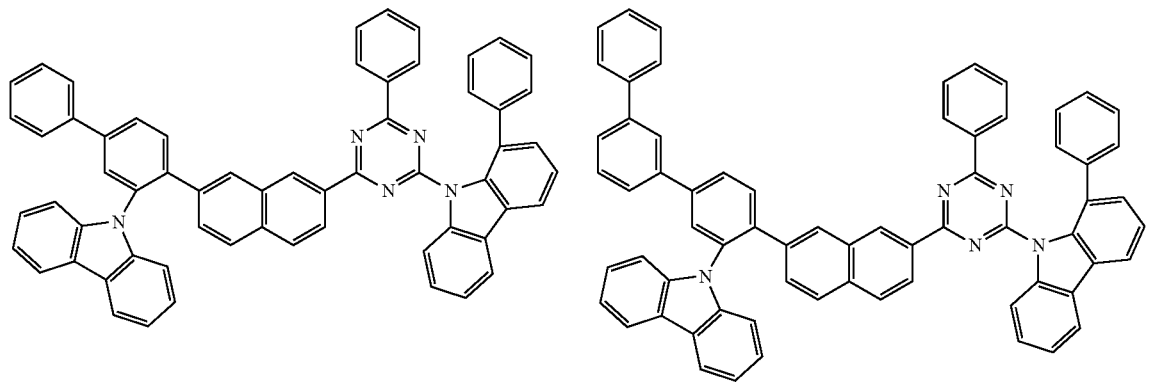
374
375
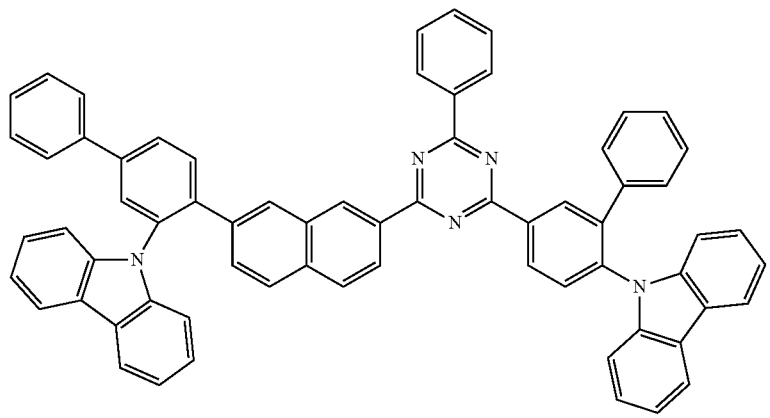
376
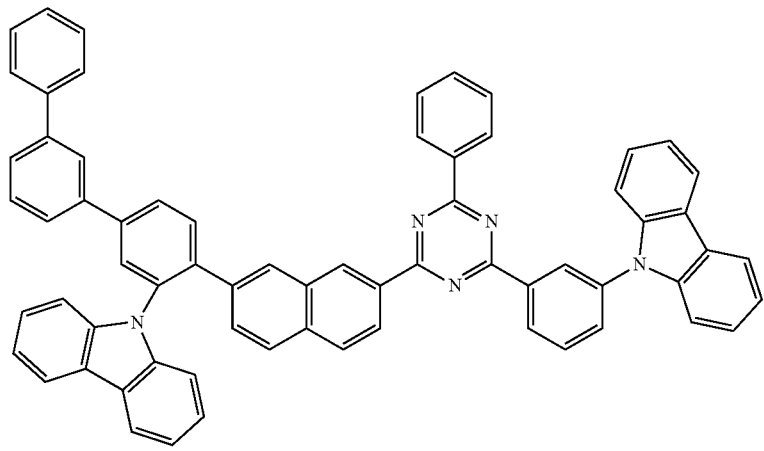
377
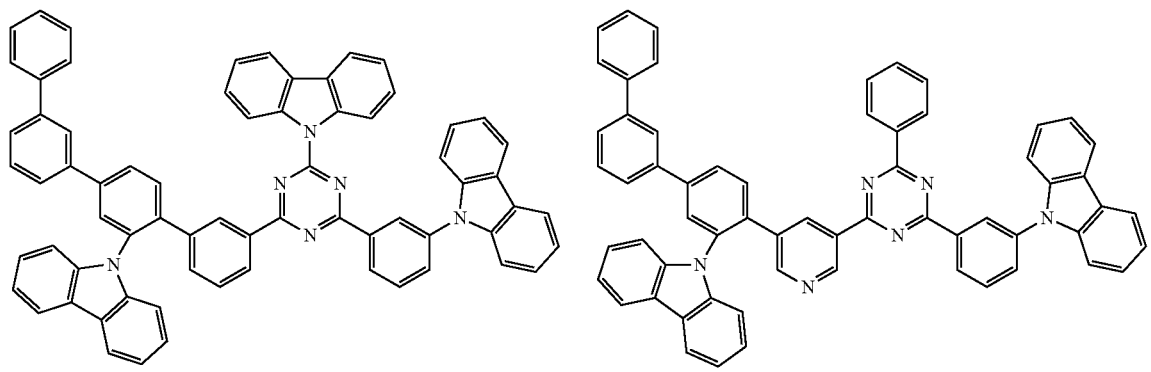
378
379

-continued
380
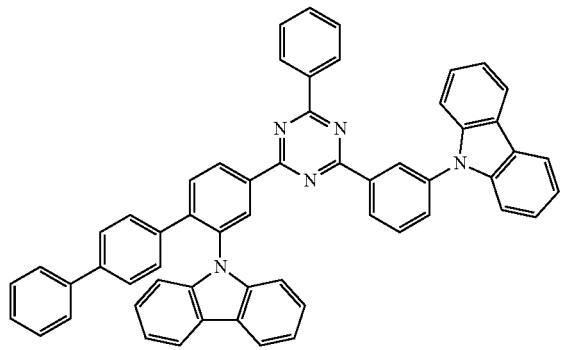
381
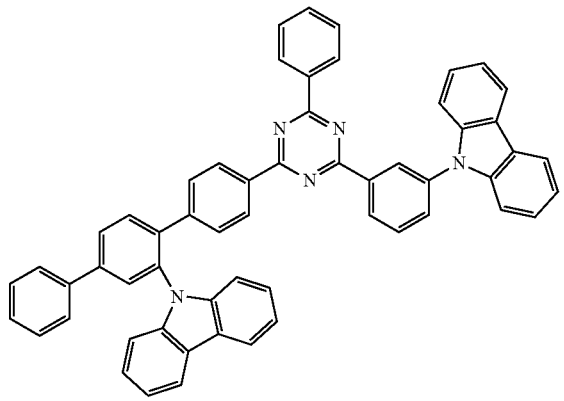
382
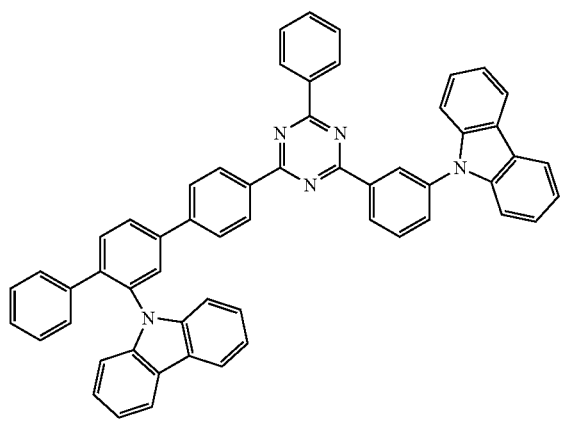
383
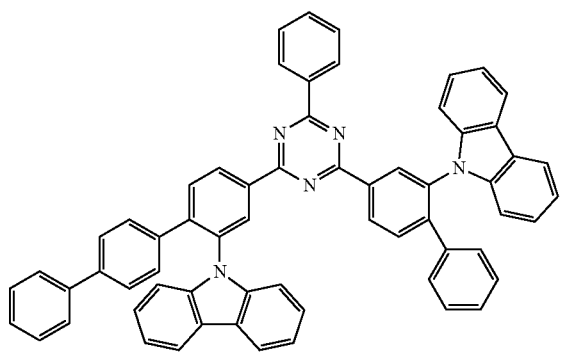
384
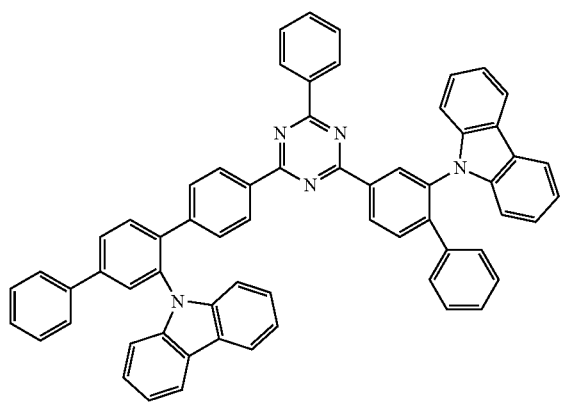
385
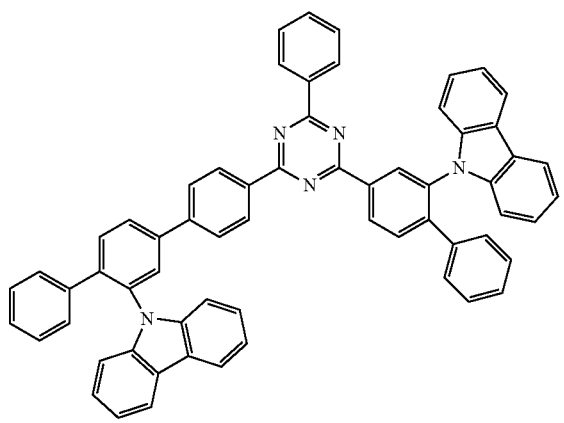

439                                           440
-continued
386
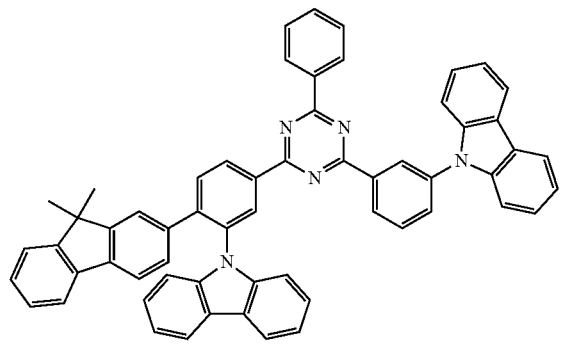
387
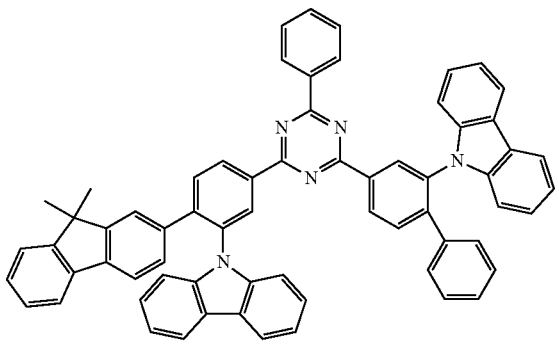
388
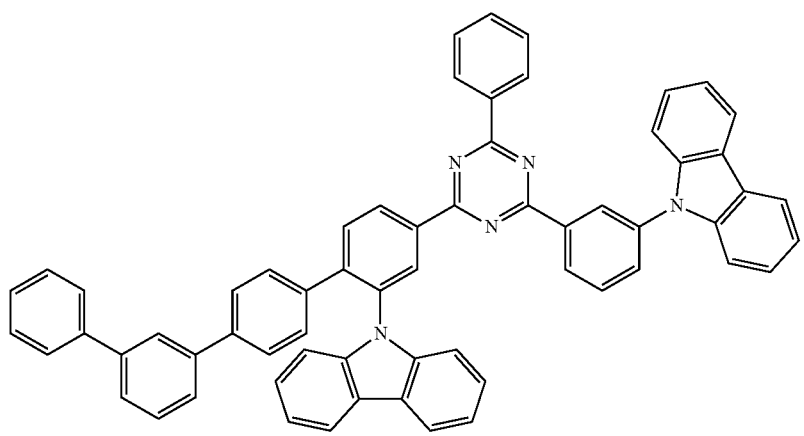
389
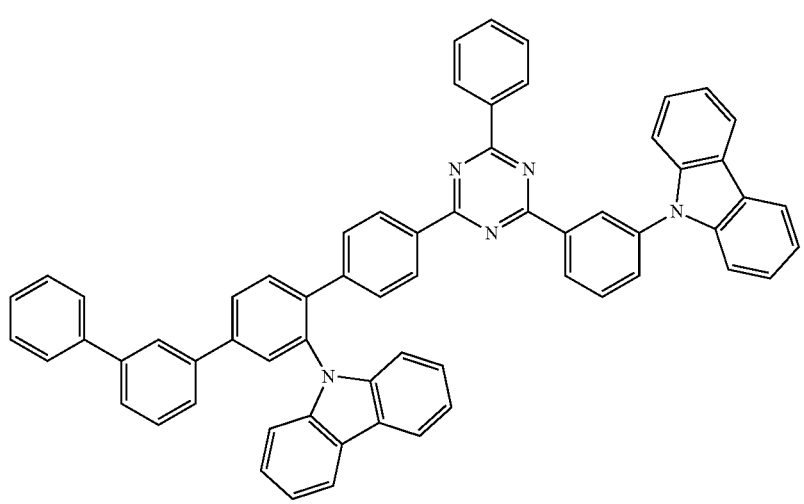

390
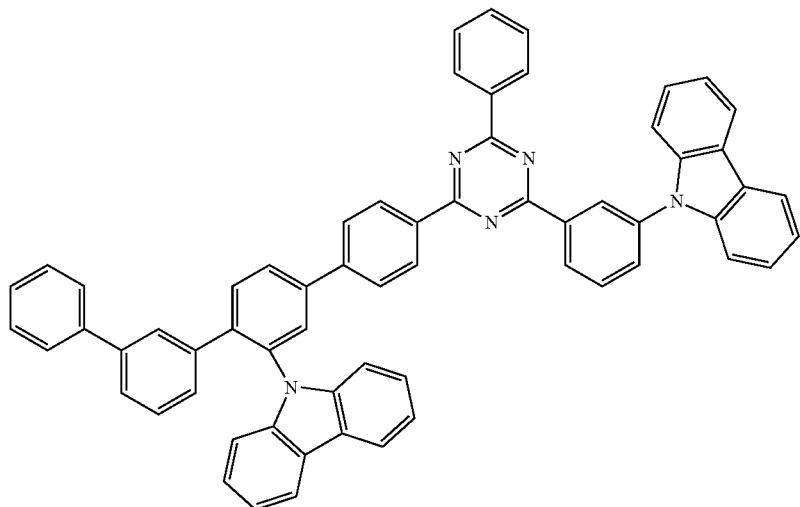
391
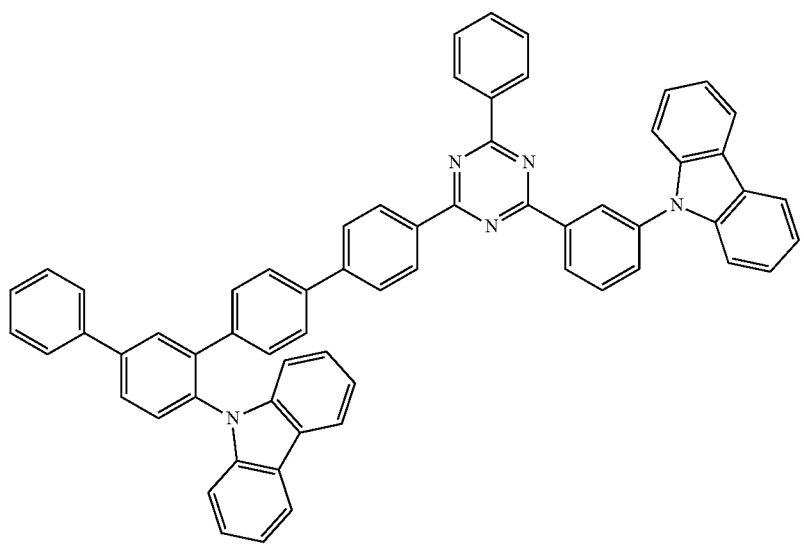
392
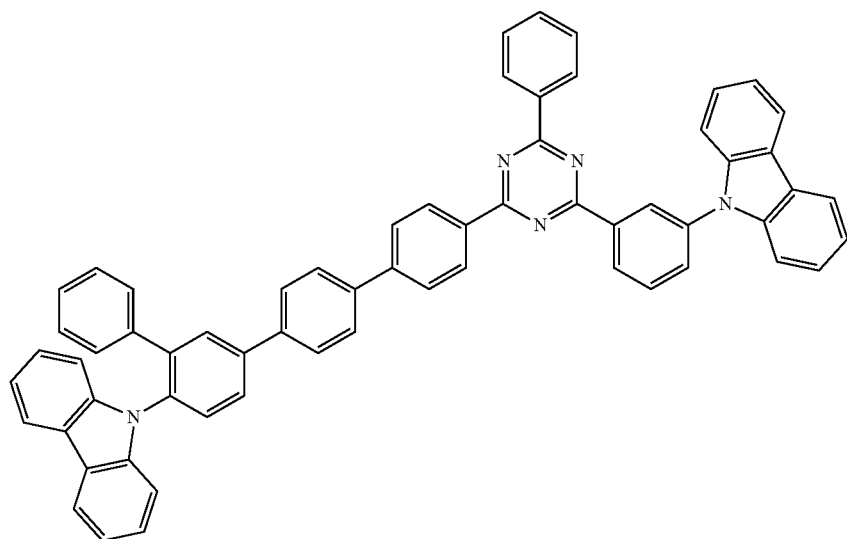

393
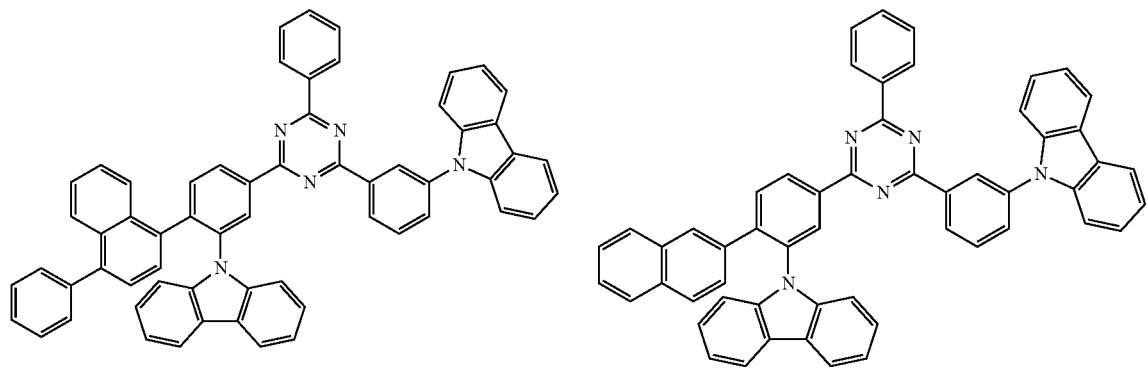
394
395
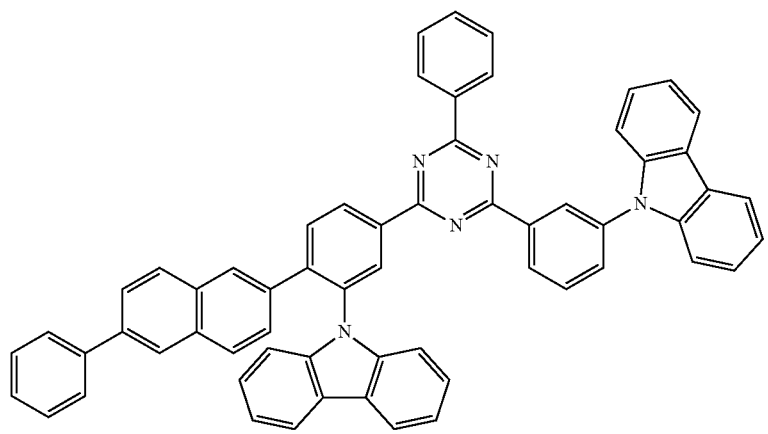
396
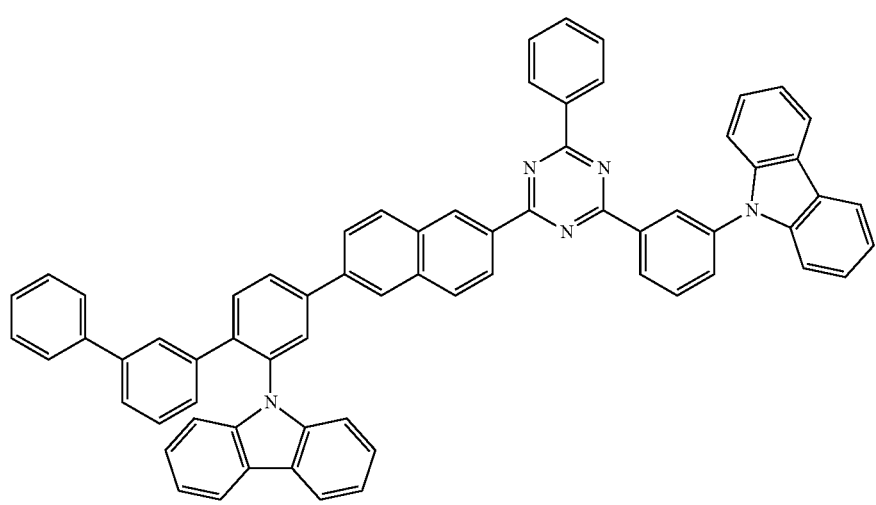

-continued
397
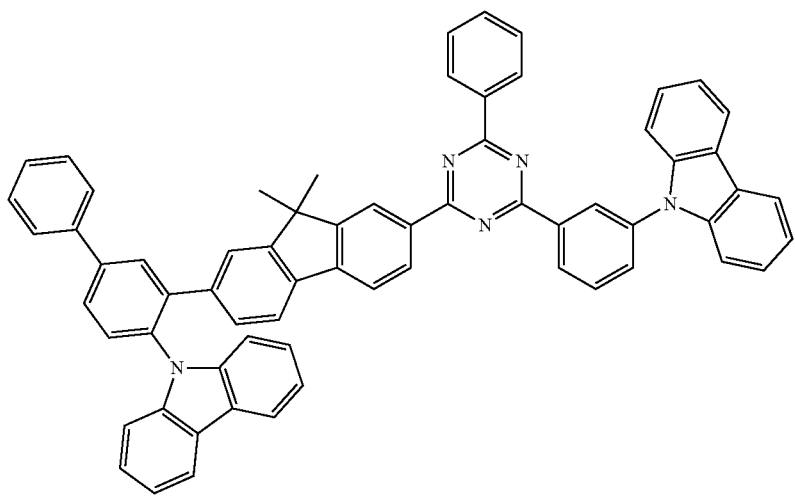
398
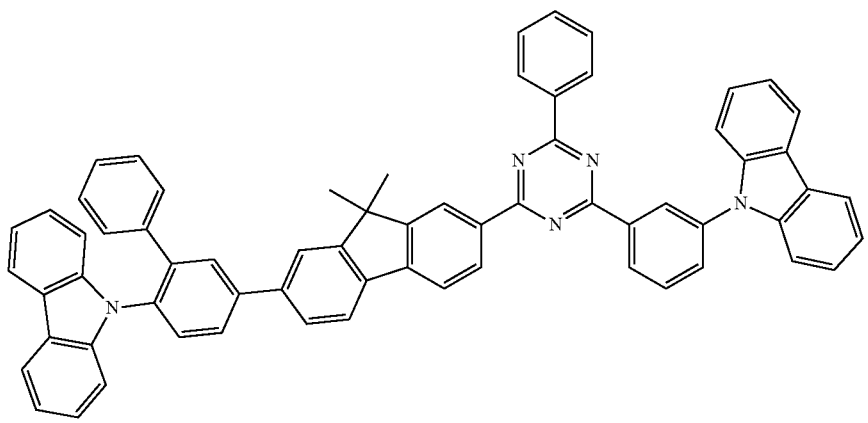
399
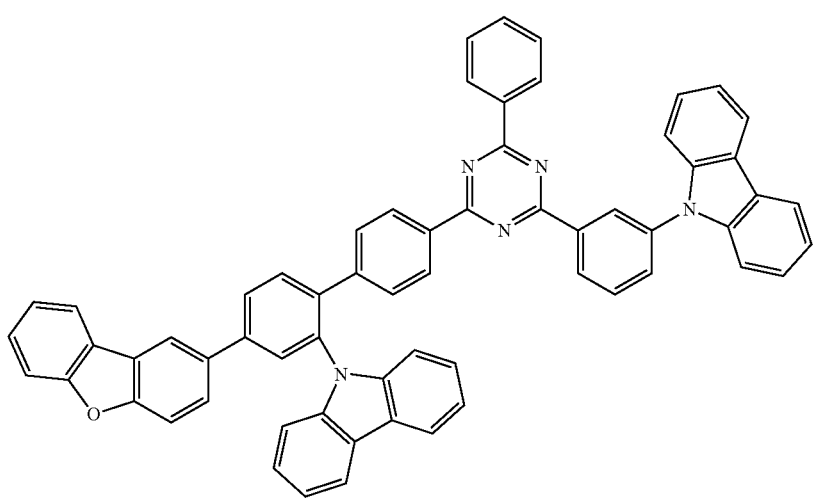

-continued
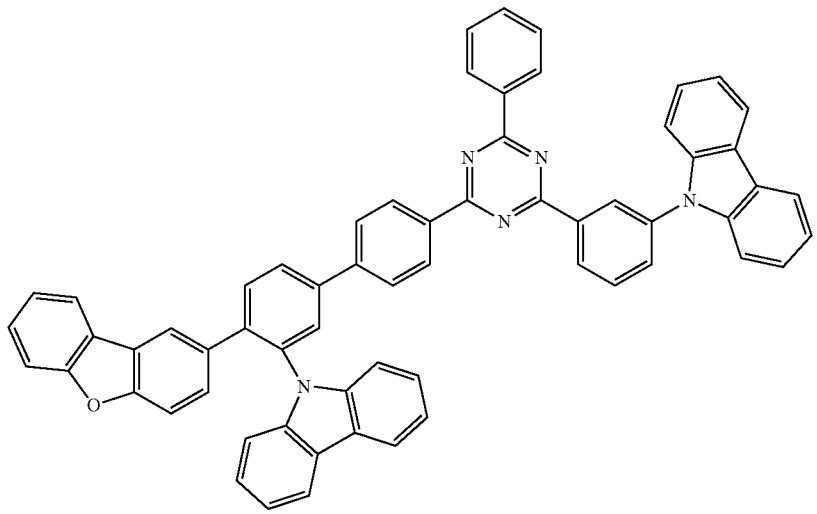
400
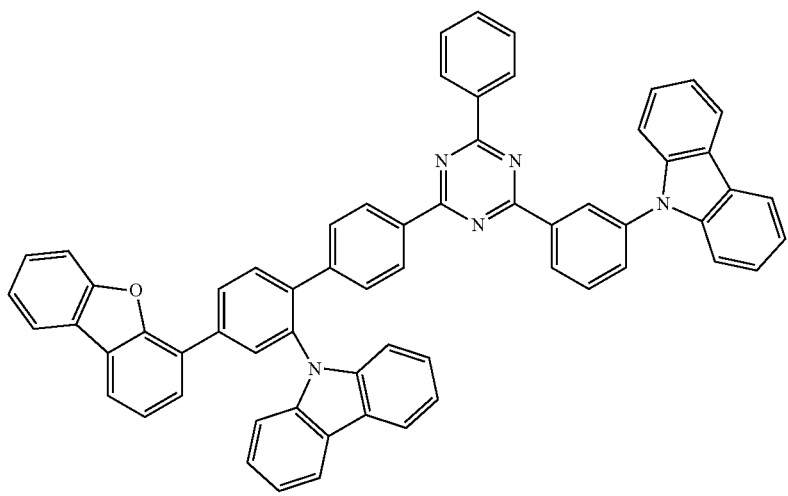
401
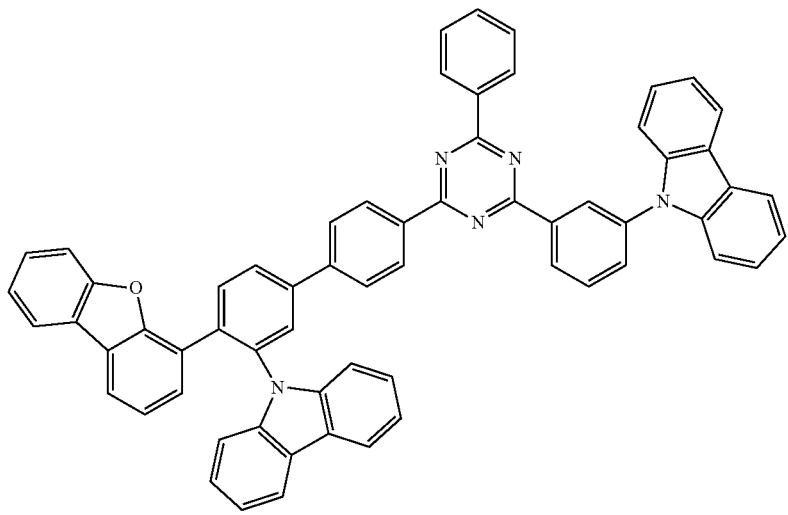
402

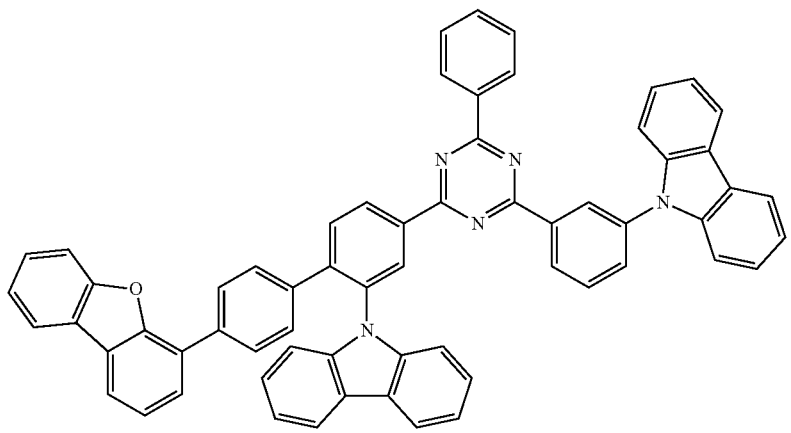
403
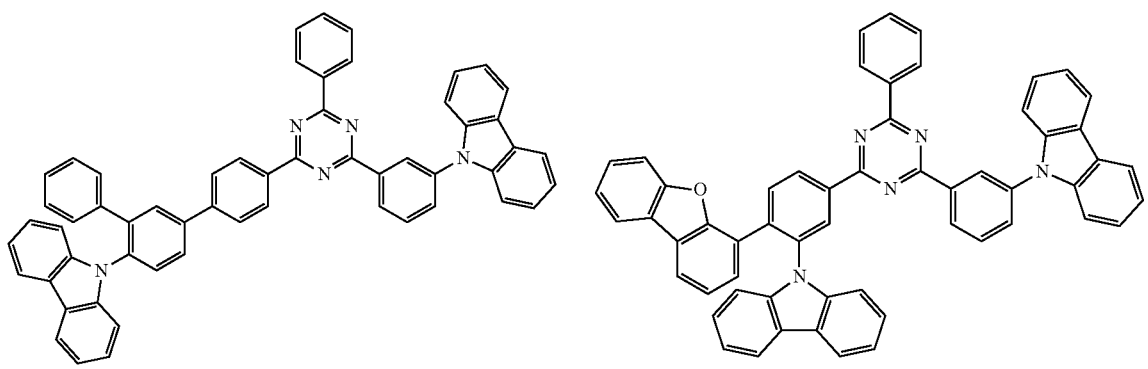
404 405
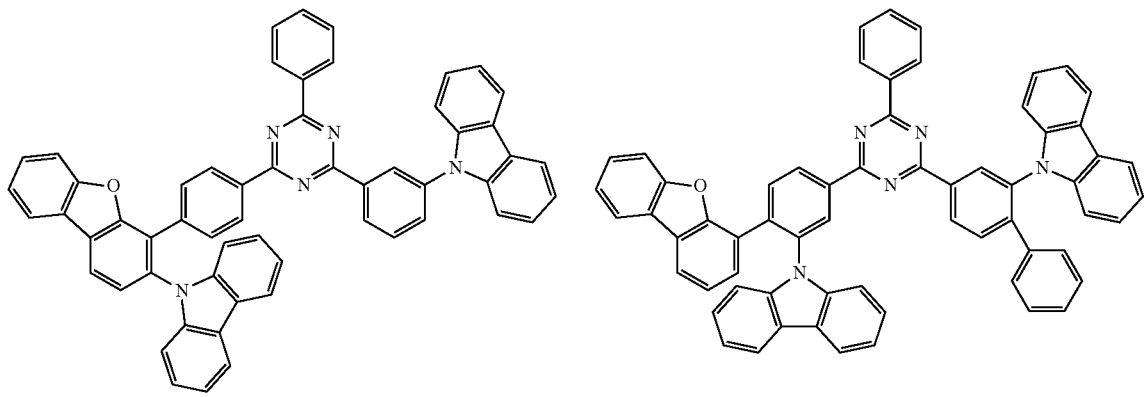
406 407
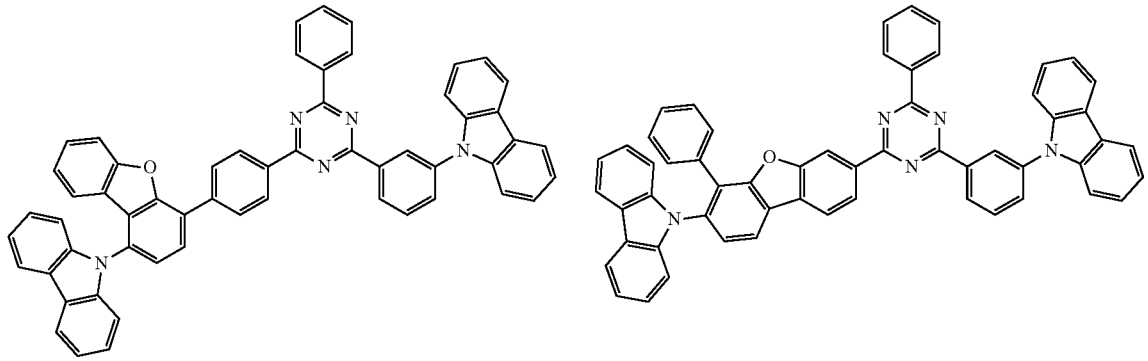
408 409

410
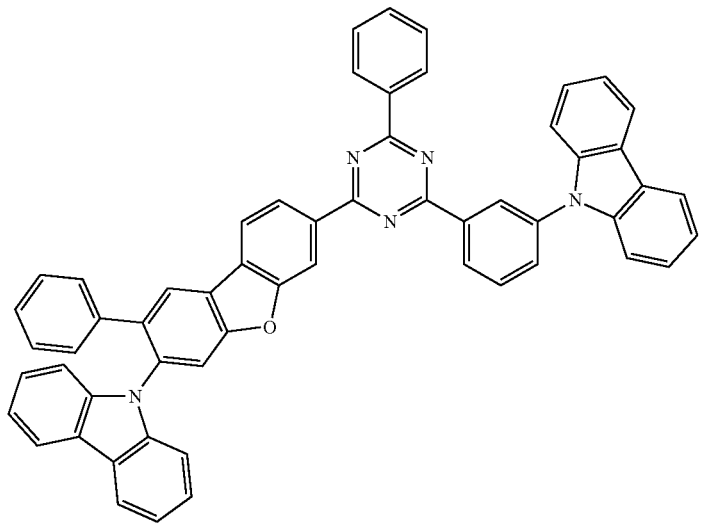
411
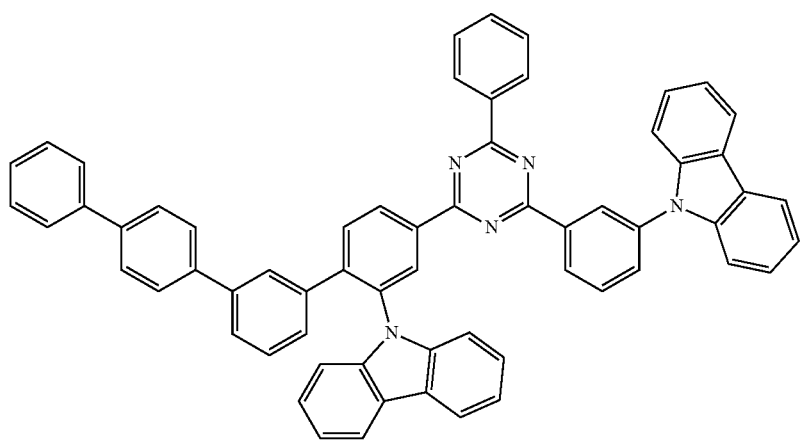
412
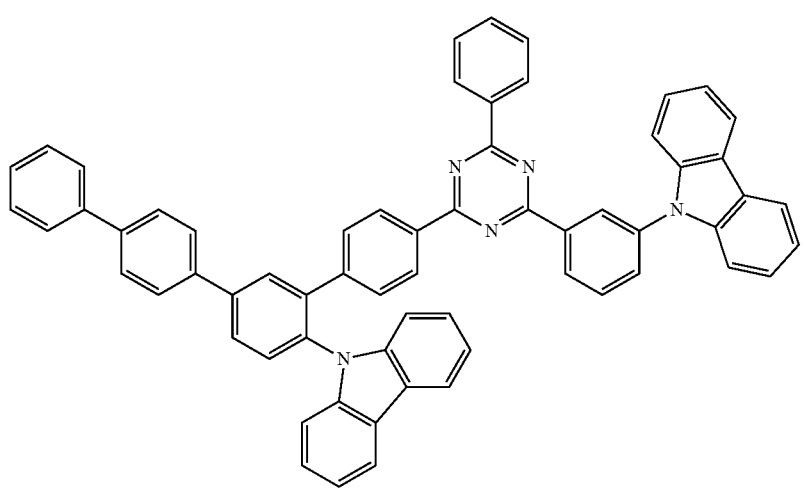

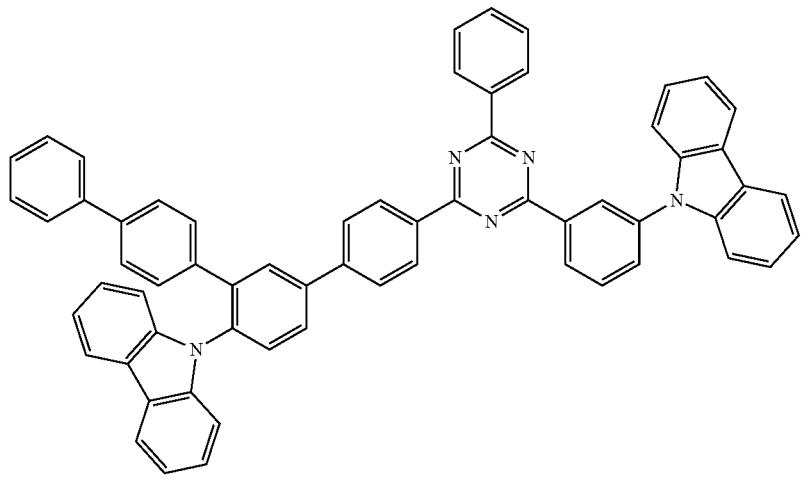
413
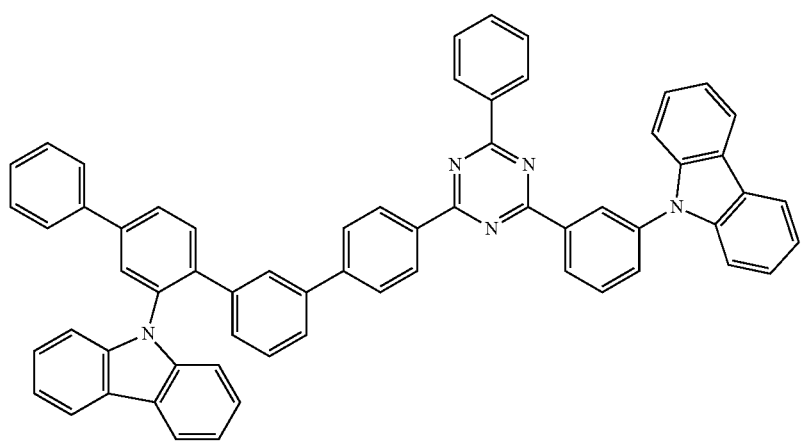
414
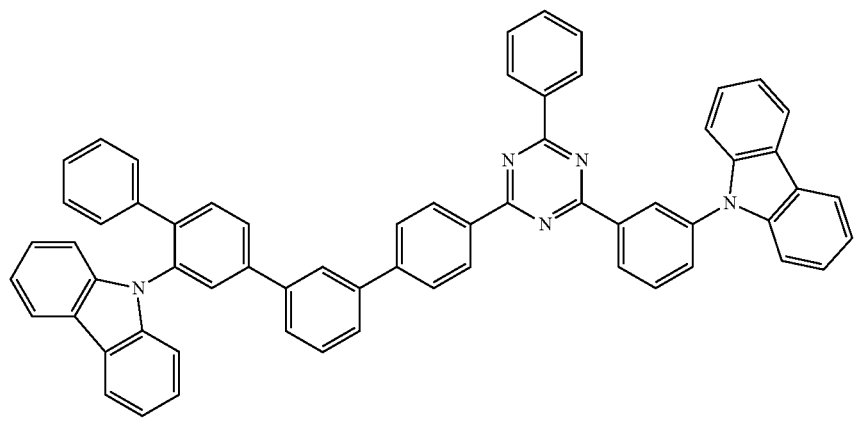
415

-continued
416
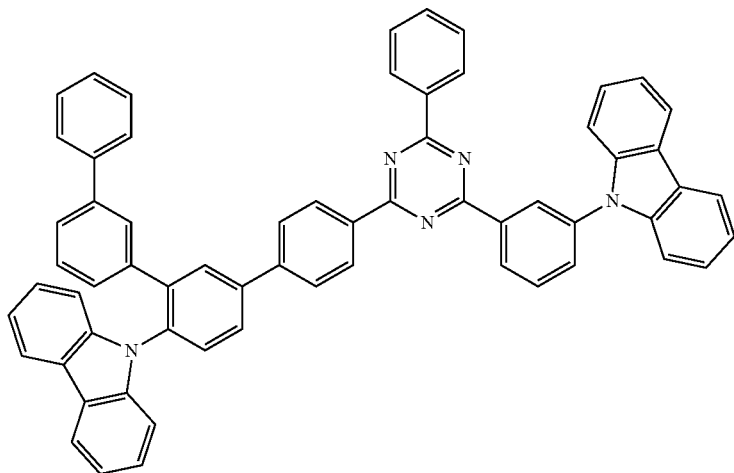
417
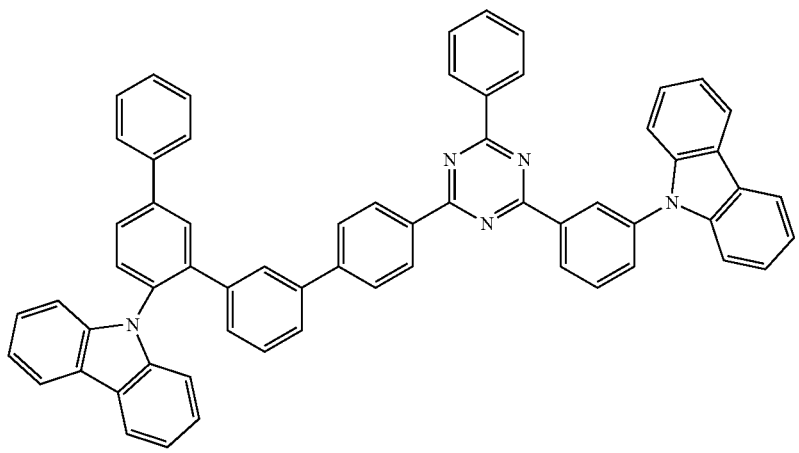
418
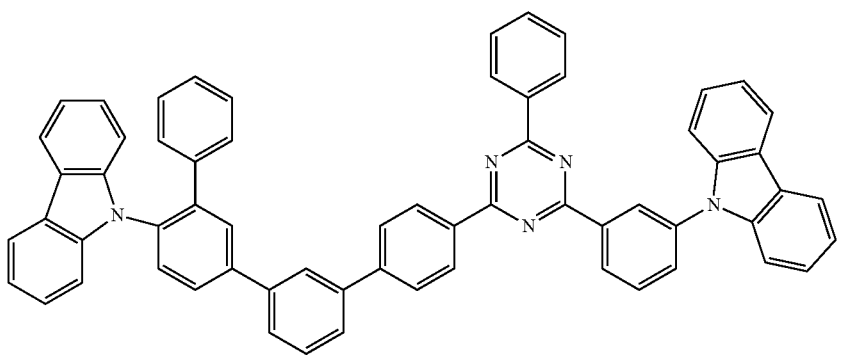
419 420
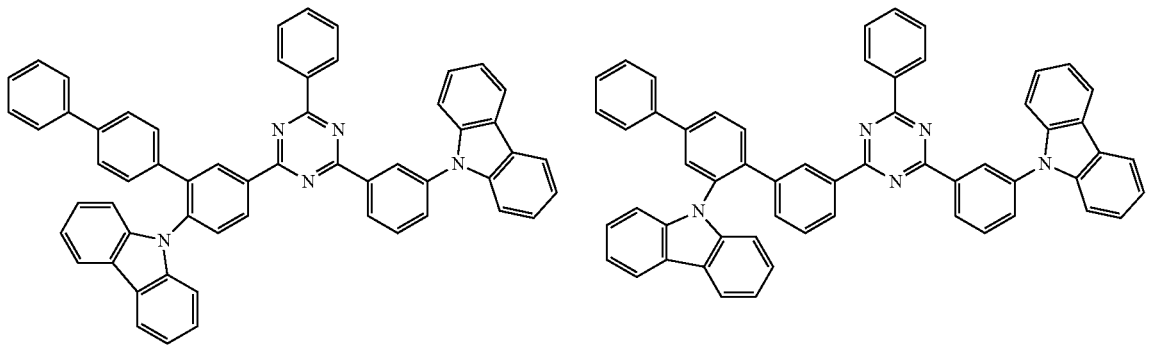

-continued
421
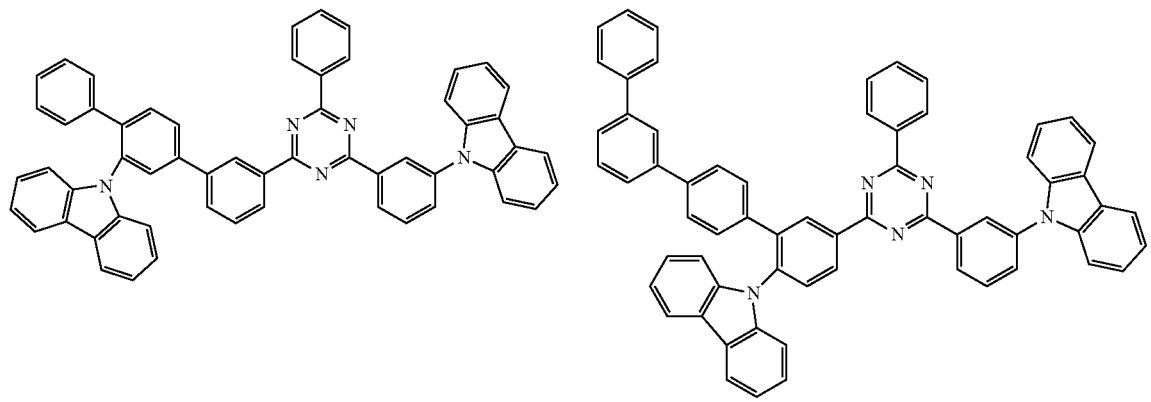
422
423
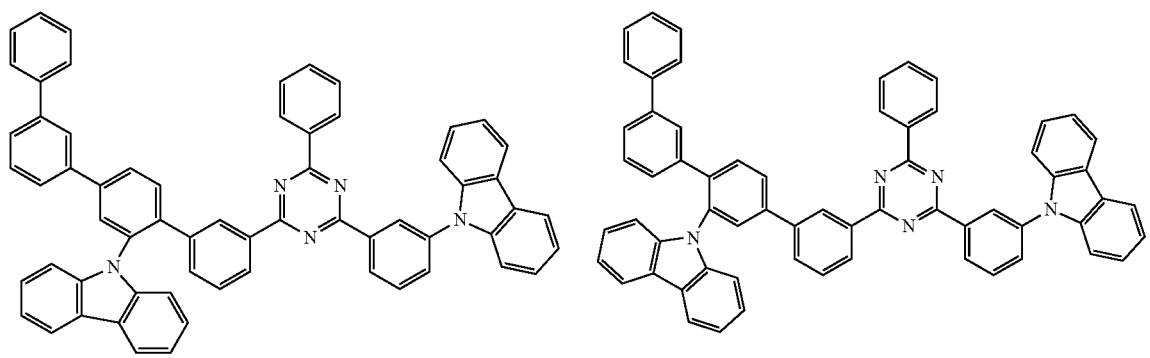
424
425
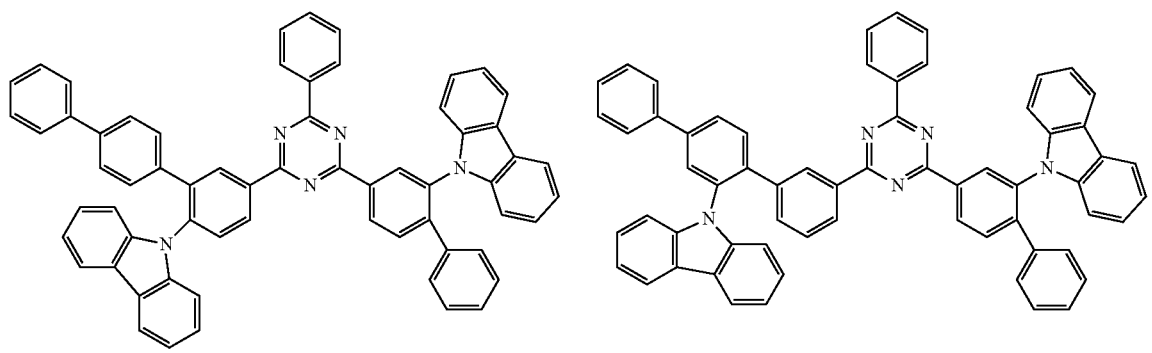
426
427
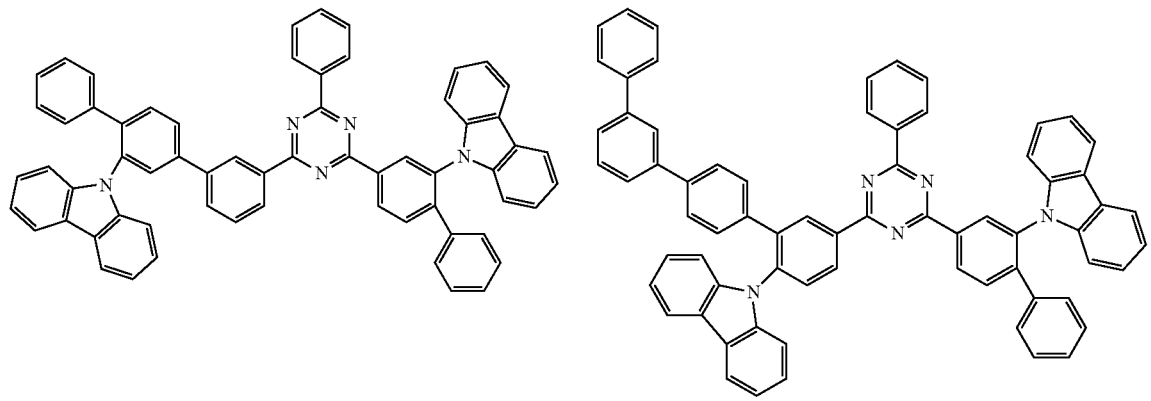
428

429
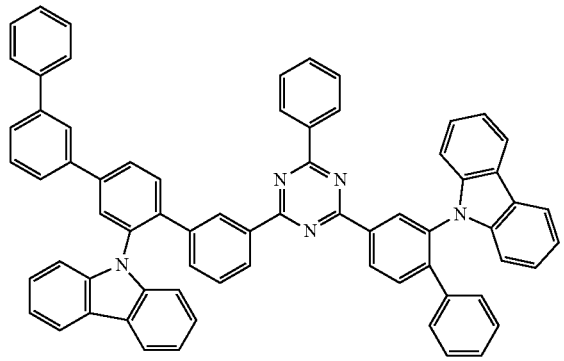
430
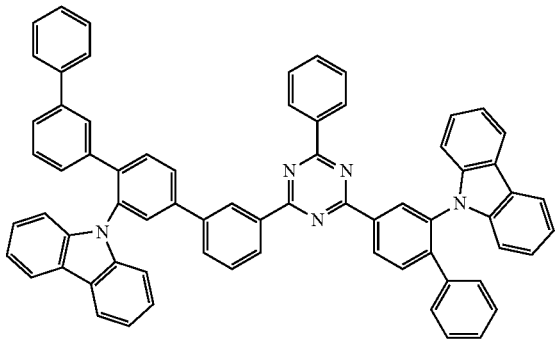
431
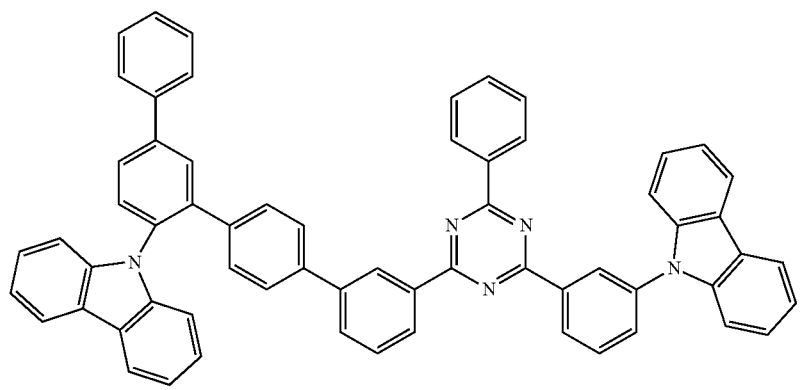
432
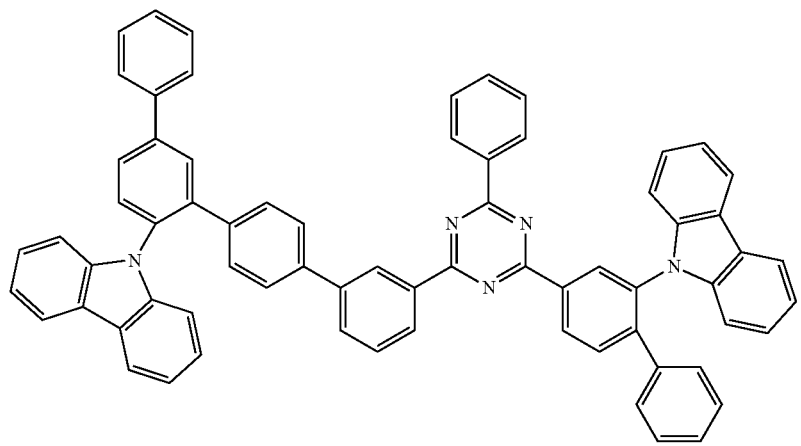

-continued
433
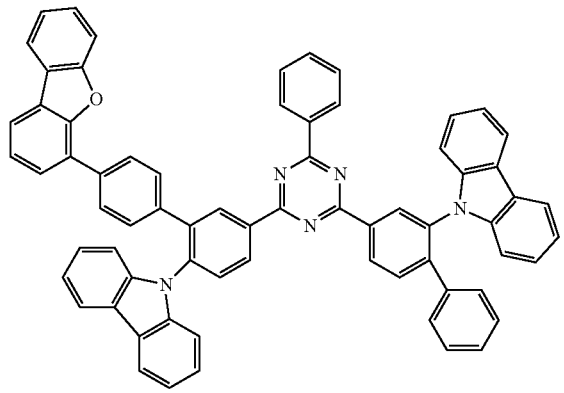
434
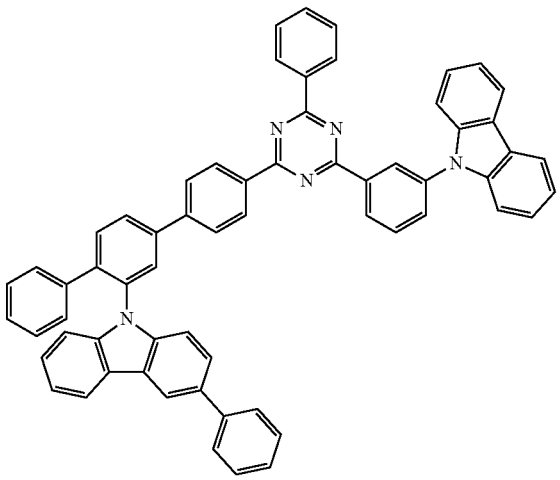
435
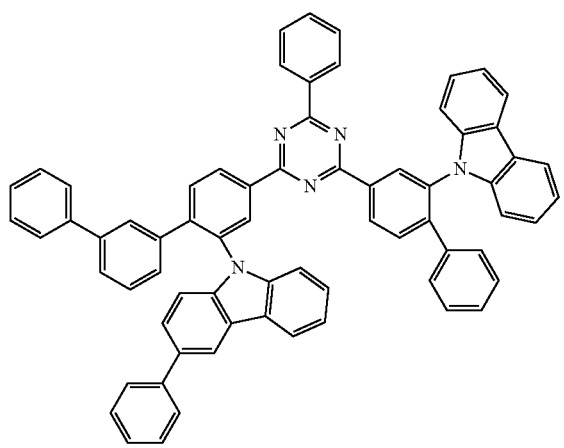
436
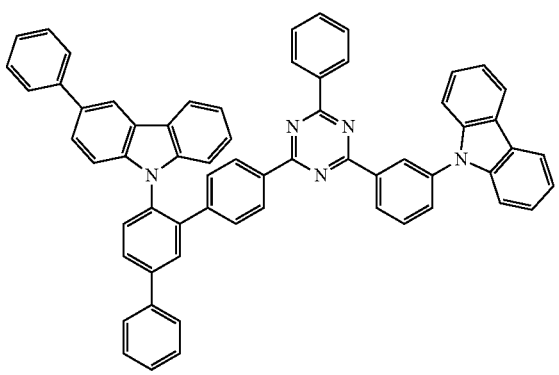
437
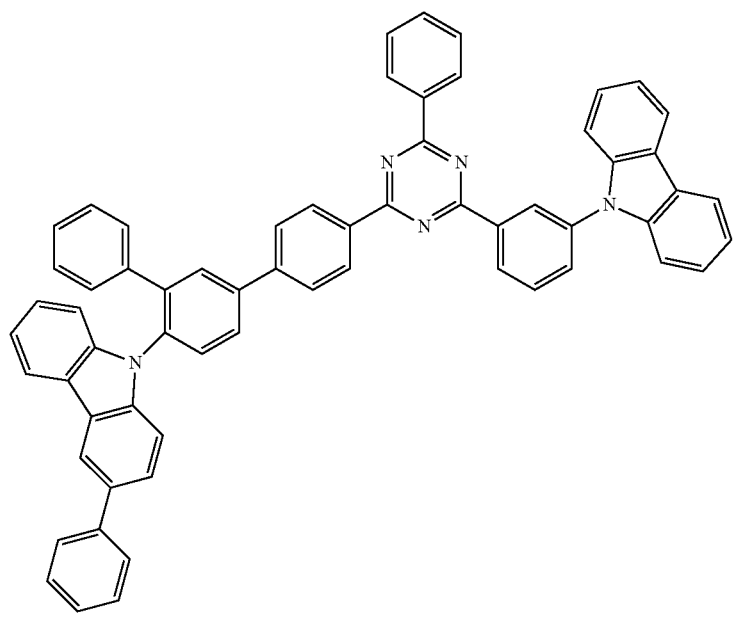

438
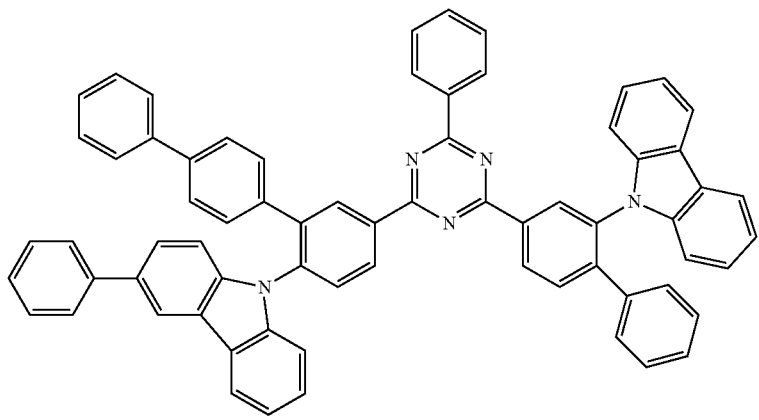
439
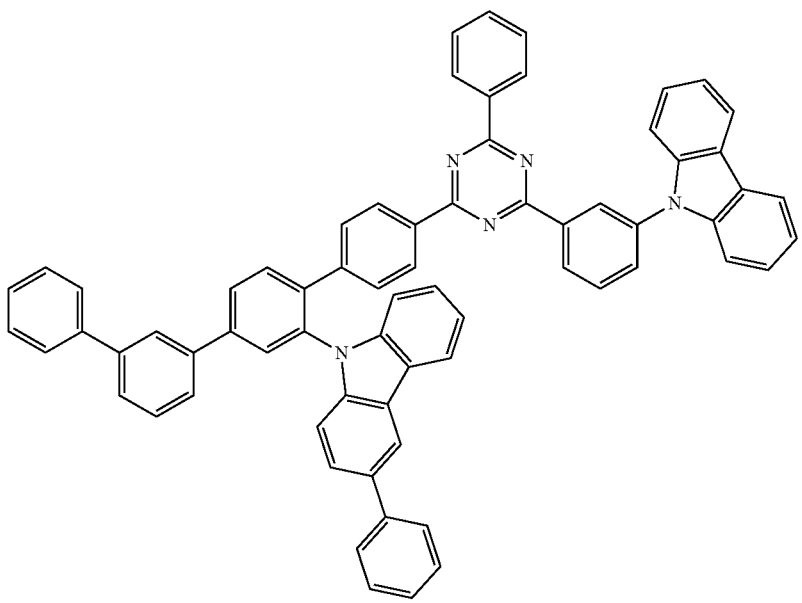
440
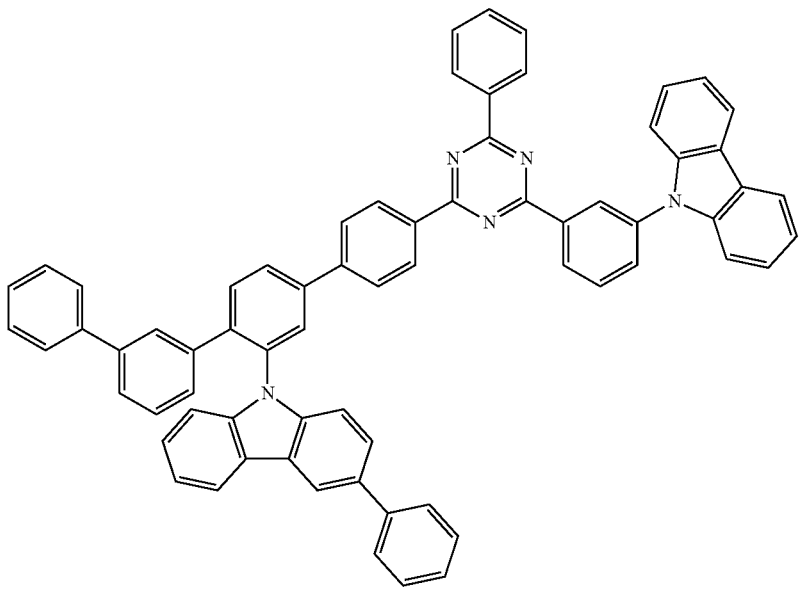

441
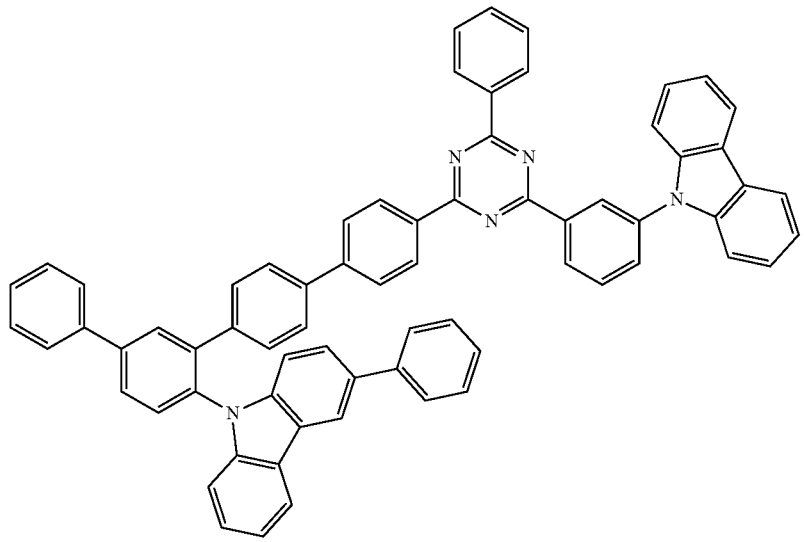
442
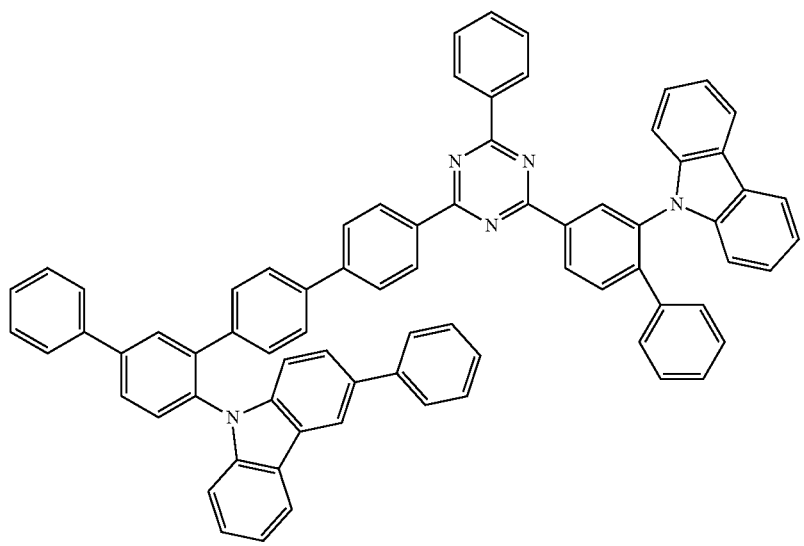
443
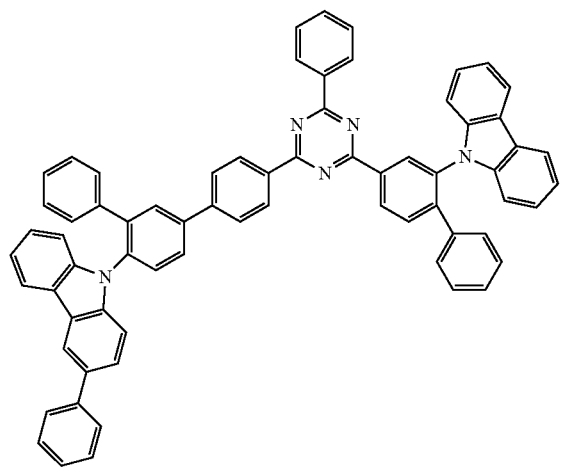
444
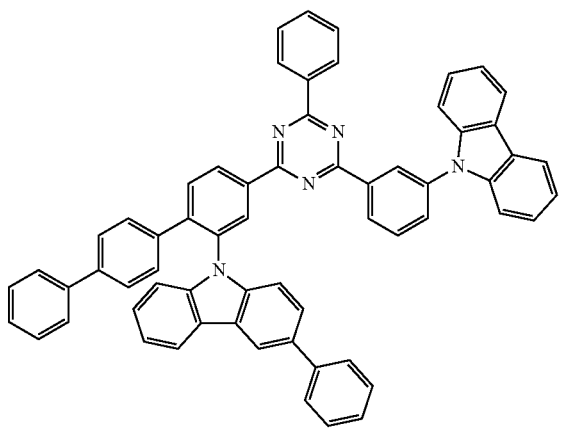

-continued
445
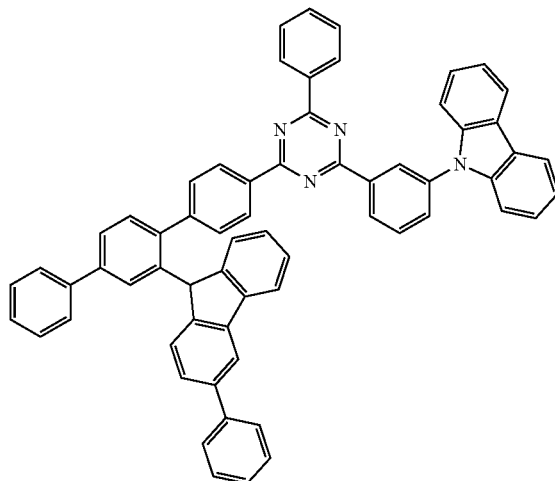
446
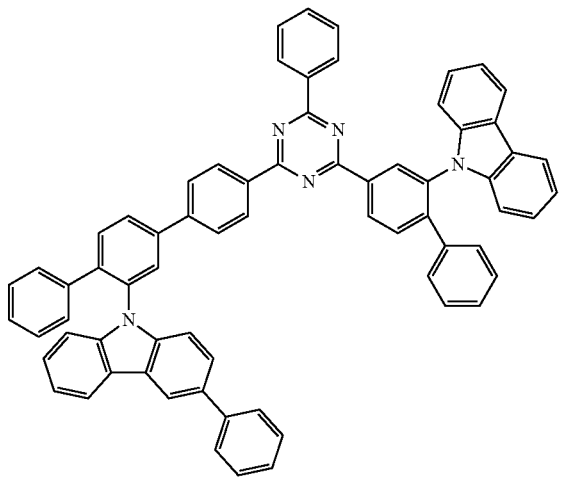
447
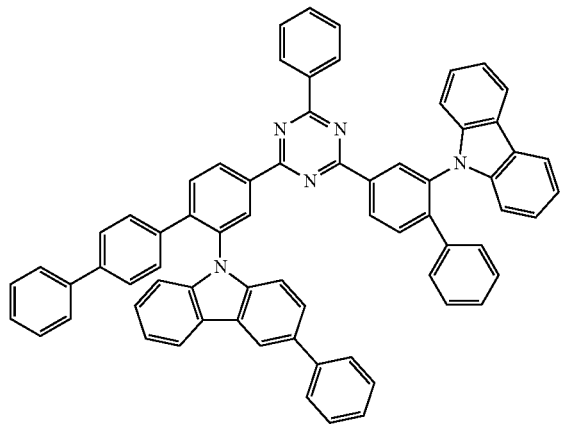
448
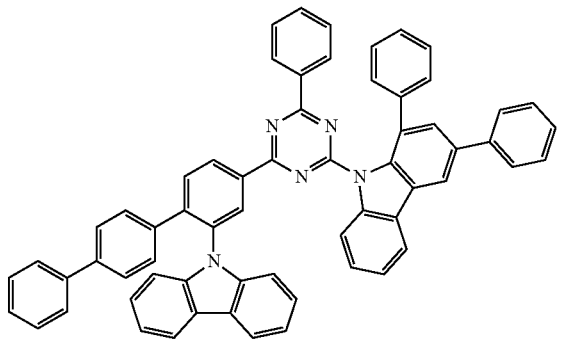
449
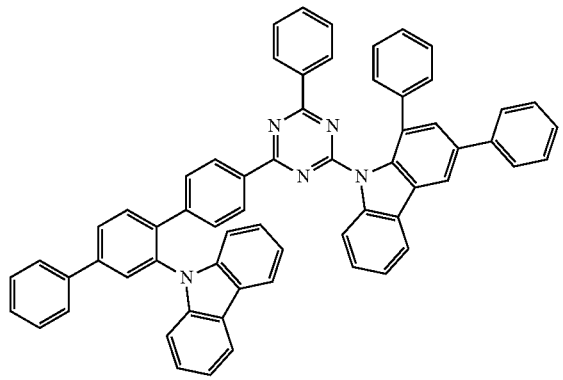
450
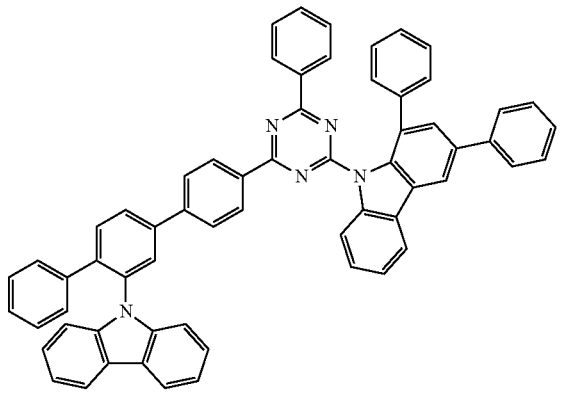

-continued
451 452
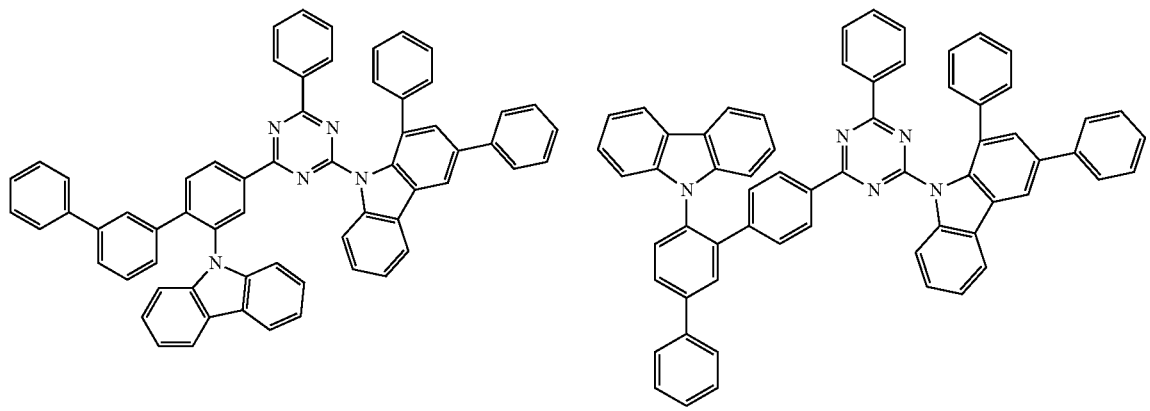
453 454
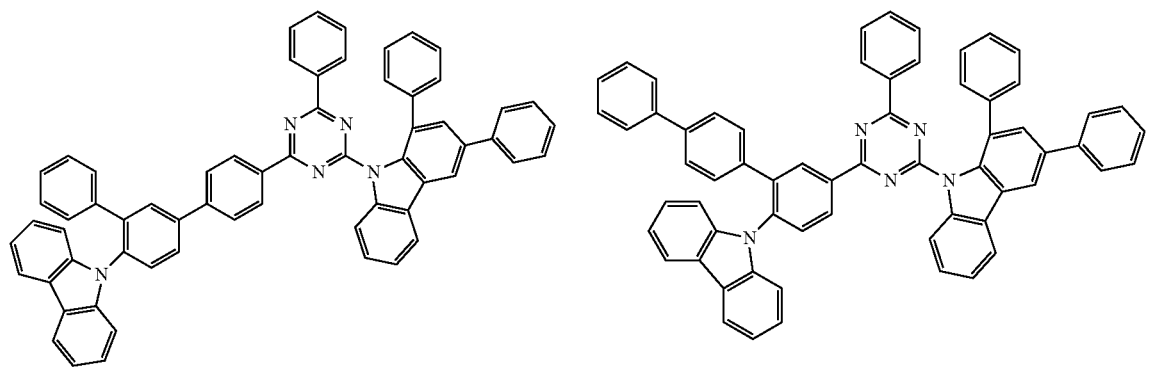
455
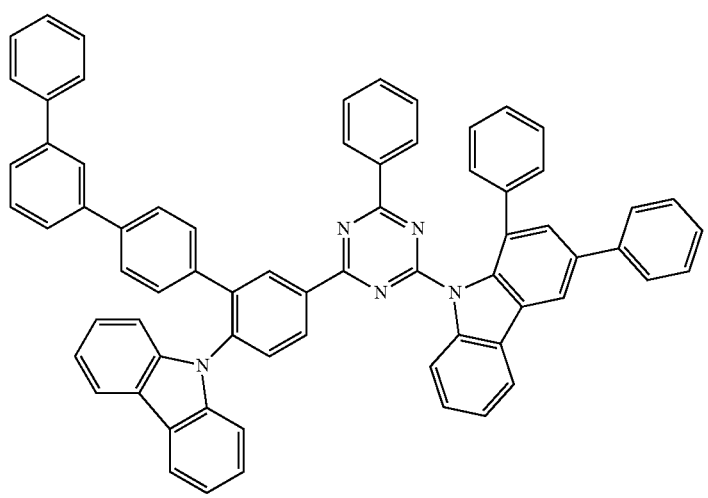

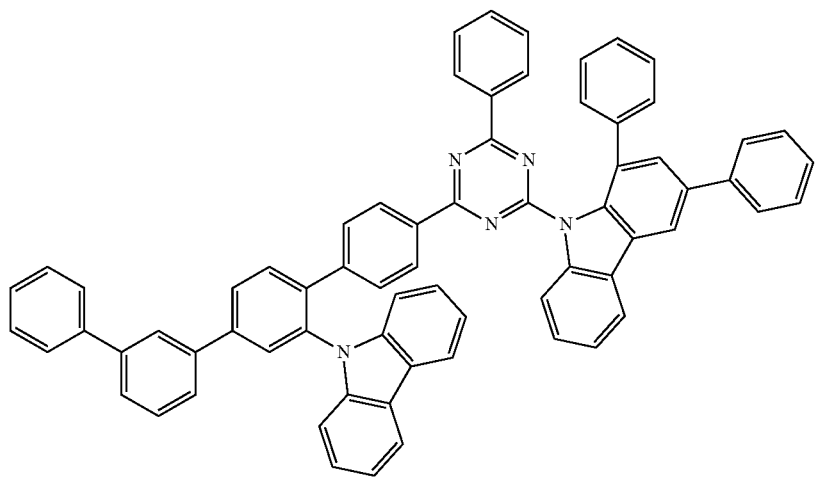
456
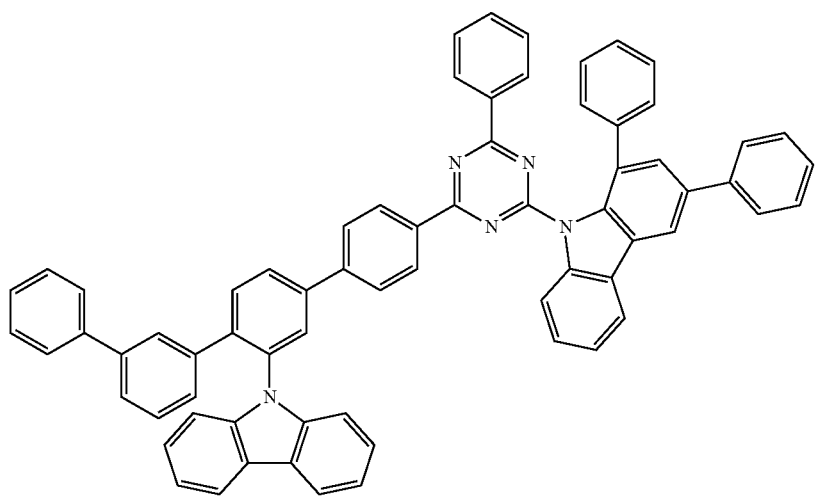
457
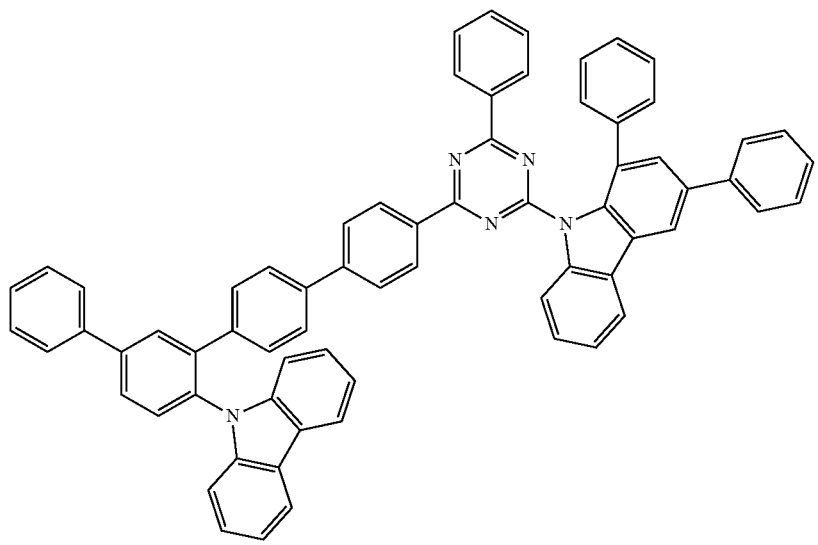
458

-continued
459
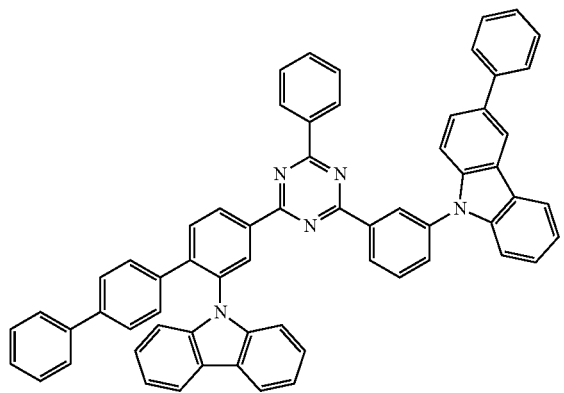
460
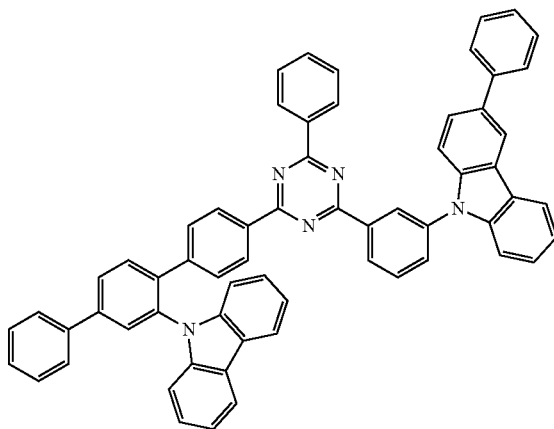
461
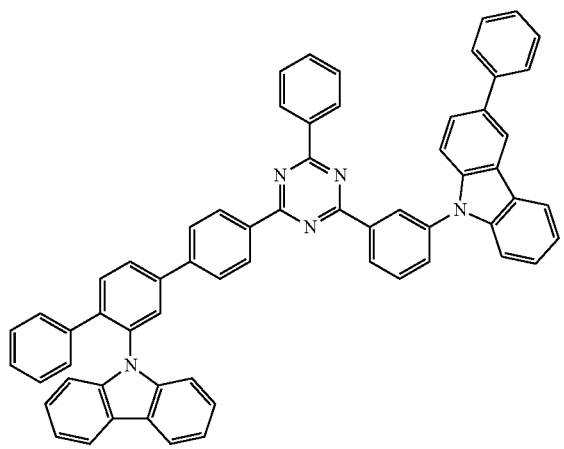
462
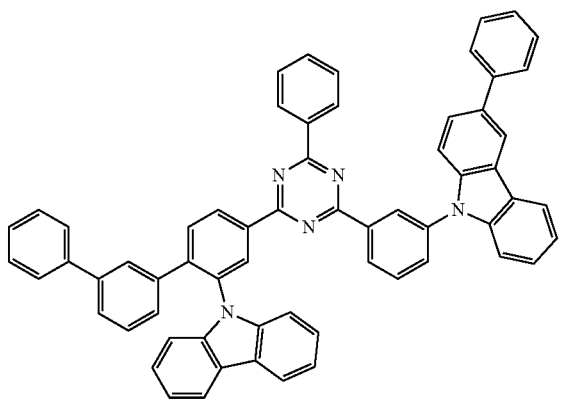
463
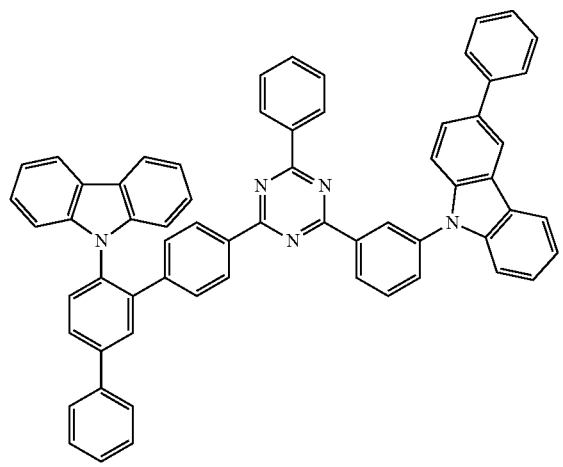
464
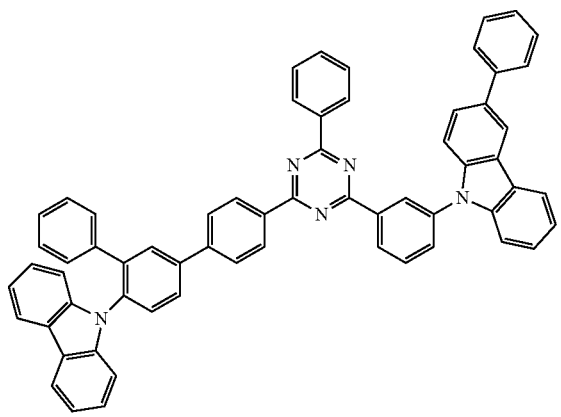

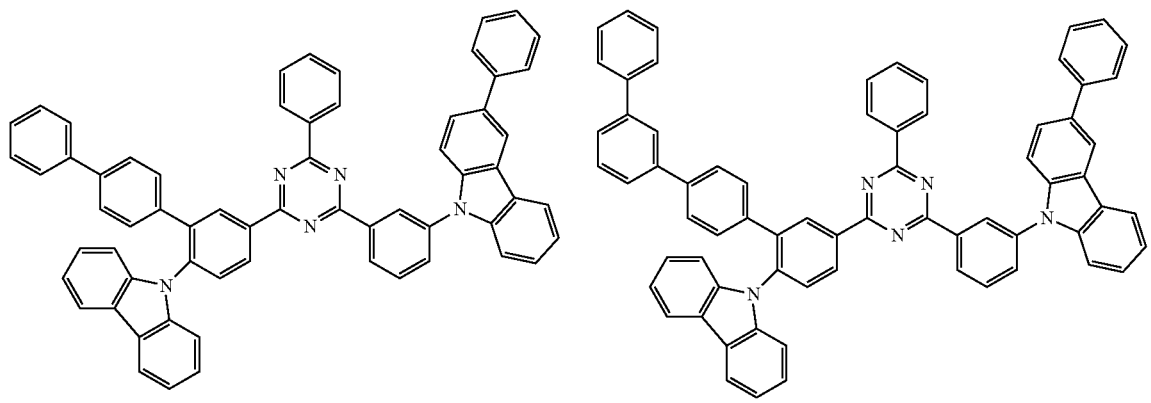
465
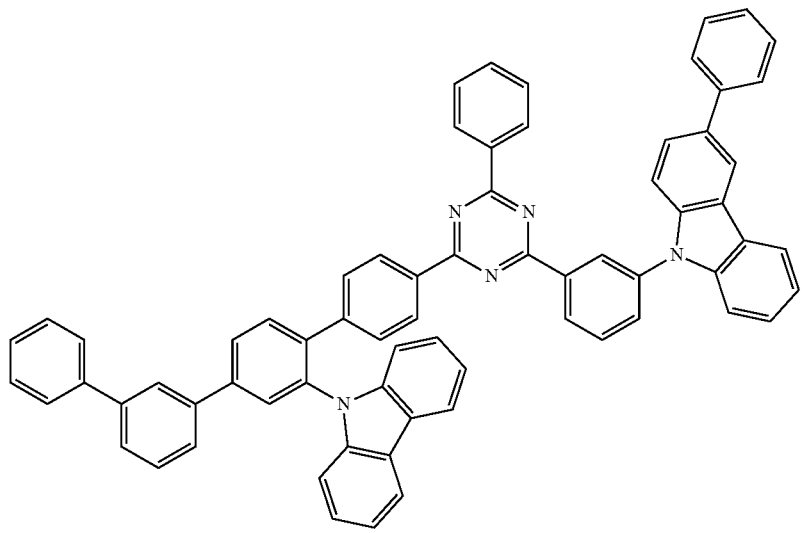
466
467
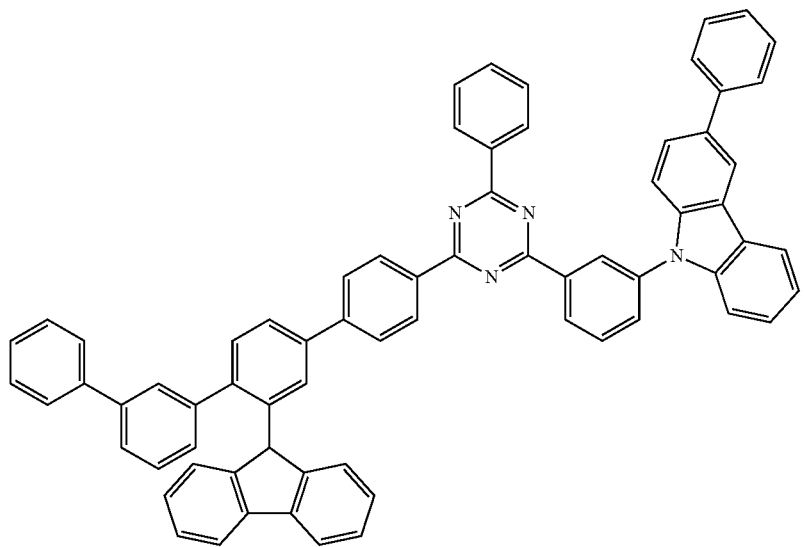
468

-continued
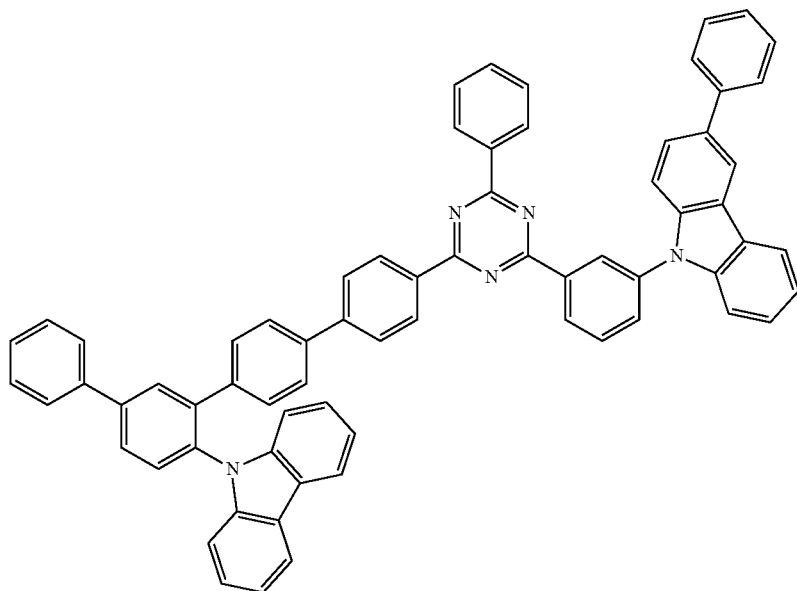
469
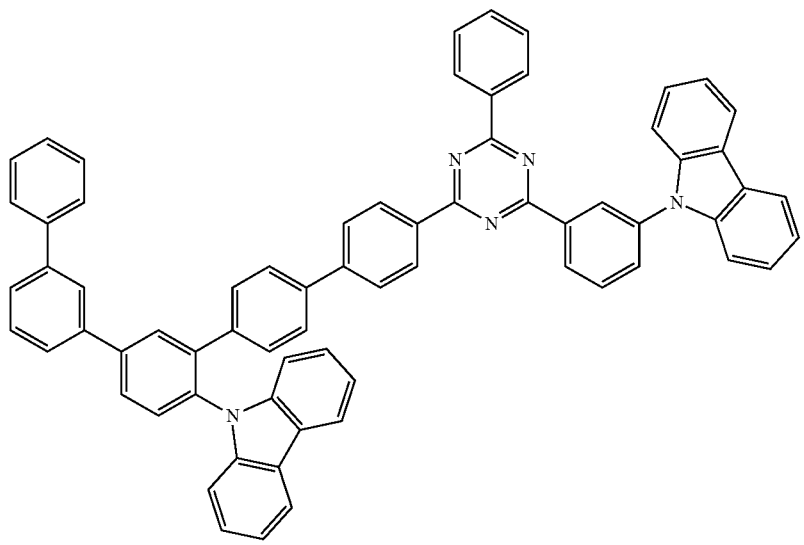
470

471
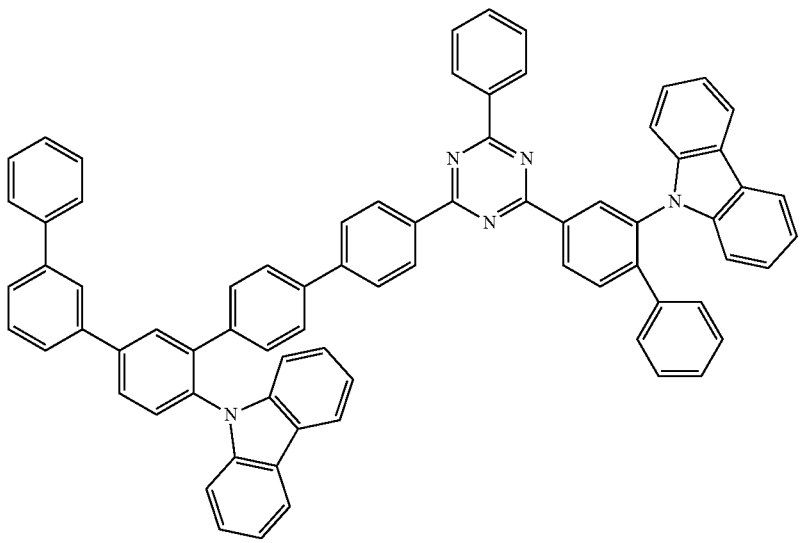
472 473
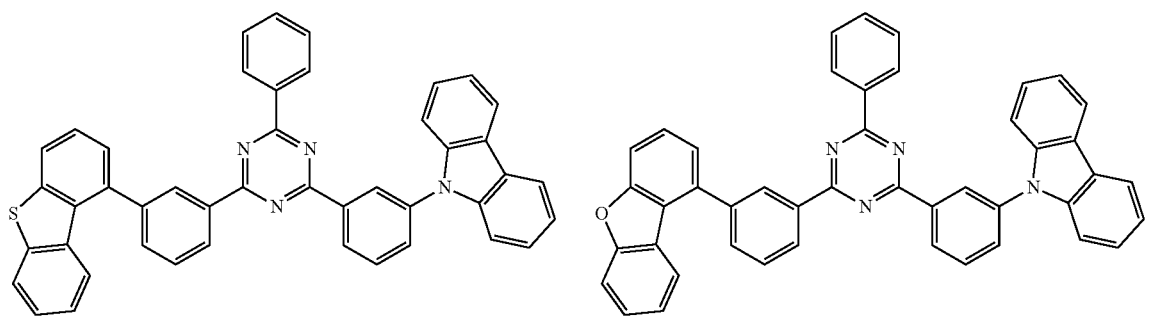
474 475
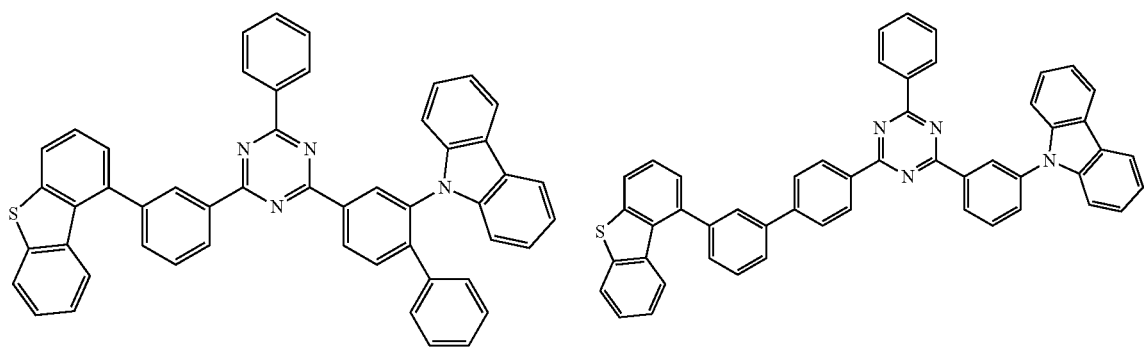
476 477
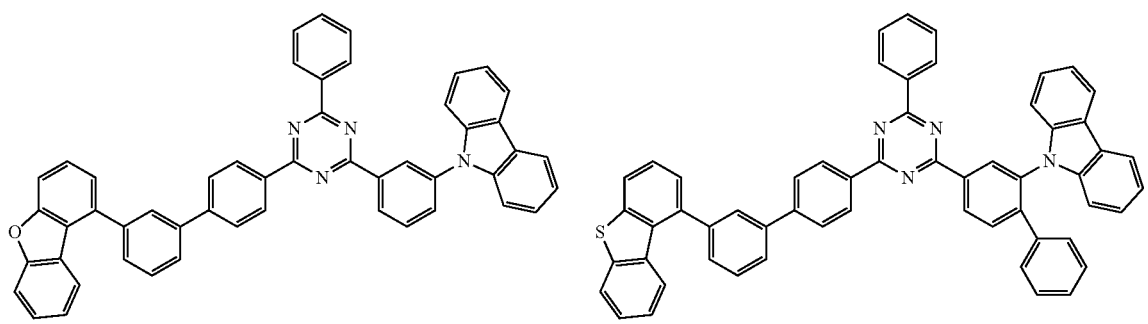

-continued
478
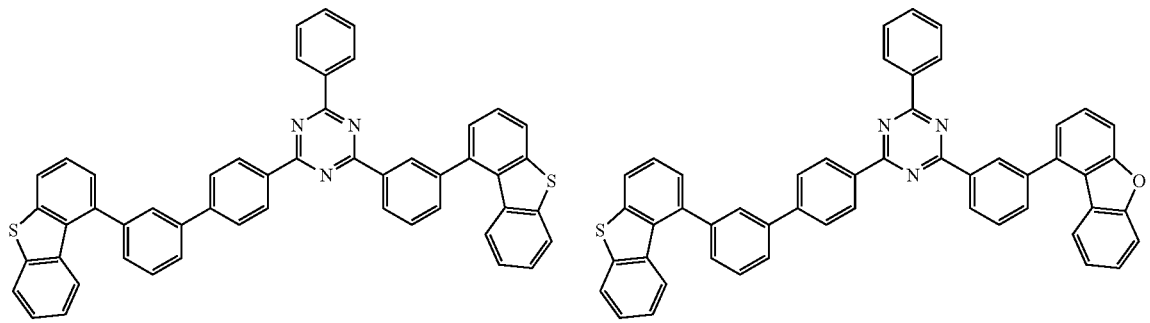
479
480
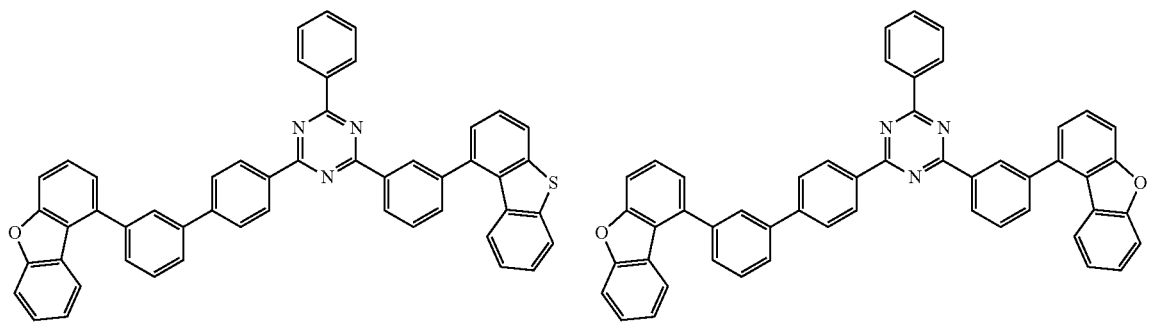
481
482
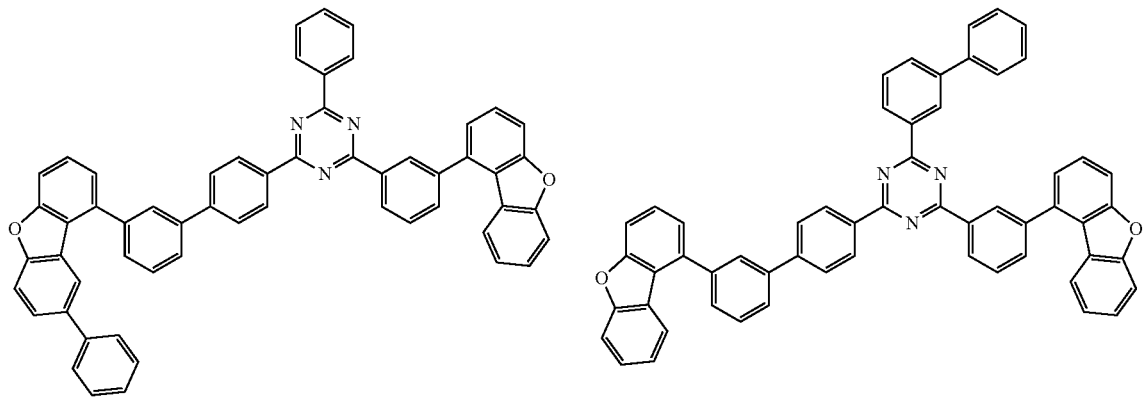
483
484
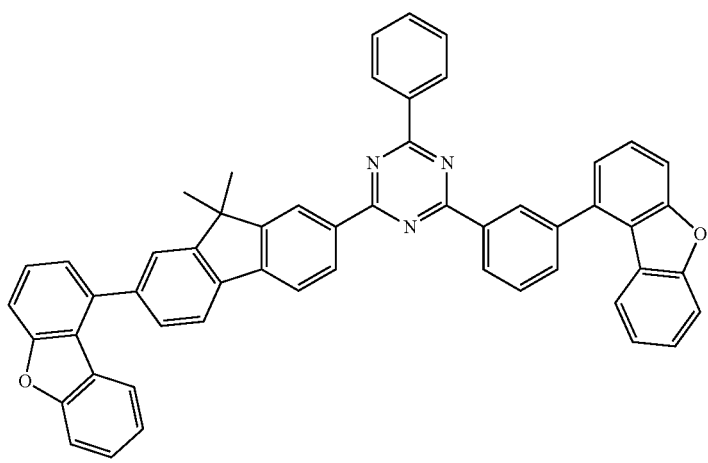

485
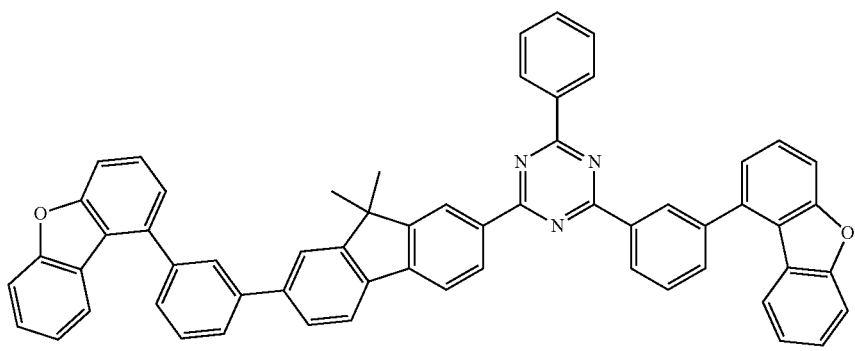
486
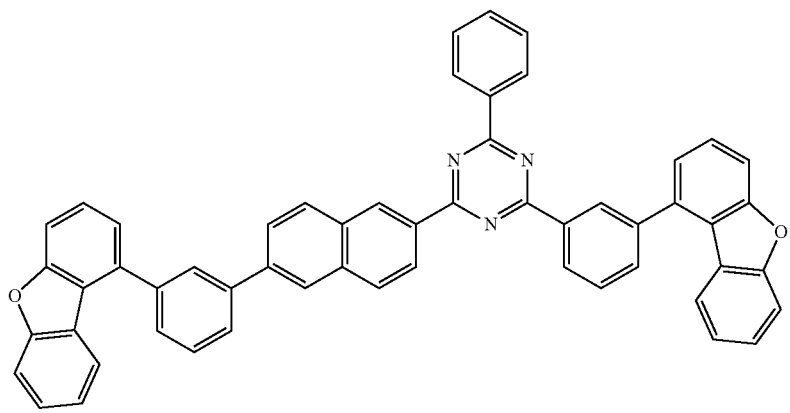
487 488
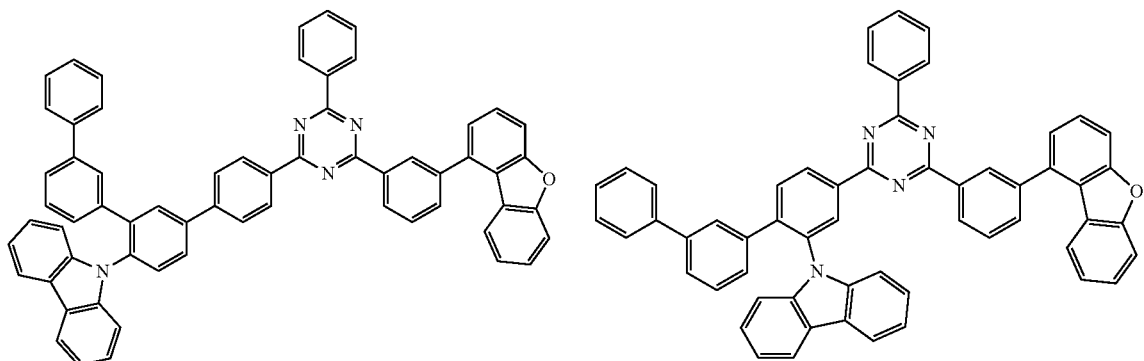
489
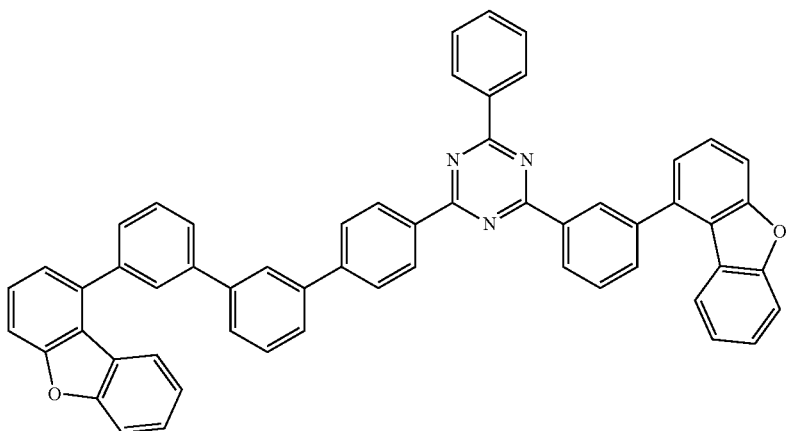

490
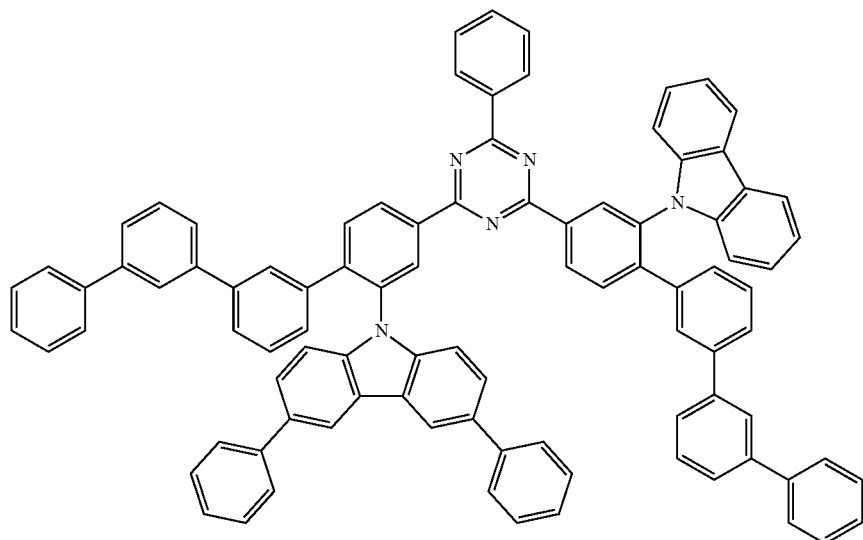
491
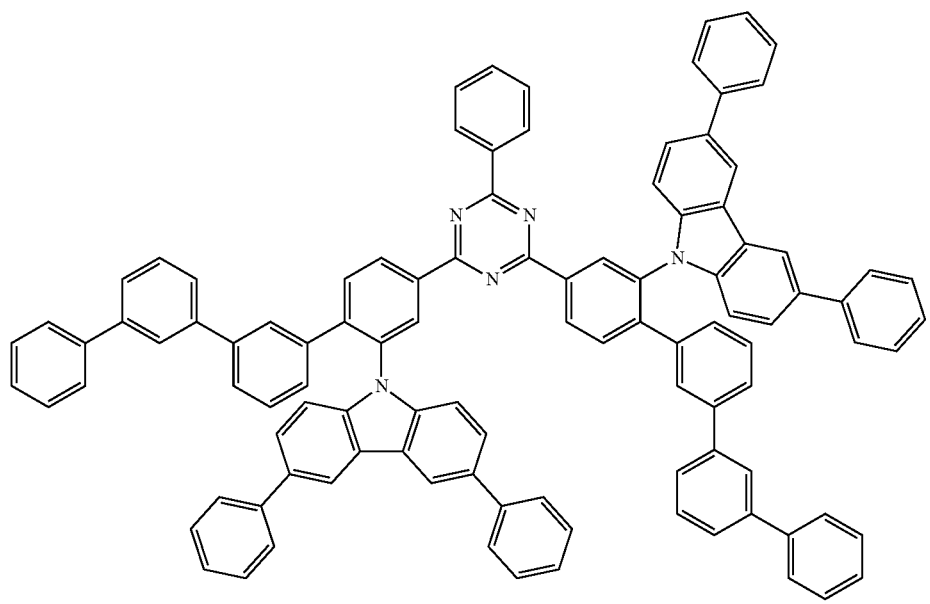
492
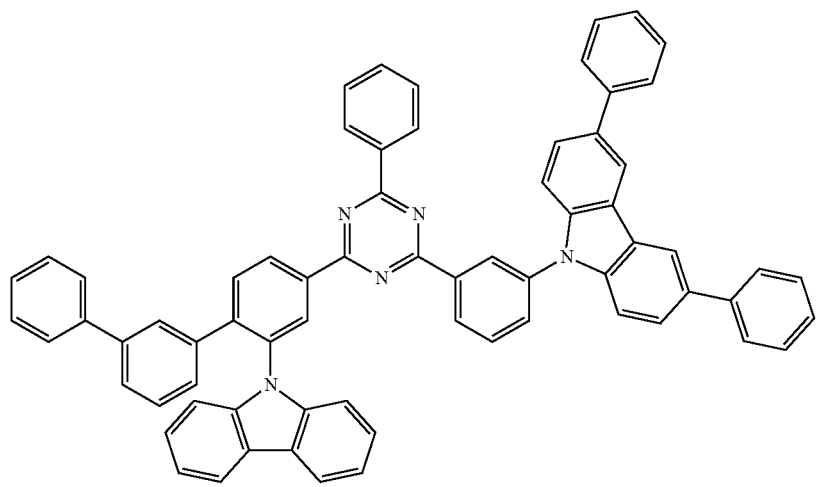

493
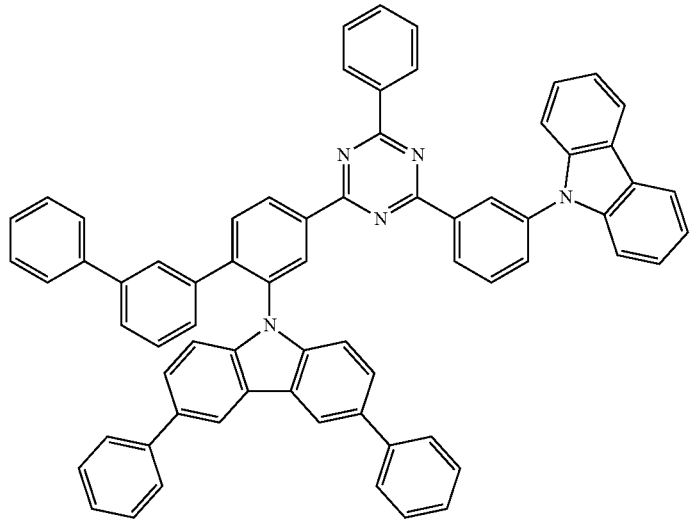
494
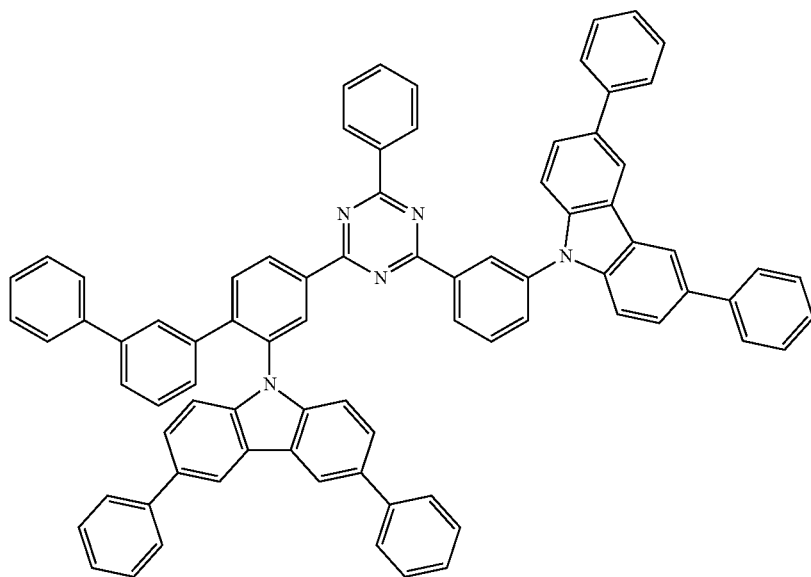
495
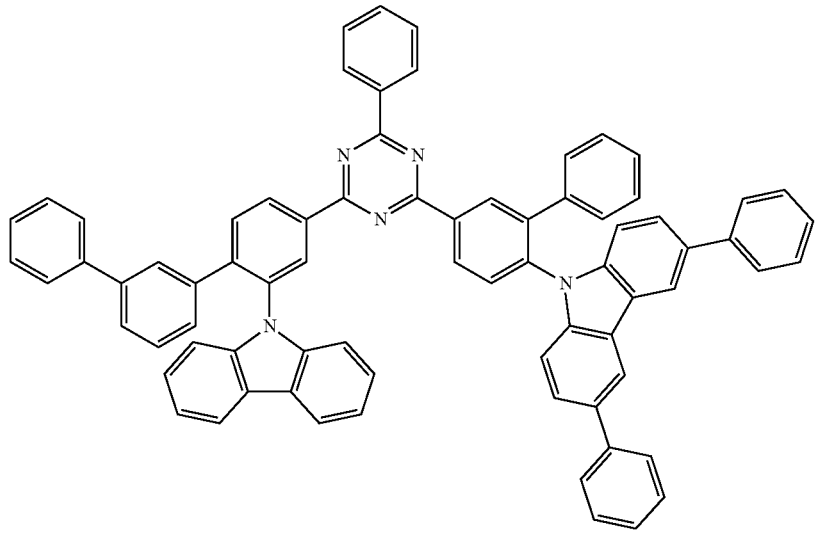

496
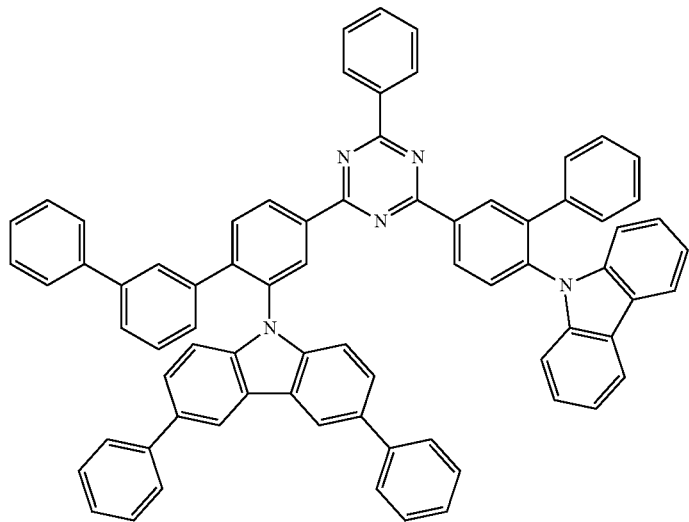
497
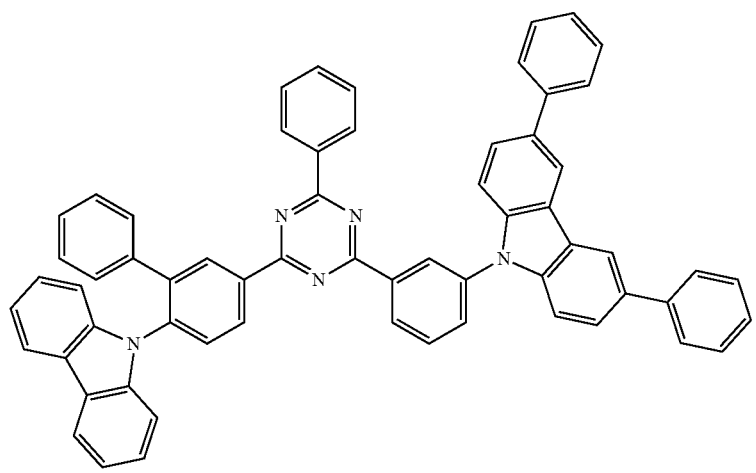
498
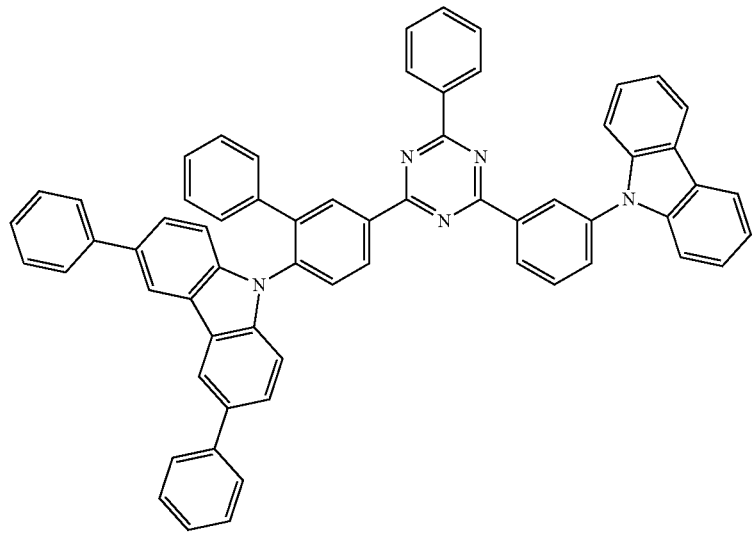

499
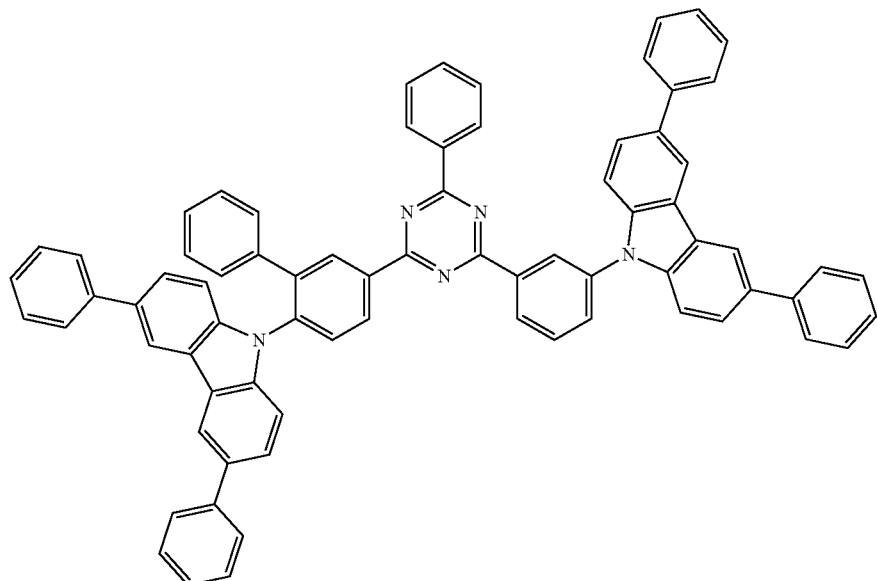
500
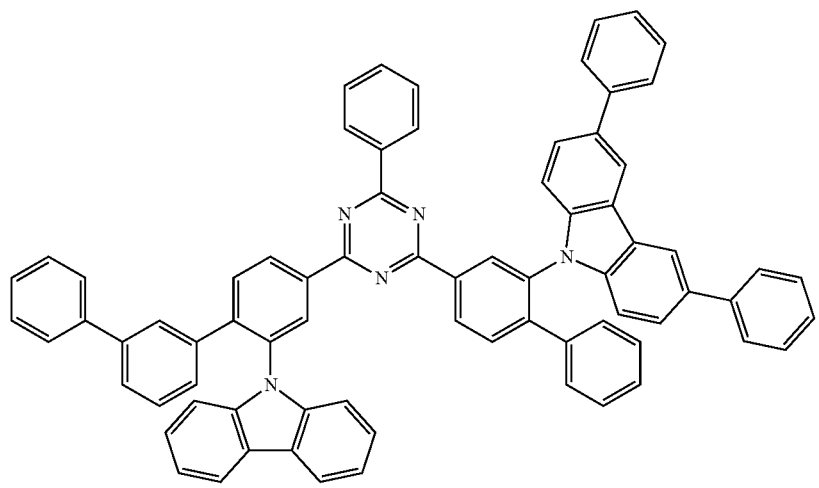
501
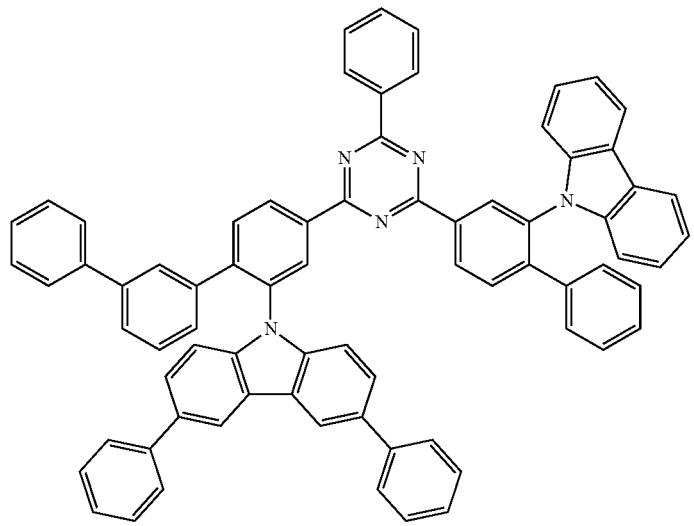

502
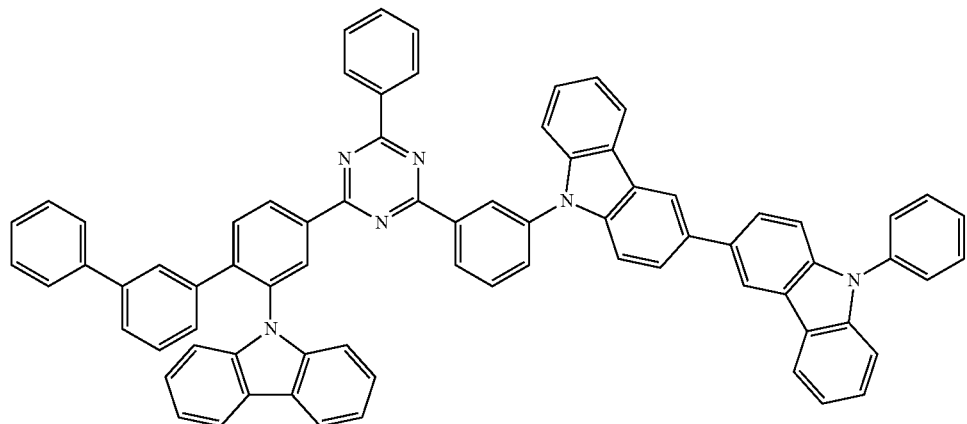
503
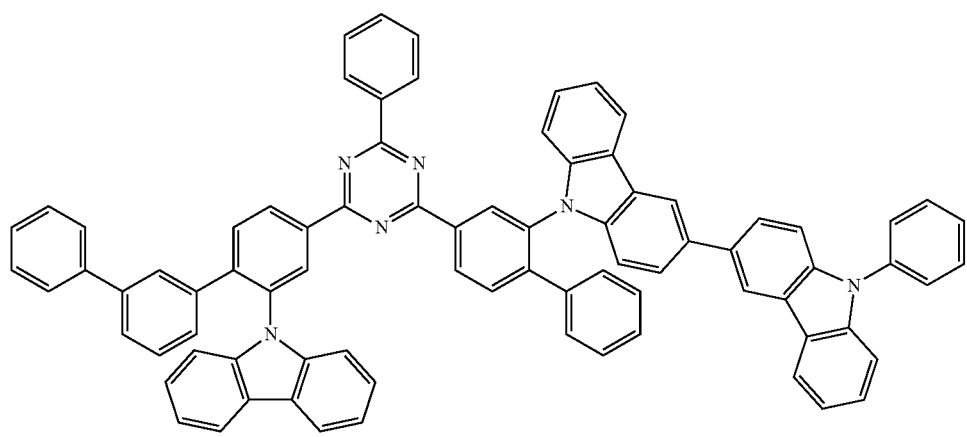
504
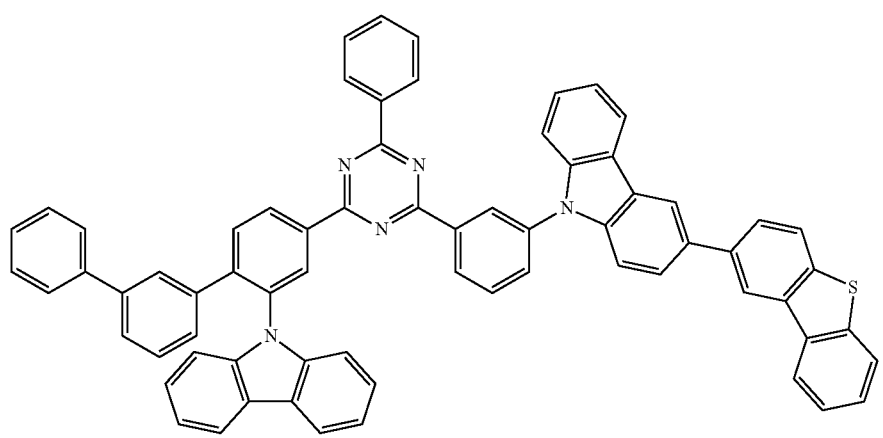

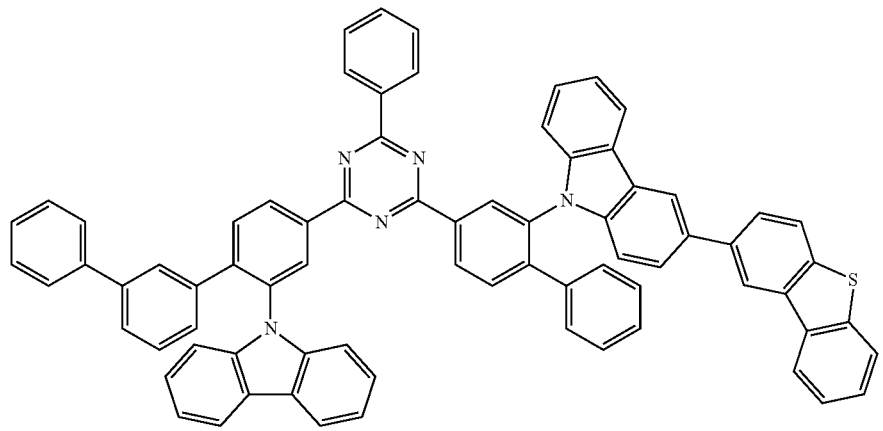
505
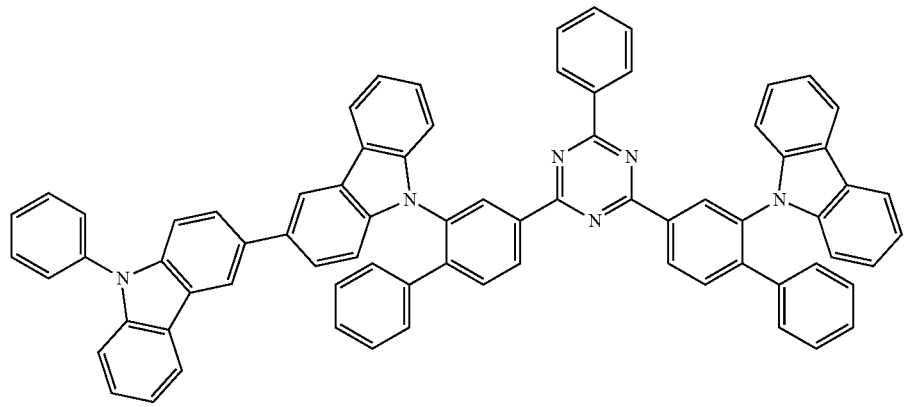
506
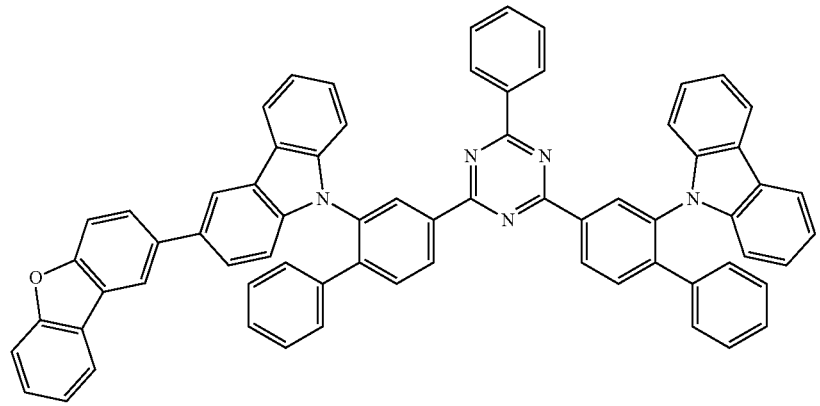
507

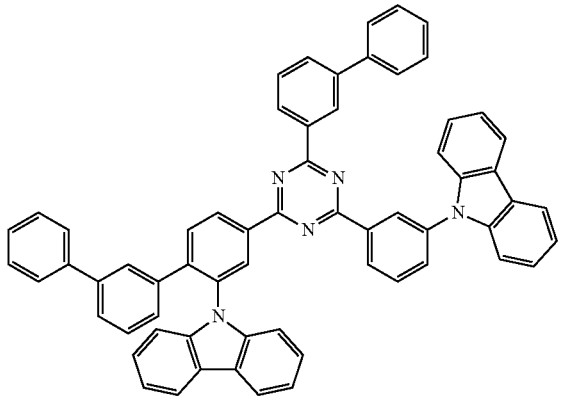

508

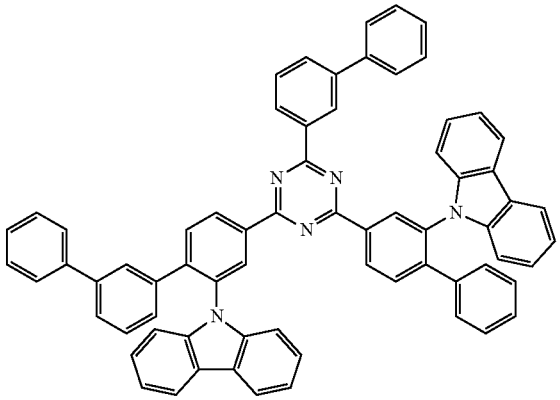

509

12. A composition comprising at least one of the heterocyclic compound represented by Formula 1 of claim 1.

13. The composition of claim 12, further comprising a first compound represented by Formula 5:

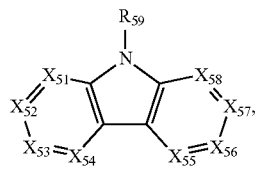

Formula 5 wherein, in Formula 5, $X_{51}$ is N or $C(R_{51})$; $X_{52}$ is N or $C(R_{52})$; $X_{53}$ is N or $C(R_{53})$; $X_{54}$ is N or $C(R_{54})$; $X_{55}$ is N or $C(R_{55})$; $X_{56}$ is N or $C(R_{56})$; $X_{57}$ is N or $C(R_{57})$; and $X_{58}$ is N or $C(R_{58})$, $X_{61}$ is N or $C(R_{61})$; $X_{62}$ is N or $C(R_{62})$; $X_{63}$ is N or $C(R_{63})$; $X_{64}$ is N or $C(R_{64})$; $X_{65}$ is N or $C(R_{65})$; $X_{66}$ is N or $C(R_{66})$, and at least one selected from $X_{61}$ to $X_{66}$ is N, $R_{51}$ to $R_{58}$ and $R_{61}$ to $R_{66}$ are each independently selected from hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and $R_{59}$ is selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

14. The composition of claim 12, further comprising a light-emitting material.

15. The composition of claim 12, further comprising a solvent.

16. An organic light-emitting device comprising:
a first electrode;
a second electrode; and
an organic layer disposed between the first electrode and the second electrode, wherein the organic layer comprises an emission layer, and
wherein the organic layer comprises at least one heterocyclic compound represented by Formula 1 of claim 1.

17. The organic light-emitting device of claim 16,
the organic layer further comprises a light-emitting material, and
the light-emitting material emits light from triplet excitons.

* * * * *